US010143734B2

(12) United States Patent
Petit

(10) Patent No.: US 10,143,734 B2
(45) Date of Patent: Dec. 4, 2018

(54) BIOMARKER DIRECTED MULTI-TARGET IMMUNOTHERAPY

(71) Applicant: Advaxis, Inc., Princeton, NJ (US)

(72) Inventor: Robert Petit, Newtown, PA (US)

(73) Assignee: Advaxis, Inc., Princeton, NJ (US)

( * ) Notice: Subject to any disclaimer, the term of this patent is extended or adjusted under 35 U.S.C. 154(b) by 118 days.

(21) Appl. No.: 15/119,661

(22) PCT Filed: Feb. 18, 2015

(86) PCT No.: PCT/US2015/016348

§ 371 (c)(1),
(2) Date: Aug. 17, 2016

(87) PCT Pub. No.: WO2015/126921

PCT Pub. Date: Aug. 27, 2015

(65) Prior Publication Data

US 2017/0106072 A1 Apr. 20, 2017

Related U.S. Application Data

(60) Provisional application No. 61/941,072, filed on Feb. 18, 2014.

(51) Int. Cl.

| | |
|---|---|
| ***A61K 39/02*** | (2006.01) |
| ***C12Q 1/6886*** | (2018.01) |
| ***G01N 33/574*** | (2006.01) |
| ***A61K 45/06*** | (2006.01) |
| ***A61K 39/00*** | (2006.01) |
| ***C07K 14/195*** | (2006.01) |

(52) U.S. Cl.

CPC ...... *A61K 39/0208* (2013.01); *A61K 39/0011* (2013.01); *A61K 45/06* (2013.01); *C07K 14/195* (2013.01); *C12Q 1/6886* (2013.01); *G01N 33/574* (2013.01); *A61K 2039/52* (2013.01); *A61K 2039/53* (2013.01); *C07K 2319/95* (2013.01); *C12Q 2600/158* (2013.01)

(58) Field of Classification Search

None

See application file for complete search history.

(56) References Cited

U.S. PATENT DOCUMENTS 5,830,702 A 11/1998 Portnoy et al.
6,051,237 A 4/2000 Paterson
6,099,848 A 8/2000 Frankel et al.
6,504,020 B1 1/2003 Frankel et al.
6,565,852 B1 5/2003 Paterson
6,635,749 B2 10/2003 Frankel
6,767,542 B2 7/2004 Paterson et al.
6,855,320 B2 2/2005 Paterson
7,135,188 B2 11/2006 Paterson
7,488,487 B2 2/2009 Frankel et al.
7,588,930 B2 9/2009 Paterson et al.
7,635,479 B2 12/2009 Paterson et al.
7,655,238 B2 2/2010 Paterson et al.
7,662,396 B2 2/2010 Paterson et al.
7,700,344 B2 4/2010 Paterson et al.
7,794,729 B2 9/2010 Paterson et al.
7,820,180 B2 10/2010 Singh et al.
7,855,064 B2 12/2010 Paterson et al.
7,858,097 B2 12/2010 Paterson et al.
8,114,414 B2 2/2012 Paterson et al.
8,241,636 B2 8/2012 Paterson et al.
8,268,326 B2 9/2012 Paterson et al.
8,337,861 B2 12/2012 Paterson et al.
8,771,702 B2 7/2014 Paterson et al.
8,778,329 B2 7/2014 Seavey et al.
8,791,237 B2 7/2014 Paterson et al.
8,906,664 B2 12/2014 Paterson et al.
8,956,621 B2 2/2015 Paterson et al.
9,012,141 B2 4/2015 Paterson et al.
9,017,660 B2 4/2015 Shahabi et al.
9,084,747 B2 7/2015 Shahabi et al.
9,226,958 B2 1/2016 Harn, Jr. et al.
9,408,898 B2 8/2016 Seavey et al.
9,463,227 B2 10/2016 Rothman et al.
9,492,527 B2 11/2016 Paterson et al.
9,499,602 B2 11/2016 Paterson et al.
9,549,973 B2 1/2017 Paterson et al.
9,644,212 B2 5/2017 Maciag et al.
9,650,639 B2 5/2017 Maciag et al.
9,700,608 B2 7/2017 Paterson et al.
(Continued)

FOREIGN PATENT DOCUMENTS

WO WO 1996/014087 A1 5/1996
WO WO 2008/140812 A2 5/1996
(Continued)

OTHER PUBLICATIONS

Supplementary European Search Report for application EP15751948.9 dated Sep. 7, 2017.

(Continued)

*Primary Examiner* — Brian Gangle
(74) *Attorney, Agent, or Firm* — Alston & Bird LLP

(57) ABSTRACT

This invention provides methods and compositions for using evaluating biomarker expression in a disease and providing a multi-targeted *Listeria*-based immunotherapeutic approach against said disease. In a related aspect, the invention relates to a method of treating a disease in a subject, the method comprising the steps of: a. obtaining a biological sample from said subject; b. evaluating the expression of a predetermined number of biomarkers in said biological sample; c. administering to said subject a composition comprising a recombinant *Listeria* strain, said strain comprising a nucleic acid sequence encoding at least one fusion protein, wherein said fusion protein comprises a biomarker identified in said biological sample, wherein said biomarker is associated with said disease, wherein said biomarker is fused to a PEST-containing polypeptide, and wherein each fusion protein within said *Listeria* comprises a different biomarker, thereby treating said disease in said subject.

29 Claims, 107 Drawing Sheets

Specification includes a Sequence Listing.

(56) References Cited

U.S. PATENT DOCUMENTS

| | | | |
|---|---|---|---|
| 2002/0025323 | A1 | 2/2002 | Paterson et al. |
| 2002/0028206 | A1 | 3/2002 | Paterson |
| 2002/0136737 | A1 | 9/2002 | Frankel |
| 2003/0202985 | A1 | 10/2003 | Paterson |
| 2005/0048081 | A1 | 3/2005 | Frankel et al. |
| 2005/0118184 | A1 | 6/2005 | Paterson et al. |
| 2005/0129715 | A1 | 6/2005 | Paterson et al. |
| 2006/0093582 | A1 | 5/2006 | Paterson et al. |
| 2006/0104991 | A1 | 5/2006 | Paterson et al. |
| 2006/0204516 | A1 | 9/2006 | Paterson et al. |
| 2006/0205067 | A1 | 9/2006 | Paterson et al. |
| 2006/0210540 | A1 | 9/2006 | Paterson et al. |
| 2006/0233835 | A1 | 10/2006 | Paterson et al. |
| 2006/0269561 | A1 | 11/2006 | Paterson et al. |
| 2007/0003567 | A1 | 1/2007 | Paterson et al. |
| 2007/0253976 | A1 | 11/2007 | Paterson et al. |
| 2007/0264279 | A1 | 11/2007 | Gravekamp et al. |
| 2008/0131456 | A1 | 6/2008 | Paterson et al. |
| 2009/0081248 | A1 | 3/2009 | Paterson et al. |
| 2009/0081250 | A1 | 3/2009 | Paterson et al. |
| 2009/0186051 | A1 | 7/2009 | Paterson et al. |
| 2009/0202587 | A1 | 8/2009 | Paterson et al. |
| 2010/0189739 | A1 | 7/2010 | Paterson et al. |
| 2010/0291140 | A1 | 11/2010 | Paterson et al. |
| 2011/0129499 | A1 | 6/2011 | Maciag et al. |
| 2011/0142791 | A1 | 6/2011 | Shahabi |
| 2011/0305724 | A1 | 12/2011 | Paterson et al. |
| 2012/0014984 | A1 | 1/2012 | Shahabi |
| 2012/0114685 | A1 | 5/2012 | Seavey et al. |
| 2012/0135033 | A1 | 5/2012 | Wallecha |
| 2012/0177678 | A1 | 7/2012 | Paterson et al. |
| 2013/0259891 | A1 | 10/2013 | Harn, Jr. et al. |
| 2014/0199258 | A1 | 7/2014 | Rothman |
| 2014/0234370 | A1 | 8/2014 | Shahabi |
| 2014/0248304 | A1 | 9/2014 | Paterson et al. |
| 2014/0314708 | A1 | 10/2014 | Maciag et al. |
| 2014/0335120 | A1 | 11/2014 | Maciag et al. |
| 2015/0079034 | A1 | 3/2015 | Seavey et al. |
| 2015/0098964 | A1 | 4/2015 | Singh et al. |
| 2015/0125480 | A1 | 5/2015 | Paterson et al. |
| 2015/0196628 | A1 | 7/2015 | Mason et al. |
| 2015/0238584 | A1 | 8/2015 | Shahabi et al. |
| 2015/0297702 | A1 | 10/2015 | Shahabi et al. |
| 2015/0335721 | A1 | 11/2015 | Paterson et al. |
| 2015/0343047 | A1 | 12/2015 | Paterson et al. |
| 2015/0366955 | A9 | 12/2015 | Shahabi et al. |
| 2016/0022814 | A1 | 1/2016 | Petit et al. |
| 2016/0024173 | A1 | 1/2016 | Paterson et al. |
| 2016/0158331 | A1 | 6/2016 | Paterson et al. |
| 2016/0206716 | A1 | 7/2016 | Seavey et al. |
| 2016/0220652 | A1 | 8/2016 | Petit et al. |
| 2016/0228530 | A1 | 8/2016 | Paterson |
| 2016/0256538 | A1 | 9/2016 | Harn, Jr. et al. |
| 2016/0324903 | A1 | 11/2016 | Rothman et al. |
| 2016/0361401 | A1 | 12/2016 | Shahabi et al. |
| 2016/0367650 | A1 | 12/2016 | Paterson |
| 2017/0028045 | A1 | 2/2017 | Paterson et al. |
| 2017/0042996 | A1 | 2/2017 | Wallecha et al. |
| 2017/0049867 | A1 | 2/2017 | Seavey et al. |
| 2017/0080064 | A1 | 3/2017 | Petit et al. |
| 2017/0100469 | A1 | 4/2017 | Paterson et al. |
| 2017/0204361 | A1 | 7/2017 | Eapen et al. |
| 2017/0246273 | A1 | 8/2017 | Wallecha et al. |
| 2017/0281691 | A1 | 10/2017 | Paterson et al. |
| 2017/0368157 | A1 | 12/2017 | Khleif et al. |

FOREIGN PATENT DOCUMENTS

| | | | |
|---|---|---|---|
| WO | WO 2016/183361 | A1 | 5/1996 |
| WO | WO 1999/025376 | A1 | 5/1999 |
| WO | WO 2016/191545 | A1 | 5/1999 |
| WO | WO 2001/072329 | A1 | 10/2001 |
| WO | WO 2016/207859 | A1 | 10/2001 |
| WO | WO 2004/062597 | A1 | 7/2004 |
| WO | WO 2017/048714 | A1 | 7/2004 |
| WO | WO 2006/017856 | A2 | 2/2006 |
| WO | WO 2017/048850 | A1 | 2/2006 |
| WO | WO 2006/0036550 | A2 | 4/2006 |
| WO | WO 2017/049218 | A2 | 4/2006 |
| WO | WO 2007/106476 | A2 | 9/2007 |
| WO | WO 2017/066706 | A1 | 9/2007 |
| WO | WO 2007/130455 | A2 | 11/2007 |
| WO | WO 2017/085691 | A1 | 11/2007 |
| WO | WO 2008/079172 | A2 | 7/2008 |
| WO | WO 2008/109155 | A2 | 9/2008 |
| WO | WO 2017/106754 | A2 | 9/2008 |
| WO | WO 2008/130551 | A2 | 10/2008 |
| WO | WO 2017/132547 | A1 | 10/2008 |
| WO | WO 2011/100754 | A1 | 11/2008 |
| WO | WO 2009/143167 | A2 | 11/2009 |
| WO | WO 2010/008782 | A1 | 1/2010 |
| WO | WO 2010/040135 | A1 | 4/2010 |
| WO | WO 2010/102140 | A1 | 9/2010 |
| WO | WO 2011/060260 | A2 | 5/2011 |
| WO | WO 2012/125551 | A1 | 9/2012 |
| WO | WO 2012/138377 | A2 | 10/2012 |
| WO | WO 2013/025925 | A1 | 2/2013 |
| WO | WO 2013/138337 | A1 | 9/2013 |
| WO | WO 2013/190321 | A1 | 12/2013 |
| WO | WO 2015/126921 | A1 | 8/2015 |
| WO | WO 2015/130810 | A2 | 9/2015 |
| WO | WO 2015/134722 | A2 | 9/2015 |
| WO | WO 2015/164121 | A2 | 10/2015 |
| WO | WO 2015/167748 | A1 | 11/2015 |
| WO | WO 2016/011320 | A1 | 1/2016 |
| WO | WO 2016/011353 | A1 | 1/2016 |
| WO | WO 2016/011357 | A1 | 1/2016 |
| WO | WO 2016/011362 | A1 | 1/2016 |
| WO | WO 2016/051277 | A1 | 4/2016 |
| WO | WO 2016/061182 | A1 | 4/2016 |
| WO | WO 2016/100924 | A1 | 6/2016 |
| WO | WO 2016/100929 | A1 | 6/2016 |
| WO | WO 2016/126876 | A2 | 8/2016 |
| WO | WO 2016/126878 | A2 | 8/2016 |
| WO | WO 2016/141121 | A1 | 9/2016 |
| WO | WO 2016/154412 | A2 | 9/2016 |
| WO | WO 2018/009461 | A1 | 1/2018 |

OTHER PUBLICATIONS

Chen et al., "Development of a *Listeria monocytogenes*-based vaccine against hepatocellular carcinoma," *Oncogene* 31:2140-2152, (2012).

Mkrtichyan et al., "Anti-PD-1 antibody significantly increases therapeutic efficacy of *Listeria monocytogenes* (Lm)-LLO immunotherapy," *Journal for ImmunoTherapy of Cancer* 1:15, (2013).

Brockstedt & Dubensky, "Promises and challenges for the development of *Listeria monocytogenes*-based immunotherapies," *Expert Rev. Vaccines* 7(7):1069-1084, (2008).

Liang et al., "Listeria monocytogenes: A promising vehicle for neonatal vaccination," *Human Vaccines & Immunotherapeutics* 10(4):1036-1046, (2014).

Pan et al., "A recombinant *Listeria monocytogenes* vaccine expressing a model tumour antigen protects mice against lethal tumour cell challenge and causes regression of established tumours," *Nature Medicine* 1(5):471-477, (1995).

Tanaka et al., "Induction of a Systemic Immune Response by a Polyvalent Melanoma-Associated Antigen DNA Vaccine for Prevention and Treatment of Malignant Melanoma," *Molecular Therapy* 5(3):291-299, (2002).

PCT International Preliminary Report on Patentability for application PCT/US2015/016348 dated Aug. 23, 2016.

PCT International Search Report and Written Opinion of the International Search Authority for application PCT/US2015/016348 dated May 14, 2015.

*atggcgcgggatggtatactatacaagcgtatggttcaaaaagatactttgaattaagaagt*
*acaataaagttaacttcattagacaaaaagaaaaacaaggaagaatagtacatagttataa*
*atacttggagagtgaggtgtaatatgggggcagctgatttttggggtttcatatatgtagtt*
*tcaagattagccattgttgcggcagtagtttacttcttatacttattgagaaaaattgcaaa*
*taaatagaaaaaaagccttgtcaaacgaggcttttttatgcaaaaaatacgacgaatgaag*
*ccatgtgagacaatttggaatagcagacaacaaggaaggtagaacatgttttgaaaaattta*
*ctgatttttcgattattattaacgcttgttaatttaaacatatcttatttttgctaacatata*
*agtatacaaagggacataaaaaggttaacagcgtttgttaaataggaagtatatgaaaatcc*
*tcttttgtgtttctaaatttattttaaggagtggaga*atgttgaaaaaaataattggtta
caaaatgcagtaatagcaatgctagtgttaattgtaggtctgtgcattaatatgggttctgg
aacaaaagtacaagctgagagtattcaacgaccaacgcctattaaccaagtttttccagatc
ccggcctagcgaatgcagtgaaacaaaatttagggaagcaaagtgttacagaccttgtatca
caaaaggaactatctggagtacaaaatttcaatggagataatagcaacattcaatctcttgc
gggaatgcaatttttcactaatttaaaagaacttcatctatcccataatcaaataagtgacc
ttagtcctttaaaggatctaactaagttagaagagctatctgtgaatagaaacagactgaaa
aatttaaacggaattccaagtgcttgtttatctcgcttgtttttagataacaacgaactcag
agatactgactcgcttattcatttgaaaaatctagaaatcttatctattcgtaataataagt
taaaaagtattgtgatgcttggtttttatcaaaactagaggtattagatttgcatggtaat
gaaataacaaatacaggtggactaactagattgaagaaagttaactggatagatttaactgg
tcagaaatgtgtgaatgaaccagtaaaataccaaccagaattgtatataacaaatactgtca
aagacccagatggaagatggatatctccatattacatcagtaatggtgggagttatgtagat
ggttgtgtcctgtgggaattgccagtttatacagatgaagtaagctataagtttagcgaata
tataaacgttggggagactgaggctatatttgatggaacagttacacaacctatcaagaatt
aggacttgtgcacacctgtatactttgagctctcgtataatcacgagagctttttaaatatg
taagtcttaattatctcttgacaaaaagaacgtttattcgtataaggttaccaagagatgaa
gaaactattttatttacaattcaccttgacaccaaaaactccatatgatatagtaaataagg
ttattaaacaagaaagaagaagcaacccgcttctcgcctcgttaacacgaacgttttcaggc
aaaaaattcaaactttcgtcgcgtagcttacgcgatttgaatgtgcgggattgctgaaaag
cagcccgtttttttatggcctccgaacgaatgagttagcaggccgcagatttgaacagctat
tttctatcttgttgtaacaaaattaagtggaggtggctcaccattagcaaagacatgttggt
aaacgatgggattcgtgcacgtgaagtaagattgatcgaccaagacggtgaacaattaggcg
tgaagagtaaaatcgatgcgcttcaaattgctgaaaaggctaatcttgatctagtgcttgtt
gctccaacagcgaaaccgccagtagctcgta

Figure 10

GAATTCatggcgcgggatggtatactatacaagcgtatggttcaaaaagatactttgaattaa
gaagtacaataaagttaacttcattagacaaaagaaaaacaaggaagaatagtacatagtt
ataaatacttggagagtgaggtgtaatatgggggcagctgatttttggggtttcatatatgta
gtttcaagattagccattgttgcggcagtagtttacttcttatacttattgagaaaaattgca
aataaatagaaaaaaagccttgtcaaacgaggctttttttatgcaaaaaatacgacgaatgaa
gccatgtgagacaatttggaatagcagacaacaaggaaggtagaacatgttttgaaaaattta
ctgattttcgattattattaacgcttgttaatttaaacatctcttatttttgctaacatataa
gtatacaaagggacataaaaaggttaacagcgtttgttaaataggaagtatatgaaaatcctc
ttttgtgtttctaaatttatttttaaggagtggagaGGATCCggacttgtgcacacctgtata
ctttgagctctcgtataatcacgagagctttttaaatatgtaagtcttaattatctcttgaca
aaaagaacgtttattcgtataaggttaccaagagatgaagaaactatttatttacaattcac
cttgacaccaaaaactccatatgatatagtaaataaggttattaaacaagaaagaagaagcaa
cccgcttctcgcctcgttaacacgaacgttttcaggcaaaaaattcaaactttcgtcgcgtag
cttacgcgattttgaatgtgcgggattgctgaaaagcagcccgtttttttatggcctccgaac
gaatgagttagcaggccgcagatttgaacagctatttttctatcttgttgtaacaaaattaagt
ggaggtggctcaccattagcaaagacatgttggtaaacgatgggattcgtgcacgtgaagtaa
gattgatcgaccaagacggtgaacaattaggcgtgaagagtaaaatcgatgcgcttcaaattg
ctgaaaaggctaatcttgatctagtgcttgttgctccaacagcgaaaccgccagtagctcgta
CTGCAG

Figure 11 gcgccaaatcattggttgattggtgaggatgtctgtgtgcgtgggtcgcgagatgggcgaataagaagcattaaagatcctgacaaatat
aatcaagcgggctcatatgaaagattacgaatcgcttccactcacagaggaaggcgactggggcggagttcattataatagtggtatccc
gaataaagcagcctataatactatcactaaacttggaaaagaaaaaacagaacagctttatttcgcgccttaaagtactatttaacgaaaa
aatcccagtttaccgatgcgaaaaaagcgcttcaacaagcagcgaaagatttatatggtgaagatgcttctaaaaaagttgctgaagctt
gggaagcagttggggttaactgattaacaaatgttagagaaaaattaattctccaagtgatattcttaaaataattcatgaatattttttcttata
ttagctaattaagaagataactaactgctaatccaattttaacggaacaaattagtgaaaatgaaggccgaattttccttgttctaaaaaggt
tgtattagcgtatcacgaggagggagtataa*gtgggattaaacagatttatgcgtgcgatgatggtggttttcattactgccaattgcatt*
*acgattaaccccgac*gtcgac*ccatacgacgttaattcttgcaatgttagctattggcgtgttctcttaggggcgtttatcaaaattatt*
*caattaagaaaaaataattc*aaaacacagaacgaaagaaaaagtgaggtgaatgatatgaaattcaaaaaggtggttctaggtatgtg
cttgatcgcaagtgttctagtctttccggtaacgataaaagcaaatgcctgttgtgatgaatacttacaaacacccgcagctccgcatgata
ttgacagcaaattaccacataaacttagttggtccgcggataacccgacaaatactgacgtaaatacgcactattggctttttaaacaagc
ggaaaaaatactagctaaagatgtaaatcatatgcgagctaatttaatgaatgaacttaaaaaattcgataaacaaatagctcaaggaata
tatgatgcggatcataaaaatccatattatgatactagtacattttatctcattttataatcctgatagagataatacttatttgccgggttttgc
taatgcgaaaataacaggagcaaagtatttcaatcaatcggtgactgattaccgagaagggaa

Figure 13

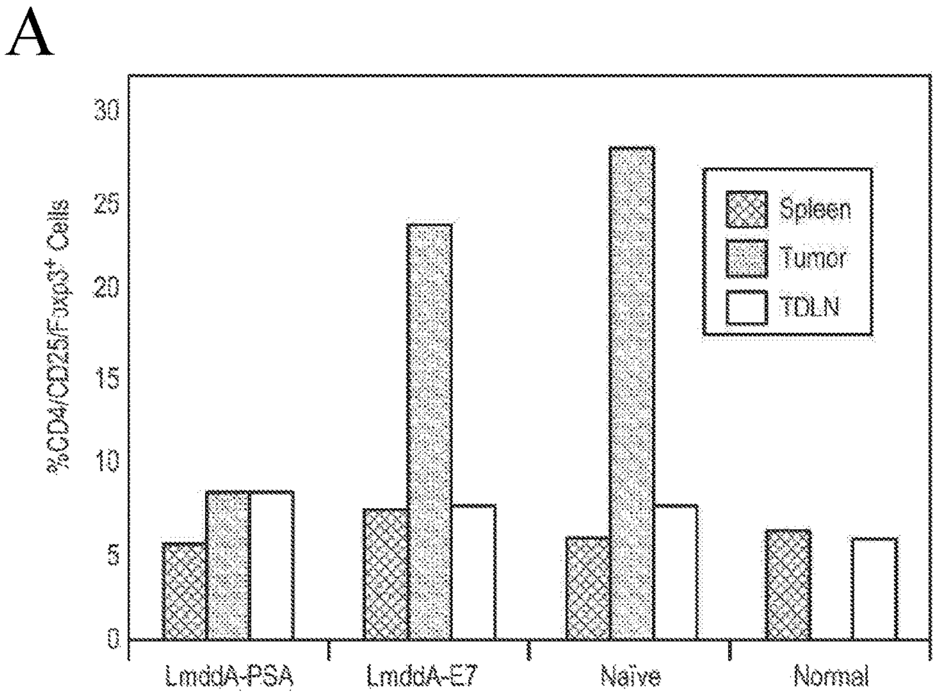
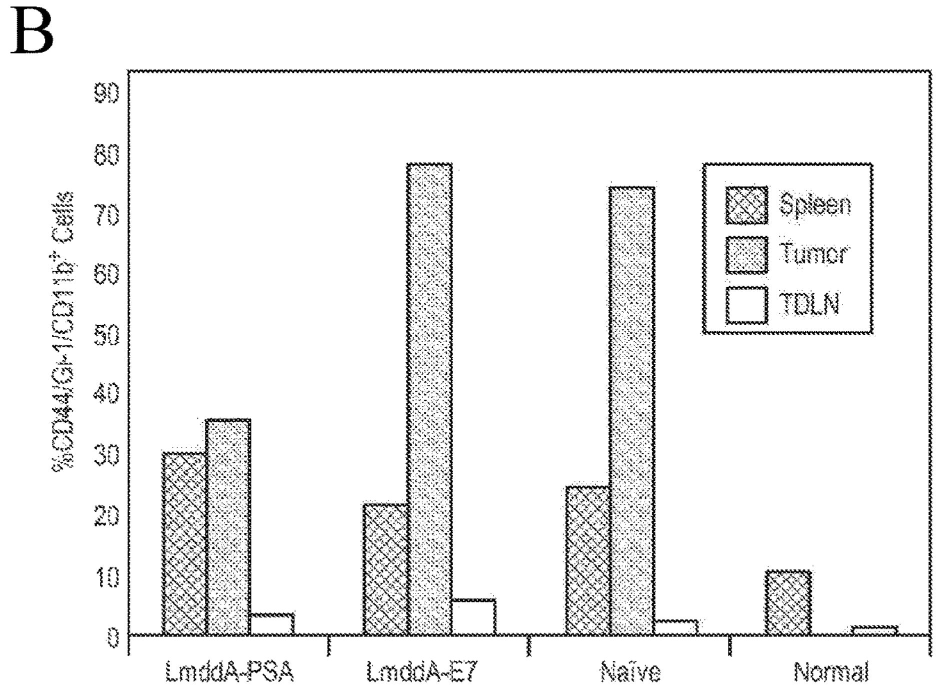
Figure 21

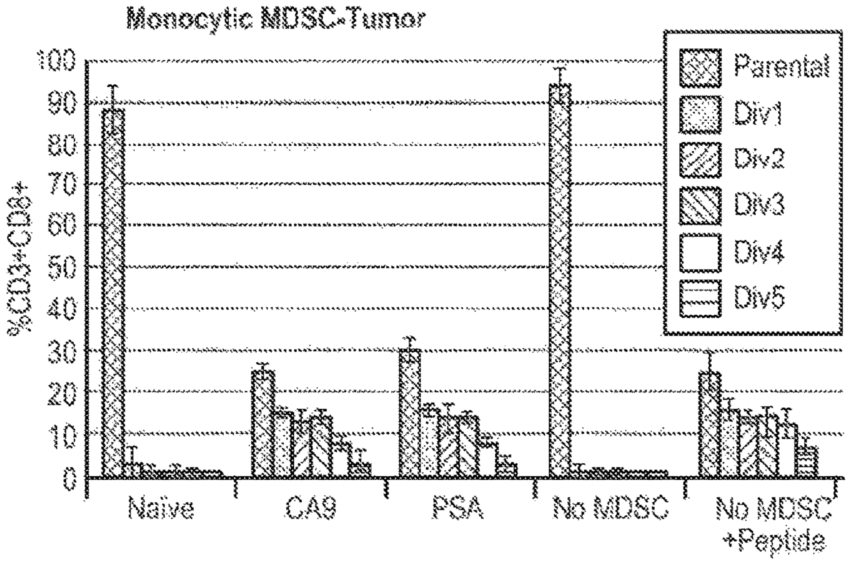
*Figure* 22 *C*
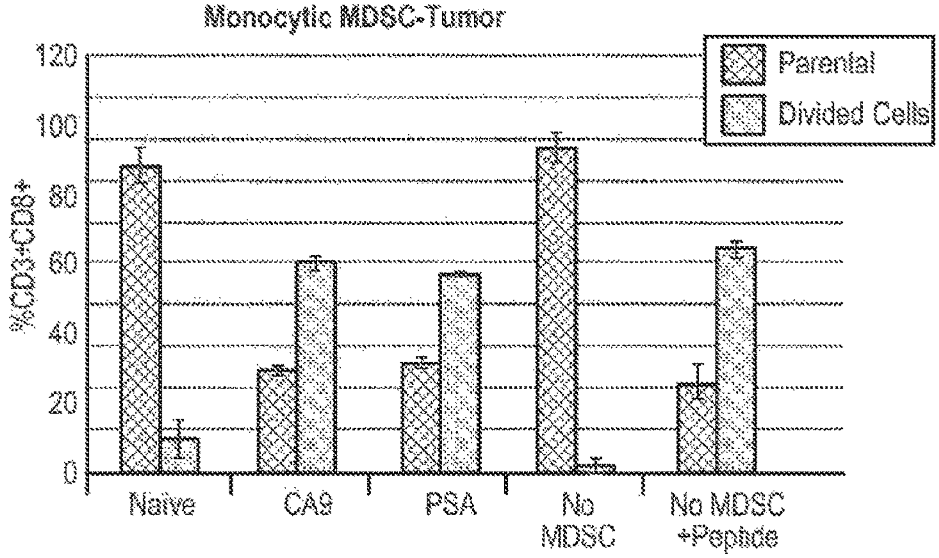
*Figure* 22 *D*

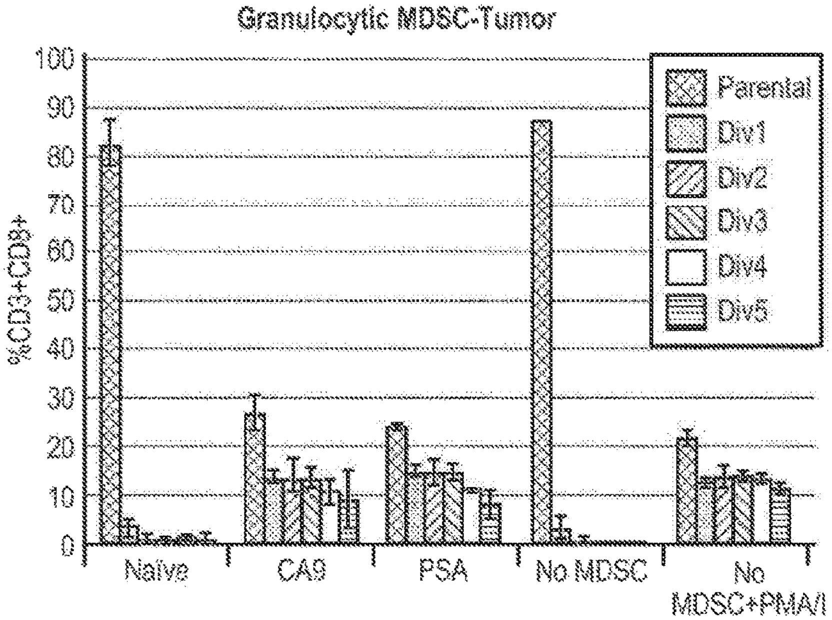
*Figure* 24 *A*
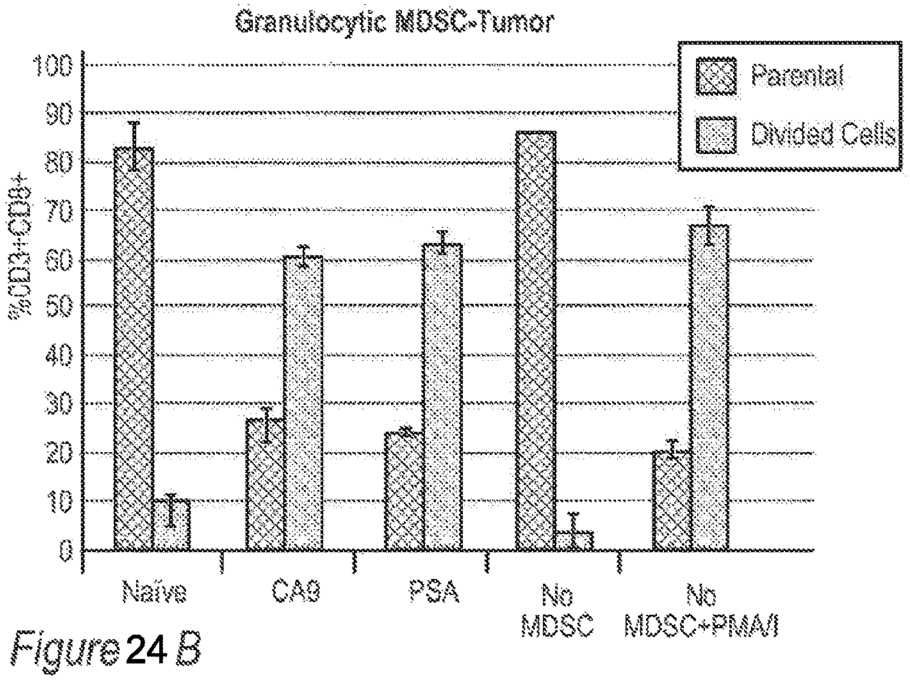
*Figure* 24 *B*

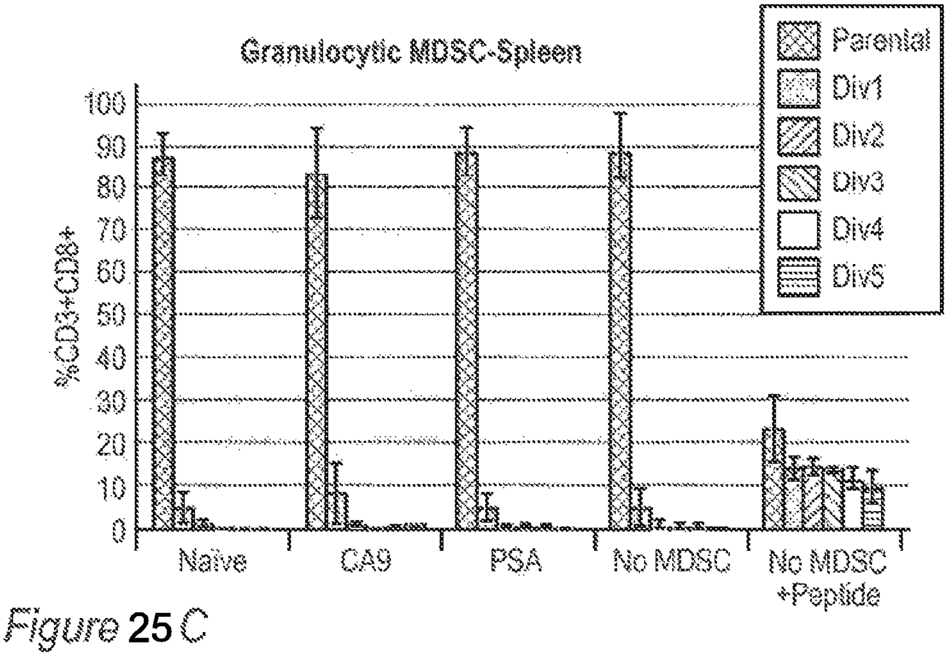
*Figure* 25 *C*
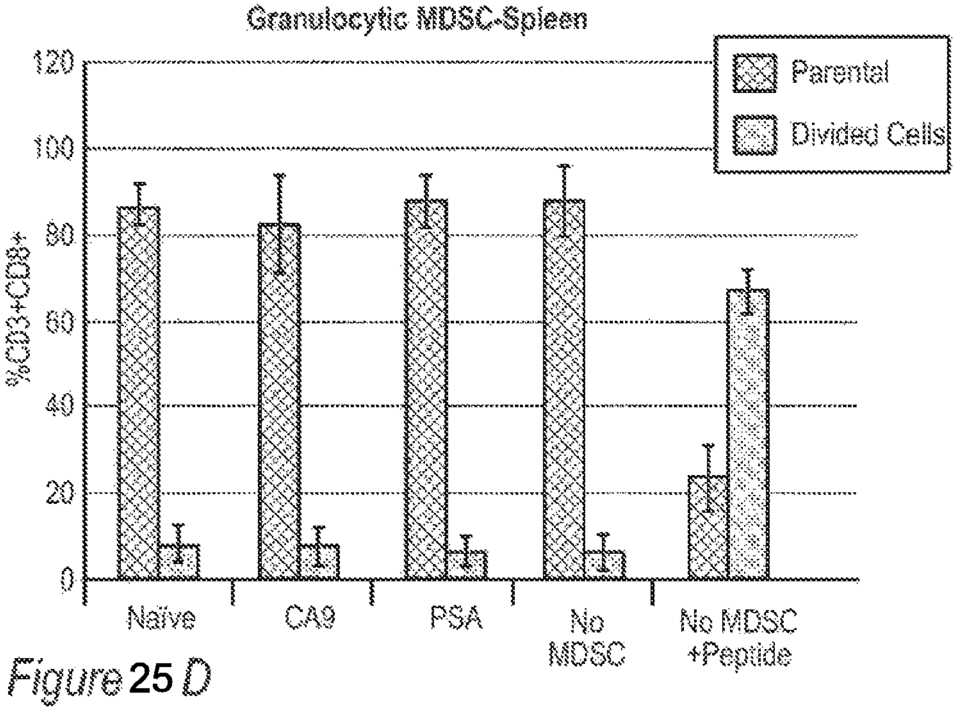
*Figure* 25 *D*

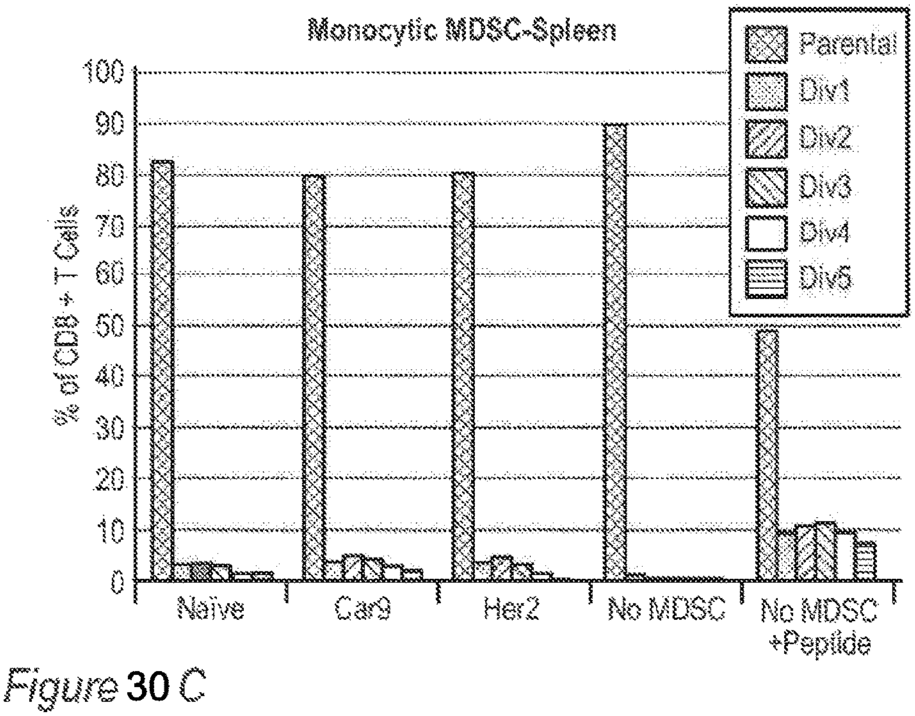
*Figure* 30 *C*
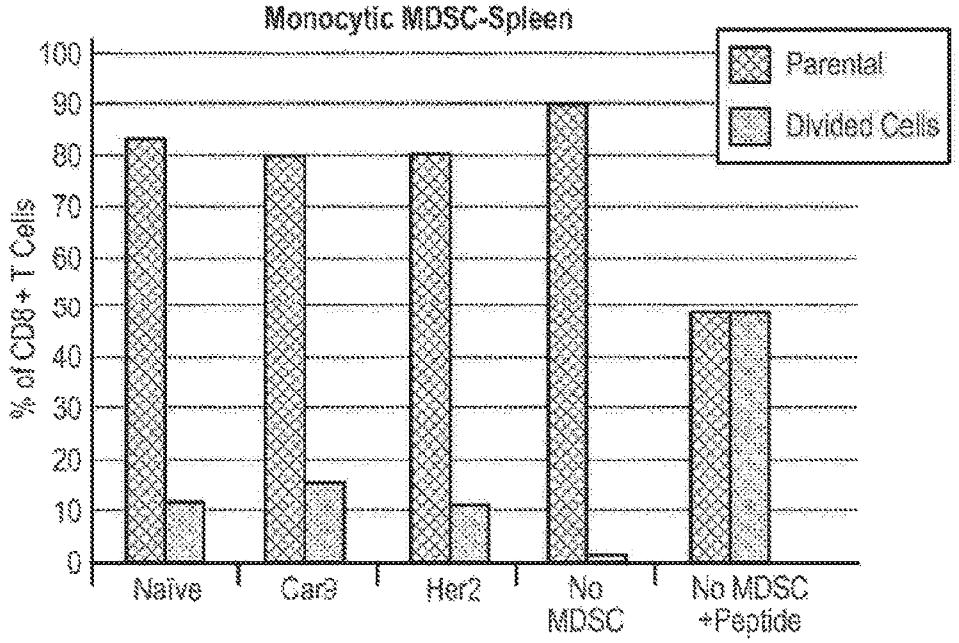
*Figure* 30 *D*

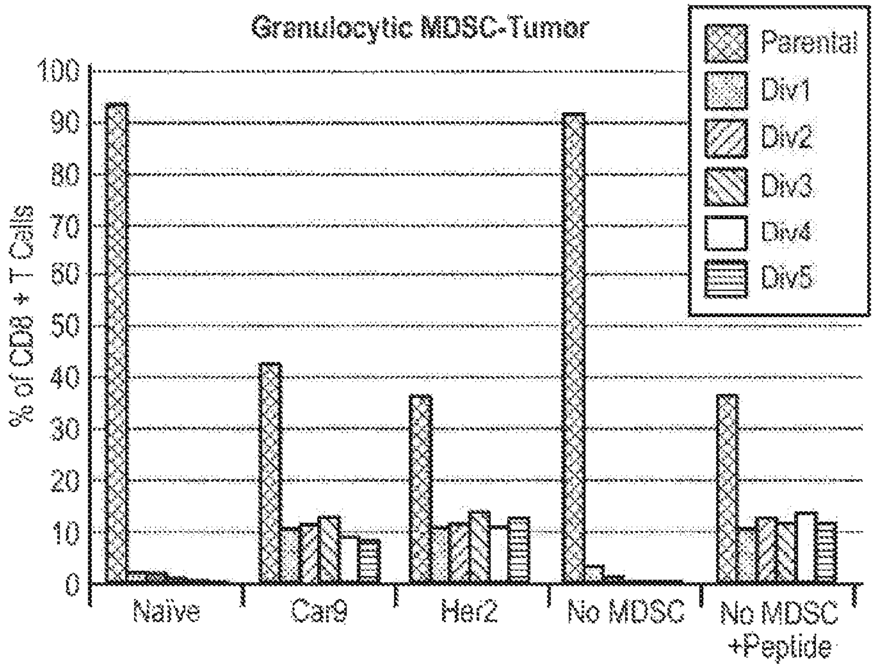
*Figure* 31 *C*
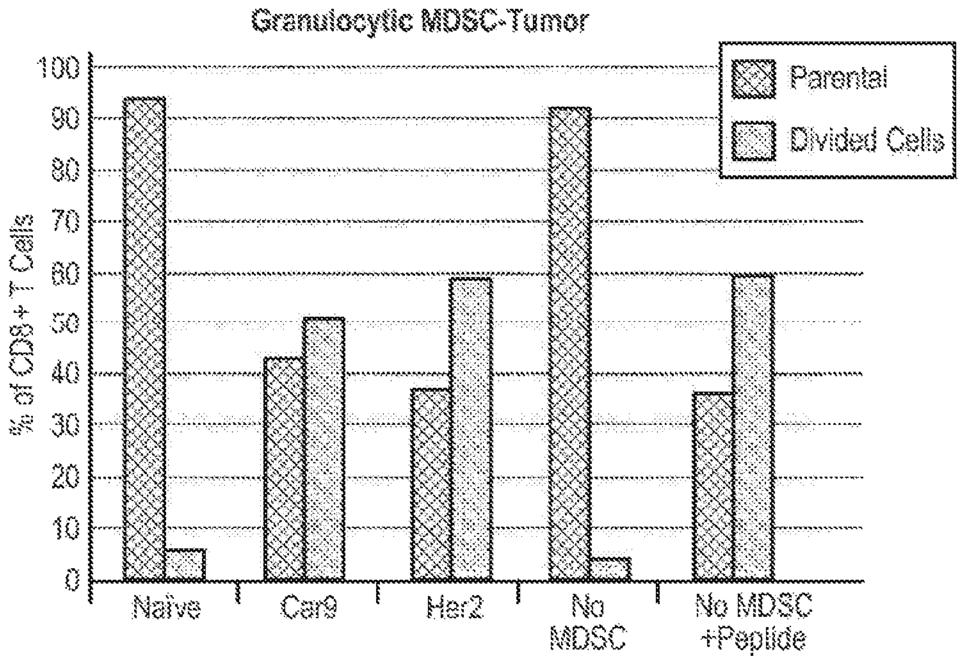
*Figure* 31 *D*

Tumor Granulocytic MDSC

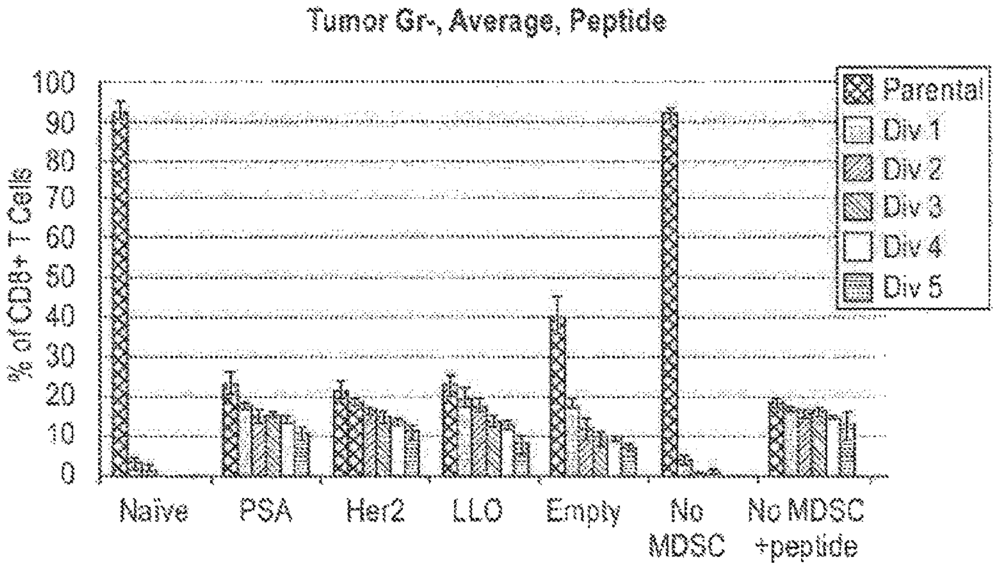
*Figure* 36 *A*
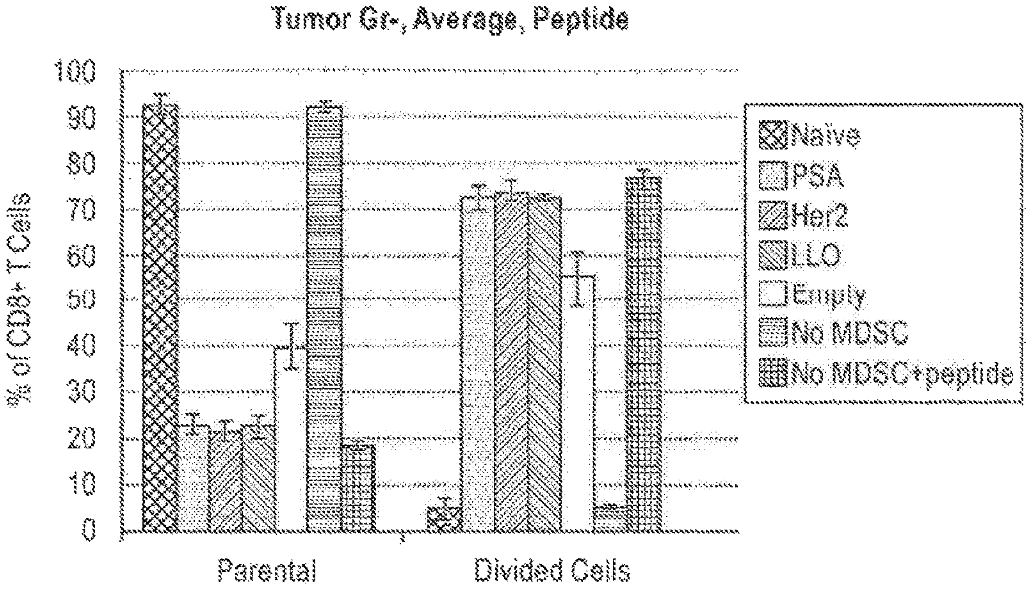
*Figure* 36 *B*

Spleen Granulocytic MDSC

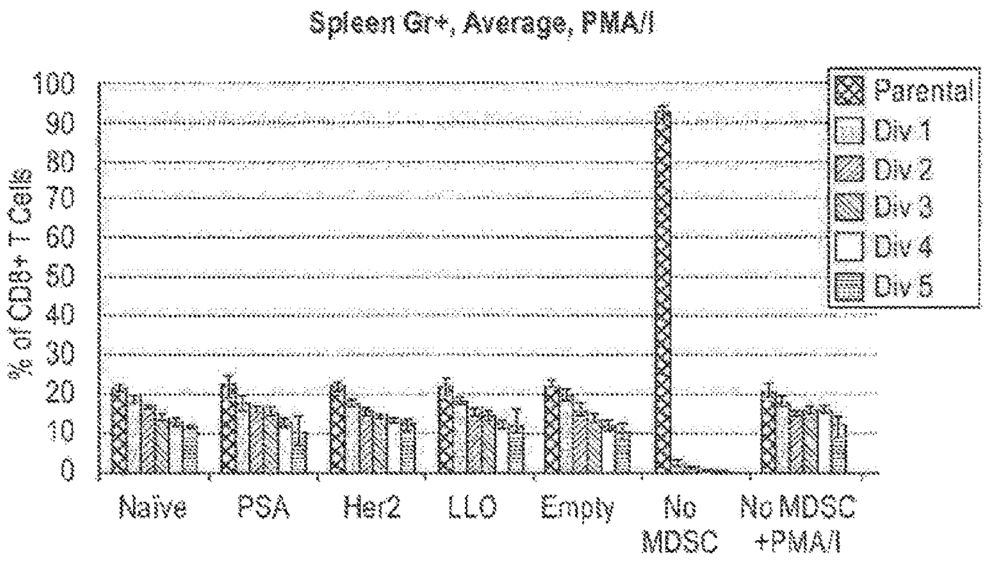
*Figure* 37 *C*
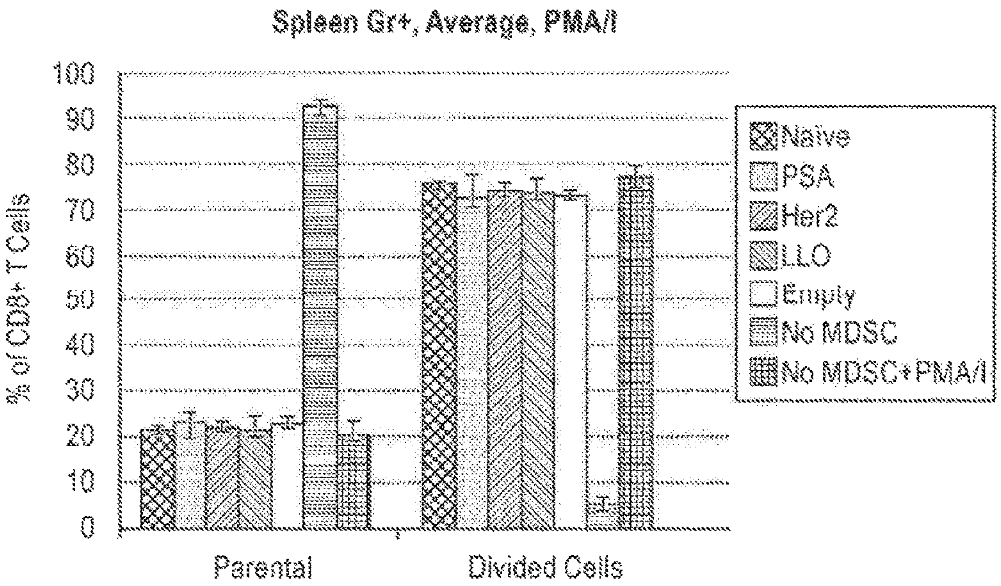
*Figure* 37 *D*

Spleen Monocytic MDSC

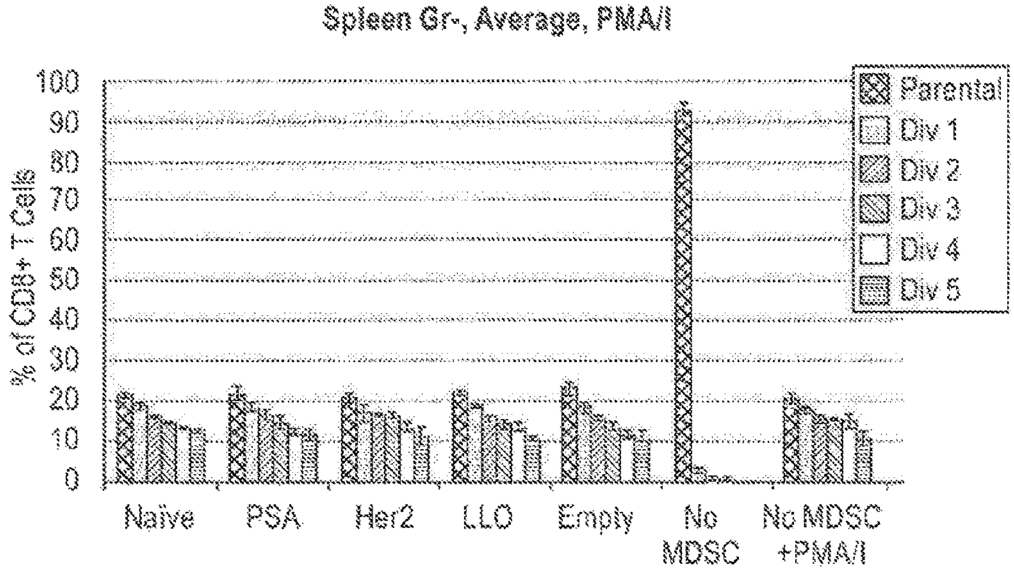
*Figure* 38 *C*
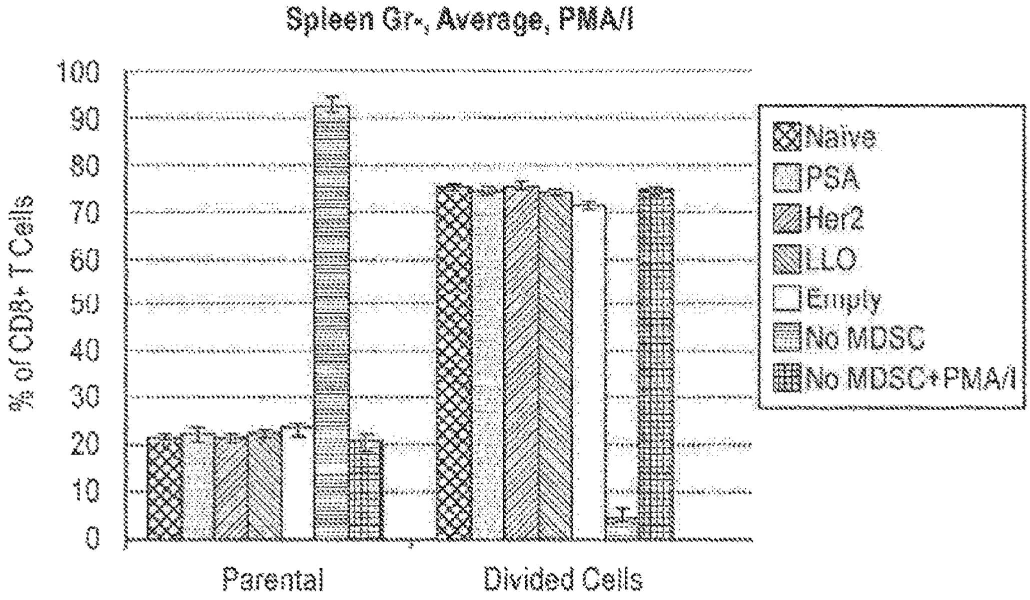
*Figure* 38 *D*

Tumor Tregs
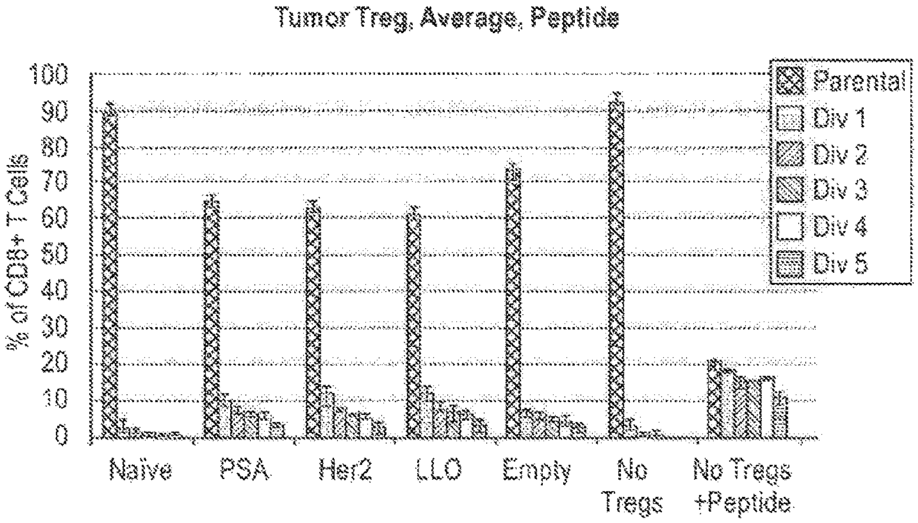
*Figure* 39 *A*
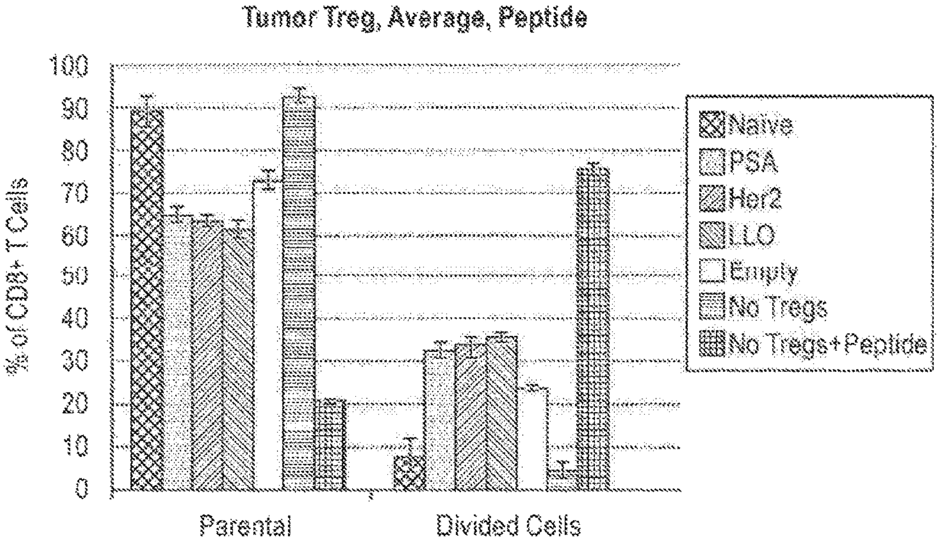
*Figure* 39 *B*

Spleen Tregs

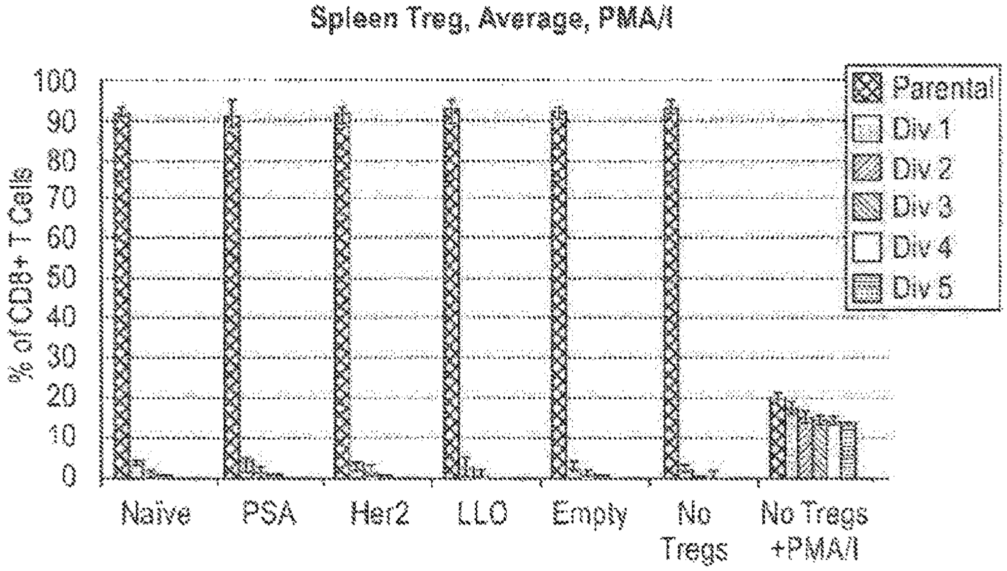
*Figure* 40 *C*
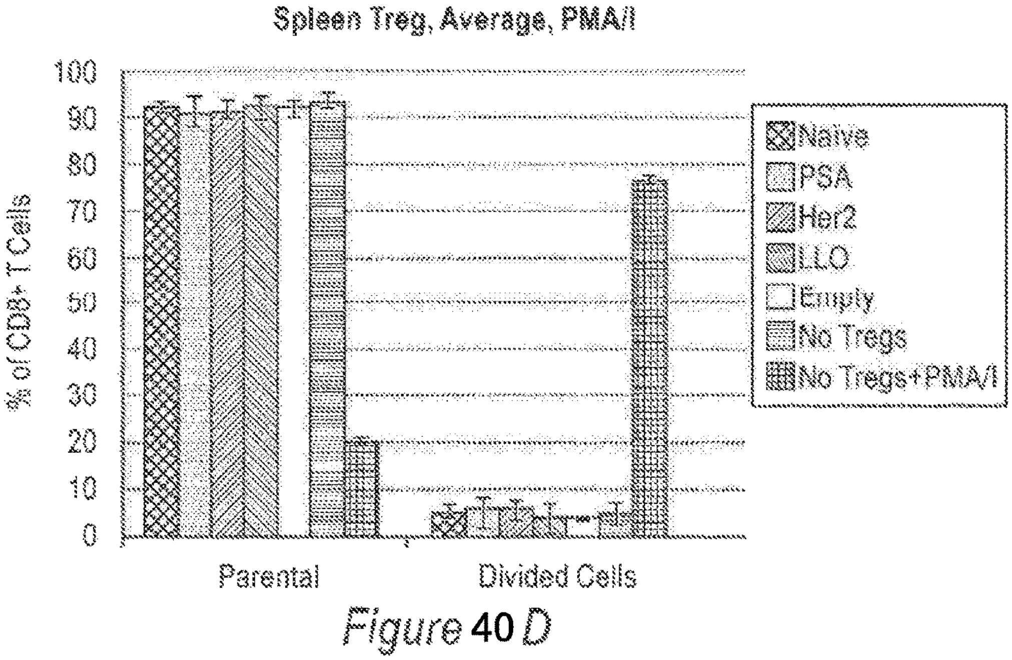
*Figure* 40 *D*

Tumor Tcon
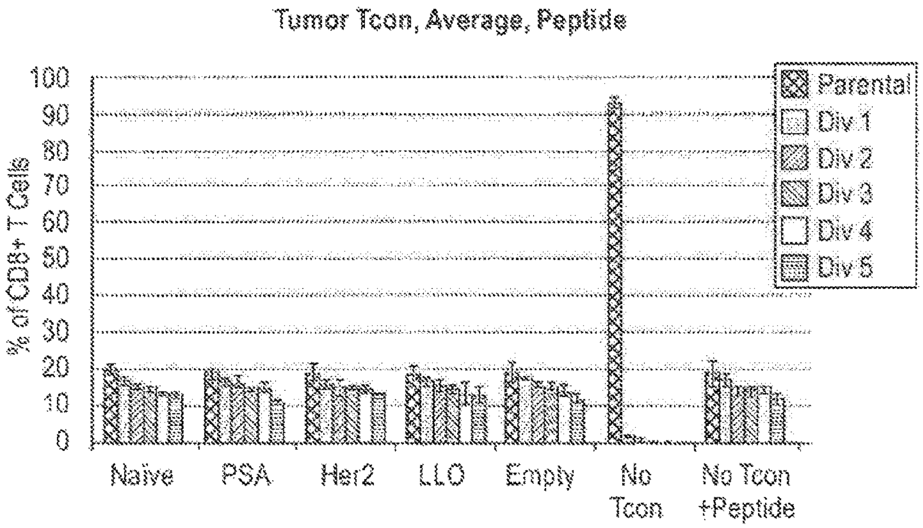
*Figure* 41 *A*
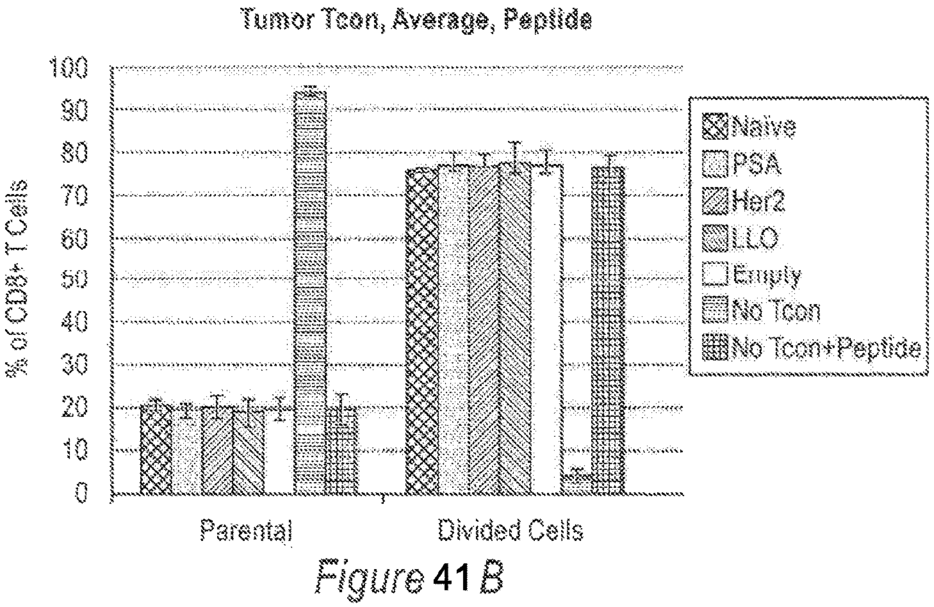
*Figure* 41 *B*

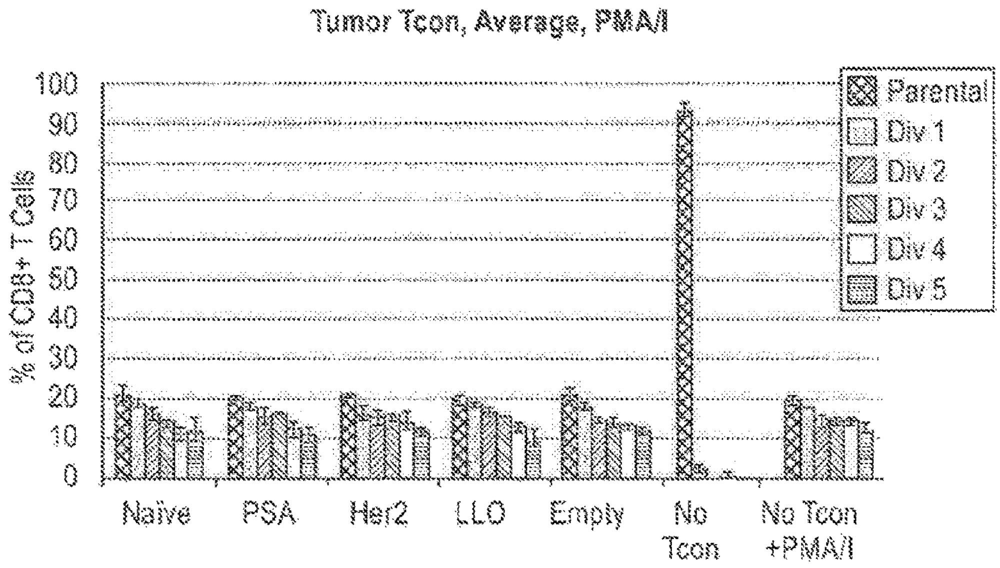
*Figure* 41 *C*
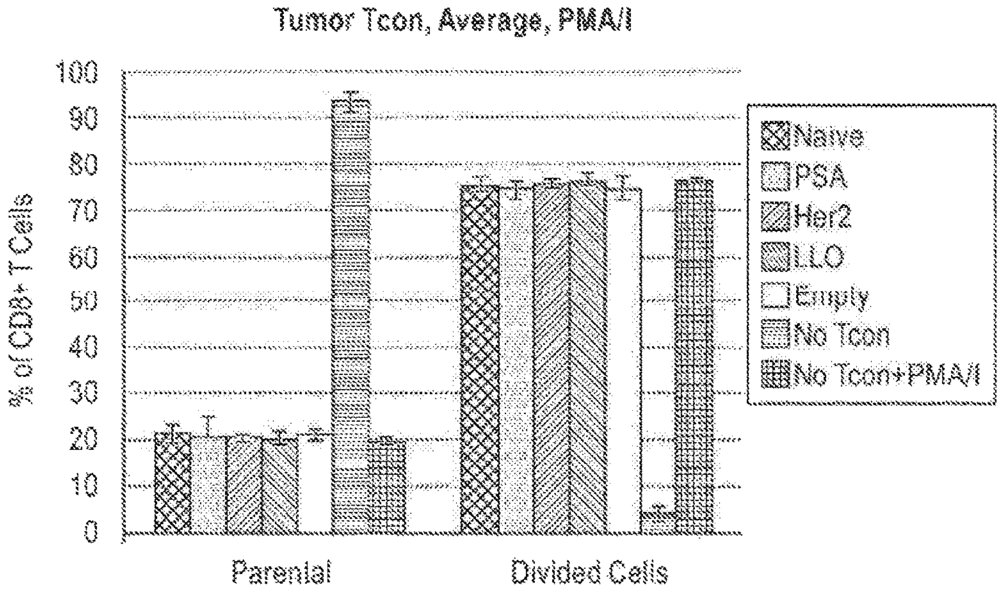
*Figure* 41 *D*

Spleen Tcon
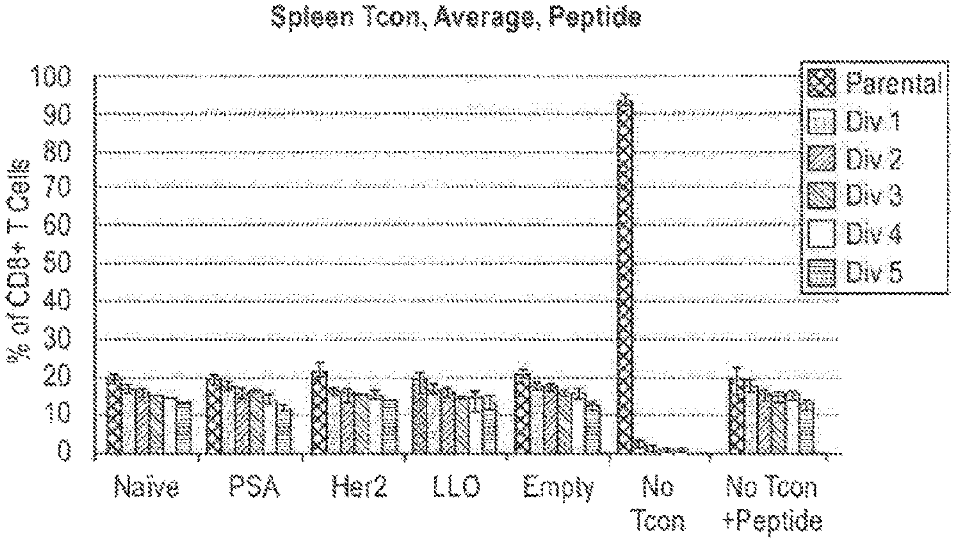
*Figure* 42 *A*
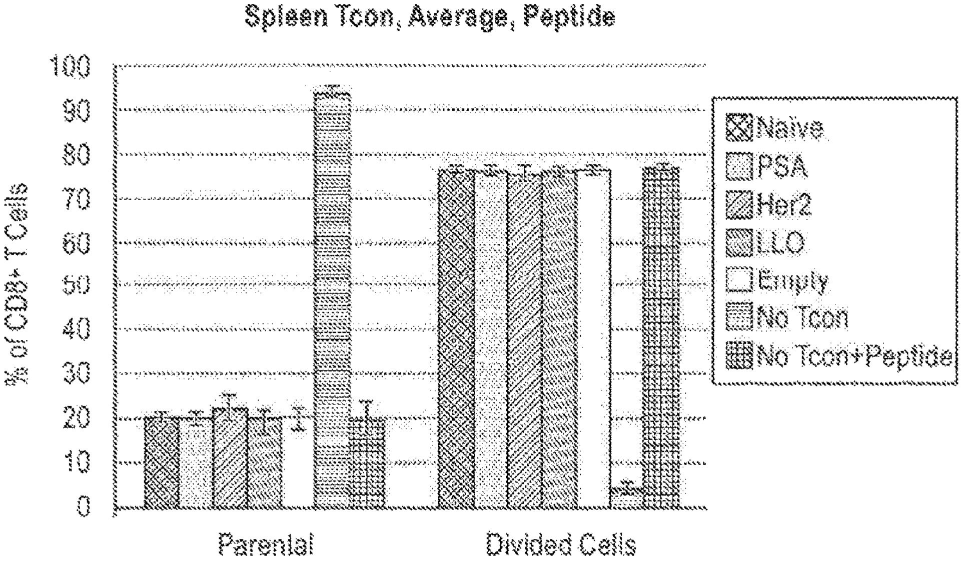
*Figure* 42 *B*

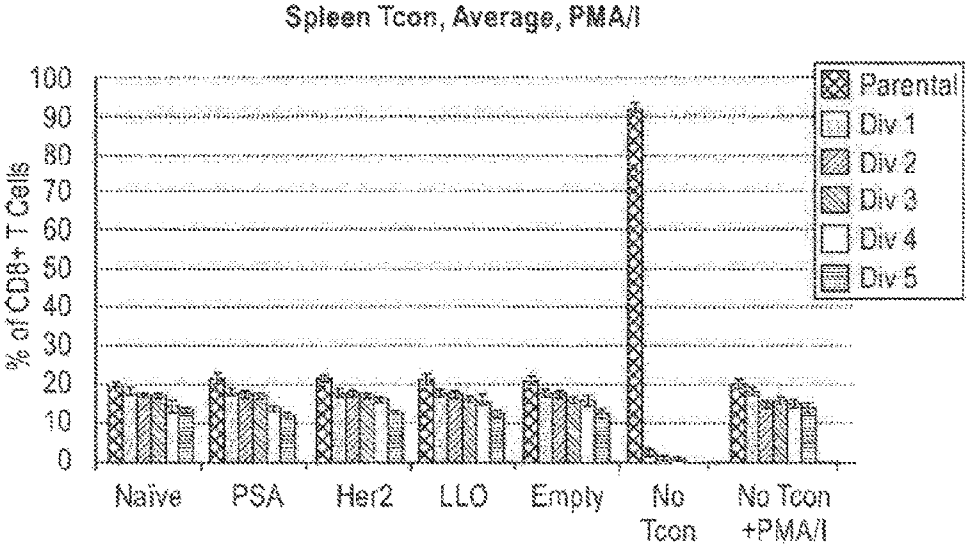
*Figure* 42 C
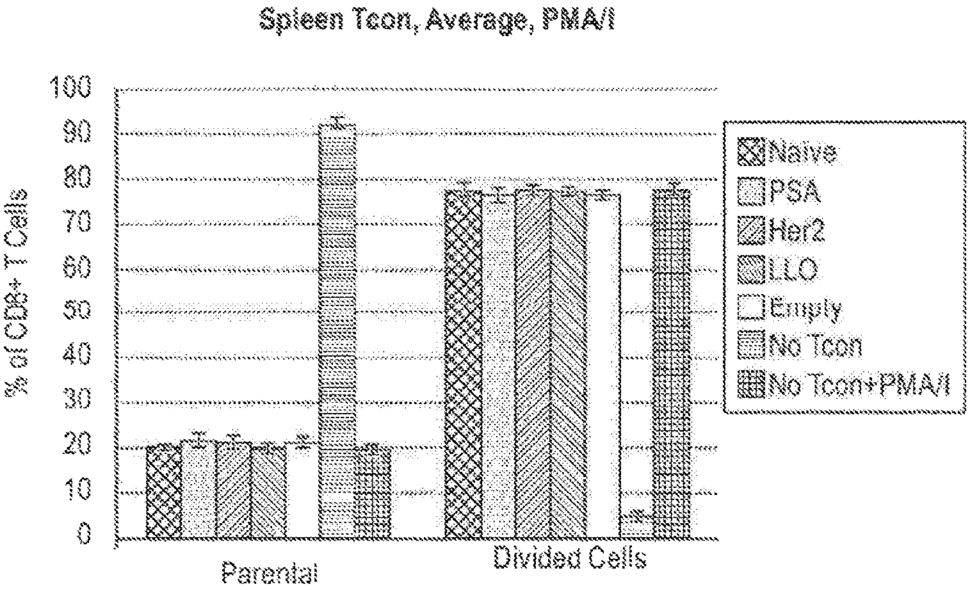
*Figure* 42 D

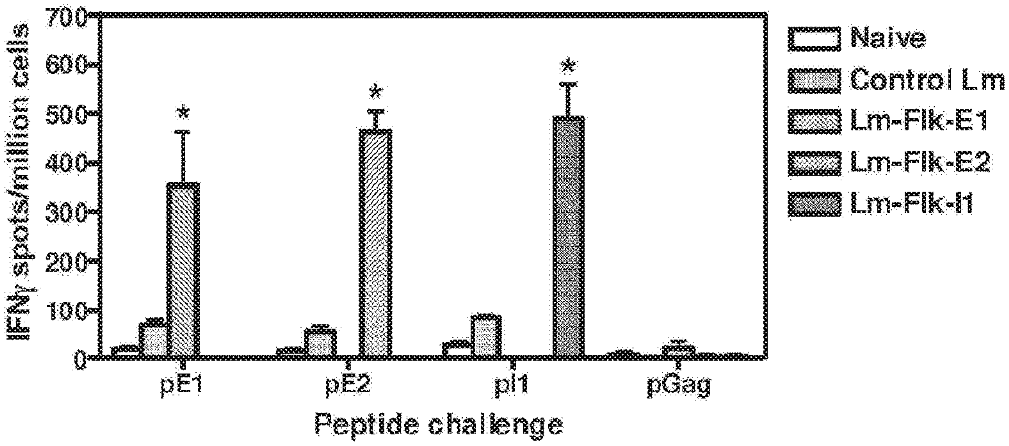

Figure 49C

MESKALLAVALWFCVETRAASVGLPGDFLHPPKLSTQKDILTILANTTLQITCRGQRDLDWLWPN
AQRDSEERVLVTECGGGDSIFCKTLTIPRVVGNDTGAYKCSYRDVDIASTVYVYVRDYRSPFIAS
VSDQHGIVYITENKNKTVVIPCRGSISNLNVSLCARYPEKRFVPDGNRISWDSEIGFTLPSYMISYA
GMVFCEAKINDETYQSIMYIVVVVGYRIYDVILSPPHEIELSAGEKLVLNCTARTELNVGLDFTWHS
PPSKSHHKKIVNRDVKPFPGTVAKMFLSTLTIESVTKSDQGEYTCVASSGRMIKRNRTFVRVHTK
PFIAFGSGMKSLVEATVGSQVRIPVKYLSYPAPDIKWYRNGRPIESNYTMIVGDELTIMEVTERDA
GNYTVILTNPISMEKQSHMVSLVVNVPPQIGEKALISPMDSYQYGTMQTLTCTVYANPPLHHIQW
YWQLEEACSYRPGQTSPYACKEWRHVEDFQGGNKIEVTKNQYALIEGKNKTVSTLVIQAANVSA
LYKCEAINKAGRGERVISFHVIRGPEITVQPAAQPTEQESVSLLCTADRNTFENLTWYKLGSQATS
VHMGESLTPVCKNLDALWKLNGTMFSNSTNDILIVAFQNASLQDQGDYVCSAQDKKTKKRHCLV
KQLIILERMAPMITGNLENQTTTIGETIEVTCPASGNPTPHITWFKDNETLVEDSGIVLRDGNRNLTI
RRVRKEDGGLYTCQACNVLGCARAETLFIIEGAQEKTNLE*VIILVGTAVIAMFFWLLLVIVLRTVKR*
*AN*EGELKTGYLSIVMDPDELPLDERCERLPYDASKWEFPRDRLKLGKPLGRGAFGQVIEADAFGI
DKTATCKTVAVKMLKEGATHSEHRALMSELKILIHIGHHLNVVNLLGACTKPGGPLMVIVEFCKFG
NLSTYLRGKRNEFVPYKSKGARFRQGKDYVGELSVDLKRRLDSITSSQSSASSGFVEEKSLSDV
EEEEASEELYKDFLTLEHLICYSFQVAKGMEFLASRKCIHRDLAARNILLSEKNVVKICDFGLARDI
YKDPDYVRKGDARLPLKWMAPETIFDRVYTIQSDVWSFGVLLWEIFSLGASPYPGVKIDEEFCRR
LKEGTRMRAPDYTTPEMYQTMLDCWHEDPNQRPSFSELVEHLGNLLQANAQQDGKDYIVLPMS
ETLSMEEDSGLSLPTSPVSCMEEEEVCDPKFHYDNTAGISHYLQNSKRKSRPVSVKTFEDIPLEE
PEVKVIPDDSQTDSGMVLASEELKTLEDRNKLSPSFGGMMPSKSRESVASEGSNQTSGYQSGY
HSDDTDTTVYSSDEAGLLKMVDAAVHADSGTTLRSPPV

Flk-E1

Flk-E2

Flk-I1

MDRGVLPLPITLLFVIYSFVPTTGLAERVGCDLQPVDPTRGEVTFTTSQVSEGCVAQAA
NAVREVHVLFLDFPGMLSHLELTLQASKQNGTETREVFLVLVSNKNVFVKFQAPEIP Lm-LLO-CD105A
LHLAYDSSLVIFQGQPRVNITVLPSLTSRKQILDWAATKGAITSIAALDDPQSIVLQLG
QDPKAPFLCLPEAHKDMGATLEWQPRAQTPVQSCRLEGVSGHKEAYILRILPGSEAG
PRTVTYMMELSCTSGDAHLILHGPPYVSWFIDINHSMQILTTGEYSVKIFPGSKVKGV
ELPDTPQGLIAEARKLNASIVTSFVELPLVSNVSLRASSCGGVFQTTPAPVVTTPPKDTCS
PVLLMSLIQPKCGNQVMTLALNKKHVQTLQCTITGLTFWDSSCQAEDTDDHLVLSS
AYSSCGMKVTAHVVSNEVIISFPSGSPPLRKKVQCIDMDSLSFQLGLYLSPHFLQASNT
IELGQQAFVQVSVSPLTSEVTVQLDSCHLDLGPEGDMVELIQSRTAKGSCVTLLSPSP Lm-LLO-CD105B
EGDPRFSFLLRVYMVPTPTAGTLSCNLALRPSTLSQEVYKTVSMRLNVVSPDLSGKG
LVLPSVLGITFGAFLIGALLTAALWYIYSHTRGPSKREPVVAVAAPASSESSSTNHSIGSTQ
STPCSTSSMA

In CD105A: AGPRTVTYM ($D^d$)
In CD105B: AYSSCGMKV ($K^d$)

B)

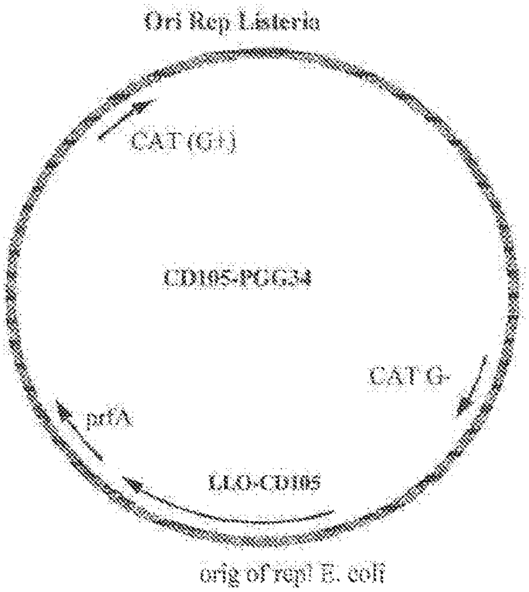

Figure 61

Tumor free on day 60
Naive 0/8
CD105A 4/8
CD105B 2/8
NYESO-1 0/8

Step II: mix the products of PCR 1 and PCR 2 and allow the annealing of the complementary region (mutated CBD) between the products from PCR 1 and 2

Clone PCR product into the pCR2.1 vector (Invitrogen)
Verify the sequence of LLO and the mutated CBD

SEQUENCE LISTING

<160> NUMBER OF SEQ ID NOS: 147

<210> SEQ ID NO 1
<211> LENGTH: 6733
<212> TYPE: DNA
<213> ORGANISM: Artificial Sequence
<220> FEATURE:
<223> OTHER INFORMATION: episomal recombinant nucleic acid backbone

<400> SEQUENCE: 1

```
ggagtgtata ctggcttact atgttggcac tgatgagggt gtcagtgaag tgcttcatgt     60

ggcaggagaa aaaaggctgc accggtgcgt cagcagaata tgtgatacag gatatattcc    120

gcttcctcgc tcactgactc gctacgctcg gtcgttcgac tgcggcgagc ggaaatggct    180

tacgaacggg gcggagattt cctggaagat gccaggaaga tacttaacag ggaagtgaga    240

gggccgcggc aaagccgttt ttccataggc tccgcccccc tgacaagcat cacgaaatct    300

gacgctcaaa tcagtggtgg cgaaacccga caggactata aagataccag gcgtttcccc    360

ctggcggctc cctcgtgcgc tctcctgttc ctgcctttcg gtttaccggt gtcattccgc    420

tgttatggcc gcgtttgtct cattccacgc ctgacactca gttccgggta ggcagttcgc    480

tccaagctgg actgtatgca cgaacccccc gttcagtccg accgctgcgc cttatccggt    540

aactatcgtc ttgagtccaa cccggaaaga catgcaaaag caccactggc agcagccact    600

ggtaattgat ttagaggagt tagtcttgaa gtcatgcgcc ggttaaggct aaactgaaag    660

gacaagtttt ggtgactgcg ctcctccaag ccagttacct cggttcaaag agttggtagc    720

tcagagaacc ttcgaaaaac cgccctgcaa ggcggttttt tcgttttcag agcaagagat    780

tacgcgcaga ccaaaacgat ctcaagaaga tcatcttatt aatcagataa aatatttcta    840

gccctccttt gattagtata ttcctatctt aaagttactt ttatgtggag gcattaacat    900

ttgttaatga cgtcaaaagg atagcaagac tagaataaag ctataaagca agcatataat    960

attgcgtttc atctttagaa gcgaatttcg ccaatattat aattatcaaa agagaggggt   1020

ggcaaacggt atttggcatt attaggttaa aaaatgtaga aggagagtga aacccatgaa   1080

aaaaataatg ctagttttta ttacacttat attagttagt ctaccaattg cgcaacaaac   1140

tgaagcaaag gatgcatctg cattcaataa agaaaattca atttcatcca tggcaccacc   1200

agcatctccg cctgcaagtc ctaagacgcc aatcgaaaag aaacacgcgg atgaaatcga   1260

taagtatata caaggattgg attacaataa aaacaatgta ttagtatacc acggagatgc   1320

agtgacaaat gtgccgccaa gaaaaggtta caaagatgga aatgaatata ttgttgtgga   1380

gaaaaagaag aaatccatca atcaaaataa tgcagacatt caagttgtga atgcaatttc   1440

gagcctaacc tatccaggtg ctctcgtaaa agcgaattcg gaattagtag aaaatcaacc   1500

agatgttctc cctgtaaaac gtgattcatt aacactcagc attgatttgc caggtatgac   1560

taatcaagac aataaaatag ttgtaaaaaa tgccactaaa tcaaacgtta acaacgcagt   1620
```

-continued

```
aaatacatta gtggaaagat ggaatgaaaa atatgctcaa gcttatccaa atgtaagtgc   1680
aaaaattgat tatgatgacg aaatggctta cagtgaatca caattaattg cgaaatttgg   1740
tacagcattt aaagctgtaa ataatagctt gaatgtaaac ttcggcgcaa tcagtgaagg   1800
gaaaatgcaa gaagaagtca ttagttttaa acaaatttac tataacgtga atgttaatga   1860
acctacaaga ccttccagat ttttcggcaa agctgttact aaagagcagt tgcaagcgct   1920
tggagtgaat gcagaaaatc ctcctgcata tatctcaagt gtggcgtatg gccgtcaagt   1980
ttatttgaaa ttatcaacta attcccatag tactaaagta aaagctgctt ttgatgctgc   2040
cgtaagcgga aaatctgtct caggtgatgt agaactaaca aatatcatca aaaattcttc   2100
cttcaaagcc gtaatttacg gaggttccgc aaaagatgaa gttcaaatca tcgacggcaa   2160
cctcggagac ttacgcgata ttttgaaaaa aggcgctact tttaatcgag aaacaccagg   2220
agttcccatt gcttatacaa caaacttcct aaaagacaat gaattagctg ttattaaaaa   2280
caactcagaa tatattgaaa caacttcaaa agcttataca gatggaaaaa ttaacatcga   2340
tcactctgga ggatacgttg ctcaattcaa catttcttgg gatgaagtaa attatgatct   2400
cgagactagt tctagattta tcacgtaccc atttccccgc atcttttatt tttttaaata   2460
ctttagggaa aaatggtttt tgatttgctt ttaaaggttg tggtgtagac tcgtctgctg   2520
actgcatgct agaatctaag tcactttcag aagcatccac aactgactct ttcgccactt   2580
ttctcttatt tgcttttgtt ggtttatctg gataagtaag gctttcaagc tcactatccg   2640
acgacgctat ggcttttctt cttttttaa tttccgctgc gctatccgat gacagacctg   2700
gatgacgacg ctccacttgc agagttggtc ggtcgactcc tgaagcctct tcatttatag   2760
ccacatttcc tgtttgctca ccgttgttat tattgttatt cggacctttc tctgcttttg   2820
ctttcaacat tgctattagg tctgctttgt tcgtattttt cactttattc gatttttcta   2880
gttcctcaat atcacgtgaa cttacttcac gtgcagtttc gtatcttggt cccgtattta   2940
cctcgcttgg ctgctcttct gtttttcttt cttcccattc atctgtgttt agactggaat   3000
cttcgctatc tgtcgctgca aatattatgt cggggttaat cgtaatgcag ttggcagtaa   3060
tgaaaactac catcatcgca cgcataaatc tgtttaatcc cacttatact ccctcctcgt   3120
gatacgctaa tacaaccttt ttagaacaag gaaaattcgg ccttcatttt cactaatttg   3180
ttccgttaaa aattggatta gcagttagtt atcttcttaa ttagctaata taagaaaaaa   3240
tattcatgaa ttattttaag aatatcactt ggagaattaa tttttctcta acatttgtta   3300
atcagttaac cccaactgct tcccaagctt cacccgggcc actaactcaa cgctagtagt   3360
ggatttaatc ccaaatgagc caacagaacc agaaccagaa acagaacaag taacattgga   3420
gttagaaatg gaagaagaaa aaagcaatga tttcgtgtga ataatgcacg aaatcattgc   3480
ttattttttt aaaaagcgat atactagata taacgaaaca acgaactgaa taaagaatac   3540
aaaaaaagag ccacgaccag ttaaagcctg agaaacttta actgcgagcc ttaattgatt   3600
accaccaatc aattaaagaa gtcgagaccc aaaatttggt aaagtattta attactttat   3660
taatcagata cttaaatatc tgtaaaccca ttatatcggg tttttgaggg gatttcaagt   3720
ctttaagaag ataccaggca atcaattaag aaaaacttag ttgattgcct tttttgttgt   3780
gattcaactt tgatcgtagc ttctaactaa ttaattttcg taagaaagga gaacagctga   3840
atgaatatcc cttttgttgt agaaactgtg cttcatgacg gcttgttaaa gtacaaattt   3900
aaaaatagta aaattcgctc aatcactacc aagccaggta aaagtaaagg ggctattttt   3960
gcgtatcgct caaaaaaaag catgattggc ggacgtggcg ttgttctgac ttccgaagaa   4020
```

```
gcgattcacg aaaatcaaga tacatttacg cattggacac caaacgttta tcgttatggt   4080
acgtatgcag acgaaaaccg ttcatacact aaaggacatt ctgaaaacaa tttaagacaa   4140
atcaatacct tctttattga ttttgatatt cacacggaaa aagaaactat ttcagcaagc   4200
gatattttaa caacagctat tgatttaggt tttatgccta cgttaattat caaatctgat   4260
aaaggttatc aagcatattt tgttttagaa acgccagtct atgtgacttc aaaatcagaa   4320
tttaaatctg tcaaagcagc caaaataatc tcgcaaaata tccgagaata ttttggaaag   4380
tctttgccag ttgatctaac gtgcaatcat tttgggattg ctcgtatacc aagaacggac   4440
aatgtagaat tttttgatcc caattaccgt tattctttca aagaatggca agattggtct   4500
ttcaaacaaa cagataataa gggctttact cgttcaagtc taacggtttt aagcggtaca   4560
gaaggcaaaa aacaagtaga tgaaccctgg tttaatctct tattgcacga aacgaaattt   4620
tcaggagaaa agggtttagt agggcgcaat agcgttatgt ttaccctctc tttagcctac   4680
tttagttcag gctattcaat cgaaacgtgc gaatataata tgtttgagtt taataatcga   4740
ttagatcaac ccttagaaga aaaagaagta atcaaaattg ttagaagtgc ctattcagaa   4800
aactatcaag gggctaatag ggaatacatt accattcttt gcaaagcttg ggtatcaagt   4860
gatttaacca gtaaagattt atttgtccgt caagggtggt ttaaattcaa gaaaaaaaga   4920
agcgaacgtc aacgtgttca tttgtcagaa tggaaagaag atttaatggc ttatattagc   4980
gaaaaaagcg atgtatacaa gccttattta gcgacgacca aaaaagagat tagagaagtg   5040
ctaggcattc ctgaacggac attagataaa ttgctgaagg tactgaaggc gaatcaggaa   5100
attttcttta agattaaacc aggaagaaat ggtggcattc aacttgctag tgttaaatca   5160
ttgttgctat cgatcattaa attaaaaaaa gaagaacgag aaagctatat aaaggcgctg   5220
acagcttcgt ttaatttaga acgtacattt attcaagaaa ctctaaacaa attggcagaa   5280
cgccccaaaa cggacccaca actcgatttg tttagctacg atacaggctg aaaataaaac   5340
ccgcactatg ccattacatt tatatctatg atacgtgttt gtttttcttt gctggctagc   5400
ttaattgctt atatttacct gcaataaagg atttcttact tccattatac tcccattttc   5460
caaaaacata cggggaacac gggaacttat tgtacaggcc acctcatagt taatggtttc   5520
gagccttcct gcaatctcat ccatggaaat atattcatcc ccctgccggc ctattaatgt   5580
gacttttgtg cccggcggat attcctgatc cagctccacc ataaattggt ccatgcaaat   5640
tcggccggca attttcaggc gttttccctt cacaaggatg tcggtccctt tcaattttcg   5700
gagccagccg tccgcatagc ctacaggcac cgtcccgatc catgtgtctt tttccgctgt   5760
gtactcggct ccgtagctga cgctctcgcc ttttctgatc agtttgacat gtgacagtgt   5820
cgaatgcagg gtaaatgccg gacgcagctg aaacggtatc tcgtccgaca tgtcagcaga   5880
cgggcgaagg ccatacatgc cgatgccgaa tctgactgca ttaaaaaagc ctttttttcag   5940
ccggagtcca gcggcgctgt tcgcgcagtg gaccattaga ttctttaacg gcagcggagc   6000
aatcagctct ttaaagcgct caaactgcat taagaaatag cctctttctt tttcatccgc   6060
tgtcgcaaaa tgggtaaata cccctttgca ctttaaacga gggttgcggt caagaattgc   6120
catcacgttc tgaacttctt cctctgtttt tacaccaagt ctgttcatcc ccgtatcgac   6180
cttcagatga aaatgaagag aaccttttttt cgtgtggcgg gctgcctcct gaagccattc   6240
aacagaataa cctgttaagg tcacgtcata ctcagcagcg attgccacat actccggggg   6300
aaccgcgcca agcaccaata taggcgcctt caatcccttt ttgcgcagtg aaatcgcttc   6360
```

atccaaaatg gccacggcca agcatgaagc acctgcgtca agagcagcct ttgctgtttc 6420
tgcatcacca tgcccgtagg cgtttgcttt cacaactgcc atcaagtgga catgttcacc 6480
gatatgtttt ttcatattgc tgacattttc ctttatcacg gacaagtcaa tttccgccca 6540
cgtatctctg taaaaaggtt ttgtgctcat ggaaaactcc tctctttttt cagaaaatcc 6600
cagtacgtaa ttaagtattt gagaattaat tttatattga ttaatactaa gtttacccag 6660
ttttcaccta aaaaacaaat gatgagataa tagctccaaa ggctaaagag gactatacca 6720
actatttgtt aat 6733

<210> SEQ ID NO 2
<211> LENGTH: 8317
<212> TYPE: DNA
<213> ORGANISM: Artificial Sequence
<220> FEATURE:
<223> OTHER INFORMATION: plasmid backbone and E7 and chimeric Her2
heterologous antigens

<400> SEQUENCE: 2
ggagtgtata ctggcttact atgttggcac tgatgagggt gtcagtgaag tgcttcatgt 60
ggcaggagaa aaaaggctgc accggtgcgt cagcagaata tgtgatacag gatatattcc 120
gcttcctcgc tcactgactc gctacgctcg gtcgttcgac tgcggcgagc ggaaatggct 180
tacgaacggg gcggagattt cctggaagat gccaggaaga tacttaacag ggaagtgaga 240
gggccgcggc aaagccgttt ttccataggc tccgcccccc tgacaagcat cacgaaatct 300
gacgctcaaa tcagtggtgg cgaaacccga caggactata aagataccag gcgtttcccc 360
ctggcggctc cctcgtgcgc tctcctgttc ctgcctttcg gtttaccggt gtcattccgc 420
tgttatggcc gcgtttgtct cattccacgc ctgacactca gttccgggta ggcagttcgc 480
tccaagctgg actgtatgca cgaacccccc gttcagtccg accgctgcgc cttatccggt 540
aactatcgtc ttgagtccaa cccggaaaga catgcaaaag caccactggc agcagccact 600
ggtaattgat ttagaggagt tagtcttgaa gtcatgcgcc ggttaaggct aaactgaaag 660
gacaagtttt ggtgactgcg ctcctccaag ccagttacct cggttcaaag agttggtagc 720
tcagagaacc ttcgaaaaac cgccctgcaa ggcggttttt tcgttttcag agcaagagat 780
tacgcgcaga ccaaaacgat ctcaagaaga tcatcttatt aatcagataa aatatttcta 840
gccctccttt gattagtata ttcctatctt aaagttactt ttatgtggag gcattaacat 900
ttgttaatga cgtcaaaagg atagcaagac tagaataaag ctataaagca agcatataat 960
attgcgtttc atctttagaa gcgaatttcg ccaatattat aattatcaaa agagaggggt 1020
ggcaaacggt atttggcatt attaggttaa aaaatgtaga aggagagtga aacccatgaa 1080
aaaaataatg ctagttttta ttacacttat attagttagt ctaccaattg cgcaacaaac 1140
tgaagcaaag gatgcatctg cattcaataa agaaaattca atttcatcca tggcaccacc 1200
agcatctccg cctgcaagtc ctaagacgcc aatcgaaaag aaacacgcgg atgaaatcga 1260
taagtatata caaggattgg attacaataa aaacaatgta ttagtatacc acggagatgc 1320
agtgacaaat gtgccgccaa gaaaaggtta caaagatgga aatgaatata ttgttgtgga 1380
gaaaaagaag aaatccatca atcaaaataa tgcagacatt caagttgtga atgcaatttc 1440
gagcctaacc tatccaggtg ctctcgtaaa agcgaattcg gaattagtag aaaatcaacc 1500
agatgttctc cctgtaaaac gtgattcatt aacactcagc attgatttgc caggtatgac 1560
taatcaagac aataaaatag ttgtaaaaaa tgccactaaa tcaaacgtta acaacgcagt 1620

-continued

```
aaatacatta gtggaaagat ggaatgaaaa atatgctcaa gcttatccaa atgtaagtgc   1680
aaaaattgat tatgatgacg aaatggctta cagtgaatca caattaattg cgaaatttgg   1740
tacagcattt aaagctgtaa ataatagctt gaatgtaaac ttcggcgcaa tcagtgaagg   1800
gaaaatgcaa gaagaagtca ttagttttaa acaaatttac tataacgtga atgttaatga   1860
acctacaaga ccttccagat tttcggcaa agctgttact aaagagcagt tgcaagcgct    1920
tggagtgaat gcagaaaatc ctcctgcata tatctcaagt gtggcgtatg gccgtcaagt   1980
ttatttgaaa ttatcaacta attcccatag tactaaagta aaagctgctt ttgatgctgc   2040
cgtaagcgga aaatctgtct caggtgatgt agaactaaca aatatcatca aaaattcttc   2100
cttcaaagcc gtaatttacg gaggttccgc aaaagatgaa gttcaaatca tcgacggcaa   2160
cctcggagac ttacgcgata ttttgaaaaa aggcgctact tttaatcgag aaacaccagg   2220
agttcccatt gcttatacaa caaacttcct aaaagacaat gaattagctg ttattaaaaa   2280
caactcagaa tatattgaaa caacttcaaa agcttataca gatggaaaaa ttaacatcga   2340
tcactctgga ggatacgttg ctcaattcaa catttcttgg gatgaagtaa attatgatct   2400
cgagcatgga gatacaccta cattgcatga atatatgtta gatttgcaac cagagacaac   2460
tgatctctac tgttatgagc aattaaatga cagctcagag gaggaggatg aaatagatgg   2520
tccagctgga caagcagaac cggacagagc ccattacaat attgtaacct tttgttgcaa   2580
gtgtgactct acgcttcggt tgtgcgtaca aagcacacac gtagacattc gtactttgga   2640
agacctgtta atgggcacac taggaattgt gtgccccatc tgttctcaga aaccataaac   2700
tagtctagtg gtgatggtga tgatggagct cagatctgtc taagaggcag ccatagggca   2760
taagctgtgt caccagctgc accgtggatg tcaggcagat gcccagaagg cgggagacat   2820
atggggagcc cacaccagcc atcacgtatg cttcgtctaa gatttctttg ttggctttgg   2880
gggatgtgtt ttccctcaac actttgatgg ccactggaat tttcacattc tccccatcag   2940
ggatccagat gcccttgtag actgtgccaa aagcgccaga tccaagcacc ttcaccttcc   3000
tcagctccgt ctctttcagg atccgcatct gcgcctggtt gggcatcgct ccgctaggtg   3060
tcagcggctc caccagctcc gtttcctgca gcagtctccg catcgtgtac ttccggatct   3120
tctgctgccc tcgggcgcac agctggtggc aggccaggcc ctcgcccaca cactcgtcct   3180
ctggccggtt ggcagtgtgg agcagagctt ggtgcgggtt ccgaaagagc tggtcccagg   3240
gcaccgtgtg cacgaagcag aggtgggtgt tatggtggat gagggccagt ccactgccca   3300
gttccctcag tgagcgcagc cccagccagc tgatgcccag cccttgcagg gtcagcgagt   3360
aggcgccatt gtgcagaatt cgtccccgga ttacttgcag gttctggaag acgctgaggt   3420
caggcaggct gtccggccat gctgagatgt ataggtaacc tgtgatctct tccagagtct   3480
caaacacttg gagctgctct ggctggagcg gggcagtgtt ggaggctggg tccccatcaa   3540
agctctccgg cagaaatgcc aggctcccaa agatcttctt gcagccagca aactcctgga   3600
tattcttcca caaaatcgtg tcctggtagc agagctgggg gttccgctgg atcaagaccc   3660
ctcctttcaa gatctctgtg aggcttcgaa gctgcagctc ccgcaggcct cctggggagg   3720
cccctgtgac aggggtggta ttgttcagcg ggtctccatt gtctagcacg gccagggcat   3780
agttgtcctc aaagagctgg gtgcctcgca caatccgcag cctctgcagt gggacctgcc   3840
tcacttggtt gtgagcgatg agcacgtagc cctgcacctc ctggatatcc tgcaggaagg   3900
acaggctggc attggtgggc aggtaggtga gttccaggtt tccctgcacc acctggcagc   3960
cctggtagag gtggcggagc atgtccaggt gggttctaga tttatcacgt acccatttcc   4020
```

-continued

```
ccgcatcttt tatttttta aatactttag ggaaaaatgg tttttgattt gcttttaaag   4080
gttgtggtgt agactcgtct gctgactgca tgctagaatc taagtcactt tcagaagcat   4140
ccacaactga ctctttcgcc acttttctct tatttgcttt tgttggttta tctggataag   4200
taaggctttc aagctcacta tccgacgacg ctatggcttt tcttcttttt ttaatttccg   4260
ctgcgctatc cgatgacaga cctggatgac gacgctccac ttgcagagtt ggtcggtcga   4320
ctcctgaagc ctcttcattt atagccacat ttcctgtttg ctcaccgttg ttattattgt   4380
tattcggacc tttctctgct tttgctttca acattgctat taggtctgct ttgttcgtat   4440
ttttcacttt attcgatttt tctagttcct caatatcacg tgaacttact tcacgtgcag   4500
tttcgtatct tggtcccgta tttacctcgc ttggctgctc ttctgttttt tcttcttccc   4560
attcatctgt gtttagactg gaatcttcgc tatctgtcgc tgcaaatatt atgtcggggt   4620
taatcgtaat gcagttggca gtaatgaaaa ctaccatcat cgcacgcata aatctgttta   4680
atcccactta tactccctcc tcgtgatacg ctaatacaac ctttttagaa caaggaaaat   4740
tcggccttca ttttcactaa tttgttccgt taaaaattgg attagcagtt agttatcttc   4800
ttaattagct aatataagaa aaaatattca tgaattattt taagaatatc acttggagaa   4860
ttaatttttc tctaacattt gttaatcagt taaccccaac tgcttcccaa gcttcacccg   4920
ggccactaac tcaacgctag tagtggattt aatcccaaat gagccaacag aaccagaacc   4980
agaaacagaa caagtaacat tggagttaga aatggaagaa gaaaaaagca atgatttcgt   5040
gtgaataatg cacgaaatca ttgcttattt ttttaaaaag cgatatacta gatataacga   5100
aacaacgaac tgaataaaga atacaaaaaa agagccacga ccagttaaag cctgagaaac   5160
tttaactgcg agccttaatt gattaccacc aatcaattaa agaagtcgag acccaaaatt   5220
tggtaaagta tttaattact ttattaatca gatacttaaa tatctgtaaa cccattatat   5280
cgggtttttg aggggatttc aagtctttaa gaagatacca ggcaatcaat taagaaaaac   5340
ttagttgatt gcctttttttg ttgtgattca actttgatcg tagcttctaa ctaattaatt   5400
ttcgtaagaa aggagaacag ctgaatgaat atccctttttg ttgtagaaac tgtgcttcat   5460
gacggcttgt taaagtacaa atttaaaaat agtaaaattc gctcaatcac taccaagcca   5520
ggtaaaagta aaggggctat ttttgcgtat cgctcaaaaa aaagcatgat tggcggacgt   5580
ggcgttgttc tgacttccga agaagcgatt cacgaaaatc aagatacatt tacgcattgg   5640
acaccaaacg tttatcgtta tggtacgtat gcagacgaaa accgttcata cactaaagga   5700
cattctgaaa acaatttaag acaaatcaat accttcttta ttgattttga tattcacacg   5760
gaaaaagaaa ctatttcagc aagcgatatt ttaacaacag ctattgattt aggttttatg   5820
cctacgttaa ttatcaaatc tgataaaggt tatcaagcat attttgtttt agaaacgcca   5880
gtctatgtga cttcaaaatc agaatttaaa tctgtcaaag cagccaaaat aatctcgcaa   5940
aatatccgag aatattttgg aaagtctttg ccagttgatc taacgtgcaa tcattttggg   6000
attgctcgta taccaagaac ggacaatgta gaattttttg atcccaatta ccgttattct   6060
ttcaaagaat ggcaagattg gtctttcaaa caaacagata ataagggctt tactcgttca   6120
agtctaacgg ttttaagcgg tacagaaggc aaaaaacaag tagatgaacc ctggtttaat   6180
ctcttattgc acgaaacgaa attttcagga gaaaagggtt tagtagggcg caatagcgtt   6240
atgtttaccc tctctttagc ctactttagt tcaggctatt caatcgaaac gtgcgaatat   6300
aatatgtttg agtttaataa tcgattagat caacccttag aagaaaaaga agtaatcaaa   6360
```

-continued

```
attgttagaa gtgcctattc agaaaactat caaggggcta atagggaata cattaccatt   6420
ctttgcaaag cttgggtatc aagtgattta accagtaaag atttatttgt ccgtcaaggg   6480
tggtttaaat tcaagaaaaa aagaagcgaa cgtcaacgtg ttcatttgtc agaatggaaa   6540
gaagatttaa tggcttatat tagcgaaaaa agcgatgtat acaagcctta tttagcgacg   6600
accaaaaaag agattagaga agtgctaggc attcctgaac ggacattaga taaattgctg   6660
aaggtactga aggcgaatca ggaaattttc tttaagatta aaccaggaag aaatggtggc   6720
attcaacttg ctagtgttaa atcattgttg ctatcgatca ttaaattaaa aaaagaagaa   6780
cgagaaagct atataaaggc gctgacagct tcgtttaatt tagaacgtac atttattcaa   6840
gaaactctaa acaaattggc agaacgcccc aaaacggacc cacaactcga tttgtttagc   6900
tacgatacag gctgaaaata aaacccgcac tatgccatta catttatatc tatgatacgt   6960
gtttgttttt ctttgctggc tagcttaatt gcttatattt acctgcaata aaggatttct   7020
tacttccatt atactcccat tttccaaaaa catacgggga acacgggaac ttattgtaca   7080
ggccacctca tagttaatgg tttcgagcct tcctgcaatc tcatccatgg aaatatattc   7140
atccccctgc cggcctatta atgtgacttt tgtgcccggc ggatattcct gatccagctc   7200
caccataaat tggtccatgc aaattcggcc ggcaattttc aggcgttttc ccttcacaag   7260
gatgtcggtc cctttcaatt ttcggagcca gccgtccgca tagcctacag gcaccgtccc   7320
gatccatgtg tctttttccg ctgtgtactc ggctccgtag ctgacgctct cgccttttct   7380
gatcagtttg acatgtgaca gtgtcgaatg cagggtaaat gccggacgca gctgaaacgg   7440
tatctcgtcc gacatgtcag cagacgggcg aaggccatac atgccgatgc cgaatctgac   7500
tgcattaaaa aagccttttt tcagccggag tccagcggcg ctgttcgcgc agtggaccat   7560
tagattcttt aacggcagcg gagcaatcag ctctttaaag cgctcaaact gcattaagaa   7620
atagcctctt tctttttcat ccgctgtcgc aaaatgggta aatacccctt tgcactttaa   7680
acgagggttg cggtcaagaa ttgccatcac gttctgaact tcttcctctg tttttacacc   7740
aagtctgttc atccccgtat cgaccttcag atgaaaatga agagaacctt ttttcgtgtg   7800
gcgggctgcc tcctgaagcc attcaacaga ataacctgtt aaggtcacgt catactcagc   7860
agcgattgcc acatactccg gggggaaccgc gccaagcacc aatataggcg ccttcaatcc   7920
ctttttgcgc agtgaaatcg cttcatccaa aatggccacg gccaagcatg aagcacctgc   7980
gtcaagagca gcctttgctg tttctgcatc accatgcccg taggcgtttg ctttcacaac   8040
tgccatcaag tggacatgtt caccgatatg tttttcata ttgctgacat tttcctttat   8100
cacggacaag tcaatttccg cccacgtatc tctgtaaaaa ggttttgtgc tcatggaaaa   8160
ctcctctctt ttttcagaaa atcccagtac gtaattaagt atttgagaat taattttata   8220
ttgattaata ctaagtttac ccagttttca cctaaaaaac aaatgatgag ataatagctc   8280
caaaggctaa agaggactat accaactatt tgttaat                             8317
```

<210> SEQ ID NO 3
<211> LENGTH: 306
<212> TYPE: DNA
<213> ORGANISM: Human papillomavirus type 16

<400> SEQUENCE: 3

```
ctcgagcatg gagatacacc tacattgcat gaatatatgt tagatttgca accagagaca     60
actgatctct actgttatga gcaattaaat gacagctcag aggaggagga tgaaatagat    120
ggtccagctg gacaagcaga accggacaga gcccattaca atattgtaac cttttgttgc    180
```

aagtgtgact ctacgcttcg gttgtgcgta caaagcacac acgtagacat tcgtactttg 240
gaagacctgt taatgggcac actaggaatt gtgtgcccca tctgttctca gaaaccataa 300
actagt 306

<210> SEQ ID NO 4
<211> LENGTH: 1297
<212> TYPE: DNA
<213> ORGANISM: Artificial Sequence
<220> FEATURE:
<223> OTHER INFORMATION: chimeric Her2-neu

<400> SEQUENCE: 4
ctagtggtga tggtgatgat ggagctcaga tctgtctaag aggcagccat agggcataag 60
ctgtgtcacc agctgcaccg tggatgtcag gcagatgccc agaaggcggg agacatatgg 120
ggagcccaca ccagccatca cgtatgcttc gtctaagatt tctttgttgg ctttggggga 180
tgtgttttcc ctcaacactt tgatggccac tggaattttc acattctccc catcagggat 240
ccagatgccc ttgtagactg tgccaaaagc gccagatcca agcaccttca ccttcctcag 300
ctccgtctct ttcaggatcc gcatctgcgc ctggttgggc atcgctccgc taggtgtcag 360
cggctccacc agctccgttt cctgcagcag tctccgcatc gtgtacttcc ggatcttctg 420
ctgccctcgg gcgcacagct ggtggcaggc caggccctcg cccacacact cgtcctctgg 480
ccggttggca gtgtggagca gagcttggtg cgggttccga aagagctggt cccagggcac 540
cgtgtgcacg aagcagaggt gggtgttatg gtggatgagg gccagtccac tgcccagttc 600
cctcagtgag cgcagcccca gccagctgat gcccagccct tgcagggtca gcgagtaggc 660
gccattgtgc agaattcgtc cccggattac ttgcaggttc tggaagacgc tgaggtcagg 720
caggctgtcc ggccatgctg agatgtatag gtaacctgtg atctcttcca gagtctcaaa 780
cacttggagc tgctctggct ggagcggggc agtgttggag gctgggtccc catcaaagct 840
ctccggcaga aatgccaggc tcccaaagat cttcttgcag ccagcaaact cctggatatt 900
cttccacaaa atcgtgtcct ggtagcagag ctgggggttc cgctggatca agacccctcc 960
tttcaagatc tctgtgaggc ttcgaagctg cagctcccgc aggcctcctg ggaggcccc 1020 tgtgacaggg gtggtattgt tcagcgggtc tccattgtct agcacggcca gggcatagtt 1080
gtcctcaaag agctgggtgc ctcgcacaat ccgcagcctc tgcagtggga cctgcctcac 1140
ttggttgtga gcgatgagca cgtagccctg cacctcctgg atatcctgca ggaaggacag 1200
gctggcattg gtgggcaggt aggtgagttc caggtttccc tgcaccacct ggcagccctg 1260
gtagaggtgg cggagcatgt ccaggtgggt tctagat 1297

<210> SEQ ID NO 5
<211> LENGTH: 1329
<212> TYPE: DNA
<213> ORGANISM: Artificial Sequence
<220> FEATURE:
<223> OTHER INFORMATION: Listeriolysin-O

<400> SEQUENCE: 5
atgaaaaaaa taatgctagt ttttattaca cttatattag ttagtctacc aattgcgcaa 60
caaactgaag caaaggatgc atctgcattc aataaagaaa attcaatttc atccatggca 120
ccaccagcat ctccgcctgc aagtcctaag acgccaatcg aaaagaaaca cgcggatgaa 180
atcgataagt atatacaagg attggattac aataaaaaca atgtattagt ataccacgga 240

-continued

```
gatgcagtga caaatgtgcc gccaagaaaa ggttacaaag atggaaatga atatattgtt    300

gtggagaaaa agaagaaatc catcaatcaa aataatgcag acattcaagt tgtgaatgca    360

atttcgagcc taacctatcc aggtgctctc gtaaaagcga attcggaatt agtagaaaat    420

caaccagatg ttctccctgt aaaacgtgat tcattaacac tcagcattga tttgccaggt    480

atgactaatc aagacaataa aatagttgta aaaaatgcca ctaaatcaaa cgttaacaac    540

gcagtaaata cattagtgga aagatggaat gaaaaatatg ctcaagctta tccaaatgta    600

agtgcaaaaa ttgattatga tgacgaaatg gcttacagtg aatcacaatt aattgcgaaa    660

tttggtacag catttaaagc tgtaaataat agcttgaatg taaacttcgg cgcaatcagt    720

gaagggaaaa tgcaagaaga agtcattagt tttaaacaaa tttactataa cgtgaatgtt    780

aatgaaccta caagaccttc cagatttttc ggcaaagctg ttactaaaga gcagttgcaa    840

gcgcttggag tgaatgcaga aaatcctcct gcatatatct caagtgtggc gtatggccgt    900

caagtttatt tgaaattatc aactaattcc catagtacta aagtaaaagc tgcttttgat    960

gctgccgtaa gcggaaaatc tgtctcaggt gatgtagaac taacaaatat catcaaaaat   1020

tcttccttca aagccgtaat ttacggaggt tccgcaaaag atgaagttca aatcatcgac   1080

ggcaacctcg gagacttacg cgatattttg aaaaaaggcg ctacttttaa tcgagaaaca   1140

ccaggagttc ccattgctta tacaacaaac ttcctaaaag acaatgaatt agctgttatt   1200

aaaaacaact cagaatatat tgaaacaact tcaaaagctt atacagatgg aaaaattaac   1260

atcgatcact ctggaggata cgttgctcaa ttcaacattt cttgggatga agtaaattat   1320

gatctcgag                                                          1329
```

```
<210> SEQ ID NO 6
<211> LENGTH: 442
<212> TYPE: PRT
<213> ORGANISM: Artificial Sequence
<220> FEATURE:
<223> OTHER INFORMATION: Listeriolysin-O

<400> SEQUENCE: 6

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
```

-continued 165 170 175

Asn Val Asn Asn Ala Val Asn Thr Leu Val Glu Arg Trp Asn Glu Lys
180 185 190

Tyr Ala Gln Ala Tyr Pro Asn Val Ser Ala Lys Ile Asp Tyr Asp Asp
195 200 205

Glu Met Ala Tyr Ser Glu Ser Gln Leu Ile Ala Lys Phe Gly Thr Ala
210 215 220

Phe Lys Ala Val Asn Asn Ser Leu Asn Val Asn Phe Gly Ala Ile Ser
225 230 235 240

Glu Gly Lys Met Gln Glu Glu Val Ile Ser Phe Lys Gln Ile Tyr Tyr
245 250 255

Asn Val Asn Val Asn Glu Pro Thr Arg Pro Ser Arg Phe Phe Gly Lys
260 265 270

Ala Val Thr Lys Glu Gln Leu Gln Ala Leu Gly Val Asn Ala Glu Asn
275 280 285

Pro Pro Ala Tyr Ile Ser Ser Val Ala Tyr Gly Arg Gln Val Tyr Leu
290 295 300

Lys Leu Ser Thr Asn Ser His Ser Thr Lys Val Lys Ala Ala Phe Asp
305 310 315 320

Ala Ala Val Ser Gly Lys Ser Val Ser Gly Asp Val Glu Leu Thr Asn
325 330 335

Ile Ile Lys Asn Ser Ser Phe Lys Ala Val Ile Tyr Gly Gly Ser Ala
340 345 350

Lys Asp Glu Val Gln Ile Ile Asp Gly Asn Leu Gly Asp Leu Arg Asp
355 360 365

Ile Leu Lys Lys Gly Ala Thr Phe Asn Arg Glu Thr Pro Gly Val Pro
370 375 380

Ile Ala Tyr Thr Thr Asn Phe Leu Lys Asp Asn Glu Leu Ala Val Ile
385 390 395 400

Lys Asn Asn Ser Glu Tyr Ile Glu Thr Thr Ser Lys Ala Tyr Thr Asp
405 410 415

Gly Lys Ile Asn Ile Asp His Ser Gly Gly Tyr Val Ala Gln Phe Asn
420 425 430

Ile Ser Trp Asp Glu Val Asn Tyr Asp Leu
435 440

<210> SEQ ID NO 7
<211> LENGTH: 390
<212> TYPE: PRT
<213> ORGANISM: Artificial Sequence
<220> FEATURE:
<223> OTHER INFORMATION: actA

<400> SEQUENCE: 7

Met Arg Ala Met Met Val Val Phe Ile Thr Ala Asn Cys Ile Thr Ile
1 5 10 15

Asn Pro Asp Ile Ile Phe Ala Ala Thr Asp Ser Glu Asp Ser Ser Leu
20 25 30

Asn Thr Asp Glu Trp Glu Glu Glu Lys Thr Glu Glu Gln Pro Ser Glu
35 40 45

Val Asn Thr Gly Pro Arg Tyr Glu Thr Ala Arg Glu Val Ser Ser Arg
50 55 60

Asp Ile Lys Glu Leu Glu Lys Ser Asn Lys Val Arg Asn Thr Asn Lys
65 70 75 80

Ala Asp Leu Ile Ala Met Leu Lys Glu Lys Ala Glu Lys Gly Pro Asn

```
                85                  90                  95

Ile Asn Asn Asn Asn Ser Glu Gln Thr Glu Asn Ala Ala Ile Asn Glu
            100                 105                 110

Glu Ala Ser Gly Ala Asp Arg Pro Ala Ile Gln Val Glu Arg Arg His
        115                 120                 125

Pro Gly Leu Pro Ser Asp Ser Ala Ala Glu Ile Lys Lys Arg Arg Lys
    130                 135                 140

Ala Ile Ala Ser Ser Asp Ser Glu Leu Glu Ser Leu Thr Tyr Pro Asp
145                 150                 155                 160

Lys Pro Thr Lys Val Asn Lys Lys Lys Val Ala Lys Glu Ser Val Ala
                165                 170                 175

Asp Ala Ser Glu Ser Asp Leu Asp Ser Ser Met Gln Ser Ala Asp Glu
            180                 185                 190

Ser Ser Pro Gln Pro Leu Lys Ala Asn Gln Gln Pro Phe Phe Pro Lys
        195                 200                 205

Val Phe Lys Lys Ile Lys Asp Ala Gly Lys Trp Val Arg Asp Lys Ile
    210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Lys Ser Glu Glu Val Asn Ala
                245                 250                 255

Ser Asp Phe Pro Pro Pro Pro Thr Asp Glu Glu Leu Arg Leu Ala Leu
            260                 265                 270

Pro Glu Thr Pro Met Leu Leu Gly Phe Asn Ala Pro Ala Thr Ser Glu
        275                 280                 285

Pro Ser Ser Phe Glu Phe Pro Pro Pro Pro Thr Asp Glu Glu Leu Arg
    290                 295                 300

Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Pro Thr Glu Asp
                325                 330                 335

Glu Leu Glu Ile Ile Arg Glu Thr Ala Ser Ser Leu Asp Ser Ser Phe
            340                 345                 350

Thr Arg Gly Asp Leu Ala Ser Leu Arg Asn Ala Ile Asn Arg His Ser
        355                 360                 365

Gln Asn Phe Ser Asp Phe Pro Pro Ile Pro Thr Glu Glu Glu Leu Asn
    370                 375                 380

Gly Arg Gly Gly Arg Pro
385                 390


<210> SEQ ID NO 8
<211> LENGTH: 1170
<212> TYPE: PRT
<213> ORGANISM: Artificial Sequence
<220> FEATURE:
<223> OTHER INFORMATION: actA

<400> SEQUENCE: 8

Ala Thr Gly Cys Gly Thr Gly Cys Gly Ala Thr Gly Ala Thr Gly Gly
1               5                   10                  15

Thr Gly Gly Thr Thr Thr Thr Cys Ala Thr Thr Ala Cys Thr Gly Cys
            20                  25                  30

Cys Ala Ala Thr Thr Gly Cys Ala Thr Thr Ala Cys Gly Ala Thr Thr
        35                  40                  45

Ala Ala Cys Cys Cys Cys Gly Ala Cys Ala Thr Ala Ala Thr Ala Thr
```

-continued

```
    50                  55                  60

Thr Thr Gly Cys Ala Gly Cys Gly Ala Cys Ala Gly Ala Thr Ala Gly
65                  70                  75                  80

Cys Gly Ala Ala Gly Ala Thr Thr Cys Thr Ala Gly Thr Cys Thr Ala
                85                  90                  95

Ala Ala Cys Ala Cys Ala Gly Ala Thr Gly Ala Ala Thr Gly Gly Gly
            100                 105                 110

Ala Ala Gly Ala Ala Gly Ala Ala Ala Ala Ala Ala Cys Ala Gly Ala
        115                 120                 125

Ala Gly Ala Gly Cys Ala Ala Cys Cys Ala Ala Gly Cys Gly Ala Gly
    130                 135                 140

Gly Thr Ala Ala Ala Thr Ala Cys Gly Gly Gly Ala Cys Cys Ala Ala
145                 150                 155                 160

Gly Ala Thr Ala Cys Gly Ala Ala Ala Cys Thr Gly Cys Ala Cys Gly
                165                 170                 175

Thr Gly Ala Ala Gly Thr Ala Ala Gly Thr Thr Cys Ala Cys Gly Thr
            180                 185                 190

Gly Ala Thr Ala Thr Thr Ala Ala Ala Gly Ala Ala Cys Thr Ala Gly
        195                 200                 205

Ala Ala Ala Ala Ala Thr Cys Gly Ala Ala Thr Ala Ala Ala Gly Thr
    210                 215                 220

Gly Ala Gly Ala Ala Ala Thr Ala Cys Gly Ala Ala Cys Ala Ala Ala
225                 230                 235                 240

Gly Cys Ala Gly Ala Cys Cys Thr Ala Ala Thr Ala Gly Cys Ala Ala
                245                 250                 255

Thr Gly Thr Thr Gly Ala Ala Ala Gly Ala Ala Ala Ala Ala Gly Cys
            260                 265                 270

Ala Gly Ala Ala Ala Ala Ala Gly Gly Thr Cys Cys Ala Ala Ala Thr
        275                 280                 285

Ala Thr Cys Ala Ala Thr Ala Ala Thr Ala Ala Cys Ala Ala Cys Ala
    290                 295                 300

Gly Thr Gly Ala Ala Cys Ala Ala Ala Cys Thr Gly Ala Gly Ala Ala
305                 310                 315                 320

Thr Gly Cys Gly Gly Cys Thr Ala Thr Ala Ala Ala Thr Gly Ala Ala
                325                 330                 335

Gly Ala Gly Gly Cys Thr Thr Cys Ala Gly Gly Ala Gly Cys Cys Gly
            340                 345                 350

Ala Cys Cys Gly Ala Cys Cys Ala Gly Cys Thr Ala Thr Ala Cys Ala
        355                 360                 365

Ala Gly Thr Gly Gly Ala Gly Cys Gly Thr Cys Gly Thr Cys Ala Thr
    370                 375                 380

Cys Cys Ala Gly Gly Ala Thr Thr Gly Cys Cys Ala Thr Cys Gly Gly
385                 390                 395                 400

Ala Thr Ala Gly Cys Gly Cys Ala Gly Cys Gly Gly Ala Ala Ala Thr
                405                 410                 415

Thr Ala Ala Ala Ala Ala Ala Ala Gly Ala Ala Gly Gly Ala Ala Ala
            420                 425                 430

Gly Cys Cys Ala Thr Ala Gly Cys Ala Thr Cys Ala Thr Cys Gly Gly
        435                 440                 445

Ala Thr Ala Gly Thr Gly Ala Gly Cys Thr Thr Gly Ala Ala Ala Gly
    450                 455                 460

Cys Cys Thr Thr Ala Cys Thr Thr Ala Thr Cys Cys Gly Gly Ala Thr
465                 470                 475                 480
```

```
Ala Ala Ala Cys Cys Ala Ala Cys Ala Ala Ala Ala Gly Thr Ala Ala
                485                 490                 495

Ala Thr Ala Ala Gly Ala Ala Ala Ala Ala Ala Gly Thr Gly Gly Cys
            500                 505                 510

Gly Ala Ala Ala Gly Ala Gly Thr Cys Ala Gly Thr Thr Gly Cys Gly
        515                 520                 525

Gly Ala Thr Gly Cys Thr Thr Cys Thr Gly Ala Ala Ala Gly Thr Gly
    530                 535                 540

Ala Cys Thr Thr Ala Gly Ala Thr Thr Cys Thr Ala Gly Cys Ala Thr
545                 550                 555                 560

Gly Cys Ala Gly Thr Cys Ala Gly Cys Ala Gly Ala Thr Gly Ala Gly
                565                 570                 575

Thr Cys Thr Thr Cys Ala Cys Cys Ala Cys Ala Ala Cys Cys Thr Thr
            580                 585                 590

Thr Ala Ala Ala Ala Gly Cys Ala Ala Ala Cys Cys Ala Ala Cys Ala
        595                 600                 605

Ala Cys Cys Ala Thr Thr Thr Thr Thr Cys Cys Cys Thr Ala Ala Ala
    610                 615                 620

Gly Thr Ala Thr Thr Thr Ala Ala Ala Ala Ala Ala Ala Thr Ala Ala
625                 630                 635                 640

Ala Ala Gly Ala Thr Gly Cys Gly Gly Gly Gly Ala Ala Ala Thr Gly
                645                 650                 655

Gly Gly Thr Ala Cys Gly Thr Gly Ala Thr Ala Ala Ala Ala Thr Cys
            660                 665                 670

Gly Ala Cys Gly Ala Ala Ala Ala Thr Cys Cys Thr Gly Ala Ala Gly
        675                 680                 685

Thr Ala Ala Ala Gly Ala Ala Ala Gly Cys Gly Ala Thr Thr Gly Thr
    690                 695                 700

Thr Gly Ala Thr Ala Ala Ala Ala Gly Thr Gly Cys Ala Gly Gly Gly
705                 710                 715                 720

Thr Thr Ala Ala Thr Thr Gly Ala Cys Cys Ala Ala Thr Thr Ala Thr
                725                 730                 735

Thr Ala Ala Cys Cys Ala Ala Ala Ala Ala Gly Ala Ala Ala Ala Gly
            740                 745                 750

Thr Gly Ala Ala Gly Ala Gly Gly Thr Ala Ala Ala Thr Gly Cys Thr
        755                 760                 765

Thr Cys Gly Gly Ala Cys Thr Thr Cys Cys Cys Gly Cys Cys Ala Cys
    770                 775                 780

Cys Ala Cys Cys Thr Ala Cys Gly Gly Ala Thr Gly Ala Ala Gly Ala
785                 790                 795                 800

Gly Thr Thr Ala Ala Gly Ala Cys Thr Thr Gly Cys Thr Thr Thr Gly
                805                 810                 815

Cys Cys Ala Gly Ala Gly Ala Cys Ala Cys Cys Ala Ala Thr Gly Cys
            820                 825                 830

Thr Thr Cys Thr Thr Gly Gly Thr Thr Thr Thr Ala Ala Thr Gly Cys
        835                 840                 845

Thr Cys Cys Thr Gly Cys Thr Ala Cys Ala Thr Cys Ala Gly Ala Ala
    850                 855                 860

Cys Cys Gly Ala Gly Cys Thr Cys Ala Thr Thr Cys Gly Ala Ala Thr
865                 870                 875                 880

Thr Thr Cys Cys Ala Cys Cys Ala Cys Cys Ala Cys Cys Thr Ala Cys
                885                 890                 895
```

-continued

```
Gly Gly Ala Thr Gly Ala Ala Gly Ala Gly Thr Thr Ala Ala Gly Ala
            900                 905                 910

Cys Thr Thr Gly Cys Thr Thr Thr Gly Cys Cys Ala Gly Ala Gly Ala
        915                 920                 925

Cys Gly Cys Cys Ala Ala Thr Gly Cys Thr Thr Cys Thr Thr Gly Gly
    930                 935                 940

Thr Thr Thr Thr Ala Ala Thr Gly Cys Thr Cys Cys Thr Gly Cys Thr
945                 950                 955                 960

Ala Cys Ala Thr Cys Gly Gly Ala Ala Cys Cys Gly Ala Gly Cys Thr
                965                 970                 975

Cys Gly Thr Thr Cys Gly Ala Ala Thr Thr Thr Cys Cys Ala Cys Cys
            980                 985                 990

Gly Cys Cys Thr Cys Cys Ala Ala  Cys Ala Gly Ala Ala  Gly Ala Thr
        995                 1000                1005

Gly Ala  Ala Cys Thr Ala Gly  Ala Ala Ala Thr Cys  Ala Thr Cys
    1010                1015                1020

Cys Gly  Gly Gly Ala Ala Ala  Cys Ala Gly Cys Ala  Thr Cys Cys
    1025                1030                1035

Thr Cys  Gly Cys Thr Ala Gly  Ala Thr Thr Cys Thr  Ala Gly Thr
    1040                1045                1050

Thr Thr  Thr Ala Cys Ala Ala  Gly Ala Gly Gly Gly  Gly Ala Thr
    1055                1060                1065

Thr Thr  Ala Gly Cys Thr Ala  Gly Thr Thr Thr Gly  Ala Gly Ala
    1070                1075                1080

Ala Ala  Thr Gly Cys Thr Ala  Thr Thr Ala Ala Thr  Cys Gly Cys
    1085                1090                1095

Cys Ala  Thr Ala Gly Thr Cys  Ala Ala Ala Ala Thr  Thr Thr Cys
    1100                1105                1110

Thr Cys  Thr Gly Ala Thr Thr  Thr Cys Cys Cys Ala  Cys Cys Ala
    1115                1120                1125

Ala Thr  Cys Cys Cys Ala Ala  Cys Ala Gly Ala Ala  Gly Ala Ala
    1130                1135                1140

Gly Ala  Gly Thr Thr Gly Ala  Ala Cys Gly Gly Gly  Ala Gly Ala
    1145                1150                1155

Gly Gly  Cys Gly Gly Thr Ala  Gly Ala Cys Cys Ala
    1160                1165                1170
```

<210> SEQ ID NO 9
<211> LENGTH: 669
<212> TYPE: DNA
<213> ORGANISM: Artificial Sequence
<220> FEATURE:
<223> OTHER INFORMATION: actA

<400> SEQUENCE: 9

```
tttatcacgt acccatttcc ccgcatcttt tattttttta aatactttag ggaaaaatgg     60

tttttgattt gcttttaaag gttgtggtgt agactcgtct gctgactgca tgctagaatc    120

taagtcactt tcagaagcat ccacaactga ctctttcgcc acttttctct tatttgcttt    180

tgttggttta tctggataag taaggctttc aagctcacta tccgacgacg ctatggcttt    240

tcttcttttt ttaatttccg ctgcgctatc cgatgacaga cctggatgac gacgctccac    300

ttgcagagtt ggtcggtcga ctcctgaagc ctcttcattt atagccacat ttcctgtttg    360

ctcaccgttg ttattattgt tattcggacc tttctctgct tttgctttca acattgctat    420

taggtctgct ttgttcgtat ttttcacttt attcgatttt tctagttcct caatatcacg    480
```

```
tgaacttact tcacgtgcag tttcgtatct tggtcccgta tttacctcgc ttggctgctc    540

ttctgttttt tcttcttccc attcatctgt gtttagactg gaatcttcgc tatctgtcgc    600

tgcaaatatt atgtcggggt taatcgtaat gcagttggca gtaatgaaaa ctaccatcat    660

cgcacgcat                                                            669


<210> SEQ ID NO 10
<211> LENGTH: 390
<212> TYPE: PRT
<213> ORGANISM: Artificial Sequence
<220> FEATURE:
<223> OTHER INFORMATION: actA

<400> SEQUENCE: 10

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
            20                  25                  30

Asn Thr Asp Glu Trp Glu Glu Glu Lys Thr Glu Glu Gln Pro Ser Glu
        35                  40                  45

Val Asn Thr Gly Pro Arg Tyr Glu Thr Ala Arg Glu Val Ser Ser Arg
    50                  55                  60

Asp Ile Lys Glu Leu Glu Lys Ser Asn Lys Val Arg Asn Thr Asn Lys
65                  70                  75                  80

Ala Asp Leu Ile Ala Met Leu Lys Glu Lys Ala Glu Lys Gly Pro Asn
                85                  90                  95

Ile Asn Asn Asn Asn Ser Glu Gln Thr Glu Asn Ala Ala Ile Asn Glu
            100                 105                 110

Glu Ala Ser Gly Ala Asp Arg Pro Ala Ile Gln Val Glu Arg Arg His
        115                 120                 125

Pro Gly Leu Pro Ser Asp Ser Ala Ala Glu Ile Lys Lys Arg Arg Lys
    130                 135                 140

Ala Ile Ala Ser Ser Asp Ser Glu Leu Glu Ser Leu Thr Tyr Pro Asp
145                 150                 155                 160

Lys Pro Thr Lys Val Asn Lys Lys Lys Val Ala Lys Glu Ser Val Ala
                165                 170                 175

Asp Ala Ser Glu Ser Asp Leu Asp Ser Ser Met Gln Ser Ala Asp Glu
            180                 185                 190

Ser Ser Pro Gln Pro Leu Lys Ala Asn Gln Gln Pro Phe Phe Pro Lys
        195                 200                 205

Val Phe Lys Lys Ile Lys Asp Ala Gly Lys Trp Val Arg Asp Lys Ile
    210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Lys Ser Glu Glu Val Asn Ala
                245                 250                 255

Ser Asp Phe Pro Pro Pro Pro Thr Asp Glu Glu Leu Arg Leu Ala Leu
            260                 265                 270

Pro Glu Thr Pro Met Leu Leu Gly Phe Asn Ala Pro Ala Thr Ser Glu
        275                 280                 285

Pro Ser Ser Phe Glu Phe Pro Pro Pro Pro Thr Asp Glu Glu Leu Arg
    290                 295                 300

Leu Ala Leu Pro Glu Thr Pro Met Leu Leu Gly Phe Asn Ala Pro Ala
305                 310                 315                 320
```

-continued

```
Thr Ser Glu Pro Ser Ser Phe Glu Phe Pro Pro Pro Pro Thr Glu Asp
                325                 330                 335

Glu Leu Glu Ile Ile Arg Glu Thr Ala Ser Ser Leu Asp Ser Ser Phe
            340                 345                 350

Thr Arg Gly Asp Leu Ala Ser Leu Arg Asn Ala Ile Asn Arg His Ser
        355                 360                 365

Gln Asn Phe Ser Asp Phe Pro Pro Ile Pro Thr Glu Glu Glu Leu Asn
    370                 375                 380

Gly Arg Gly Gly Arg Pro
385                 390


<210> SEQ ID NO 11
<211> LENGTH: 1170
<212> TYPE: DNA
<213> ORGANISM: Artificial Sequence
<220> FEATURE:
<223> OTHER INFORMATION: actA

<400> SEQUENCE: 11

atgcgtgcga tgatggtggt tttcattact gccaattgca ttacgattaa ccccgacata     60

atatttgcag cgacagatag cgaagattct agtctaaaca cagatgaatg ggaagaagaa    120

aaaacagaag agcaaccaag cgaggtaaat acgggaccaa gatacgaaac tgcacgtgaa    180

gtaagttcac gtgatattaa agaactagaa aaatcgaata aagtgagaaa tacgaacaaa    240

gcagacctaa tagcaatgtt gaaagaaaaa gcagaaaaag gtccaaatat caataataac    300

aacagtgaac aaactgagaa tgcggctata aatgaagagg cttcaggagc cgaccgacca    360

gctatacaag tggagcgtcg tcatccagga ttgccatcgg atagcgcagc ggaaattaaa    420

aaaagaagga aagccatagc atcatcggat agtgagcttg aaagccttac ttatccggat    480

aaaccaacaa aagtaaataa gaaaaaagtg gcgaaagagt cagttgcgga tgcttctgaa    540

agtgacttag attctagcat gcagtcagca gatgagtctt caccacaacc tttaaaagca    600

aaccaacaac catttttccc taaagtattt aaaaaaataa aagatgcggg gaaatgggta    660

cgtgataaaa tcgacgaaaa tcctgaagta aagaaagcga ttgttgataa aagtgcaggg    720

ttaattgacc aattattaac caaaaagaaa agtgaagagg taaatgcttc ggacttcccg    780

ccaccaccta cggatgaaga gttaagactt gctttgccag agacaccaat gcttcttggt    840

tttaatgctc ctgctacatc agaaccgagc tcattcgaat ttccaccacc acctacggat    900

gaagagttaa gacttgcttt gccagagacg ccaatgcttc ttggttttaa tgctcctgct    960

acatcggaac cgagctcgtt cgaatttcca ccgcctccaa cagaagatga actagaaatc   1020

atccgggaaa cagcatcctc gctagattct agttttacaa gaggggattt agctagtttg   1080

agaaatgcta ttaatcgcca tagtcaaaat ttctctgatt tcccaccaat cccaacagaa   1140

gaagagttga acgggagagg cggtagacca                                    1170


<210> SEQ ID NO 12
<211> LENGTH: 32
<212> TYPE: PRT
<213> ORGANISM: Listeria monocytogenes

<400> SEQUENCE: 12

Lys Glu Asn Ser Ile Ser Ser Met Ala Pro Pro Ala Ser Pro Pro Ala
1               5                   10                  15

Ser Pro Lys Thr Pro Ile Glu Lys Lys His Ala Asp Glu Ile Asp Lys
            20                  25                  30
```

<210> SEQ ID NO 13
<211> LENGTH: 19
<212> TYPE: PRT
<213> ORGANISM: Listeria monocytogenes

<400> SEQUENCE: 13

```
Lys Glu Asn Ser Ile Ser Ser Met Ala Pro Pro Ala Ser Pro Pro Ala
1               5                   10                  15

Ser Pro Lys
```

<210> SEQ ID NO 14
<211> LENGTH: 14
<212> TYPE: PRT
<213> ORGANISM: Listeria monocytogenes

<400> SEQUENCE: 14

```
Lys Thr Glu Glu Gln Pro Ser Glu Val Asn Thr Gly Pro Arg
1               5                   10
```

<210> SEQ ID NO 15
<211> LENGTH: 28
<212> TYPE: PRT
<213> ORGANISM: Listeria monocytogenes

<400> SEQUENCE: 15

```
Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25
```

<210> SEQ ID NO 16
<211> LENGTH: 20
<212> TYPE: PRT
<213> ORGANISM: Listeria monocytogenes

<400> SEQUENCE: 16

```
Lys Asn Glu Glu Val Asn Ala Ser Asp Phe Pro Pro Pro Pro Thr Asp
1               5                   10                  15

Glu Glu Leu Arg
            20
```

<210> SEQ ID NO 17
<211> LENGTH: 33
<212> TYPE: PRT
<213> ORGANISM: Listeria monocytogenes

<400> SEQUENCE: 17

```
Arg Gly Gly Ile Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
            20                  25                  30

Arg
```

<210> SEQ ID NO 18
<211> LENGTH: 28
<212> TYPE: PRT
<213> ORGANISM: Listeria monocytogenes

<400> SEQUENCE: 18

```
Lys Glu Ser Val Val Asp Ala Ser Glu Ser Asp Leu Asp Ser Ser Met
1               5                   10                  15
```

-continued

```
Gln Ser Ala Asp Glu Ser Thr Pro Gln Pro Leu Lys
            20                  25


<210> SEQ ID NO 19
<211> LENGTH: 20
<212> TYPE: PRT
<213> ORGANISM: Listeria monocytogenes

<400> SEQUENCE: 19

Lys Ser Glu Glu Val Asn Ala Ser Asp Phe Pro Pro Pro Pro Thr Asp
1               5                   10                  15

Glu Glu Leu Arg
            20


<210> SEQ ID NO 20
<211> LENGTH: 33
<212> TYPE: PRT
<213> ORGANISM: Listeria monocytogenes

<400> SEQUENCE: 20

Arg Gly Gly Arg Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
            20                  25                  30

Arg


<210> SEQ ID NO 21
<211> LENGTH: 19
<212> TYPE: PRT
<213> ORGANISM: Listeria monocytogenes

<400> SEQUENCE: 21

Arg Ser Glu Val Thr Ile Ser Pro Ala Glu Thr Pro Glu Ser Pro Pro
1               5                   10                  15

Ala Thr Pro


<210> SEQ ID NO 22
<211> LENGTH: 17
<212> TYPE: PRT
<213> ORGANISM: Streptococcus pyogenes

<400> SEQUENCE: 22

Lys Gln Asn Thr Ala Ser Thr Glu Thr Thr Thr Thr Asn Glu Gln Pro
1               5                   10                  15

Lys


<210> SEQ ID NO 23
<211> LENGTH: 17
<212> TYPE: PRT
<213> ORGANISM: Streptococcus equisimilis

<400> SEQUENCE: 23

Lys Gln Asn Thr Ala Asn Thr Glu Thr Thr Thr Thr Asn Glu Gln Pro
1               5                   10                  15

Lys


<210> SEQ ID NO 24
<211> LENGTH: 22
<212> TYPE: DNA
<213> ORGANISM: Artificial Sequence
<220> FEATURE:
<223> OTHER INFORMATION: E7 primer sequence
```

<400> SEQUENCE: 24
ggctcgagca tggagataca cc 22

<210> SEQ ID NO 25
<211> LENGTH: 28
<212> TYPE: DNA
<213> ORGANISM: Artificial Sequence
<220> FEATURE:
<223> OTHER INFORMATION: E7 primer sequence

<400> SEQUENCE: 25
ggggactagt ttatggtttc tgagaaca 28

<210> SEQ ID NO 26
<211> LENGTH: 31
<212> TYPE: DNA
<213> ORGANISM: Artificial Sequence
<220> FEATURE:
<223> OTHER INFORMATION: hly promoter and gene fragment F primer

<400> SEQUENCE: 26
gggggctagc cctcctttga ttagtatatt c 31

<210> SEQ ID NO 27
<211> LENGTH: 28
<212> TYPE: DNA
<213> ORGANISM: Artificial Sequence
<220> FEATURE:
<223> OTHER INFORMATION: hly promoter and gene fragment R primer

<400> SEQUENCE: 27
ctccctcgag atcataattt acttcatc 28

<210> SEQ ID NO 28
<211> LENGTH: 55
<212> TYPE: DNA
<213> ORGANISM: Artificial Sequence
<220> FEATURE:
<223> OTHER INFORMATION: prfA gene amplification F primer

<400> SEQUENCE: 28
gactacaagg acgatgaccg acaagtgata acccgggatc taaataaatc cgttt 55

<210> SEQ ID NO 29
<211> LENGTH: 27
<212> TYPE: DNA
<213> ORGANISM: Artificial Sequence
<220> FEATURE:
<223> OTHER INFORMATION: prfA gene amplification R primer

<400> SEQUENCE: 29
cccgtcgacc agctcttctt ggtgaag 27

<210> SEQ ID NO 30
<211> LENGTH: 25
<212> TYPE: DNA
<213> ORGANISM: Artificial Sequence
<220> FEATURE:
<223> OTHER INFORMATION: E7 F primer sequence

<400> SEQUENCE: 30
gcggatccca tggagataca cctac 25

<210> SEQ ID NO 31

<211> LENGTH: 22
<212> TYPE: DNA
<213> ORGANISM: Artificial Sequence
<220> FEATURE:
<223> OTHER INFORMATION: E7 R primer sequence

<400> SEQUENCE: 31
gctctagatt atggtttctg ag 22

<210> SEQ ID NO 32
<211> LENGTH: 9
<212> TYPE: PRT
<213> ORGANISM: Artificial Sequence
<220> FEATURE:
<223> OTHER INFORMATION: (PE)-conjugated E7 peptide

<400> SEQUENCE: 32

Arg Ala His Tyr Asn Ile Val Thr Phe
1 5

<210> SEQ ID NO 33
<211> LENGTH: 31
<212> TYPE: DNA
<213> ORGANISM: Artificial Sequence
<220> FEATURE:
<223> OTHER INFORMATION: hly promoter and gene fragment F primer

<400> SEQUENCE: 33
ggggtctaga cctcctttga ttagtatatt c 31

<210> SEQ ID NO 34
<211> LENGTH: 45
<212> TYPE: DNA
<213> ORGANISM: Artificial Sequence
<220> FEATURE:
<223> OTHER INFORMATION: hly promoter and gene fragment R primer

<400> SEQUENCE: 34
atcttcgcta tctgtcgccg cggcgcgtgc ttcagtttgt tgcgc 45

<210> SEQ ID NO 35
<211> LENGTH: 45
<212> TYPE: DNA
<213> ORGANISM: Artificial Sequence
<220> FEATURE:
<223> OTHER INFORMATION: ActA gene amplification F primer

<400> SEQUENCE: 35
gcgcaacaaa ctgaagcagc ggccgcggcg acagatagcg aagat 45

<210> SEQ ID NO 36
<211> LENGTH: 42
<212> TYPE: DNA
<213> ORGANISM: Artificial Sequence
<220> FEATURE:
<223> OTHER INFORMATION: ActA gene amplification R primer

<400> SEQUENCE: 36
tgtaggtgta tctccatgct cgagagctag gcgatcaatt tc 42

<210> SEQ ID NO 37
<211> LENGTH: 42
<212> TYPE: DNA
<213> ORGANISM: Artificial Sequence
<220> FEATURE:
<223> OTHER INFORMATION: E7 F primer sequence

<400> SEQUENCE: 37
ggaattgatc gcctagctct cgagcatgga gatacaccta ca 42

<210> SEQ ID NO 38
<211> LENGTH: 42
<212> TYPE: DNA
<213> ORGANISM: Artificial Sequence
<220> FEATURE:
<223> OTHER INFORMATION: E7 R primer sequence

<400> SEQUENCE: 38
aaacggattt atttagatcc cgggttatgg tttctgagaa ca 42

<210> SEQ ID NO 39
<211> LENGTH: 42
<212> TYPE: DNA
<213> ORGANISM: Artificial Sequence
<220> FEATURE:
<223> OTHER INFORMATION: prfA gene amplification F primer

<400> SEQUENCE: 39
tgttctcaga aaccataacc cgggatctaa ataaatccgt tt 42

<210> SEQ ID NO 40
<211> LENGTH: 28
<212> TYPE: DNA
<213> ORGANISM: Artificial Sequence
<220> FEATURE:
<223> OTHER INFORMATION: prfA gene amplification R primer

<400> SEQUENCE: 40
gggggtcgac cagctcttct tggtgaag 28

<210> SEQ ID NO 41
<211> LENGTH: 21
<212> TYPE: DNA
<213> ORGANISM: Artificial Sequence
<220> FEATURE:
<223> OTHER INFORMATION: dal gene forward primer

<400> SEQUENCE: 41
ccatggtgac aggctggcat c 21

<210> SEQ ID NO 42
<211> LENGTH: 27
<212> TYPE: DNA
<213> ORGANISM: Artificial Sequence
<220> FEATURE:
<223> OTHER INFORMATION: dal gene reverse primer

<400> SEQUENCE: 42
gctagcctaa tggatgtatt ttctagg 27

<210> SEQ ID NO 43
<211> LENGTH: 27
<212> TYPE: DNA
<213> ORGANISM: Artificial Sequence
<220> FEATURE:
<223> OTHER INFORMATION: minimal p60 promoter sequence forward primer

<400> SEQUENCE: 43
ttaattaaca aatagttggt atagtcc 27

<210> SEQ ID NO 44
<211> LENGTH: 36

<212> TYPE: DNA
<213> ORGANISM: Artificial Sequence
<220> FEATURE:
<223> OTHER INFORMATION: minimal p60 promoter sequence forward primer

<400> SEQUENCE: 44
gacgatgcca gcctgtcacc atggaaaact cctctc 36

<210> SEQ ID NO 45
<211> LENGTH: 156
<212> TYPE: DNA
<213> ORGANISM: Artificial Sequence
<220> FEATURE:
<223> OTHER INFORMATION: truncated p60 promoter

<400> SEQUENCE: 45
caaatagttg gtatagtcct ctttagcctt tggagtatta tctcatcatt tgttttttag 60
gtgaaaactg ggtaaactta gtattatcaa tataaaatta attctcaaat acttaattac 120
gtactgggat tttctgaaaa aagagaggag ttttcc 156

<210> SEQ ID NO 46
<211> LENGTH: 25
<212> TYPE: DNA
<213> ORGANISM: Artificial Sequence
<220> FEATURE:
<223> OTHER INFORMATION: oriRep forward primer

<400> SEQUENCE: 46
ggcgccacta actcaacgct agtag 25

<210> SEQ ID NO 47
<211> LENGTH: 27
<212> TYPE: DNA
<213> ORGANISM: Artificial Sequence
<220> FEATURE:
<223> OTHER INFORMATION: oriRep reverse primer

<400> SEQUENCE: 47
gctagccagc aaagaaaaac aaacacg 27

<210> SEQ ID NO 48
<211> LENGTH: 38
<212> TYPE: DNA
<213> ORGANISM: Artificial Sequence
<220> FEATURE:
<223> OTHER INFORMATION: oriRep forward primer

<400> SEQUENCE: 48
gtcgacggtc accggcgcca ctaactcaac gctagtag 38

<210> SEQ ID NO 49
<211> LENGTH: 35
<212> TYPE: DNA
<213> ORGANISM: Artificial Sequence
<220> FEATURE:
<223> OTHER INFORMATION: oriRep reverse primer

<400> SEQUENCE: 49
ttaattaagc tagccagcaa agaaaaacaa acacg 35

<210> SEQ ID NO 50
<211> LENGTH: 29
<212> TYPE: DNA
<213> ORGANISM: Artificial Sequence
<220> FEATURE:

<223> OTHER INFORMATION: LLO-E7 gene forward amplification primer

<400> SEQUENCE: 50
atgaaaaaaa taatgctagt ttttattac 29

<210> SEQ ID NO 51
<211> LENGTH: 48
<212> TYPE: DNA
<213> ORGANISM: Artificial Sequence
<220> FEATURE:
<223> OTHER INFORMATION: LLO-E7 gene reverse amplification primer

<400> SEQUENCE: 51
gcggccgctt aatgatgatg atgatgatgt ggtttctgag aacagatg 48

<210> SEQ ID NO 52
<211> LENGTH: 22
<212> TYPE: DNA
<213> ORGANISM: Artificial Sequence
<220> FEATURE:
<223> OTHER INFORMATION: Taqman primer-probe sets

<400> SEQUENCE: 52
gcaagtgtga ctctacgctt cg 22

<210> SEQ ID NO 53
<211> LENGTH: 21
<212> TYPE: DNA
<213> ORGANISM: Artificial Sequence
<220> FEATURE:
<223> OTHER INFORMATION: Taqman primer-probe sets

<400> SEQUENCE: 53
tgcccattaa caggtcttcc a 21

<210> SEQ ID NO 54
<211> LENGTH: 32
<212> TYPE: DNA
<213> ORGANISM: Artificial Sequence
<220> FEATURE:
<223> OTHER INFORMATION: Taqman primer-probe sets

<400> SEQUENCE: 54
tgcgtacaaa gcacacacgt agacattcgt ac 32

<210> SEQ ID NO 55
<211> LENGTH: 24
<212> TYPE: DNA
<213> ORGANISM: Artificial Sequence
<220> FEATURE:
<223> OTHER INFORMATION: Taqman primer-probe sets

<400> SEQUENCE: 55
tgacatcgtt tgtgtttgag ctag 24

<210> SEQ ID NO 56
<211> LENGTH: 23
<212> TYPE: DNA
<213> ORGANISM: Artificial Sequence
<220> FEATURE:
<223> OTHER INFORMATION: Taqman primer-probe sets

<400> SEQUENCE: 56
gcagcgctct ctataccagg tac 23

<210> SEQ ID NO 57
<211> LENGTH: 38
<212> TYPE: DNA
<213> ORGANISM: Artificial Sequence
<220> FEATURE:
<223> OTHER INFORMATION: Taqman primer-probe sets

<400> SEQUENCE: 57
ttaatgtcca tgttatgtct ccgttatagc tcatcgta 38

<210> SEQ ID NO 58
<211> LENGTH: 19
<212> TYPE: DNA
<213> ORGANISM: Artificial Sequence
<220> FEATURE:
<223> OTHER INFORMATION: primer to verify deletion of ActA

<400> SEQUENCE: 58
tgggatggcc aagaaattc 19

<210> SEQ ID NO 59
<211> LENGTH: 22
<212> TYPE: DNA
<213> ORGANISM: Artificial Sequence
<220> FEATURE:
<223> OTHER INFORMATION: primer to verify deletion of ActA

<400> SEQUENCE: 59
ctaccatgtc ttccgttgct tg 22

<210> SEQ ID NO 60
<211> LENGTH: 1256
<212> TYPE: DNA
<213> ORGANISM: Artificial Sequence
<220> FEATURE:
<223> OTHER INFORMATION: Lm-dd actA

<400> SEQUENCE: 60
gcgccaaatc attggttgat tggtgaggat gtctgtgtgc gtgggtcgcg agatgggcga 60
ataagaagca ttaaagatcc tgacaaatat aatcaagcgg ctcatatgaa agattacgaa 120
tcgcttccac tcacagagga aggcgactgg ggcggagttc attataatag tggtatcccg 180
aataaagcag cctataatac tatcactaaa cttggaaaag aaaaaacaga acagctttat 240
tttcgcgcct taaagtacta tttaacgaaa aaatcccagt ttaccgatgc gaaaaaagcg 300
cttcaacaag cagcgaaaga tttatatggt gaagatgctt ctaaaaaagt tgctgaagct 360
tgggaagcag ttggggttaa ctgattaaca aatgttagag aaaaattaat tctccaagtg 420
atattcttaa aataattcat gaatattttt tcttatatta gctaattaag aagataacta 480
actgctaatc caatttttaa cggaacaaat tagtgaaaat gaaggccgaa ttttccttgt 540
tctaaaaagg ttgtattagc gtatcacgag gagggagtat aagtgggatt aaacagattt 600
atgcgtgcga tgatggtggt tttcattact gccaattgca ttacgattaa ccccgacgtc 660
gacccatacg acgttaattc ttgcaatgtt agctattggc gtgttctctt taggggcgtt 720
tatcaaaatt attcaattaa gaaaaaataa ttaaaaacac agaacgaaag aaaaagtgag 780
gtgaatgata tgaaattcaa aaaggtggtt ctaggtatgt gcttgatcgc aagtgttcta 840
gtctttccgg taacgataaa agcaaatgcc tgttgtgatg aatacttaca aacacccgca 900
gctccgcatg atattgacag caaattacca cataaactta gttggtccgc ggataacccg 960
acaaatactg acgtaaatac gcactattgg ctttttaaac aagcggaaaa aatactagct 1020

-continued

```
aaagatgtaa atcatatgcg agctaattta atgaatgaac ttaaaaaatt cgataaacaa   1080

atagctcaag gaatatatga tgcggatcat aaaaatccat attatgatac tagtacattt   1140

ttatctcatt tttataatcc tgatagagat aatacttatt tgccgggttt tgctaatgcg   1200

aaaataacag gagcaaagta tttcaatcaa tcggtgactg attaccgaga agggaa       1256


<210> SEQ ID NO 61
<211> LENGTH: 28
<212> TYPE: DNA
<213> ORGANISM: Artificial Sequence
<220> FEATURE:
<223> OTHER INFORMATION: Her-2-Chimera (F) primer

<400> SEQUENCE: 61

tgatctcgag acccacctgg acatgctc                                        28


<210> SEQ ID NO 62
<211> LENGTH: 49
<212> TYPE: DNA
<213> ORGANISM: Artificial Sequence
<220> FEATURE:
<223> OTHER INFORMATION: HerEC1-EC2F primer

<400> SEQUENCE: 62

ctaccaggac acgattttgt ggaagaatat ccaggagttt gctggctgc                 49


<210> SEQ ID NO 63
<211> LENGTH: 49
<212> TYPE: DNA
<213> ORGANISM: Artificial Sequence
<220> FEATURE:
<223> OTHER INFORMATION: HerEC1-EC2R primer

<400> SEQUENCE: 63

gcagccagca aactcctgga tattcttcca caaaatcgtg tcctggtag                 49


<210> SEQ ID NO 64
<211> LENGTH: 50
<212> TYPE: DNA
<213> ORGANISM: Artificial Sequence
<220> FEATURE:
<223> OTHER INFORMATION: HerEC2-ICIF primer

<400> SEQUENCE: 64

ctgccaccag ctgtgcgccc gagggcagca gaagatccgg aagtacacga                50


<210> SEQ ID NO 65
<211> LENGTH: 50
<212> TYPE: DNA
<213> ORGANISM: Artificial Sequence
<220> FEATURE:
<223> OTHER INFORMATION: HerEC2-ICIR primer

<400> SEQUENCE: 65

tcgtgtactt ccggatcttc tgctgccctc gggcgcacag ctggtggcag                50


<210> SEQ ID NO 66
<211> LENGTH: 39
<212> TYPE: DNA
<213> ORGANISM: Artificial Sequence
<220> FEATURE:
<223> OTHER INFORMATION: Her-2-Chimera (R) primer

<400> SEQUENCE: 66

gtggcccggg tctagattag tctaagaggc agccatagg                            39
```

<210> SEQ ID NO 67
<211> LENGTH: 28
<212> TYPE: DNA
<213> ORGANISM: Artificial Sequence
<220> FEATURE:
<223> OTHER INFORMATION: Her-2-EC1(F) primer

<400> SEQUENCE: 67
ccgcctcgag gccgcgagca cccaagtg 28

<210> SEQ ID NO 68
<211> LENGTH: 31
<212> TYPE: DNA
<213> ORGANISM: Artificial Sequence
<220> FEATURE:
<223> OTHER INFORMATION: Her-2-EC1(R)

<400> SEQUENCE: 68
cgcgactagt ttaatcctct gctgtcacct c 31

<210> SEQ ID NO 69
<211> LENGTH: 28
<212> TYPE: DNA
<213> ORGANISM: Artificial Sequence
<220> FEATURE:
<223> OTHER INFORMATION: Her-2-EC2(F) primer

<400> SEQUENCE: 69
ccgcctcgag tacctttcta cggacgtg 28

<210> SEQ ID NO 70
<211> LENGTH: 30
<212> TYPE: DNA
<213> ORGANISM: Artificial Sequence
<220> FEATURE:
<223> OTHER INFORMATION: Her- 2- EC2(R) primer

<400> SEQUENCE: 70
cgcgactagt ttactctggc cggttggcag 30

<210> SEQ ID NO 71
<211> LENGTH: 31
<212> TYPE: DNA
<213> ORGANISM: Artificial Sequence
<220> FEATURE:
<223> OTHER INFORMATION: Her-2- IC1(F) primer

<400> SEQUENCE: 71
ccgcctcgag cagcagaaga tccggaagta c 31

<210> SEQ ID NO 72
<211> LENGTH: 30
<212> TYPE: DNA
<213> ORGANISM: Artificial Sequence
<220> FEATURE:
<223> OTHER INFORMATION: Her-2-IC1(R) primer

<400> SEQUENCE: 72
cgcgactagt ttaagcccct tcggagggtg 30

<210> SEQ ID NO 73
<211> LENGTH: 7075
<212> TYPE: DNA
<213> ORGANISM: Artificial Sequence
<220> FEATURE:

<223> OTHER INFORMATION: pAdv164 sequence

<400> SEQUENCE: 73

```
cggagtgtat actggcttac tatgttggca ctgatgaggg tgtcagtgaa gtgcttcatg     60
tggcaggaga aaaaaggctg caccggtgcg tcagcagaat atgtgataca ggatatattc    120
cgcttcctcg ctcactgact cgctacgctc ggtcgttcga ctgcggcgag cggaaatggc    180
ttacgaacgg ggcggagatt tcctggaaga tgccaggaag atacttaaca gggaagtgag    240
agggccgcgg caaagccgtt tttccatagg ctccgccccc ctgacaagca tcacgaaatc    300
tgacgctcaa atcagtggtg gcgaaacccg acaggactat aaagatacca ggcgtttccc    360
cctggcggct ccctcgtgcg ctctcctgtt cctgcctttc ggtttaccgg tgtcattccg    420
ctgttatggc cgcgtttgtc tcattccacg cctgacactc agttccgggt aggcagttcg    480
ctccaagctg gactgtatgc acgaaccccc cgttcagtcc gaccgctgcg ccttatccgg    540
taactatcgt cttgagtcca acccggaaag acatgcaaaa gcaccactgg cagcagccac    600
tggtaattga tttagaggag ttagtcttga agtcatgcgc cggttaaggc taaactgaaa    660
ggacaagttt tggtgactgc gctcctccaa gccagttacc tcggttcaaa gagttggtag    720
ctcagagaac cttcgaaaaa ccgccctgca aggcggtttt ttcgttttca gagcaagaga    780
ttacgcgcag accaaaacga tctcaagaag atcatcttat taatcagata aaatatttct    840
agccctcctt tgattagtat attcctatct taaagttact tttatgtgga ggcattaaca    900
tttgttaatg acgtcaaaag gatagcaaga ctagaataaa gctataaagc aagcatataa    960
tattgcgttt catctttaga agcgaatttc gccaatatta taattatcaa aagagagggg   1020
tggcaaacgg tatttggcat tattaggtta aaaaatgtag aaggagagtg aaacccatga   1080
aaaaaataat gctagttttt attacactta tattagttag tctaccaatt gcgcaacaaa   1140
ctgaagcaaa ggatgcatct gcattcaata aagaaaattc aatttcatcc atggcaccac   1200
cagcatctcc gcctgcaagt cctaagacgc caatcgaaaa gaaacacgcg gatgaaatcg   1260
ataagtatat acaaggattg gattacaata aaaacaatgt attagtatac cacggagatg   1320
cagtgacaaa tgtgccgcca agaaaaggtt acaaagatgg aaatgaatat attgttgtgg   1380
agaaaaagaa gaaatccatc aatcaaaata atgcagacat tcaagttgtg aatgcaattt   1440
cgagcctaac ctatccaggt gctctcgtaa aagcgaattc ggaattagta gaaaatcaac   1500
cagatgttct ccctgtaaaa cgtgattcat taacactcag cattgatttg ccaggtatga   1560
ctaatcaaga caataaaata gttgtaaaaa atgccactaa atcaaacgtt aacaacgcag   1620
taaatacatt agtggaaaga tggaatgaaa aatatgctca agcttatcca aatgtaagtg   1680
caaaaattga ttatgatgac gaaatggctt acagtgaatc acaattaatt gcgaaatttg   1740
gtacagcatt taaagctgta aataatagct tgaatgtaaa cttcggcgca atcagtgaag   1800
ggaaaatgca agaagaagtc attagtttta aacaaattta ctataacgtg aatgttaatg   1860
aacctacaag accttccaga tttttcggca aagctgttac taaagagcag ttgcaagcgc   1920
ttggagtgaa tgcagaaaat cctcctgcat atatctcaag tgtggcgtat ggccgtcaag   1980
tttatttgaa attatcaact aattcccata gtactaaagt aaaagctgct tttgatgctg   2040
ccgtaagcgg aaaatctgtc tcaggtgatg tagaactaac aaatatcatc aaaaaattctt  2100
ccttcaaagc cgtaatttac ggaggttccg caaaagatga agttcaaatc atcgacggca   2160
acctcggaga cttacgcgat attttgaaaa aaggcgctac ttttaatcga gaaacaccag   2220
gagttcccat tgcttataca acaaacttcc taaaagacaa tgaattagct gttattaaaa   2280
```

-continued

```
acaactcaga atatattgaa acaacttcaa aagcttatac agatggaaaa attaacatcg   2340
atcactctgg aggatacgtt gctcaattca acatttcttg ggatgaagta aattatgatc   2400
tcgagaccca cctggacatg ctccgccacc tctaccaggg ctgccaggtg gtgcagggaa   2460
acctggaact cacctacctg cccaccaatg ccagcctgtc cttcctgcag gatatccagg   2520
aggtgcaggg ctacgtgctc atcgctcaca accaagtgag gcaggtccca ctgcagaggc   2580
tgcggattgt gcgaggcacc cagctctttg aggacaacta tgccctggcc gtgctagaca   2640
atggagaccc gctgaacaat accacccctg tcacaggggc ctccccagga ggcctgcggg   2700
agctgcagct tcgaagcctc acagagatct tgaaaggagg ggtcttgatc cagcggaacc   2760
cccagctctg ctaccaggac acgattttgt ggaagaatat ccaggagttt gctggctgca   2820
agaagatctt tgggagcctg gcatttctgc cggagagctt tgatggggac ccagcctcca   2880
acactgcccc gctccagcca gagcagctcc aagtgtttga gactctggaa gagatcacag   2940
gttacctata catctcagca tggccggaca gcctgcctga cctcagcgtc ttccagaacc   3000
tgcaagtaat ccggggacga attctgcaca atggcgccta ctcgctgacc ctgcaagggc   3060
tgggcatcag ctggctgggg ctgcgctcac tgagggaact gggcagtgga ctggccctca   3120
tccaccataa cacccacctc tgcttcgtgc acacggtgcc ctgggaccag ctctttcgga   3180
acccgcacca agctctgctc cacactgcca accggccaga ggacgagtgt gtgggcgagg   3240
gcctggcctg ccaccagctg tgcgcccgag ggcagcagaa gatccggaag tacacgatgc   3300
ggagactgct gcaggaaacg gagctggtgg agccgctgac acctagcgga gcgatgccca   3360
accaggcgca gatgcggatc ctgaaagaga cggagctgag gaaggtgaag gtgcttggat   3420
ctggcgcttt tggcacagtc tacaagggca tctggatccc tgatggggag aatgtgaaaa   3480
ttccagtggc catcaaagtg ttgagggaaa acacatcccc caaagccaac aaagaaatct   3540
tagacgaagc atacgtgatg gctggtgtgg gctccccata tgtctcccgc cttctgggca   3600
tctgcctgac atccacggtg cagctggtga cacagcttat gccctatggc tgcctcttag   3660
actaatctag acccgggcca ctaactcaac gctagtagtg gatttaatcc caaatgagcc   3720
aacagaacca gaaccagaaa cagaacaagt aacattggag ttagaaatgg aagaagaaaa   3780
aagcaatgat ttcgtgtgaa taatgcacga aatcattgct tatttttta aaaagcgata   3840
tactagatat aacgaaacaa cgaactgaat aaagaataca aaaaaagagc cacgaccagt   3900
taaagcctga gaaactttaa ctgcgagcct taattgatta ccaccaatca attaaagaag   3960
tcgagaccca aaatttggta aagtatttaa ttactttatt aatcagatac ttaaatatct   4020
gtaaacccat tatatcgggt ttttgagggg atttcaagtc tttaagaaga taccaggcaa   4080
tcaattaaga aaaacttagt tgattgcctt ttttgttgtg attcaacttt gatcgtagct   4140
tctaactaat taattttcgt aagaaaggag aacagctgaa tgaatatccc ttttgttgta   4200
gaaactgtgc ttcatgacgg cttgttaaag tacaaattta aaaatagtaa aattcgctca   4260
atcactacca agccaggtaa aagtaaaggg gctatttttg cgtatcgctc aaaaaaaagc   4320
atgattggcg gacgtggcgt tgttctgact tccgaagaag cgattcacga aaatcaagat   4380
acatttacgc attggacacc aaacgtttat cgttatggta cgtatgcaga cgaaaaccgt   4440
tcatacacta aaggacattc tgaaaacaat ttaagacaaa tcaatacctt ctttattgat   4500
tttgatattc acacggaaaa agaaactatt tcagcaagcg atattttaac aacagctatt   4560
gatttaggtt ttatgcctac gttaattatc aaatctgata aaggttatca agcatatttt   4620
```

-continued gttttagaaa cgccagtcta tgtgacttca aaatcagaat ttaaatctgt caaagcagcc 4680
aaaataatct cgcaaaatat ccgagaatat tttggaaagt ctttgccagt tgatctaacg 4740
tgcaatcatt ttgggattgc tcgtatacca agaacggaca atgtagaatt ttttgatccc 4800
aattaccgtt attctttcaa agaatggcaa gattggtctt tcaaacaaac agataataag 4860
ggctttactc gttcaagtct aacggtttta agcggtacag aaggcaaaaa acaagtagat 4920
gaaccctggt ttaatctctt attgcacgaa acgaaatttt caggagaaaa gggtttagta 4980
gggcgcaata gcgttatgtt taccctctct ttagcctact ttagttcagg ctattcaatc 5040
gaaacgtgcg aatataatat gtttgagttt aataatcgat tagatcaacc cttagaagaa 5100
aaagaagtaa tcaaaattgt tagaagtgcc tattcagaaa actatcaagg ggctaatagg 5160
gaatacatta ccattctttg caaagcttgg gtatcaagtg atttaaccag taaagattta 5220
tttgtccgtc aagggtggtt taaattcaag aaaaaaagaa gcgaacgtca acgtgttcat 5280
ttgtcagaat ggaaagaaga tttaatggct tatattagcg aaaaaagcga tgtatacaag 5340
ccttatttag cgacgaccaa aaaagagatt agagaagtgc taggcattcc tgaacggaca 5400
ttagataaat tgctgaaggt actgaaggcg aatcaggaaa ttttctttaa gattaaacca 5460
ggaagaaatg gtggcattca acttgctagt gttaaatcat tgttgctatc gatcattaaa 5520
ttaaaaaaag aagaacgaga aagctatata aaggcgctga cagcttcgtt taatttagaa 5580
cgtacattta ttcaagaaac tctaaacaaa ttggcagaac gccccaaaac ggacccacaa 5640
ctcgatttgt ttagctacga tacaggctga aaataaaacc cgcactatgc cattacattt 5700
atatctatga tacgtgtttg tttttctttg ctggctagct taattgctta tatttacctg 5760
caataaagga tttcttactt ccattatact cccattttcc aaaaacatac ggggaacacg 5820
ggaacttatt gtacaggcca cctcatagtt aatggtttcg agccttcctg caatctcatc 5880
catggaaata tattcatccc cctgccggcc tattaatgtg acttttgtgc ccggcggata 5940
ttcctgatcc agctccacca taaattggtc catgcaaatt cggccggcaa ttttcaggcg 6000
ttttcccttc acaaggatgt cggtcccttt caattttcgg agccagccgt ccgcatagcc 6060
tacaggcacc gtcccgatcc atgtgtcttt ttccgctgtg tactcggctc cgtagctgac 6120
gctctcgcct tttctgatca gtttgacatg tgacagtgtc gaatgcaggg taaatgccgg 6180
acgcagctga aacggtatct cgtccgacat gtcagcagac gggcgaaggc catacatgcc 6240
gatgccgaat ctgactgcat taaaaaagcc tttttcagc cggagtccag cggcgctgtt 6300
cgcgcagtgg accattagat tctttaacgg cagcggagca atcagctctt taaagcgctc 6360
aaactgcatt aagaaatagc ctctttcttt ttcatccgct gtcgcaaaat gggtaaatac 6420
ccctttgcac tttaaacgag ggttgcggtc aagaattgcc atcacgttct gaacttcttc 6480
ctctgttttt acaccaagtc tgttcatccc cgtatcgacc ttcagatgaa aatgaagaga 6540
acctttttc gtgtggcggg ctgcctcctg aagccattca acagaataac ctgttaaggt 6600
cacgtcatac tcagcagcga ttgccacata ctccggggga accgcgccaa gcaccaatat 6660
aggcgccttc aatccctttt tgcgcagtga aatcgcttca tccaaaatgg ccacggccaa 6720
gcatgaagca cctgcgtcaa gagcagcctt tgctgtttct gcatcaccat gcccgtaggc 6780
gtttgctttc acaactgcca tcaagtggac atgttcaccg atatgttttt tcatattgct 6840
gacattttcc tttatcgcgg acaagtcaat ttccgcccac gtatctctgt aaaaaggttt 6900
tgtgctcatg gaaaactcct ctcttttttc agaaaatccc agtacgtaat taagtatttg 6960
agaattaatt ttatattgat taatactaag tttacccagt tttcacctaa aaaacaaatg 7020
atgagataat agctccaaag gctaaagagg actataccaa ctatttgtta attaa 7075

<210> SEQ ID NO 74
<211> LENGTH: 9
<212> TYPE: PRT
<213> ORGANISM: Artificial Sequence
<220> FEATURE:
<223> OTHER INFORMATION: HLA-A2 restricted epitopes

<400> SEQUENCE: 74

His Leu Tyr Gln Gly Cys Gln Val Val
1 5

<210> SEQ ID NO 75
<211> LENGTH: 9
<212> TYPE: PRT
<213> ORGANISM: Artificial Sequence
<220> FEATURE:
<223> OTHER INFORMATION: HLA-A2 restricted epitopes

<400> SEQUENCE: 75

Lys Ile Phe Gly Ser Leu Ala Phe Leu
1 5

<210> SEQ ID NO 76
<211> LENGTH: 9
<212> TYPE: PRT
<213> ORGANISM: Artificial Sequence
<220> FEATURE:
<223> OTHER INFORMATION: HLA-A2 restricted epitopes

<400> SEQUENCE: 76

Arg Leu Leu Gln Glu Thr Glu Leu Val
1 5

<210> SEQ ID NO 77
<211> LENGTH: 30
<212> TYPE: DNA
<213> ORGANISM: Artificial Sequence
<220> FEATURE:
<223> OTHER INFORMATION: forward amplification primer actA promoter region

<400> SEQUENCE: 77
atcccgggtg aagcttggga agcagttggg 30

<210> SEQ ID NO 78
<211> LENGTH: 32
<212> TYPE: DNA
<213> ORGANISM: Artificial Sequence
<220> FEATURE:
<223> OTHER INFORMATION: reverse amplification primer actA promoter region

<400> SEQUENCE: 78
attctagatt tatcacgtac ccatttcccc gc 32

<210> SEQ ID NO 79
<211> LENGTH: 32
<212> TYPE: DNA
<213> ORGANISM: Artificial Sequence
<220> FEATURE:
<223> OTHER INFORMATION: chimera Her2/neu amplification F primer

<400> SEQUENCE: 79
attctagaac ccacctggac atgctccgcc ac 32

<210> SEQ ID NO 80
<211> LENGTH: 67
<212> TYPE: DNA
<213> ORGANISM: Artificial Sequence
<220> FEATURE:
<223> OTHER INFORMATION: chimera Her2/neu amplification R primer

<400> SEQUENCE: 80
gtcgacacta gtctagtggt gatggtgatg atggagctca gatctgtcta agaggcagcc 60
atagggc 67

<210> SEQ ID NO 81
<211> LENGTH: 2015
<212> TYPE: DNA
<213> ORGANISM: Listeria monocytogenes

<400> SEQUENCE: 81
atggcgcggg atggtatact atacaagcgt atggttcaaa aagatacttt gaattaagaa 60
gtacaataaa gttaacttca ttagacaaaa agaaaaaaca aggaagaata gtacatagtt 120
ataaatactt ggagagtgag gtgtaatatg ggggcagctg atttttgggg tttcatatat 180
gtagtttcaa gattagccat tgttgcggca gtagtttact tcttatactt attgagaaaa 240
attgcaaata aatagaaaaa aagccttgtc aaacgaggct ttttttatgc aaaaaatacg 300
acgaatgaag ccatgtgaga caatttggaa tagcagacaa caaggaaggt agaacatgtt 360
ttgaaaaatt tactgatttt cgattattat taacgcttgt taatttaaac atctcttatt 420
tttgctaaca tataagtata caaagggaca taaaaaggtt aacagcgttt gttaaatagg 480
aagtatatga aaatcctctt ttgtgtttct aaatttattt ttaaggagtg gagaatgttg 540
aaaaaaaata attggttaca aaatgcagta atagcaatgc tagtgttaat tgtaggtctg 600
tgcattaata tgggttctgg aacaaaagta caagctgaga gtattcaacg accaacgcct 660
attaaccaag tttttccaga tcccggccta gcgaatgcag tgaaacaaaa tttagggaag 720
caaagtgtta cagaccttgt atcacaaaag gaactatctg gagtacaaaa tttcaatgga 780
gataatagca acattcaatc tcttgcggga atgcaatttt tcactaattt aaaagaactt 840
catctatccc ataatcaaat aagtgacctt agtcctttaa aggatctaac taagttagaa 900
gagctatctg tgaatagaaa cagactgaaa aatttaaacg gaattccaag tgcttgttta 960
tctcgcttgt ttttagataa caacgaactc agagatactg actcgcttat tcatttgaaa 1020
aatctagaaa tcttatctat tcgtaataat aagttaaaaa gtattgtgat gcttggtttt 1080
ttatcaaaac tagaggtatt agatttgcat ggtaatgaaa taacaaatac aggtggacta 1140
actagattga agaaagttaa ctggatagat ttaactggtc agaaatgtgt gaatgaacca 1200
gtaaaatacc aaccagaatt gtatataaca aatactgtca aagacccaga tggaagatgg 1260
atatctccat attacatcag taatggtggg agttatgtag atggttgtgt cctgtgggaa 1320
ttgccagttt atacagatga agtaagctat aagtttagcg aatatataaa cgttggggag 1380
actgaggcta tatttgatgg aacagttaca caacctatca agaattagga cttgtgcaca 1440
cctgtatact ttgagctctc gtataatcac gagagctttt taaatatgta agtcttaatt 1500
atctcttgac aaaaagaacg tttattcgta taaggttacc aagagatgaa gaaactattt 1560
tatttacaat tcaccttgac accaaaaact ccatatgata tagtaaataa ggttattaaa 1620
caagaaagaa gaagcaaccc gcttctcgcc tcgttaacac gaacgttttc aggcaaaaaa 1680

-continued ttcaaacttt cgtcgcgtag cttacgcgat tttgaatgtg cgggattgct gaaaagcagc 1740
ccgttttttt atggcctccg aacgaatgag ttagcaggcc gcagatttga acagctattt 1800
tctatcttgt tgtaacaaaa ttaagtggag gtggctcacc attagcaaag acatgttggt 1860
aaacgatggg attcgtgcac gtgaagtaag attgatcgac caagacggtg aacaattagg 1920
cgtgaagagt aaaatcgatg cgcttcaaat tgctgaaaag gctaatcttg atctagtgct 1980
tgttgctcca acagcgaaac cgccagtagc tcgta 2015

<210> SEQ ID NO 82
<211> LENGTH: 1140
<212> TYPE: DNA
<213> ORGANISM: Artificial Sequence
<220> FEATURE:
<223> OTHER INFORMATION: sequence of DNA that is cloned in the temperature sensitive plasmid, pKSV7 to create inl C deletion mutant

<400> SEQUENCE: 82
gaattcatgg cgcgggatgg tatactatac aagcgtatgg ttcaaaaaga tactttgaat 60
taagaagtac aataaagtta acttcattag acaaaaagaa aaaacaagga agaatagtac 120
atagttataa atacttggag agtgaggtgt aatatggggg cagctgattt ttggggtttc 180
atatatgtag tttcaagatt agccattgtt gcggcagtag tttacttctt atacttattg 240
agaaaaattg caaataaata gaaaaaaagc cttgtcaaac gaggcttttt ttatgcaaaa 300
aatacgacga atgaagccat gtgagacaat ttggaatagc agacaacaag gaaggtagaa 360
catgttttga aaaatttact gattttcgat tattattaac gcttgttaat ttaaacatct 420
cttatttttg ctaacatata agtatacaaa gggacataaa aaggttaaca gcgtttgtta 480
aataggaagt atatgaaaat cctcttttgt gtttctaaat ttatttttaa ggagtggaga 540
ggatccggac ttgtgcacac ctgtatactt tgagctctcg tataatcacg agagcttttt 600
aaatatgtaa gtcttaatta tctcttgaca aaaagaacgt ttattcgtat aaggttacca 660
agagatgaag aaactatttt atttacaatt caccttgaca ccaaaaactc catatgatat 720
agtaaataag gttattaaac aagaaagaag aagcaacccg cttctcgcct cgttaacacg 780
aacgttttca ggcaaaaaat tcaaactttc gtcgcgtagc ttacgcgatt ttgaatgtgc 840
gggattgctg aaaagcagcc cgttttttta tggcctccga acgaatgagt tagcaggccg 900
cagatttgaa cagctatttt ctatcttgtt gtaacaaaat taagtggagg tggctcacca 960
ttagcaaaga catgttggta aacgatggga ttcgtgcacg tgaagtaaga ttgatcgacc 1020
aagacggtga acaattaggc gtgaagagta aaatcgatgc gcttcaaatt gctgaaaagg 1080
ctaatcttga tctagtgctt gttgctccaa cagcgaaacc gccagtagct cgtactgcag 1140

<210> SEQ ID NO 83
<211> LENGTH: 28
<212> TYPE: DNA
<213> ORGANISM: Artificial Sequence
<220> FEATURE:
<223> OTHER INFORMATION: Lm-LLO-ISG15.Forward primer

<400> SEQUENCE: 83
taatctcgag atggcctggg acctaaag 28

<210> SEQ ID NO 84
<211> LENGTH: 28
<212> TYPE: DNA
<213> ORGANISM: Artificial Sequence
<220> FEATURE:
<223> OTHER INFORMATION: Lm-LLO-ISG15.Reverse primer

<400> SEQUENCE: 84
attaactagt ttaggcacac tggtcccc 28

<210> SEQ ID NO 85
<211> LENGTH: 18
<212> TYPE: DNA
<213> ORGANISM: Artificial Sequence
<220> FEATURE:
<223> OTHER INFORMATION: Forward primers specific for ISG15

<400> SEQUENCE: 85
atggcctggg acctaaag 18

<210> SEQ ID NO 86
<211> LENGTH: 18
<212> TYPE: DNA
<213> ORGANISM: Artificial Sequence
<220> FEATURE:
<223> OTHER INFORMATION: Forward primers specific for ISG15

<400> SEQUENCE: 86
ttaggcacac tggtcccc 18

<210> SEQ ID NO 87
<211> LENGTH: 20
<212> TYPE: DNA
<213> ORGANISM: Artificial Sequence
<220> FEATURE:
<223> OTHER INFORMATION: 18S rRNA 18SRNA. Forward primer

<400> SEQUENCE: 87
cggctaccac atccaaggaa 20

<210> SEQ ID NO 88
<211> LENGTH: 18
<212> TYPE: DNA
<213> ORGANISM: Artificial Sequence
<220> FEATURE:
<223> OTHER INFORMATION: 18S rRNA 18SRNA. Reverse primer

<400> SEQUENCE: 88
gctggaatta ccgcggct 18

<210> SEQ ID NO 89
<211> LENGTH: 21
<212> TYPE: DNA
<213> ORGANISM: Artificial Sequence
<220> FEATURE:
<223> OTHER INFORMATION: beta-actin ACTIN. Forward primer

<400> SEQUENCE: 89
gtgggccgct ctaggcacca a 21

<210> SEQ ID NO 90
<211> LENGTH: 24
<212> TYPE: DNA
<213> ORGANISM: Artificial Sequence
<220> FEATURE:
<223> OTHER INFORMATION: beta-actin ACTIN. Reverse primer

<400> SEQUENCE: 90
ctctttgatg tcacgcacga tttc 24

-continued

<210> SEQ ID NO 91
<211> LENGTH: 9
<212> TYPE: PRT
<213> ORGANISM: Artificial Sequence
<220> FEATURE:
<223> OTHER INFORMATION: HIV-gag H-2Kd CTL epitope

<400> SEQUENCE: 91

Ala Met Gln Met Leu Lys Glu Thr Ile
1               5

<210> SEQ ID NO 92
<211> LENGTH: 9
<212> TYPE: PRT
<213> ORGANISM: Artificial Sequence
<220> FEATURE:
<223> OTHER INFORMATION: ISG15 d1 primer

<400> SEQUENCE: 92

Arg Gly His Ser Asn Ile Tyr Glu Val
1               5

<210> SEQ ID NO 93
<211> LENGTH: 9
<212> TYPE: PRT
<213> ORGANISM: Artificial Sequence
<220> FEATURE:
<223> OTHER INFORMATION: ISG15 d2 primer

<400> SEQUENCE: 93

Leu Gly Pro Ser Ser Thr Val Met Leu
1               5

<210> SEQ ID NO 94
<211> LENGTH: 9
<212> TYPE: PRT
<213> ORGANISM: Artificial Sequence
<220> FEATURE:
<223> OTHER INFORMATION: Her2/neu-specific H-2Kd epitope peptides
      Her2-EC1

<400> SEQUENCE: 94

Pro Tyr Asn Tyr Leu Ser Thr Glu Val
1               5

<210> SEQ ID NO 95
<211> LENGTH: 10
<212> TYPE: PRT
<213> ORGANISM: Artificial Sequence
<220> FEATURE:
<223> OTHER INFORMATION: Her2-EC2

<400> SEQUENCE: 95

Leu Phe Arg Asn Pro His Gln Ala Leu Leu
1               5                   10

<210> SEQ ID NO 96
<211> LENGTH: 9
<212> TYPE: PRT
<213> ORGANISM: Artificial Sequence
<220> FEATURE:
<223> OTHER INFORMATION: Her2-IC1

<400> SEQUENCE: 96

Pro Tyr Val Ser Arg Leu Leu Gly Ile
1               5

<210> SEQ ID NO 97
<211> LENGTH: 10
<212> TYPE: PRT
<213> ORGANISM: Artificial Sequence
<220> FEATURE:
<223> OTHER INFORMATION: her-2/neu EC2

<400> SEQUENCE: 97

Pro Asp Ser Leu Arg Asp Leu Ser Val Phe
1 5 10

<210> SEQ ID NO 98
<211> LENGTH: 10
<212> TYPE: PRT
<213> ORGANISM: Artificial Sequence
<220> FEATURE:
<223> OTHER INFORMATION: Her-2/neu EC1

<400> SEQUENCE: 98

Ala Ser Pro Glu Thr His Leu Asp Met Leu
1 5 10

<210> SEQ ID NO 99
<211> LENGTH: 10
<212> TYPE: PRT
<213> ORGANISM: Artificial Sequence
<220> FEATURE:
<223> OTHER INFORMATION: her-2/neu IC1

<400> SEQUENCE: 99

Gly Ser Gly Ala Phe Gly Thr Val Tyr Lys
1 5 10

<210> SEQ ID NO 100
<211> LENGTH: 9
<212> TYPE: PRT
<213> ORGANISM: Artificial Sequence
<220> FEATURE:
<223> OTHER INFORMATION: Flk-E1

<400> SEQUENCE: 100

Thr Tyr Gln Ser Ile Met Tyr Ile Val
1 5

<210> SEQ ID NO 101
<211> LENGTH: 9
<212> TYPE: PRT
<213> ORGANISM: Artificial Sequence
<220> FEATURE:
<223> OTHER INFORMATION: Flk-E2

<400> SEQUENCE: 101

Met Phe Ser Asn Ser Thr Asn Asp Ile
1 5

<210> SEQ ID NO 102
<211> LENGTH: 9
<212> TYPE: PRT
<213> ORGANISM: Artificial Sequence
<220> FEATURE:
<223> OTHER INFORMATION: FLK-I1 906-915

<400> SEQUENCE: 102

Pro Gly Gly Pro Leu Met Val Ile Val
1 5

-continued

<210> SEQ ID NO 103
<211> LENGTH: 9
<212> TYPE: PRT
<213> ORGANISM: Artificial Sequence
<220> FEATURE:
<223> OTHER INFORMATION: Flk-I1 839-848

<400> SEQUENCE: 103

Gly Arg Gly Ala Phe Gly Gln Val Ile
1               5

<210> SEQ ID NO 104
<211> LENGTH: 32
<212> TYPE: DNA
<213> ORGANISM: Artificial Sequence
<220> FEATURE:
<223> OTHER INFORMATION: Flk-E1 primer (F)

<400> SEQUENCE: 104
gggctcgagc gtgattctga ggaaagggta tt 32

<210> SEQ ID NO 105
<211> LENGTH: 33
<212> TYPE: DNA
<213> ORGANISM: Artificial Sequence
<220> FEATURE:
<223> OTHER INFORMATION: Flk-E1 (R)

<400> SEQUENCE: 105
gggactagtt tacccggttt acaatcttct tat 33

<210> SEQ ID NO 106
<211> LENGTH: 31
<212> TYPE: DNA
<213> ORGANISM: Artificial Sequence
<220> FEATURE:
<223> OTHER INFORMATION: Flk-E2 (F)

<400> SEQUENCE: 106
gggctcgagg tgatcagggg tcctgaaatt a 31

<210> SEQ ID NO 107
<211> LENGTH: 30
<212> TYPE: DNA
<213> ORGANISM: Artificial Sequence
<220> FEATURE:
<223> OTHER INFORMATION: Flk-E2 (R)

<400> SEQUENCE: 107
gggactagtt tagcctccat cctccttcct 30

<210> SEQ ID NO 108
<211> LENGTH: 30
<212> TYPE: DNA
<213> ORGANISM: Artificial Sequence
<220> FEATURE:
<223> OTHER INFORMATION: Flk-I1 (F)

<400> SEQUENCE: 108
gggctcgagg aaggggaact gaagacagcc 30

<210> SEQ ID NO 109
<211> LENGTH: 39
<212> TYPE: DNA
<213> ORGANISM: Artificial Sequence
<220> FEATURE:
<223> OTHER INFORMATION: Flk-I1 (R)

<400> SEQUENCE: 109
gggactagtt tatgtgtata ctctgtcaaa aatggtttc 39

<210> SEQ ID NO 110
<211> LENGTH: 18
<212> TYPE: DNA
<213> ORGANISM: Artificial Sequence
<220> FEATURE:
<223> OTHER INFORMATION: EC1FP FP =reverse primer RP= reverse primer

<400> SEQUENCE: 110
agggctgtca ggtagtgc 18

<210> SEQ ID NO 111
<211> LENGTH: 18
<212> TYPE: DNA
<213> ORGANISM: Artificial Sequence
<220> FEATURE:
<223> OTHER INFORMATION: EC1RP

<400> SEQUENCE: 111
tgacctcttg gttattcg 18

<210> SEQ ID NO 112
<211> LENGTH: 18
<212> TYPE: DNA
<213> ORGANISM: Artificial Sequence
<220> FEATURE:
<223> OTHER INFORMATION: EC2FP

<400> SEQUENCE: 112
acctgcccct acaactac 18

<210> SEQ ID NO 113
<211> LENGTH: 18
<212> TYPE: DNA
<213> ORGANISM: Artificial Sequence
<220> FEATURE:
<223> OTHER INFORMATION: EC3 FP

<400> SEQUENCE: 113
gacgccctct acagttgc 18

<210> SEQ ID NO 114
<211> LENGTH: 18
<212> TYPE: DNA
<213> ORGANISM: Artificial Sequence
<220> FEATURE:
<223> OTHER INFORMATION: EC2 RP

<400> SEQUENCE: 114
gtggattggc tctgattc 18

<210> SEQ ID NO 115
<211> LENGTH: 18
<212> TYPE: DNA
<213> ORGANISM: Artificial Sequence
<220> FEATURE:
<223> OTHER INFORMATION: EC3RP

<400> SEQUENCE: 115
tgagttacag accaagcc 18

<210> SEQ ID NO 116

<211> LENGTH: 19
<212> TYPE: DNA
<213> ORGANISM: Artificial Sequence
<220> FEATURE:
<223> OTHER INFORMATION: IC1FP

<400> SEQUENCE: 116
caaacgaagg agacagaag 19

<210> SEQ ID NO 117
<211> LENGTH: 18
<212> TYPE: DNA
<213> ORGANISM: Artificial Sequence
<220> FEATURE:
<223> OTHER INFORMATION: IC1 RP

<400> SEQUENCE: 117
caccatcaaa cacatcgg 18

<210> SEQ ID NO 118
<211> LENGTH: 18
<212> TYPE: DNA
<213> ORGANISM: Artificial Sequence
<220> FEATURE:
<223> OTHER INFORMATION: IC2 FP

<400> SEQUENCE: 118
cactgctgga agatgatg 18

<210> SEQ ID NO 119
<211> LENGTH: 18
<212> TYPE: DNA
<213> ORGANISM: Artificial Sequence
<220> FEATURE:
<223> OTHER INFORMATION: IC2 RP

<400> SEQUENCE: 119
tttgtggcga tggagacc 18

<210> SEQ ID NO 120
<211> LENGTH: 9
<212> TYPE: PRT
<213> ORGANISM: Artificial Sequence
<220> FEATURE:
<223> OTHER INFORMATION: CD105A peptide

<400> SEQUENCE: 120

Ala Gly Pro Arg Thr Val Thr Val Met
1               5

<210> SEQ ID NO 121
<211> LENGTH: 9
<212> TYPE: PRT
<213> ORGANISM: Artificial Sequence
<220> FEATURE:
<223> OTHER INFORMATION: Cd105B peptide

<400> SEQUENCE: 121

Ala Tyr Ser Ser Cys Gly Met Lys Val
1               5

<210> SEQ ID NO 122
<211> LENGTH: 9
<212> TYPE: PRT
<213> ORGANISM: Artificial Sequence
<220> FEATURE:
<223> OTHER INFORMATION: AH1 peptide

<400> SEQUENCE: 122

Ser Pro Ser Tyr Val Tyr His Gln Phe
1 5

<210> SEQ ID NO 123
<211> LENGTH: 529
<212> TYPE: PRT
<213> ORGANISM: Listeria monocytogenes

<400> SEQUENCE: 123

Met Lys Lys Ile Met Leu Val Phe Ile Thr Leu Ile Leu Val Ser Leu
1 5 10 15

Pro Ile Ala Gln Gln Thr Glu Ala Lys Asp Ala Ser Ala Phe Asn Lys
20 25 30

Glu Asn Ser Ile Ser Ser Val Ala Pro Pro Ala Ser Pro Pro Ala Ser
35 40 45

Pro Lys Thr Pro Ile Glu Lys Lys His Ala Asp Glu Ile Asp Lys Tyr
50 55 60

Ile Gln Gly Leu Asp Tyr Asn Lys Asn Asn Val Leu Val Tyr His Gly
65 70 75 80

Asp Ala Val Thr Asn Val Pro Pro Arg Lys Gly Tyr Lys Asp Gly Asn
85 90 95

Glu Tyr Ile Val Val Glu Lys Lys Lys Lys Ser Ile Asn Gln Asn Asn
100 105 110

Ala Asp Ile Gln Val Val Asn Ala Ile Ser Ser Leu Thr Tyr Pro Gly
115 120 125

Ala Leu Val Lys Ala Asn Ser Glu Leu Val Glu Asn Gln Pro Asp Val
130 135 140

Leu Pro Val Lys Arg Asp Ser Leu Thr Leu Ser Ile Asp Leu Pro Gly
145 150 155 160

Met Thr Asn Gln Asp Asn Lys Ile Val Val Lys Asn Ala Thr Lys Ser
165 170 175

Asn Val Asn Asn Ala Val Asn Thr Leu Val Glu Arg Trp Asn Glu Lys
180 185 190

Tyr Ala Gln Ala Tyr Ser Asn Val Ser Ala Lys Ile Asp Tyr Asp Asp
195 200 205

Glu Met Ala Tyr Ser Glu Ser Gln Leu Ile Ala Lys Phe Gly Thr Ala
210 215 220

Phe Lys Ala Val Asn Asn Ser Leu Asn Val Asn Phe Gly Ala Ile Ser
225 230 235 240

Glu Gly Lys Met Gln Glu Glu Val Ile Ser Phe Lys Gln Ile Tyr Tyr
245 250 255

Asn Val Asn Val Asn Glu Pro Thr Arg Pro Ser Arg Phe Phe Gly Lys
260 265 270

Ala Val Thr Lys Glu Gln Leu Gln Ala Leu Gly Val Asn Ala Glu Asn
275 280 285

Pro Pro Ala Tyr Ile Ser Ser Val Ala Tyr Gly Arg Gln Val Tyr Leu
290 295 300

Lys Leu Ser Thr Asn Ser His Ser Thr Lys Val Lys Ala Ala Phe Asp
305 310 315 320

Ala Ala Val Ser Gly Lys Ser Val Ser Gly Asp Val Glu Leu Thr Asn
325 330 335

Ile Ile Lys Asn Ser Ser Phe Lys Ala Val Ile Tyr Gly Gly Ser Ala
340 345 350

```
Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Glu Gly Asn Glu Ile Val
        435                 440                 445

Gln His Lys Asn Trp Ser Glu Asn Asn Lys Ser Lys Leu Ala His Phe
    450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
                485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
        515                 520                 525

Glu


<210> SEQ ID NO 124
<211> LENGTH: 535
<212> TYPE: PRT
<213> ORGANISM: Listeria monocytogenes

<400> SEQUENCE: 124

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190
```

Tyr Ala Gln Ala Tyr Ser Asn Val Ser Ala Lys Ile Asp Tyr Asp Asp
195 200 205

Glu Met Ala Tyr Ser Glu Ser Gln Leu Ile Ala Lys Phe Gly Thr Ala
210 215 220

Phe Lys Ala Val Asn Asn Ser Leu Asn Val Asn Phe Gly Ala Ile Ser
225 230 235 240

Glu Gly Lys Met Gln Glu Glu Val Ile Ser Phe Lys Gln Ile Tyr Tyr
245 250 255

Asn Val Asn Val Asn Glu Pro Thr Arg Pro Ser Arg Phe Phe Gly Lys
260 265 270

Ala Val Thr Lys Glu Gln Leu Gln Ala Leu Gly Val Asn Ala Glu Asn
275 280 285

Pro Pro Ala Tyr Ile Ser Ser Val Ala Tyr Gly Arg Gln Val Tyr Leu
290 295 300

Lys Leu Ser Thr Asn Ser His Ser Thr Lys Val Lys Ala Ala Phe Asp
305 310 315 320

Ala Ala Val Ser Gly Lys Ser Val Ser Gly Asp Val Glu Leu Thr Asn
325 330 335

Ile Ile Lys Asn Ser Ser Phe Lys Ala Val Ile Tyr Gly Gly Ser Ala
340 345 350

Lys Asp Glu Val Gln Ile Ile Asp Gly Asn Leu Gly Asp Leu Arg Asp
355 360 365

Ile Leu Lys Lys Gly Ala Thr Phe Asn Arg Glu Thr Pro Gly Val Pro
370 375 380

Ile Ala Tyr Thr Thr Asn Phe Leu Lys Asp Asn Glu Leu Ala Val Ile
385 390 395 400

Lys Asn Asn Ser Glu Tyr Ile Glu Thr Thr Ser Lys Ala Tyr Thr Asp
405 410 415

Gly Lys Ile Asn Ile Asp His Ser Gly Gly Tyr Val Ala Gln Phe Asn
420 425 430

Ile Ser Trp Asp Glu Val Asn Tyr Asp Pro Glu Gly Asn Glu Ile Val
435 440 445

Gln His Lys Asn Trp Ser Glu Asn Asn Lys Ser Lys Leu Ala His Phe
450 455 460

Thr Ser Ser Ile Tyr Leu Pro Gly Asn Ala Arg Asn Ile Asn Val Tyr
465 470 475 480

Ala Lys Glu Cys Thr Gly Leu Ala Trp Glu Trp Trp Arg Thr Val Ile
485 490 495

Asp Asp Arg Asn Leu Pro Leu Val Lys Asn Arg Asn Ile Ser Ile Trp
500 505 510

Gly Thr Thr Leu Tyr Pro Lys Tyr Ser Asn Lys Val Asp Asn Pro Ile
515 520 525

Glu His His His His His His
530 535

<210> SEQ ID NO 125
<211> LENGTH: 1551
<212> TYPE: DNA
<213> ORGANISM: Listeria monocytogenes

<400> SEQUENCE: 125
catatgaagg atgcatctgc attcaataaa gaaaattcaa tttcatccgt ggcaccacca 60
gcatctccgc ctgcaagtcc taagacgcca atcgaaaaga aacacgcgga tgaaatcgat 120
aagtatatac aaggattgga ttacaataaa aacaatgtat tagtatacca cggagatgca 180
gtgacaaatg tgccgccaag aaaaggttac aaagatggaa atgaatatat tgttgtggag 240
aaaaagaaga aatccatcaa tcaaaataat gcagacattc aagttgtgaa tgcaatttcg 300
agcctaacct atccaggtgc tctcgtaaaa gcgaattcgg aattagtaga aaatcaacca 360
gatgttctcc ctgtaaaacg tgattcatta acactcagca ttgatttgcc aggtatgact 420
aatcaagaca ataaaatagt tgtaaaaaat gccactaaat caaacgttaa caacgcagta 480
aatacattag tggaaagatg gaatgaaaaa tatgctcaag cttattcaaa tgtaagtgca 540
aaaattgatt atgatgacga aatggcttac agtgaatcac aattaattgc gaaatttggt 600
acagcattta aagctgtaaa taatagcttg aatgtaaact tcggcgcaat cagtgaaggg 660
aaaatgcaag aagaagtcat tagttttaaa caaatttact ataacgtgaa tgttaatgaa 720
cctacaagac cttccagatt tttcggcaaa gctgttacta aagagcagtt gcaagcgctt 780
ggagtgaatg cagaaaatcc tcctgcatat atctcaagtg tggcgtatgg ccgtcaagtt 840
tatttgaaat tatcaactaa ttcccatagt actaaagtaa aagctgcttt tgatgctgcc 900
gtaagcggaa aatctgtctc aggtgatgta gaactaacaa atatcatcaa aaattcttcc 960
ttcaaagccg taatttacgg aggttccgca aaagatgaag ttcaaatcat cgacggcaac 1020
ctcggagact tacgcgatat tttgaaaaaa ggcgctactt ttaatcgaga aacaccagga 1080
gttcccattg cttatacaac aaacttccta aaagacaatg aattagctgt tattaaaaac 1140
aactcagaat atattgaaac aacttcaaaa gcttatacag atggaaaaat taacatcgat 1200
cactctggag gatacgttgc tcaattcaac atttcttggg atgaagtaaa ttatgatcct 1260
gaaggtaacg aaattgttca acataaaaac tggagcgaaa acaataaaag caagctagct 1320
catttcacat cgtccatcta tttgcctggt aacgcgagaa atattaatgt ttacgctaaa 1380
gaatgcactg gtttagcttg ggaatggtgg agaacggtaa ttgatgaccg gaacttacca 1440
cttgtgaaaa atagaaatat ctccatctgg ggcaccacgc tttatccgaa atatagtaat 1500
aaagtagata atccaatcga acaccaccac caccaccact aataaggatc c 1551

<210> SEQ ID NO 126
<211> LENGTH: 20
<212> TYPE: DNA
<213> ORGANISM: Artificial Sequence
<220> FEATURE:
<223> OTHER INFORMATION: Primer

<400> SEQUENCE: 126
gctagctcat ttcacatcgt 20

<210> SEQ ID NO 127
<211> LENGTH: 54
<212> TYPE: DNA
<213> ORGANISM: Artificial Sequence
<220> FEATURE:
<223> OTHER INFORMATION: Primer

<400> SEQUENCE: 127
tcttgcagct tcccaagcta aaccagtcgc ttctttagcg taaacattaa tatt 54

<210> SEQ ID NO 128
<211> LENGTH: 54
<212> TYPE: DNA
<213> ORGANISM: Artificial Sequence
<220> FEATURE:
<223> OTHER INFORMATION: Primer

<400> SEQUENCE: 128
gaagcgactg gtttagcttg ggaagctgca agaacggtaa ttgatgaccg gaac 54

<210> SEQ ID NO 129
<211> LENGTH: 39
<212> TYPE: DNA
<213> ORGANISM: Artificial Sequence
<220> FEATURE:
<223> OTHER INFORMATION: Primer

<400> SEQUENCE: 129
ggatccttat tagtggtggt ggtggtggtg ttcgattgg 39

<210> SEQ ID NO 130
<211> LENGTH: 11
<212> TYPE: PRT
<213> ORGANISM: Listeria monocytogenes

<400> SEQUENCE: 130

Glu Cys Thr Gly Leu Ala Trp Glu Trp Trp Arg
1 5 10

<210> SEQ ID NO 131
<211> LENGTH: 11
<212> TYPE: PRT
<213> ORGANISM: Listeria monocytogenes

<400> SEQUENCE: 131

Glu Ala Thr Gly Leu Ala Trp Glu Ala Ala Arg
1 5 10

<210> SEQ ID NO 132
<211> LENGTH: 238
<212> TYPE: DNA
<213> ORGANISM: Listeria monocytogenes

<400> SEQUENCE: 132
gctagctcat ttcacatcgt ccatctattt gcctggtaac gcgagaaata ttaatgttta 60
cgctaaagaa gcgactggtt tagcttggga agctgcaaga acggtaattg atgaccggaa 120
cttaccactt gtgaaaaata gaaatatctc catctggggc accacgcttt atccgaaata 180
tagtaataaa gtagataatc caatcgaaca ccaccaccac caccactaat aaggatcc 238

<210> SEQ ID NO 133
<211> LENGTH: 11
<212> TYPE: PRT
<213> ORGANISM: Listeria monocytogenes

<400> SEQUENCE: 133

Glu Ser Leu Leu Met Trp Ile Thr Gln Cys Arg
1 5 10

<210> SEQ ID NO 134
<211> LENGTH: 54
<212> TYPE: DNA
<213> ORGANISM: Artificial Sequence
<220> FEATURE:
<223> OTHER INFORMATION: Primer

<400> SEQUENCE: 134
tctgcactgg gtgatccaca tcagcaggct ttctttagcg taaacattaa tatt 54

<210> SEQ ID NO 135
<211> LENGTH: 54
<212> TYPE: DNA
<213> ORGANISM: Artificial Sequence
<220> FEATURE:
<223> OTHER INFORMATION: Primer

<400> SEQUENCE: 135
gaaagcctgc tgatgtggat cacccagtgc agaacggtaa ttgatgaccg gaac 54

<210> SEQ ID NO 136
<211> LENGTH: 238
<212> TYPE: DNA
<213> ORGANISM: Listeria monocytogenes

<400> SEQUENCE: 136
gctagctcat ttcacatcgt ccatctattt gcctggtaac gcgagaaata ttaatgttta 60
cgctaaagaa agcctgctga tgtggatcac ccagtgcaga acggtaattg atgaccggaa 120
cttaccactt gtgaaaaata gaaatatctc catctggggc accacgcttt atccgaaata 180
tagtaataaa gtagataatc caatcgaaca ccaccaccac caccactaat aaggatcc 238

<210> SEQ ID NO 137
<211> LENGTH: 1345
<212> TYPE: PRT
<213> ORGANISM: Mus musculus

<400> SEQUENCE: 137

Met Glu Ser Lys Ala Leu Leu Ala Val Ala Leu Trp Phe Cys Val Glu
1 5 10 15

Thr Arg Ala Ala Ser Val Gly Leu Pro Gly Asp Phe Leu His Pro Pro
20 25 30

Lys Leu Ser Thr Gln Lys Asp Ile Leu Thr Ile Leu Ala Asn Thr Thr
35 40 45

Leu Gln Ile Thr Cys Arg Gly Gln Arg Asp Leu Asp Trp Leu Trp Pro
50 55 60

Asn Ala Gln Arg Asp Ser Glu Glu Arg Val Leu Val Thr Glu Cys Gly
65 70 75 80

Gly Gly Asp Ser Ile Phe Cys Lys Thr Leu Thr Ile Pro Arg Val Val
85 90 95

Gly Asn Asp Thr Gly Ala Tyr Lys Cys Ser Tyr Arg Asp Val Asp Ile
100 105 110

Ala Ser Thr Val Tyr Val Tyr Val Arg Asp Tyr Arg Ser Pro Phe Ile
115 120 125

Ala Ser Val Ser Asp Gln His Gly Ile Val Tyr Ile Thr Glu Asn Lys
130 135 140

Asn Lys Thr Val Val Ile Pro Cys Arg Gly Ser Ile Ser Asn Leu Asn
145 150 155 160

Val Ser Leu Cys Ala Arg Tyr Pro Glu Lys Arg Phe Val Pro Asp Gly
165 170 175

Asn Arg Ile Ser Trp Asp Ser Glu Ile Gly Phe Thr Leu Pro Ser Tyr
180 185 190

Met Ile Ser Tyr Ala Gly Met Val Phe Cys Glu Ala Lys Ile Asn Asp
195 200 205

Glu Thr Tyr Gln Ser Ile Met Tyr Ile Val Val Val Val Gly Tyr Arg
210 215 220

Ile Tyr Asp Val Ile Leu Ser Pro Pro His Glu Ile Glu Leu Ser Ala
225 230 235 240

-continued

```
Gly Glu Lys Leu Val Leu Asn Cys Thr Ala Arg Thr Glu Leu Asn Val
                245                 250                 255

Gly Leu Asp Phe Thr Trp His Ser Pro Pro Ser Lys Ser His His Lys
            260                 265                 270

Lys Ile Val Asn Arg Asp Val Lys Pro Phe Pro Gly Thr Val Ala Lys
        275                 280                 285

Met Phe Leu Ser Thr Leu Thr Ile Glu Ser Val Thr Lys Ser Asp Gln
    290                 295                 300

Gly Glu Tyr Thr Cys Val Ala Ser Ser Gly Arg Met Ile Lys Arg Asn
305                 310                 315                 320

Arg Thr Phe Val Arg Val His Thr Lys Pro Phe Ile Ala Phe Gly Ser
                325                 330                 335

Gly Met Lys Ser Leu Val Glu Ala Thr Val Gly Ser Gln Val Arg Ile
            340                 345                 350

Pro Val Lys Tyr Leu Ser Tyr Pro Ala Pro Asp Ile Lys Trp Tyr Arg
        355                 360                 365

Asn Gly Arg Pro Ile Glu Ser Asn Tyr Thr Met Ile Val Gly Asp Glu
    370                 375                 380

Leu Thr Ile Met Glu Val Thr Glu Arg Asp Ala Gly Asn Tyr Thr Val
385                 390                 395                 400

Ile Leu Thr Asn Pro Ile Ser Met Glu Lys Gln Ser His Met Val Ser
                405                 410                 415

Leu Val Val Asn Val Pro Pro Gln Ile Gly Glu Lys Ala Leu Ile Ser
            420                 425                 430

Pro Met Asp Ser Tyr Gln Tyr Gly Thr Met Gln Thr Leu Thr Cys Thr
        435                 440                 445

Val Tyr Ala Asn Pro Pro Leu His His Ile Gln Trp Tyr Trp Gln Leu
    450                 455                 460

Glu Glu Ala Cys Ser Tyr Arg Pro Gly Gln Thr Ser Pro Tyr Ala Cys
465                 470                 475                 480

Lys Glu Trp Arg His Val Glu Asp Phe Gln Gly Gly Asn Lys Ile Glu
                485                 490                 495

Val Thr Lys Asn Gln Tyr Ala Leu Ile Glu Gly Lys Asn Lys Thr Val
            500                 505                 510

Ser Thr Leu Val Ile Gln Ala Ala Asn Val Ser Ala Leu Tyr Lys Cys
        515                 520                 525

Glu Ala Ile Asn Lys Ala Gly Arg Gly Glu Arg Val Ile Ser Phe His
    530                 535                 540

Val Ile Arg Gly Pro Glu Ile Thr Val Gln Pro Ala Ala Gln Pro Thr
545                 550                 555                 560

Glu Gln Glu Ser Val Ser Leu Leu Cys Thr Ala Asp Arg Asn Thr Phe
                565                 570                 575

Glu Asn Leu Thr Trp Tyr Lys Leu Gly Ser Gln Ala Thr Ser Val His
            580                 585                 590

Met Gly Glu Ser Leu Thr Pro Val Cys Lys Asn Leu Asp Ala Leu Trp
        595                 600                 605

Lys Leu Asn Gly Thr Met Phe Ser Asn Ser Thr Asn Asp Ile Leu Ile
    610                 615                 620

Val Ala Phe Gln Asn Ala Ser Leu Gln Asp Gln Gly Asp Tyr Val Cys
625                 630                 635                 640

Ser Ala Gln Asp Lys Lys Thr Lys Lys Arg His Cys Leu Val Lys Gln
                645                 650                 655
```

-continued

```
Leu Ile Ile Leu Glu Arg Met Ala Pro Met Ile Thr Gly Asn Leu Glu
            660                 665                 670

Asn Gln Thr Thr Thr Ile Gly Glu Thr Ile Glu Val Thr Cys Pro Ala
        675                 680                 685

Ser Gly Asn Pro Thr Pro His Ile Thr Trp Phe Lys Asp Asn Glu Thr
    690                 695                 700

Leu Val Glu Asp Ser Gly Ile Val Leu Arg Asp Gly Asn Arg Asn Leu
705                 710                 715                 720

Thr Ile Arg Arg Val Arg Lys Glu Asp Gly Gly Leu Tyr Thr Cys Gln
                725                 730                 735

Ala Cys Asn Val Leu Gly Cys Ala Arg Ala Glu Thr Leu Phe Ile Ile
            740                 745                 750

Glu Gly Ala Gln Glu Lys Thr Asn Leu Glu Val Ile Ile Leu Val Gly
        755                 760                 765

Thr Ala Val Ile Ala Met Phe Phe Trp Leu Leu Leu Val Ile Val Leu
    770                 775                 780

Arg Thr Val Lys Arg Ala Asn Glu Gly Glu Leu Lys Thr Gly Tyr Leu
785                 790                 795                 800

Ser Ile Val Met Asp Pro Asp Glu Leu Pro Leu Asp Glu Arg Cys Glu
                805                 810                 815

Arg Leu Pro Tyr Asp Ala Ser Lys Trp Glu Phe Pro Arg Asp Arg Leu
            820                 825                 830

Lys Leu Gly Lys Pro Leu Gly Arg Gly Ala Phe Gly Gln Val Ile Glu
        835                 840                 845

Ala Asp Ala Phe Gly Ile Asp Lys Thr Ala Thr Cys Lys Thr Val Ala
    850                 855                 860

Val Lys Met Leu Lys Glu Gly Ala Thr His Ser Glu His Arg Ala Leu
865                 870                 875                 880

Met Ser Glu Leu Lys Ile Leu Ile His Ile Gly His His Leu Asn Val
                885                 890                 895

Val Asn Leu Leu Gly Ala Cys Thr Lys Pro Gly Gly Pro Leu Met Val
            900                 905                 910

Ile Val Glu Phe Cys Lys Phe Gly Asn Leu Ser Thr Tyr Leu Arg Gly
        915                 920                 925

Lys Arg Asn Glu Phe Val Pro Tyr Lys Ser Lys Gly Ala Arg Phe Arg
    930                 935                 940

Gln Gly Lys Asp Tyr Val Gly Glu Leu Ser Val Asp Leu Lys Arg Arg
945                 950                 955                 960

Leu Asp Ser Ile Thr Ser Ser Gln Ser Ser Ala Ser Ser Gly Phe Val
                965                 970                 975

Glu Glu Lys Ser Leu Ser Asp Val Glu Glu Glu Glu Ala Ser Glu Glu
            980                 985                 990

Leu Tyr Lys Asp Phe Leu Thr Leu  Glu His Leu Ile Cys  Tyr Ser Phe
        995                 1000                 1005

Gln Val  Ala Lys Gly Met Glu  Phe Leu Ala Ser Arg  Lys Cys Ile
    1010                 1015                 1020

His Arg  Asp Leu Ala Ala Arg  Asn Ile Leu Leu Ser  Glu Lys Asn
    1025                 1030                 1035

Val Val  Lys Ile Cys Asp Phe  Gly Leu Ala Arg Asp  Ile Tyr Lys
    1040                 1045                 1050

Asp Pro  Asp Tyr Val Arg Lys  Gly Asp Ala Arg Leu  Pro Leu Lys
    1055                 1060                 1065

Trp Met  Ala Pro Glu Thr Ile  Phe Asp Arg Val Tyr  Thr Ile Gln
```

```
    1070                1075                1080

Ser Asp  Val Trp Ser Phe Gly  Val Leu Leu Trp Glu  Ile Phe Ser
    1085                1090                1095

Leu Gly  Ala Ser Pro Tyr Pro  Gly Val Lys Ile Asp  Glu Glu Phe
    1100                1105                1110

Cys Arg  Arg Leu Lys Glu Gly  Thr Arg Met Arg Ala  Pro Asp Tyr
    1115                1120                1125

Thr Thr  Pro Glu Met Tyr Gln  Thr Met Leu Asp Cys  Trp His Glu
    1130                1135                1140

Asp Pro  Asn Gln Arg Pro Ser  Phe Ser Glu Leu Val  Glu His Leu
    1145                1150                1155

Gly Asn  Leu Leu Gln Ala Asn  Ala Gln Gln Asp Gly  Lys Asp Tyr
    1160                1165                1170

Ile Val  Leu Pro Met Ser Glu  Thr Leu Ser Met Glu  Glu Asp Ser
    1175                1180                1185

Gly Leu  Ser Leu Pro Thr Ser  Pro Val Ser Cys Met  Glu Glu Glu
    1190                1195                1200

Glu Val  Cys Asp Pro Lys Phe  His Tyr Asp Asn Thr  Ala Gly Ile
    1205                1210                1215

Ser His  Tyr Leu Gln Asn Ser  Lys Arg Lys Ser Arg  Pro Val Ser
    1220                1225                1230

Val Lys  Thr Phe Glu Asp Ile  Pro Leu Glu Glu Pro  Glu Val Lys
    1235                1240                1245

Val Ile  Pro Asp Asp Ser Gln  Thr Asp Ser Gly Met  Val Leu Ala
    1250                1255                1260

Ser Glu  Glu Leu Lys Thr Leu  Glu Asp Arg Asn Lys  Leu Ser Pro
    1265                1270                1275

Ser Phe  Gly Gly Met Met Pro  Ser Lys Ser Arg Glu  Ser Val Ala
    1280                1285                1290

Ser Glu  Gly Ser Asn Gln Thr  Ser Gly Tyr Gln Ser  Gly Tyr His
    1295                1300                1305

Ser Asp  Asp Thr Asp Thr Thr  Val Tyr Ser Ser Asp  Glu Ala Gly
    1310                1315                1320

Leu Leu  Lys Met Val Asp Ala  Ala Val His Ala Asp  Ser Gly Thr
    1325                1330                1335

Thr Leu  Arg Ser Pro Pro Val
    1340                1345
```

<210> SEQ ID NO 138
<211> LENGTH: 210
<212> TYPE: PRT
<213> ORGANISM: Artificial Sequence
<220> FEATURE:
<223> OTHER INFORMATION: VEGFR2 protein fragment

<400> SEQUENCE: 138

```
Arg Asp Ser Glu Glu Arg Val Leu Val Thr Glu Cys Gly Gly Gly Asp
1               5                   10                  15

Ser Ile Phe Cys Lys Thr Leu Thr Ile Pro Arg Val Val Gly Asn Asp
            20                  25                  30

Thr Gly Ala Tyr Lys Cys Ser Tyr Arg Asp Val Asp Ile Ala Ser Thr
        35                  40                  45

Val Tyr Val Tyr Val Arg Asp Tyr Arg Ser Pro Phe Ile Ala Ser Val
    50                  55                  60

Ser Asp Gln His Gly Ile Val Tyr Ile Thr Glu Asn Lys Asn Lys Thr
```

65 70 75 80

Val Val Ile Pro Cys Arg Gly Ser Ile Ser Asn Leu Asn Val Ser Leu
85 90 95

Cys Ala Arg Tyr Pro Glu Lys Arg Phe Val Pro Asp Gly Asn Arg Ile
100 105 110

Ser Trp Asp Ser Glu Ile Gly Phe Thr Leu Pro Ser Tyr Met Ile Ser
115 120 125

Tyr Ala Gly Met Val Phe Cys Glu Ala Lys Ile Asn Asp Glu Thr Tyr
130 135 140

Gln Ser Ile Met Tyr Ile Val Val Val Val Gly Tyr Arg Ile Tyr Asp
145 150 155 160

Val Ile Leu Ser Pro Pro His Glu Ile Glu Leu Ser Ala Gly Glu Lys
165 170 175

Leu Val Leu Asn Cys Thr Ala Arg Thr Glu Leu Asn Val Gly Leu Asp
180 185 190

Phe Thr Trp His Ser Pro Pro Ser Lys Ser His His Lys Lys Ile Val
195 200 205

Asn Arg
210

<210> SEQ ID NO 139
<211> LENGTH: 186
<212> TYPE: PRT
<213> ORGANISM: Artificial Sequence
<220> FEATURE:
<223> OTHER INFORMATION: VEGFR2 protein fragment

<400> SEQUENCE: 139

Val Ile Arg Gly Pro Glu Ile Thr Val Gln Pro Ala Ala Gln Pro Thr
1 5 10 15

Glu Gln Glu Ser Val Ser Leu Leu Cys Thr Ala Asp Arg Asn Thr Phe
20 25 30

Glu Asn Leu Thr Trp Tyr Lys Leu Gly Ser Gln Ala Thr Ser Val His
35 40 45

Met Gly Glu Ser Leu Thr Pro Val Cys Lys Asn Leu Asp Ala Leu Trp
50 55 60

Lys Leu Asn Gly Thr Met Phe Ser Asn Ser Thr Asn Asp Ile Leu Ile
65 70 75 80

Val Ala Phe Gln Asn Ala Ser Leu Gln Asp Gln Gly Asp Tyr Val Cys
85 90 95

Ser Ala Gln Asp Lys Lys Thr Lys Lys Arg His Cys Leu Val Lys Gln
100 105 110

Leu Ile Ile Leu Glu Arg Met Ala Pro Met Ile Thr Gly Asn Leu Glu
115 120 125

Asn Gln Thr Thr Thr Ile Gly Glu Thr Ile Glu Val Thr Cys Pro Ala
130 135 140

Ser Gly Asn Pro Thr Pro His Ile Thr Trp Phe Lys Asp Asn Glu Thr
145 150 155 160

Leu Val Glu Asp Ser Gly Ile Val Leu Arg Asp Gly Asn Arg Asn Leu
165 170 175

Thr Ile Arg Arg Val Arg Lys Glu Asp Gly
180 185

<210> SEQ ID NO 140
<211> LENGTH: 290
<212> TYPE: PRT

<213> ORGANISM: Artificial Sequence
<220> FEATURE:
<223> OTHER INFORMATION: VEGFR2 protein fragment

<400> SEQUENCE: 140

Glu Gly Glu Leu Lys Thr Gly Tyr Leu Ser Ile Val Met Asp Pro Asp
1 5 10 15

Glu Leu Pro Leu Asp Glu Arg Cys Glu Arg Leu Pro Tyr Asp Ala Ser
20 25 30

Lys Trp Glu Phe Pro Arg Asp Arg Leu Lys Leu Gly Lys Pro Leu Gly
35 40 45

Arg Gly Ala Phe Gly Gln Val Ile Glu Ala Asp Ala Phe Gly Ile Asp
50 55 60

Lys Thr Ala Thr Cys Lys Thr Val Ala Val Lys Met Leu Lys Glu Gly
65 70 75 80

Ala Thr His Ser Glu His Arg Ala Leu Met Ser Glu Leu Lys Ile Leu
85 90 95

Ile His Ile Gly His His Leu Asn Val Val Asn Leu Leu Gly Ala Cys
100 105 110

Thr Lys Pro Gly Gly Pro Leu Met Val Ile Val Glu Phe Cys Lys Phe
115 120 125

Gly Asn Leu Ser Thr Tyr Leu Arg Gly Lys Arg Asn Glu Phe Val Pro
130 135 140

Tyr Lys Ser Lys Gly Ala Arg Phe Arg Gln Gly Lys Asp Tyr Val Gly
145 150 155 160

Glu Leu Ser Val Asp Leu Lys Arg Arg Leu Asp Ser Ile Thr Ser Ser
165 170 175

Gln Ser Ser Ala Ser Ser Gly Phe Val Glu Glu Lys Ser Leu Ser Asp
180 185 190

Val Glu Glu Glu Glu Ala Ser Glu Glu Leu Tyr Lys Asp Phe Leu Thr
195 200 205

Leu Glu His Leu Ile Cys Tyr Ser Phe Gln Val Ala Lys Gly Met Glu
210 215 220

Phe Leu Ala Ser Arg Lys Cys Ile His Arg Asp Leu Ala Ala Arg Asn
225 230 235 240

Ile Leu Leu Ser Glu Lys Asn Val Val Lys Ile Cys Asp Phe Gly Leu
245 250 255

Ala Arg Asp Ile Tyr Lys Asp Pro Asp Tyr Val Arg Lys Gly Asp Ala
260 265 270

Arg Leu Pro Leu Lys Trp Met Ala Pro Glu Thr Ile Phe Asp Arg Val
275 280 285

Tyr Thr
290

<210> SEQ ID NO 141
<211> LENGTH: 156
<212> TYPE: PRT
<213> ORGANISM: Artificial Sequence
<220> FEATURE:
<223> OTHER INFORMATION: VEGFR2 protein

<400> SEQUENCE: 141

Ile Gln Ser Asp Val Trp Ser Phe Gly Val Leu Leu Trp Glu Ile Phe
1 5 10 15

Ser Leu Gly Ala Ser Pro Tyr Pro Gly Val Lys Ile Asp Glu Glu Phe
20 25 30

Cys Arg Arg Leu Lys Glu Gly Thr Arg Met Arg Ala Pro Asp Tyr Thr
35 40 45

Thr Pro Glu Met Tyr Gln Thr Met Leu Asp Cys Trp His Glu Asp Pro
50 55 60

Asn Gln Arg Pro Ser Phe Ser Glu Leu Val Glu His Leu Gly Asn Leu
65 70 75 80

Leu Gln Ala Asn Ala Gln Gln Asp Gly Lys Asp Tyr Ile Val Leu Pro
85 90 95

Met Ser Glu Thr Leu Ser Met Glu Glu Asp Ser Gly Leu Ser Leu Pro
100 105 110

Thr Ser Pro Val Ser Cys Met Glu Glu Glu Glu Val Cys Asp Pro Lys
115 120 125

Phe His Tyr Asp Asn Thr Ala Gly Ile Ser His Tyr Leu Gln Asn Ser
130 135 140

Lys Arg Lys Ser Arg Pro Val Ser Val Lys Thr Phe
145 150 155

<210> SEQ ID NO 142
<211> LENGTH: 9
<212> TYPE: PRT
<213> ORGANISM: Artificial Sequence
<220> FEATURE:
<223> OTHER INFORMATION: VEGFR2 fragment

<400> SEQUENCE: 142

Ile Ile Leu Val Gly Thr Ala Val Ile
1 5

<210> SEQ ID NO 143
<211> LENGTH: 9
<212> TYPE: PRT
<213> ORGANISM: Artificial Sequence
<220> FEATURE:
<223> OTHER INFORMATION: VEGFR2 fragment

<400> SEQUENCE: 143

Leu Leu Val Ile Ile Leu Arg Thr Val
1 5

<210> SEQ ID NO 144
<211> LENGTH: 9
<212> TYPE: PRT
<213> ORGANISM: Artificial Sequence
<220> FEATURE:
<223> OTHER INFORMATION: VEGFR2 fragment

<400> SEQUENCE: 144

Ile Leu Leu Ser Glu Lys Asn Val Val
1 5

<210> SEQ ID NO 145
<211> LENGTH: 9
<212> TYPE: PRT
<213> ORGANISM: Artificial Sequence
<220> FEATURE:
<223> OTHER INFORMATION: VEGFR2 fragment

<400> SEQUENCE: 145

Thr Ile Phe Asp Arg Val Tyr Thr Ile
1 5

<210> SEQ ID NO 146
<211> LENGTH: 9
<212> TYPE: PRT
<213> ORGANISM: Artificial Sequence
<220> FEATURE:
<223> OTHER INFORMATION: VEGFR2 fragment

<400> SEQUENCE: 146

Val Leu Leu Trp Glu Ile Phe Ser Leu
1 5

<210> SEQ ID NO 147
<211> LENGTH: 654
<212> TYPE: PRT
<213> ORGANISM: Mus musculus

<400> SEQUENCE: 147

Met Asp Arg Gly Val Leu Pro Leu Pro Ile Thr Leu Leu Leu Phe Glu
1 5 10 15

Ile Tyr Ser Phe Glu Pro Thr Thr Gly Leu Ala Glu Arg Val Gly Cys
20 25 30

Asp Leu Gln Pro Val Asp Pro Thr Arg Gly Glu Val Thr Phe Thr Thr
35 40 45

Ser Gln Val Ser Glu Gly Cys Val Ala Gln Ala Ala Asn Ala Val Arg
50 55 60

Glu Val His Val Leu Phe Leu Asp Phe Pro Gly Met Leu Ser His Leu
65 70 75 80

Glu Leu Thr Leu Gln Ala Ser Lys Gln Asn Gly Thr Glu Thr Arg Glu
85 90 95

Val Phe Leu Val Leu Val Ser Asn Lys Asn Val Phe Val Lys Phe Gln
100 105 110

Ala Pro Glu Ile Pro Leu His Leu Ala Tyr Asp Ser Ser Leu Val Ile
115 120 125

Phe Gln Gly Gln Pro Arg Val Asn Ile Thr Val Leu Pro Ser Leu Thr
130 135 140

Ser Arg Lys Gln Ile Leu Asp Trp Ala Ala Thr Lys Gly Ala Ile Thr
145 150 155 160

Ser Ile Ala Ala Leu Asp Asp Pro Gln Ser Ile Val Leu Gln Leu Gly
165 170 175

Gln Asp Pro Lys Ala Pro Phe Leu Cys Leu Pro Glu Ala His Lys Asp
180 185 190

Met Gly Ala Thr Leu Glu Trp Gln Pro Arg Ala Gln Thr Pro Val Gln
195 200 205

Ser Cys Arg Leu Glu Gly Val Ser Gly His Lys Glu Ala Tyr Ile Leu
210 215 220

Arg Ile Leu Pro Gly Ser Glu Ala Gly Pro Arg Thr Val Thr Val Met
225 230 235 240

Met Glu Leu Ser Cys Thr Ser Gly Asp Ala Ile Leu Ile Leu His Gly
245 250 255

Pro Pro Tyr Val Ser Trp Phe Ile Asp Ile Asn His Ser Met Gln Ile
260 265 270

Leu Thr Thr Gly Glu Tyr Ser Val Lys Ile Phe Pro Gly Ser Lys Val
275 280 285

Lys Gly Val Glu Leu Pro Asp Thr Pro Gln Gly Leu Ile Ala Glu Ala
290 295 300

Arg Lys Leu Asn Ala Ser Ile Val Thr Ser Phe Val Glu Leu Pro Leu
305 310 315 320

-continued

```
Val Ser Asn Val Ser Leu Arg Ala Ser Ser Cys Gly Gly Val Phe Gln
                325                 330                 335

Thr Thr Pro Ala Pro Val Val Thr Thr Pro Pro Lys Asp Thr Cys Ser
            340                 345                 350

Pro Val Leu Leu Met Ser Leu Ile Gln Pro Lys Cys Gly Asn Gln Val
        355                 360                 365

Met Thr Leu Ala Leu Asn Lys Lys His Val Gln Thr Leu Gln Cys Thr
    370                 375                 380

Ile Thr Gly Leu Thr Phe Trp Asp Ser Ser Cys Gln Ala Glu Asp Thr
385                 390                 395                 400

Asp Asp His Leu Val Leu Ser Ser Ala Tyr Ser Ser Cys Gly Met Lys
                405                 410                 415

Val Thr Ala His Val Val Ser Asn Glu Val Ile Ile Ser Phe Pro Ser
            420                 425                 430

Gly Ser Pro Pro Leu Arg Lys Lys Val Gln Cys Ile Asp Met Asp Ser
        435                 440                 445

Leu Ser Phe Gln Leu Gly Leu Tyr Leu Ser Pro His Phe Leu Gln Ala
    450                 455                 460

Ser Asn Thr Ile Glu Leu Gly Gln Gln Ala Phe Val Gln Val Ser Val
465                 470                 475                 480

Ser Pro Leu Thr Ser Glu Val Thr Val Gln Leu Asp Ser Cys His Leu
                485                 490                 495

Asp Leu Gly Pro Glu Gly Asp Met Val Glu Leu Ile Gln Ser Arg Thr
            500                 505                 510

Ala Lys Gly Ser Cys Val Thr Leu Leu Ser Pro Ser Pro Glu Gly Asp
        515                 520                 525

Pro Arg Phe Ser Phe Leu Leu Arg Val Tyr Met Val Pro Thr Pro Thr
    530                 535                 540

Ala Gly Thr Leu Ser Cys Asn Leu Ala Leu Arg Pro Ser Thr Leu Ser
545                 550                 555                 560

Gln Glu Val Tyr Lys Thr Val Ser Met Arg Leu Asn Val Val Ser Pro
                565                 570                 575

Asp Leu Ser Gly Lys Gly Leu Val Leu Pro Ser Val Leu Gly Ile Thr
            580                 585                 590

Phe Gly Ala Phe Leu Ile Gly Ala Leu Leu Thr Ala Ala Leu Trp Tyr
        595                 600                 605

Ile Tyr Ser His Thr Arg Gly Pro Ser Lys Arg Glu Pro Val Val Ala
    610                 615                 620

Val Ala Ala Pro Ala Ser Ser Glu Ser Ser Ser Thr Asn His Ser Ile
625                 630                 635                 640

Gly Ser Thr Gln Ser Thr Pro Cys Ser Thr Ser Ser Met Ala
                645                 650
```

BIOMARKER DIRECTED MULTI-TARGET IMMUNOTHERAPY

CROSS REFERENCE TO RELATED APPLICATIONS

This application is a U.S. National Stage entry of PCT/US2015/016348 filed Feb. 18, 2015, which claims the benefit of US Provisional Application No. 61/941,072, filed Feb. 18, 2014.

REFERENCE TO A SEQUENCE LISTING

This application includes an electronic sequence listing in a file named 482683_ SEQLIST.TXT, created Dec. 6, 2016, and containing 122 kilobytes, which is herein incorporated by reference in its entirety for all purposes.

FIELD OF INVENTION

This invention provides methods and compositions for evaluating biomarker expression in a disease and providing a multi-targeted *Listeria*-based immunotherapeutic approach against said disease.

BACKGROUND OF THE INVENTION

A biomarker is a measurable characteristic that reflects the severity or presence of or is associated with some disease state and that can be used as an indicator of a particular disease state or some other physiological state of an organism. Biomarkers can be specific cells, molecules, genes, gene products, enzymes, receptors, mutated versions of any of these cellular elements or hormones that can be used to identify and/or measure the presence or progress of disease state, such as a particular cancer or tumor. Further, it is well known that tumors and cancers can express a set of tumor biomarkers that can be used to identify the presence of or measure the progress of or the effects of treatment on the tumor or cancer.

Despite the abundant use of biomarkers for diagnosing disease and monitoring progression of the same, there remains a need for developing therapeutic approaches that make use of this information to specifically target biomarkers expressed by the disease that are directly associated with the proliferation or existence of the diseased state and subsequent deterioration of a subject's overall health

*Listeria monocytogenes* (Lm) is an intracellular pathogen that primarily infects antigen presenting cells and has adapted for life in the cytoplasm of these cells. *Listeria monocytogenes* and a protein it produces named listeriolysin O (LLO) have strong adjuvant properties that unlike the majority of adjuvants used for cellular based immunotherapies, can be administered after providing an antigen specific treatment or can be used to itself provide antigen-specific treatment when fusing an antigen of interest to an adjuvant protein expressed by the *Listeria*, such as LLO or an ActA protein.

The present invention addresses this need by providing a combinatorial, multi-target immunotherapeutic approach wherein individual compositions each comprising a recombinant *Listeria*-strain expressing a different disease-associated antigen than a counterpart *Listeria* present in a separate composition, are administered separately to a subject having a disease, or the compositions are administered in combination as single bolus administration. The present invention further addresses this need by providing a predetermined number disease-associated antigens or fragments thereof by using a recombinant *Listeria* expressing at least one fusion protein comprising the antigen fused to an immunogenic *Listeria* peptide such as an N-terminal LLO, truncated LLO, an ActA protein fragment, or a PEST peptide. Use of such compositions will allow diseases, including tumors, cancers, or others having sub-populations of diseased cells expressing more than one biomarker to be successfully treated.

SUMMARY OF THE INVENTION

In one aspect, the invention relates to a method of inducing an immune response against a disease in a subject having said disease, the method comprising the steps of: a. obtaining a biological sample from said subject; b. evaluating the expression of a predetermined number of biomarkers in said biological sample; c. administering to said subject a composition comprising a recombinant *Listeria* strain, said strain comprising a nucleic acid sequence encoding at least one fusion protein, wherein said fusion protein comprises a biomarker identified in said biological sample, wherein said biomarker is associated with said disease, wherein said biomarker is fused to a PEST-containing polypeptide, and wherein each fusion protein within said *Listeria* comprises a different biomarker, thereby inducing a multi-target anti-disease immune response in said subject.

In one aspect, the invention relates to a method of inducing an immune response against a disease in a subject having said disease, the method comprising the steps of: a. obtaining a biological sample from said subject; b. evaluating the expression of a predetermined number of biomarkers in said biological sample; c. administering to said subject a mixture of compositions each comprising a recombinant *Listeria* strain, said strain comprising a nucleic acid sequence encoding fusion protein, wherein said fusion protein comprises a biomarker identified in said biological sample, wherein said biomarker is associated with said disease, wherein said biomarker is fused to a PEST-containing polypeptide, and wherein each *Listeria* strain within each composition comprises a different biomarker in said fusion protein, thereby inducing a multi-target anti-disease immune response in said subject.

In a related aspect, the invention relates to a method of treating a disease in a subject, the method comprising the steps of: a. obtaining a biological sample from said subject; b. evaluating the expression of a predetermined number of biomarkers in said biological sample; c. administering to said subject a composition comprising a recombinant *Listeria* strain, said strain comprising a nucleic acid sequence encoding at least one fusion protein, wherein said fusion protein comprises a biomarker identified in said biological sample, wherein said biomarker is associated with said disease, wherein said biomarker is fused to a PEST-containing polypeptide, and wherein each fusion protein within said *Listeria* comprises a different biomarker, thereby treating said disease in said subject.

In a related aspect, the invention relates to a method of treating a disease in a subject, the method comprising the steps of: a. obtaining a biological sample from said subject; b. evaluating the expression of a predetermined number of biomarkers in said biological sample; c. administering to said subject a mixture of compositions each comprising a recombinant *Listeria* strain, said strain comprising a nucleic acid sequence encoding fusion protein, wherein said fusion protein comprises a biomarker identified in said biological sample, wherein said biomarker is associated with said disease, wherein said biomarker is fused to a PEST-containing polypeptide, and wherein each *Listeria* strain within each composition comprises a different biomarker, thereby treating said disease in said subject.

In another aspect, the invention relates to a method of preventing a recurrence of a disease in a subject, the method comprising the steps of: a. obtaining a biological sample from said subject; b. evaluating the expression of a predetermined number of biomarkers in said biological sample; c. administering to said subject a composition comprising a recombinant *Listeria* strain, said strain comprising a nucleic acid sequence encoding at least one fusion protein, wherein said fusion protein comprises a biomarker identified in said biological sample, wherein said biomarker is associated with said disease, wherein said biomarker is fused to a PEST-containing polypeptide, and wherein each fusion protein within said *Listeria* comprises a different biomarker, thereby preventing a recurrence of said disease in said subject.

In another aspect, the invention relates to a method of preventing a recurrence of a disease in a subject, the method comprising the steps of: a. obtaining a biological sample from said subject; b. evaluating the expression of a predetermined number of biomarkers in said biological sample; c. administering to said subject a mixture of compositions each comprising a recombinant *Listeria* strain, said strain comprising nucleic acid sequence encoding a fusion protein, wherein said fusion protein comprises a biomarker identified in said biological sample, wherein said biomarker is associated with said disease, wherein said biomarker is fused to a PEST-containing polypeptide, and wherein each *Listeria* strain within each composition comprises a different biomarker, thereby preventing a recurrence of said disease in said subject.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present disclosure, the inventions of which can be better understood by reference to one or more of these drawings in combination with the detailed description of specific embodiments presented herein.

In FIG. 1A, Lm-E7 was generated by introducing a gene cassette into the orfZ domain of the *L. monocytogenes* genome. The hly promoter drives expression of the hly signal sequence and the first five amino acids (AA) of LLO followed by HPV-16 E7. In FIG. 1B, Lm-LLO-E7 was generated by transforming the prfA- strain XFL-7 with the plasmid pGG-55. pGG-55 has the hly promoter driving expression of a non-hemolytic fusion of LLO-E7. pGG-55 also contains the prfA gene to select for retention of the plasmid by XFL-7 in vivo.

FIG. 6B Top panel: *Listeria* constructs containing PEST regions induce tumor regression. Bottom panel: Average tumor sizes at day 28 post-tumor challenge in 2 separate experiments.

FIG. 10 shows the DNA sequence (SEQ ID NO: 81) present upstream and downstream of the inlC region on the genome of *Listeria* strain EGD. DNA-up (red), inlC gene (blue) and DNA-down (black).

FIG. 11 shows the sequence of DNA (SEQ ID NO: 82) that is cloned in the temperature sensitive plasmid, pKSV7 to create inl C deletion mutant. The restriction enzyme sites used for cloning of these regions are indicated in caps and underlined. GAATTC-EcoRI, GGATCC-BamHI and CTGCAg-PstI. The EcoRI-PstI insert is cloned in the vector, pKSV7.

FIG. 13 shows the DNA sequence (SEQ ID NO: 60) present upstream and downstream of the actA gene in the *Listeria* chromosome. The region in italics contains the residual actA sequence element that is present in the LmddΔactA strain. The underlined sequence gtcgac represent the restriction site of XhoI, which is the junction between the N-T and C-T region of actA.

FIG. 21 shows a decrease in MDSCs and Tregs in tumors. The number of MDSCs on right-hand panel (B) and Tregs on left-hand panel (A) following Lm vaccination (LmddAPSA and LmddAE7).

In FIGS. 22A and 22B Phorbol-Myristate-Acetate and lonomycin (PMA/I) represents non-specific stimulation. In FIGS. 22C and 22D the term "peptide" represents specific antigen stimulation. Percent (%) CD3+CD22+ represents % effector (responder) T cells. The No MDSC group shows the lack of division of the responder T cells when they are left unstimulated and the last group (PMA/I or peptide added) shows the division of stimulated cells in the absence of MDSCs. FIGS. 22A and 22C show individual cell division cycles for each group. FIGS. 22B and 22D show pooled division cycles.

In FIGS. 23A and 23B PMA/I represents non-specific stimulation. In FIGS. 23C and 23D the term "peptide" represents specific antigen stimulation. Percent (%) CD3+CD8+ represents % effector (responder) T cells. The No MDSC group shows the lack of division of the responder T cells when they are left unstimulated and the last group (PMA/I or peptide added) shows the division of stimulated cells in the absence of MDSCs. FIGS. 23A and 23C show individual cell division cycles for each group. FIGS. 23B and 23D show pooled division cycles.

In FIGS. 24A and 24B PMA/I represents non-specific stimulation. In FIGS. 24C and 24D the term "peptide" represents specific antigen stimulation. Percent (%) CD3+CD8+ represents % effector (responder) T cells. The No MDSC group shows the lack of division of the responder T cells when they are left unstimulated and the last group (PMA/I or peptide added) shows the division of stimulated cells in the absence of MDSCs. FIGS. 24A and 24C show individual cell division cycles for each group. FIGS. 24B and 24D show pooled percentage division.

In FIGS. 25A and 25B PMA/I represents non-specific stimulation. In FIGS. 25C and 25D the term "peptide" represents specific antigen stimulation. Percent (%) CD3+CD8+ represents % effector (responder) T cells. The No MDSC group shows the lack of division of the responder T cells when they are left unstimulated and the last group (PMA/I or peptide added) shows the division of stimulated cells in the absence of MDSCs. FIGS. 25A and 25C show individual cell division cycles for each group. FIGS. 25B and 25D show pooled percentage division.

In FIGS. 26A and 26B PMA/I represents non-specific stimulation. In FIGS. 26C and 26D the term "peptide" represents specific antigen stimulation. Percent (%) CD3+CD8+ represents % effector (responder) T cells. The No Treg group shows the lack of division of the responder T cells when they are left unstimulated and the last group (PMA/I or peptide added) shows the division of stimulated cells in the absence of Tregs. FIGS. 26A and 26C show individual cell division cycles for each group. FIGS. 26B and 26D show pooled percentage division.

In FIGS. 27A and 27B PMA/I represents non-specific stimulation. In FIGS. 27C and 27D the term "peptide" represents specific antigen stimulation. Percent (%) CD3+CD8+ represents % effector (responder) T cells. The No Treg group shows the lack of division of the responder T cells when they are left unstimulated and the last group (PMA/I or peptide added) shows the division of stimulated cells in the absence of Tregs. FIGS. 27A and 27C show individual cell division cycles for each group. FIGS. 27B and 27D show pooled percentage division.

In FIGS. 28A and 28B PMA/I represents non-specific stimulation. In FIGS. 28C and 28D the term "peptide" represents specific antigen stimulation. Percent (%) CD3+CD8+ represents % effector (responder) T cells. The No Treg group shows the lack of division of the responder T cells when they are left unstimulated and the last group (PMA/I or peptide added) shows the division of stimulated cells in the absence of Tregs. FIGS. 28C-28D show data from pooled percentage division.

In FIGS. 29A and 29B PMA/I represents non-specific stimulation. In FIGS. 29C and 29D the term "peptide" represents specific antigen stimulation. Percent (%) CD8+ represents % effector (responder) T cells. The No MDSC group shows the lack of division of the responder T cells when they are left unstimulated and the last group (PMA/I or peptide added) shows the division of stimulated cells in the absence of MDSCs. FIGS. 29A and 29C show individual cell division cycles for each group. FIGS. 29B and 29D show pooled percentage division.

In FIGS. 30A and 30B PMA/I represents non-specific stimulation. In FIGS. 30C and 30D the term "peptide" represents specific antigen stimulation. Percent (%) CD8+ represents % effector (responder) T cells. The No MDSC group shows the lack of division of the responder T cells when they are left unstimulated and the last group (PMA/I or peptide added) shows the division of stimulated cells in the absence of MDSC. FIGS. 30A and 30C show individual cell division cycles for each group. FIGS. 30B and 30D show pooled percentage division.

In FIGS. 31A and 31B PMA/I represents non-specific stimulation. In FIGS. 31C and 31D the term "peptide" represents specific antigen stimulation. Percent (%) CD8+ represents % effector (responder) T cells. The No MDSC group shows the lack of division of the responder T cells when they are left unstimulated and the last group (PMA/I or peptide added) shows the division of stimulated cells in the absence of MDSCs. FIGS. 31A and 31C show individual cell division cycles for each group. FIGS. 31B and 31D shows pooled percentage division.

In FIGS. 32A and 32B PMA/I represents non-specific stimulation. In FIGS. 32C and 32D the term "peptide" represents specific antigen stimulation. Percent (%) CD8+ represents % effector (responder) T cells. The No MDSC group shows the lack of division of the responder T cells when they are left unstimulated and the last group (PMA/I or peptide added) shows the division of stimulated cells in the absence of MDSCs. FIGS. 32A and 32C show individual cell division cycles for each group. FIGS. 32B and 32D show pooled percentage division.

In FIGS. 33A and 33B PMA/I represents non-specific stimulation. In FIGS. 33C and 33D the term "peptide" represents specific antigen stimulation. Percent (%) CD8+ represents % effector (responder) T cells. This decrease is not antigen specific, as the change in Treg suppressive ability is seen with both Her2/neu-specific and non-specific responder T cells. FIGS. 33A and 33C show individual cell division cycles for each group. FIGS. 33B and 33D show pooled percentage division.

In FIGS. 34A and 34B PMA/I represents non-specific stimulation. In FIGS. 34C and 34D the term "peptide" represents specific antigen stimulation. Percent (%) CD8+ represents % effector (responder) T cells. FIGS. 34A and 34C show individual cell division cycles for each group. FIGS. 34B and 34D show pooled percentage division.

FIGS. 41A-41D show suppressor assay data demonstrating that tumor Tcon cells are not capable of suppressing the division of T cells regardless of whether the responder cells are antigens specific (FIGS. 41A and 41B) or non-specifically activated (FIGS. 41C and 41D).

FIGS. 42A-42D show suppressor assay data demonstrating that spleen Tcon cells are not capable of suppressing the division of T cells regardless of whether the responder cells are antigens specific (FIGS. 42A and 42B) or non-specifically activated (FIGS. 42C and 42D).

FIG. 49C shows the design of the Flk-1/VEGFR2 expressing Lm-based constructs. IFN-g ELISpot showing $CD8^+$ T cell restricted responses ex vivo after immunization with each construct. The naive group was injected with PBS alone; all groups contained a control Lm group. Responses are to the corresponding mapped epitopes for each Flk fragment. N=5 per group. Graphs show Mean±SEM; *$p<0.05$, Mann-Whitney statistical test, experiment repeated once.

FIG. 50A shows the design of the Flk-1/VEGFR2 expressing Lm-based constructs. Cloned regions boxed for each construct built, highlighted/bold amino acids show mapped CTL epitopes for $H2^{d/q}$ MHC I haplotype.

FIG. 61. The design of the novel CD105A and CD105B-expressing *Listeria* constructs. A. Cloned regions for each construct are in bold and two putative epitopes are underlined; Lm-LLO-CD105A and Lm-LLOCD105B together span nearly the entire endoglin gene and encompass more potential CTL epitopes. B. Each underlined fragment was cloned into the expression vector pGG34 fused to adjuvant LLO.

Figures 1A, 1B:
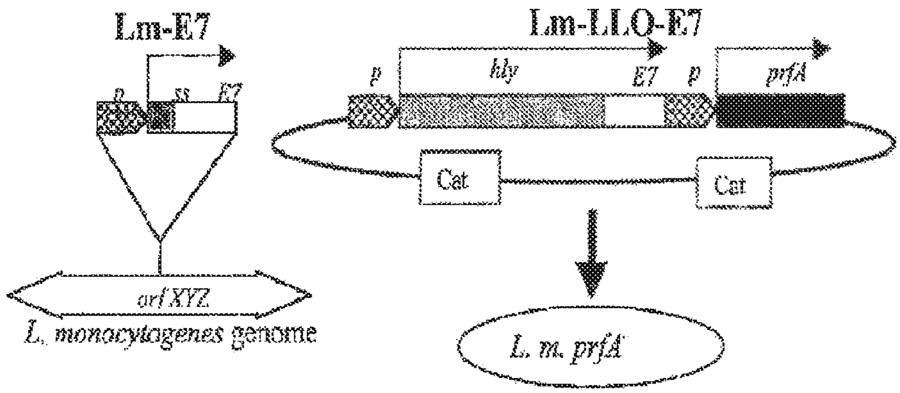
FIGS. 1A and 1B show that Lm-E7 and Lm-LLO-E7 use different expression systems to express and secrete E7.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In one embodiment, the invention provided herein aims to evaluate the expression of or presence of biomarkers associated with a disease in a subject and that are expressed in a biological sample obtained from the subject in order to identify and target biomarkers that are associated with the disease, and consequently treat the disease in the subject. In another embodiment, the method of treating the subject comprises administering a composition or a mixture of compositions that target two or more biomarkers expressed by a disease in a subject.

In one embodiment, a composition provided herein comprises a recombinant *Listeria* strain, said strain comprising a nucleic acid sequence encoding a fusion protein, wherein said fusion protein comprises a biomarker identified in a biological sample obtained from a subject having a disease, wherein said biomarker is associated with said disease, and wherein said biomarker is fused to a PEST-containing polypeptide. In another embodiment, the recombinant *Listeria* comprises a nucleic acid encoding a recombinant polypeptide comprising a fusion protein. In another embodiment, the recombinant polypeptide is a fusion protein.

In one embodiment, when a single composition (as opposed to a mixture of compositions—i.e., independent of being administered as part of a mixture regiment) is being administered to a subject having a disease, the composition comprises a recombinant *Listeria* comprising a nucleic acid sequence encoding at least one fusion protein comprising a biomarker identified in a biological sample obtained from the subject, wherein said biomarker is associated with said disease, wherein said biomarker is fused to a PEST-containing polypeptide. In another embodiment, the *Listeria* comprises a nucleic acid sequence encoding one to three, one to four, or one to six fusion proteins each comprising a different biomarker associated with a disease. In another embodiment, the *Listeria* comprises a nucleic acid sequence comprising one to three, one to four, or one to six open reading frames (ORFs) each encoding a fusion protein comprising a biomarker that is associated with a disease. In another embodiment, each biomarker in each of said at least one fusion protein is different than another biomarker present in another fusion protein expressed from a different open reading frame within the nucleic acid sequence.

In another embodiment, when a composition is being administered to a subject as part of a mixture, each composition in the mixture comprises a recombinant *Listeria* strain, said strain comprising a nucleic acid sequence encoding a fusion protein, wherein said fusion protein comprises a biomarker identified in a biological sample obtained from the subject, wherein said biomarker is associated with said disease, wherein said biomarker is fused to a PEST-containing polypeptide, and wherein each recombinant *Listeria* strain within each composition comprises a different biomarker from the rest. In one embodiment, a mixture is a vaccine mixture. In another embodiment, a mixture comprises a predetermined number of compositions each comprising a recombinant *Listeria* expressing a fusion protein of a biomarker expressed in said disease and a PEST-containing polypeptide. In another embodiment, a mixture of compositions is a combination of compositions.

It will be appreciated by a skilled artisan that each composition in a mixture of compositions may all be administered concurrently in a single bolus dose or separately over time and would target more than one biomarker expressed by a disease. In another embodiment, each composition in a mixture of compositions may all be administered concurrently in a single bolus dose and would target more than one biomarker expressed by a disease at the same time. In another embodiment, a composition comprising a recombinant *Listeria* expressing at least one fusion protein targets more than one biomarker expressed by a disease at the same time. In one embodiment, a predetermined number of compositions in a mixture of compositions comprising a recombinant *Listeria* expressing at least one fusion protein are administered to a subject concurrently or separately over time.

In one embodiment, when a mixture of compositions is being administered to a subject having a disease, each composition in the mixture may be administered one to two days apart, one to three days apart, one to five days apart, one to ten days apart, or one to fourteen days apart.

In one embodiment, when a mixture of compositions is being administered to a subject having a disease, each composition may be administered at a predetermined dose that has been previously determined to been an optimal for the subject receiving the administration. Such an optimal dose may be experimentally determined by a clinician or skilled artisan prior to administering the mixture. In another embodiment, a mixture comprises a predetermined number of compositions each comprising a recombinant *Listeria* expressing a fusion protein of a biomarker and a PEST-containing polypeptide. In another embodiment, a mixture of compositions is a combination of compositions each comprising a recombinant *Listeria* strain expressing a single fusion protein of a biomarker fused to a PEST-containing polypeptide.

In one aspect, the invention relates to a method of inducing an immune response against a disease in a subject having said disease, the method comprising the steps of: a. obtaining a biological sample from said subject; b. evaluating the expression of a predetermined number of biomarkers in said biological sample; c. administering to said subject a composition comprising a recombinant *Listeria* strain, said strain comprising a nucleic acid sequence encoding at least one fusion protein, wherein said fusion protein comprises a biomarker identified in said biological sample obtained from said subject, wherein said biomarker is associated with said disease, wherein said biomarker is fused to a PEST-containing polypeptide, and wherein each fusion protein within said *Listeria* comprises a different biomarker, thereby inducing a multi-target anti-disease immune response in said subject.

In one embodiment, a *Listeria* strain comprising a nucleic acid sequence encoding a at least one fusion protein, encodes one to two fusion proteins. In another embodiment, the nucleic acid sequence encodes one to three fusion proteins, one to four fusion proteins, one to five fusion proteins, one to ten fusion proteins, two to three fusion proteins, two to four fusion proteins, two to five fusion proteins, or two to ten fusion proteins.

In one aspect, the invention relates to a method of inducing an immune response against a disease in a subject having said disease, the method comprising the steps of: a. obtaining a biological sample from said subject; b. evaluating the expression of a predetermined number of biomarkers in said biological sample; c. administering to said subject a predetermined number of compositions each comprising a recombinant *Listeria* strain, said strain comprising a nucleic acid sequence encoding fusion protein, wherein said fusion protein comprises a biomarker identified in said biological sample obtained from said subject, wherein said biomarker is associated with said disease, wherein said biomarker is fused to a PEST-containing polypeptide, and wherein each *Listeria* strain within each composition comprises a different biomarker in said fusion protein, thereby inducing a multi-target anti-disease immune response in said subject.

In one embodiment, the invention relates to a method of treating a disease in a subject, the method comprising the steps of: a. obtaining a biological sample from said subject; b. evaluating the expression of a predetermined number of biomarkers in said biological sample; c. administering to said subject a composition comprising a recombinant *Listeria* strain, said strain comprising a nucleic acid sequence encoding at least one fusion protein, wherein said fusion protein comprises a biomarker identified in said biological sample obtained from said subject, wherein said biomarker is associated with said disease, wherein said biomarker is fused to a PEST-containing polypeptide, and wherein each fusion protein within said *Listeria* comprises a different biomarker, thereby treating said disease in said subject.

In another embodiment, the invention relates to a method of treating a disease in a subject, the method comprising the steps of: a. obtaining a biological sample from said subject; b. evaluating the expression of a predetermined number of biomarkers in said biological sample; c. administering to said subject a predetermined number of compositions each comprising a recombinant *Listeria* strain, said strain comprising a nucleic acid sequence encoding fusion protein, wherein said fusion protein comprises a biomarker identified in said biological sample, wherein said biomarker is associated with said disease, wherein said biomarker is fused to a PEST-containing polypeptide, and wherein each *Listeria* strain within each composition comprises a different biomarker, thereby treating said disease in said subject.

In another embodiment, the invention relates to a method of preventing a recurrence of a disease in a subject, the method comprising the steps of: a. obtaining a biological sample from said subject; b. evaluating the expression of a predetermined number of biomarkers in said biological sample; c. administering to said subject a composition comprising a recombinant *Listeria* strain, said strain comprising a nucleic acid sequence encoding at least one fusion protein, wherein said fusion protein comprises a biomarker identified in said biological sample, wherein said biomarker is associated with said disease, wherein said biomarker is fused to a PEST-containing polypeptide, and wherein each fusion protein within said *Listeria* comprises a different biomarker, thereby preventing a recurrence of said disease in said subject.

In one embodiment, a disease provided herein is cancer or a tumor growth. In another embodiment, a disease provided herein is an infectious disease, a respiratory disease, an inflammatory disease, or a disease where the subject has a Th2 persistent profile. In another embodiment, the disease is a localized disease, i.e., to a specific disease site or is a systemic disease.

In one embodiment, the fusion protein is a transcribed fusion protein. In another embodiment, the *Listeria* provided herein expresses the fusion protein comprising the biomarker fused to a PEST-containing peptide provided herein. In another embodiment, the fusion protein expresses the biomarker provided herein.

In one embodiment, the *Listeria* of methods and compositions of the present invention is *Listeria monocytogenes*. In another embodiment, the *Listeria* is *Listeria ivanovii*. In another embodiment, the *Listeria* is *Listeria welshimeri*. In another embodiment, the *Listeria* is *Listeria seeligeri*. Each type of *Listeria* represents a separate embodiment of the present invention.

In one embodiment, provided herein are mixtures of compositions wherein each composition comprises a recombinant *Listeria* strain expressing an biomarker that targets an immunologic response to each individual biomarker present in a disease. In another embodiment, the biomarker is present on the surface of a tissue that is associated with said disease. In another embodiment, a disease provided herein is a tumor or cancer. In another embodiment, a biomarker is a surface biomarker. In another embodiment, a biomarker is an intracellular biomarker. In another embodiment, where a disease is a tumor or cancer, the biomarker is an angioneic biomarker that is associated with a tumor or cancer vasculature.

In one embodiment, a predetermined number of compositions each comprising a *Listeria* strain is at least 1 to about 10 compositions. In another embodiment, a predetermined number of compositions is at least 1 to about 20 compositions. In another embodiment, a predetermined number of compositions is 2 to 5 compositions, 3-6 compositions, 4-7 compositions 5-10 compositions, 6-11 compositions or 7-12 compositions.

In one embodiment, a predetermined number of biomarkers is at least 1 to about 10 biomarkers. In another embodiment, a predetermined number of biomarkers is at least 1 to about 20 biomarkers, at least 1 to about 30 biomarkers, at least 1 to about 40 biomarkers, at least 1 to about 50 biomarkers, at least 51 to about 60 biomarkers, at least 71 to about 80 biomarkers, at least 81 to about 90 biomarkers, or at least 1 to about 100 biomarkers.

It will be appreciated by a skilled artisan that the term "biomarker" may encompass antigens, including heterologous antigens, tumor antigens, angiogenic antigens, and the like. The term may also encompass proteins, DNA, RNA, peptides, that are associated with or are expressed by a disease, including, but not limited to, cancers, tumors, infectious diseases, autoimmune diseases, congenital diseases, and the like. It will also be appreciated that such biomarkers may be overexpressed in subjects having a disease as compared to normal levels of expression of the biomarker in healthy hosts. In another embodiment, a subject is tolerant to a biomarker such that a disease expressing the biomarker can freely progress without a proper immune response being mounted against it. In another embodiment, the term "biomarker" refers to an antigen expressed by a disease. In another embodiment, the biomarker is a heterologous antigen or a fragment thereof. In one embodiment, the biomarker is a tumor antigen or a fragment thereof. In another embodiment, the biomarker provided herein is an allergen that causes an allergic or inflammatory reaction in a host.

In one embodiment, the term "tumor marker," and "tumor antigen" are used interchangeably herein and refer to an antigen expressed by a tumor. In another embodiment, a tumor marker is a heterologous tumor antigen or a fragment thereof. In one embodiment, a tumor marker is associated with a formation of or proliferation of said tumor. In another embodiment, a tumor marker is expressed by said tumor or by a vasculature of said tumor. In another embodiment, a tumor marker is secreted by a tumor. In another embodiment, a tumor maker provided herein is associated with a local tissue environment that is further associated with a development of or metastasis of cancer. In another embodiment, a tumor marker is associated with tumor evasion or resistance to cancer, or is an angiogenic antigen. In another embodiment, a tumor marker is expressed by a tumor on the surface of a tumor. In another embodiment, a tumor marker is present inside a tumor and is released to the extracellular milieu upon lysis of a tumor cell.

In one embodiment, evaluation of a biomarker profile or biomarker expression level comprises obtaining a biological sample from a subject having a disease and detecting an expression level of the biomarker in said sample. In one embodiment, the biomarker profile provided herein is a tumor marker profile. In another embodiment, evaluation of a tumor marker profile or tumor marker expression level comprises obtaining a biological sample from a subject having a tumor and obtaining the expression level of the tumor markers in said sample.

It will be well appreciated by a skilled artisan that a biomarker expression profile may be measured by using any assay known in the art to be useful for measuring expression levels of a biomarker. Such assays include but are not limited to, immunoassays (e.g. ELISAs), FACS, immunohistochemical assays, fluorescence-based assays, PCR, quantitative HPLC alone or in combination with mass spectrometry, or any other assay known in the art. The measured expression profile can then be compared with a control profile such as one from a healthy subject to effectively diagnose a disease (e.g., a tumor or cancer) in a subject. In another embodiment, the biomarker is detectable in a biological sample obtained from a subject having a disease prior to administering a composition comprising a recombinant *Listeria* strain.

In another embodiment, provided herein is a method of monitoring disease progression in a subject in order to determine an optimal time to administer a composition or mixture of compositions of the present invention, the method comprising the step of obtaining a biological sample from the subject and measuring the expression profile of a biomarker in the biological sample, wherein measuring a biomarker expression level in the subject over the levels observed in that of a control sample enables the monitoring the progress of the disease in the subject, and wherein a composition or mixture of compositions of the present invention is administered at predetermined time that will maximize therapeutic efficacy. Diseases encompassed by the present invention include, but are not limited to, cancer, a tumor growth, an infectious disease, or a disease where the subject has a Th2-skewed profile. These diseases are further characterized or staged according to the progression of the disease in a subject. Such information can be used to determine an optimal period for administering a composition or compositions of the present invention.

It is to be understood by a skilled artisan that the biological sample may include, but is not limited to, tissue, blood, serum, DNA, RNA, urine, semen, synovial fluid, sputa, or cerebrospinal fluid (CSF).

In one embodiment, a "Th2-skewed subject," also known as, a subject having a Th2 phenotypic profile, is one in which the Th1 immune response is defective, lacking, or repressed a result of an infectious disease, including but not limited to parasitic infections, or a cancer in the subject. In another embodiment, a Th2-skewed subject refers to a subject wherein a Th2 response is not exclusively present in the subject, but predominates over the Th1 response in the subject. In another embodiment, a Th2-skewed subject refer to a subject wherein a Th2 response is exclusively present in the subject and there are minimal or insignificant levels of indicators (i.e. cytokines, chemokines or other known markers) of a Th1 response.

In one embodiment, a mixture of compositions comprising each comprises 1-5 compositions each comprising a recombinant *Listeria* strain expressing a single fusion protein. In another embodiment, the mixture comprises, 1-10 compositions, 1-15 compositions, 5-10 compositions, 5-15 compositions or 5-20 compositions, each comprising a recombinant *Listeria* strain expressing a single fusion protein of a PEST-containing polypeptide and a biomarker. In another embodiment, each composition in the mixture comprises a *Listeria* expressing a different biomarker.

In another embodiment, a composition or mixture of compositions provided herein is administered concurrently with the administration of an alternate form of a vaccine or composition different from the original composition or mixture of compositions. In another embodiment, the alternate form of a vaccine is administered separately from an administration of a composition or mixture of compositions provided herein. It will be appreciated by a skilled artisan that the alternate forms of a vaccine or composition may include, but are not limited to, a DNA vaccine encoding a fusion protein comprising a biomarker and a PEST-containing peptide or a fragment thereof, a viral vector comprising said fusion protein, a viral vector comprising a biomarker provided herein, a virus-like particle comprising said fusion protein, a virus-like particle comprising a biomarker provided herein, a recombinant peptide or a recombinant polypeptide comprising said fusion protein, a cell-based vaccine expressing a biomarker provided herein, or a live recombinant non-*Listeria* bacterial vector comprising a biomarker provided herein alone or in fusion protein form as further provided herein. It will also be appreciated by the skilled artisan that such alternate forms may not only be used in combination with a composition or mixture of compositions provided herein, but may be administered prior to, or following a dose of the same.

In one embodiment, a recombinant polypeptide provided herein comprises a fusion protein provided herein. In another embodiment, a recombinant polypeptide provided herein is a fusion protein provided herein.

In another embodiment, a composition or combination of compositions utilized in any of the methods described above have any of the characteristics of vaccines and compositions of the present invention.

The terms "immunogenic composition," "composition" and "pharmaceutical composition" may be used interchangeably. For example, in one embodiment, a composition of this invention may encompass a recombinant *Listeria* described herein, and an adjuvant. In another embodiment, an immunogenic composition comprises a recombinant *Listeria* provided herein. In another embodiment, an immunogenic composition comprises an adjuvant known in the art or as provided herein. It is also to be understood that administration of such compositions enhance an immune response, or increase a T effector cell to regulatory T cell ratio or elicit an anti-tumor immune response, as further provided herein.

The term "pharmaceutical composition" may encompass a therapeutically effective amount of the active ingredient or ingredients including a composition comprising a *Listeria* strain together with a pharmaceutically acceptable carrier or diluent.

It will be understood by the skilled artisan that the term "administering" may encompass bringing a subject in contact with a composition of the present invention. In one embodiment, administration can be accomplished in vitro, i.e. in a test tube, or in vivo, i.e. in cells or tissues of living organisms, for example humans. In one embodiment, the present invention encompasses administering the *Listeria* strains and compositions thereof of the present invention to a subject.

In one embodiment, a bacterial vector is an intracellular pathogen. In another embodiment, a vector is derived from a cytosolic pathogen. In another embodiment, a vector is derived from an intracellular pathogen. In another embodiment, an intracellular pathogen induces a predominantly cell-mediated immune response. In another embodiment, the vector is a *Salmonella* strain. In another embodiment, the vector is a BCG strain. In another embodiment, the vector is a bacterial vector. In another embodiment, dendritic cells transduced with a vector of the present invention may be administered to the subject to upregulate the subject's immune response, which in one embodiment is accomplished by upregulating CTL activity.

In another embodiment, a recombinant vaccine vector induces a predominantly Th1-type immune response.

In another embodiment, a vector is selected from *Salmonella* sp., *Shigella* sp., BCG, *L. monocytogenes, E. coli*, and *S. gordonii*. In another embodiment, fusion proteins are delivered by recombinant bacterial vectors modified to escape phagolysosomal fusion and live in the cytoplasm of the cell. In another embodiment, a vector is a viral vector. In other embodiments, a vector is selected from Vaccinia, Avipox, Adenovirus, AAV, Vaccinia virus NYVAC, Modified vaccinia strain Ankara (MVA), Semliki Forest virus, Venezuelan equine encephalitis virus, herpes viruses, and retroviruses. In another embodiment, a vector is a naked DNA vector. In another embodiment, a vector is any other vector known in the art. Each possibility represents a separate embodiment of the present invention.

In one embodiment, a viral vector is an adenoviral vector, a retroviral vector, a lentiviral vector, a poxviral vector, a baculoviral vector, a herpes simplex viral vector, an adeno-associated viral vector, a nano-engineered virus-like substance or any viral vector known in the art for use in vaccines. In another embodiment, the viral vector is a vaccinia virus vector.

It will be appreciated by the skilled artisan that a cell-based vaccine may include live cells or dead cells and may also include tumor cells of autologous or heterologous origin.

In one embodiment, a biomarker expression profile is obtained prior to the administration of any of the vaccines provided herein.

In one embodiment, a peptide-based vaccine comprises a detox LLO having a mutated or deleted cholesterol binding domain (see Examples 38-39) fused to a tumor marker or antigen provided herein. In another embodiment, a peptide-based vaccine is combined with a composition comprising a recombinant *Listeria* strain provided herein for use in providing multi-targeted immunotherapy of a disease, including cancer.

In another embodiment, the methods of the present invention further comprise the step of administering a booster dose to a subject receiving an immunotherapy provided herein. In another embodiment, the booster dose is administered following initial administration of a composition or mixture of compositions provided herein. In another embodiment, the method further comprises the step of obtaining a biomarker profile from said subject subsequent to the first administration of a composition or mixture of compositions provided herein, and administering a booster dose. In another embodiment, the booster dose that is administered comprises a composition provided herein and an alternate form of a vaccine as further provided herein. In another embodiment, the method further comprises obtaining a second, third, fourth, fifth, etc., biomarker profile following a previous administration of a composition or mixture of compositions provided herein and administering a booster dose or in combination with an alternate form of a vaccine or composition following obtaining said third, fourth, fifth, etc., biomarker profile. In another embodiment, the biomarker is a tumor marker and the biomarker profile is a tumor marker profile. In another embodiment, the booster dose is the same or different as the initial dose of a composition or any one of the compositions in the mixture of compositions provided herein.

In one embodiment, a booster vaccination follows a single priming vaccination or administration. In another embodiment, a single booster vaccination is administered after a priming vaccination. In another embodiment, two booster vaccinations are administered after the priming vaccination. In another embodiment, three booster vaccinations are administered after the priming vaccination. In one embodiment, the period between a prime and a boost vaccine is experimentally determined by a skilled artisan. In another embodiment, the period between a prime and a boost vaccine is 1 week, in another embodiment it is 2 weeks, in another embodiment, it is 3 weeks, in another embodiment, it is 4 weeks, in another embodiment, it is 5 weeks, in another embodiment it is 6-8 weeks, in yet another embodiment, the boost vaccine is administered 8-10 weeks after the prime vaccine.

Heterologous "prime boost" strategies have been effective for enhancing immune responses and protection against numerous pathogens. Schneider et al., Immunol. Rev. 170: 29-38 (1999); Robinson, H. L., Nat. Rev. Immunol. 2:239-50 (2002); Gonzalo, R. M. et al., Vaccine 20:1226-31 (2002); Tanghe, A., Infect. Immun. 69:3041-7 (2001). Providing antigen in different forms in the prime and the boost injections appears to maximize the immune response to the antigen. DNA vaccine priming followed by boosting with protein in adjuvant or by viral vector delivery of DNA encoding antigen appears to be the most effective way of improving antigen specific antibody and CD4+ T-cell responses or CD8+ T-cell responses respectively. Shiver J. W. et al., Nature 415: 331-5 (2002); Gilbert, S. C. et al., Vaccine 20:1039-45 (2002); Billaut-Mulot, O. et al., Vaccine 19:95-102 (2000); Sin, J. I. et al., DNA Cell Biol. 18:771-9 (1999). Recent data from monkey vaccination studies suggests that adding CRL1005 poloxamer (12 kDa, 5% POE), to DNA encoding the HIV gag antigen enhances T-cell responses when monkeys are vaccinated with an HIV gag DNA prime followed by a boost with an adenoviral vector expressing HIV gag (Ad5-gag). The cellular immune responses for a DNA/poloxamer prime followed by an Ad5-gag boost were greater than the responses induced with a DNA (without poloxamer) prime followed by Ad5-gag boost or for Ad5-gag only. Shiver, J. W. et al. Nature 415:331-5 (2002). U.S. Patent Appl. Publication No. US 2002/0165172 A1 describes simultaneous administration of a vector construct encoding an immunogenic portion of an antigen and a protein comprising the immunogenic portion of an antigen such that an immune response is generated. The document is limited to hepatitis B antigens and HIV antigens. Moreover, U.S. Pat. No. 6,500,432 is directed to methods of enhancing an immune response of nucleic acid vaccination by simultaneous administration of a polynucleotide and polypeptide of interest. According to the patent, simultaneous administration means administration of the polynucleotide and the polypeptide during the same immune response, preferably within 0-10 or 3-7 days of each other. The antigens contemplated by the patent include, among others, those of Hepatitis (all forms), HSV, HIV, CMV, EBV, RSV, VZV, HPV, polio, influenza, parasites (e.g., from the genus *Plasmodium*), and pathogenic bacteria (including but not limited to *M. tuberculosis, M. leprae, Chlamydia, Shigella, B. burgdorferi*, enterotoxigenic *E. coli, S. typhosa, H. pylori, V. cholerae, B. pertussis*, etc.). All of the above references are herein incorporated by reference in their entireties.

In one embodiment, the composition provided herein may be referred to as a vaccine and the mixture of compositions or combination of compositions provided herein may be referred to as a vaccine combination. In other embodiments, a vaccine combination may comprise an alternate form of a vaccine in addition to a composition or combination of compositions provided herein.

It will be well appreciated by a skilled artisan that a vaccine combination or administration may adjusted (to target additional or new tumor markers) based on the changes detected in resistant tumor or recurrent tumor or data gathered at a time point subsequent to the original treatment or administration. For example, if a tumor expresses markers A, B, C, and D, then the total dose of an immunotherapy given would be comprised of composition or a mixture of compositions comprising a recombinant *Listeria* strain as provided herein that target an immunologic response to each individual marker. In one embodiment, where a mixture of compositions is administered, a single bolus is administered at the same time, at least one composition in a mixture of compositions is administered at different times, that is, where one composition from the mixture comprising a specific *Listeria* strain targets biomarkers A and B and at a different time another composition from the mixture comprising another recombinant *Listeria*-strains targets biomarkers C and D.

In another embodiment, 2-4 compositions of a 10 composition mixture are administered before the rest of the compositions in the mixture. In another embodiment, 2-6 compositions of a 10 composition mixture are administered before the rest of the compositions in the mixture. In another embodiment, 5-8 compositions of a 10 composition mixture are administered before the rest of the compositions in the mixture. In another embodiment, all compositions of a 10 composition mixture are administered at different time points. In another embodiment, all compositions of a 10 composition mixture are administered concomitantly. In another embodiment, the mixture comprises 5-10 compositions, 11-15 compositions, or 16-20 compositions.

In one embodiment, the methods provided herein increase the infiltrating T lymphocytes/suppressor cells ratio in a subject having a disease or in a disease site within the subject. In another embodiment, the methods provided herein increasing the ratio of CD8+ T cells/suppressor cells in a subject having a disease or in a disease site within the subject. In another embodiment, the methods provided herein increasing the infiltrating T lymphocyte/suppressor cells or CD8+ T cells/suppressor cells ratio comprises the step of administering to the subject a composition comprising the vaccine or composition provided herein.

In one embodiment, the methods provided herein increase the infiltrating T lymphocyte/Myeloid-derived suppressor cell (MDSC) ratio in a subject having a disease or in a disease site within the subject. In another embodiment, the methods provided herein increase the ratio of CD8+ T cells/Myeloid-derived suppressor cells (MDSC) in a subject having a disease or in a disease site within the subject. In another embodiment, the method of increasing the infiltrating T lymphocyte/Myeloid-derived suppressor cells (MDSC) or CD8+ T cell/Myeloid-derived suppressor cell (MDSC) ratio comprises the step of administering to the subject a composition comprising the vaccine or composition provided herein.

In one embodiment, the infiltrating T lymphocyte is a Tumor infiltrating T lymphocyte (TIL). In one embodiment, the suppressor cells provided herein are T regulatory cells (Tregs). In another embodiment, the suppressor cells are myeloid-derived suppressor cells (MDSCs).

In one embodiment, the methods provided herein reduce the amount of cells that suppress an immune response against a disease. In another embodiment, the cells that suppress the immune response are suppressive cells. In another embodiment, the suppressive cells are myeloid-derived suppressor cells (MDSC). In another embodiment, the suppressive cells are T regulatory cells (Tregs).

In one embodiment, tumor MDSCs can unexpectedly inhibit both, the function of antigen-specific and non-specific T cell function, while spleen MDSCs can only inhibit the function of antigen-specific T cells. As demonstrated in the Examples below (see Examples 17-20), the live attenuated *Listeria* provided herein reduces the percent of suppressor cells in a disease compared to the population of TILs at the disease site, for example, a tumor site.

In one embodiment, the recombinant *Listeria* strains comprised by the *Listeria monocytogenes* (Lm)-based vaccines provided herein reduce the percentage of Tregs and MDSCs at sites of disease, with a corresponding shift in the ratio of effector to suppressor cells at sites of disease. In another embodiment, Lm-based vaccines provided herein are useful for improving immune responses by reducing the percentage of Tregs and MDSCs and the absolute number of MDSC at a specific site of disease in a subject. Such a site can be an inflammation site due to allergy, trauma, infection, disease or the site can be a tumor site.

In another embodiment, both monocytic and granulocytic MDSCs purified from the tumors of *Listeria*-treated mice are less able to suppress the division of CD8+ T cells than MDSCs purified from the tumors of untreated mice, whereas monocytic and granulocytic MDSCs purified from the spleens of these same tumor-bearing mice show no change in their function after vaccination with *Listeria* (See Examples 17-20 herein). In one embodiment, this effect is seen because splenic MDSCs are suppressive in an antigen-specific manner. Hence, treatment with *Listeria* has the distinct advantage that it allows for tumor-specific inhibition of tumor suppressive cells such as Tregs and MDSCs. Another unexpected advantage provided by the live attenuated *Listeria* strains of the methods and compositions provided herein is that there are lower amount of Tregs in the tumor, and the ones that persist lose the ability to suppress T cell replication.

In another embodiment, both monocytic and granulocytic MDSCs purified from the tumors of truncated LLO-expressing *Listeria*-treated mice are less able to suppress the division of CD8+ T cells than MDSCs purified from the tumors of untreated mice, whereas monocytic and granulocytic MDSCs purified from the spleens of these same tumor-bearing mice show no change in their function after vaccination with truncated LLO-expressing *Listeria* (See Example 21 herein). In one embodiment, this effect is seen because splenic MDSCs are only suppressive in an antigen-specific manner. Hence, treatment with truncated LLO-expressing *Listeria* has the distinct advantage that it allows for tumor-specific inhibition of tumor suppressive cells such as Tregs and MDSCs. Another unexpected advantage provided by the truncated LLO-expressing live attenuated *Listeria* of the methods and compositions provided herein is that there are lower amount of Tregs and MDSCs in the tumor, and the ones that persist lose the ability to suppress T cell replication, and this effect is observed even in the absence of an LLO fusion partner, such as a heterologous antigen.

In another embodiment, administering a truncated LLO-expressing live attenuated *Listeria* strain enhances an anti-tumor T cell response by suppressing Treg- and MDSC-mediated T cell suppression (see Example 21 herein).

In one embodiment, provided herein is a method of reducing the percentage of suppressor cells in a disease site in a subject, the method comprising the step of administering a composition comprising a live attenuated *Listeria* strain or mixture of compositions comprising live attenuated *Listeria* vaccine strains provided herein to the subject.

In another embodiment, provided herein is a method of reducing suppressor cells' ability to suppress T cell replication in a disease site in a subject, the method comprising the step of administering a composition comprising a live attenuated *Listeria* strain or mixture of compositions comprising live attenuated *Listeria* vaccine strains provided herein to the subject.

In one embodiment, reducing the number of suppressor cells at a disease site effectively treats a disease. In another embodiment, reducing the number of the suppressor cells at the disease site enhances an anti-disease immune response in the subject having the disease at the disease site. In another embodiment, an immune response is a cell-mediated immune response. In another embodiment, an immune response is a tumor infiltrating T-lymphocytes (TILs) immune response.

In one embodiment, the methods provided herein reduce a percentage of suppressor cells in a disease in a subject and enhances a therapeutic response against a disease in the subject.

In another embodiment, the methods provided herein reduce suppressor cells' ability to suppress replication of T cells in a disease in a subject and enhancing a therapeutic response against a disease in the subject.

In one embodiment, the term "reducing the percentage of" is representative of the amount suppressor cells, either Tregs or MDSCs whose presence at a disease site is diminished or reduced in relation to the presence of T infiltrating cells as measured in an assay or in an immune response.

In another embodiment, the term "reducing the number of" refers to the absolute number of suppressor cells, either Tregs, or MDSCs that been diminished or reduced as a result of administration of the live attenuated *Listeria* strain comprised by the *Listeria*-based vaccines provided herein or an alternate form of this vaccine that achieve a similar effect, also described elsewhere herein.

In one embodiment, provided herein is a PEST-containing polypeptide to which the biomarker or tumor marker is fused to. In another embodiment, the PEST-containing polypeptide is an N-terminal Listeriolysin O (LLO) or truncated LLO, a PEST amino acid sequence or PEST-sequence, or an N-terminal ActA sequence or truncated ActA.

In another, the invention includes an isolated nucleic acid encoding a truncated ActA, a truncated LLO, or a PEST amino acid sequence and an isolated nucleic acid encoding a tumor marker or an immunogenic fragment thereof operably linked to a nucleic acid comprising a promoter/regulatory sequence such that the nucleic acid is preferably capable of directing expression of the protein encoded by the nucleic acid. The invention also includes a vector comprising an isolated nucleic acid of the present invention. Thus, the invention encompasses expression vectors and methods for the introduction of exogenous DNA into cells with concomitant expression of the exogenous DNA in the cells such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

In another embodiment, the term "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA is, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). DNA can be, in other embodiments, in form of plasmid DNA, viral DNA, linear DNA, or chromosomal DNA or derivatives of these groups. In addition, these forms of DNA and RNA can be single, double, triple, or quadruple stranded. The term also includes, in another embodiment, artificial nucleic acids that contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

It will be appreciated by the skilled artisan that the term "isolated nucleic acid" may encompass a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In one embodiment, nucleic acids encoding the recombinant polypeptides or fusion proteins provided herein also comprise a signal peptide or sequence. In one embodiment, a heterologous antigen may be expressed through the use of a signal sequence, such as a Listerial signal sequence, for example, the hemolysin signal sequence or the actA signal sequence. Alternatively, for example, foreign genes can be expressed downstream from a *L. monocytogenes* promoter without creating a fusion protein. In another embodiment, the signal peptide is bacterial (Listerial or non-Listerial). In one embodiment, the signal peptide is native to the bacterium. In another embodiment, the signal peptide is foreign to the bacterium. In another embodiment, the signal peptide is a signal peptide from *Listeria monocytogenes*, such as a secA1 signal peptide. In another embodiment, the signal peptide is a Usp45 signal peptide from *Lactococcus lactis*, or a Protective Antigen signal peptide from *Bacillus anthracis*. In another embodiment, the signal peptide is a secA2 signal peptide, such the p60 signal peptide from *Listeria monocytogenes*. In addition, the recombinant nucleic acid molecule optionally comprises a third polynucleotide sequence encoding p60, or a fragment thereof. In another embodiment, the signal peptide is a Tat signal peptide, such as a *B. subtilis* Tat signal peptide (e.g., PhoD). In one embodiment, the signal peptide is in the same translational reading frame encoding the recombinant polypeptide.

In another embodiment, the present invention provides an isolated nucleic acid encoding a signal peptide or a recombinant polypeptide of the present invention. In one embodiment, the isolated nucleic acid comprises a sequence sharing at least 65% homology with a nucleic acid encoding the signal peptide or the recombinant polypeptide of the present invention. In another embodiment, the isolated nucleic acid comprises a sequence sharing at least 75% homology with a nucleic acid encoding the signal peptide or the recombinant polypeptide of the present invention. In another embodiment, the isolated nucleic acid comprises a sequence sharing at least 85% homology with a nucleic acid encoding the signal peptide or the recombinant polypeptide of the present invention. In another embodiment, the isolated nucleic acid comprises a sequence sharing at least 90% homology with a nucleic acid encoding the signal peptide or the recombinant polypeptide of the present invention. In another embodiment, the isolated nucleic acid comprises a sequence sharing at least 95% homology with a nucleic acid encoding the signal peptide or the recombinant polypeptide of the present invention. In another embodiment, the isolated nucleic acid comprises a sequence sharing at least 97% homology with a nucleic acid encoding the signal peptide or the recombinant polypeptide of the present invention. In another embodiment, the isolated nucleic acid comprises a sequence sharing at least 99% homology with a nucleic acid encoding the signal peptide or the recombinant polypeptide of the present invention.

In one embodiment, the present invention provides a vector comprising an oligonucleotide encoding a polypeptide of the present invention. In one embodiment, the term "oligonucleotide" refers to a short nucleic acid polymer, typically with twenty or fewer bases. In one embodiment, the present invention provides a vector comprising an polynucleotide encoding a polypeptide of the present invention. In one embodiment, the term "polynucleotide" refers to a chain of many nucleotides, which in one embodiment, is more than 5, in another embodiment, more than 10, in another embodiment, more than 20, in another embodiment, more than 50. In one embodiment, an oligonucleotide or polynucleotide or nucleic acid may refer to prokaryotic sequences, eukaryotic mRNA, cDNA from eukaryotic mRNA, genomic DNA sequences from eukaryotic (e.g., mammalian) DNA, or synthetic DNA sequences. The term also refers to sequences that include any of the known base analogs of DNA and RNA.

In one embodiment, the present invention provides a *Listeria*, which in one embodiment, is a *Listeria* vaccine strain comprising an isolated nucleic acid or vector of the present invention.

In one embodiment, a recombinant polypeptide or fusion protein provided herein is expressed by a *Listeria* strain provided herein. In another embodiment, a recombinant polypeptide or fusion protein is expressed from a plasmid present within said *Listeria* strain. In another embodiment, the recombinant polypeptide is expressed from the chromosome of said *Listeria*. In one embodiment, the recombinant polypeptide comprises a fusion protein provided herein. In another embodiment, the recombinant polypeptide is a fusion protein provided herein.

In another embodiment, z live attenuated *Listeria* strains comprised by the compositions provided herein comprise a recombinant nucleic acid sequence comprising a first and a second open reading frame each encoding a first and a second polypeptide, wherein the first and the second polypeptide each comprise a heterologous antigen or a fragment thereof fused to an PEST-containing polypeptide.

In one embodiment, provided herein is a recombinant *Listeria* strain comprising an episomal recombinant nucleic acid molecule, the nucleic acid molecule comprising a first and a second open reading frame each encoding a first and a second polypeptide, wherein the first and the second polypeptide each comprise a heterologous antigen or a fragment thereof fused to an PEST-containing polypeptide, and wherein the nucleic acid further comprises an open reading frame encoding a metabolic enzyme. In one embodiment, the term "episomal" or "episome" refers to a plasmid that is present within a host cell such as a *Listeria*.

In another embodiment, the *Listeria* strains comprise a recombinant nucleotide comprising one to five open reading frames each encoding a heterologous antigen or a fragment thereof, fused to PEST-containing polypeptide. In one embodiment, the heterologous antigen or fragments thereof and the PEST-containing polypeptides provided herein are translated in a single open reading frame. In another embodiment each heterologous antigenic polypeptides and the PEST-containing polypeptide provided herein are fused after being translated separately.

In one embodiment, a composition comprising a recombinant *Listeria* strain comprise one to five recombinant nucleic acids each encoding a heterologous antigen or a fragment thereof, fused to a PEST-containing polypeptide.

In another embodiment, a PEST-containing polypeptide is an N-terminal truncated LLO polypeptide, an N-terminal ActA polypeptide, or PEST-peptide, or a fragment thereof. In another embodiment, the fragment is a functional fragment. In another embodiment, the fragment is an immunogenic fragment.

In one embodiment, a nucleic acid molecule provided herein comprises a first open reading frame encoding a heterologous antigen. In another embodiment, the nucleic acid molecule provided herein further comprises a second open reading frame encoding a metabolic enzyme. In another embodiment, the metabolic enzyme complements an endogenous gene that is lacking in the chromosome of the recombinant *Listeria* strain. In another embodiment, the metabolic enzyme encoded by the second open reading frame is an alanine racemase enzyme (dal). In another embodiment, the metabolic enzyme encoded by the second open reading frame is a D-amino acid transferase enzyme (dat). In one embodiment, the *Listeria* further comprises a third open reading frame encoding an additional metabolic enzyme. In another embodiment, the metabolic enzyme encoded by the third open reading frame is a D-amino acid transferase enzyme. In another embodiment, the nucleic acid molecule comprises a fourth reading frame encoding a heterologous antigen or fragment thereof. In another embodiment, a recombinant *Listeria* strain provided herein comprise a mutation or a deletion in the genomic dal/dat genes. In another embodiment, a recombinant *Listeria* strain lack dal/dat genes. In another embodiment, the dal/dat genes are inactivated in the recombinant *Listeria* provided herein. In one embodiment, the term "lack(s)" when in reference to a genomic virulence gene means that the virulence gene is either mutated, or is otherwise not functionally expressed from the chromosome. Such a term may also encompass a partial deletion or a whole gene deletion of the virulence gene in the chromosome.

In another embodiment, a nucleic acid molecule of the methods and compositions of the present invention is operably linked to a promoter/regulatory sequence. In another embodiment, the first open reading frame of methods and compositions of the present invention is operably linked to a promoter/regulatory sequence. In another embodiment, the second open reading frame of methods and compositions of the present invention is operably linked to a promoter/regulatory sequence. In another embodiment, each of the open reading frames are operably linked to a promoter/regulatory sequence. Each possibility represents a separate embodiment of the present invention.

"Metabolic enzyme" refers, in another embodiment, to an enzyme involved in synthesis of a nutrient required by the host bacteria. In another embodiment, the term refers to an enzyme required for synthesis of a nutrient required by the host bacteria. In another embodiment, the term refers to an enzyme involved in synthesis of a nutrient utilized by the host bacteria. In another embodiment, the term refers to an enzyme involved in synthesis of a nutrient required for sustained growth of the host bacteria. In another embodiment, the enzyme is required for synthesis of the nutrient. Each possibility represents a separate embodiment of the present invention.

In another embodiment, the recombinant *Listeria* is an attenuated auxotrophic strain.

In one embodiment an attenuated *Listeria* strain is Lm dal(−)dat(−) (Lmdd). In another embodiment, the attenuated strains is Lm dal(−)dat(−)ΔactA (LmddA). LmddA is based on a *Listeria* vaccine vector which is attenuated due to the deletion of virulence gene actA and retains the plasmid for a desired heterologous antigen or truncated LLO expression in vivo and in vitro by complementation of dal gene. In another embodiment, the attenuated strain is LmΔactA. In another embodiment, the attenuated strain is LmΔPrfA. In another embodiment, the attenuated strain is LmΔPlcB. In another embodiment, the attenuated strain is LmΔPlcA. In another embodiment, the strain is the double mutant or triple mutant of any of the above-mentioned strains. In another embodiment, this strain exerts a strong adjuvant effect which is an inherent property of *Listeria*-based vaccines. In another embodiment, this strain is constructed from the EGD *Listeria* backbone. In another embodiment, the strain used in the invention is a *Listeria* strain that expresses a non-hemolytic LLO.

In another embodiment, a *Listeria* strain provided herein is an auxotrophic mutant. In another embodiment, the *Listeria* strain is deficient in a gene encoding a vitamin synthesis gene. In another embodiment, the *Listeria* strain is deficient in a gene encoding pantothenic acid synthase.

In another embodiment, a *Listeria* strain provided herein is deficient in an AA metabolism enzyme. In another embodiment, the *Listeria* strain is deficient in a D-glutamic acid synthase gene. In another embodiment, the *Listeria* strain is deficient in the dat gene. In another embodiment, the *Listeria* strain is deficient in the dal gene. In another embodiment, the *Listeria* strain is deficient in the dga gene. In another embodiment, the *Listeria* strain is deficient in a gene involved in the synthesis of diaminopimelic acid. CysK. In another embodiment, the gene is vitamin-B12 independent methionine synthase. In another embodiment, the gene is trpA. In another embodiment, the gene is trpB. In another embodiment, the gene is trpE. In another embodiment, the gene is asnB. In another embodiment, the gene is gltD. In another embodiment, the gene is gltB. In another embodiment, the gene is leuA. In another embodiment, the gene is argG. In another embodiment, the gene is thrC. In another embodiment, the *Listeria* strain is deficient in one or more of the genes described hereinabove.

In another embodiment, a *Listeria* strain provided herein is deficient in a synthase gene. In another embodiment, the gene is an AA synthesis gene. In another embodiment, the gene is folP. In another embodiment, the gene is dihydrouridine synthase family protein. In another embodiment, the gene is ispD. In another embodiment, the gene is ispF. In another embodiment, the gene is phosphoenolpyruvate synthase. In another embodiment, the gene is hisF. In another embodiment, the gene is hisH. In another embodiment, the gene is fliI. In another embodiment, the gene is ribosomal large subunit pseudouridine synthase. In another embodiment, the gene is ispD. In another embodiment, the gene is bifunctional GMP synthase/glutamine amidotransferase protein. In another embodiment, the gene is cobS. In another embodiment, the gene is cobB. In another embodiment, the gene is cbiD. In another embodiment, the gene is uroporphyrin-III C-methyltransferase/uroporphyrinogen-III synthase. In another embodiment, the gene is cobQ. In another embodiment, the gene is uppS. In another embodiment, the gene is truB. In another embodiment, the gene is dxs. In another embodiment, the gene is mvaS. In another embodiment, the gene is dapA. In another embodiment, the gene is ispG. In another embodiment, the gene is folC. In another embodiment, the gene is citrate synthase. In another embodiment, the gene is argJ. In another embodiment, the gene is 3-deoxy-7-phosphoheptulonate synthase. In another embodiment, the gene is indole-3-glycerol-phosphate synthase. In another embodiment, the gene is anthranilate synthase/glutamine amidotransferase component. In another embodiment, the gene is menB. In another embodiment, the gene is menaquinone-specific isochorismate synthase. In another embodiment, the gene is phosphoribosylformylglycinamidine synthase I or II. In another embodiment, the gene is phosphoribosylaminoimidazole-succinocarboxamide synthase. In another embodiment, the gene is carB. In another embodiment, the gene is carA. In another embodiment, the gene is thyA. In another embodiment, the gene is mgsA. In another embodiment, the gene is aroB. In another embodiment, the gene is hepB. In another embodiment, the gene is rluB. In another embodiment, the gene is ilvB. In another embodiment, the gene is ilvN. In another embodiment, the gene is alsS. In another embodiment, the gene is fabF. In another embodiment, the gene is fabH. In another embodiment, the gene is pseudouridine synthase. In another embodiment, the gene is pyrG. In another embodiment, the gene is truA. In another embodiment, the gene is pabB. In another embodiment, the gene is an atp synthase gene (e.g. atpC, atpD-2, aptG, atpA-2, etc).

In another embodiment, the gene is phoP. In another embodiment, the gene is aroA. In another embodiment, the gene is aroC. In another embodiment, the gene is aroD. In another embodiment, the gene is plcB.

In another embodiment, the *Listeria* strain is deficient in a peptide transporter. In another embodiment, the gene is ABC transporter/ATP-binding/permease protein. In another embodiment, the gene is oligopeptide ABC transporter/oligopeptide-binding protein. In another embodiment, the gene is oligopeptide ABC transporter/permease protein. In another embodiment, the gene is zinc ABC transporter/zinc-binding protein. In another embodiment, the gene is sugar ABC transporter. In another embodiment, the gene is phosphate transporter. In another embodiment, the gene is ZIP zinc transporter. In another embodiment, the gene is drug resistance transporter of the EmrB/QacA family. In another embodiment, the gene is sulfate transporter. In another embodiment, the gene is proton-dependent oligopeptide transporter. In another embodiment, the gene is magnesium transporter. In another embodiment, the gene is formate/nitrite transporter. In another embodiment, the gene is spermidine/putrescine ABC transporter. In another embodiment, the gene is Na/Pi-cotransporter. In another embodiment, the gene is sugar phosphate transporter. In another embodiment, the gene is glutamine ABC transporter. In another embodiment, the gene is major facilitator family transporter. In another embodiment, the gene is glycine betaine/L-proline ABC transporter. In another embodiment, the gene is molybdenum ABC transporter. In another embodiment, the gene is techoic acid ABC transporter. In another embodiment, the gene is cobalt ABC transporter. In another embodiment, the gene is ammonium transporter. In another embodiment, the gene is amino acid ABC transporter. In another embodiment, the gene is cell division ABC transporter. In another embodiment, the gene is manganese ABC transporter. In another embodiment, the gene is iron compound ABC transporter. In another embodiment, the gene is maltose/maltodextrin ABC transporter. In another embodiment, the gene is drug resistance transporter of the Bcr/CflA family. In another embodiment, the gene is a subunit of one of the above proteins.

In one embodiment, provided herein is a nucleic acid molecule that is used to transform the *Listeria* in order to arrive at a recombinant *Listeria*. In another embodiment, the nucleic acid provided herein used to transform *Listeria* lacks a virulence gene. In another embodiment, the nucleic acid molecule is integrated into the *Listeria* genome and carries a non-functional virulence gene. In another embodiment, the virulence gene is mutated in the recombinant *Listeria*. In yet another embodiment, the nucleic acid molecule is used to inactivate the endogenous gene present in the *Listeria* genome. In yet another embodiment, the virulence gene is an actA gene, an inlA gene, and inlB gene, an inlC gene, inlJ gene, a plbC gene, a bsh gene, or a prfA gene. It is to be understood by a skilled artisan, that the virulence gene can be any gene known in the art to be associated with virulence in the recombinant *Listeria*

In yet another embodiment, a *Listeria* strain provided herein is an inlA mutant, an inlB mutant, an inlC mutant, an inlJ mutant, prfA mutant, ActA mutant, a prfA mutant, a plcB deletion mutant, or a double mutant lacking both plcA and plcB. In another embodiment, the *Listeria* comprise a deletion or mutation of these genes individually or in combination. In another embodiment, the *Listeria* provided herein lack each one of genes. In another embodiment, the *Listeria* provided herein lack at least one and up to ten of any gene provided herein, including the actA, prfA, and dal/dat genes. In one embodiment, the live attenuated *Listeria* is a recombinant *Listeria*. In another embodiment, the recombinant *Listeria* comprises a mutation or a deletion of a genomic internalin B (inlB) gene. In another embodiment, the recombinant *Listeria* comprises a mutation or a deletion of a genomic actA gene and a genomic internalin B gene. In another embodiment, the recombinant *Listeria* comprises a mutation or a deletion of a genomic internalin C (inlC) gene In one embodiment, translocation of *Listeria* to adjacent cells is inhibited by the deletion of the actA gene and/or the inlC gene, which are involved in the process, thereby resulting in unexpectedly high levels of attenuation with increased immunogenicity and utility as a vaccine backbone.

Each possibility represents a separate embodiment of the present invention.

In one embodiment, the metabolic gene, the virulence gene, etc. is lacking in a chromosome of the *Listeria* strain. In another embodiment, the metabolic gene, virulence gene, etc. is lacking in the chromosome and in any episomal genetic element of the *Listeria* strain. In another embodiment, the metabolic gene, virulence gene, etc. is lacking in the genome of the virulence strain. In one embodiment, the virulence gene is mutated in the chromosome. In another embodiment, the virulence gene is deleted from the chromosome. Each possibility represents a separate embodiment of the present invention.

In one embodiment, in order to select for an auxotrophic bacteria comprising a plasmid encoding a metabolic enzyme or a complementing gene provided herein, transformed auxotrophic bacteria are grown on a media that will select for expression of the amino acid metabolism gene or the complementing gene. In another embodiment, a bacteria auxotrophic for D-glutamic acid synthesis is transformed with a plasmid comprising a gene for D-glutamic acid synthesis, and the auxotrophic bacteria will grow in the absence of D-glutamic acid, whereas auxotrophic bacteria that have not been transformed with the plasmid, or are not expressing the plasmid encoding a protein for D-glutamic acid synthesis, will not grow. In another embodiment, a bacterium auxotrophic for D-alanine synthesis will grow in the absence of D-alanine when transformed and expressing the plasmid of the present invention if the plasmid comprises an isolated nucleic acid encoding an amino acid metabolism enzyme for D-alanine synthesis. Such methods for making appropriate media comprising or lacking necessary growth factors, supplements, amino acids, vitamins, antibiotics, and the like are well known in the art, and are available commercially (Becton-Dickinson, Franklin Lakes, N.J.). Each method represents a separate embodiment of the present invention.

In another embodiment, once an auxotrophic bacteria comprising the plasmid of the present invention have been selected on appropriate media, the bacteria are propagated in the presence of a selective pressure. Such propagation comprises growing the bacteria in media without the auxotrophic factor. The presence of the plasmid expressing an amino acid metabolism enzyme in the auxotrophic bacteria ensures that the plasmid will replicate along with the bacteria, thus continually selecting for bacteria harboring the plasmid. The skilled artisan, when equipped with the present disclosure and methods herein will be readily able to scale-up the production of the *Listeria* vaccine vector by adjusting the volume of the media in which the auxotrophic bacteria comprising the plasmid are growing.

The skilled artisan will appreciate that, in another embodiment, other auxotroph strains and complementation systems are adopted for the use with this invention.

In another embodiment, the construct or nucleic acid molecule provided herein is integrated into the Listerial chromosome using homologous recombination. Techniques for homologous recombination are well known in the art, and are described, for example, in Baloglu S, Boyle S M, et al. (Immune responses of mice to vaccinia virus recombinants expressing either *Listeria monocytogenes* partial listeriolysin or *Brucella abortus* ribosomal L7/L12 protein. Vet Microbiol 2005, 109(1-2): 11-7); and Jiang L L, Song H H, et al., (Characterization of a mutant *Listeria monocytogenes* strain expressing green fluorescent protein. Acta Biochim Biophys Sin (Shanghai) 2005, 37(1): 19-24). In another embodiment, homologous recombination is performed as described in U.S. Pat. No. 6,855,320. In this case, a recombinant Lm strain that expresses E7 was made by chromosomal integration of the E7 gene under the control of the hly promoter and with the inclusion of the hly signal sequence to ensure secretion of the gene product, yielding the recombinant referred to as Lm-AZ/E7. In another embodiment, a temperature sensitive plasmid is used to select the recombinants. Each technique represents a separate embodiment of the present invention.

In another embodiment, the construct or nucleic acid molecule is integrated into the Listerial chromosome using transposon insertion. Techniques for transposon insertion are well known in the art, and are described, inter alia, by Sun et al. (Infection and Immunity 1990, 58: 3770-3778) in the construction of DP-L967. Transposon mutagenesis has the advantage, in another embodiment, that a stable genomic insertion mutant can be formed but the disadvantage that the position in the genome where the foreign gene has been inserted is unknown.

In another embodiment, the construct or nucleic acid molecule is integrated into the Listerial chromosome using phage integration sites (Lauer P, Chow M Y et al, Construction, characterization, and use of two *Listeria monocytogenes* site-specific phage integration vectors. J Bacteriol 2002; 184(15): 4177-86). In certain embodiments of this method, an integrase gene and attachment site of a bacteriophage (e.g. U153 or PSA listeriophage) is used to insert the heterologous gene into the corresponding attachment site, which may be any appropriate site in the genome (e.g. comK or the 3' end of the arg tRNA gene). In another embodiment, endogenous prophages are cured from the attachment site utilized prior to integration of the construct or heterologous gene. In another embodiment, this method results in single-copy integrants. In another embodiment, the present invention further comprises a phage based chromosomal integration system for clinical applications, where a host strain that is auxotrophic for essential enzymes, including, but not limited to, d-alanine racemase can be used, for example Lmdal(−) dat(−). In another embodiment, in order to avoid a "phage curing step," a phage integration system based on PSA is used. This requires, in another embodiment, continuous selection by antibiotics to maintain the integrated gene. Thus, in another embodiment, the current invention enables the establishment of a phage based chromosomal integration system that does not require selection with antibiotics. Instead, an auxotrophic host strain can be complemented. Each possibility represents a separate embodiment of the present invention.

A "phage expression vector" or "phagemid" refers to any phage-based recombinant expression system for the purpose of expressing a nucleic acid sequence of the methods and compositions as provided herein in vitro or in vivo, constitutively or inducibly, in any cell, including prokaryotic, yeast, fungal, plant, insect or mammalian cell. A phage expression vector typically can both reproduce in a bacterial cell and, under proper conditions, produce phage particles. The term includes linear or circular expression systems and encompasses both phage-based expression vectors that remain episomal or integrate into the host cell genome.

In another embodiment, the construct or nucleic acid molecule is expressed from an episomal or plasmid vector, with an endogenous nucleic acid sequence encoding an LLO, PEST or ActA sequence or fragments thereof. In another embodiment, the plasmid is stably maintained in the recombinant *Listeria* vaccine strain in the absence of antibiotic selection. In another embodiment, the plasmid does not confer antibiotic resistance upon the recombinant *Listeria*. In another embodiment, the fragment is a functional fragment. In another embodiment, the fragment is an immunogenic fragment. In another embodiment, the construct or nucleic acid molecule comprises a first and at least a second open reading frame each encoding a first and at least a second polypeptide, wherein the first and the second polypeptide each comprise a heterologous antigen or a functional fragment thereof fused to a PEST-containing polypeptide.

In one embodiment, an "open reading frame" or "ORF" is a portion of an organism's genome which contains a sequence of bases that could potentially encode a protein. In another embodiment, the start and stop ends of the ORF are not equivalent to the ends of the mRNA, but they are usually contained within the mRNA. In one embodiment, ORFs are located between the start-code sequence (initiation codon) and the stop-codon sequence (termination codon) of a gene. Thus, in one embodiment, a nucleic acid molecule operably integrated into a genome as an open reading frame with an endogenous polypeptide is a nucleic acid molecule that has integrated into a genome in the same open reading frame as an endogenous polypeptide.

"Stably maintained" refers, in another embodiment, to maintenance of a nucleic acid molecule or plasmid in the absence of selection (e.g. antibiotic selection) for 10 generations, without detectable loss. In another embodiment, the period is 15 generations. In another embodiment, the period is 20 generations. In another embodiment, the period is 25 generations. In another embodiment, the period is 30 generations. In another embodiment, the period is 40 generations. In another embodiment, the period is 50 generations. In another embodiment, the period is 60 generations. In another embodiment, the period is 80 generations. In another embodiment, the period is 100 generations. In another embodiment, the period is 150 generations. In another embodiment, the period is 200 generations. In another embodiment, the period is 300 generations. In another embodiment, the period is 500 generations. In another embodiment, the period is more than generations. In another embodiment, the nucleic acid molecule or plasmid is maintained stably in vitro (e.g. in culture). In another embodiment, the nucleic acid molecule or plasmid is maintained stably in vivo. In another embodiment, the nucleic acid molecule or plasmid is maintained stably both in vitro and in vitro. Each possibility represents a separate embodiment of the present invention.

In another embodiment, a "functional fragment" is an immunogenic fragment capable of eliciting an immune response when administered to a subject alone or in a vaccine or composition provided herein. In another embodiment, a functional fragment has biological activity as will be understood by a skilled artisan and as further provided herein.

In other embodiments, an antigen provided herein is associated with one of the following diseases; cholera, diphtheria, *Haemophilus*, hepatitis A, hepatitis B, influenza, measles, meningitis, mumps, pertussis, small pox, pneumococcal pneumonia, polio, rabies, rubella, tetanus, tuberculosis, typhoid, Varicella-zoster, whooping cough, yellow fever, the immunogens and antigens from Addison's disease, allergies, anaphylaxis, Bruton's syndrome, cancer, including solid and blood borne tumors, eczema, Hashimoto's thyroiditis, polymyositis, dermatomyositis, type 1 diabetes mellitus, acquired immune deficiency syndrome, transplant rejection, such as kidney, heart, pancreas, lung, bone, and liver transplants, Graves' disease, polyendocrine autoimmune disease, hepatitis, microscopic polyarteritis, polyarteritis *nodosa*, pemphigus, primary biliary cirrhosis, pernicious anemia, coeliac disease, antibody-mediated nephritis, glomerulonephritis, rheumatic diseases, systemic lupus erthematosus, rheumatoid arthritis, seronegative spondylarthritides, rhinitis, sjogren's syndrome, systemic sclerosis, sclerosing cholangitis, Wegener's granulomatosis, dermatitis herpetiformis, psoriasis, vitiligo, multiple sclerosis, encephalomyelitis, Guillain-Barre syndrome, myasthenia gravis, Lambert-Eaton syndrome, sclera, episclera, uveitis, chronic mucocutaneous candidiasis, urticaria, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutropenia, Waldenstrom's macroglobulinemia, amyloidosis, chronic lymphocytic leukemia, non-Hodgkin's lymphoma, malarial circumsporozite protein, microbial antigens, viral antigens, autoantigens, and listeriosis.

In one embodiment, a disease provided herein is an infectious disease. In one embodiment, an infectious disease is one caused by, but not limited to, any one of the following pathogens: BCG/Tuberculosis, Malaria, *Plasmodium falciparum, plasmodium malariae, plasmodium vivax*, Rotavirus, Cholera, Diptheria-Tetanus, Pertussis, *Haemophilus influenzae*, Hepatitis B, Human papilloma virus, Influenza seasonal), Influenza A (H1N1) Pandemic, Measles and Rubella, Mumps, Meningococcus A+C, Oral Polio Vaccines, mono, bi and trivalent, Pneumococcal, Rabies, Tetanus Toxoid, Yellow Fever, *Bacillus anthracis* (anthrax), *Clostridium botulinum* toxin (botulism), *Yersinia pestis* (plague), Variola major (smallpox) and other related pox viruses, *Francisella tularensis* (tularemia), Viral hemorrhagic fevers, Arenaviruses (LCM, Junin virus, Machupo virus, Guanarito virus, Lassa Fever), Bunyaviruses (Hantaviruses, Rift Valley Fever), Flaviruses (Dengue), Filoviruses (Ebola, Marburg), *Burkholderia pseudomallei, Coxiella burnetii* (Q fever), *Brucella* species (brucellosis), *Burkholderia mallei* (glanders), *Chlamydia psittaci* (Psittacosis), Ricin toxin (from *Ricinus communis*), Epsilon toxin of *Clostridium perfringens, Staphylococcus* enterotoxin B, Typhus fever (*Rickettsia prowazekii*), other Rickettsias, Food- and Waterborne Pathogens, Bacteria (Diarrheagenic *E. coli*, Pathogenic Vibrios, *Shigella* species, *Salmonella* BCG/, *Campylobacter jejuni, Yersinia enterocolitica*), Viruses (Caliciviruses, Hepatitis A, West Nile Virus, LaCrosse, Calif. encephalitis, VEE, EEE, WEE, Japanese Encephalitis Virus, Kyasanur Forest Virus, Nipah virus, hantaviruses, Tickborne hemorrhagic fever viruses, Chikungunya virus, Crimean-Congo Hemorrhagic fever virus, Tickborne encephalitis viruses, Hepatitis B virus, Hepatitis C virus, Herpes Simplex virus (HSV), Human immunodeficiency virus (HIV), Human papillomavirus (HPV)), Protozoa (*Cryptosporidium parvum, Cyclospora cayatanensis, Giardia lamblia, Entamoeba histolytica, Toxoplasma*), Fungi (Microsporidia), Yellow fever, Tuberculosis, including drug-resistant TB, Rabies, Prions, Severe acute respiratory syndrome associated coronavirus (SARS-CoV), *Coccidioides posadasii, Coccidioides immitis, Bacterial vaginosis, Chlamydia trachomatis*, Cytomegalovirus, Granuloma inguinale, Hemophilus *ducreyi, Neisseria gonorrhea, Treponema pallidum, Trichomonas vaginalis*, or any other infectious disease known in the art that is not listed herein.

In another embodiment, an infectious disease is a livestock infectious disease. In another embodiment, livestock diseases can be transmitted to man and are called "zoonotic diseases." In another embodiment, these diseases include, but are not limited to, Foot and mouth disease, West Nile Virus, rabies, canine parvovirus, feline leukemia virus, equine influenza virus, infectious bovine rhinotracheitis (IBR), pseudorabies, classical swine fever (CSF), IBR, caused by bovine herpesvirus type 1 (BHV-1) infection of cattle, and pseudorabies (Aujeszky's disease) in pigs, toxoplasmosis, anthrax, vesicular stomatitis virus, *rhodococcus equi*, Tularemia, Plague (*Yersinia pestis*), *trichomonas*.

In another embodiment, a disease provided herein is a respiratory or inflammatory disease. In another embodiment, the respiratory or inflammatory disease is chronic obstructive pulmonary disease (COPD). In another embodiment, the disease is asthma.

In one embodiment, live attenuated *Listeria* strains are capable of alleviating asthma symptoms without co-administration of other therapeutic agents, such as anti-inflammatory agents or bronchodilators. In another embodiment, the methods provided herein further comprise the step of co-administering to a subject the live attenuated *Listeria* strain and one or more therapeutic agents. In another embodiment, the therapeutic agent is an anti-asthmatic agent. In another embodiment, the agent is an anti-inflammatory agent, a non-steroidal anti-inflammatory agent, an antibiotic, an anti-chlolinerginc agent, a bronchodilator, a corticosteroid, a short-acting beta-agonist, a long-acting beta-agonist, combination inhalers, an antihistamine, or combinations thereof.

In one embodiment, a disease provided herein is a cancer or a tumor. In one embodiment, the cancer treated by a method of the present invention is breast cancer. In another embodiment, the cancer is a cervical cancer. In another embodiment, the cancer is a HER2 containing cancer. In another embodiment, the cancer is a melanoma. In another embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, it is a glioblastoma multiforme. In another embodiment, it is a mesothelioma. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is non-smallcell lung carcinoma. In another embodiment, the cancer is an endometrial carcinoma. In another embodiment, the cancer is a bladder cancer. In another embodiment, the cancer is a head and neck cancer. In another embodiment, the cancer is a prostate carcinoma. In another embodiment, the cancer is oropharyngeal cancer. In another embodiment, the cancer is lung cancer. In another embodiment, the cancer is anal cancer. In another embodiment, the cancer is colorectal cancer. In another embodiment, the cancer is esophageal cancer. Each possibility represents a separate embodiment of the present invention.

In one embodiment, a tumor marker provided herein is a heterologous tumor antigen, which is also referred to herein as "tumor antigen" "antigenic polypeptide," or "antigen." In another embodiment, the antigen is Human Papilloma Virus-E7 (HPV-E7) antigen, which in one embodiment, is from HPV16 (in one embodiment, GenBank Accession No. AAD33253) and in another embodiment, from HPV18 (in one embodiment, GenBank Accession No. P06788). In another embodiment, the antigenic polypeptide is HPV-E6, which in one embodiment, is from HPV16 (in one embodiment, GenBank Accession No. AAD33252, AAM51854, AAM51853, or AAB67615) and in another embodiment, from HPV18 (in one embodiment, GenBank Accession No. P06463). In another embodiment, the antigenic polypeptide is a Her/2-neu antigen. In another embodiment, the antigenic polypeptide is Prostate Specific Antigen (PSA) (in one embodiment, GenBank Accession No. CAD30844, CAD54617, AAA58802, or NP_001639). In another embodiment, the antigenic polypeptide is Stratum Corneum Chymotryptic Enzyme (SCCE) antigen (in one embodiment, GenBank Accession No. AAK69652, AAK69624, AAG33360, AAF01139, or AAC37551). In another embodiment, the antigenic polypeptide is Wilms tumor antigen 1, which in another embodiment is WT-1 Telomerase (GenBank Accession. No. P49952, P22561, NP_659032, CAC39220.2, or EAW68222.1). In another embodiment, the antigenic polypeptide is hTERT or Telomerase (GenBank Accession. No. NM003219 (variant 1), NM198255 (variant 2), NM 198253 (variant 3), or NM 198254 (variant 4). In another embodiment, the antigenic polypeptide is Proteinase 3 (in one embodiment, GenBank Accession No. M29142, M75154, M96839, X55668, NM 00277, M96628 or X56606). In another embodiment, the antigenic polypeptide is Tyrosinase Related Protein 2 (TRP2) (in one embodiment, GenBank Accession No. NP_001913, ABI73976, AAP33051, or Q95119). In another embodiment, the antigenic polypeptide is High Molecular Weight Melanoma Associated Antigen (HMW-MAA) (in one embodiment, GenBank Accession No. NP_001888, AAI28111, or AAQ62842). In another embodiment, the antigenic polypeptide is Testisin (in one embodiment, GenBank Accession No. AAF79020, AAF79019, AAG02255, AAK29360, AAD41588, or NP_659206). In another embodiment, the antigenic polypeptide is NY-ESO-1 antigen (in one embodiment, GenBank Accession No. CAA05908, P78358, AAB49693, or NP_640343). In another embodiment, the antigenic polypeptide is PSCA (in one embodiment, GenBank Accession No. AAH65183, NP_005663, NP_082492, 043653, or CAB97347). In another embodiment, the antigenic polypeptide is Interleukin (IL) 13 Receptor alpha (in one embodiment, GenBank Accession No. NP_000631, NP_001551, NP_032382, NP_598751, NP_001003075, or NP_999506). In another embodiment, the antigenic polypeptide is Carbonic anhydrase IX (CAIX) (in one embodiment, GenBank Accession No. CAI13455, CAI10985, EAW58359, NP_001207, NP_647466, or NP_001101426). In another embodiment, the antigenic polypeptide is carcinoembryonic antigen (CEA) (in one embodiment, GenBank Accession No. AAA66186, CAA79884, CAA66955, AAA51966, AAD15250, or AAA51970.). In another embodiment, the antigenic polypeptide is MAGE-A (in one embodiment, GenBank Accession No. NP_786885, NP_786884, NP_005352, NP_004979, NP_005358, or NP 005353). In another embodiment, the antigenic polypeptide is survivin (in one embodiment, GenBank Accession No. AAC51660, AAY15202, ABF60110, NP_001003019, or NP 001082350). In another embodiment, the antigenic polypeptide is GP100 (in one embodiment, GenBank Accession No. AAC60634, YP_655861, or AAB31176). In another embodiment, the antigenic polypeptide is any other antigenic polypeptide known in the art. In another embodiment, the antigenic peptide of the compositions and methods of the present invention comprise an immunogenic portion of the antigenic polypeptide. Each possibility represents a separate embodiment of the present invention.

In another embodiment, an antigen provided herein is HPV-E6. In another embodiment, the antigen is telomerase (TERT). In another embodiment, the antigen is LMP-1. In another embodiment, the antigen is p53. In another embodiment, the antigen is mesothelin. In another embodiment, the antigen is EGFRVIII. In another embodiment, the antigen is carboxic anhydrase IX (CAIX). In another embodiment, the antigen is PSMA. In another embodiment, the antigen is HMW-MAA. In another embodiment, the antigen is HIV-1 Gag. In another embodiment, the antigen is Tyrosinase related protein 2. In another embodiment, the antigen is selected from HPV-E7, HPV-E6, Her-2, HIV-1 Gag, LMP-1, p53, PSMA, carcinoembryonic antigen (CEA), LMP-1, kallikrein-related peptidase 3 (KLK3), KLK9, Muc, Tyrosinase related protein 2, Muc 1, FAP, IL-13R alpha 2, PSA (prostate-specific antigen), MAGE-1, MAGE-3, gp-100, heat-shock protein 70 (HSP-70), beta-HCG, EGFR-III, VEGFR2, Granulocyte colony-stimulating factor (G-CSF), Angiogenin, Angiopoietin-1, Del-1, Fibroblast growth factors: acidic (aFGF) or basic (bFGF), Follistatin, Granulocyte colony-stimulating factor (G-CSF), Hepatocyte growth factor (HGF)/scatter factor (SF), Interleukin-8 (IL-8), Leptin, Midkine, Placental growth factor, Platelet-derived endothelial cell growth factor (PD-ECGF), Platelet-derived growth factor-BB (PDGF-BB), Pleiotrophin (PTN), Progranulin, Proliferin, Transforming growth factor-alpha (TGF-alpha), Transforming growth factor-beta (TGF-beta), Tumor necrosis factor-alpha (TNF-alpha), Vascular endothelial growth factor (VEGF)/vascular permeability factor (VPF), VEGFR, VEGFR2 (KDR/FLK-1) or a fragment thereof, FLK-1 or an epitope thereof, FLK-E1, FLK-E2, FLK-I1, endoglin or a fragment thereof, Neuropilin 1 (NRP-1), Angiopoietin 1 (Ang1), Tie2, Platelet-derived growth factor (PDGF), Platelet-derived growth factor receptor (PDGFR), Transforming growth factor-beta (TGF-β), endoglin, TGF-β receptors, monocyte chemotactic protein-1 (MCP-1), VE-cadherin, CD31, ephrin, ICAM-1, V-CAM-1, VAP-1, E-selectin, plasminogen activators, plasminogen activator inhibitor-1, Nitric oxide synthase (NOS), COX-2, AC133, or Id1/Id3, Angiopoietin 3, Angiopoietin 4, Angiopoietin 6, CD105, EDG, HHT1, ORW, ORW1 or a TGFbeta co-receptor, or a combination thereof. The use of fragments of antigens provided herein is also encompassed by the present invention.

In another embodiment, a heterologous antigen provided herein is a tumor-associated antigen, which in one embodiment, is one of the following tumor antigens: a MAGE (Melanoma-Associated Antigen E) protein, e.g. MAGE 1, MAGE 2, MAGE 3, MAGE 4, a tyrosinase; a mutant ras protein; a mutant p53 protein; p97 melanoma antigen, a ras peptide or p53 peptide associated with advanced cancers; the HPV 16/18 antigens associated with cervical cancers, KLH antigen associated with breast carcinoma, CEA (carcinoembryonic antigen) associated with colorectal cancer, a MART1 antigen associated with melanoma, or the PSA antigen associated with prostate cancer. In another embodiment, the antigen for the compositions and methods provided herein are melanoma-associated antigens, which in one embodiment are TRP-2, MAGE-1, MAGE-3, gp-100, tyrosinase, HSP-70, beta-HCG, or a combination thereof. In one embodiment, the antigen is a chimeric Her2 antigen described in US patent application publication US2011/0142791, which is hereby incorporated by reference herein in its entirety.

It is to be understood that a skilled artisan will be able to use any heterologous antigen not mentioned herein but known in the art for use in the methods and compositions provided herein.

In other embodiments, an antigen is derived from a fungal pathogen, bacteria, parasite, helminth, or viruses. In other embodiments, the antigen is selected from tetanus toxoid, hemagglutinin molecules from influenza virus, diphtheria toxoid, HIV gp120, HIV gag protein, IgA protease, insulin peptide B, *Spongospora subterranea* antigen, vibriose antigens, *Salmonella* antigens, pneumococcus antigens, respiratory syncytial virus antigens, *Haemophilus* influenza outer membrane proteins, *Helicobacter pylori* urease, *Neisseria meningitidis* pilins, *N. gonorrhoeae* pilins, the melanoma-associated antigens (TRP-2, MAGE-1, MAGE-3, gp-100, tyrosinase, MART-1, HSP-70, beta-HCG), human papilloma virus antigens E1 and E2 from type HPV-16, -18, -31, -33, -35 or -45 human papilloma viruses, the tumor antigens CEA, the ras protein, mutated or otherwise, the p53 protein, mutated or otherwise, Mucl, mesothelin, EGFRVIII or pSA.

In one embodiment, an angiogenic factor for use in the compositions and methods of the present invention is VEGFR2.

In one embodiment, vascular endothelial growth factor (VEGF) is an important signaling protein involved in both vasculogenesis (the formation of the embryonic circulatory system) and angiogenesis (the growth of blood vessels from pre-existing vasculature). In one embodiment, VEGF activity is restricted mainly to cells of the vascular endothelium, although it does have effects on a limited number of other cell types (e.g. stimulation monocyte/macrophage migration). In vitro, VEGF has been shown to stimulate endothelial cell mitogenesis and cell migration. VEGF also enhances microvascular permeability and is sometimes referred to as vascular permeability factor.

In one embodiment, all of the members of the VEGF family stimulate cellular responses by binding to tyrosine kinase receptors (the VEGFRs) on the cell surface, causing them to dimerize and become activated through transphosphorylation. The VEGF receptors have an extracellular portion consisting of 7 immunoglobulin-like domains, a single transmembrane spanning region and an intracellular portion containing a split tyrosine-kinase domain.

In one embodiment, VEGF-A is a VEGFR-2 (KDR/Flk-1) ligand as well as a VEGFR-1 (Flt-1) ligand. In one embodiment, VEGFR-mediates almost all of the known cellular responses to VEGF. The function of VEGFR-1 is less well defined, although it is thought to modulate VEGFR-2 signaling, in one embodiment, via sequestration of VEGF from VEGFR-2 binding, which in one embodiment, is particularly important during vasculogenesis in the embryo. In one embodiment, VEGF-C and VEGF-D are ligands of the VEGFR-3 receptor, which in one embodiment, mediates lymphangiogenesis.

In one embodiment, a recombinant *Listeria* of the present invention express a VEGF receptor or a fragment thereof, which in one embodiment, is a VEGFR-2 and, in another embodiment, a VEGFR-1, and, in another embodiment, VEGFR-3.

In one embodiment, vascular Endothelial Growth Factor Receptor 2 (VEGFR2) is highly expressed on activated endothelial cells (ECs) and participates in the formation of new blood vessels. In one embodiment, VEGFR2 binds all 5 isoforms of VEGF. In one embodiment, signaling of VEGF through VEGFR2 on ECs induces proliferation, migration, and eventual differentiation. In one embodiment, the mouse homologue of VEGFR2 is the fetal liver kinase gene-1 (Flk-1), which is a strong therapeutic target, and has important roles in tumor growth, invasion, and metastasis. In one embodiment, VEGFR2 is also referred to as kinase insert domain receptor (a type III receptor tyrosine kinase) (KDR), cluster of differentiation 309 (CD309), FLK1, Ly73, Krd-1, VEGFR, VEGFR-2, or 6130401C07.

In another embodiment, the VEGFR2 protein used in the compositions of the present invention has the following sequence:

MESKALLAVALWFCVETRAASVGLPGDFLHPPKLSTQKDILTILANTT
LQITCRGQRDLDWLWPNAQRDSEERVLVTECGGGDSIFCKTLTIPRVV
GNDTGAYKCSYRDVDIASTVYVYVRDYRSPFIASVSDQHGIVYITENK
NKTVVIPCRGSISNLNVSLCARYPEKRFVPDGNRISWDSEIGFTLPSY
MISYAGMVFCEAKINDETYQSIMYIVVVVGYRIYDVILSPPHEIELSA
GEKLVLNCTARTELNVGLDFTWHSPPSKSHHKKIVNRDVKPFPGTVAK
MFLSTLTIESVTKSDQGEYTCVASSGRMIKRNRTFVRVHTKPFIAFGS
GMKSLVEATVGSQVRIPVKYLSYPAPDIKWYRNGRPIESNYTMIVGDE
LTIMEVTERDAGNYTVILTNPISMEKQSHMVSLVVNVPPQIGEKALIS
PMDSYQYGTMQTLTCTVYANPPLHHIQWYWQLEEACSYRPGQTSPYAC
KEWRHVEDFQGGNKIEVTKNQYALIEGKNKTVSTLVIQAANVSALYKC
EAINKAGRGERVISFHVIRGPEITVQPAAQPTEQESVSLLCTADRNTF
ENLTWYKLGSQATSVHMGESLTPVCKNLDALWKLNGTMFSNSTNDILI
VAFQNASLQDQGDYVCSAQDKKTKKRHCLVKQLIILERMAPMITGNLE
NQTTTIGETIEVTPASGNPTPHITWFKDNETLVEDSGIVLRDGNRNLT
IRRVRKEDGGLYTCQACNVLGCARAETLFIIEGAQEKTNLEVIILVGT
AVIAMFFWLLLVIVLRTVKRANEGELKTGYLSIVMDPDELPLDERCER
LPYDASKWEFPRDRLKLGKPLGRGAFGQVIEADAFGIDKTATCKTVAV
KMLKEGATHSEHRALMSELKILIHIGHHLNVVNLLGACTKPGGPLMVI
VEFCKFGNLSTYLRGKRNEFVPYKSKGARFRQGKDYVGELSVDLKRRL
DSITSSQSSASSGFVEEKSLSDVEEEEASEELYKDFLTLEHLICYSFQ
VAKGMEFLASRKCIHRDLAARNILLSEKNVVKICDFGLARDIYKDPDY
VRKGDARLPLKWMAPETIFDRVYTIQSDVWSFGVLLWEIFSLGASPYP
GVKIDEEFCRRLKEGTRMRAPDYTTPEMYQTMLDCWHEDPNQRPSFSE

-continued

```
LVEHLGNLLQANAQQDGKDYIVLPMSETLSMEEDSGLSLPTSPVSCME

EEEVCDPKFHYDNTAGISHYLQNSKRKSRPVSVKTFEDIPLEEPEVKV

IPDDSQTDSGMVLASEELKTLEDRNKLSPSFGGMMPSKSRESVASEGS

NQTSGYQSGYHSDDTDTTVYSSDEAGLLKMVDAAVHADSGTTLRSPPV
```

(GenBank Accession No. NP_034742.2, AAH20530.1, or EDL37891.1; SEQ ID NO: 137; the nucleic acid sequence is set forth in GenBank Accession No. NM_010612.2 or BC020530.1). In one embodiment, AA 68-277 corresponds to E1 described herein, AA 545-730 corresponds to E2 described herein, and AA 792-1081 corresponds to I1 described herein. In another embodiment, the above sequence is used as the source of the VEGFR2 fragment incorporated in a vaccine of the present invention. In another embodiment, a VEGFR2 AA sequence of methods and compositions of the present invention is a homologue of SEQ ID NO: 137. In another embodiment, the VEGFR2 AA sequence is a variant of SEQ ID NO: 137. In another embodiment, the VEGFR2 AA sequence is a fragment of SEQ ID NO: 137. In another embodiment, the VEGFR2 AA sequence is an isoform of SEQ ID NO: 137. Each possibility represents a separate embodiment of the present invention.

In another embodiment, the VEGFR2 has an amino acid sequence set forth in one of the following GenBank entries: EDL37891.1; CAA61917.1; BAC27532.1; BAE24892.1; AAH20530.1; AAB25043.1; CAA42040.1; or CAA50192.1. In another embodiment, the VEGFR2 has an amino acid sequence set forth in one of the following GenBank entries: EAX05462.1; EAX05463.1; EAX05464.1; CAA61916.1; BAD93138.1; AAB88005.1; AAC16450.1; BAG57114.1; AAI31823.1; ACF47599.1; AAA59459.1; or CAA43837.1. In another embodiment, the VEGFR2 has an amino acid sequence set forth in one of the following GenBank entries: EDL89914.1; EDL89915.1; EDL89916.1; AAH87029.1; AAB97508.1; or AAB97509.1. In another embodiment, the VEGFR2 has an amino acid sequence set forth in one of the following GenBank entries: CAQ13438.1; AAF03237.1; AAN47136.1; AAL16381.1; AAI29159.1; CAM73177.1; AAB18415.1; AAB41042.1; or AAB62405.1. In another embodiment, the VEGFR2 has any VEGFR2 amino acid sequence known in the art. In another embodiment, the VEGFR2 is a homologue of a sequence from one of the above GenBank entries. In another embodiment, the VEGFR2 is a variant of a sequence from one of the above GenBank entries. In another embodiment, the VEGFR2 is an isoform of a sequence from one of the above GenBank entries. In another embodiment, the VEGFR2 is a fragment of a sequence from one of the above GenBank entries. Each possibility represents a separate embodiment of the present invention.

In another embodiment, the VEGFR2 has a nucleic acid sequence set forth in one of the following GenBank entries: AC124615.11; AC134903.4; AC160723.2; AF061804.1; AF153058.1; CH466524.1; X89777.1; AK031739.1; AK054510.1; AK141938.1; BCO20530.1; 553103.1; X59397.1; or X70842.1. In another embodiment, the VEGFR2 has a nucleic acid sequence set forth in one of the following GenBank entries: ACO21220.7; AC111194.4; CH471057.1; EAX05463.1; EAX05464.1; X89776.1; AB209901.1; AF035121.1; AF063658.1; AK293668.1; BC131822.1; BP280621.1; CR606055.1; EU826563.1; L04947.1; or X61656.1. In another embodiment, the VEGFR2 has a nucleic acid sequence set forth in one of the following GenBank entries: CH473981.1; BC087029.1; U93306.1; or U93307.1. In another embodiment, the VEGFR2 has a nucleic acid sequence set forth in one of the following GenBank entries: AL935131.7; BX247946.6; CR759732.9; AF180354.1; AF487829.1; AY056466.1; BC129158.1; CU458916.1; U75995.1; U82383.1; U89515.1 In another embodiment, the VEGFR2 has any VEGFR2 nucleic acid sequence known in the art. In another embodiment, the VEGFR2 is a homologue of a sequence from one of the above GenBank entries. In another embodiment, the VEGFR2 is a variant of a sequence from one of the above GenBank entries. In another embodiment, the VEGFR2 is an isoform of a sequence from one of the above GenBank entries. In another embodiment, the VEGFR2 is a fragment of a sequence from one of the above GenBank entries. Each possibility represents a separate embodiment of the present invention.

In another embodiment, a VEGFR2 polypeptide fragment is utilized in compositions and methods of the present invention. In another embodiment, the VEGFR2 fragment comprises amino acids 68-277 of the VEGFR2 protein, which in one embodiment, is referred to as Flk1-E1. In another embodiment, the VEGFR2 polypeptide fragment has the sequence:

RDSEERVLVTECGGGDSIFCKTLTIPRVVGNDT-GAYKCSYRDVDIASTVYVYVRDYRSPFIASVSDQH-GIVYITENKNKTVVIPCRGSISNLNVSLCARY-PEKRFVPDGNRISWDSEIGFTLPSYMISYAGMVF-CEAKINDETYQSIMYIVVVVGYRIYDVILSPPHEIEL-SAGEKLVLNCTARTELNVGLDFTWHSPPSKSHHK-KIVNR (SEQ ID NO: 138). In another embodiment, a VEGFR2 AA sequence of methods and compositions of the present invention comprises the sequence set forth in SEQ ID NO: 138. In another embodiment, the VEGFR2 AA sequence is a homologue of SEQ ID NO: 138. In another embodiment, the VEGFR2 AA sequence is a variant of SEQ ID NO: 138. In another embodiment, the VEGFR2 AA sequence is a fragment of SEQ ID NO: 138. In another embodiment, the VEGFR2 AA sequence is an isoform of SEQ ID NO: 138. Each possibility represents a separate embodiment of the present invention.

In another embodiment, the VEGFR2 fragment comprises amino acids 545-730 of the VEGFR2 protein, which in one embodiment, is referred to as Flk1-E2. In another embodiment, the VEGFR2 polypeptide fragment has the sequence:

VIRGPEITVQPAAQPTEQESVSLLCTADRNTFEN-LTWYKLGSQATSVHMGESLTPVCKNLDALWKLNGT-MFSNSTNDILIVAFQNASLQDQGDYVCSAQDKKTK-KRHCLVKQLIILERMAPMITGNLENQTTTIGETIEVT-CPASGNPTPHITWFKDNETLVEDSGIVLRDGNRN-LTIRRVRKEDG (SEQ ID NO: 139). In another embodiment, a VEGFR2 AA sequence of methods and compositions of the present invention comprises the sequence set forth in SEQ ID NO: 139. In another embodiment, the VEGFR2 AA sequence is a homologue of SEQ ID NO: 139. In another embodiment, the VEGFR2 AA sequence is a variant of SEQ ID NO: 139. In another embodiment, the VEGFR2 AA sequence is a fragment of SEQ ID NO: 139. In another embodiment, the VEGFR2 AA sequence is an isoform of SEQ ID NO: 139. Each possibility represents a separate embodiment of the present invention.

In another embodiment, the VEGFR2 fragment comprises amino acids 792-1081 of the VEGFR2 protein, which in one embodiment, is referred to as Flk1-I1. In another embodiment, the VEGFR2 polypeptide fragment has the sequence:

EGELKTGYLSIVMDPDELPLDERCERLPYDASK-WEFPRDRLKLGKPLGRGAFGQVIEADAFGIDK-TATCKTVAVKMLKEGATHSEHRALMSELKILIHIGH-

HLNVVNLLGACTKPGGPLMVIVEFCKFGNLSTYLRG-KRNEFVPYKSKGARFRQGKDYVGELSVDLKRRLD-SITSSQSSASSGFVEEKSLSDVEEEEASEELYKD-FLTLEHLICYSFQVAKGMEFLASRKCIHRDLAAR-NILLSEKNVVKICDFGLARDIYKDPDYVRKGDARLP-LKWMAPETIFDRVYT (SEQ ID NO: 140). In another embodiment, a VEGFR2 AA sequence of methods and compositions of the present invention comprises the sequence set forth in SEQ ID NO: 140. In another embodiment, the VEGFR2 AA sequence is a homologue of SEQ ID NO: 140. In another embodiment, the VEGFR2 AA sequence is a variant of SEQ ID NO: 140. In another embodiment, the VEGFR2 AA sequence is a fragment of SEQ ID NO: 140. In another embodiment, the VEGFR2 AA sequence is an isoform of SEQ ID NO: 140. Each possibility represents a separate embodiment of the present invention.

In another embodiment, the VEGFR2 fragment comprises amino acids 1082-1237 of the VEGFR2 protein, which in one embodiment, is referred to as Flk1-I2. In another embodiment, the VEGFR2 polypeptide fragment has the sequence:

IQSDVWSFGVLLWEIFSLGASPYPGVKIDEEFCR-RLKEGTRMRAPDYTTPEMYQTMLDCWHEDPN-QRPSFSELVEHLGNLLQANAQQDGKDYIVLPM-SETLSMEEDSGLSLPTSPVSCMEEEEVCDPKFHYD-NTAGISHYLQNSKRKSRPVSVKTF (SEQ ID NO: 141). In another embodiment, a VEGFR2 AA sequence of methods and compositions of the present invention comprises the sequence set forth in SEQ ID NO: 141. In another embodiment, the VEGFR2 AA sequence is a homologue of SEQ ID NO: 141. In another embodiment, the VEGFR2 AA sequence is a variant of SEQ ID NO: 141. In another embodiment, the VEGFR2 AA sequence is a fragment of SEQ ID NO: 141. In another embodiment, the VEGFR2 AA sequence is an isoform of SEQ ID NO: 141. Each possibility represents a separate embodiment of the present invention.

In another embodiment, the VEGFR2 fragment used in the compositions and methods of the present invention are based on analyzing the VEGFR2 amino acid sequence for regions that contain T cell epitopes, which in one embodiment, are determined by running the VEGFR2 sequence through an epitope predictor program, several of which are known in the art, and in another embodiment, are determined by predictive epitope mapping. In another embodiment, the VEGFR2 fragment is used by using human sequences that are homologous to VEGFR2 sequences in other species, in one embodiment, mice or rats, which are known to comprise T cell epitopes. In another embodiment, the VEGFR2 fragment used in the compositions and methods of the present invention are based on knowledge in the art regarding regions of VEGFR2 that contain T cell epitopes.

In one embodiment, a human HLA-A0201 fragment for use in the compositions and methods of the present invention comprises amino acids 766-774 of the VEGFR2 protein. In another embodiment, the VEGFR2 polypeptide fragment comprises the sequence IILVGTAVI (SEQ ID NO: 142). In another embodiment, a human HLA-A0201 fragment for use in the compositions and methods of the present invention comprises amino acids 781-789 of the VEGFR2 protein. In another embodiment, the VEGFR2 polypeptide fragment comprises the sequence LLVIILRTV (SEQ ID NO: 143). In another embodiment, a human HLA-A0201 fragment for use in the compositions and methods of the present invention comprises amino acids 1034-1042 of the VEGFR2 protein. In another embodiment, the VEGFR2 polypeptide fragment comprises the sequence ILLSEKNVV (SEQ ID NO: 144). In another embodiment, a human HLA-A0201 fragment for use in the compositions and methods of the present invention comprises amino acids 1076-1084 of the VEGFR2 protein. In another embodiment, the VEGFR2 polypeptide fragment comprises the sequence TIFDRVYTI (SEQ ID NO: 145). In another embodiment, a human HLA-A0201 fragment for use in the compositions and methods of the present invention comprises amino acids 1093-1101 of the VEGFR2 protein. In another embodiment, the VEGFR2 polypeptide fragment comprises the sequence VLLWEIFSL (SEQ ID NO: 146).

Figure 60:
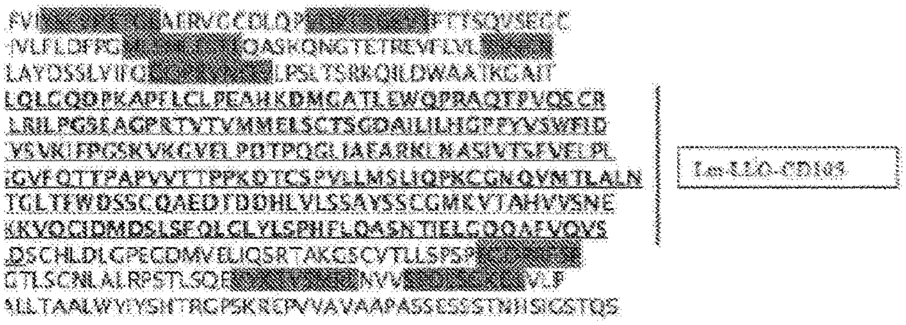
FIG. 60. Sequence of endoglin (CD105). The original fragment, based on the sequence cloned by Reisfeld's group, which was cloned into Lm-LLO-CD5 is in bold and underlined. Note that Rankpep and other MHC epitope predicting program have shown that there are several alternative, putative CTL epitopes (highlighted in red) for the b, d, and k H-2 haplotypes, that lie outside this region.

In one embodiment, an endoglin protein is set forth in the following sequence:

MDRGVLPLPITLLLFEIYSFEPTTG-LAERVGCDLQPVDPTRGEVTFTTSQVSEGCVAQAA-NAVREVHVLFLDFPGMLSHLELTLQASKQNGTET-REVFLVLVSNKNVFVKFQAPEIPLHLAYDSSLVIFQ-GQPRVNITVLPSLTSRKQILDWAATKGAITSIAALD-DPQSIVLQLGQDPKAPFLCLPEAHKDMGA-TLEWQPRAQTPVQSCRLEGVSGHKEAYILRILPG SEAGPRTVTVMMELSCTSGDAILILHGPPYVSWFID-INHSMQILTTGEYSVKIFPGSKVKGVELPDTPQGLI-AEARKLNASIVTSFVELPLVSNVSLRASSCGGVFQTT-PAPVVTTPPKDTCSPVLLMSLIQPKCGNQVMTLAL-NKKHVQTLQCTITGLTFWDSSCQAEDTDDHLV-LSSAYSSCGMKVTAHVVSNEVIISFPSGSPPLRKKVQ-CIDMDSLSFQLGLYLSPHFLQASNTIELGQQAFVQVS-VSPLTSEVTVQLDSCHLDLGPEGDMVELIQSRTAKG-SCVTLLSPSPEGDPRFSFLLRVYMVPTPTAGTLSCN-LALRPSTLSQEVYKTVSMRLNVVSPDLSGKGLVLPS-VLGITFGAFLIGALLTAALWYIYSHTRGPSKREPVVA-VAAPASSESSSTNHSIGSTQSTPCSTSSMA (SEQ ID NO: 147; FIG. 60). In one embodiment, the endoglin is any endoglin available in the art which include but is not limited to the following accession numbers: CAA54917.1, NP_001010968.1, NP_001074356.1, AAC63386.1, CAA50891. In another embodiment, aa 17-319 correspond to the construct CD105A. In another embodiment, aa 359-599 correspond to the construct CD105B.

The *Listeria*-based vaccine may contain both the mixture of live attenuated *Listeria* strains and a co-administered therapeutic agents. The live attenuated *Listeria* strain and the co-administered therapeutic agents may also be in different pharmaceutical compositions.

In one embodiment, the agent includes inhaled corticosteroids, which include fluticasone (Flovent Diskus, Flovent HFA), budesonide (Pulmicort Flexhaler), mometasone (Asmanex), flunisolide (Aerobid), beclomethasone (Qvar) and others. They are the most commonly prescribed type of long-term asthma medication. Unlike oral corticosteroids, these corticosteroid medications have a relatively low risk of side effects and are generally safe for long-term use.

The agent can be a Leukotriene modifier. These oral medications include montelukast (Singulair), zafirlukast (Accolate) and zileuton (Zyflo, Zyflo CR). They help prevent asthma symptoms for up to 24 hours.

Moreover, the agent can be long-acting beta agonists (LABAs). These inhaled medications include salmeterol (Serevent Diskus) and formoterol (Foradil Aerolizer). LABAs open the airways and reduce inflammation. However, they've been linked to severe asthma attacks. LABAs should be taken only in combination with an inhaled corticosteroid.

In one embodiment, a composition or mixture of compositions provided herein comprises an adjuvant. In another embodiment, the adjuvant is a granulocyte/macrophage colony-stimulating factor (GM-CSF) protein. In another embodiment, the adjuvant comprises a GM-CSF protein. In another embodiment, the adjuvant is a nucleotide molecule encoding GM-CSF. In another embodiment, the adjuvant comprises a nucleotide molecule encoding GM-CSF. In another embodiment, the adjuvant is saponin QS21. In another embodiment, the adjuvant comprises saponin QS21. In another embodiment, the adjuvant is monophosphoryl lipid A. In another embodiment, the adjuvant comprises monophosphoryl lipid A. In another embodiment, the adjuvant is SBAS2. In another embodiment, the adjuvant comprises SBAS2. In another embodiment, the adjuvant is an unmethylated CpG-containing oligonucleotide. In another embodiment, the adjuvant comprises an unmethylated CpG-containing oligonucleotide. In another embodiment, the adjuvant is an immune-stimulating cytokine. In another embodiment, the adjuvant comprises an immune-stimulating cytokine. In another embodiment, the adjuvant is a nucleotide molecule encoding an immune-stimulating cytokine. In another embodiment, the adjuvant comprises a nucleotide molecule encoding an immune-stimulating cytokine. In another embodiment, the adjuvant is or comprises a quill glycoside. In another embodiment, the adjuvant is or comprises a bacterial mitogen. In another embodiment, the adjuvant is or comprises a bacterial toxin. In another embodiment, the adjuvant is or comprises any other adjuvant known in the art. Each possibility represents a separate embodiment of the present invention.

In one embodiment, a composition or mixture of compositions provided herein comprise an additional active agent. In one embodiment said additional active agent comprises an oncolytic virus. In another embodiment, the additional active agent comprises a T cell receptor engineered T cell (Receptor engineered T cells). In another embodiment, the additional active agent comprises a chimeric antigen receptor engineered cells (CAR T cells). In another embodiment, the additional active agent comprises a therapeutic or immunomodulating monoclonal antibody. In another embodiment, the additional active agent comprises a targeting thymidine kinase inhibitor (TKI). In another embodiment, the additional active agent comprises an adoptively transferred cell incorporating engineered T cell receptors. In another embodiment, an additional active agent of this invention comprises an attenuated oncolytic virus, a T cell receptor engineered T cell (Receptor engineered T cells), a chimeric antigen receptor engineered T cell (CAR T cells), a therapeutic or immunomodulating monoclonal antibody, a targeting thymidine kinase inhibitor (TKI), or an adoptively transferred cells incorporating engineered T cell receptors, or any combination thereof.

In another embodiment, a composition or mixture of compositions provided herein comprise an additional active agent. In another embodiment, the active agent is an immune checkpoint inhibitor.

In one embodiment, the immune checkpoint protein inhibitor is a Programmed Death 1 (PD-1) signaling pathway inhibitor. In another embodiment, the PD-1 signaling pathway inhibitor is a molecule blocking PD-1 receptor interactions with PD-1 Ligand 1 (PD-L1) and PD-1 Ligand 2 (PD-L2). In another embodiment, PD-L1 is also known as CD274 or B7-H1. In another embodiment, PD-L2 is also known as CD273 or B7-DC. In another embodiment, the molecule blocking PD-1 receptor interactions with PD-1 Ligand 1 (PD-L1) and PD-1 Ligand 2 (PD-L2) is a molecule interacting with PD-1, PD-L1 or PD-L2. In another embodiment, the molecule blocking PD-1 receptor interactions with PD-1 Ligand 1 (PD-L1) or PD-1 Ligand 2 (PD-L2) is a molecule interacting with PD-1, PD-L1 or PD-L2. The term "interacts" or grammatical equivalents thereof may encompass binding, or coming into contact with another molecule. In another embodiment, the molecule binds to PD-1. In another embodiment, the PD-1 signaling pathway inhibitor is an anti-PD1 antibody. In another embodiment, molecule interacting with PD-L2 is an anti-PD-L1 antibody, or a small molecule that binds PD-L1. In another embodiment, molecule interacting with PD-L2 is an anti-PD-L2 antibody, or a small molecule that binds PD-L2.

In one embodiment, the molecule that interacts with PD-1 is a truncated PD-L1 protein. In another embodiment, the truncated PD-L1 protein comprises the cytoplasmic domain of PD-L1 protein. In another embodiment, the molecule interacting with PD-1 is a truncated PD-L2 protein. In another embodiment, the truncated PD-L2 protein comprises the cytoplasmic domain of PD-L2 protein. In another embodiment, the molecule blocking PD-1 receptor interactions with PD-1 Ligand 1 (PD-L1) and PD-1 Ligand 2 (PD-L2) is a molecule interacting with PD-L1 and PD-L2. In another embodiment, the molecule interacting with PD-L1 or PD-L2 is a truncated PD-1 protein, a PD-1 mimic or a small molecule that binds PD-L1 or PD-L2. In another embodiment, the truncated PD-1 protein comprises the cytoplasmic domain of the PD-1 protein.

In one embodiment, the immune checkpoint inhibitor is a CD80/86 signaling pathway inhibitor. In another embodiment, CD80 is also known as B7.1. In another embodiment, CD86 is also known as B7.2. In another embodiment, the CD80 signaling pathway inhibitor is a small molecule that interacts with CD80. In another embodiment, the CD80 inhibitor is an anti-CD80 antibody. In another embodiment, the CD86 signaling pathway inhibitor is a small molecule that interacts with CD86. In another embodiment, the CD86 inhibitor is an anti-CD86 antibody.

In one embodiment, the immune checkpoint inhibitor is a CTLA-4 signaling pathway inhibitor. In another embodiment, CTLA-4 is also known as CD152. In another embodiment, the CTLA-4 signaling pathway inhibitor is a small molecule that interacts with CTLA-4. In another embodiment, the CTLA-4 inhibitor is an anti-CTLA-4 antibody. In another embodiment, the immune checkpoint inhibitor is a CD40 signaling pathway inhibitor. In another embodiment, the immune checkpoint inhibitor is any other antigen-presenting cell:Tcell signaling pathway inhibitor known in the art.

It will be appreciated by the skilled artisan that any immune checkpoint protein known in the art can be targeted by an immune check point inhibitor. An immune checkpoint protein may be selected from, but is not limited to the following: programmed cell death protein 1 (PD1), T cell membrane protein 3 (TIM3), adenosine A2a receptor (A2aR) and lymphocyte activation gene 3 (LAG3), killer immunoglobulin receptor (KIR) or cytotoxic T-lymphocyte antigen-4 (CTLA-4). In another embodiment, the checkpoint inhibitor protein is one belonging to the B7/CD28 receptor superfamily. In one embodiment, the T cell stimulator is an antigen presenting cell (APC)/T cell agonist. In another embodiment, the T cell stimulator is a CD134 or a ligand thereof or a fragment thereof, a CD-137 or a ligand thereof or a fragment thereof, or an Includible T cell costimulator (ICOS) or a ligand thereof or a fragment thereof.

In one embodiment, the methods provided herein further comprise the step of co-administering an immunogenic composition provided herein with a indoleamine 2,3-dioxygenase (IDO) pathway inhibitor. IDO pathway inhibitors for use in the present invention include any IDO pathway inhibitor known in the art, including but not limited to, 1-methyltryptophan (1MT), 1-methyltryptophan (1MT), Necrostatin-1, Pyridoxal Isonicotinoyl Hydrazone, Ebselen, 5-Methylindole-3-carboxaldehyde, CAY10581, an anti-IDO antibody or a small molecule IDO inhibitor. In another embodiment, the compositions and methods provided herein are also used in conjunction with, prior to, or following a chemotherapeutic or radiotherapeutic regiment.

In one embodiment, the methods provided herein further comprise the step of co-administering an immunogenic composition provided herein with a tumor kinase inhibitor that enhances an anti-tumor immune response in said subject. Tumor kinase inhibitors (TKIs) serve to interfere with specific cell signaling pathways and thus allow target-specific therapy for selected malignancies. TKI's are well known and will be appreciated by the skilled artisan to include those set forth in Table 1 below and any other TKI known to enhance an anti-tumor immune response.

TABLE 1

| Name | Target | Class |
|---|---|---|
| Afatinib | EGFR/ErbB2 | Small molecule |
| Axitinib | VEGFR1/VEGFR2/ VEGFR3/PDGFRB/c-KIT | Small molecule |
| Bevacizumab | VEGF | Monoclonal antibody |
| Bosutinib | BcrAbl/SRC | Small molecule |
| Cetuximab | ErbB1 | Monoclonal antibody |
| Crizotinib | ALK/Met | Small molecule |
| Dasatinib | multiple targets | Small molecule |
| Erlotinib | ErbB1 | Small molecule |
| Fostamatinib | Syk | Small molecule |
| Gefitinib | EGFR | Small molecule |
| Ibrutinib | BTK | Small molecule |
| Imatinib | Bcr-Abl | Small molecule |
| Lapatinib | ErbB1/ErbB2 | Small molecule |
| Lenvatinib | VEGFR2/VEGFR2 | Small molecule |
| Mubritinib | N/A | Small molecule |
| Nilotinib | Bcr-Abl | Small molecule |
| Panitumumab | EGFR | Monoclonal antibody |
| Pazopanib | VEGFR2/PDGFR/c-kit | Small molecule |
| Pegaptanib | VEGF | RNA Aptamer |
| Ranibizumab | VEGF | Monoclonal antibody |
| Ruxolitinib | JAK | Small molecule |
| Sorafenib | multiple targets | Small molecule |
| SU6656 | multiple targets | Small molecule |
| Sunitinib | multiple targets | Small molecule |
| Tofacitinib | JAK | Small molecule |
| Trastuzumab | Erb2 | Monoclonal antibody |
| Vandetanib | RET/VEGFR/EGFR | Small molecule |
| Vemurafenib | BRAF | Small molecule |

In another embodiment, the dose of an immune checkpoint inhibitor (e.g., a PD-1 signaling pathway inhibitor) present in the immunogenic composition provided herein that is administered to a subject is 5-10 mg/kg every 2 weeks, 5-10 mg/kg every 3 weeks, or 1-2 mg/kg every 3 weeks. In another embodiment, the dose ranges from 1-10 mg/kg every week. In another embodiment, the dose ranges from 1-10 mg/kg every 2 weeks. In another embodiment, the dose ranges from 1-10 mg/kg every 3 weeks. In another embodiment, the dose ranges from 1-10 mg/kg every 4 weeks. These doses are exemplary and are not meant to be limiting.

In one embodiment, a composition or a mixture of compositions of the present invention comprise an antibody or a functional fragment thereof, which specifically binds GITR or a portion thereof. In another embodiment, a composition or a mixture of compositions of the present invention comprise an antibody or functional fragment thereof, which specifically binds OX40 or a portion thereof. In another embodiment, a composition or a mixture of compositions of the present invention comprise an antibody that specifically bind GITR or a portion thereof, and an antibody that specifically binds OX40. In another embodiment, a composition or a mixture of compositions of the present invention comprises an Lm strain and an antibody or a functional fragment thereof that specifically binds GITR. In another embodiment, a composition or a mixture of compositions of the present invention comprises an Lm strain and an antibody or a functional fragment thereof that specifically binds OX40. In another embodiment, a composition or a mixture of compositions of the present invention comprises an Lm strain and an antibody that specifically binds GITR or a portion thereof, and an antibody that specifically binds OX40 or a portion thereof.

Different antibodies present in the same or different compositions need not have the same form, for example one antibody may be a monoclonal antibody and another may be a FAb fragment. Each possibility represents a different embodiment of this invention.

The term "antibody functional fragment" refers to a portion of an intact antibody that is capable of specifically binding to an antigen. Examples of antibody fragments include, but are not limited to, Fab, Fab', $F(ab')_2$, and Fv fragments, linear antibodies, scFv antibodies, and multispecific antibodies formed from antibody fragments.

It will be appreciated by a skilled artisan that the term "binds" or "specifically binds," with respect to an antibody, encompasses an antibody or functional fragment thereof, which recognizes a specific antigen, but does not substantially recognize or bind other molecules in a sample. For example, an antibody that specifically binds to an antigen from one species may also bind to that antigen from one or more species, but, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than a specific amino acid sequence.

In one embodiment, a composition of this invention comprises a recombinant *Listeria monocytogenes* (Lm) strain. In another embodiment, a composition of this invention comprises an antibody or functional fragment thereof, as described herein.

In one embodiment, a composition provided herein as either part of a single composition administration or as part of a mixture of compositions comprises an antibody or a functional fragment thereof, as provided herein, and a recombinant attenuated *Listeria*, as provided herein. In another embodiment, each component of the compositions provided herein is administered prior to, concurrently with, or after another component of the compositions provided herein. In one embodiment, even when administered concurrently, a *Listeria*-based composition and an antibody or functional fragment thereof may be administered as two separate compositions. Alternately, in another embodiment, a *Listeria*-based composition may comprise an antibody or a functional fragment thereof.

In one embodiment, any of the compositions of the present invention induce a strong innate stimulation of interferon-gamma, which in one embodiment, has anti-angiogenic properties. In one embodiment, a *Listeria* of the present invention induces a strong innate stimulation of interferon-gamma, which in one embodiment, has anti-angiogenic properties (Dominiecki et al., Cancer Immunol Immunother. 2005 May; 54(5):477-88. Epub 2004 Oct. 6, incorporated herein by reference in its entirety; Beatty and Paterson, J Immunol. 2001 Feb. 15; 166(4):2276-82, incorporated herein by reference in its entirety). In one embodiment, anti-angiogenic properties of *Listeria* are mediated by $CD4^+$ T cells (Beatty and Paterson, 2001). In another embodiment, anti-angiogenic properties of *Listeria* are mediated by $CD8^+$ T cells. In another embodiment, IFN-gamma secretion as a result of *Listeria* vaccination is mediated by NK cells, NKT cells, Th1 $CD4^+$ T cells, TC1 $CD8^+$ T cells, or a combination thereof.

In another embodiment, any of the compositions of the present invention induce production of one or more anti-angiogenic proteins or factors. In one embodiment, the anti-angiogenic protein is IFN-gamma. In another embodiment, the anti-angiogenic protein is pigment epithelium-derived factor (PEDF); angiostatin; endostatin; fms-like tyrosine kinase (sFlt)-1; or soluble endoglin (sEng). In one embodiment, a *Listeria* of the present invention is involved in the release of anti-angiogenic factors, and, therefore, in one embodiment, has a therapeutic role in addition to its role as a vector for introducing an antigen to a subject. Each *Listeria* strain and type thereof represents a separate embodiment of the present invention.

In another embodiment, the present invention provides a recombinant *Listeria* strain comprising an episomal recombinant nucleic acid molecule, the nucleic acid molecule comprising a first and at least a second open reading frame each encoding a first and at least a second polypeptide, wherein the first and the at least second polypeptide each comprise a heterologous antigen or a functional fragment thereof fused to a PEST-containing polypeptide, wherein the nucleic acids further comprise a plasmid replication control region. In another embodiment, the plasmid control region regulates expression from the first and least second open reading frame. In another embodiment, the plasmid control region comprises an open reading frame encoding a transcription repressor that represses heterologous antigen expression from the first or at least second open reading frame. In another embodiment, the plasmid control region comprises an open reading frame encoding a transcription inducer that induces heterologous antigen expression from the first and at least second open reading frame. In another embodiment, the nucleic acid molecule comprises 1-4 open reading frames each encoding 1-4 recombinant polypeptides, wherein said recombinant polypeptides each comprise a heterologous antigen or a functional fragment thereof fused to a PEST-containing polypeptide. In another embodiment, a plasmid control region represses heterologous antigen expression from the first through fourth open reading frames. In another embodiment, the plasmid control region comprises an open reading frame encoding a transcription inducer that induces heterologous antigen expression from the first through fourth open reading frames.

In one embodiment, there are different types of transcription regulation mechanisms known in the art and these include, but are not limited to, "negative control" and "positive control." In negative control, a regulatory protein or repressor protein binds to the operator and prevents RNA polymerase from binding properly to the promoter sequence. Alternatively, the repressor protein can be synthesized in an inactive form in that it cannot block RNA polymerase binding to the promoter; the repressor is then activated to prevent RNA polymerase binding to the promoter by the binding of a corepressor. This type of control is seen most often in anabolic pathways (e.g., arginine biosynthesis), where the corepressor is often the end product of the anabolic pathway. Alternatively, the repressor protein is synthesized in an active form, binds to the operator and prevents RNA polymerase from binding to promoter. When an inducer binds to the repressor, the repressor becomes inactive, therefore RNA polymerase is now free to initiate transcription. This type of control is seen most often in catabolic pathways (e.g., lactose catabolism). The inducer is often a form of the substrate that will be degraded. In positive control, a regulatory protein, called an activator protein, binds to the operator and the activator molecular stabilizes RNA polymerase binding to the promoter region. An example of this includes the arabinose catabolism. Regulatory proteins (for both positive and negative regulation) are encoded by regulatory genes and can be synthesized continuously at low levels. They can be made to be self-regulated whereby high concentrations of the regulatory protein (associated with high plasmid production) binds to its own operator and represses RNA polymerase from binding to the promoter sequence. This stops transcription until its level drops. Several examples of these types of regulation include the lactose operon, the arginine operon, the diphtheria toxin gene regulation system, etc. Transcription repressors and methods of use thereof are readily known in the art and are contemplated for use in the present invention.

In one embodiment, the methods provided herein comprise the step of measuring metabolic burden in the recombinant Listerias expressing multiple fusion proteins provided herein prior to using them in a clinical setting. In doing so, a skilled artisan can readily determine which optimal conditions to use for expression of fusion proteins comprising a heterologous antigen provided herein. In another embodiment, measuring metabolic burden is accomplished by any means know in the art at the time of the invention which include but are not limited to, measuring growth rates of the vaccine strain, optical density readings, colony forming unit (CFU) plating, and the like. In another embodiment, the metabolic burden on the bacterial cell is determined by measuring the viability of the bacterial cell. Methods of measuring bacteria viability are readily known and available in the art, some of which include but are not limited to, bacteria plating for viability count, measuring ATP, and flow cytometry. In ATP staining, detection is based on using the luciferase reaction to measure the amount of ATP from viable cells, wherein the amount of ATP in cells correlates with cell viability. As to flow cytometry, this method can be used in various ways, also known in the art, for example after employing the use of viability dyes which are excluded by live bacterial cells and are absorbed or adsorbed by a dead bacterial cells. A skilled artisan would readily understand that these and any other methods known in the art for measuring bacterial viability can be used in the present invention. It is to be understood that a skilled artisan would be able to implement the knowledge available in the art at the time of the invention for measuring growth rates of a *Listeria* strain or expression of marker genes by the *Listeria* strain that allow determining the metabolic burden of the *Listeria* strain expressing multiple heterologous antigens or functional fragments thereof.

In one embodiment, the term "at least second nucleic acid molecule" refers to two or more nucleic acid molecules, alternatively it refers to three, four, five, and so on nucleic acid molecules. In another embodiment, the term refers to up to ten nucleic acid molecules, or up to twenty or up to thirty nucleic acid molecules.

Figure 20:
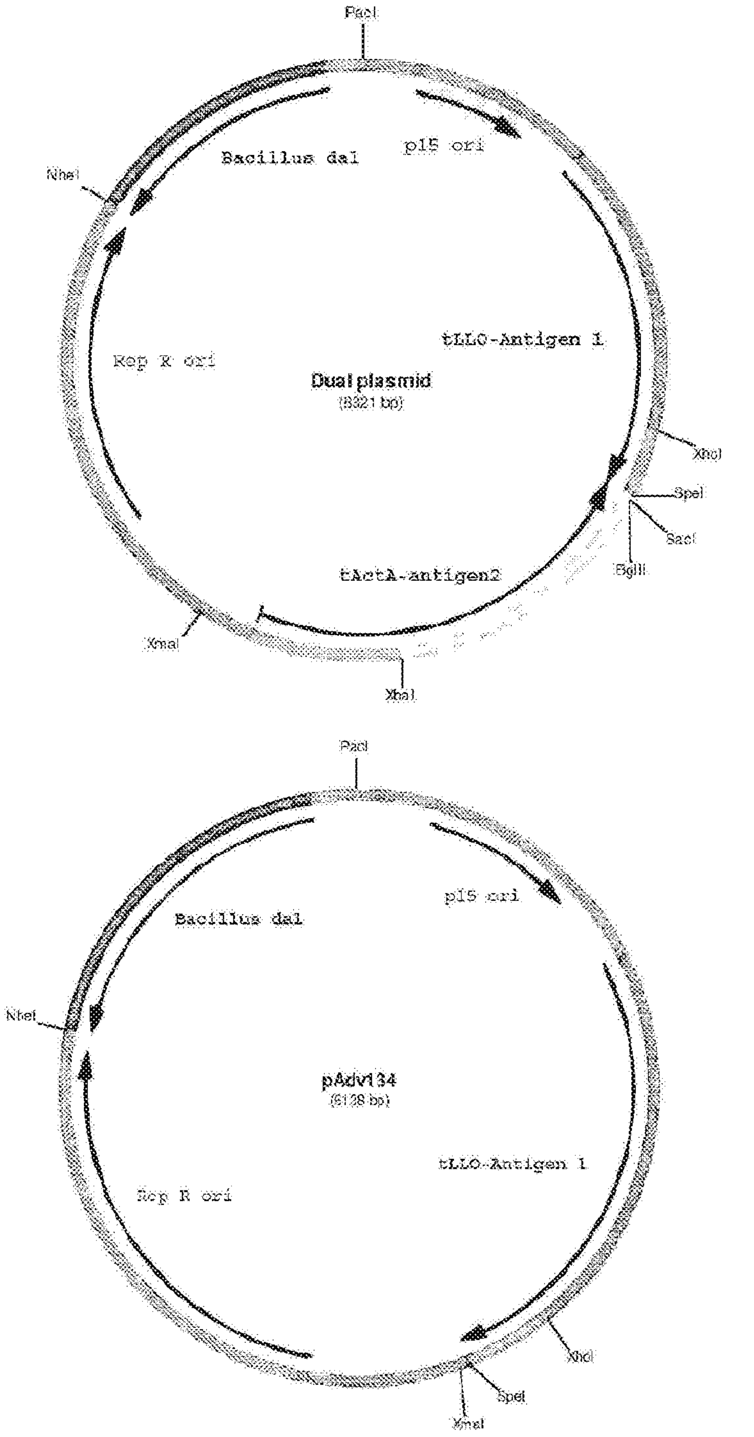
FIG. 20 shows a schematic representation of pAdv134 plasmid and dual plasmid. The restriction sites that will be used for cloning of antigen 1 (Xho I and SpeI) and antigen 2 (XbaI and SacI or BglII) genes are indicated. The black arrow represents the direction of transcription. p15 ori and RepR refer to *Listeria* and *E. coli* origin of replication. tLLO is truncated Listeriolysin O protein (1-441 aa) and tActA is truncated ActA (1-233 aa) protein. *Bacillus*-dal gene codes for D-alanine racemase which complements for the synthesis of D-alanine in LmΔdal dat strain.

In one embodiment, a recombinant *Listeria* strain provided herein comprises a multivalent plasmid that delivers two or more antigens. In another embodiment, the plasmid is a dual plasmid described herein (see FIG. 20 and Example 40). In another embodiment, provided herein is an episomal recombinant nucleic acid encoding the multivalent plasmid. In another embodiment, the multivalent plasmid delivers two to five antigens. In another embodiment, the multivalent plasmid delivers two to ten antigens. In another embodiment, the antigens in the multivalent plasmid are fused to a PEST-containing amino acid sequence.

In one embodiment, a plasmid provided herein remains extra-chromosomal or episomal, that is, it does not integrate into a host's bacteria's chromosome once transfected into a bacteria. In another embodiment, a plasmid provided herein is an integrative plasmid that integrates into a host bacteria's chromosomal sequence (specifically or randomly) once transfected into a bacteria.

In another embodiment, an episomal recombinant nucleic acid backbone is encoded by the sequence comprising SEQ ID NO: 1. In another embodiment, the episomal recombinant nucleic acid provided herein is encoded by the sequence consisting of SEQ ID NO: 1. In another embodiment, the episomal recombinant nucleic acid provided herein is encoded by the sequence set forth in SEQ ID NO: 1.

(SEQ ID NO: 1)

```
ggagtgtatactggcttactatgttggcactgatgagggtgtcagtgaa
gtgcttcatgtggcaggagaaaaaaggctgcaccggtgcgtcagcagaa
tatgtgatacaggatatattccgcttcctcgctcactgactcgctacgc
tcggtcgttcgactgcggcgagcggaaatggcttacgaacggggcggag
atttcctggaagatgccaggaagatacttaacagggaagtgagagggcc
gcggcaaagccgtttttccataggctccgcccccctgacaagcatcacg
aaatctgacgctcaaatcagtggtggcgaaacccgacaggactataaag
ataccaggcgtttccccctggcggctccctcgtgcgctctcctgttcct
gcctttcggtttaccggtgtcattccgctgttatggccgcgtttgtctc
attccacgcctgacactcagttccgggtaggcagttcgctccaagctgg
actgtatgcacgaaccccccgttcagtccgaccgctgcgccttatccgg
taactatcgtcttgagtccaacccggaaagacatgcaaaagcaccactg
gcagcagccactggtaattgatttagaggagttagtcttgaagtcatgc
gccggttaaggctaaactgaaaggacaagttttggtgactgcgctcctc
caagccagttacctcggttcaaagagttggtagctcagagaaccttcga
aaaaccgccctgcaaggcggttttttcgttttcagagcaagagattacg
cgcagaccaaaacgatctcaagaagatcatcttattaatcagataaaat
atttctagccctcctttgattagtatattcctatcttaaagttactttt
atgtggaggcattaacatttgttaatgacgtcaaaaggatagcaagact
agaataaagctataaagcaagcatataatattgcgtttcatctttagaa
gcgaatttcgccaatattataattatcaaaagagaggggtggcaaacgg
```

-continued

```
tatttggcattattaggttaaaaaatgtagaaggagagtgaaacccatg
aaaaaaataatgctagtttttattacacttatattagttagtctaccaa
ttgcgcaacaaactgaagcaaaggatgcatctgcattcaataaagaaaa
ttcaatttcatccatggcaccaccagcatctccgcctgcaagtcctaag
acgccaatcgaaaagaaacacgcggatgaaatcgataagtatatacaag
gattggattacaataaaaacaatgtattagtataccacggagatgcagt
gacaaatgtgccgccaagaaaaggttacaaagatggaaatgaatatatt
gttgtggagaaaaagaagaaatccatcaatcaaaataatgcagacattc
aagttgtgaatgcaatttcgagcctaacctatccaggtgctctcgtaaa
agcgaattcggaattagtagaaaatcaaccagatgttctccctgtaaaa
cgtgattcattaacactcagcattgatttgccaggtatgactaatcaag
acaataaaatagttgtaaaaaatgccactaaatcaaacgttaacaacgc
agtaaatacattagtggaaagatggaatgaaaaatatgctcaagcttat
ccaaatgtaagtgcaaaaattgattatgatgacgaaatggcttacagtg
aatcacaattaattgcgaaatttggtacagcatttaaagctgtaaataa
tagcttgaatgtaaacttcggcgcaatcagtgaagggaaaatgcaagaa
gaagtcattagttttaaacaaatttactataacgtgaatgttaatgaac
ctacaagaccttccagatttttcggcaaagctgttactaaagagcagtt
gcaagcgcttggagtgaatgcagaaaatcctcctgcatatatctcaagt
gtggcgtatggccgtcaagtttatttgaaattatcaactaattcccata
gtactaaagtaaaagctgcttttgatgctgccgtaagcggaaaatctgt
ctcaggtgatgtagaactaacaaatatcatcaaaaattcttccttcaaa
gccgtaatttacggaggttccgcaaaagatgaagttcaaatcatcgacg
gcaacctcggagacttacgcgatattttgaaaaaaggcgctacttttaa
tcgagaaacaccaggagttcccattgcttatacaacaaacttcctaaaa
gacaatgaattagctgttattaaaaacaactcagaatatattgaaacaa
cttcaaaagcttatacagatggaaaaattaacatcgatcactctggagg
atacgttgctcaattcaacatttcttgggatgaagtaaattatgatctc
gagactagttctagatttatcacgtacccatttccccgcatcttttatt
tttttaaatactttagggaaaaatggtttttgatttgcttttaaaggtt
gtggtgtagactcgtctgctgactgcatgctagaatctaagtcactttc
agaagcatccacaactgactctttcgccacttttctcttatttgctttt
gttggtttatctggataagtaaggctttcaagctcactatccgacgacg
ctatggcttttcttctttttttaatttccgctgcgctatccgatgacag
acctggatgacgacgctccacttgcagagttggtcggtcgactcctgaa
gcctcttcatttatagccacatttcctgtttgctcaccgttgttattat
tgttattcggacctttctctgcttttgctttcaacattgctattaggtc
tgctttgttcgtatttttcactttattcgatttttctagttcctcaata
tcacgtgaacttacttcacgtgcagtttcgtatcttggtcccgtattta
cctcgcttggctgctcttctgtttttcttcttcccattcatctgtgtt
tagactggaatcttcgctatctgtcgctgcaaatattatgtcggggtta
```

-continued atcgtaatgcagttggcagtaatgaaaactaccatcatcgcacgcataa atctgtttaatcccacttatactccctcctcgtgatacgctaatacaac ctttttagaacaaggaaaattcggccttcattttcactaatttgttccg ttaaaaattggattagcagttagttatcttcttaattagctaatataag aaaaaatattcatgaattattttaagaatatcacttggagaattaattt ttctctaacatttgttaatcagttaaccccaactgcttcccaagcttca cccgggccactaactcaacgctagtagtggatttaatcccaaatgagcc aacagaaccagaaccagaaacagaacaagtaacattggagttagaaatg gaagaagaaaaaagcaatgatttcgtgtgaataatgcacgaaatcattg cttattttttaaaaagcgatatactagatataacgaaacaacgaactg aataaagaatacaaaaaaagagccacgaccagttaaagcctgagaaact ttaactgcgagccttaattgattaccaccaatcaattaaagaagtcgag acccaaaatttggtaaagtatttaattactttattaatcagatacttaa atatctgtaaacccattatatcgggtttttgaggggatttcaagtcttt aagaagataccaggcaatcaattaagaaaaacttagttgattgcctttt ttgttgtgattcaactttgatcgtagcttctaactaattaattttcgta agaaaggagaacagctgaatgaatatcccttttgttgtagaaactgtgc ttcatgacggcttgttaaagtacaaatttaaaaatagtaaaattcgctc aatcactaccaagccaggtaaaagtaaaggggctatttttgcgtatcgc tcaaaaaaaagcatgattggcggacgtggcgttgttctgacttccgaag aagcgattcacgaaaatcaagatacatttacgcattggacaccaaacgt ttatcgttatggtacgtatgcagacgaaaaccgttcatacactaaagga cattctgaaaacaatttaagacaaatcaataccttctttattgattttg atattcacacggaaaaagaaactatttcagcaagcgatattttaacaac agctattgatttaggttttatgcctacgttaattatcaaatctgataaa ggttatcaagcatattttgttttagaaacgccagtctatgtgacttcaa aatcagaatttaaatctgtcaaagcagccaaaataatctcgcaaaatat ccgagaatattttggaaagtctttgccagttgatctaacgtgcaatcat tttgggattgctcgtataccaagaacggacaatgtagaatttttttgatc ccaattaccgttattctttcaaagaatggcaagattggtctttcaaaca aacagataataagggctttactcgttcaagtctaacggttttaagcggt acagaaggcaaaaaacaagtagatgaaccctggtttaatctcttattgc acgaaacgaaattttcaggagaaaagggtttagtagggcgcaatagcgt tatgtttaccctctctttagcctactttagttcaggctattcaatcgaa acgtgcgaatataatatgtttgagtttaataatcgattagatcaaccct tagaagaaaaagaagtaatcaaaattgttagaagtgcctattcagaaaa ctatcaaggggctaatagggaatacattaccattctttgcaaagcttgg gtatcaagtgatttaaccagtaaagatttatttgtccgtcaagggtggt ttaaattcaagaaaaaaagaagcgaacgtcaacgtgttcatttgtcaga atggaaagaagatttaatggcttatattagcgaaaaaagcgatgtatac aagccttatttagcgacgaccaaaaaagagattagagaagtgctaggca -continued ttcctgaacggacattagataaattgctgaaggtactgaaggcgaatca ggaaattttctttaagattaaaccaggaagaaatggtggcattcaactt gctagtgttaaatcattgttgctatcgatcattaaattaaaaaaagaag aacgagaaagctatataaaggcgctgacagcttcgtttaatttagaacg tacatttattcaagaaactctaaacaaattggcagaacgccccaaaacg gacccacaactcgatttgtttagctacgatacaggctgaaaataaaacc cgcactatgccattacatttatatctatgatacgtgtttgtttttcttt gctggctagcttaattgcttatatttacctgcaataaaggatttcttac ttccattatactcccattttccaaaaacatacggggaacacgggaactt attgtacaggccacctcatagttaatggtttcgagccttcctgcaatct catccatggaaatatattcatcccccctgccggcctattaatgtgacttt tgtgcccggcggatattcctgatccagctccaccataaattggtccatg caaattcggccggcaattttcaggcgttttcccttcacaaggatgtcgg tccctttcaattttcggagccagccgtccgcatagcctacaggcaccgt cccgatccatgtgtctttttccgctgtgtactcggctccgtagctgacg ctctcgccttttctgatcagtttgacatgtgacagtgtcgaatgcaggg taaatgccggacgcagctgaaacggtatctcgtccgacatgtcagcaga cgggcgaaggccatacatgccgatgccgaatctgactgcattaaaaaag cctttttcagccggagtccagcggcgctgttcgcgcagtggaccatta gattctttaacggcagcggagcaatcagctctttaaagcgctcaaactg cattaagaaatagcctctttctttttcatccgctgtcgcaaaatgggta aatacccctttgcactttaaacgagggttgcggtcaagaattgccatca cgttctgaacttcttcctctgtttttacaccaagtctgttcatccccgt atcgaccttcagatgaaaatgaagagaacctttttttcgtgtggcgggct gcctcctgaagccattcaacagaataacctgttaaggtcacgtcatact cagcagcgattgccacatactccgggggaaccgcgccaagcaccaatat aggcgccttcaatcccttttgcgcagtgaaatcgcttcatccaaaatg gccacggccaagcatgaagcacctgcgtcaagagcagcctttgctgttt ctgcatcaccatgcccgtaggcgtttgctttcacaactgccatcaagtg gacatgttcaccgatatgtttttcatattgctgacattttcctttatc acggacaagtcaatttccgcccacgtatctctgtaaaaaggttttgtgc tcatggaaaactcctctctttttcagaaaatcccagtacgtaattaag tatttgagaattaattttatattgattaatactaagtttacccagtttt cacctaaaaaacaaatgatgagataatagctccaaaggctaaagaggac tataccaactatttgttaat.

In one embodiment, a multivalent plasmid backbone comprises at least two nucleic acid sequences encoding at least two antigens. In another embodiment, the recombinant episomal nucleic acid encodes a plasmid backbone sequence and at least two antigens. In another embodiment, the antigens are heterologous antigens to the bacteria host carrying the plasmid. In another embodiment, the antigens are heterologous antigens to the *Listeria* host carrying the plasmid. In another embodiment, the recombinant episomal nucleic acid sequence encoding the plasmid backbone and at least two heterologous antigens comprises SEQ ID NO: 2. In another embodiment, the recombinant episomal nucleic acid sequence encoding the plasmid backbone and at least two heterologous antigens consists of SEQ ID NO: 2.

(SEQ ID NO: 2)

ggagtgtatactggcttactatgttggcactgatgagggtgtcagtgaag
tgcttcatgtggcaggagaaaaaaggctgcaccggtgcgtcagcagaata
tgtgatacaggatatattccgcttcctcgctcactgactcgctacgctcg
gtcgttcgactgcggcgagcggaaatggcttacgaacggggcggagattt
cctggaagatgccaggaagatacttaacagggaagtgagagggccgcggc
aaagccgtttttccataggctccgcccccctgacaagcatcacgaaatct
gacgctcaaatcagtggtggcgaaacccgacaggactataaagataccag
gcgtttccccctggcggctccctcgtgcgctctcctgttcctgcctttcg
gtttaccggtgtcattccgctgttatggccgcgtttgtctcattccacgc
ctgacactcagttccgggtaggcagttcgctccaagctggactgtatgca
cgaaccccccgttcagtccgaccgctgcgccttatccggtaactatcgtc
ttgagtccaacccggaaagacatgcaaaagcaccactggcagcagccact
ggtaattgatttagaggagttagtcttgaagtcatgcgccggttaaggct
aaactgaaaggacaagttttggtgactgcgctcctccaagccagttacct
cggttcaaagagttggtagctcagagaaccttcgaaaaaccgccctgcaa
ggcggttttttcgttttcagagcaagagattacgcgcagaccaaaacgat
ctcaagaagatcatcttattaatcagataaaatatttctagccctccttt
gattagtatattcctatcttaaagttacttttatgtggaggcattaacat
ttgttaatgacgtcaaaaggatagcaagactagaataaagctataaagca
agcatataatattgcgtttcatctttagaagcgaatttcgccaatattat
aattatcaaaagagaggggtggcaaacggtatttggcattattaggttaa
aaaatgtagaaggagagtgaaacccatgaaaaaaataatgctagtttta
ttacacttatattagttagtctaccaattgcgcaacaaactgaagcaaag
gatgcatctgcattcaataaagaaaattcaatttcatccatggcaccacc
agcatctccgcctgcaagtcctaagacgccaatcgaaaagaaacacgcgg
atgaaatcgataagtatatacaaggattggattacaataaaaacaatgta
ttagtataccacggagatgcagtgacaaatgtgccgccaagaaaaggtta
caaagatggaaatgaatatattgttgtggagaaaaagaagaaatccatca
atcaaaataatgcagacattcaagttgtgaatgcaatttcgagcctaacc
tatccaggtgctctcgtaaaagcgaattcggaattagtagaaaatcaacc
agatgttctccctgtaaaacgtgattcattaacactcagcattgatttgc
caggtatgactaatcaagacaataaaatagttgtaaaaaatgccactaaa
tcaaacgttaacaacgcagtaaatacattagtggaaagatggaatgaaaa
atatgctcaagcttatccaaatgtaagtgcaaaaattgattatgatgacg
aaatggcttacagtgaatcacaattaattgcgaaatttggtacagcattt
aaagctgtaaataatagcttgaatgtaaacttcggcgcaatcagtgaagg
gaaaatgcaagaagaagtcattagttttaaacaaatttactataacgtga -continued atgttaatgaacctacaagaccttccagattttttcggcaaagctgttact
aaagagcagttgcaagcgcttggagtgaatgcagaaaatcctcctgcata
tatctcaagtgtggcgtatggccgtcaagtttatttgaaattatcaacta
attcccatagtactaaagtaaaagctgcttttgatgctgccgtaagcgga
aaatctgtctcaggtgatgtagaactaacaaatatcatcaaaaattcttc
cttcaaagccgtaatttacggaggttccgcaaaagatgaagttcaaatca
tcgacggcaacctcggagacttacgcgatattttgaaaaaaggcgctact
tttaatcgagaaacaccaggagttcccattgcttatacaacaaacttcct
aaaagacaatgaattagctgttattaaaaacaactcagaatatattgaaa
caacttcaaaagcttatacagatggaaaaattaacatcgatcactctgga
ggatacgttgctcaattcaacatttcttgggatgaagtaaattatgatct
cgagcatggagatacacctacattgcatgaatatatgttagatttgcaac
cagagacaactgatctctactgttatgagcaattaaatgacagctcagag
gaggaggatgaaatagatggtccagctggacaagcagaaccggacagagc
ccattacaatattgtaaccttttgttgcaagtgtgactctacgcttcggt
tgtgcgtacaaagcacacacgtagacattcgtactttggaagacctgtta
atgggcacactaggaattgtgtgccccatctgttctcagaaaccataaac
tagt*ctagtggtgatggtgatgatggagctcagatctgtctaagaggcag*
*ccatagggcataagctgtgtcaccagctgcaccgtggatgtcaggcagat*
*gcccagaaggcgggagacatatggggagcccacaccagccatcacgtatg*
*cttcgtctaagatttctttgttggctttgggggatgtgttttccctcaac*
*actttgatggccactggaattttcacattctccccatcagggatccagat*
*gccccttgtagactgtgccaaaagcgccagatccaagcaccttcaccttcc*
*tcagctccgtctctttcaggatccgcatctgcgcctggttgggcatcgct*
*ccgctaggtgtcagcggctccaccagctccgtttcctgcagcagtctccg*
*catcgtgtacttccggatcttctgctgccctcgggcgcacagctggtggc*
*aggccaggccctcgcccacacactcgtcctctggccggttggcagtgtgg*
*agcagagcttggtgcgggttccgaaagagctggtcccagggcaccgtgtg*
*cacgaagcagaggtgggtgttatggtggatgagggccagtccactgccca*
*gttccctcagtgagcgcagccccagccagctgatgcccagcccttgcagg*
*gtcagcgagtaggcgccattgtgcagaattcgtccccggattacttgcag*
*gttctggaagacgctgaggtcaggcaggctgtccggccatgctgagatgt*
*ataggtaacctgtgatctcttccagagtctcaaacacttggagctgctct*
*ggctggagcggggcagtgttggaggctgggtccccatcaaagctctccgg*
*cagaaatgccaggctcccaaagatcttcttgcagccagcaaactcctgga*
*tattcttccacaaaatcgtgtcctggtagcagagctgggggttccgctgg*
*atcaagacccctcctttcaagatctctgtgaggcttcgaagctgcagctc*
*ccgcaggcctcctggggaggcccctgtgacaggggtggtattgttcagcg*
*ggtctccattgtctagcacggccagggcatagttgtcctcaaagagctgg*
*gtgcctcgcacaatccgcagcctctgcagtgggacctgcctcacttggtt*
*gtgagcgatgagcacgtagccctgcacctcctggatatcctgcaggaagg*

-continued

*acaggctggcattggtgggcaggtaggtgagttccaggtttccctgcacc*

*acctggcagccctggtagaggtggcggagcatgtccaggtgggttctaga* tttatcacgtacccatttccccgcatcttttatttttttaaatactttag ggaaaaatggtttttgatttgcttttaaaggttgtggtgtagactcgtct gctgactgcatgctagaatctaagtcactttcagaagcatccacaactga ctctttcgccacttttctcttatttgcttttgttggtttatctggataag taaggctttcaagctcactatccgacgacgctatggcttttcttcttttt ttaatttccgctgcgctatccgatgacagacctggatgacgacgctccac ttgcagagttggtcggtcgactcctgaagcctcttcatttatagccacat ttcctgtttgctcaccgttgttattattgttattcggacctttctctgct tttgctttcaacattgctattaggtctgctttgttcgtatttttcacttt attcgatttttctagttcctcaatatcacgtgaacttacttcacgtgcag tttcgtatcttggtcccgtatttacctcgcttggctgctcttctgttttt tcttcttcccattcatctgtgtttagactggaatcttcgctatctgtcgc tgcaaatattatgtcggggttaatcgtaatgcagttggcagtaatgaaaa ctaccatcatcgcacgcataaatctgtttaatcccacttatactccctcc tcgtgatacgctaatacaacctttttagaacaaggaaaattcggccttca ttttcactaatttgttccgttaaaaattggattagcagttagttatcttc ttaattagctaatataagaaaaaatattcatgaattattttaagaatatc acttggagaattaatttttctctaacatttgttaatcagttaaccccaac tgcttcccaagcttcacccgggccactaactcaacgctagtagtggattt aatcccaaatgagccaacagaaccagaaccagaaacagaacaagtaacat tggagttagaaatggaagaagaaaaaagcaatgatttcgtgtgaataatg cacgaaatcattgcttatttttttaaaaagcgatatactagatataacga aacaacgaactgaataaagaatacaaaaaaagagccacgaccagttaaag cctgagaaactttaactgcgagccttaattgattaccaccaatcaattaa agaagtcgagacccaaaatttggtaaagtatttaattactttattaatca gatacttaaatatctgtaaacccattatatcgggtttttgaggggatttc aagtctttaagaagataccaggcaatcaattaagaaaaacttagttgatt gcctttttttgttgtgattcaactttgatcgtagcttctaactaattaatt ttcgtaagaaaggagaacagctgaatgaatatccctttttgttgtagaaac tgtgcttcatgacggcttgttaaagtacaaatttaaaaatagtaaaattc gctcaatcactaccaagccaggtaaaagtaaaggggctatttttgcgtat cgctcaaaaaaaagcatgattggcggacgtggcgttgttctgacttccga agaagcgattcacgaaaatcaagatacatttacgcattggacaccaaacg tttatcgttatggtacgtatgcagacgaaaaccgttcatacactaaagga cattctgaaaacaatttaagacaaatcaataccttctttattgattttga tattcacacggaaaaagaaactatttcagcaagcgatattttaacaacag ctattgatttaggttttatgcctacgttaattatcaaatctgataaaggt tatcaagcatattttgttttagaaacgccagtctatgtgacttcaaaatc agaatttaaatctgtcaaagcagccaaaataatctcgcaaaatatccgag -continued aatattttggaaagtctttgccagttgatctaacgtgcaatcattttggg attgctcgtataccaagaacggacaatgtagaatttttttgatcccaatta ccgttattctttcaaagaatggcaagattggtctttcaaacaaacagata ataagggctttactcgttcaagtctaacggttttaagcggtacagaaggc aaaaaacaagtagatgaaccctggtttaatctcttattgcacgaaacgaa attttcaggagaaaagggtttagtagggcgcaatagcgttatgtttaccc tctctttagcctactttagttcaggctattcaatcgaaacgtgcgaatat aatatgtttgagtttaataatcgattagatcaacccttagaagaaaaaga agtaatcaaaattgttagaagtgcctattcagaaaactatcaaggggcta atagggaatacattaccattctttgcaaagcttgggtatcaagtgattta accagtaaagatttatttgtccgtcaagggtggtttaaattcaagaaaaa aagaagcgaacgtcaacgtgttcatttgtcagaatggaaagaagatttaa tggcttatattagcgaaaaaagcgatgtatacaagccttatttagcgacg accaaaaaagagattagagaagtgctaggcattcctgaacggacattaga taaattgctgaaggtactgaaggcgaatcaggaaattttctttaagatta aaccaggaagaaatggtggcattcaacttgctagtgttaaatcattgttg ctatcgatcattaaattaaaaaaagaagaacgagaaagctatataaaggc gctgacagcttcgtttaatttagaacgtacatttattcaagaaactctaa acaaattggcagaacgccccaaaacggacccacaactcgatttgtttagc tacgatacaggctgaaaataaaacccgcactatgccattacatttatatc tatgatacgtgtttgtttttctttgctggctagcttaattgcttatattt acctgcaataaaggatttcttacttccattatactcccattttccaaaaa catacggggaacacgggaacttattgtacaggccacctcatagttaatgg tttcgagccttcctgcaatctcatccatggaaatatattcatccccctgc cggcctattaatgtgacttttgtgcccggcggatattcctgatccagctc caccataaattggtccatgcaaattcggccggcaattttcaggcgttttc ccttcacaaggatgtcggtccctttcaattttcggagccagccgtccgca tagcctacaggcaccgtcccgatccatgtgtctttttccgctgtgtactc ggctccgtagctgacgctctcgccttttctgatcagtttgacatgtgaca gtgtcgaatgcagggtaaatgccggacgcagctgaaacggtatctcgtcc gacatgtcagcagacgggcgaaggccatacatgccgatgccgaatctgac tgcattaaaaaagcctttttttcagccggagtccagcggcgctgttcgcgc agtggaccattagattctttaacggcagcggagcaatcagctctttaaag cgctcaaactgcattaagaaatagcctctttctttttcatccgctgtcgc aaaatgggtaaataccccttttgcactttaaacgagggttgcggtcaagaa ttgccatcacgttctgaacttcttcctctgtttttacaccaagtctgttc atccccgtatcgaccttcagatgaaaatgaagagaacctttttttcgtgtg gcgggctgcctcctgaagccattcaacagaataacctgttaaggtcacgt catactcagcagcgattgccacatactccgggggaaccgcgccaagcacc aatataggcgccttcaatccctttttgcgcagtgaaatcgcttcatccaa aatggccacggccaagcatgaagcacctgcgtcaagagcagcctttgctg -continued

```
tttctgcatcaccatgcccgtaggcgtttgctttcacaactgccatcaag
tggacatgttcaccgatatgtttttcatattgctgacattttcctttat
cacggacaagtcaatttccgcccacgtatctctgtaaaaggttttgtgc
tcatggaaaactcctctctttttcagaaaatcccagtacgtaattaagt
atttgagaattaattttatattgattaatactaagtttacccagttttca
cctaaaaaacaaatgatgagataatagctccaaaggctaaagaggactat
accaactatttgttaat.
```

In another embodiment, one of the antigens encoded by a sequence within SEQ ID NO: 2 is E7 (bolded in SEQ ID NO:2). In another embodiment, the E7 sequence is set forth in SEQ ID NO: 3

```
                                        (SEQ ID NO: 3)
Ctcgagcatggagatacacctacattgcatgaatatatgttagatttgc
aaccagagacaactgatctctactgttatgagcaattaaatgacagctc
agaggaggaggatgaaatagatggtccagctggacaagcagaaccggac
agagcccattacaatattgtaaccttttgttgcaagtgtgactctacgc
ttcggttgtgcgtacaaagcacacacgtagacattcgtactttggaaga
cctgttaatgggcacactaggaattgtgtgccccatctgttctcagaaa
ccataaactagt.
```

In one embodiment, one of the antigens encoded by a sequence within SEQ ID NO: 2 is a chimeric Her2-neu antigen (italicized in SEQ ID NO: 2). In another embodiment, the chimeric Her2-neu sequence is set forth in SEQ ID NO: 4.

```
                                        (SEQ ID NO: 4)
ctagtggtgatggtgatgatggagctcagatctgtctaagaggcagccat
agggcataagctgtgtcaccagctgcaccgtggatgtcaggcagatgccc
agaaggcgggagacatatggggagcccacaccagccatcacgtatgcttc
gtctaagatttctttgttggctttgggggatgtgttttccctcaacactt
tgatggccactggaattttcacattctccccatcagggatccagatgccc
ttgtagactgtgccaaaagcgccagatccaagcaccttcaccttcctcag
ctccgtctctttcaggatccgcatctgcgcctggttgggcatcgctccgc
taggtgtcagcggctccaccagctccgtttcctgcagcagtctccgcatc
gtgtacttccggatcttctgctgccctcgggcgcacagctggtggcaggc
caggccctcgcccacacactcgtcctctggccggttggcagtgtggagca
gagcttggtgcgggttccgaaagagctggtcccagggcaccgtgtgcacg
aagcagaggtgggtgttatggtggatgagggccagtccactgcccagttc
cctcagtgagcgcagccccagccagctgatgcccagcccttgcagggtca
gcgagtaggcgccattgtgcagaattcgtccccggattacttgcaggttc
tggaagacgctgaggtcaggcaggctgtccggccatgctgagatgtatag
gtaacctgtgatctcttccagagtctcaaacacttggagctgctctggct
ggagcggggcagtgttggaggctgggtccccatcaaagctctccggcaga
aatgccaggctcccaaagatcttcttgcagccagcaaactcctggatatt
```

-continued

```
cttccacaaaatcgtgtcctggtagcagagctgggggttccgctggatca
agacccctcctttcaagatctctgtgaggcttcgaagctgcagctcccgc
aggcctcctggggaggcccctgtgacaggggtggtattgttcagcgggtc
tccattgtctagcacggccagggcatagttgtcctcaaagagctgggtgc
ctcgcacaatccgcagcctctgcagtgggacctgcctcacttggttgtga
gcgatgagcacgtagccctgcacctcctggatatcctgcaggaaggacag
gctggcattggtgggcaggtaggtgagttccaggtttccctgcaccacct
ggcagccctggtagaggtggcggagcatgtccaggtgggttctagat.
```

In another embodiment, a gene encoding the metabolic enzyme provided herein is expressed under the control of the *Listeria* p60 promoter. In another embodiment, the inlA (encodes internalin) promoter is used. In another embodiment, the hly promoter is used. In another embodiment, the actA promoter is used. A skilled artisan, when equipped with the present disclosure and the methods provided herein, will readily understand that different transcriptional promoters, terminators, carrier vectors or specific gene sequences (e.g. those in commercially available cloning vectors) can be used successfully in methods and compositions of the present invention. As is contemplated in the present invention, these functionalities are provided in, for example, the commercially available vectors known as the pUC series. In another embodiment, non-essential DNA sequences (e.g. antibiotic resistance genes) are removed. Each possibility represents a separate embodiment of the present invention.

In another embodiment, the integrase gene is expressed under the control of any other gram positive promoter. In another embodiment, the gene encoding the metabolic enzyme is expressed under the control of any other promoter that functions in *Listeria*. The skilled artisan will appreciate that other promoters or polycistronic expression cassettes may be used to drive the expression of the gene. Each possibility represents a separate embodiment of the present invention.

In one embodiment, a "constitutive" promoter is a nucleotide sequence which, when operably linked with a polynucleotide which encodes or specifies a gene product, causes the gene product to be produced in a living human cell under most or all physiological conditions of the cell.

In one embodiment, an "inducible" promoter is a nucleotide sequence which, when operably linked with a polynucleotide which encodes or specifies a gene product, causes the gene product to be produced in a living cell substantially only when an inducer which corresponds to the promoter is present in the cell.

In one embodiment, a "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

In one embodiment, a recombinant *Listeria* strain provided herein has been passaged through an animal host. In another embodiment, the animal host is a non-human animal host. In another embodiment, the passaging maximizes efficacy of the strain as a vaccine vector. In another embodiment, the passaging stabilizes the immunogenicity of the *Listeria* strain. In another embodiment, the passaging stabilizes the virulence of the *Listeria* strain. In another embodiment, the passaging increases the immunogenicity of the *Listeria* strain. In another embodiment, the passaging increases the virulence of the *Listeria* strain. In another embodiment, the passaging removes unstable sub-strains of the *Listeria* strain. In another embodiment, the passaging reduces the prevalence of unstable sub-strains of the *Listeria* strain. In another embodiment, the passaging attenuates the strain, or in another embodiment, makes the strain less virulent. Methods for passaging a recombinant *Listeria* strain through an animal host are well known in the art, and are described, for example, in U.S. patent application Ser. No. 10/541,614. In one embodiment, the animal through which the *Listeria* is passaged is a mammal, which, in one embodiment, is a mouse. The present invention contemplates the use of mammals for passaging such as mice, rabbits, guinea pigs, hamsters, gerbils, rats, and the like. Such mammals are well known in the art and are available to the skilled artisan through a variety of wholesalers, distributors, and laboratories, for example, Jackson Laboratories (Bar Harbor, Me.). Methods for passaging a recombinant *Listeria* strain through an animal host are known in the art, and are described, for example, in U.S. patent application Ser. No. 10/541,614. Each possibility represents a separate embodiment of the present invention.

In one embodiment, provided herein are methods and compositions for preventing disease, treating disease and vaccinating a human subject. In another embodiment, this invention provides methods and compositions for preventing disease, treating disease and vaccinating an animal subject.

In another embodiment, the present invention is directed to enhancing an anti-tumor immune response of a human or animal. In another embodiment, the methods of enhancing an anti-tumor response in a subject by administering a composition provided herein or a mixture of compositions provided herein can be combined with other known anti-tumor or anti-cancer therapies. In another embodiment, the compositions of the invention can be used alone, or in combination with any therapy in which an adjuvant is appropriate, and may have utility in settings where no adjuvant has been commonly used, such as chemotherapy or radiotherapy.

In another embodiment, the methods provided herein further provide methods of overcoming or "breaking" tolerance toward a heterologous antigen that is a self-antigen. Such antigens may be aberrantly expressed by various tumors which are subject to treatment or prophylaxis under the scope of the present invention by using the methods and compositions provided herein.

In one embodiment, an immune response induced by the methods and compositions provided herein is a therapeutic one. In another embodiment it is a prophylactic immune response. In another embodiment, it is an enhanced immune response over methods available in the art for inducing an immune response in a subject afflicted with the conditions provided herein. In another embodiment, the immune response leads to clearance of a tumor provided herein that is afflicting the subject.

In one embodiment, a tumor is a hypoxic solid tumor. In another embodiment, the tumor is solid tumor. In another embodiment, the tumor is any tumor associated with any cancer provided herein and known in the art.

In one embodiment, recombinant attenuated, *Listeria* expressing truncated listeriolysin O in combination with other therapeutic modalities are useful for enhancing an immune response, and for preventing, and treating a disease including cancer or solid tumors. In one embodiment, recombinant attenuated, *Listeria* expressing truncated ActA in combination with other therapeutic modalities are useful for enhancing an immune response, and for preventing, and treating a disease including cancer or solid tumors. In one embodiment, recombinant attenuated, *Listeria* expressing PEST amino acid sequence in combination with other therapeutic modalities are useful for enhancing an immune response, and for preventing, and treating a disease including cancer or solid tumors.

In another embodiment, provided herein is a method of improving the immunogenicity of a therapeutic vaccine, the method comprising co-administering the vaccine and a composition comprising a single recombinant *Listeria* expressing multiple fusion proteins or a mixture of compositions each comprising a recombinant *Listeria* expressing a fusion protein of the present invention, to a subject, wherein each composition or mixture of compositions enhances the immunogenicity of the vaccine and elicits an antigen-specific immune response, thereby improving the immunogenicity of the vaccine. In one embodiment, the method allows treating a tumor for which the vaccine is specific against. In another embodiment, the vaccine is a drug vaccine, a chemotherapeutic agent, a peptide vaccine, or any other type of vaccine known in the art.

In another embodiment, the LLO utilized in the methods and compositions provided herein is a *Listeria* LLO. In one embodiment, the *Listeria* from which the LLO is derived is *Listeria monocytogenes* (Lm). In another embodiment, the *Listeria* is *Listeria ivanovii*. In another embodiment, the *Listeria* is *Listeria welshimeri*. In another embodiment, the *Listeria* is *Listeria seeligeri*.

In one embodiment, the LLO protein is encoded by the following nucleic acid sequence set forth in (SEQ ID NO: 5).

```
                                        (SEQ ID NO: 5)
atgaaaaaaataatgctagtttttattacacttatattagttagtctac

caattgcgcaacaaactgaagcaaaggatgcatctgcattcaataaaga

aaattcaatttcatccatggcaccaccagcatctccgcctgcaagtcct

aagacgccaatcgaaaagaaacacgcggatgaaatcgataagtatatac

aaggattggattacaataaaaacaatgtattagtataccacggagatgc

agtgacaaatgtgccgccaagaaaaggttacaaagatggaaatgaatat

attgttgtggagaaaaagaagaaatccatcaatcaaaataatgcagaca

ttcaagttgtgaatgcaatttcgagcctaacctatccaggtgctctcgt

aaaagcgaattcggaattagtagaaaatcaaccagatgttctccctgta

aaacgtgattcattaacactcagcattgatttgccaggtatgactaatc

aagacaataaaatagttgtaaaaaatgccactaaatcaaacgttaacaa

cgcagtaaatacattagtggaaagatggaatgaaaaatatgctcaagct

tatccaaatgtaagtgcaaaaattgattatgatgacgaaatggcttaca

gtgaatcacaattaattgcgaaatttggtacagcatttaaagctgtaaa

taatagcttgaatgtaaacttcggcgcaatcagtgaagggaaaatgcaa

gaagaagtcattagttttaaacaaatttactataacgtgaatgttaatg

aacctacaagaccttccagatttttcggcaaagctgttactaaagagca

gttgcaagcgcttggagtgaatgcagaaaatcctcctgcatatatctca

agtgtggcgtatggccgtcaagtttatttgaaattatcaactaattccc

atagtactaaagtaaaagctgcttttgatgctgccgtaagcggaaaatc
```

-continued

```
tgtctcaggtgatgtagaactaacaaatatcatcaaaaattcttccttc
aaagccgtaatttacggaggttccgcaaaagatgaagttcaaatcatcg
acggcaacctcggagacttacgcgatattttgaaaaaaggcgctacttt
taatcgagaaacaccaggagttcccattgcttatacaacaaacttccta
aaagacaatgaattagctgttattaaaaacaactcagaatatattgaaa
caacttcaaaagcttatacagatggaaaaattaacatcgatcactctgg
aggatacgttgctcaattcaacatttcttgggatgaagtaaattatgat
ctcgag.
```

In another embodiment, the LLO protein has the sequence SEQ ID NO: 6. In another embodiment, the LLO protein comprises the sequence set forth in SEQ ID NO: 6.

```
(SEQ ID NO: 6)
MKKIMLVFITLILVSLPIAQQTEAKDASAFNKENS
ISSMAPPASPPASPKTPIEKKHADEIDKYIQGLDY
NKNNVLVYHGDAVTNVPPRKGYKDGNEYIVVEK
KKKSINQNNADIQVVNAISSLTYPGALVKANSEL
VENQPDVLPVKRDSLTLSIDLPGMTNQDNKIVVK
NATKSNVNNAVNTLVERWNEKYAQAYPNVSAKI
DYDDEMAYSESQLIAKFGTAFKAVNNSLNVNFG
AISEGKMQEEVISFKQIYYNVNVNEPTRPSRFFG
KAVTKEQLQALGVNAENPPAYISS VAYGRQVYL
KLSTNSHSTKVKAAFDAAVSGKSVSGDVELTNII
KNSSFKAVIYGGSAKDEVQIIDGNLGDLRDILKK
GATFNRETPGVPIAYTTNFLKDNELAVIKNNSEY
IETTSKAYTDGKINIDHSGGYVAQFNISWDEVNY
DL
```

The first 25 amino acids of the proprotein corresponding to this sequence are the signal sequence and are cleaved from LLO when it is secreted by the bacterium. Thus, in this embodiment, the full length active LLO protein is 504 residues long. In another embodiment, the LLO protein has a sequence set forth in GenBank Accession No. DQ054588, DQ054589, AY878649, U25452, or U25452. In another embodiment, the LLO protein is a variant of an LLO protein. In another embodiment, the LLO protein is a homologue of an LLO protein. Each possibility represents a separate embodiment of the present invention.

In another embodiment, the LLO protein utilized to construct a composition (in any form) of the present invention (in another embodiment, used as the source of the LLO fragment incorporated in the compositions provided herein) has, in another embodiment, the sequence:

```
MKKIMLVFITLILVSLPIAQQTEAKDASAFNKENSISSMAPPASPPASP
KTPIEKKHADEIDKYIQGLDYNKNNVLVYHGDAVTNVPPRKGYKDGNEY
IVVEKKKKSINQNNADIQVVNAISSLTYPGALVKANSELVENQPDVLPV
KRDSLTLSIDLPGMTNQDNKIVVKNATKSNVNNAVNTLVERWNEKYAQA
```

-continued

```
YPNVSAKIDYDDEMAYSESQLIAKFGTAFKAVNNSLNVNFGAISEGKMQ
EEVISFKQIYYNVNVNEPTRPSRFFGKAVTKEQLQALGVNAENPPAYIS
SVAYGRQVYLKLSTNSHSTKVKAAFDAAVSGKSVSGDVELTNIIKNSSF
KAVIYGGSAKDEVQIIDGNLGDLRDILKKGATFNRETPGVPIAYTTNFL
KDNELAVIKNNSEYIETTSKAYTDGKINIDHSGGYVAQFNISWDEVNYD
PEGNEIVQHKNWSENNKSKLAHFTSSIYLPGNARNINVYAKECTGLAWE
WWRTVIDDRNLPLVKNRNISIWGTTLYPKYSNKVDNPIE
```

(GenBank Accession No. P13128; SEQ ID NO: 123; nucleic acid sequence is set forth in GenBank Accession No. X15127). The first 25 AA of the proprotein corresponding to this sequence are the signal sequence and are cleaved from LLO when it is secreted by the bacterium. Thus, in this embodiment, the full-length active LLO protein is 504 residues long. In another embodiment, the LLO protein is a homologue of SEQ ID NO: 123. In another embodiment, the LLO protein is a variant of SEQ ID NO: 123. In another embodiment, the LLO protein is an isomer of SEQ ID NO: 123. In another embodiment, the LLO protein is a fragment of SEQ ID NO: 123. In another embodiment, the LLO protein is a fragment of a homologue of SEQ ID NO: 123. In another embodiment, the LLO protein is a fragment of a variant of SEQ ID NO: 123. In another embodiment, the LLO protein is a fragment of an isomer of SEQ ID NO: 123. Each possibility represents a separate embodiment of the present invention.

In another embodiment, "truncated LLO" or "tLLO" refers to a fragment of LLO that comprises a PEST amino acid sequence domain. In another embodiment, the terms refer to an LLO fragment that does not contain the activation domain at the amino terminus and does not include cystine 484. In another embodiment, the LLO protein is a ctLLO. In another embodiment ctLLO is full length LLO in which the cholesterol binding domain (CBD) has been replaced by an antigen peptide or epitope thereof. In another embodiment "replaced" in can mean via a substitution, or deletion mutation. In another embodiment, the LLO protein is a mutLLO. In another embodiment, a mutLLO is one in which the CBD has been mutated. In another embodiment, the mutLLO is one in which the amino acids in the CBD have been mutated. In another embodiment the mutation is a point mutation, a deletion, an inversion, a substitution, or a combination thereof. In another embodiment the mutation is any mutation known in the art. In another embodiment, the mutated LLO protein comprises any combination of deletions, substitutions, or point mutations in the CBD and/or deletions of the signal sequence of LLO. In another embodiment, mutating the CBD reduces the hemolytic activity of LLO. In another embodiment, the CBD is replaced by known HLA class I restricted epitopes to be used as a vaccine. In another embodiment, the mutated LLO is expressed and purified from *E. coli* expression systems.

In another embodiment, the LLO fragment consists of a PEST sequence. In another embodiment, the LLO fragment comprises a PEST sequence. In another embodiment, the LLO fragment consists of about the first 400 to 441 amino acids of the 529 amino acid full-length LLO protein. In another embodiment, the LLO fragment is a non-hemolytic form of the LLO protein.

In another embodiment, the present invention provides a recombinant polypeptide comprising (a) a mutated LLO protein, wherein the mutated LLO protein contains an internal deletion, the internal deletion comprising the cholesterol-binding domain of the mutated LLO protein; and (b) a heterologous peptide of interest. In another embodiment, the sequence of the LLO cholesterol-binding domain is well known in the art and is described in U.S. Pat. No. 8,771,702, which is incorporated by reference herein. In another embodiment, the internal deletion is an 11-50 amino acid internal deletion. In another embodiment, the internal deletion is inactivating with regard to the hemolytic activity of the recombinant protein or polypeptide. In another embodiment, the recombinant protein or polypeptide exhibits a reduction in hemolytic activity relative to wild-type LLO. In another embodiment, provided herein is a recombinant *Listeria* comprising a recombinant protein or recombinant polypeptide provided herein. Each possibility represents another embodiment of the present invention.

In another embodiment, the present invention provides a recombinant protein or polypeptide comprising (a) a mutated LLO protein, wherein the mutated LLO protein contains an internal deletion, the internal deletion comprising a fragment of the cholesterol-binding domain of the mutated LLO protein; and (b) a heterologous peptide of interest. In another embodiment, the internal deletion is a 1-11 amino acid internal deletion. In another embodiment, the sequence of the cholesterol-binding domain is set forth in SEQ ID NO: 130. In another embodiment, the internal deletion is inactivating with regard to the hemolytic activity of the recombinant protein or polypeptide. In another embodiment, the recombinant protein or polypeptide exhibits a reduction in hemolytic activity relative to wild-type LLO. Each possibility represents another embodiment of the present invention.

The mutated region of methods and compositions of the present invention comprises, in another embodiment, residue C484 of SEQ ID NO: 123. In another embodiment, the mutated region comprises a corresponding cysteine residue of a homologous LLO protein. In another embodiment, the mutated region comprises residue W491 of SEQ ID NO: 123. In another embodiment, the mutated region comprises a corresponding tryptophan residue of a homologous LLO protein. In another embodiment, the mutated region comprises residue W492 of SEQ ID NO: 123. In another embodiment, the mutated region comprises residues C484, W491 and W492 of SEQ ID NO: 123. In another embodiment, the mutated region comprises a corresponding tryptophan residue of a homologous LLO protein. Methods for identifying corresponding residues of a homologous protein are well known in the art, and include, for example, sequence alignment. Each possibility represents a separate embodiment of the present invention.

In another embodiment, the mutated region comprises residues C484 and W491. In another embodiment, the mutated region comprises residues C484 and W492. In another embodiment, the mutated region comprises residues W491 and W492. In another embodiment, the mutated region comprises residues C484, W491, and W492. Each possibility represents a separate embodiment of the present invention.

In another embodiment, the mutated region of an LLO protein provided in the methods and compositions of the present invention comprises the cholesterol-binding domain of the mutated LLO protein or fragment thereof. For example, a mutated region consisting of residues 470-500, 470-510, or 480-500 of SEQ ID NO: 37 comprises the CBD thereof (residues 483-493). In another embodiment, the mutated region is a fragment of the CBD of the mutated LLO protein or fragment thereof. For example, as provided herein, residues C484, W491, and W492, each of which is a fragment of the CBD, were mutated to alanine residues (Example 38). Further, as provided herein, a fragment of the CBD, residues 484-492, was replaced with a heterologous sequence from NY-ESO-1 (Example 39). In another embodiment, the mutated region overlaps the CBD of the mutated LLO protein or fragment thereof. For example, a mutated region consisting of residues 470-490, 480-488, 490-500, or 486-510 of SEQ ID NO: 123 comprises the CBD thereof. In another embodiment, a single peptide may have a deletion in the signal sequence and a mutation or substitution in the CBD. Each possibility represents a separate embodiment of the present invention.

In another embodiment, an internal deletion in an LLO protein of the methods and compositions of the present invention comprises the CBD of an LLO protein or fragment thereof. For example, an internal deletion consisting of residues 470-500, 470-510, or 480-500 of SEQ ID NO: 37 comprises the CBD thereof (residues 483-493). In another embodiment, the internal deletion is a fragment of the CBD of the mutated LLO protein or fragment thereof. For example, residues 484-492, 485-490, and 486-488 are all fragments of the CBD of SEQ ID NO: 123. In another embodiment, the internal deletion overlaps the CBD of the mutated LLO protein or fragment thereof. For example, an internal deletion consisting of residues 470-490, 480-488, 490-500, or 486-510 of SEQ ID NO: 123 comprises the CBD thereof. Each possibility represents a separate embodiment of the present invention.

In one embodiment, the LLO fragment consists of about residues 1-25. In another embodiment, the LLO fragment consists of about residues 1-50. In another embodiment, the LLO fragment consists of about residues 1-75. In another embodiment, the LLO fragment consists of about residues 1-100. In another embodiment, the LLO fragment consists of about residues 1-125. In another embodiment, the LLO fragment consists of about residues 1-150. In another embodiment, the LLO fragment consists of about residues 1175. In another embodiment, the LLO fragment consists of about residues 1-200. In another embodiment, the LLO fragment consists of about residues 1-225. In another embodiment, the LLO fragment consists of about residues 1-250. In another embodiment, the LLO fragment consists of about residues 1-275. In another embodiment, the LLO fragment consists of about residues 1-300. In another embodiment, the LLO fragment consists of about residues 1-325. In another embodiment, the LLO fragment consists of about residues 1-350. In another embodiment, the LLO fragment consists of about residues 1-375. In another embodiment, the LLO fragment consists of about residues 1-400. In another embodiment, the LLO fragment consists of about residues 1-425. In another embodiment, the LLO fragment consists of about residues 1-441. Each possibility represents a separate embodiment of the present invention.

In another embodiment, the LLO fragment contains residues of a homologous LLO protein that correspond to one of the above AA ranges. The residue numbers need not, in another embodiment, correspond exactly with the residue numbers enumerated above; e.g. if the homologous LLO protein has an insertion or deletion, relative to an LLO protein utilized herein.

In another embodiment, homologues of LLO from other species, including known lysins, such as streptolysin O, perfringolysin O, pneumolysin, etc, or fragments thereof may be used in the invention.

In one embodiment, the live attenuated *Listeria* or recombinant *Listeria* provided herein expresses an ActA protein or a fragment thereof. In another embodiment of the methods and compositions of the present invention, a fragment of an ActA protein is fused to the heterologous antigen or a fragment thereof also provided herein. In another embodiment, the fragment of an ActA protein has the sequence:

MRAMMVVFITANCITINPDIIFAATDSEDSSLNT-
DEWEEEKTEEQPSEVNTGPRY-
ETAREVSSRDIKELEKSNKVRNTNKADLIAMLKEKA-
EKGPNINNNNSEQTENAAINEEASGADRPAIQVER-
RHPGLPSDSAAEIKKRRKAIASSDSELESLTYPDKPT-
KVNKKKVAKESVADASESDLDSSMQSADESSPQPL-
KANQQPFFPKVFKKIKDAGKWVRDKIDENPE
VKKAIVDKSAGLIDQLLTKKKSEEVNASDFPPPPT-
DEELRLALPETPMLLGFNAPATSEPSSFEFPPPPT-
DEELRLALPETPMLLGFNAPATSEPSSFEFPPPPT-
EDELEIIRETASSLDSSFTRGDLASLRNAINRHSQN-
FSDFPPIPTEEELNGRGGRP (SEQ ID No: 7). In another embodiment, an ActA AA sequence of methods and compositions of the present invention comprises the sequence set forth in SEQ ID No: 7. In another embodiment, the ActA AA sequence is a homologue of SEQ ID No: 7. In another embodiment, the ActA AA sequence is a variant of SEQ ID No: 7. In another embodiment, the ActA AA sequence is a fragment of SEQ ID No: 7. In another embodiment, the ActA AA sequence is an isoform of SEQ ID No: 5. Each possibility represents a separate embodiment of the present invention.

In another embodiment, the ActA fragment is encoded by a recombinant nucleotide comprising the sequence:
ATGCGTGCGATGATGGTGGTTTTCATTACTGCCAAT-
TGCATTACGATTAACCCCGACATAATATTTGCAGC-
GACAGATAGCGAAGATTCTAGTCTAAACACAGAT-
GAATGGGAAGAAGAAAAAACAGAAGAGCAACC-
AAGCGAGGTAAATACGGGACCAAGATACGAAACT-
GCACGTGAAGTAAGTTCACGTGATAT-
TAAAGAACTAGAAAAATCGAATAAAGTGAGAA
ATACGAACAAAGCAGACCTAATAGCAATGTT-
GAAAGAAAAAGCAGAAAAAGGTCCAAATAT-
CAATAATAACAACAGTGAACAAACTGAGAATGCG-
GCTATAAATGAAGAGGCTTCAGGAGCCGACCGA-
CCAGCTATACAAGTGGAGCGTCGTCATCCAGGATT-
GCCATCGGATAGCGCAGCGGAAAT-
TAAAAAAAGAAGGAAAGCCATAGCATCATCGGA-
TAGTGAGCT
TGAAAGCCTTACTTATCCGGATAAACCAACAAAAG-
TAAATAAGAAAAAAGTGGCGAAAGAGTCAGTT-
GCGGATGCTTCTGAAAGTGACTTAGATTCTAGCAT-
GCAGTCAGCAGATGAGTCTTCACCACAACCTTTA-
AAAGCAAACCAACAACCATTTTTCCCTAAAGTATT-
TAAAAAAATAAAAGATGCGGGGAAATGGGTACGT-
GATAAAATCGACGAAAATCCTGAA
GTAAAGAAAGCGATTGTTGATAAAAGTGCAGGGT-
TAATTGACCAATTATTAACCAAAAAGAAAAGT-
GAAGAGGTAAATGCTTCGGACTTCCCGCCACCAC-
CTACGGATGAAGAGTTAAGACTTGCTTTGCCAGA-
GACACCAATGCTTCTTGGTTTTAATGCTCCTGCTA-
CATCAGAACCGAGCTCATTCGAATTTCCACCAC-
CACCTACGGATGAAGAGTTAAGACTTGCTTTGCCA-
GAGACGCCAATGCTTCTTGGTTTAATGCTCC-
TGCTACATCGGAACCGAGCTCGTTCGAATTTCCAC-
CGCCTCCAACAGAAGATGAACTAGAAATCATC-
CGGGAAACAGCATCCTCGCTAGATTCTAGTTTTA-
CAAGAGGGGATTTAGCTAGTTTGAGAAATGCTAT-
TAATCGCCATAGTCAAAATTTCTCTGATTTCCCAC-
CAATCCCAACAGAAGAAGA GTTGAA CGGGAGAG-
GCGGTAGACCA (SEQ ID NO: 8). In another embodiment, the recombinant nucleotide has the sequence set forth in SEQ ID NO: 8. In another embodiment, an ActA-encoding nucleotide of methods and compositions of the present invention comprises the sequence set forth in SEQ ID No: 8. In another embodiment, the ActA-encoding nucleotide is a homologue of SEQ ID No: 8. In another embodiment, the ActA-encoding nucleotide is a variant of SEQ ID No: 8. In another embodiment, the ActA-encoding nucleotide is a fragment of SEQ ID No: 8. In another embodiment, the ActA-encoding nucleotide is an isoform of SEQ ID No: 8. Each possibility represents a separate embodiment of the present invention.

In another embodiment, the ActA fragment is encoded by a recombinant nucleotide comprising the sequence:

Tttatcacgtacccatttccccgcatcttttatttttttaaatactt-
tagggaaaaatggtttttgatttgcttttaaaggttgtggtgtagactcgtctgctgact-
gcatgctagaatctaagtcactttcagaagcatccacaactgactctttcgc-
cacttttctcttatttgcttttgttggtttatctggataagtaaggctttcaagctcacta-
tccgacgac gctatggcttttcttctttttttaatttccgctgcgctatccgatgaca-
gacctggatgacgacgctccacttgcagagttggtcggtcgactcctgaagcctct-
tcatttatagccacatttcctgtttgctcaccgttgttattattgttattcggac-
ctttctctgcttttgctttcaacattgctattaggtctgctttgttcgtatttttcacttta-
ttcgatt tttctagttcctcaatatcacgtgaacttacttcacgtgcagtttcgtatcttg-
gtcccgtatttacctcgcttggctgctcttctgtttttcttcttcccattcatctgt-
gtttagactggaatcttcgctatctgtcgctgcaaatattatgtcggggttaatcg-
taatgcagttggcagtaatgaaaactaccatcatcgcacgcat (SEQ ID NO: 9). In another embodiment, the recombinant nucleotide has the sequence set forth in SEQ ID NO: 9. In another embodiment, an ActA-encoding nucleotide of methods and compositions of the present invention comprises the sequence set forth in SEQ ID No: 9. In another embodiment, the ActA-encoding nucleotide is a homologue of SEQ ID No: 9. In another embodiment, the ActA-encoding nucleotide is a variant of SEQ ID No: 9. In another embodiment, the ActA-encoding nucleotide is a fragment of SEQ ID No: 9. In another embodiment, the ActA-encoding nucleotide is an isoform of SEQ ID No: 9. In another embodiment SEQ ID NO: 9 is used to arrive at the construct of SEQ ID NO: 2, also provided herein. Each possibility represents a separate embodiment of the present invention.

In another embodiment of methods and compositions of the present invention, a fragment of an ActA protein is fused to a heterologous antigen or fragment thereof. In another embodiment, the fragment of an ActA protein has the sequence as set forth in Genbank Accession No. AAF04762. In another embodiment, an ActA AA sequence of methods and compositions of the present invention comprises the sequence set forth in Genbank Accession No. AAF04762. In another embodiment, the ActA AA sequence is a homologue of Genbank Accession No. AAF04762. In another embodiment, the ActA AA sequence is a variant of Genbank Accession No. AAF04762. In another embodiment, the ActA AA sequence is a fragment of Genbank Accession No. AAF04762. In another embodiment, the ActA AA sequence is an isoform of Genbank Accession No. AAF04762. Each possibility represents a separate embodiment of the present invention.

An N-terminal fragment of an ActA protein utilized in methods and compositions of the present invention has, in another embodiment, the sequence set forth in SEQ ID NO: 10: MRAMMVVFITANCITINPDIIFAATDSEDSSLNT-
DEWEEEKTEEQPSEVNTGPRY-
ETAREVSSRDIKELEKSNKVRNTNKADLIAMLKEKA-
EKGPNINNNNSEQTENAAINEEASGADRPAIQVER-
RHPGLPSDSAAEIKKRRKAIASSDSELESLTYPDKPT-
KVNKKKVAKESVADASESDLDSSMQSADESSPQPL-
KANQQPFFPKVFKKIKDAGKWVRDKIDENPE
VKKAIVDKSAGLIDQLLTKKKSEEVNASDFPPPPT- DEELRLALPETPMLLGFNAPATSEPSSFEFPPPPT-DEELRLALPETPMLLGFNAPATSEPSSFEFPPPPT-EDELEIIRETASSLDSSFTRGDLASLRNAINRHSQN-FSDFPPIPTEEELNGRGGRP. In another embodiment, the ActA fragment comprises the sequence set forth in SEQ ID NO: 10. In another embodiment, the ActA fragment is any other ActA fragment known in the art. Each possibility represents a separate embodiment of the present invention.

In another embodiment, the recombinant nucleotide encoding a fragment of an ActA protein comprises the sequence set forth in SEQ ID NO: 11: Atgcgtgcgatgatggtg-gttttcattactgccaattgcattacgattaaccccgacataatatttgcagcgaca-gatagcgaagattctagtctaaacacagatgaatgggaagaagaaaaaca-gaagagcaaccaagcgaggtaaatacgggaccaagatacgaaactgcacgt-gaagtaagttcacgtgatattaaagaactagaaaaatcgaataaagtgagaa atacgaacaaagcagacctaatagcaatgttgaaagaaaaagcagaaaaaggtc-caaatatcaataataacaacagtgaacaaactgagaatgcggctataaat-gaagaggcttcaggagccgaccgaccagctatacaagtggagcgtcgtcatcca-ggattgccatcggatagcgcagcggaaattaaaaaaagaaggaaagccatag-catcatcggatagtgagcttgaaagccttacttatccggataaaccaacaaaag-taaataagaaaaaagtggcgaaagagtcagttgcggatgcttctgaaagtgactta-gattctagcatgcagtcagcagatgagtcttcaccacaacctttaaaagcaaac-caacaaccatttttccctaaagtatttaaaaaaataaaagatgcggggaaatggg-tacgtgataaaatcgacgaaaatcctgaa gtaaagaaagcgattgttgataaaagt-gcagggttaattgaccaattattaaccaaaaagaaaagtgaagaggtaaatgct-tcggacttcccgccaccacctacggatgaagagttaagacttgctttgccagaga-caccaatgcttcttggttttaatgctcctgctacatcagaaccgagctcattcgaat-ttccaccaccacctacggatgaagagttaagacttg ctttgccagagacgccaat-gcttcttggttttaatgctcctgctacatcggaaccgagctcgttcgaatttccac-cgcctccaacagaagatgaactagaaatcatccgggaaacagcatcctcgcta-gattctagttttacaagaggggatttagctagtttgagaaatgctattaatcgccata-gtcaaaatttctctgatttcccaccaatcccaacagaagaagagttgaacggga-gaggcggtagacca. In another embodiment, the recombinant nucleotide has the sequence set forth in SEQ ID NO: 11. In another embodiment, the recombinant nucleotide comprises any other sequence that encodes a fragment of an ActA protein. Each possibility represents a separate embodiment of the present invention.

In another embodiment, the ActA fragment is encoded by a recombinant nucleotide comprising the sequence as set forth in Genbank Accession No. AF103807. In another embodiment, the recombinant nucleotide has the sequence set forth in Genbank Accession No. AF103807. In another embodiment, an ActA-encoding nucleotide of methods and compositions of the present invention comprises the sequence set forth in Genbank Accession No. AF103807. In another embodiment, the ActA-encoding nucleotide is a homologue of Genbank Accession No. AF103807. In another embodiment, the ActA-encoding nucleotide is a variant of Genbank Accession No. AF103807. In another embodiment, the ActA-encoding nucleotide is a fragment of Genbank Accession No. AF103807. In another embodiment, the ActA-encoding nucleotide is an isoform of Genbank Accession No. AF103807. Each possibility represents a separate embodiment of the present invention. In another embodiment, a truncated ActA is an ActA-N100 or a modified version thereof (referred to as ActA-N100*) in which a PEST motif has been deleted and containing the nonconservative QDNKR substitution as described in US Patent Publication Serial No. 2014/0186387.

In another embodiment, the ActA fragment is any other ActA fragment known in the art. In another embodiment, a recombinant nucleotide of the present invention comprises any other sequence that encodes a fragment of an ActA protein. In another embodiment, the recombinant nucleotide comprises any other sequence that encodes an entire ActA protein. Each possibility represents a separate embodiment of the present invention.

In one embodiment, the live attenuated *Listeria* or recombinant *Listeria* provided herein expresses a PEST sequence peptide. In another embodiment of methods and compositions of the present invention, a PEST AA sequence is fused to the heterologous antigen or fragment thereof. In another embodiment, a PEST AA sequence is KENSISSMAPPASP-PASPKTPIEKKHADEIDK (SEQ ID NO: 12). In another embodiment, the PEST sequence is KENSISSMAPPASP-PASPK (SEQ ID No: 13). In another embodiment, fusion of an antigen to any LLO sequence that includes one of the PEST AA sequences enumerated herein can enhance cell mediated immunity against an antigen.

In another embodiment, a PEST AA sequence is a PEST sequence from a *Listeria* ActA protein. In another embodiment, the PEST sequence is KTEEQPSEVNTGPR (SEQ ID NO: 14), KASVTDTSEGDLDSSMQSADESTPQPLK (SEQ ID NO: 15), KNEEVNASDFPPPPTDEELR (SEQ ID NO: 16), or RGGIPTSEEFSSLNSGDFTDDENSETTEEE-IDR (SEQ ID NO: 17). In another embodiment, the PEST sequence is a variant of the PEST sequence described hereinabove, which in one embodiment, is KESVVDASE SDLDSSMQSADESTPQPLK (SEQ ID NO: 18), K SEEVNASDFPPPPTDEELR (SEQ ID NO: 19), or RGG RPTSEEFSSLNSGDFTDDENSETTEEEIDR (SEQ ID NO: 20), as would be understood by a skilled artisan. In another embodiment, the PEST sequence is from *Listeria seeligeri* cytolysin, encoded by the lso gene. In another embodiment, the PEST sequence is RSEVTISPAETPESP-PATP (SEQ ID NO: 21). In another embodiment, the PEST sequence is from Streptolysin O protein of *Streptococcus* sp. In another embodiment, the PEST sequence is from *Streptococcus pyogenes* Streptolysin O, e.g. KQN-TASTETTTTNEQPK (SEQ ID NO: 22) at AA 35-51. In another embodiment, the PEST sequence is from *Streptococcus equisimilis* Streptolysin O, e.g. KQNTAN-TETTTTNEQPK (SEQ ID NO: 23) at AA 38-54. In another embodiment, the PEST sequence has a sequence selected from SEQ ID NO: 14-23. In another embodiment, the PEST sequence is another PEST AA sequence derived from a prokaryotic organism.

Identification of PEST amino acid sequences or "PEST sequences" is well known in the art, and is described, for example in Rogers S et al (Amino acid sequences common to rapidly degraded proteins: the PEST hypothesis. Science 1986; 234(4774):364-8) and Rechsteiner M et al (PEST sequences and regulation by proteolysis. Trends Biochem Sci 1996; 21(7):267-71). "PEST sequence" refers, in another embodiment, to a region rich in proline (P), glutamic acid (E), serine (S), and threonine (T) residues. In another embodiment, the PEST sequence is flanked by one or more clusters containing several positively charged amino acids. In another embodiment, the PEST sequence mediates rapid intracellular degradation of proteins containing it. In another embodiment, the PEST sequence fits an algorithm disclosed in Rogers et al. In another embodiment, the PEST sequence fits an algorithm disclosed in Rechsteiner et al. In another embodiment, the PEST sequence contains one or more internal phosphorylation sites, and phosphorylation at these sites precedes protein degradation.

In one embodiment, PEST sequences of prokaryotic organisms are identified in accordance with methods such as described by, for example Rechsteiner and Rogers (1996, Trends Biochem. Sci. 21:267-271) for LM and in Rogers S et al (Science 1986; 234(4774):364-8). Alternatively, PEST AA sequences from other prokaryotic organisms can also be identified based on this method. Other prokaryotic organisms wherein PEST AA sequences would be expected to include, but are not limited to, other *Listeria* species. In one embodiment, the PEST sequence fits an algorithm disclosed in Rogers et al. In another embodiment, the PEST sequence fits an algorithm disclosed in Rechsteiner et al. In another embodiment, the PEST sequence is identified using the PEST-find program.

In another embodiment, identification of PEST motifs is achieved by an initial scan for positively charged AA R, H, and K within the specified protein sequence. All AA between the positively charged flanks are counted and only those motifs are considered further, which contain a number of AA equal to or higher than the window-size parameter. In another embodiment, a PEST-like sequence must contain at least 1 P, 1 D or E, and at least 1 S or T.

In another embodiment, the quality of a PEST motif is refined by means of a scoring parameter based on the local enrichment of critical AA as well as the motifs hydrophobicity. Enrichment of D, E, P, S and T is expressed in mass percent (w/w) and corrected for 1 equivalent of D or E, 1 of P and 1 of S or T. In another embodiment, calculation of hydrophobicity follows in principle the method of J. Kyte and R. F. Doolittle (Kyte, J and Dootlittle, R F. J. Mol. Biol. 157, 105 (1982).

In another embodiment, a potential PEST motif's hydrophobicity is calculated as the sum over the products of mole percent and hydrophobicity index for each AA species. The desired PEST score is obtained as combination of local enrichment term and hydrophobicity term as expressed by the following equation:

$$\text{PEST score}=0.55*\text{DEPST}-0.5*\text{hydrophobicity index.}$$

It will be appreciated that the terms "PEST amino acid sequence", "PEST sequence", "PEST-like sequence" or "PEST-like sequence peptide" can encompass peptides having a score of at least +5, using the above algorithm. In another embodiment, the term refers to a peptide having a score of at least 6. In another embodiment, the peptide has a score of at least 7. In another embodiment, the score is at least 8. In another embodiment, the score is at least 9. In another embodiment, the score is at least 10. In another embodiment, the score is at least 11. In another embodiment, the score is at least 12. In another embodiment, the score is at least 13. In another embodiment, the score is at least 14. In another embodiment, the score is at least 15. In another embodiment, the score is at least 16. In another embodiment, the score is at least 17. In another embodiment, the score is at least 18. In another embodiment, the score is at least 19. In another embodiment, the score is at least 20. In another embodiment, the score is at least 21. In another embodiment, the score is at least 22. In another embodiment, the score is at least 22. In another embodiment, the score is at least 24. In another embodiment, the score is at least 24. In another embodiment, the score is at least 25. In another embodiment, the score is at least 26. In another embodiment, the score is at least 27. In another embodiment, the score is at least 28. In another embodiment, the score is at least 29. In another embodiment, the score is at least 30. In another embodiment, the score is at least 32. In another embodiment, the score is at least 35. In another embodiment, the score is at least 38. In another embodiment, the score is at least 40. In another embodiment, the score is at least 45. Each possibility represents a separate embodiment of the present invention.

In another embodiment, the PEST sequence is identified using any other method or algorithm known in the art, e.g the CaSPredictor (Garay-Malpartida H M, Occhiucci J M, Alves J, Belizario J E. Bioinformatics. 2005 June; 21 Suppl 1:i169-76). In another embodiment, the following method is used:

A PEST index is calculated for each stretch of appropriate length (e.g. a 30-35 AA stretch) by assigning a value of 1 to the AA Ser, Thr, Pro, Glu, Asp, Asn, or Gln. The coefficient value (CV) for each of the PEST residue is 1 and for each of the other AA (non-PEST) is 0.

Each method for identifying a PEST-like sequence represents a separate embodiment of the present invention.

In another embodiment, the PEST sequence is any other PEST sequence known in the art. Each PEST sequence and type thereof represents a separate embodiment of the present invention.

It will be appreciated that the term "Fusion to a PEST sequence" may encompass fusion to a protein fragment comprising a PEST sequence. In another embodiment, the term includes cases wherein the protein fragment comprises surrounding sequence other than the PEST sequence. In another embodiment, the protein fragment consists of the PEST sequence. It will also be appreciated that the term "fusion" encompasses fusion to two peptides or protein fragments either linked together at their respective ends or embedded one within the other.

In another embodiment, provided herein is a vaccine comprising a recombinant form of *Listeria* of the present invention.

In another embodiment, provided herein, is a culture of a recombinant form of *Listeria* of the present invention.

Another embodiment is a plasmid such as pCR2.1 (Invitrogen, La Jolla, Calif.), which is a prokaryotic expression vector with a prokaryotic origin of replication and promoter/regulatory elements to facilitate expression in a prokaryotic organism. In another embodiment, extraneous nucleotide sequences are removed to decrease the size of the plasmid and increase the size of the cassette that can be placed therein.

Such methods are well known in the art, and are described in, for example, Sambrook et al. (1989, Molecular Cloning: A Laboratory Manual, Cold Spring Harbor Laboratory Press, New York) and Ausubei et al. (1997, Current Protocols in Molecular Biology, Green & Wiley, New York).

Antibiotic resistance genes are used in the conventional selection and cloning processes commonly employed in molecular biology and vaccine preparation. Antibiotic resistance genes contemplated in the present invention include, but are not limited to, gene products that confer resistance to ampicillin, penicillin, methicillin, streptomycin, erythromycin, kanamycin, tetracycline, cloramphenicol (CAT), neomycin, hygromycin, gentamicin and others well known in the art. Each gene represents a separate embodiment of the present invention.

Methods for transforming bacteria are well known in the art, and include calcium-chloride competent cell-based methods, electroporation methods, bacteriophage-mediated transduction, chemical, and physical transformation techniques (de Boer et al, 1989, Cell 56:641-649; Miller et al, 1995, FASEB J., 9:190-199; Sambrook et al. 1989, Molecular Cloning: A Laboratory Manual, Cold Spring Harbor Laboratory, New York; Ausubel et al., 1997, Current Protocols in Molecular Biology, John Wiley & Sons, New York; Gerhardt et al., eds., 1994, Methods for General and Molecular Bacteriology, American Society for Microbiology, Washington, D.C.; Miller, 1992, A Short Course in Bacterial Genetics, Cold Spring Harbor Laboratory Press, Cold Spring Harbor, N.Y.) In another embodiment, the

*Listeria* vaccine strain of the present invention is transformed by electroporation. Each method represents a separate embodiment of the present invention.

In another embodiment, conjugation is used to introduce genetic material and/or plasmids into bacteria. Methods for conjugation are well known in the art, and are described, for example, in Nikodinovic J et al. (A second generation snp-derived *Escherichia coli-Streptomyces* shuttle expression vector that is generally transferable by conjugation. Plasmid. 2006 November; 56(3):223-7) and Auchtung J M et al (Regulation of a *Bacillus subtilis* mobile genetic element by intercellular signaling and the global DNA damage response. Proc Natl Acad Sci USA. 2005 Aug. 30; 102 (35):12554-9). Each method represents a separate embodiment of the present invention.

It will be appreciated that the term "transforming," can be used identically with the term "transfecting," and refers to engineering a bacterial cell to take up a plasmid or other heterologous DNA molecule. It is also to be understood that the term "transforming" can refer to engineering a bacterial cell to express a gene of a plasmid or other heterologous DNA molecule.

In one embodiment, a commercially available plasmid is used in the present invention. Such plasmids are available from a variety of sources, for example, Invitrogen (La Jolla, Calif.), Stratagene (La Jolla, Calif.), Clontech (Palo Alto, Calif.), or can be constructed using methods well known in the art. Plasmids and other expression vectors useful in the present invention are described elsewhere herein, and can include such features as a promoter/regulatory sequence, an origin of replication for gram negative and gram positive bacteria, an isolated nucleic acid encoding a fusion protein and an isolated nucleic acid encoding an amino acid metabolism gene. Further, an isolated nucleic acid encoding a fusion protein and an amino acid metabolism gene will have a promoter suitable for driving expression of such an isolated nucleic acid. Promoters useful for driving expression in a bacterial system are well known in the art, and include bacteriophage lambda, the bla promoter of the beta-lactamase gene of pBR322, and the CAT promoter of the chloramphenicol acetyl transferase gene of pBR325. Further examples of prokaryotic promoters include the major right and left promoters of 5 bacteriophage lambda (PL and PR), the trp, recA, lacZ, lad, and gal promoters of *E. coli*, the alpha-amylase (Ulmanen et al, 1985. J. Bacteriol. 162:176-182) and the S28-specific promoters of *B. subtilis* (Gilman et al, 1984 Gene 32:11-20), the promoters of the bacteriophages of *Bacillus* (Gryczan, 1982, In: The Molecular Biology of the Bacilli, Academic Press, Inc., New York), and *Streptomyces* promoters (Ward et al, 1986, Mol. Gen. Genet. 203:468-478). Additional prokaryotic promoters contemplated in the present invention are reviewed in, for example, Glick (1987, J. Ind. Microbiol. 1:277-282); Cenatiempo, (1986, Biochimie, 68:505-516); and Gottesman, (1984, Ann. Rev. Genet. 18:415-442). Further examples of promoter/regulatory elements contemplated in the present invention include, but are not limited to the *Listerial* prfA promoter, the *Listerial* hly promoter, the *Listerial* p60 promoter and the Listerial ActA promoter (GenBank Acc. No. NC_003210) or fragments thereof.

Recombinant proteins of the present invention are synthesized, in another embodiment, using recombinant DNA methodology. This involves, in one embodiment, creating a DNA sequence, placing the DNA in an expression cassette, such as the plasmid of the present invention, under the control of a particular promoter/regulatory element, and expressing the protein. DNA encoding a recombinant protein (e.g. non-hemolytic LLO) of the present invention is prepared, in another embodiment, by any suitable method, including, for example, cloning and restriction of appropriate sequences or direct chemical synthesis by methods such as the phosphotriester method of Narang et al. (1979, Meth. Enzymol. 68: 90-99); the phosphodiester method of Brown et al. (1979, Meth. Enzymol 68: 109-151); the diethylphosphoramidite method of Beaucage et al. (1981, Tetra. Lett., 22: 15 1859-1862); and the solid support method of U.S. Pat. No. 4,458,066.

In another embodiment, chemical synthesis is used to produce a single stranded oligonucleotide. This single stranded oligonucleotide is converted, in various embodiments, into double stranded DNA by hybridization with a complementary sequence, or by polymerization with a DNA polymerase using the single strand as a template. One of skill in the art would recognize that while chemical synthesis of DNA is limited to sequences of about 100 bases, longer sequences can be obtained by the ligation of shorter sequences. In another embodiment, subsequences are cloned and the appropriate subsequences cleaved using appropriate restriction enzymes. The fragments are then be ligated to produce the desired DNA sequence.

In another embodiment, DNA encoding the recombinant protein of the present invention is cloned using DNA amplification methods such as polymerase chain reaction (PCR). Thus, the gene for non-hemolytic LLO is PCR amplified, using a sense primer comprising a suitable restriction site and an antisense primer comprising another restriction site, e.g. a non-identical restriction site to facilitate cloning.

In another embodiment, a recombinant gene encoding a fusion protein is operably linked to appropriate expression control sequences for each host. Promoter/regulatory sequences are described in detail elsewhere herein. In another embodiment, the plasmid further comprises additional promoter regulatory elements, as well as a ribosome binding site and a transcription termination signal. For eukaryotic cells, the control sequences will include a promoter and an enhancer derived from e.g. immunoglobulin genes, SV40, cytomegalovirus, etc., and a polyadenylation sequence. In another embodiment, the sequences include splice donor and acceptor sequences.

In one embodiment, the term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

In one embodiment, provided herein is a method of administering a composition or mixture of compositions of the present invention. In another embodiment, provided herein is a method of administering a vaccine of the present invention. In another embodiment, provided herein is a method of administering the immunotherapeutic compositions of the present invention. In another embodiment, provided herein is a method of administering the attenuated recombinant form of *Listeria* of the present invention.

In one embodiment, an immune response elicited by methods and compositions of the present invention comprises a $CD8^+$ T cell-mediated response. In another embodiment, the immune response consists primarily of a $CD8^+$ T cell-mediated response. In another embodiment, the only detectable component of the immune response is a $CD8^+$ T cell-mediated response.

In another embodiment, an immune response elicited by methods and compositions of the present invention comprises a $CD4^+$ T cell-mediated response. In another embodiment, the immune response consists primarily of a $CD4^+$ T cell-mediated response. In another embodiment, the only detectable component of the immune response is a $CD4^+$ T cell-mediated response.

In another embodiment, an immune response elicited by methods and compositions of the present invention comprises an innate immune response. In another embodiment, the immune response consists primarily of an innate immune response. In another embodiment, the only detectable component of the immune response is an innate immune response. It will be appreciated by the skilled artisan that the activation of an innate immune response may involve the activation of macrophages such as M1 macrophages, natural killer cells and also of dendritic cells (DC).

In another embodiment, the present invention provides a method of reducing an incidence of cancer or infectious disease or allergy, comprising administering a composition of the present invention. In another embodiment, the present invention provides a method of ameliorating cancer or infectious disease or allergy, comprising administering a composition of the present invention. Each possibility represents a separate embodiment of the present invention.

In one embodiment, a recombinant *Listeria monocytogenes* for use in the present invention secretes a heterologous peptide. In another embodiment, a recombinant *Listeria monocytogenes* for use in the present invention expresses a heterologous peptide.

In another embodiment, a recombinant *Listeria monocytogenes* for use in the present invention expresses and secretes a PEST-containing polypeptide (e.g. non-hemolytic LLO), as described herein.

In one embodiment, a treatment protocol of the present invention is therapeutic. In another embodiment, the protocol is prophylactic. In another embodiment, the vaccines of the present invention are used to protect people at risk for cancer such as breast cancer or other types of tumors because of familial genetics or other circumstances that predispose them to these types of ailments as will be understood by a skilled artisan. In another embodiment, the vaccines of the present invention are used to treat people having cancer such as breast cancer or other types of tumors because of familial genetics or other circumstances that predispose them to these types of ailments as will be understood by a skilled artisan. In another embodiment, the vaccines of the present invention are used prior to or following an alternative treatment in people having cancer such as breast cancer or other types of tumors because of familial genetics or other circumstances that predispose them to these types of ailments as will be understood by a skilled artisan. In another embodiment, such treatments include chemotherapy, surgery, radiation, and the like. Following such treatments, the vaccines of the present invention are administered so that the CTL response to the tumor antigen of the vaccine destroys remaining metastases and prolongs remission from the cancer. In another embodiment, vaccines of the present invention are used to effect the growth of previously established tumors and to kill existing tumor cells. Each possibility represents a separate embodiment of the present invention.

Various embodiments of dosage ranges are contemplated by this invention. In one embodiment, in the case of vaccine vectors, the dosage is in the range of 0.4 $LD_{50}$/dose. In another embodiment, the dosage is from about 0.4-4.9 $LD_{50}$/dose. In another embodiment the dosage is from about 0.5-0.59 $LD_{50}$/dose. In another embodiment the dosage is from about 0.6-0.69 $LD_{50}$/dose. In another embodiment the dosage is from about 0.7-0.79 $LD_{50}$/dose. In another embodiment the dosage is about 0.8 $LD_{50}$/dose. In another embodiment, the dosage is 0.4 $LD_{50}$/dose to 0.8 of the $LD_{50}$/dose.

In another embodiment, the dosage is $10^7$ bacteria/dose. In another embodiment, the dosage is $1.5\times10^7$ bacteria/dose. In another embodiment, the dosage is $2\times10^7$ bacteria/dose. In another embodiment, the dosage is $3\times10^7$ bacteria/dose. In another embodiment, the dosage is $4\times10^7$ bacteria/dose. In another embodiment, the dosage is $6\times10^7$ bacteria/dose. In another embodiment, the dosage is $8\times10^7$ bacteria/dose. In another embodiment, the dosage is $1\times10^8$ bacteria/dose. In another embodiment, the dosage is $1.5\times10^8$ bacteria/dose. In another embodiment, the dosage is $2\times10^8$ bacteria/dose. In another embodiment, the dosage is $3\times10^8$ bacteria/dose. In another embodiment, the dosage is $4\times10^8$ bacteria/dose. In another embodiment, the dosage is $6\times10^8$ bacteria/dose. In another embodiment, the dosage is $8\times10^8$ bacteria/dose. In another embodiment, the dosage is $1\times10^9$ bacteria/dose. In another embodiment, the dosage is $1.5\times10^9$ bacteria/dose. In another embodiment, the dosage is $2\times10^9$ bacteria/dose. In another embodiment, the dosage is $3\times10^9$ bacteria/dose. In another embodiment, the dosage is $5\times10^9$ bacteria/dose. In another embodiment, the dosage is $6\times10^9$ bacteria/dose. In another embodiment, the dosage is $8\times10^9$ bacteria/dose. In another embodiment, the dosage is $1\times10^{10}$ bacteria/dose. In another embodiment, the dosage is $1.5\times10^{10}$ bacteria/dose. In another embodiment, the dosage is $2\times10^{10}$ bacteria/dose. In another embodiment, the dosage is $3\times10^{10}$ bacteria/dose. In another embodiment, the dosage is $5\times10^{10}$ bacteria/dose. In another embodiment, the dosage is $6\times10^{10}$ bacteria/dose. In another embodiment, the dosage is $8\times10^{10}$ bacteria/dose. In another embodiment, the dosage is $8\times10^9$ bacteria/dose. In another embodiment, the dosage is $1\times10^{11}$ bacteria/dose. In another embodiment, the dosage is $1.5\times10^{11}$ bacteria/dose. In another embodiment, the dosage is $2\times10^{11}$ bacteria/dose. In another embodiment, the dosage is $3\times10^{11}$ bacteria/dose. In another embodiment, the dosage is $5\times10^{11}$ bacteria/dose. In another embodiment, the dosage is $6\times10^{11}$ bacteria/dose. In another embodiment, the dosage is $8\times10^{11}$ bacteria/dose. Each possibility represents a separate embodiment of the present invention.

The terms "homology," "homologous," etc, when in reference to any protein or peptide provided herein, refer in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art. In another embodiment, methods and compositions of the present invention utilize a homologue of a heterologous antigen or LLO sequence of the present invention.

In another embodiment, the term "homology," when in reference to any nucleic acid sequence similarly indicates a percentage of nucleotides in a candidate sequence that are identical with the nucleotides of a corresponding native nucleic acid sequence.

In another embodiment, the term "homology" refers to an isolated nucleic acid encoding a signal peptide or a recombinant polypeptide of the present invention that shares at least 65% homology with a nucleic acid encoding the signal peptide or the recombinant polypeptide of the present invention. In another embodiment, the isolated nucleic acid comprises a sequence sharing at least 75% homology with a nucleic acid encoding the signal peptide or the recombinant polypeptide of the present invention. In another embodiment, the isolated nucleic acid comprises a sequence sharing at least 85% homology with a nucleic acid encoding the signal peptide or the recombinant polypeptide of the present invention. In another embodiment, the isolated nucleic acid comprises a sequence sharing at least 90% homology with a nucleic acid encoding the signal peptide or the recombinant polypeptide of the present invention. In another embodiment, the isolated nucleic acid comprises a sequence sharing at least 95% homology with a nucleic acid encoding the signal peptide or the recombinant polypeptide of the present invention. In another embodiment, the isolated nucleic acid comprises a sequence sharing at least 97% homology with a nucleic acid encoding the signal peptide or the recombinant polypeptide of the present invention. In another embodiment, the isolated nucleic acid comprises a sequence sharing at least 99% homology with a nucleic acid encoding the signal peptide or the recombinant polypeptide of the present invention. In another embodiment, the above ranges in homology apply to shared between amino acid sequences of a signal peptide or recombinant polypeptide with that of amino acid sequences of a signal peptide or recombinant polypeptide provided herein. In another embodiment, a PEST-containing polypeptide provided herein is a recombinant polypeptide.

Homology is, in one embodiment, determined by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from a sequence provided herein of greater than 60%. In another embodiment, "homology" refers to identity to a sequence selected from a sequence provided herein of greater than 70%. In another embodiment, the identity is greater than 75%. In another embodiment, the identity is greater than 78%. In another embodiment, the identity is greater than 80%. In another embodiment, the identity is greater than 82%. In another embodiment, the identity is greater than 83%. In another embodiment, the identity is greater than 85%. In another embodiment, the identity is greater than 87%. In another embodiment, the identity is greater than 88%. In another embodiment, the identity is greater than 90%. In another embodiment, the identity is greater than 92%. In another embodiment, the identity is greater than 93%. In another embodiment, the identity is greater than 95%. In another embodiment, the identity is greater than 96%. In another embodiment, the identity is greater than 97%. In another embodiment, the identity is greater than 98%. In another embodiment, the identity is greater than 99%. In another embodiment, the identity is 100%. Each possibility represents a separate embodiment of the present invention.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). For example methods of hybridization may be carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example. Each method of determining homology represents a separate embodiment of the present invention.

In another embodiment, the present invention provides a kit comprising a reagent utilized in performing a method of the present invention. In another embodiment, the present invention provides a kit comprising a composition, tool, or instrument of the present invention.

It will be well appreciated that the terms "contacting" or "administering," can encompass directly contacting the cancer cell, subject, tumor, or site of disease with a composition of the present invention. In another embodiment, the terms refer to indirectly contacting the cancer cell, tumor, or site of disease with a composition of the present invention. In another embodiment, methods of the present invention include methods in which the subject is contacted with a composition of the present invention after which the composition is brought in contact with the cancer cell, tumor, or site of disease by diffusion or any other active transport or passive transport process known in the art by which compounds circulate within the body. Each possibility represents a separate embodiment of the present invention.

In another embodiment, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals or organisms. This can be readily carried out by using hybridization probes to identify the same genetic locus in a variety of individuals or organisms. Any and all such nucleotide variations and resulting amino acid polymorphisms or variations that are the result of natural allelic variation and that do not alter the functional activity are intended to be within the scope of the invention.

The compositions of this invention, in another embodiment, are administered to a subject by any method known to a person skilled in the art, such as parenterally, paracancerally, transmucosally, transdermally, intramuscularly, intravenously, intra-dermally, subcutaneously, intra-peritonealy, intra-ventricularly, intra-cranially, intra-vaginally or intratumorally.

In another embodiment of the methods and compositions provided herein, the vaccines or compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a gelatin capsule.

In another embodiment, the vaccines or compositions are administered by intravenous, intra-arterial, or intra-muscular injection of a liquid preparation. Suitable liquid formulations include solutions, suspensions, dispersions, emulsions, oils and the like. In one embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intramuscularly and are thus formulated in a form suitable for intra-muscular administration.

In some embodiments, when an antibody or functional fragment thereof is administered separately from a composition comprising a recombinant Lm strain, the antibody may be injected intravenously, subcutaneously, or directly into the tumor or tumor bed. In one embodiment, a composition comprising an antibody is injected into the space left after a tumor has been surgically removed, e.g., the space in a prostate gland following removal of a prostate tumor.

In one embodiment, the term "immunogenic composition" may encompass the recombinant *Listeria* provided herein, and an adjuvant, and an antibody or functional fragment thereof, or any combination thereof. In another embodiment, an immunogenic composition comprises a recombinant *Listeria* provided herein. In another embodiment, an immunogenic composition comprises an adjuvant known in the art or as provided herein. It is also to be understood that administration of such compositions enhance an immune response, or increase a T effector cell to regulatory T cell ratio or elicit an anti-tumor immune response, as further provided herein.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

It will be appreciated by a skilled artisan that the term "treating" may encompass curing a disease, preventing a disease, reducing the incidence of a disease, ameliorating symptoms of a disease, inducing remission of a disease, slowing the progression of a disease. The terms "reducing," "suppressing" and "inhibiting" refer in another embodiment to lessening or decreasing.

It will be well appreciated by a skilled artisan that the term "therapeutically effective dose" or "therapeutic effective amount" may encompass a dose that produces the desired effect for which it is administered. The exact dose will be ascertainable by one skilled in the art using known techniques.

It will be well appreciated by a skilled artisan that the term "about" may encompass in quantitative terms plus or minus 5%, or in another embodiment plus or minus 10%, or in another embodiment plus or minus 15%, or in another embodiment plus or minus 20%.

It will be well appreciated by a skilled artisan that the term "subject" may encompass a mammal including a human in need of therapy for, or susceptible to, a condition or its sequelae, and also may include dogs, cats, pigs, cows, sheep, goats, horses, rats, and mice and humans. It will also be appreciated that the term may encompass livestock. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Materials and Experimental Methods (Examples 1-2)

Example 1

LLO-Antigen Fusions Induce Anti-Tumor Immunity

Cell Lines

The C57BL/6 syngeneic TC-1 tumor was immortalized with HPV-16 E6 and E7 and transformed with the c-Ha-ras oncogene. TC-1, provided by T. C. Wu (Johns Hopkins University School of Medicine, Baltimore, Md.) is a highly tumorigenic lung epithelial cell expressing low levels of with HPV-16 E6 and E7 and transformed with the c-Ha-ras oncogene. TC-1 was grown in RPMI 1640, 10% FCS, 2 mM L-glutamine, 100 U/ml penicillin, 100 μg/ml streptomycin, 100 μM nonessential amino acids, 1 mM sodium pyruvate, 50 micromolar (mcM) 2-ME, 400 microgram (mcg)/ml G418, and 10% National Collection Type Culture-109 medium at 37° with 10% $CO_2$. C3 is a mouse embryo cell from C57BL/6 mice immortalized with the complete genome of HPV 16 and transformed with pEJ-ras. EL-4/E7 is the thymoma EL-4 retrovirally transduced with E7.

*L. monocytogenes* Strains and Propagation

Figure 2:
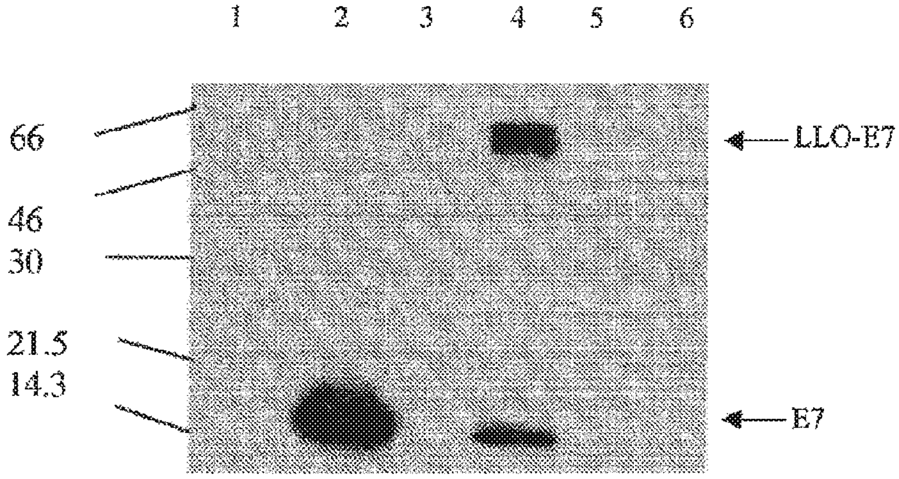
FIG. 2 shows that Lm-E7 and Lm-LLO-E7 secrete E7. Lm-Gag (lane 1), Lm-E7 (lane 2), Lm-LLO-NP (lane 3), Lm-LLO-E7 (lane 4), XFL-7 (lane 5), and 10403S (lane 6) were grown overnight at 37° C. in Luria-Bertoni broth. Equivalent numbers of bacteria, as determined by OD at 600 nm absorbance, were pelleted and 18 ml of each supernatant was TCA precipitated. E7 expression was analyzed by Western blot. The blot was probed with an anti-E7 mAb, followed by HRP-conjugated anti-mouse (Amersham), and then developed using ECL detection reagents.

*Listeria* strains used were Lm-LLO-E7 (hly-E7 fusion gene in an episomal expression system; FIG. 1A), Lm-E7 (single-copy E7 gene cassette integrated into *Listeria* genome), Lm-LLO-NP ("DP-L2028"; hly-NP fusion gene in an episomal expression system), and Lm-Gag ("ZY-18"; single-copy HIV-1 Gag gene cassette integrated into the chromosome). E7 was amplified by PCR using the primers 5'-GGCTCGAGCATGGAGATACACC-3' (SEQ ID No: 24; XhoI site is underlined) and 5'-GGGGACTAGTTTATGGTTTCTGAGAACA-3' (SEQ ID No: 25; SpeI site is underlined) and ligated into pCR2.1 (Invitrogen, San Diego, Calif.). E7 was excised from pCR2.1 by XhoI/SpeI digestion and ligated into pGG-55. The hly-E7 fusion gene and the pluripotential transcription factor prfA were cloned into pAM401, a multicopy shuttle plasmid (Wirth R et al, J Bacteriol, 165: 831, 1986), generating pGG-55. The hly promoter drives the expression of the first 441 AA of the hly gene product, (lacking the hemolytic C-terminus, referred to below as "ΔLLO"), which is joined by the XhoI site to the E7 gene, yielding a hly-E7 fusion gene that is transcribed and secreted as LLO-E7. Transformation of a prfA negative strain of *Listeria*, XFL-7 (provided by Dr. Hao Shen, University of Pennsylvania), with pGG-55 selected for the retention of the plasmid in vivo (FIGS. 1A-B). The hly promoter and gene fragment were generated using primers 5'-GGGGGCTAGCCCTCCTTTGATTAGTATATTC-3' (SEQ ID No: 26; NheI site is underlined) and 5'-CTCCCTCGAGATCATAATTTACTTCATC-3' (SEQ ID No: 27; XhoI site is underlined). The prfA gene was PCR amplified using primers 5'-GACTACAAGGACGATGACCGACAAGTGATAACCCGGGATCTAAATAAATCCGTTT-3' (SEQ ID No: 28; XbaI site is underlined) and 5'-CCCGTCGACCAGCTCTTCTTGGTGAAG-3' (SEQ ID No: 29; SalI site is underlined). Lm-E7 was generated by introducing an expression cassette containing the hly promoter and signal sequence driving the expression and secretion of E7 into the orfZ domain of the LM genome. E7 was amplified by PCR using the primers 5'-GCGGATCCCATGGAGATACACCTAC-3' (SEQ ID No: 30; BamHI site is underlined) and 5'-GCTCTAGATTATGGTTTCTGAG-3' (SEQ ID No: 31; XbaI site is underlined). E7 was then ligated into the pZY-21 shuttle vector. LM strain 10403S was transformed with the resulting plasmid, pZY-21-E7, which includes an expression cassette inserted in the middle of a 1.6-kb sequence that corresponds to the orfX, Y, Z domain of the LM genome. The homology domain allows for insertion of the E7 gene cassette into the orfZ domain by homologous recombination. Clones were screened for integration of the E7 gene cassette into the orfZ domain. Bacteria were grown in brain heart infusion medium with (Lm-LLO-E7 and Lm-LLO-NP) or without (Lm-E7 and ZY-18) chloramphenicol (20 µg/ml). Bacteria were frozen in aliquots at −80° C. Expression was verified by Western blotting (FIG. 2).

Western Blotting

*Listeria* strains were grown in Luria-Bertoni medium at 37° C. and were harvested at the same optical density measured at 600 nm. The supernatants were TCA precipitated and resuspended in 1× sample buffer supplemented with 0.1 N NaOH. Identical amounts of each cell pellet or each TCA-precipitated supernatant were loaded on 4-20% Tris-glycine SDS-PAGE gels (NOVEX, San Diego, Calif.). The gels were transferred to polyvinylidene difluoride and probed with an anti-E7 monoclonal antibody (mAb) (Zymed Laboratories, South San Francisco, Calif.), then incubated with HRP-conjugated anti-mouse secondary Ab (Amersham Pharmacia Biotech, Little Chalfont, U.K.), developed with Amersham ECL detection reagents, and exposed to Hyperfilm (Amersham Pharmacia Biotech).

Measurement of Tumor Growth

Tumors were measured every other day with calipers spanning the shortest and longest surface diameters. The mean of these two measurements was plotted as the mean tumor diameter in millimeters against various time points. Mice were sacrificed when the tumor diameter reached 20 mm. Tumor measurements for each time point are shown only for surviving mice.

Effects of *Listeria* Recombinants on Established Tumor Growth

Six- to 8-wk-old C57BL/6 mice (Charles River) received $2\times10^5$ TC-1 cells s.c. on the left flank. One week following tumor inoculation, the tumors had reached a palpable size of 4-5 mm in diameter. Groups of eight mice were then treated with 0.1 $LD_{50}$ i.p. Lm-LLO-E7 ($10^7$ CFU), Lm-E7 ($10^6$ CFU), Lm-LLO-NP ($10^7$ CFU), or Lm-Gag ($5\times10^5$ CFU) on days 7 and 14.

$^{51}$Cr Release Assay

C57BL/6 mice, 6-8 wk old, were immunized i.p. with 0.1 $LD_{50}$ Lm-LLO-E7, Lm-E7, Lm-LLO-NP, or Lm-Gag. Ten days post-immunization, spleens were harvested. Splenocytes were established in culture with irradiated TC-1 cells (100:1, splenocytes:TC-1) as feeder cells; stimulated in vitro for 5 days, then used in a standard $^{51}$Cr release assay, using the following targets: EL-4, EL-4/E7, or EL-4 pulsed with E7 H-2b peptide (RAHYNIVTF) (SEQ ID NO:32). E:T cell ratios, performed in triplicate, were 80:1, 40:1, 20:1, 10:1, 5:1, and 2.5:1. Following a 4-h incubation at 37° C., cells were pelleted, and 50 µl supernatant was removed from each well. Samples were assayed with a Wallac 1450 scintillation counter (Gaithersburg, Md.). The percent specific lysis was determined as [(experimental counts per minute (cpm)−spontaneous cpm)/(total cpm−spontaneous cpm)]×100.

TC-1-specific Proliferation

C57BL/6 mice were immunized with 0.1 $LD_{50}$ and boosted by i.p. injection 20 days later with 1 $LD_{50}$ Lm-LLO-E7, Lm-E7, Lm-LLO-NP, or Lm-Gag. Six days after boosting, spleens were harvested from immunized and naive mice. Splenocytes were established in culture at $5\times10^5$/well in flat-bottom 96-well plates with $2.5\times10^4$, $1.25\times10^4$, $6\times10^3$, or $3\times10^3$ irradiated TC-1 cells/well as a source of E7 Ag, or without TC-1 cells or with 10 µg/ml Con A. Cells were pulsed 45 h later with 0.5 µCi [$^3$H]thymidine/well. Plates were harvested 18 h later using a Tomtec harvester 96 (Orange, Conn.), and proliferation was assessed with a Wallac 1450 scintillation counter. The change in cpm was calculated as experimental cpm−no Ag cpm.

Flow Cytometric Analysis

C57BL/6 mice were immunized intravenously (i.v.) with 0.1 $LD_{50}$ Lm-LLO-E7 or Lm-E7 and boosted 30 days later. Three-color flow cytometry for CD8 (53-6.7, PE conjugated), CD62 ligand (CD62L; MEL-14, APC conjugated), and E7 H-2Db tetramer was performed using a FACSCalibur® flow cytometer with CellQuest® software (Becton Dickinson, Mountain View, Calif.). Splenocytes harvested 5 days after the boost were stained at room temperature (rt) with H-2Db tetramers loaded with the E7 peptide (RAHYNIVTF) (SEQ ID NO:32) or a control (HIV-Gag) peptide. Tetramers were used at a 1/200 dilution and were provided by Dr. Larry R. Pease (Mayo Clinic, Rochester, Minn.) and by the NIAID Tetramer Core Facility and the NIH AIDS Research and Reference Reagent Program. Tetramer$^+$, CD8$^+$, CD62L$^{low}$ cells were analyzed.

B16F0-Ova Experiment

24 C57BL/6 mice were inoculated with $5\times10^5$ B16F0-Ova cells. On days 3, 10 and 17, groups of 8 mice were immunized with 0.1 $LD_{50}$ Lm-OVA ($10^6$ cfu), Lm-LLO-OVA ($10^8$ cfu) and eight animals were left untreated.

Statistics

For comparisons of tumor diameters, mean and SD of tumor size for each group were determined, and statistical significance was determined by Student's t test. $p<0.05$ was considered significant.

Results

Figure 3:
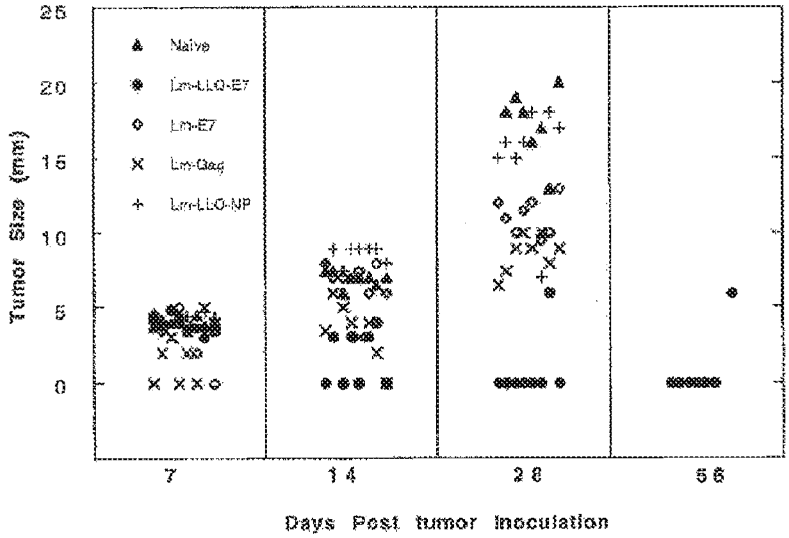
FIG. 3 shows that tumor immunotherapeutic efficacy of LLO-E7 fusions. Tumor size in millimeters in mice is shown at 7, 14, 21, 28 and 56 days post tumor-inoculation. Naive mice: open-circles; Lm-LLO-E7: filled circles; Lm-E7: squares; Lm-Gag: open diamonds; and Lm-LLO-NP: filled triangles.

Lm-E7 and Lm-LLO-E7 were compared for their abilities to impact on TC-1 growth. Subcutaneous tumors were established on the left flank of C57BL/6 mice. Seven days later tumors had reached a palpable size (4-5 mm). Mice were vaccinated on days 7 and 14 with 0.1 $LD_{50}$ Lm-E7, Lm-LLO-E7, or, as controls, Lm-Gag and Lm-LLO-NP. Lm-LLO-E7 induced complete regression of 75% of established TC-1 tumors, while tumor growth was controlled in the other 2 mice in the group (FIG. 3). By contrast, immunization with Lm-E7 and Lm-Gag did not induce tumor regression. This experiment was repeated multiple times, always with very similar results. In addition, similar results were achieved for Lm-LLO-E7 under different immunization protocols. In another experiment, a single immunization was able to cure mice of established 5 mm TC-1 tumors.

In other experiments, similar results were obtained with 2 other E7-expressing tumor cell lines: C3 and EL-4/E7. To confirm the efficacy of vaccination with Lm-LLO-E7, animals that had eliminated their tumors were re-challenged with TC-1 or EL-4/E7 tumor cells on day 60 or day 40, respectively. Animals immunized with Lm-LLO-E7 remained tumor free until termination of the experiment (day 124 in the case of TC-1 and day 54 for EL-4/E7).

Thus, expression of an antigen as a fusion protein with ΔLLO enhances the immunogenicity of the antigen.

Example 2

LM-LLO-E7 Treatment Elicits TC-1 Specific Splenocyte Proliferation

Figure 4:
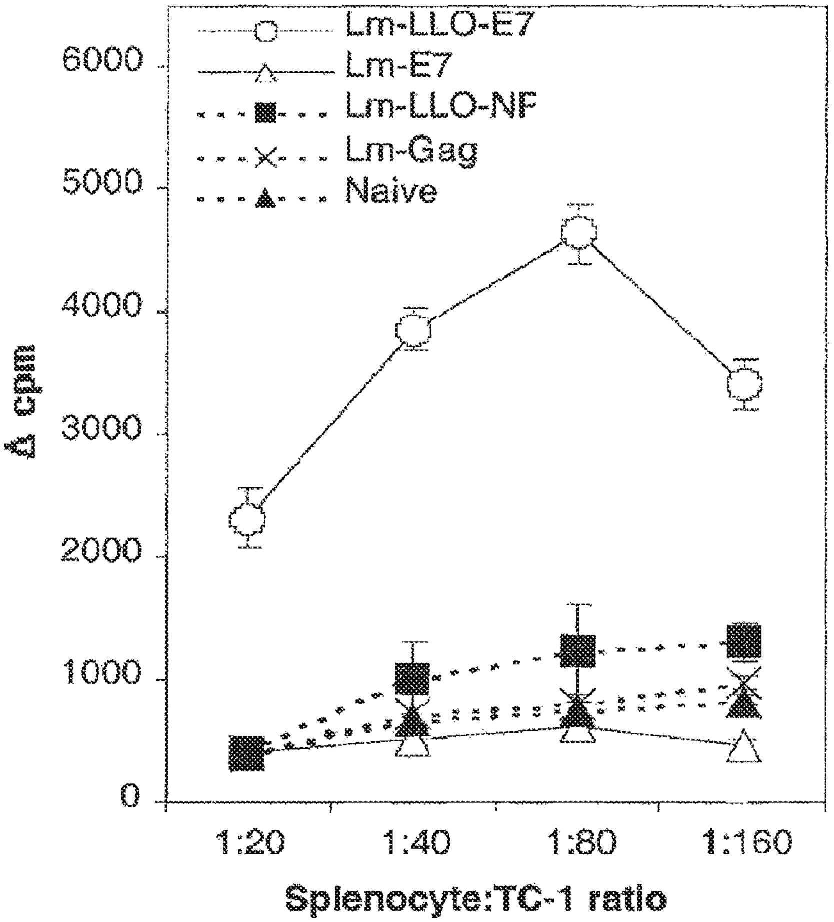
FIG. 4 shows that splenocytes from Lm-LLO-E7-immunized mice proliferate when exposed to TC-1 cells. C57BL/6 mice were immunized and boosted with Lm-LLO-E7, Lm-E7, or control rLm strains. Splenocytes were harvested 6 days after the boost and plated with irradiated TC-1 cells at the ratios shown. The cells were pulsed with $^3$H thymidine and harvested. Cpm is defined as (experimental cpm)−(no-TC-1 control).

To measure induction of T cells by Lm-E7 with Lm-LLO-E7, E7-specific proliferative responses, a measure of antigen-specific immunocompetence, were measured in immunized mice. Splenocytes from Lm-LLO-E7-immunized mice proliferated when exposed to irradiated TC-1 cells as a source of E7, at splenocyte: TC-1 ratios of 20:1, 40:1, 80:1, and 160:1 (FIG. 4). Conversely, splenocytes from Lm-E7 and rLm control-immunized mice exhibited only background levels of proliferation.

Example 3

ActA-E7 and Pest-E7 Fusions Confer Anti-Tumor Immunity

Materials and Experimental Methods

Construction of Lm-ActA-E7

Lm-ActA-E7 is a recombinant strain of LM, comprising a plasmid that expresses the E7 protein fused to a truncated version of the actA protein. Lm-actA-E7 was generated by introducing a plasmid vector pDD-1, constructed by modifying pDP-2028, into *Listeria*. pDD-1 comprises an expression cassette expressing a copy of the 310 bp hly promoter and the hly signal sequence (ss), which drives the expression and secretion of ActA-E7; 1170 bp of the actA gene that comprises four PEST sequences (SEQ ID NO: 11) (the truncated ActA polypeptide consists of the first 390 AA of the molecule, SEQ ID NO: 10); the 300 bp HPV E7 gene; the 1019 bp prfA gene (controls expression of the virulence genes); and the CAT gene (chloramphenicol resistance gene) for selection of transformed bacteria clones (Sewell et al. (2004), Arch. Otolaryngol. Head Neck Surg., 130: 92-97).

The hly promoter (pHly) and gene fragment were PCR amplified from pGG55 (Example 1) using primer 5'-GGGGTCTAGACCTCCTTTGATTAGTATATTC-3' (Xba I site is underlined; SEQ ID NO: 33) and primer 5'-ATCTTCGCTATCTGTCGCCGCGGCGCGTGCTTCAGTTTGTTGCGC-'3 (Not I site is underlined. The first 18 nucleotides are the ActA gene overlap; SEQ ID NO: 34). The actA gene was PCR amplified from the LM 10403s wildtype genome using primer 5'-GCGCAACAAACTGAAGCAGCGGCCGCGGCGACAGATAGCGAAGAT-3' (NotI site is underlined; SEQ ID NO: 35) and primer 5'-TGTAGGTGTATCTCCATGCTCGAGAGCTAGGCGATCAATTTC-3' (XhoI site is underlined; SEQ ID NO: 36). The E7 gene was PCR amplified from pGG55 (pLLO-E7) using primer 5'-GGAATTGATCGCCTAGCTCTCGAGCATGGAGATACACCTACA-3' (XhoI site is underlined; SEQ ID NO: 37) and primer 5'-AAACGGATTTATTTAGATCCCGGGTTATGGTTTCTGAGAACA-3' (XmaI site is underlined; SEQ ID NO: 38). The prfA gene was PCR amplified from the LM 10403s wild-type genome using primer 5'-TGTTCTCAGAAACCATAACCCGGGATCTAAATAAATCCGTTT-3' (XmaI site is underlined; SEQ ID NO: 39) and primer 5'-GGGGGTCGACCAGCTCTTCTTGGTGAAG-3' (SalI site is underlined; SEQ ID NO: 40). The hly promoter-actA gene fusion (pHly-actA) was PCR generated and amplified from purified pHly DNA and purified actA DNA using the upstream pHly primer (SEQ ID NO: 33) and downstream actA primer (SEQ ID NO: 36).

The E7 gene fused to the prfA gene (E7-prfA) was PCR generated and amplified from purified E7 DNA and purified prfA DNA using the upstream E7 primer (SEQ ID NO: 37) and downstream prfA gene primer (SEQ ID NO: 40).

The pHly-actA fusion product fused to the E7-prfA fusion product was PCR generated and amplified from purified fused pHly-actA DNA product and purified fused E7-prfA DNA product using the upstream pHly primer (SEQ ID NO: 33) and downstream prfA gene primer (SEQ ID NO: 40) and ligated into pCRII (Invitrogen, La Jolla, Calif.). Competent *E. coli* (TOP10'F, Invitrogen, La Jolla, Calif.) were transformed with pCRII-*ActAE7*. After lysis and isolation, the plasmid was screened by restriction analysis using BamHI (expected fragment sizes 770 bp and 6400 bp (or when the insert was reversed into the vector: 2500 bp and 4100 bp)) and BstXI (expected fragment sizes 2800 bp and 3900 bp) and also screened with PCR analysis using the upstream pHly primer (SEQ ID NO: 33) and the downstream prfA gene primer (SEQ ID NO: 40).

The pHly-actA-E7-prfA DNA insert was excised from pCRII by double digestion with Xba I and Sal I and ligated into pDP-2028 also digested with Xba I and Sal I. After transforming TOP10'F competent *E. coli* (Invitrogen, La Jolla, Calif.) with expression system pActAE7, chloramphenicol resistant clones were screened by PCR analysis using the upstream pHly primer (SEQ ID NO: 33) and the downstream PrfA gene primer (SEQ ID NO: 40). A clone comprising pActAE7 was grown in brain heart infusion medium (with chloramphenicol (20 mcg (microgram)/ml (milliliter), Difco, Detroit, Mich.) and pActAE7 was isolated from the bacteria cell using a midiprep DNA purification system kit (Promega, Madison, Wis.). A prfA-negative strain of penicillin-treated *Listeria* (strain XFL-7) was transformed with expression system pActAE7, as described in Ikonomidis et al. (1994, J. Exp. Med. 180: 2209-2218) and clones were selected for the retention of the plasmid in vivo. Clones were grown in brain heart infusion with chloramphenicol (20 mcg/ml) at 37° C. Bacteria were frozen in aliquots at −80° C.

Immunoblot Verification of Antigen Expression

Figure 5A:
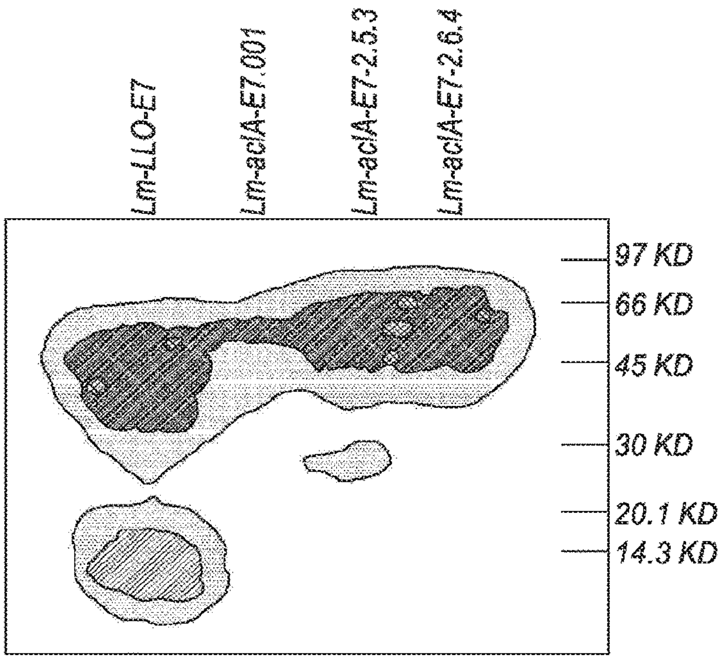
FIG. 5A shows (A) Western blot demonstrating that Lm-ActA-E7 secretes E7. Lane 1: Lm-LLO-E7; lane 2: Lm-ActA-E7.001; lane 3; Lm-ActA-E7-2.5.3; lane 4: Lm-ActA-E7-2.5.4.

To verify that Lm-ActA-E7 secretes ActA-E7, (about 64 kD), *Listeria* strains were grown in Luria-Bertoni (LB) medium at 37° C. Protein was precipitated from the culture supernatant with trichloroacetic acid (TCA) and resuspended in 1× sample buffer with 0.1N sodium hydroxide. Identical amounts of each TCA precipitated supernatant were loaded on 4% to 20% Tris-glycine sodium dodecyl sulfate-polyacrylamide gels (NOVEX, San Diego, Calif.). Gels were transferred to polyvinylidene difluoride membranes and probed with 1:2500 anti-E7 monoclonal antibody (Zymed Laboratories, South San Francisco, Calif.), then with 1:5000 horseradish peroxidase-conjugated anti-mouse IgG (Amersham Pharmacia Biotech, Little Chalfont, England). Blots were developed with Amersham enhanced chemiluminescence detection reagents and exposed to autoradiography film (Amersham) (FIG. 5A).

Figure 6A:
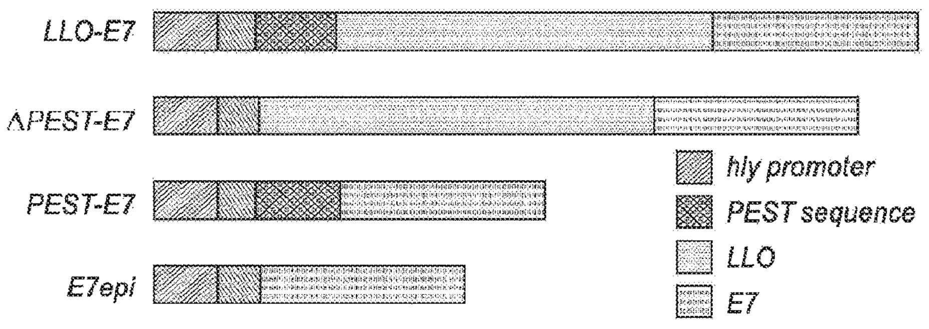
FIG. 6A shows schematic representation of the plasmid inserts used to create 4 LM vaccines. Lm-LLO-E7 insert contains all of the *Listeria* genes used. It contains the hly promoter, the first 1.3 kb of the hly gene (which encodes the protein LLO), and the HPV-16 E7 gene. The first 1.3 kb of hly includes the signal sequence (ss) and the PEST region. Lm-PEST-E7 includes the hly promoter, the signal sequence, and PEST and E7 sequences but excludes the remainder of the truncated LLO gene. Lm-ΔPEST-E7 excludes the PEST region, but contains the hly promoter, the signal sequence, E7, and the remainder of the truncated LLO. Lm-E7epi has only the hly promoter, the signal sequence, and E7.

Construction of Lm-PEST-E7, Lm-ΔPEST-E7, and Lm-E7epi (FIG. 6A)

Lm-PEST-E7 is identical to Lm-LLO-E7, except that it contains only the promoter and PEST sequence of the hly gene, specifically the first 50 AA of LLO. To construct Lm-PEST-E7, the hly promoter and PEST regions were fused to the full-length E7 gene using the SOE (gene splicing by overlap extension) PCR technique. The E7 gene and the hly-PEST gene fragment were amplified from the plasmid pGG-55, which contains the first 441 AA of LLO, and spliced together by conventional PCR techniques. To create a final plasmid, pVS 16.5, the hly-PEST-E7 fragment and the prfA gene were subcloned into the plasmid pAM401, which includes a chloramphenicol resistance gene for selection in vitro, and the resultant plasmid was used to transform XFL-7.

Lm-ΔPEST-E7 is a recombinant *Listeria* strain that is identical to Lm-LLO-E7 except that it lacks the PEST sequence. It was made essentially as described for Lm-PEST-E7, except that the episomal expression system was constructed using primers designed to remove the PEST-containing region (bp 333-387) from the hly-E7 fusion gene. Lm-E7epi is a recombinant strain that secretes E7 without the PEST region or LLO. The plasmid used to transform this strain contains a gene fragment of the hly promoter and signal sequence fused to the E7 gene. This construct differs from the original Lm-E7, which expressed a single copy of the E7 gene integrated into the chromosome. Lm-E7epi is completely isogenic to Lm-LLO-E7, Lm-PEST-E7, and Lm-ΔPEST-E7 except for the form of the E7 antigen expressed.

Results

Figure 5B:
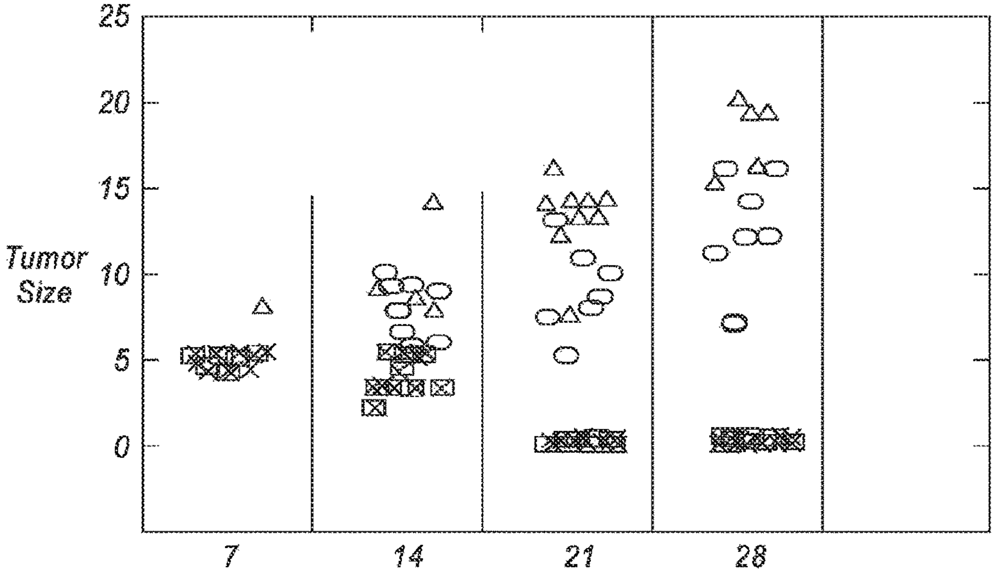
FIG. 5B shows Tumor size in mice administered Lm-ActA-E7 (rectangles), Lm-E7 (ovals), Lm-LLO-E7 (X), and naive mice (non-vaccinated; solid triangles).

To compare the anti-tumor immunity induced by Lm-ActA-E7 versus Lm-LLO-E7, $2\times10^5$ TC-1 tumor cells were implanted subcutaneously in mice and allowed to grow to a palpable size (approximately 5 millimeters [mm]). Mice were immunized i.p. with one $LD_{50}$ of either Lm-ActA-E7 ($5\times10^8$ CFU), (crosses) Lm-LLO-E7 ($10^8$ CFU) (squares) or Lm-E7 ($10^6$ CFU) (circles) on days 7 and 14. By day 26, all of the animals in the Lm-LLO-E7 and Lm-ActA-E7 were tumor free and remained so, whereas all of the naive animals (triangles) and the animals immunized with Lm-E7 grew large tumors (FIG. 5B). Thus, vaccination with ActA-E7 fusions causes tumor regression.

Figure 6B:
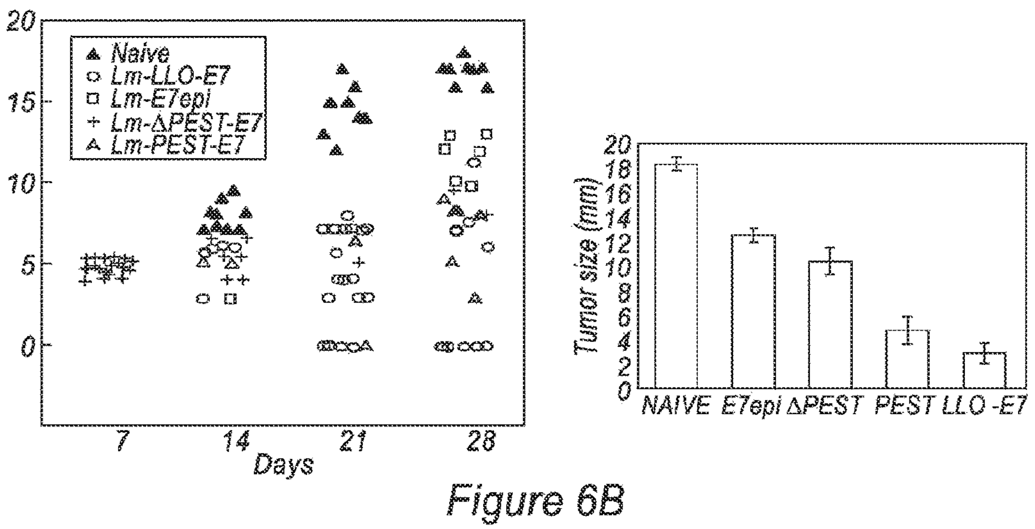
Figure 6C:
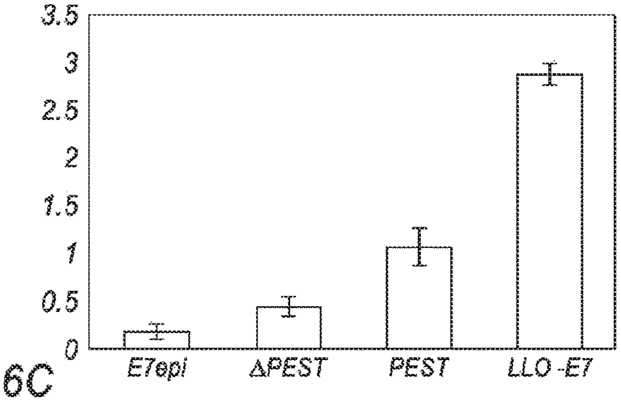
FIG. 6C shows *Listeria* constructs containing PEST regions induce a higher percentage of E7-specific lymphocytes in the spleen. Average and SE of data from 3 experiments are depicted.

In addition, Lm-LLO-E7, Lm-PEST-E7, Lm-ΔPEST-E7, and Lm-E7epi were compared for their ability to cause regression of E7-expressing tumors. S.c. TC-1 tumors were established on the left flank of 40 C57BL/6 mice. After tumors had reached 4-5 mm, mice were divided into 5 groups of 8 mice. Each groups was treated with 1 of 4 recombinant LM vaccines, and 1 group was left untreated. Lm-LLO-E7 and Lm-PEST-E7 induced regression of established tumors in 5/8 and 3/8 cases, respectively. There was no statistical difference between the average tumor size of mice treated with Lm-PEST-E7 or Lm-LLO-E7 at any time point. However, the vaccines that expressed E7 without the PEST sequences, Lm-ΔPEST-E7 and Lm-E7epi, failed to cause tumor regression in all mice except one (FIG. 6B, top panel). This was representative of 2 experiments, wherein a statistically significant difference in mean tumor sizes at day 28 was observed between tumors treated with Lm-LLO-E7 or Lm-PEST-E7 and those treated with Lm-E7epi or Lm-ΔPEST-E7; $P<0.001$, Student's t test; FIG. 6B, bottom panel). In addition, increased percentages of tetramer-positive splenocytes were seen reproducibly over 3 experiments in the spleens of mice vaccinated with PEST-containing vaccines (FIG. 6C). Thus, vaccination with PEST-E7 fusions causes tumor regression.

Example 4

Fusion of E7 to LLO, ActA, or a Pest-Like Sequence Enhances E7-Specific Immunity and Generates Tumor-Infiltrating E7-Specific $CD8^+$ Cells Materials and Experimental Methods 500 mcl (microliter) of MATRIGEL®, comprising 100 mcl of $2\times10^5$ TC-1 tumor cells in phosphate buffered saline (PBS) plus 400 mcl of MATRIGEL® (BD Biosciences, Franklin Lakes, N.J.) were implanted subcutaneously on the left flank of 12 C57BL/6 mice (n=3). Mice were immunized intraperitoneally on day 7, 14 and 21, and spleens and tumors were harvested on day 28. Tumor MATRIGELs were removed from the mice and incubated at 4° C. overnight in tubes containing 2 milliliters (ml) of RP 10 medium on ice. Tumors were minced with forceps, cut into 2 mm blocks, and incubated at 37° C. for 1 hour with 3 ml of enzyme mixture (0.2 mg/ml collagenase-P, 1 mg/ml DNAse-1 in PBS). The tissue suspension was filtered through nylon mesh and washed with 5% fetal bovine serum+0.05% of $NaN_3$ in PBS for tetramer and IFN-gamma staining.

Splenocytes and tumor cells were incubated with 1 micromole (mcm) E7 peptide for 5 hours in the presence of brefeldin A at $10^7$ cells/ml. Cells were washed twice and incubated in 50 mcl of anti-mouse Fc receptor supernatant (2.4 G2) for 1 hour or overnight at 4° C. Cells were stained for surface molecules CD8 and CD62L, permeabilized, fixed using the permeabilization kit Golgi-Stop® or Golgi-Plug® (Pharmingen, San Diego, Calif.), and stained for IFN-gamma. 500,000 events were acquired using two-laser flow cytometer FACSCalibur and analyzed using Cellquest Software (Becton Dickinson, Franklin Lakes, N.J.). Percentages of IFN-gamma secreting cells within the activated ($CD62L^{low}$) $CD8^+$ T cells were calculated.

For tetramer staining, $H\text{-}2D^b$ tetramer was loaded with phycoerythrin (PE)-conjugated E7 peptide (RAHYNIVTF, SEQ ID NO: 32), stained at rt for 1 hour, and stained with anti-allophycocyanin (APC) conjugated MEL-14 (CD62L) and FITC-conjugated CD8β at 4° C. for 30 min. Cells were analyzed comparing $tetramer^+CD8^+$ $CD62L^{low}$ cells in the spleen and in the tumor.

Results

Figure 7A:
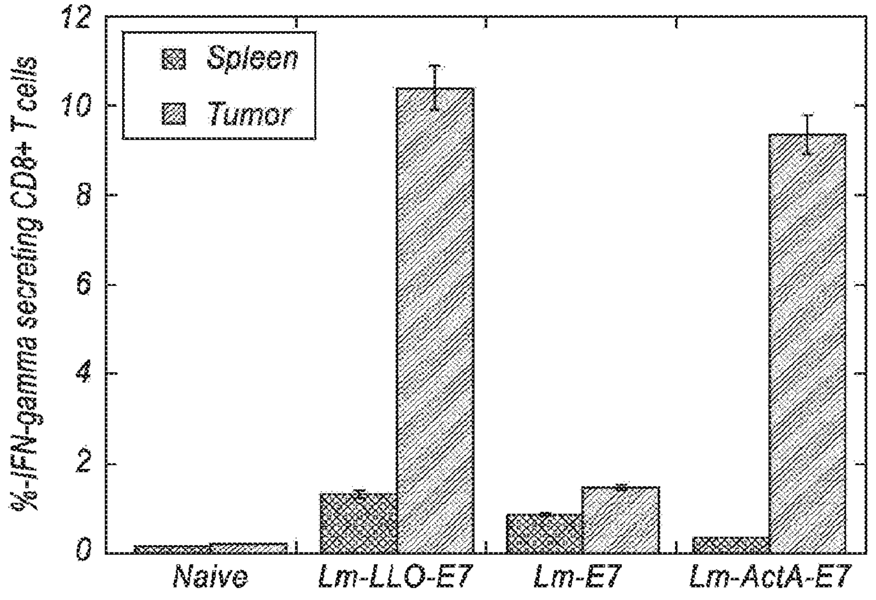
FIG. 7A shows Induction of E7-specific IFN-gamma-secreting $CD8^+$ T cells in the spleens and the numbers penetrating the tumors, in mice administered TC-1 tumor cells and subsequently administered Lm-E7, Lm-LLO-E7, Lm-ActA-E7, or no vaccine (naive).
Figure 7B:
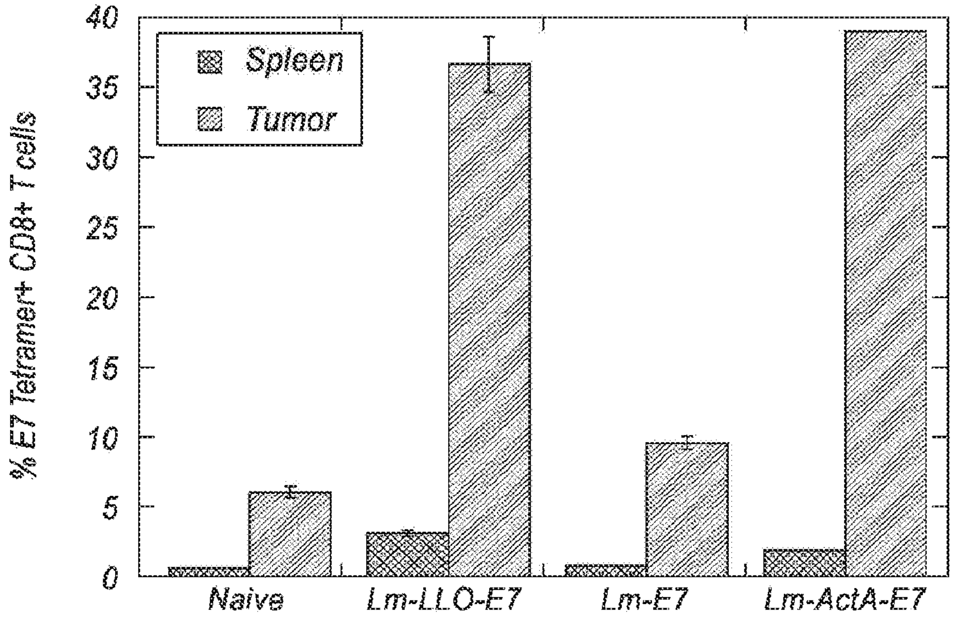
FIG. 7B shows induction and penetration of E7 specific $CD8^+$ cells in the spleens and tumors of the mice described for (A).

To analyze the ability of Lm-ActA-E7 to enhance antigen specific immunity, mice were implanted with TC-1 tumor cells and immunized with either Lm-LLO-E7 ($1\times10^7$ CFU), Lm-E7 ($1\times10^6$ CFU), or Lm-ActA-E7 ($2\times10^8$ CFU), or were untreated (naïve). Tumors of mice from the Lm-LLO-E7 and Lm-ActA-E7 groups contained a higher percentage of IFN-gamma-secreting $CD8^+$ T cells (FIG. 7A) and tetramer-specific $CD8^+$ cells (FIG. 7B) than in Lm-E7 or naive mice.

Figure 8:
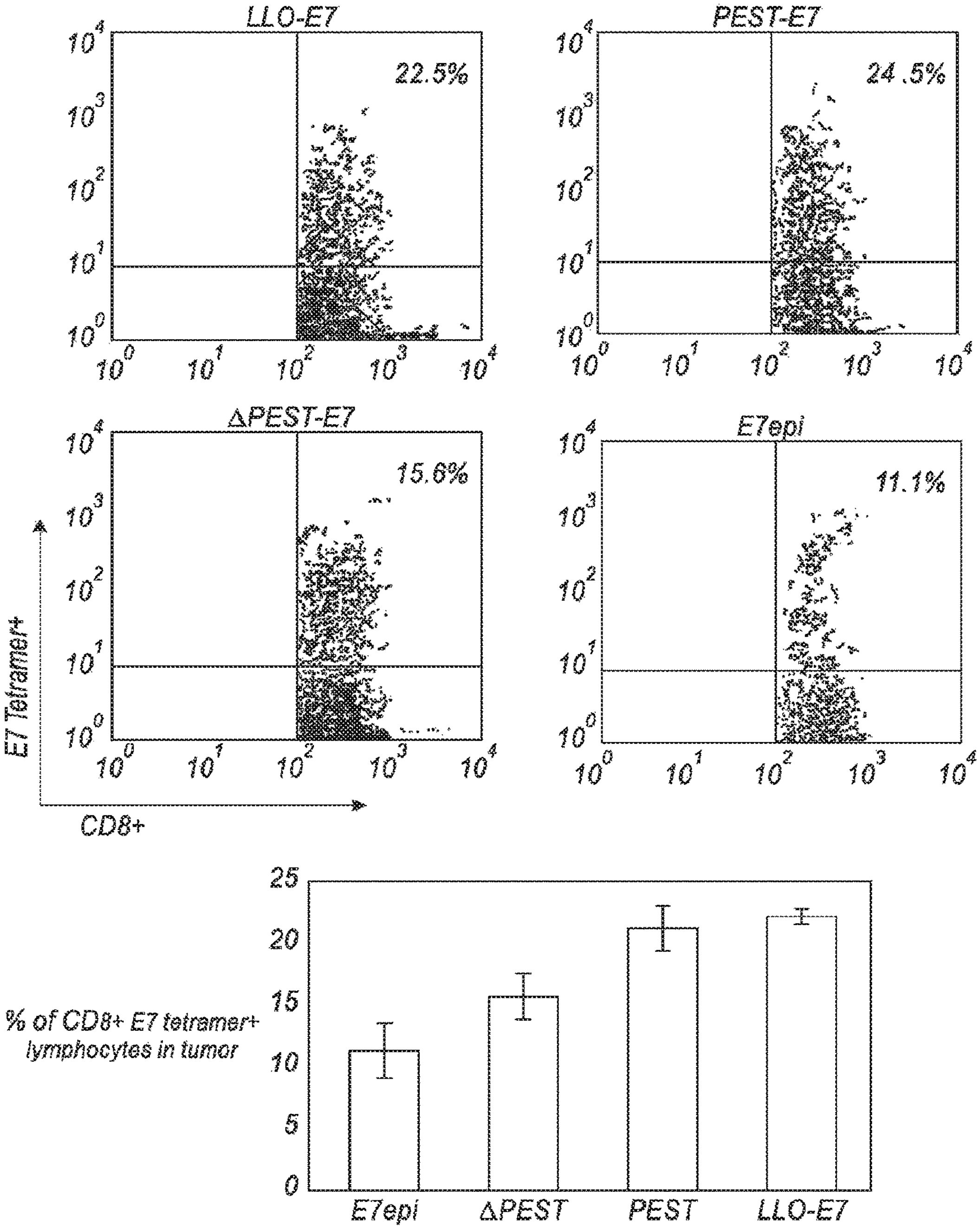
FIG. 8 shows *Listeria* constructs containing PEST regions induce a higher percentage of E7-specific lymphocytes within the tumor. (A) representative data from 1 experiment. (B) average and SE of data from all 3 experiments.

In another experiment, tumor-bearing mice were administered Lm-LLO-E7, Lm-PEST-E7, Lm-ΔPEST-E7, or Lm-E7epi, and levels of E7-specific lymphocytes within the tumor were measured. Mice were treated on days 7 and 14 with 0.1 $LD_{50}$ of the 4 vaccines. Tumors were harvested on day 21 and stained with antibodies to CD62L, CD8, and with the E7/Db tetramer. An increased percentage of tetramer-positive lymphocytes within the tumor were seen in mice vaccinated with Lm-LLO-E7 and Lm-PEST-E7 (FIG. 8A). This result was reproducible over three experiments (FIG. 8B).

Thus, Lm-LLO-E7, Lm-ActA-E7, and Lm-PEST-E7 are each efficacious at induction of tumor-infiltrating $CD8^+$ T cells and tumor regression.

Materials and Experimental Methods (Examples 5-10)

Bacterial Strains, Transformation and Selection

*E. coli* strain MB2159 was used for transformations, using standard protocols. Bacterial cells were prepared for electroporation by washing with $H_2O$.

*E. coli* strain MB2159 (Strych U et al, FEMS Microbiol Lett. 2001 Mar. 15; 196(2):93-8) is an alr (−)/dadX (−) deficient mutant that is not able to synthesize D-alanine racemase. *Listeria* strain Lm dal(−)/dat(−) (Lmdd) similarly is not able to synthesize D-alanine racemase due to partial deletions of the dal and the dat genes.

Plasmid Constructions

Using the published sequence of the plcA gene (Mengaud et al., Infect. Immun. 1989 57, 3695-3701), PCR was used to amplify the gene from chromosomal DNA. The amplified product was then ligated into pAM401 using SalI- and XbaI-generated DNA ends to generate pDP1462.

Plasmid pDP1500, containing prfA alone, was constructed by deleting the plcA gene, bases 429 to 1349 (Mengaud et al., supra), from pDP1462 after restriction with XbaI and PstI, treatment of the DNA ends with T4 DNA polymerase to make them blunt, and intramolecular ligation.

Plasmid pDP1499, containing the plcA promoter and a portion of the 3' end of plcA, was constructed by deleting a plcA internal fragment, bases 428 to 882 (Mengaud et al., Infect. Immun. 1989 57, 3695-3701), from pDP1339 after restriction with PstI and NsiI and intramolecular ligation.

pDP1526 (pKSV7::ΔplcA) was constructed by a single three-part ligation of pKSV7 restricted with BAMHI and XbaI, the 468 bp XbaI and NsiI-generated fragment from pAM401::plcA containing the 5' end of plcA (bases 882 to 1351; Mengaud et al., supra) and, the 501 bp PstI- and BamHI-generated fragment from pAM401::plcA prfA containing the 3' end of plcA (bases 77 to 429; Mengaud et al., supra).

The prfA promoter, bases 1-429 (Mengaud et al., supra), was isolated by EcoRI and PstI double digestion of pDP1462 and the fragment was subsequently ligated into EcoRI- and PstI-restricted pKSV7 to generate pDP1498. Two random HindIII-generated 10403S chromosomal DNA fragments, approximately 3 kb in length, were ligated into HindIII-restricted pKSV7, to generate the random integration control plasmids pDP1519 and pDP1521.

Construction of *L. monocytogenes* Mutant Strains

*L. monocytogenes* strain DP-L1387 was isolated as a mutant with reduced lecithinase (PC-PLC) from a Tn917-LTV3 bank of SLCC 5764, constructed as previously described (Camilli et al., J. Bacteriol. 1990, 172, 3738-3744). The site of Tn917-LTV3 insertion was determined by sequencing one transposon-chromosomal DNA junction as previously described (Sun et al., Infect. Immun. 1990 58, 3770-3778). *L. monocytogenes* was transformed with plasmid DNA as previously described (Camilli et al., supra). Selective pressure for maintenance of pAM401, pKSV7, and their derivatives in *L. monocytogenes* was exerted in the presence of 10 μg of chloramphenicol per ml of media. In addition, maintenance of pKSV7 derivatives required growth at 30° C., a permissive temperature for plasmid replication in Gram-positive bacteria.

Integration of pKSV7 derivatives into the *L. monocytogenes* chromosome occurred by homologous recombination between *L. monocytogenes* DNA sequences on the plasmids and their corresponding chromosomal alleles. Integration mutants were enriched by growth for approximately 30 generations at 40° C., a non-permissive temperature for pKSV7 replication, in Brain Heart Infusion (BHI) broth containing 10 μg chloramphenicol per ml of media. Each integration strain was subsequently colony purified on BHI agar containing 10 μg chloramphenicol per ml of media and incubated at 40° C. Southern blot analyses of chromosomal DNA isolated from each integration strain confirmed the presence of the integrated plasmid.

Construction of DP-L1552 is achieved by integration of the pKSV7 derivative, pDP1526, to generate a merodiploid intermediate as described above. Spontaneous excision of the integrated plasmid, through intramolecular homologous recombination, occurred at a low frequency. Bacteria in which the plasmid had excised from the chromosome were enriched by growth at 30° C. in BHI broth for approximately 50 generations. The nature of the selective pressure during this step was not known but may be due to a slight growth defect of strains containing integrated temperature-sensitive plasmids. Approximately 50% of excision events, i.e., those resulting from homologous recombination between sequences 3' of the deletion, resulted in allelic exchange of ΔplcA for the wild-type allele on the chromosome.

The excised plasmids were cured by growing the bacteria at 40° C. in BHI for approximately 30 generations. Bacteria cured of the plasmid retaining the ΔplcA allele on the chromosome were identified by their failure to produce a zone of turbidity surrounding colonies after growth on BHI agar plates containing a 5 ml overlay of BHI agar/2.5% egg yolk/2.5% phosphate-buffered saline (PBS) (BHI/egg yolk agar). The turbid zones resulted from PI-PLC hydrolysis of PI in the egg yolk, giving an insoluble diacylglycerol precipitate. The correct plcA deletion on the *L. monocytogenes* chromosome was confirmed by amplifying the deleted allele using PCR and sequencing across the deletion.

Thus, PI-PLC negative mutants (plcA deletion mutants) may be used according to the present invention to generate attenuated *L. monocytogenes* vaccines. Other mutants were made using the same method, namely, an actA deletion mutant, a plcB deletion mutant, and a double mutant lacking both plcA and plcB, all of which may also be used according to the present disclosure to generate attenuated *L. monocytogenes* vaccines. Given the present disclosure, one skilled in the art would be able to create other attenuated mutants in addition to those mentioned above.

Construction of Lmdd

The dal gene was initially inactivated by means of a double-allelic exchange between the chromosomal gene and the temperature-sensitive shuttle plasmid pKSV7 (Smith K et al, Biochimie. 1992 July-August; 74(7-8):705-11) carrying an erythromycin resistance gene between a 450-bp fragment from the 5' end of the original 850-bp dal gene PCR product and a 450-bp fragment from the 3' end of the dal gene PCR product. Subsequently, a dal deletion mutant covering 82% of the gene was constructed by a similar exchange reaction with pKSV7 carrying homology regions from the 5' and 3' ends of the intact gene (including sequences upstream and downstream of the gene) surrounding the desired deletion. PCR analysis was used to confirm the structure of this chromosomal deletion.

The chromosomal dat gene was inactivated by a similar allelic exchange reaction. pKSV7 was modified to carry 450-bp fragments derived by PCR from both the 5' and 3' ends of the intact dat gene (including sequences upstream and downstream of the gene). These two fragments were ligated by appropriate PCR. Exchange of this construct into the chromosome resulted in the deletion of 30% of the central bases of the dat gene, which was confirmed by PCR analysis.

Bacterial Culture and In Vivo Passaging of *Listeria*

*E. coli* were cultured following standard methods. *Listeria* were grown at 37° C., 250 rpm shaking in LB media (Difco, Detroit, Mich.). +50 μg/ml streptomycin, and harvested during exponential growth phase. For Lm-LLOE7, 37 μg/ml chloramphenicol was added to the media. For growth kinetics determinations, bacteria were grown for 16 hours in 10 ml of LB+antibiotics. The $OD_{600nm}$. was measured and culture densities were normalized between the strains. The culture was diluted 1:50 into LB+suitable antibiotics and D-alanine if applicable.

Passaging of LM in Mice $1\times10^8$ CFU were injected intraperitoneally (i.p.) into C57BL/6 mice. On day three, spleens were isolated and homogenized in PBS. An aliquot of the spleen suspension was plated on LB plates with antibiotics as applicable. Several colonies were expanded and mixed to establish an injection stock.

Construction of Antibiotic Resistance Factor Free Plasmid pTV3

Construction of p60-dal cassette. The first step in the construction of the antibiotic resistance gene-free vector was construction of a fusion of a truncated p60 promoter to the dal gene. The LM alanine racemase (dal) gene (forward primer: 5'-CCA TGG TGA CAG GCT GGC ATC-3'; SEQ ID NO: 41) (reverse primer: 5'-GCT AGC CTA ATG GAT GTA TTT TCT AGG-3'; SEQ ID NO: 42) and a minimal p60 promoter sequence (forward primer: 5'-TTA ATT AAC AAA TAG TTG GTA TAG TCC-3'; SEQ ID No: 43) (reverse primer: 5'-GAC GAT GCC AGC CTG TCA CCA TGG AAA ACT CCT CTC-3'; SEQ ID No: 44) were isolated by PCR amplification from the genome of LM strain 10403S. The primers introduced a PacI site upstream of the p60 sequence, an NheI site downstream of the dal sequence (restriction sites in bold type), and an overlapping dal sequence (the first 18 bp) downstream of the p60 promoter for subsequent fusion of p60 and dal by splice overlap extension (SOE)-PCR. The sequence of the truncated p60 promoter was: CAAATAGTTGGTATAGTCCTCTTTAGCCTTTGGAGTATTATCTCATCATTTGTTTTTTAGGTGAAAACTGGGTAAACTTAGTATTATCAATATAAAATTAATTCTCAAATACTTAATTACGTACTGGGATTTTCTGAAAAAAGAGAGGAGTTTTCC (SEQ ID NO: 45) (Kohler et al, J Bacteriol 173: 4668-74, 1991). Using SOE-PCR, the p60 and dal PCR products were fused and cloned into cloning vector pCR2.1 (Invitrogen, La Jolla, Calif.).

Removal of antibiotic resistance genes from pGG55. The subsequent cloning strategy for removing the Chloramphenicol acetyltransferase (CAT) genes from pGG55 and introducing the p60-dal cassette also intermittently resulted in the removal of the gram-positive replication region (oriRep; Brantl et al, Nucleic Acid Res 18: 4783-4790, 1990). In order to re-introduce the gram-positive oriRep, the oriRep was PCR-amplified from pGG55, using a 5'-primer that added a NarI/EheI site upstream of the sequence (GGCGCCACTAACTCAACGCTAGTAG, SEQ ID NO: 46) and a 3'-primer that added a NheI site downstream of the sequence (GCTAGCCAGCAAAGAAAAACAAACACG, SEQ ID NO: 47). The PCR product was cloned into cloning vector pCR2.1 and sequence verified.

In order to incorporate the p60-dal sequence into the pGG55 vector, the p60-dal expression cassette was excised from pCR-p60dal by PacI/NheI double digestion. The replication region for gram-positive bacteria in pGG55 was amplified from pCR-oriRep by PCR (primer 1, 5'-GTC GAC GGT CAC CGG CGC CAC TAA CTC AAC GCT AGT AG-3'; SEQ ID No: 48); (primer 2, 5'-TTA ATT AAG CTA GCC AGC AAA GAA AAA CAA ACA CG-3'; SEQ ID No: 49) to introduce additional restriction sites for EheI and NheI. The PCR product was ligated into pCR2.1-TOPO (Invitrogen, Carlsbad, Calif.), and the sequence was verified. The replication region was excised by EheI/NheI digestion, and vector pGG55 was double digested with EheI and NheI, removing both CAT genes from the plasmid simultaneously. The two inserts, p60-dal and oriRep, and the pGG55 fragment were ligated together, yielding pTV3 (FIG. 9). pTV3 also contains a prfA (pathogenicity regulating factor A) gene. This gene is not necessary for the function of pTV3, but can be used in situations wherein an additional selected marker is required or desired.

Preparation of DNA for Real-time PCR

Total *Listeria* DNA was prepared using the Masterpure® Total DNA kit (Epicentre, Madison, Wis.). *Listeria* were cultured for 24 hours at 37° C. and shaken at 250 rpm in 25 ml of Luria-Bertoni broth (LB). Bacterial cells were pelleted by centrifugation, resuspended in PBS supplemented with 5 mg/ml of lysozyme and incubated for 20 minutes at 37° C., after which DNA was isolated.

In order to obtain standard target DNA for real-time PCR, the LLO-E7 gene was PCR amplified from pGG55 (5'-ATGAAAAAAATAATGCTAGTTTTTATTAC-3' (SEQ ID NO: 50); 5'-GCGGCCGCTTAATGATGATGATGATGATGTGGTTTCTGAGAACAGATG-3' (SEQ ID NO: 51)) and cloned into vector pETblue1 (Novagen, San Diego, Calif.). Similarly, the plcA amplicon was cloned into pCR2.1. *E. coli* were transformed with pET-LLOE7 and pCR-plcA, respectively, and purified plasmid DNA was prepared for use in real-time PCR.

Real-time PCR

Taqman primer-probe sets (Applied Biosystems, Foster City, Calif.) were designed using the ABI PrimerExpress software (Applied Biosystems) with E7 as a plasmid target, using the following primers: 5'-GCAAGTGTGACTCTACGCTTCG-3' (SEQ ID NO: 52); 5'-TGCCCATTAACAGGTCTTCCA-3' (SEQ ID NO: 53); 5'-FAM-TGCGTACAAAGCACACACGTAGACATTCGTAC-TAMRA-3' (SEQ ID NO: 54) and the one-copy gene plcA (TGACATCGTTTGTGTTTGAGCTAG-3' (SEQ ID NO: 55), 5'-GCAGCGCTCTCTATACCAGGTAC-3' (SEQ ID NO: 56); 5'-TET-TTAATGTCCATGTTATGTCTCCGT-TATAGCTCATCGTA-TAMRA-3'; SEQ ID NO: 57) as a *Listeria* genome target.

0.4 μM primer and 0.05 mM probe were mixed with PuRE Taq RTG PCR beads (Amersham, Piscataway, N.J.) as recommended by the manufacturer. Standard curves were prepared for each target with purified plasmid DNA, pET-LLOE7 and pCR-plcA (internal standard) and used to calculate gene copy numbers in unknown samples. Mean ratios of E7 copies/plcA copies were calculated based on the standard curves and calibrated by dividing the results for Lmdd-TV3 and Lm-LLOE7 with the results from Lm-E7, a *Listeria* strain with a single copy of the E7 gene integrated into the genome. All samples were run in triplicate in each qPCR assay which was repeated three times. Variation between samples was analyzed by Two-Way ANOVA using the KyPlot software. Results were deemed statistically significant if $p<0.05$.

Growth Measurements

Bacteria were grown at 37° C., 250 rpm shaking in Luria Bertani (LB) Medium+/−100 micrograms (μg)/ml D-alanine and/or 37 μg/ml chloramphenicol. The starting inoculum was adjusted based on $OD_{600}$ nm measurements to be the same for all strains.

Hemolytic Lysis Assay $4\times10^9$ CFU of *Listeria* were thawed, pelleted by centrifugation (1 minute, 14000 rpm) and resuspended in 100 μl PBS, pH 5.5 with 1 M cysteine. Bacteria were serially diluted 1:2 and incubated for 45 minutes at 37° C. in order to activate secreted LLO. Defibrinated total sheep blood (Cedarlane, Hornby, Ontario, Canada) was washed twice with 5 volumes of PBS and three to four times with 6 volumes of PBS-Cysteine until the supernatant remained clear, pelleting cells at 3000×g for 8 minutes between wash steps, then resuspended to a final concentration of 10% (v/v) in PBS-Cysteine. 100 μl of 10% washed blood cells were mixed with 100 μl of *Listeria* suspension and incubated for additional 45 minutes at 37° C. Un-lysed blood cells were then pelleted by centrifugation (10 minutes, 1000×g). 100 μl of supernatant was transferred into a new plate and the $OD_{530nm}$ was determined and plotted against the sample dilution.

Therapeutic Efficacy of Lmdd-Tv3

$10^5$ TC-1 (ATCC, Manassas, Va.) were implanted subcutaneously in C57BL/6 mice (n=8) and allowed to grow for about 7 days, after which tumors were palpable. TC-1 is a C57BL/6 epithelial cell line that was immortalized with HPV E6 and E7 and transformed with activated ras, which forms tumors upon subcutaneous implantation. Mice were immunized with 0.1 $LD_{50}$ of the appropriate *Listeria* strain on days 7 and 14 following implantation of tumor cells. A non-immunized control group (naïve) was also included. Tumor growth was measured with electronic calipers.

Generation of an ActA Deletion Mutant

Figure 12:
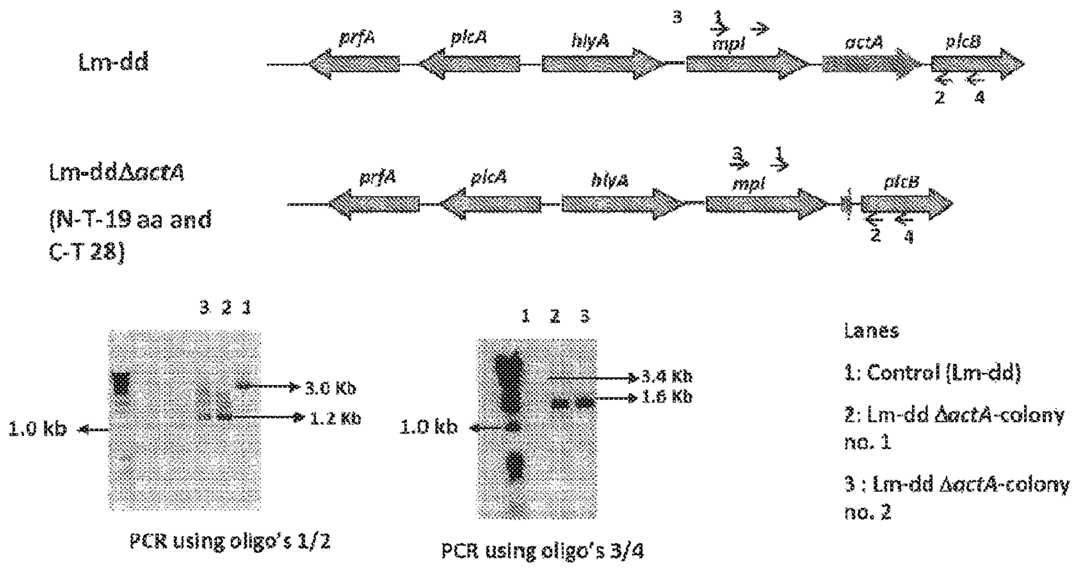
FIG. 12 shows a Schematic representation of the Lm-dd and Lm-ddD actA strains. The gel showing the size of PCR products using oligo's ½ and oligo's ¾ obtained using e chromosomal DNA of the strains, Lm-dd and Lm-ddΔactA as template.

The strain Lm dal dat (Lmdd) was attenuated by the irreversible deletion of the virulence factor, ActA. An in frame deletion of actA in the Lmdaldat (Lmdd) background was constructed to avoid any polar effects on the expression of downstream genes. The Lm dal dat ΔactA contains the first 19 amino acids at the N-terminal and 28 amino acid residues of the C-terminal with a deletion of 591 amino acids of ActA. The deletion of the gene into the chromosomal spot was verified using primers that anneal external to the actA deletion region. These are primers 3 (Adv 305-tgggatggc-caagaaattc) (SEQ ID NO: 58) and 4 (Adv304-ctaccatgtctc-cgttgcttg) (SEQ ID NO: 59) as shown in the FIG. 12. The PCR analysis was performed on the chromosomal DNA isolated from Lmdd and Lm-ddΔactA. The sizes of the DNA fragments after amplification with two different set of primer pairs 1, 2 and 3, 4 in Lm-dd chromosomal DNA was expected to be 3.0 Kb and 3.4 Kb. However, for the Lm-ddΔactA the expected sizes of PCR using the primer pairs 1, 2 and 3, 4 was 1.2 Kb and 1.6 Kb. Thus, PCR analysis in FIG. 12 confirms that 1.8 kb region of actA was deleted in the strain, Lm-ddΔactA. DNA sequencing was also performed on PCR products to confirm the deletion of actA containing region in the strain, Lm-ddΔactA (FIG. 13, SEQ ID NO: 60).

(SEQ ID NO: 60)

gcgccaaatcattggttgattggtgaggatgtctgtgtgcgtgggtcgcg
agatgggcgaataagaagcattaaagatcctgacaaatataatcaagcgg
ctcatatgaaagattacgaatcgcttccactcacagaggaaggcgactgg
ggcggagttcattataatagtggtatcccgaataaagcagcctataatac
tatcactaaacttggaaaagaaaaaacagaacagctttattttcgcgcct
taaagtactatttaacgaaaaaatcccagtttaccgatgcgaaaaaagcg
cttcaacaagcagcgaaagatttatatggtgaagatgcttctaaaaaagt
tgctgaagcttgggaagcagttggggttaactgattaacaaatgttagag
aaaaattaattctccaagtgatattcttaaaataattcatgaatattttt
tcttatattagctaattaagaagataactaactgctaatccaatttttaa
cggaacaaattagtgaaaatgaaggccgaattttccttgttctaaaaagg
ttgtattagcgtatcacgaggagggagtataa*gtgggattaaacagattt*
*atgcgtgcgatgatggtggttttcattactgccaattgcattacgattaa*
*ccccgac*<u>gtcgac</u>*ccatacgacgttaattcttgcaatgttagctattggc*
*gtgttctctttaggggcgtttatcaaaattattcaattaagaaaaaataa*
*tta*aaaacacagaacgaaagaaaaagtgaggtgaatgatatgaaattcaa
aaaggtggttctaggtatgtgcttgatcgcaagtgttctagtctttccgg
taacgataaaagcaaatgcctgttgtgatgaatacttacaaacacccgca
gctccgcatgatattgacagcaaattaccacataaacttagttggtccgc
ggataacccgacaaatactgacgtaaatacgcactattggctttttaaac
aagcggaaaaaatactagctaaagatgtaaatcatatgcgagctaattta
atgaatgaacttaaaaaattcgataaacaaatagctcaaggaatatatga
tgcggatcataaaaatccatattatgatactagtacatttttatctcatt
tttataatcctgatagagataatacttatttgccgggttttgctaatgcg
aaaataacaggagcaaagtatttcaatcaatcggtgactgattaccgaga
agggaa.

Production of Inflammatory Cytokines:

Macrophages such as RAW 264.7 are infected with different *Listeria* backbones such as Lm prfA-(pGG55), Lm dal dat, Lm dal dat actA, Lm dal dat actA Δ inlC and Lm dal dat Δ inlC and supernatant is harvested at different time points to quantify the level of various cytokines using different ELISA based kits. The cytokines that are quantified include IFN-γ, TNF-α and IL-6.

In Vivo Cytokine Production:

To measure the in vivo cytokine production and recruitment of neutrophils, C57BL/6 mice are injected intraperitoneally with different $10^8$ CFU of Lm prfA-(pGG55), Lm dal dat, Lm dal dat actA, Lm dal dat actA Δ inlC and Lm dal dat Δ inlC, *Listeria* control or an equivalent volume of saline. After 12 h mice are killed and peritoneal cavities are washed with 2 mL of PBS. The peritoneal washes are examined for bacterial load after plating on growth medium and analysis of proinflammatory cytokines such as MIP-1α, KC, MCP etc. Using flow cytometry the number of neutrophils and macrophages is determine after staining with markers such as Gr-1, CD11b and F4/80 and further these populations are quantified using CellQuest software.

Transwell Migration Assay:

This assay is done to determine if there is an increase in the migration of neutrophils following infection of bone marrow derived macrophages or dendritic cells with the inlC deletion strain. Bone marrow-derived macrophages or dendritic cells are isolated from mice such as C57BL/6 and are infected with the inlC deletion mutants or control *Listeria*. Using infected cells the transwell assay is set up using corning costar Transwell plates. The assay is initially standardized using 3, 5, or 8 micron pore transwell plates. To test neutrophil migration, plate the infected APCs in the bottom of the plate and the neutrophils in the top of the well in the chamber. At different time points the cells are counted to determine the number of neutrophils that have migrated to the bottom.

Therapeutic Efficacy of the Lm Dal Dat actA Δ inlC Mutant:

To determine the therapeutic efficacy of inlC mutant, human Prostate specific antigen (PSA) is used as tumor antigen as proof of concept. The backbone Lm dal dat actA inlC are transformed with the plasmid, pAdv142 that contains expression cassette for human PSA resulting in LmddAinlC142. The strain LmddAinlC142 is characterized for the expression and secretion of fusion protein, tLLO-PSA. Further the strain LmddAinlC142 are passaged twice in vivo in mice and the colonies obtained after two in vivo passages are examined for the expression and secretion of fusion protein, tLLO-PSA. The vaccine working stock are prepared from the colonies obtained after second in vivo passage and this are used for the assessment of therapeutic effects and immunogenicity. —

Impact on Tumor Microenvironment:

The ability of LmddA, LmddAΔactA, LmddAΔPlcA, LmddAΔPlcB, LmddAΔprfA, LmddAinlC142, LmddA142 and other control strains to cause infiltration of immune cells in the tumor microenvironment are determined. In this study mice are inoculated with $1\times10^6$ TPSA23 tumor cells on day 0 and are vaccinated on day 7, 14 and 21 with $10^8$ CFU of LmddAinlC142, LmddA142 and other control strains. Tumors are harvested on day 28 and processed for further staining with different cell surface markers such as Gr-1, CD11b, CD3, CD4, CD8, CD25, Foxp3, NK1.1 and CD62L. Using these markers different cell populations that are examined include macrophages ($CD11b^+$), NK cells ($NK1.1^+$), neutrophils ($Gr\text{-}1^+$ $CD11b^+$), myeloid derived suppressor cells (MDSCs) ($Gr\text{-}1^+$ $CD11b^+$), regulatory T cells ($CD4^+$ $CD25^+$ $Foxp3^+$) and effector T cells ($CD8^+$ $CD3^+$ $CD62L^{low}$). Further effector T cells are characterized for their functional ability to produce effector cytokines such as IFN-γ, TNF-α and IL-2. The intratumoral regulatory T cells and MDSCs are tested for their ability to cause suppression of T cell proliferation.

Results

Example 5

Figure 9A:
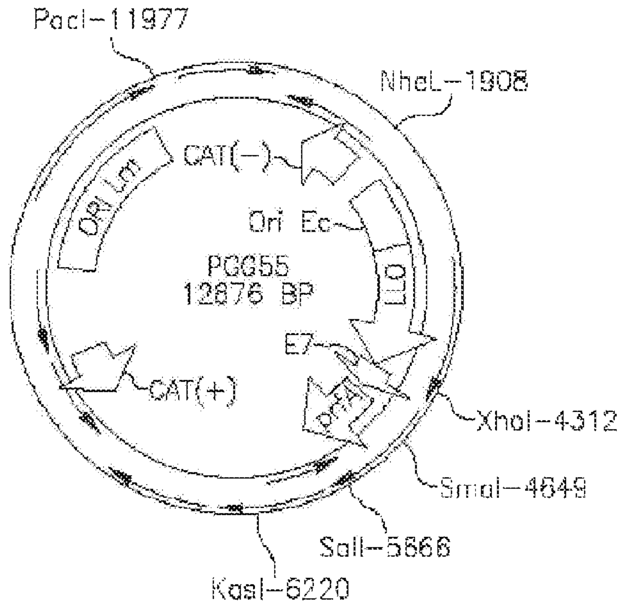
FIG. 9A shows a schematic map of *E. coli-Listeria* shuttle plasmid pGG55. CAT(−): *E. coli* chloramphenicol transferase; CAT(+): *Listeria* chloramphenicol transferase; On Lm: replication origin for *Listeria*; On Ec: p15 origin of replication for *E. coli*; prfA: *Listeria* pathogenicity regulating factor A; LLO: C-terminally truncated listeriolysin O, including its promoter; E7: HPV E7. Selected restriction sites are also depicted.
Figure 9B:
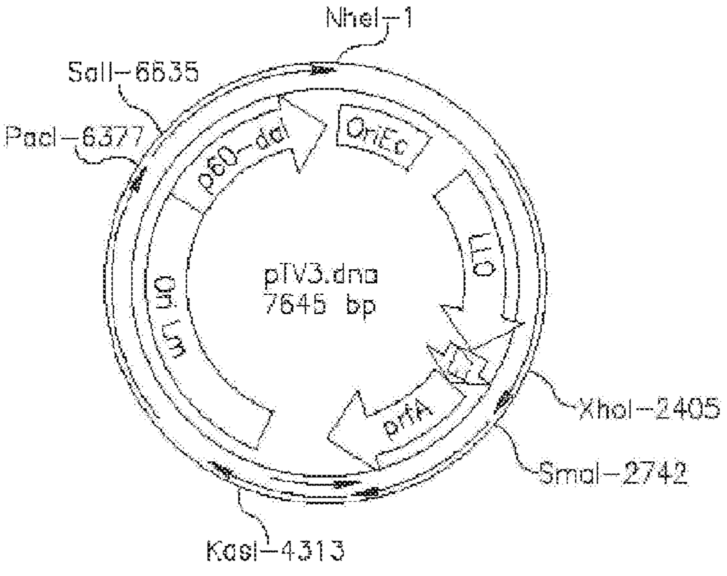
FIG. 9B shows a schematic map of *E. coli-Listeria* shuttle plasmid pTV3 (below). CAT(−): *E. coli* chloramphenicol transferase; CAT(+): *Listeria* chloramphenicol transferase; On Lm: replication origin for *Listeria*; On Ec: p15 origin of replication for *E. coli*; prfA: *Listeria* pathogenicity regulating factor A; LLO: C-terminally truncated listeriolysin O, including its promoter; E7: HPV E7; p60-dal; expression cassette of p60 promoter and *Listeria* dal gene. Selected restriction sites are also depicted.

A Plasmid Containing an Amino Acid Metabolism Enzyme Instead of an Antibiotic Resistance Gene is Retained in E. *Coli* and Lm Both In Vitro and In Vivo An auxotroph complementation system based on D-alanine racemase was utilized to mediate plasmid retention in LM without the use of an antibiotic resistance gene. *E. coli* strain MB2159 is an alr (−)/dadX (−) deficient mutant that is not able to synthesize D-alanine racemase. *Listeria* strain Lm dal(−)/dat(−) (Lmdd) similarly is not able to synthesize D-alanine racemase due to partial deletions of the dal and the dat genes. Plasmid pGG55, which is based on *E. coli-Listeria* shuttle vector pAM401, was modified by removing both CAT genes and replacing them with a p60-dal expression cassette under control of the *Listeria* p60 promoter to generate pTV3 (FIG. 9). DNA was purified from several colonies.

Example 6

Plasmids Containing a Metabolic Enzyme do not Increase the Virulence of Bacteria As virulence is linked to LLO function, the hemolytic lysis activity between Lmdd-TV3 and Lm-LLOE7 was compared. This assay tests LLO function by lysis of red blood cells and can be performed with culture supernatant, purified LLO or bacterial cells. Lmdd-TV3 displayed higher hemolytic lysis activity than Lm-LLOE7.

In vivo virulence was also measured by determining $LD_{50}$ values, a more direct, and therefore accurate, means of measuring virulence. The $LD_{50}$ of Lmdd-TV3 ($0.75\times10^9$) was very close to that of Lm-LLOE7 ($1\times10^9$), showing that plasmids containing a metabolic enzyme do not increase the virulence of bacteria.

Example 7

Induction of Anti-Tumor Immunity by Plasmids Containing a Metabolic Enzyme

Figure 14:
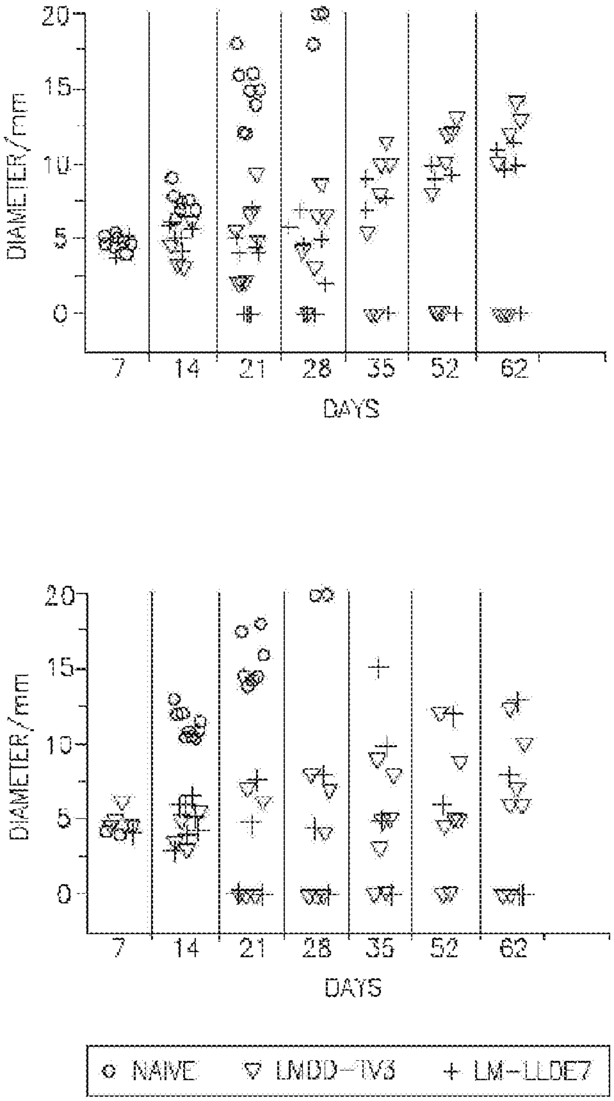
FIG. 14 depicts tumor regression in response to administration of LM vaccine strains (A). Circles represent naive mice, inverted triangles represent mice administered Lmdd-TV3, and crosses represent mice administered Lm-LLOE7.

Efficacy of the metabolic enzyme-containing plasmid as a cancer vaccine was determined in a tumor regression model. The TC-1 cell line model, which is well characterized for HPV vaccine development and which allowed for a controlled comparison of the regression of established tumors of similar size after immunization with Lmdd-TV3 or Lm-LLOE7, was used. In two separate experiments, immunization of mice with Lmdd-TV3 and Lm-LLOE7 resulted in similar tumor regression (FIG. 14) with no statistically significant difference ($p<0.05$) between vaccinated groups. All immunized mice were still alive after 63 days, whereas non-immunized mice had to be sacrificed when their tumors reached 20 mm diameter. Cured mice remained tumor-free until the termination of the experiment.

Thus, metabolic enzyme-containing plasmids are efficacious as a therapeutic cancer vaccine. Because immune responses required for a therapeutic cancer vaccine are stronger than those required for a prophylactic cancer vaccine, these results demonstrate utility as well for a prophylactic cancer vaccine.

Example 8 inlC-Deletion Mutant Generate Significantly High Levels of the Chemokines and Cytokines inlC deletion mutant generates significantly high levels of the chemokines such as MIP-1α, KC (mouse homolog of IL-8), MCP resulting in infiltration of neutrophils and leukocytes towards the site of infection. Thus when different *Listeria* strains are administered intraperitoneally, the inlC mutant demonstrate an increase production of these cytokines and chemokines, which attract neutrophils and macrophages in the peritoneal fluid obtained 12 h after injection. Further, inlC deletion mutant generate significantly high levels of the inflammatory cytokines when compared to control strains.

Example 9 inlC-Deletion Mutants Induce Neutrophil Migration

The macrophages infected with inlC deletion mutant show significant increase in the migration of neutrophils at different time points when compared to other control strains. The results of this experiment strongly support the ability of this strain to attract immune cells such as neutrophils during infection.

Example 10 inlC-Deletion Mutants Effect a Therapeutic Anti-Tumor Response

The results of anti-tumor studies using both LmddA142 and LmddAinlC142 are very comparable to each other and therapeutic regression of tumors is observed. Further, two doses of LmddAinlC142 are comparable to three doses of the strain LmddA142 because of its ability to generate high levels of innate responses and increased secretion of proinflammatory cytokines.

Materials and Methods (Examples 11-16)

Oligonucleotides were synthesized by Invitrogen (Carlsbad, Calif.) and DNA sequencing was done by Genewiz Inc, South Plainfield, N.J. Flow cytometry reagents were purchased from Becton Dickinson Biosciences (BD, San Diego, Calif.). Cell culture media, supplements and all other reagents, unless indicated, were from Sigma (St. Louise, Mo.). Her2/neu HLA-A2 peptides were synthesized by EZbiolabs (Westfield, Ind.). Complete RPMI 1640 (C-RPMI) medium contained 2 mM glutamine, 0.1 mM non-essential amino acids, and 1 mM sodium pyruvate, 10% fetal bovine serum, penicillin/streptomycin, Hepes (25 mM). The polyclonal anti-LLO antibody was described previously and anti-Her2/neu antibody was purchased from Sigma.

Mice and Cell Lines

All animal experiments were performed according to approved protocols by IACUC at the University of Pennsylvania or Rutgers University. FVB/N mice were purchased from Jackson laboratories (Bar Harbor, Me.). The FVB/N Her2/neu transgenic mice, which overexpress the rat Her2/neu onco-protein were housed and bred at the animal core facility at the University of Pennsylvania. The NT-2 tumor cell line expresses high levels of rat Her2/neu protein, was derived from a spontaneous mammary tumor in these mice and grown as described previously. DHFR-G8 (3T3/neu) cells were obtained from ATCC and were grown according to the ATCC recommendations. The EMT6-Luc cell line was a generous gift from Dr. John Ohlfest (University of Minnesota, MN) and was grown in complete C-RPMI medium. Bioluminescent work was conducted under guidance by the Small Animal Imaging Facility (SAIF) at the University of Pennsylvania (Philadelphia, Pa.).

*Listeria* Constructs and Antigen Expression

Her2/neu-pGEM7Z was kindly provided by Dr. Mark Greene at the University of Pennsylvania and contained the full-length human Her2/neu (hHer2) gene cloned into the pGEM7Z plasmid (Promega, Madison Wis.). This plasmid was used as a template to amplify three segments of hHer-2/neu, namely, EC1, EC2, and IC1, by PCR using pfx DNA polymerase (Invitrogen) and the oligos indicated in Table 2.

TABLE 2

Primers for cloning of Human her-2-Chimera

| | DNA sequence | Base pair region | Amino acid region or junctions |
|---|---|---|---|
| Her-2-Chimera (F) | TGATCTCGAGACCCACCTGGACATGCTC (SEQ ID NO: 61) | 120-510 | 40-170 |
| HerEC1-EC2F (Junction) | CTACCAGGACACGATTTTGTGGAAG-AATATCCA GGAGTTTGCTGGCTGC (SEQ ID NO: 62) | 510/1077 | 170/359 |
| HerEC1-EC2R (Junction) | GCAGCCAGCAAACTCCTGGATATT-CTTCCACAA AATCGTGTCCTGGTAG (SEQ ID NO: 63) | | |
| HerEC2-ICIF (Junction) | CTGCCACCAGCTGTGCGCCCGAGGG-CAGCAGAAGATCCGGAAGTACACGA (SEQ ID NO: 64) | 1554/2034 | 518/679 |
| HerEC2-ICIR (Junction) | TCGTGTACTTCCGGATCTTCTGCTG CCCTCGGGC GCACAGCTGGTGGCAG (SEQ ID NO: 65) | | |
| Her-2-Chimera (R) | GTGGCCCGGGTCTAGATTAGTCTAAGAGGCAGCCATAGG (SEQ ID NO: 66) | 2034-2424 | 679-808 |

The Her-2/neu chimera construct was generated by direct fusion by the SOEing PCR method and each separate hHer-2/neu segment as templates. Primers are shown in Table 3.

Sequence of primers for amplification of different segments human Her2 regions.

| | DNA sequence | Base pair region | Amino acid region |
|---|---|---|---|
| Her-2-EC1(F) | CCGCCTCGAGGCCGCGAGCACCCAAGTG (SEQ ID NO: 67) | 58-979 | 20-326 |
| Her-2-EC1(R) | CGCGACTAGTTTAATCCTCTGCTGTCACCTC (SEQ ID NO: 68) | | |
| Her-2-EC2(F) | CCGCCTCGAGTACCTTTCTACGGACGTG (SEQ ID NO: 69) | 907-1504 | 303-501 |
| Her-2-EC2(R) | CGCGACTAGTTTACTCTGGCCGGTTGGCAG (SEQ ID NO: 70) | | |
| Her-2-IC1(F) | CCGCCTCGAGCAGCAGAAGATCCGGAAGTAC (SEQ ID NO: 71) | 2034-3243 | 679-1081 |
| Her-2-IC1(R) | CGCGACTAGTTTAAGCCCCTTCGGAGGGTG (SEQ ID NO: 72) | | |

Sequence of primers for amplification of different segments human Her2 regions.

ChHer2 gene was excised from pAdv138 using XhoI and SpeI restriction enzymes, and cloned in frame with a truncated, non-hemolytic fragment of LLO in the Lmdd shuttle vector, pAdv134. The sequences of the insert, LLO and hly promoter were confirmed by DNA sequencing analysis. This plasmid was electroporated into electro-competent actA, dal, dat mutant *Listeria monocytogenes* strain, LmddA and positive clones were selected on Brain Heart infusion (BHI) agar plates containing streptomycin (250 μg/ml). In some experiments similar *Listeria* strains expressing hHer2/neu (Lm-hHer2) fragments were used for comparative purposes. These have been previously described. In all studies, an irrelevant *Listeria* construct (Lm-control) was included to account for the antigen independent effects of *Listeria* on the immune system. Lm-controls were based on the same *Listeria* platform as ADXS31-164, but expressed a different antigen such as HPV16-E7 or NY-ESO-1. Expression and secretion of fusion proteins from *Listeria* were tested. Each construct was passaged twice in vivo.

Cytotoxicity Assay

Groups of 3-5 FVB/N mice were immunized three times with one week intervals with $1\times10^8$ colony forming units (CFU) of Lm-LLO-ChHer2, ADXS31-164, Lm-hHer2 ICI or Lm-control (expressing an irrelevant antigen) or were left naïve. NT-2 cells were grown in vitro, detached by trypsin and treated with mitomycin C (250 μg/ml in serum free C-RPMI medium) at 37° C. for 45 minutes. After 5 washes, they were co-incubated with splenocytes harvested from immunized or naïve animals at a ratio of 1:5 (Stimulator: Responder) for 5 days at 37° C. and 5% $CO_2$. A standard cytotoxicity assay was performed using europium labeled 3T3/neu (DHFR-G8) cells as targets according to the method previously described. Released europium from killed target cells was measured after 4 hour incubation using a spectrophotometer (Perkin Elmer, Victor$^2$) at 590 nm. Percent specific lysis was defined as (lysis in experimental group-spontaneous lysis)/(Maximum lysis-spontaneous lysis).

Interferon-γ Secretion by Splenocytes from Immunized Mice

Groups of 3-5 FVB/N or HLA-A2 transgenic mice were immunized three times with one week intervals with $1\times10^8$ CFU of ADXS31-164, a negative *Listeria* control (expressing an irrelevant antigen) or were left naïve. Splenocytes from FVB/N mice were isolated one week after the last immunization and co-cultured in 24 well plates at $5\times10^6$ cells/well in the presence of mitomycin C treated NT-2 cells in C-RPMI medium. Splenocytes from the HLA-A2 transgenic mice were incubated in the presence of 1 μM of HLA-A2 specific peptides or 1 μg/ml of a recombinant His-tagged ChHer2 protein, produced in *E. coli* and purified by a nickel based affinity chromatography system. Samples from supernatants were obtained 24 or 72 hours later and tested for the presence of interferon-γ (IFN-γ) using mouse IFN-γ Enzyme-linked immunosorbent assay (ELISA) kit according to manufacturer's recommendations.

Tumor Studies in HER2 Transgenic Animals

Six weeks old FVB/N rat Her2/neu transgenic mice (9-14/group) were immunized 6 times with $5\times10^8$ CFU of Lm-LLO-ChHer2, ADXS31-164 or Lm-control. They were observed twice a week for the emergence of spontaneous mammary tumors, which were measured using an electronic caliper, for up to 52 weeks. Escaped tumors were excised when they reached a size 1 $cm^2$ in average diameter and preserved in RNAlater at −20° C. In order to determine the effect of mutations in the Her2/neu protein on the escape of these tumors, genomic DNA was extracted using a genomic DNA isolation kit, and sequenced.

Effect of ADXS31-164 on Regulatory T Cells in Spleens and Tumors

Mice were implanted subcutaneously (s.c.) with $1\times10^6$ NT-2 cells. On days 7, 14 and 21, they were immunized with $1\times10^8$ CFUs of ADXS31-164, LmddA-control or left naïve. Tumors and spleens were extracted on day 28 and tested for the presence of $CD3^+/CD4^+/FoxP3^+$ Tregs by FACS analysis. Briefly, splenocytes were isolated by homogenizing the spleens between two glass slides in C-RPMI medium. Tumors were minced using a sterile razor blade and digested with a buffer containing DNase (12 U/ml), and collagenase (2 mg/ml) in PBS. After 60 min incubation at RT with agitation, cells were separated by vigorous pipetting. Red blood cells were lysed by RBC lysis buffer followed by several washes with complete RPMI-1640 medium containing 10% FBS. After filtration through a nylon mesh, tumor cells and splenocytes were resuspended in FACS buffer (2% FBS/PBS) and stained with anti-CD3-PerCP-Cy5.5, CD4-FITC, CD25-APC antibodies followed by permeabilization and staining with anti-Foxp3-PE. Flow cytometry analysis was performed using 4-color FACS calibur (BD) and data were analyzed using cell quest software (BD).

Statistical Analysis

The log-rank Chi-Squared test was used for survival data and student's t-test for the CTL and ELISA assays, which were done in triplicates. A p-value of less than 0.05 (marked as *) was considered statistically significant in these analyzes. All statistical analysis was done with either Prism software, V.4.0a (2006) or SPSS software, V.15.0 (2006). For all FVB/N rat Her2/neu transgenic studies we used 8-14 mice per group, for all wild-type FVB/N studies we used at least 8 mice per group unless otherwise stated. All studies were repeated at least once except for the long term tumor study in Her2/neu transgenic mouse model.

Results

Example 11

Generation of L. *Monocytogenes* Strains that Secrete LLO Fragments Fused to Her-2 Fragments: Construction of ADXS31-164

Figure 15:
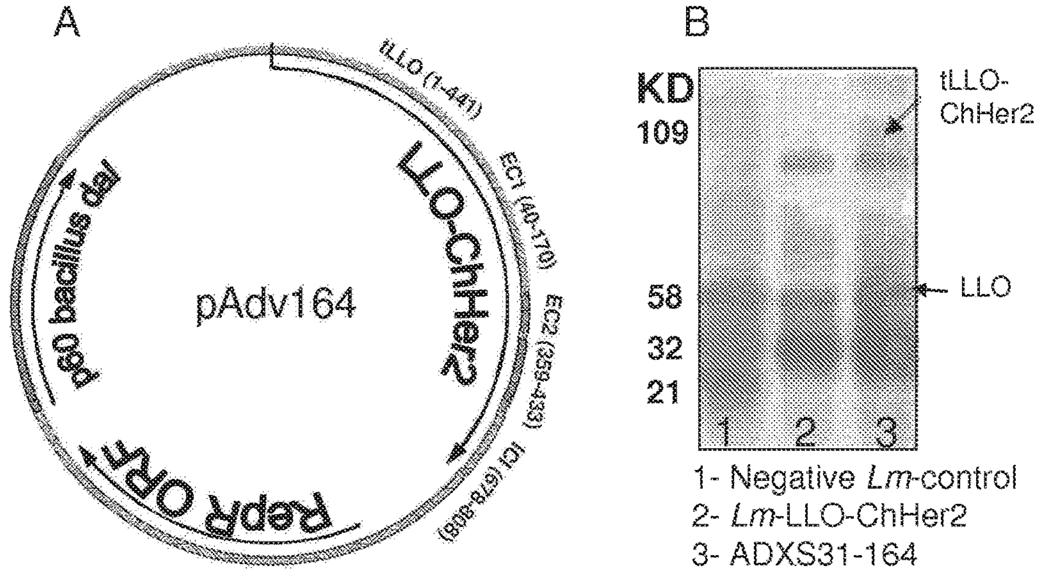
FIG. 15 shows (A) Plasmid map of pAdv164, which harbors *bacillus subtilis* dal gene under the control of constitutive *Listeria* p60 promoter for complementation of the chromosomal dal-dat deletion in LmddA strain. It also contains the fusion of truncated $LLO_{(1-441)}$ to the chimeric human Her2/neu gene, which was constructed by the direct fusion of 3 fragments the Her2/neu: EC1 (aa 40-170), EC2 (aa 359-518) and ICI (aa 679-808). (B) Expression and secretion of tLLO-ChHer2 was detected in Lm-LLO-ChHer2 (Lm-LLO-138) and LmddA-LLO-ChHer2 (ADXS31-164) by western blot analysis of the TCA precipitated cell culture supernatants blotted with anti-LLO antibody. A differential band of ~104 KD corresponds to tLLO-ChHer2. The endogenous LLO is detected as a 58 KD band. *Listeria* control lacked ChHer2 expression.

Construction of the chimeric Her2/neu gene (ChHer2) was described previously. Briefly, ChHer2 gene was generated by direct fusion of two extracellular (aa 40-170 and aa 359-433) and one intracellular fragment (aa 678-808) of the Her2/neu protein by SOEing PCR method. The chimeric protein harbors most of the known human MHC class I epitopes of the protein. ChHer2 gene was excised from the plasmid, pAdv138 (which was used to construct Lm-LLO-ChHer2) and cloned into LmddA shuttle plasmid, resulting in the plasmid pAdv164 (FIG. 15A). There are two major differences between these two plasmid backbones. 1) Whereas pAdv138 uses the chloramphenicol resistance marker (cat) for in vitro selection of recombinant bacteria, pAdv164 harbors the D-alanine racemase gene (dal) from *bacillus subtilis*, which uses a metabolic complementation pathway for in vitro selection and in vivo plasmid retention in LmddA strain which lacks the dal-dat genes. This vaccine platform was designed and developed to address FDA concerns about the antibiotic resistance of the engineered *Listeria* vaccine strains. 2) Unlike pAdv138, pAdv164 does not harbor a copy of the prfA gene in the plasmid (see sequence below and FIG. 15A), as this is not necessary for in vivo complementation of the Lmdd strain. The LmddA vaccine strain also lacks the actA gene (responsible for the intracellular movement and cell-to-cell spread of *Listeria*) so the recombinant vaccine strains derived from this backbone are 100 times less virulent than those derived from the Lmdd, its parent strain. LmddA-based vaccines are also cleared much faster (in less than 48 hours) than the Lmdd-based vaccines from the spleens of the immunized mice. The expression and secretion of the fusion protein tLLO-ChHer2 from this strain was comparable to that of the Lm-LLO-ChHer2 in TCA precipitated cell culture supernatants after 8 hours of in vitro growth (FIG. 15B) as a band of ~104 KD was detected by an anti-LLO antibody using Western Blot analysis. The *Listeria* backbone strain expressing only tLLO was used as negative control.

pAdv164 sequence (7075 base pairs) (see FIG. 15):

(SEQ ID NO: 73)

```
cggagtgtatactggcttactatgttggcactgatgagggtgtcagtga
agtgcttcatgtggcaggagaaaaaaggctgcaccggtgcgtcagcaga
atatgtgatacaggatatattccgcttcctcgctcactgactcgctacg
ctcggtcgttcgactgcggcgagcggaaatggcttacgaacggggcgga
gatttcctggaagatgccaggaagatacttaacagggaagtgagagggc
cgcggcaaagccgtttttccataggctccgcccccctgacaagcatcac
gaaatctgacgctcaaatcagtggtggcgaaacccgacaggactataaa
gataccaggcgtttccccctggcggctccctcgtgcgctctcctgttcc
tgcctttcggtttaccggtgtcattccgctgttatggccgcgtttgtct
cattccacgcctgacactcagttccgggtaggcagttcgctccaagctg
gactgtatgcacgaaccccccgttcagtccgaccgctgcgccttatccg
gtaactatcgtcttgagtccaacccggaaagacatgcaaaagcaccact
ggcagcagccactggtaattgatttagaggagttagtcttgaagtcatg
cgccggttaaggctaaactgaaaggacaagttttggtgactgcgctcct
ccaagccagttacctcggttcaaagagttggtagctcagagaaccttcg
aaaaaccgccctgcaaggcggttttttcgttttcagagcaagagattac
gcgcagaccaaaacgatctcaagaagatcatcttattaatcagataaaa
tatttctagccctcctttgattagtatattcctatcttaaagttacttt
tatgtggaggcattaacatttgttaatgacgtcaaaaggatagcaagac
tagaataaagctataaagcaagcatataatattgcgtttcatctttaga
agcgaatttcgccaatattataattatcaaaagagaggggtggcaaacg
gtatttggcattattaggttaaaaaatgtagaaggagagtgaaacccat
gaaaaaaataatgctagtttttattacacttatattagttagtctacca
attgcgcaacaaactgaagcaaaggatgcatctgcattcaataaagaaa
attcaatttcatccatggcaccaccagcatctccgcctgcaagtcctaa
gacgccaatcgaaaagaaacacgcggatgaaatcgataagtatatacaa
ggattggattacaataaaaacaatgtattagtataccacggagatgcag
tgacaaatgtgccgccaagaaaaggttacaaagatggaaatgaatatat
tgttgtggagaaaaagaagaaatccatcaatcaaaataatgcagacatt
caagttgtgaatgcaatttcgagcctaacctatccaggtgctctcgtaa
aagcgaattcggaattagtagaaaatcaaccagatgttctccctgtaaa
acgtgattcattaacactcagcattgatttgccaggtatgactaatcaa
gacaataaaatagttgtaaaaaatgccactaaatcaaacgttaacaacg
cagtaaatacattagtggaaagatggaatgaaaaatatgctcaagctta
tccaaatgtaagtgcaaaaattgattatgatgacgaaatggcttacagt
gaatcacaattaattgcgaaatttggtacagcatttaaagctgtaaata
atagcttgaatgtaaacttcggcgcaatcagtgaagggaaaatgcaaga
agaagtcattagttttaaacaaatttactataacgtgaatgttaatgaa
cctacaagaccttccagattttcggcaaagctgttactaaagagcagt
```

-continued tgcaagcgcttggagtgaatgcagaaaatcctcctgcatatatctcaag
tgtggcgtatggccgtcaagtttatttgaaattatcaactaattcccat
agtactaaagtaaaagctgcttttgatgctgccgtaagcggaaaatctg
tctcaggtgatgtagaactaacaaatatcatcaaaaattcttccttcaa
agccgtaatttacggaggttccgcaaaagatgaagttcaaatcatcgac
ggcaacctcggagacttacgcgatattttgaaaaaaggcgctactttta
atcgagaaacaccaggagttcccattgcttatacaacaaacttcctaaa
agacaatgaattagctgttattaaaaacaactcagaatatattgaaaca
acttcaaaagcttatacagatggaaaaattaacatcgatcactctggag
gatacgttgctcaattcaacatttcttgggatgaagtaaattatgatct
cgagacccacctggacatgctccgccacctctaccagggctgccaggtg
gtgcagggaaacctggaactcacctacctgcccaccaatgccagcctgt
ccttcctgcaggatatccaggaggtgcagggctacgtgctcatcgctca
caaccaagtgaggcaggtcccactgcagaggctgcggattgtgcgaggc
acccagctctttgaggacaactatgccctggccgtgctagacaatggag
acccgctgaacaataccacccctgtcacaggggcctccccaggaggcct
gcgggagctgcagcttcgaagcctcacagagatcttgaaaggaggggtc
ttgatccagcggaaccccagctctgctaccaggacacgatttgtgga
agaatatccaggagtttgctggctgcaagaagatctttgggagcctggc
atttctgccggagagctttgatggggacccagcctccaacactgccccg
ctccagccagagcagctccaagtgtttgagactctggaagagatcacag
gttacctatacatctcagcatggccggacagcctgcctgacctcagcgt
cttccagaacctgcaagtaatccggggacgaattctgcacaatggcgcc
tactcgctgaccctgcaagggctgggcatcagctggctggggctgcgct
cactgagggaactgggcagtggactggccctcatccaccataacaccca
cctctgcttcgtgcacacggtgccctgggaccagctctttcggaacccg
caccaagctctgctccacactgccaaccggccagaggacgagtgtgtgg
gcgagggcctggcctgccaccagctgtgcgcccgagggcagcagaagat
ccggaagtacacgatgcggagactgctgcaggaaacggagctggtggag
ccgctgacacctagcggagcgatgcccaaccaggcgcagatgcggatcc
tgaaagagacggagctgaggaaggtgaaggtgcttggatctggcgcttt
tggcacagtctacaagggcatctggatccctgatggggagaatgtgaaa
attccagtggccatcaaagtgttgagggaaaacacatcccccaaagcca
acaaagaaatcttagacgaagcatacgtgatggctggtgtgggctcccc
atatgtctcccgccttctgggcatctgcctgacatccacggtgcagctg
gtgacacagcttatgccctatggctgcctcttagactaatctagacccg
ggccactaactcaacgctagtagtggatttaatcccaaatgagccaaca
gaaccagaaccagaaacagaacaagtaacattggagttagaaatggaag
aagaaaaaaagcaatgatttcgtgtgaataatgcacgaaatcattgctta
ttttttttaaaaagcgatatactagatataacgaaacaacgaactgaata
aagaatacaaaaaaagagccacgaccagttaaagcctgagaaactttaa
ctgcgagccttaattgattaccaccaatcaattaaagaagtcgagaccc
aaaatttggtaaagtatttaattactttattaatcagatacttaaatat
ctgtaaacccattatatcgggtttttgaggggatttcaagtctttaaga
agataccaggcaatcaattaagaaaaacttagttgattgcctttttttgt
tgtgattcaactttgatcgtagcttctaactaattaattttcgtaagaa
aggagaacagctgaatgaatatccctttttgttgtagaaactgtgcttca
tgacggcttgttaaagtacaaatttaaaaatagtaaaattcgctcaatc
actaccaagccaggtaaaagtaaaggggctatttttgcgtatcgctcaa
aaaaaagcatgattggcggacgtggcgttgttctgacttccgaagaagc
gattcacgaaaatcaagatacatttacgcattggacaccaaacgtttat
cgttatggtacgtatgcagacgaaaaccgttcatacactaaaggacatt
ctgaaaacaatttaagacaaatcaataccttctttattgattttgatat
tcacacggaaaaagaaactatttcagcaagcgatattttaacaacagct
attgatttaggttttatgcctacgttaattatcaaatctgataaaggtt
atcaagcatattttgttttagaaacgccagtctatgtgacttcaaaatc
agaatttaaatctgtcaaagcagccaaaataatctcgcaaaatatccga
gaatattttggaaagtctttgccagttgatctaacgtgcaatcattttg
ggattgctcgtataccaagaacggacaatgtagaatttttttgatcccaa
ttaccgttattctttcaaagaatggcaagattggtctttcaaacaaaca
gataataagggctttactcgttcaagtctaacggttttaagcggtacag
aaggcaaaaaacaagtagatgaaccctggtttaatctcttattgcacga
aacgaaattttcaggagaaaagggtttagtagggcgcaatagcgttatg
tttaccctctctttagcctactttagttcaggctattcaatcgaaacgt
gcgaatataatatgtttgagtttaataatcgattagatcaacccttaga
agaaaaagaagtaatcaaaattgttagaagtgcctattcagaaaactat
caaggggctaatagggaatacattaccattctttgcaaagcttgggtat
caagtgatttaaccagtaaagatttatttgtccgtcaagggtggtttaa
attcaagaaaaaaagaagcgaacgtcaacgtgttcatttgtcagaatgg
aaagaagatttaatggcttatattagcgaaaaaagcgatgtatacaagc
cttatttagcgacgaccaaaaaagagattagagaagtgctaggcattcc
tgaacggacattagataaattgctgaaggtactgaaggcgaatcaggaa
attttctttaagattaaaccaggaagaaatggtggcattcaacttgcta
gtgttaaatcattgttgctatcgatcattaaattaaaaaaagaagaacg
agaaagctatataaaggcgctgacagcttcgtttaatttagaacgtaca
tttattcaagaaactctaaacaaattggcagaacgccccaaaacggacc
cacaactcgatttgtttagctacgatacaggctgaaaataaaacccgca
ctatgccattacatttatatctatgatacgtgtttgtttttctttgctg
gctagcttaattgcttatatttacctgcaataaaggatttcttacttcc
attatactcccattttccaaaaacatacggggaacacgggaacttattg
tacaggccacctcatagttaatggtttcgagccttcctgcaatctcatc
catggaaatatattcatccccctgccggcctattaatgtgacttttgtg -continued

```
cccggcggatattcctgatccagctccaccataaattggtccatgcaaa
ttcggccggcaattttcaggcgttttcccttcacaaggatgtcggtccc
tttcaattttcggagccagccgtccgcatagcctacaggcaccgtcccg
atccatgtgtctttttccgctgtgtactcggctccgtagctgacgctct
cgccttttctgatcagtttgacatgtgacagtgtcgaatgcagggtaaa
tgccggacgcagctgaaacggtatctcgtccgacatgtcagcagacggg
cgaaggccatacatgccgatgccgaatctgactgcattaaaaaagcctt
ttttcagccggagtccagcggcgctgttcgcgcagtggaccattagatt
ctttaacggcagcggagcaatcagctctttaaagcgctcaaactgcatt
aagaaatagcctctttctttttcatccgctgtcgcaaaatgggtaaata
cccctttgcactttaaacgagggttgcggtcaagaattgccatcacgtt
ctgaacttcttcctctgtttttacaccaagtctgttcatccccgtatcg
accttcagatgaaaatgaagagaacctttttttcgtgtggcgggctgcct
cctgaagccattcaacagaataacctgttaaggtcacgtcatactcagc
agcgattgccacatactccgggggaaccgcgccaagcaccaatataggc
gccttcaatccctttttgcgcagtgaaatcgcttcatccaaaatggcca
cggccaagcatgaagcacctgcgtcaagagcagcctttgctgtttctgc
atcaccatgcccgtaggcgtttgctttcacaactgccatcaagtggaca
tgttcaccgatatgtttttcatattgctgacattttcctttatcgcgg
acaagtcaatttccgcccacgtatctctgtaaaaaggttttgtgctcat
ggaaaactcctctctttttttcagaaaatcccagtacgtaattaagtatt
tgagaattaattttatattgattaatactaagtttacccagttttcacc
taaaaaacaaatgatgagataatagctccaaaggctaaagaggactata
ccaactatttgttaattaa
```

Example 12

ADXS31-164 is as Immunogenic as LM-LLO-ChHER2

Figure 16:
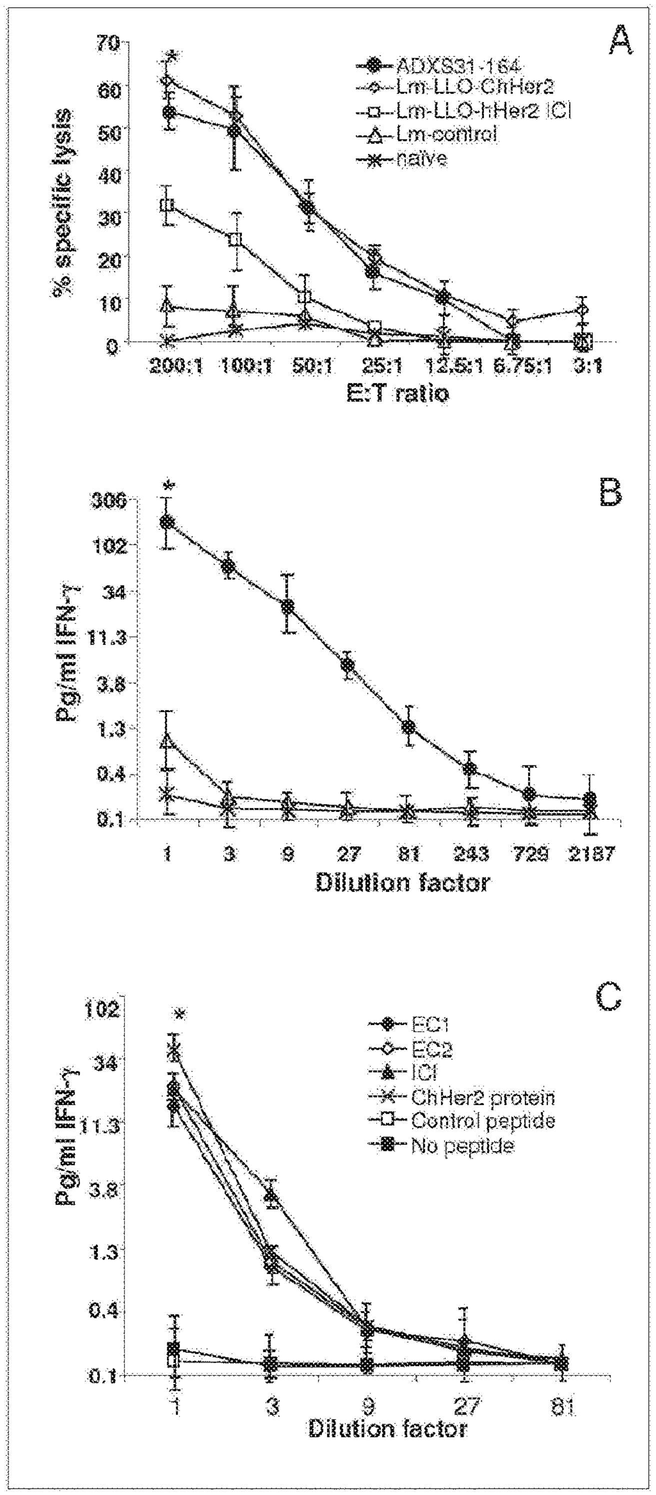
FIG. 16 (A) Cytotoxic T cell responses elicited by Her2/neu *Listeria*-based vaccines in splenocytes from immunized mice were tested using NT-2 cells as stimulators and 3T3/neu cells as targets. Lm-control was based on the LmddA background that was identical in all ways but expressed an irrelevant antigen (HPV16-E7). (B) IFN-γ secreted by the splenocytes from immunized FVB/N mice into the cell culture medium, measured by ELISA, after 24 hours of in vitro stimulation with mitomycin C treated NT-2 cells. (C) IFN-γ secretion by splenocytes from HLA-A2 transgenic mice immunized with the chimeric vaccine, in response to in vitro incubation with peptides from different regions of the protein. A recombinant ChHer2 protein was used as positive control and an irrelevant peptide or no peptide groups constituted the negative controls as listed in the figure legend. IFN-γ secretion was detected by an ELISA assay using cell culture supernatants harvested after 72 hours of co-incubation. Each data point was an average of triplicate data +/−standard error. *P value<0.001.
Figure 19:
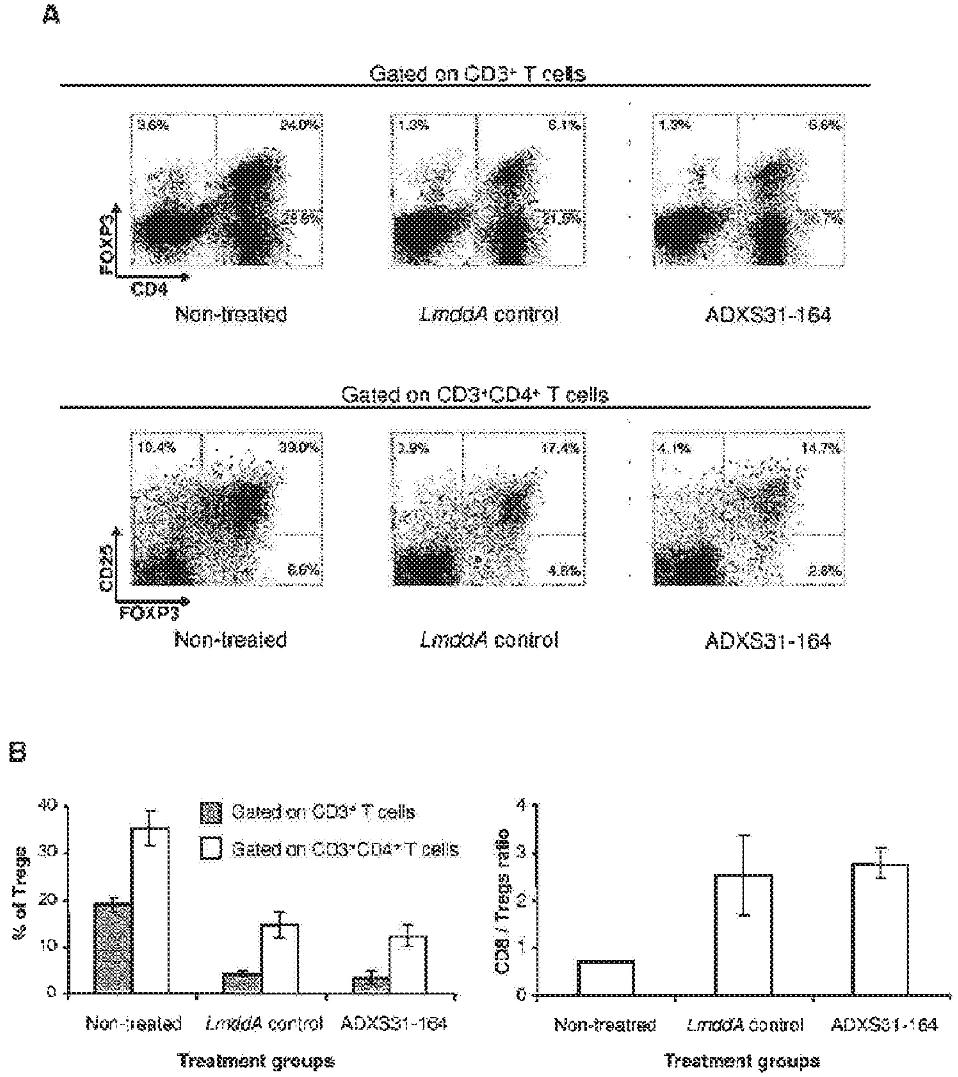
FIG. 19 shows FVB/N mice were inoculated s.c. with $1\times10^6$ NT-2 cells and immunized three times with each vaccine at one week intervals. Tumors were harvested 7 days after the second immunization. After isolation of the immune cells, they were stained for detection of Tregs by anti CD3, CD4, CD25 and FoxP3 antibodies. (A). dot-plots of the Tregs from a representative experiment. (B). Frequency of $CD25^+$/$FoxP3^+$ T cells, expressed as percentages of the total $CD3^+$ or $CD3^+CD4^+$ T cells (left panel) and intratumoral CD8/Tregs ratio (right panel) across the different treatment groups. Data is shown as mean±SEM obtained from 2 independent experiments.

Immunogenic properties of ADXS31-164 in generating anti-Her2/neu specific cytotoxic T cells were compared to those of the Lm-LLO-ChHer2 vaccine in a standard CTL assay. Both vaccines elicited strong but comparable cytotoxic T cell responses toward Her2/neu antigen expressed by 3T3/neu target cells. Accordingly, mice immunized with a *Listeria* expressing only an intracellular fragment of Her2-fused to LLO showed lower lytic activity than the chimeras which contain more MHC class I epitopes. No CTL activity was detected in naïve animals or mice injected with the irrelevant *Listeria* vaccine (FIG. 16A). ADXS31-164 was also able to stimulate the secretion of IFN-γ by the splenocytes from wild type FVB/N mice (FIG. 16B). This was detected in the culture supernatants of these cells that were co-cultured with mitomycin C treated NT-2 cells, which express high levels of Her2/neu antigen (FIG. 19C).

Proper processing and presentation of the human MHC class I epitopes after immunizations with ADXS31-164 was tested in HLA-A2 mice. Splenocytes from immunized HLA-A2 transgenics were co-incubated for 72 hours with peptides corresponding to mapped HLA-A2 restricted epitopes located at the extracellular (HLYQGCQVV SEQ ID NO: 74 or KIFGSLAFL SEQ ID NO: 75) or intracellular (RLLQETELV SEQ ID NO: 76) domains of the Her2/neu molecule (FIG. 16C). A recombinant ChHer2 protein was used as positive control and an irrelevant peptide or no peptide as negative controls. The data from this experiment show that ADXS31-164 is able to elicit anti-Her2/neu specific immune responses to human epitopes that are located at different domains of the targeted antigen.

Example 13

Figure 17:
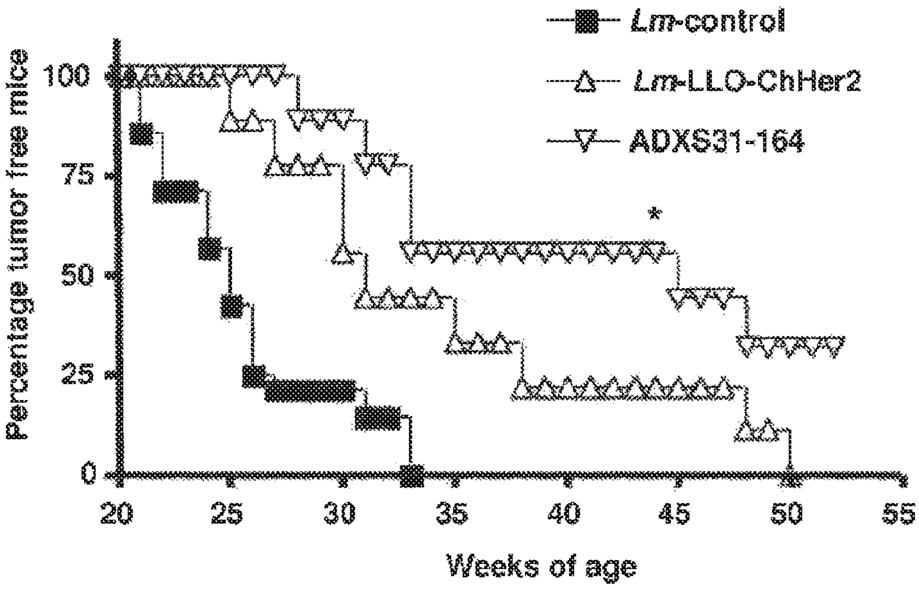
FIG. 17 represents results from Her2/neu transgenic mice that were injected six times with each recombinant *Listeria*-ChHer2 or a control *Listeria* vaccine. Immunizations started at 6 weeks of age and continued every three weeks until week 21. Appearance of tumors was monitored on a weekly basis and expressed as percentage of tumor free mice. *p<0.05, N=9 per group.

ADXS31-164 was More Efficacious than LM-LLO-ChHER2 in Preventing the Onset of Spontaneous Mammary Tumors Anti-tumor effects of ADXS31-164 were compared to those of Lm-LLO-ChHer2 in Her2/neu transgenic animals which develop slow growing, spontaneous mammary tumors at 20-25 weeks of age. All animals immunized with the irrelevant *Listeria*-control vaccine developed breast tumors within weeks 21-25 and were sacrificed before week 33. In contrast, Liseria-Her2/neu recombinant vaccines caused a significant delay in the formation of the mammary tumors. On week 45, more than 50% of ADXS31-164 vaccinated mice (5 out of 9) were still tumor free, as compared to 25% of mice immunized with Lm-LLO-ChHer2. At week 52, 2 out of 8 mice immunized with ADXS31-164 still remained tumor free, whereas all mice from other experimental groups had already succumbed to their disease (FIG. 17). These results indicate that despite being more attenuated, ADXS31-164 is more efficacious than Lm-LLO-ChHer2 in preventing the onset of spontaneous mammary tumors in Her2/neu transgenic animals.

Example 14

Mutations in HER2/Neu Gene Upon Immunization with ADXS31-164

Mutations in the MHC class I epitopes of Her2/neu have been considered responsible for tumor escape upon immunization with small fragment vaccines or trastuzumab (Herceptin), a monoclonal antibody that targets an epitope in the extracellular domain of Her2/neu. To assess this, genomic material was extracted from the escaped tumors in the transgenic animals and sequenced the corresponding fragments of the neu gene in tumors immunized with the chimeric or control vaccines. Mutations were not observed within the Her-2/neu gene of any vaccinated tumor samples suggesting alternative escape mechanisms (data not shown).

Example 15

Figure 18:
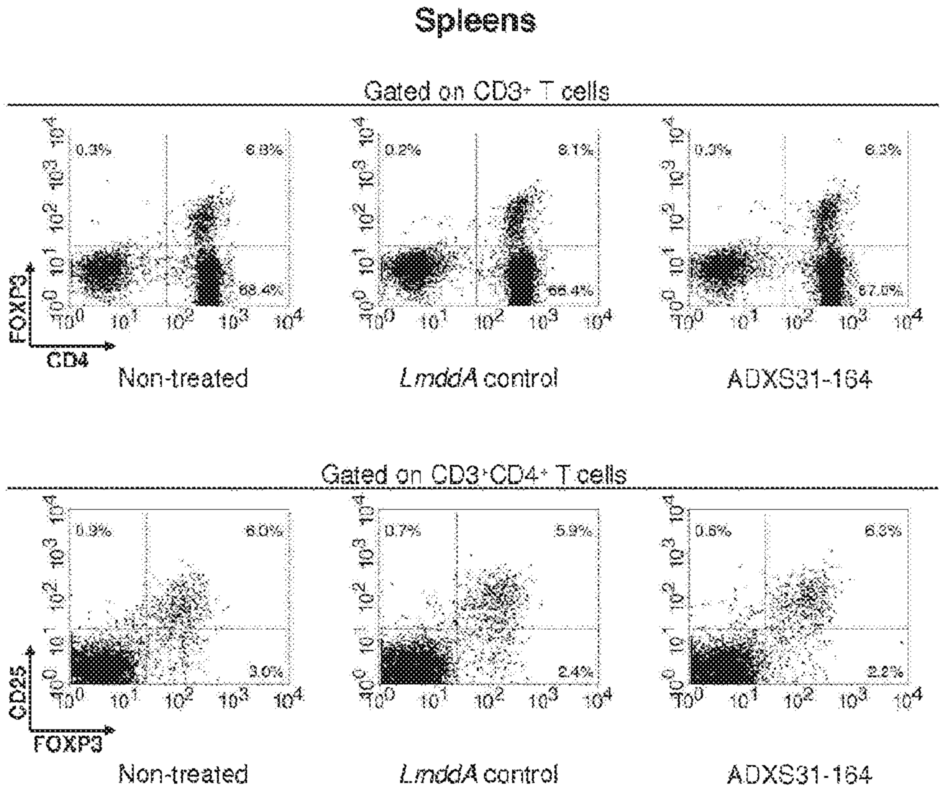
FIG. 18 shows FVB/N mice were inoculated s.c. with $1\times10^6$ NT-2 cells and immunized three times with each vaccine at one week intervals. Spleens were harvested 7 days after the second immunization. After isolation of the immune cells, they were stained for detection of Tregs by anti CD3, CD4, CD25 and FoxP3 antibodies. dot-plots of the Tregs from a representative experiment showing the frequency of $CD25^+$/$FoxP3^+$ T cells, expressed as percentages of the total $CD3^+$ or $CD3^+CD4^+$ T cells across the different treatment groups.

ADXS31-164 Causes a Significant Decrease in Intra-Tumoral T Regulatory Cells To elucidate the effect of ADXS31-164 on the frequency of regulatory T cells in spleens and tumors, mice were implanted with NT-2 tumor cells. Splenocytes and intra-tumoral lymphocytes were isolated after three immunizations and stained for Tregs, which were defined as $CD3^+$/$CD4^+$/$CD25^+$/$FoxP3^+$ cells, although comparable results were obtained with either FoxP3 or CD25 markers when analyzed separately. The results indicated that immunization with ADXS31-164 had no effect on the frequency of Tregs in the spleens, as compared to an irrelevant *Listeria* vaccine or the naïve animals (See FIG. 18). In contrast, immunization with the *Listeria* vaccines caused a considerable impact on the presence of Tregs in the tumors (FIG. 19A). Whereas in average 19.0% of all $CD3^+$ T cells in untreated tumors were Tregs, this frequency was reduced to 4.2% for the irrelevant vaccine and 3.4% for ADXS31-164, a 5-fold reduction in the frequency of intra-tumoral Tregs (FIG. 19B). The decrease in the frequency of intra-tumoral Tregs in mice treated with either of the LmddA vaccines could not be attributed to differences in the sizes of the tumors. In a representative experiment, the tumors from mice immunized with ADXS31-164 were significantly smaller [mean diameter (mm)±SD, 6.71±0.43, n=5] than the tumors from untreated mice (8.69±0.98, n=5, p<0.01) or treated with the irrelevant vaccine (8.41±1.47, n=5, p=0.04), whereas comparison of these last two groups showed no statistically significant difference in tumor size (p=0.73). The lower frequency of Tregs in tumors treated with LmddA vaccines resulted in an increased intratumoral CD8/Tregs ratio, suggesting that a more favorable tumor microenvironment can be obtained after immunization with LmddA vaccines. However, only the vaccine expressing the target antigen HER2/neu (ADXS31-164) was able to reduce tumor growth, indicating that the decrease in Tregs has an effect only in the presence on antigen-specific responses in the tumor.

Example 16

Construction of Dual Plasmid that Concomitantly Delivers Two Heterologous Antigens DNA corresponding to the actA promoter region and 1-233 amino acids of N-terminus of ActA is amplified from *Listeria* genomic DNA by Polymerase Chain Reaction (PCR) using the following primers ActA-F-5'-at cccgggtgaagcttgggaagcagttggg-3' (XmaI) (SEQ ID NO: 77) and ActA-R-attctagatttatcacgtacccatttccccgc (XbaI)(SEQ ID NO:78). The restriction sites used for cloning are underlined. XmaI/XbaI segment is cloned in plasmid pNEB193 to create pNEB193-ActA. Further antigen 2, which is Chimera Her2 is PCR amplified using the primers Ch-Her2-F-5'-at tctagaacccacctggacatgctccgccac-3' (XbaI)(SEQ ID NO: 79) and Ch-Her2-R-5'-gtcgacactagtctagtggtgatggtgatgatg gagctcagatctgtctaagaggcagccatagggc-3' (RE sites-SalI-SpeI-SacI-BglII)(SEQ ID NO: 80). The XbaI and SalI fragment of Ch-Her2 is cloned in the plasmid pNEB193-ActA to create pNEB193-ActA-Ch-Her2 plasmid. His tag DNA sequence is included in the Ch-Her2 reverse primer sequence between SacI and SpeI restriction site. The XmaI/SpeI fragment corresponding to tActA-Ch-Her2-His from the plasmid pNEB193-ActA-Ch-Her2 is excised for cloning in XmaI/SpeI restricted pAdv134 to create dual plasmid.

A *Listeria*-based plasmid that delivers two recombinant antigens concomitantly as fusion proteins is then generated. The two fusion proteins that are expressed by this plasmid include tLLO-antigen 1 and tActA-antigen 2. The expression and secretion of the antigen 1 is under the control of hly promoter and LLO signal sequence and it is expressed as a fusion to non-hemolytic fragment of Listeriolysin O (truncated LLO or tLLO). The expression and secretion of antigen 2 is under the control of actA promoter and ActA signal sequence and it is expressed as fusion to 1-233 amino acids of ActA (truncated ActA or tActA). The construction of antibiotic-marker free plasmid pAdv134 has been described previously and it contains the gene cassette for the expression of tLLO-antigen 1 fusion protein. The SpeI and Xma I restriction sites present downstream of the tLLO-antigen 1 in pAdv134 are used for the cloning of actA promoter-tActA-antigen 2 DNA segment FIG. 20. The restriction sites XbaI, SacI and BglII are added in the cassette to facilitate cloning of the antigen 2 insert at XbaI/SacI or XbaI/BglII. A DNA sequence coding for His tag is added after SacI site to facilitate the detection of tActA-antigen 2-his fusion protein. The dual plasmid is able to concomitantly express and secrete two different antigens as fusion proteins.

Materials and Methods (Examples 17-21)

MDSC and Treg Function

Tumors were implanted in mice on the flank or a physiological site depending on the tumor model. After 7 days, mice were then vaccinated, the initial vaccination day depends on the tumor model being used. The mice were then administered a booster vaccine one week after the vaccine was given.

Mice were then sacrificed and tumors and spleen were harvested 1 week after the boost or, in the case of an aggressive tumor model, 3-4 days after the boost. Five days before harvesting the tumor, non-tumor bearing mice were vaccinated to use for responder T cells. Splenocytes were prepared using standard methodology.

Briefly, single cell suspensions of both the tumors and the spleens were prepared. Spleens were crushed manually and red blood cells were lysed. Tumors were minced and incubated with collagenase/DNase. Alternatively, the GENTLEMACS™ dissociator was used with the tumor dissociation kit.

MDSCs or Tregs were purified from tumors and spleens using a Miltenyi kit and columns or the autoMACs separator. Cells were then counted.

Single cell suspension was prepared and the red blood cells were lysed. Responder T cells were then labeled with CFSE.

Cells were plated together at a 2:1 ratio of responder T cells (from all division cycle stages) to MDSCs or Tregs at a density of $1\times10^5$ T cells per well in 96 well plates. Responder T cells were then stimulated with either the appropriate peptide (PSA OR CA9) or non-specifically with PMA/ionomycin. Cells were incubated in the dark for 2 days at 37° C. with 5% $CO_2$. Two days later, the cells were stained for FACS and analyzed on a FACS machine.

Analysis of T-cell Responses

For cytokine analysis by ELISA, splenocytes were harvested and plated at 1.5 million cells per well in 48-well plates in the presence of media, SEA or conA (as a positive control). After incubation for 72 hours, supernatants were harvested and analyzed for cytokine level by ELISA (BD). For antigen-specific IFN-γ ELISpot, splenocytes were harvested and plated at 300K and 150K cells per well in IFN-γ ELISpot plates in the presence of media, specific CTL peptide, irrelevant peptide, specific helper peptide or conA (as a positive control). After incubation for 20 hours, ELISpots (BD) were performed and spots counted by the Immunospot analyzer (C.T.L.). Number of spots per million splenocytes were graphed.

Splenocytes were counted using a Coulter Counter, Z1. The frequency of IFN-γ producing CD8+ T cells after re-stimulation with gag-CTL, gag-helper, medium, an irrelevant antigen, and con A (positive control) was determined using a standard IFN-γ-based ELISPOT assay.

Briefly, IFN-γ was detected using the mAb R46-A2 at 5 mg/ml and polyclonal rabbit anti-IFN-γ used at an optimal dilution (kindly provided by Dr. Phillip Scott, University of Pennsylvania, Philadelphia, Pa.). The levels of IFN-γ were calculated by comparison with a standard curve using murine rIFN-γ (Life Technologies, Gaithersburg, Md.). Plates were developed using a peroxidase-conjugated goat anti-rabbit IgG Ab (IFN-γ). Plates were then read at 405 nm. The lower limit of detection for the assays was 30 pg/ml.

Results

Example 17

Suppressor Cell Function after *Listeria* Vaccine Treatment

At day 0 tumors were implanted in mice. At day 7 mice were vaccinated with Lmdda-E7 or LmddA-PSA. At day 14 tumors were harvested and the number and percentages of infiltrating MDSCs and Treg were measured for vaccinated and naïve groups. It was found that there is a decrease in the percentages of both MDSC and Tregs in the tumors of *Listeria*-treated mice, and the absolute number of MDSC, whereas the same effect is not observed in the spleens or the draining lymph nodes (TLDN) (FIG. 21).

Isolated splenocytes and tumor-infiltrating lymphocytes (TILs) extracted from tumor bearing mice in the above experiment were pooled and stained for CD3, and CD8 to elucidate the effect of immunization with Lm-LLO-E7, Lm-LLO-PSA and Lm-LLO-CA9, Lm-LLO-Her2 (FIG. 22-34) on the presence of MDSCs and Tregs (both splenic and tumoral MDSCs and Tregs) in the tumor. Each column represents the % of T cell population at a particular cell division stage and is subgrouped under a particular treatment group (naïve, peptide-CA9 or PSA-treated, no MDSC/Treg, and no MDSC+PMA/ionomycin) (see FIGS. 22-34).

Blood from tumor-bearing mice was analyzed for the percentages of Tregs and MDSCs present. There is a decrease in both MDSC and Tregs in the blood of mice after Lm vaccination.

Example 18

Figure 22:
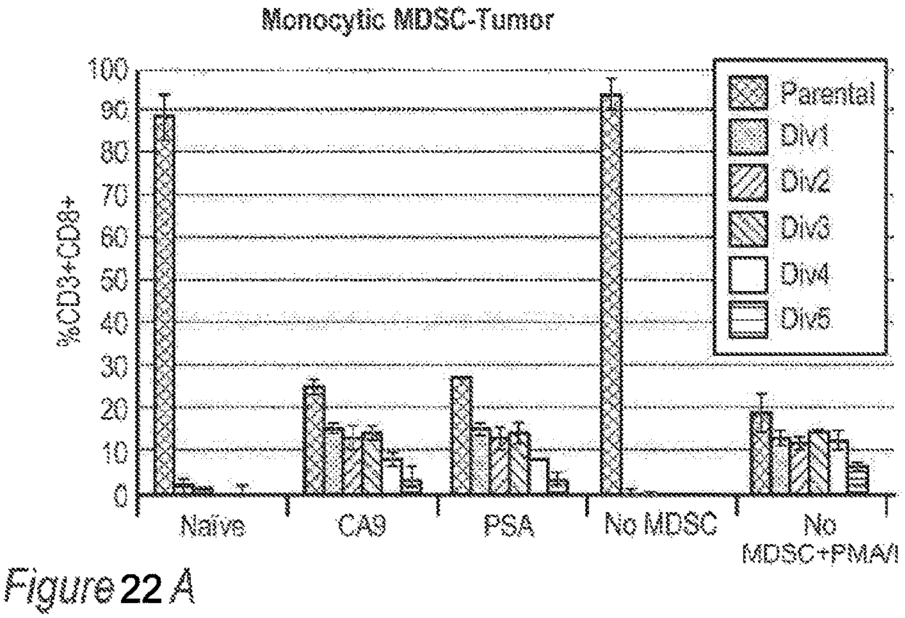
FIGS. 22A-22D show suppressor assay data demonstrating that monocytic MDSCs from TPSA23 tumors (PSA expressing tumor) are less suppressive after *Listeria* vaccination. This change in the suppressive ability of the MDSCs is not antigen specific as the same decrease in suppression is seen with PSA-antigen specific T cells and also with non-specifically stimulated T cells.
Figure 22:
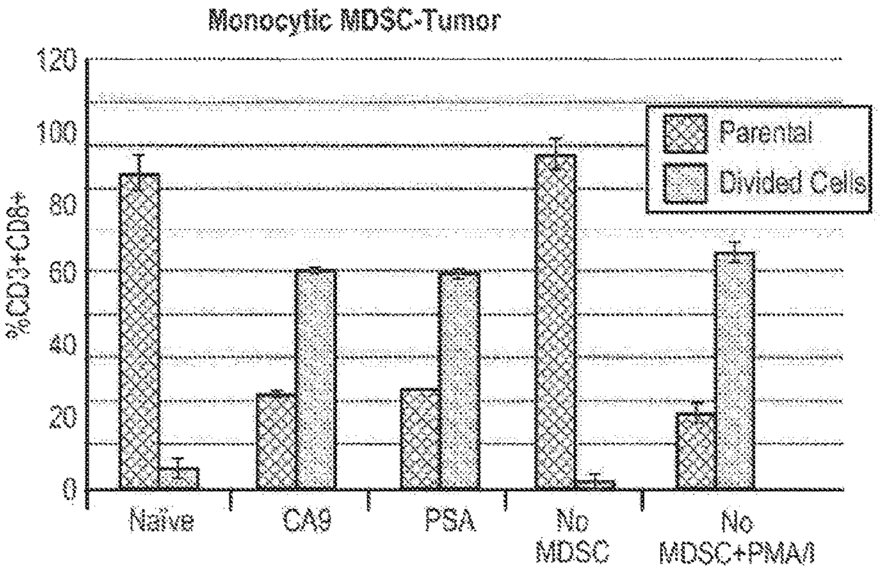
Figure 24:
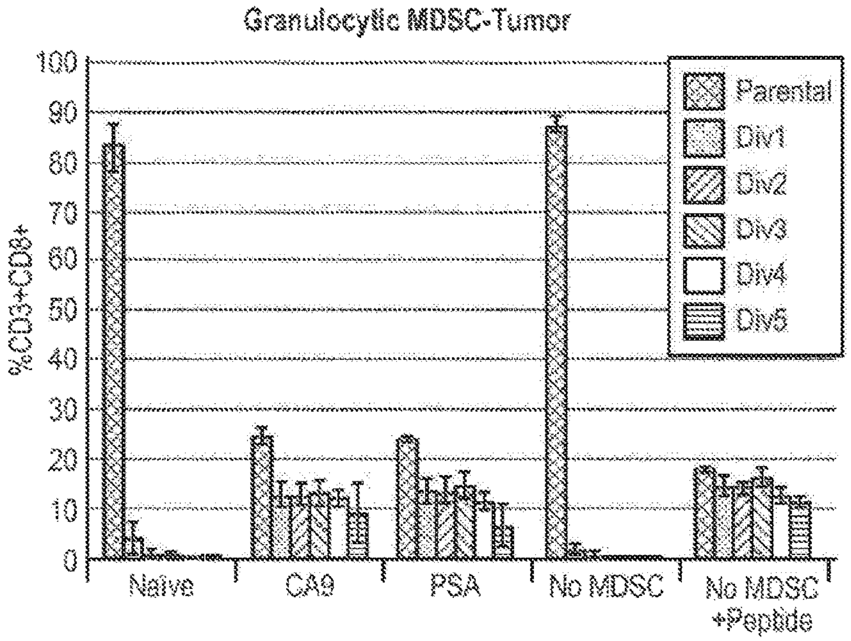
FIGS. 24A-24D show suppressor assay data demonstrating that granulocytic MDSCs from tumors have a reduced ability to suppress T cells after *Listeria* vaccination. This change in the suppressive ability of the MDSCs is not antigen specific as the same decrease in suppression is seen with PSA-antigen specific T cells and also with non-specifically stimulated T cells.
Figure 24:
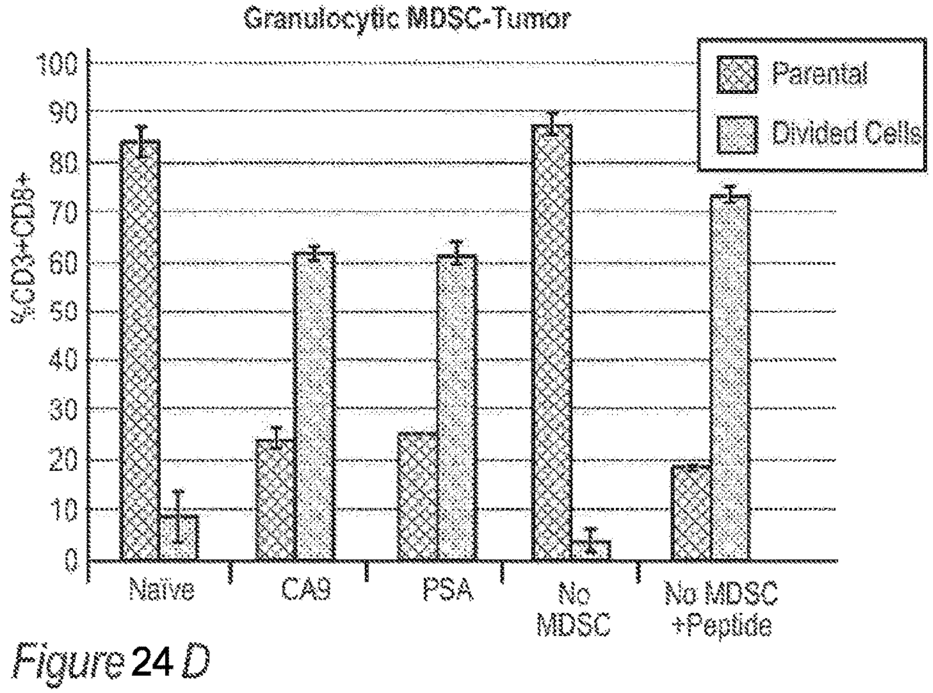

MDSCS from TPSA23 Tumors but not Spleen are Less Suppressive after *Listeria* Vaccination Suppressor assays were carried out using monocytic and granulocytic MDSCs isolated from TPSA23 tumors with non-specifically activated naïve murine cells, and specifically activated cells (PSA, CA9, PMA/ionomycyn). Results demonstrated that the MDSCs isolated from tumors from the Lm vaccinated groups have a diminished capacity to suppress the division of activated T cells as compared to MDSC from the tumors of naïve mice. (see Lm-LLO-PSA and Lm-LLO-treated Groups in FIGS. 22 & 24, right-hand panel in figures represents pooled cell division data from left-hand panel). In addition, T responder cells from untreated mice where no MDSCs were present and where the cells were unstimulated/activated, remained in their parental (resting) state (FIGS. 22 & 24), whereas T cells stimulated with PMA or ionomycin were observed to replicate (FIGS. 22 & 24). Further, it was observed that both, the Gr+Ly6G+ and the $Gr_{dim}$Ly6G-MDSCs are less suppressive after treatment with *Listeria* vaccines. This applies to their decreased abilities to suppress both the division of activated PSA-specific T cells and non-specific (PMA/Ionomycin stimulated) T cells.

Moreover, suppressor assays carried out using MDSCs isolated from TPSA23 tumors with non-specifically activated naïve murine cells demonstrated that the MDSCs isolated from tumors from the Lm vaccinated groups have a diminished capacity to suppress the division of activated T cells as compared to MDSC from the tumors of naïve mice (see FIGS. 22 & 24).

Figure 23:
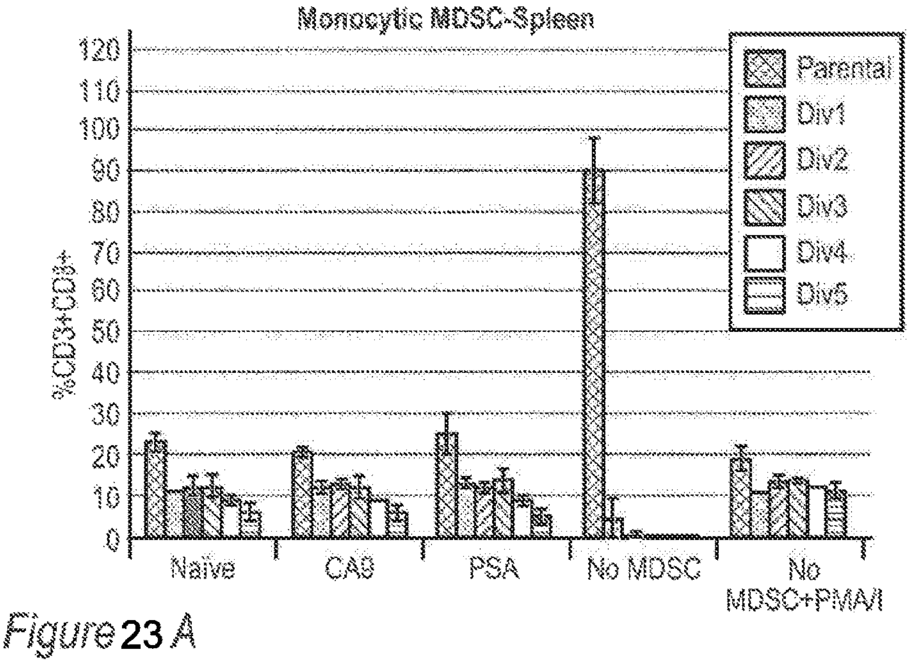
FIGS. 23A-23D show suppressor assay data demonstrating that *Listeria* has no effect on splenic monocytic MDSCs and they are only suppressive in an antigen-specific manner.
Figure 23:
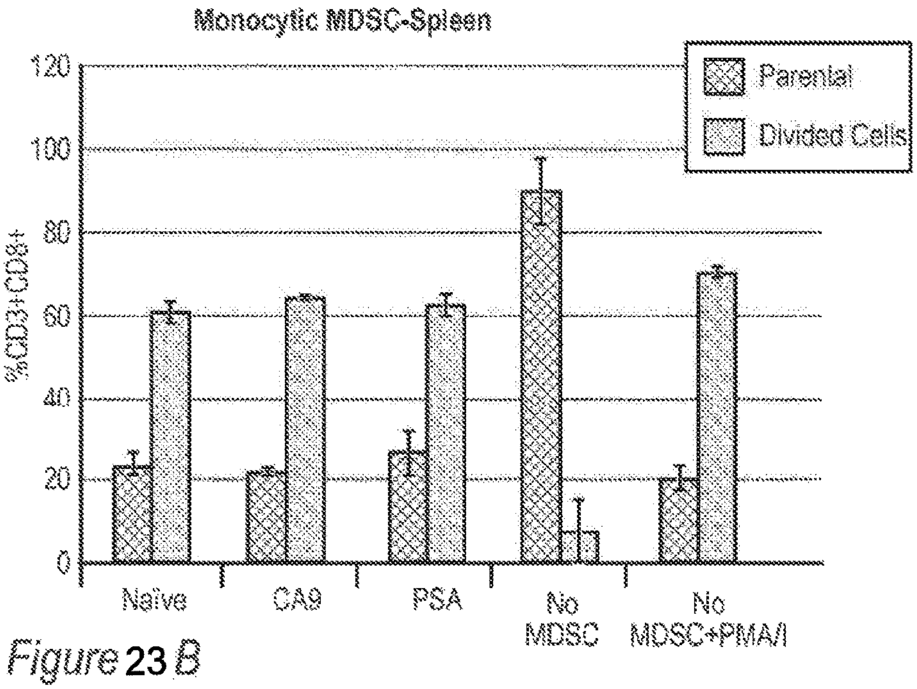
Figure 23:
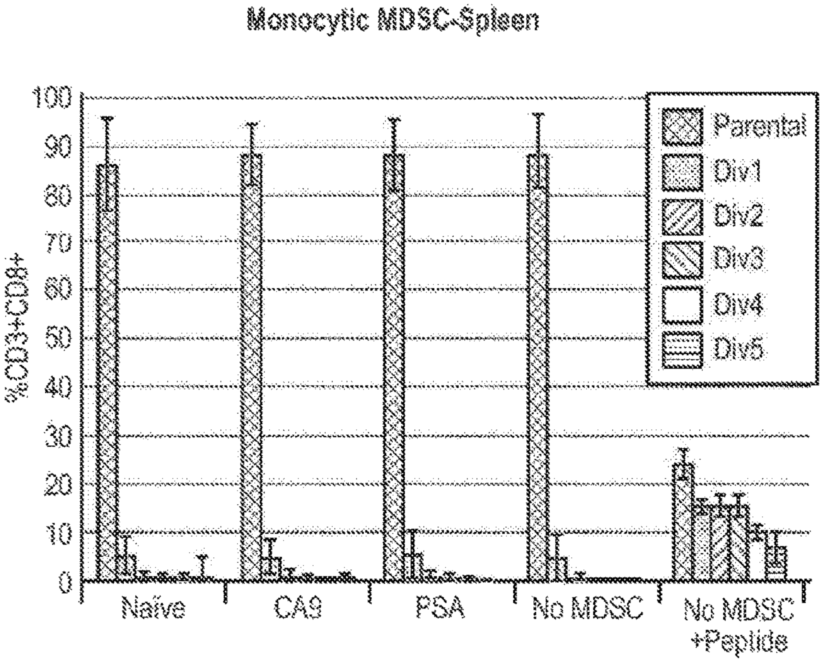
Figure 23:
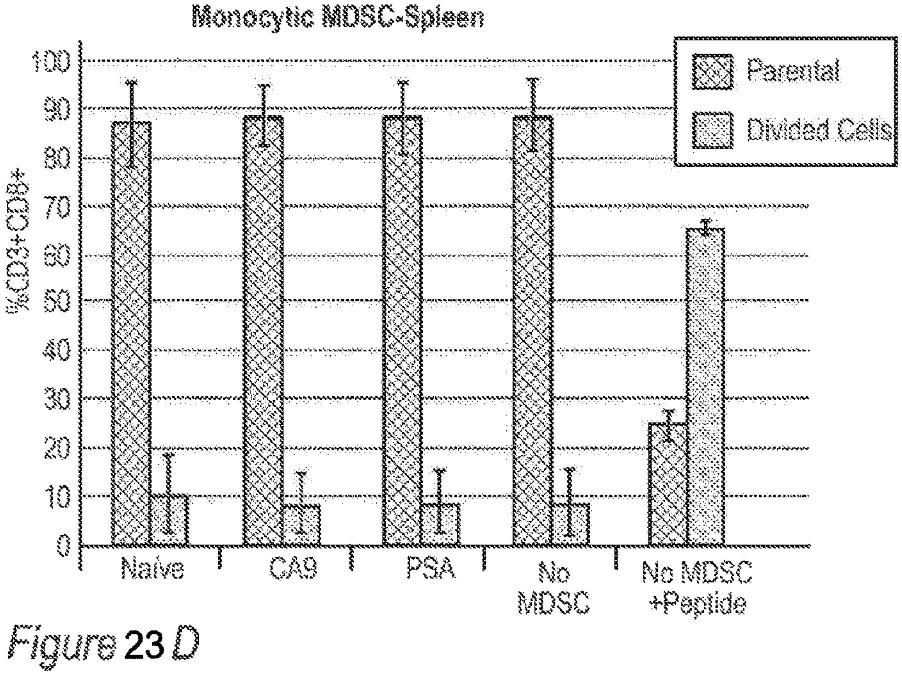
Figure 25:
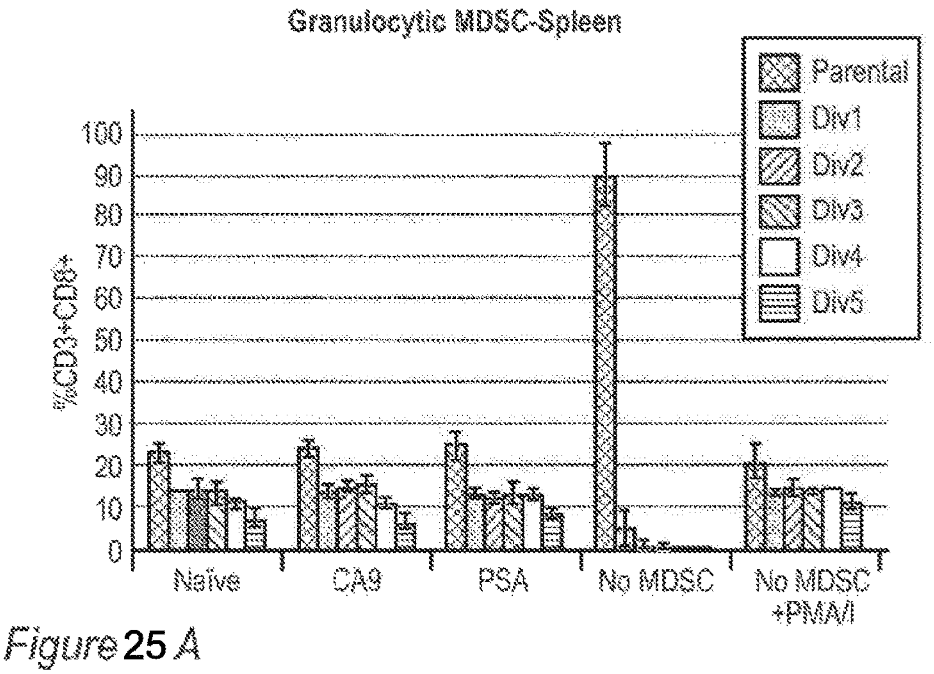
FIGS. 25A-25D show suppressor assay data demonstrating that *Listeria* has no effect on splenic granulocytic MDSCs and they are only suppressive in an antigen-specific manner.
Figure 25:
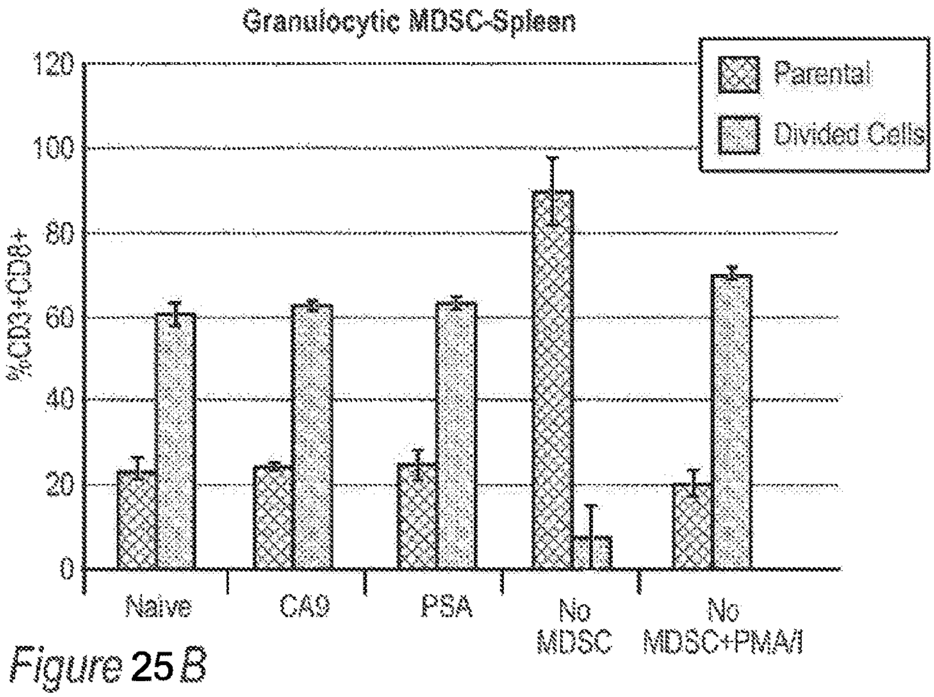
Figure 26:
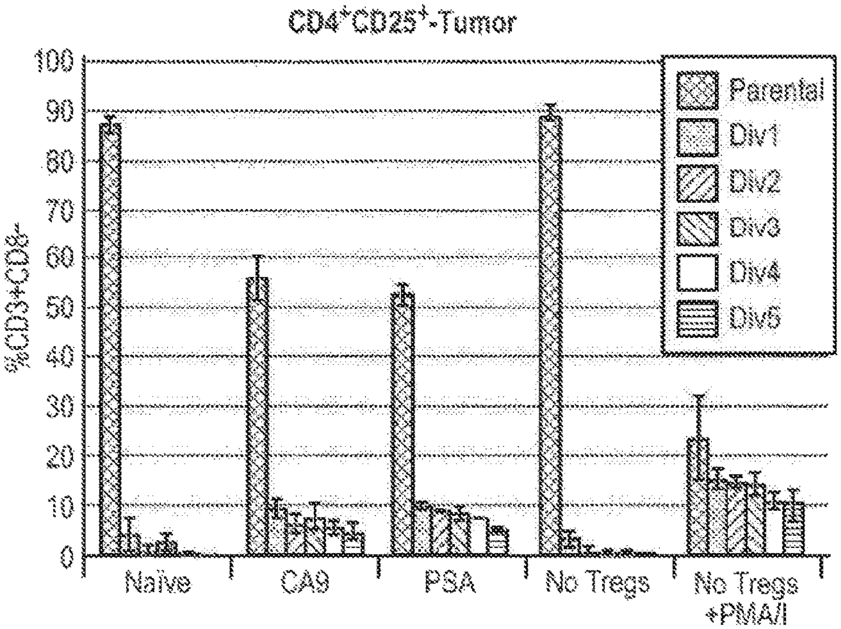
FIGS. 26A-26D show suppressor assay data demonstrating that Tregs from tumors are still suppressive. There is a slight decrease in the suppressive ability of Tregs in a non-antigen specific manner, in this tumor model.
Figure 26:
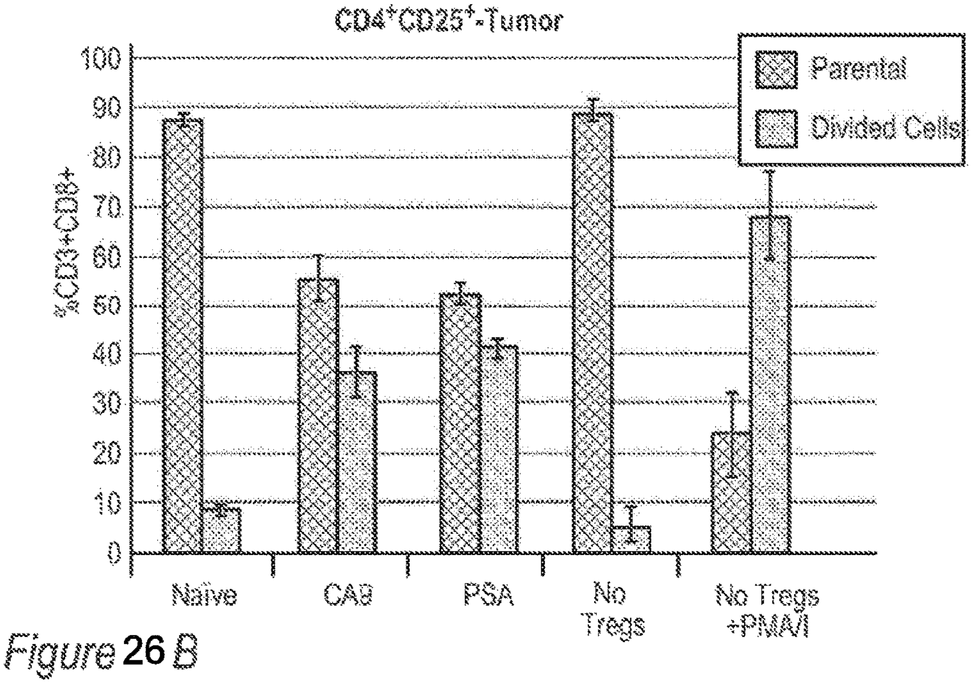
Figure 26:
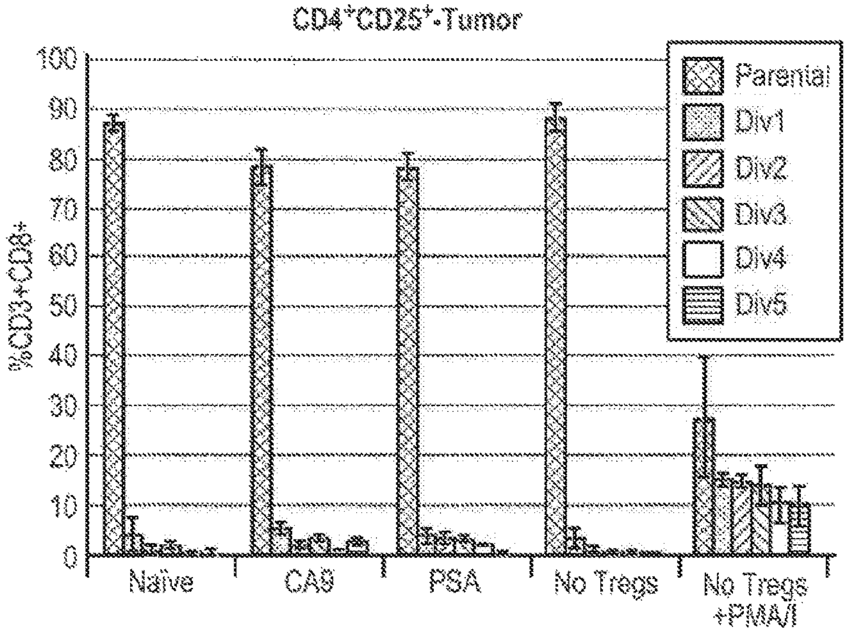
Figure 26:
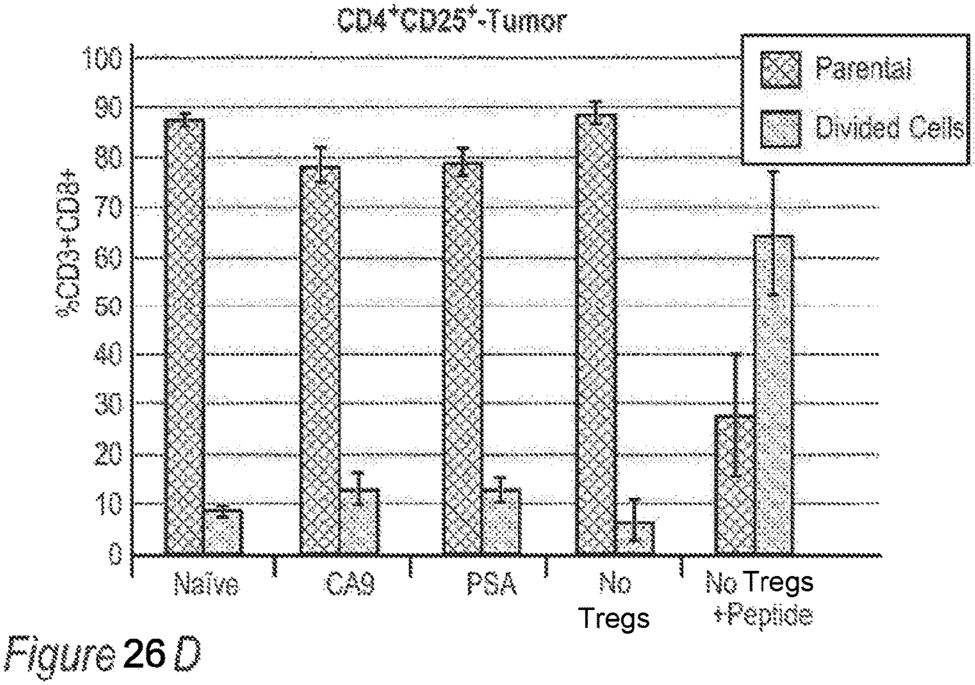

In addition, the observations discussed immediately above relating to FIGS. 22 and 24 were not observed when using splenic MDSCs. In the latter, splenocytes/T cells from the naïve group, the *Listeria*-treated group (PSA, CA9), and the PMA/ionomycin stimulated group (positive control) all demonstrated the same level of replication (FIGS. 23 & 25). Hence, these results show that *Listeria*-mediated inhibition of suppressor cells in tumors worked in an antigen-specific and non-specific manner, whereas *Listeria* has no effect on splenic granulocytic MDSCs as they are only suppressive in an antigen-specific manner.

Example 19

Tumor T Regulatory Cells' Reduced Suppression

Figure 27:
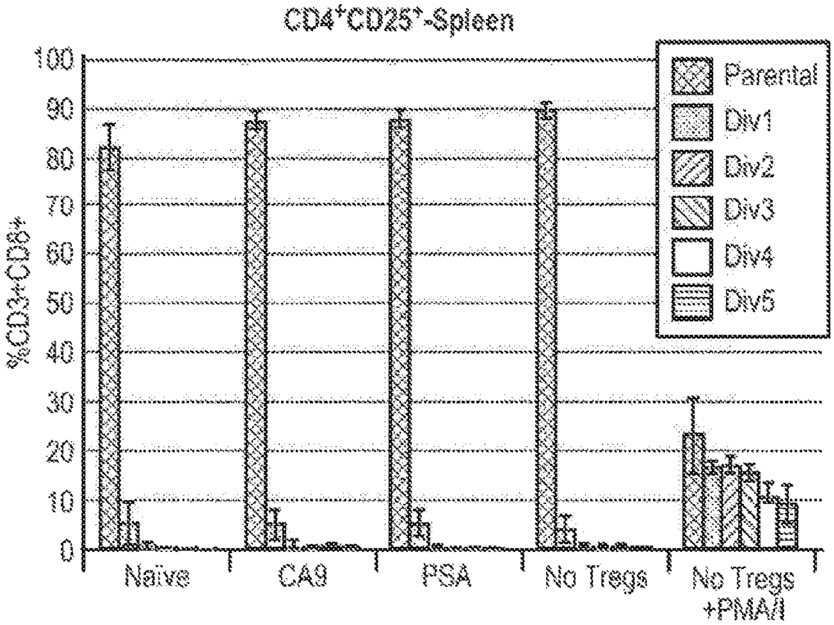
FIGS. 27A-27D shows suppressor assay data demonstrating that splenic Tregs are still suppressive.
Figure 27:
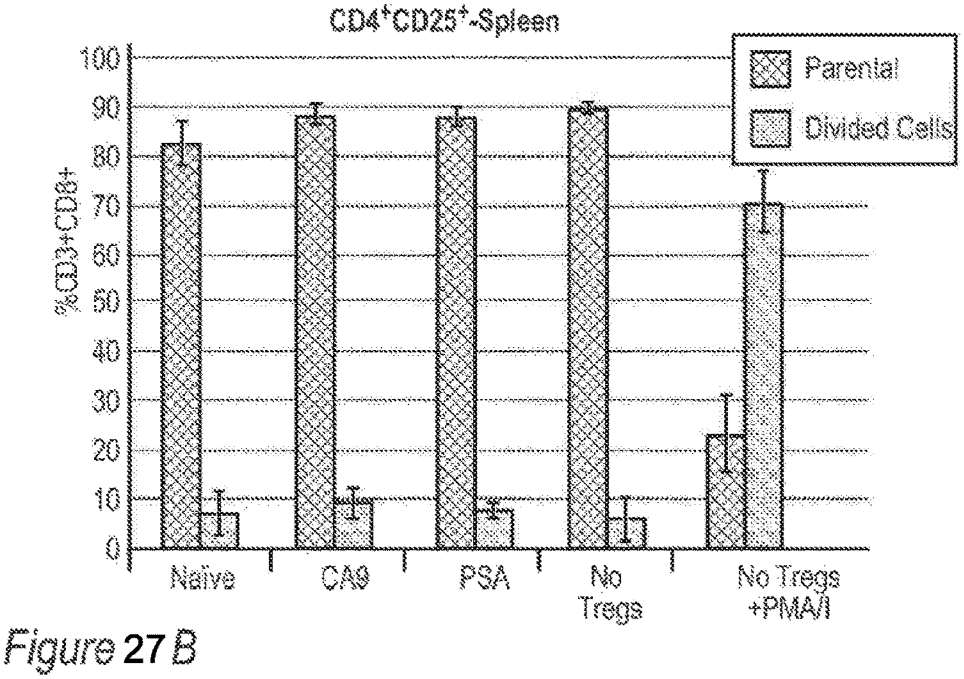
Figure 27:
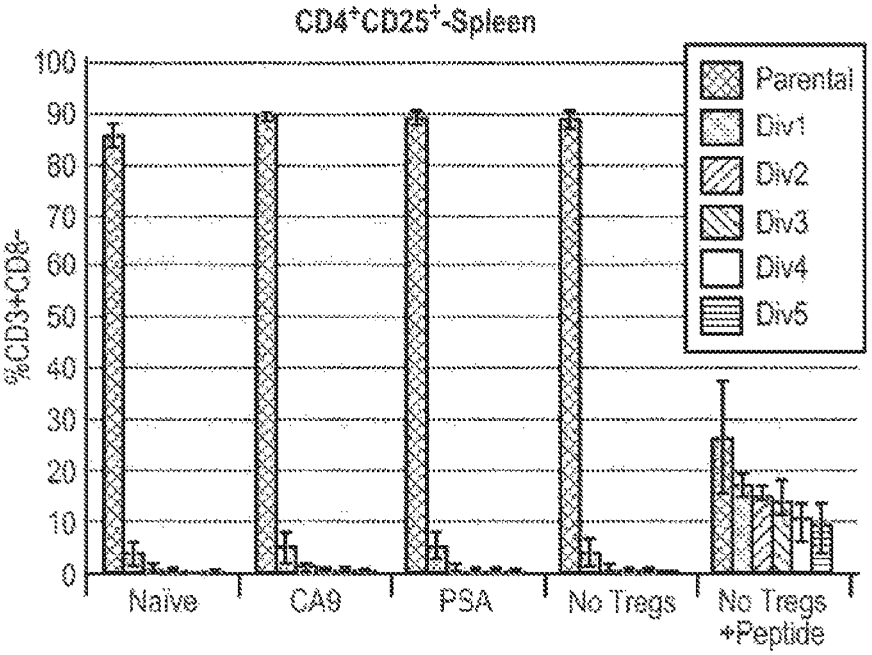
Figure 27:
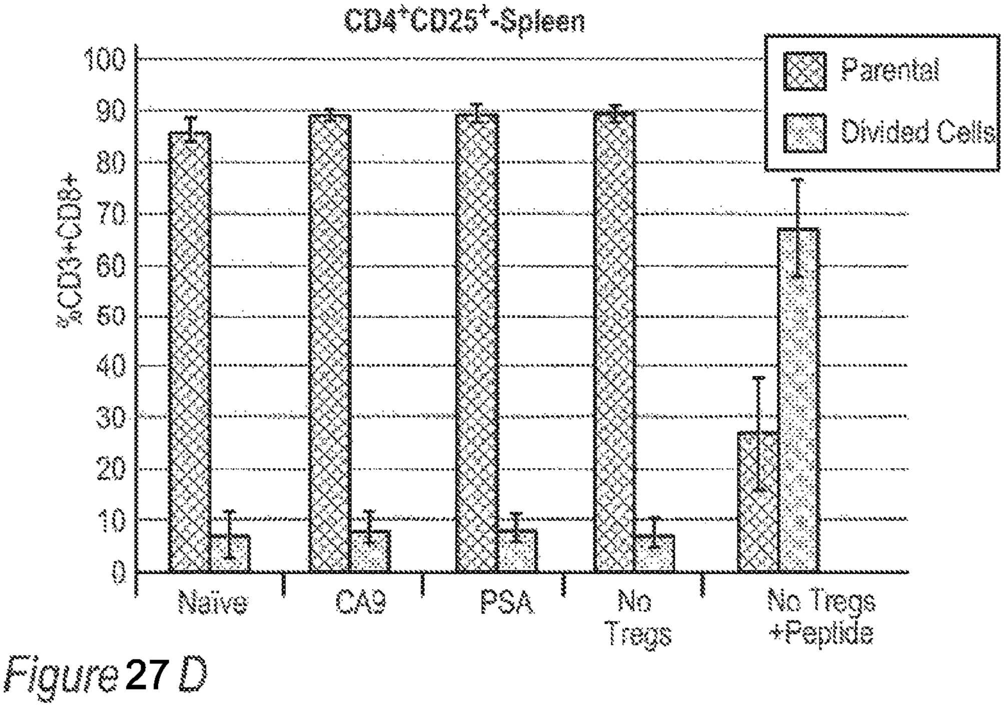

Suppressor assays were carried out using Tregs isolated from TPSA23 tumors after *Listeria* treatment. It was observed that after treatment with *Listeria* there is a reduction of the suppressive ability of Tregs from tumors (FIG. 26), however, it was found that splenic Tregs are still suppressive (FIG. 27).

Figure 28:
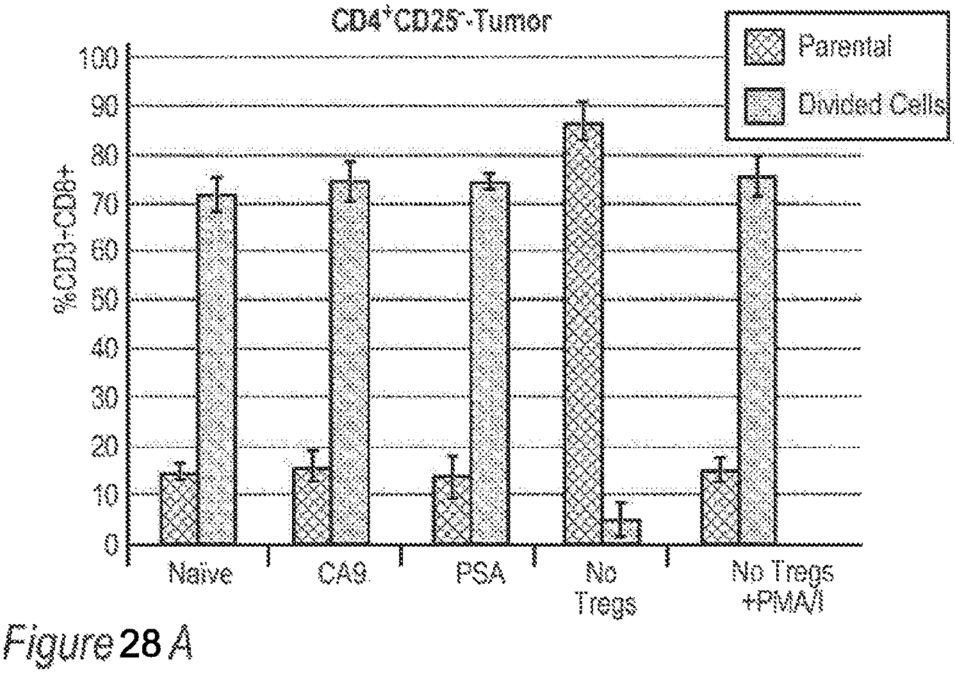
FIGS. 28A-28D show suppressor assay data demonstrating that conventional CD4+ T cells have no effect on cell division regardless whether they are found in the tumors or spleens of mice.
Figure 28:
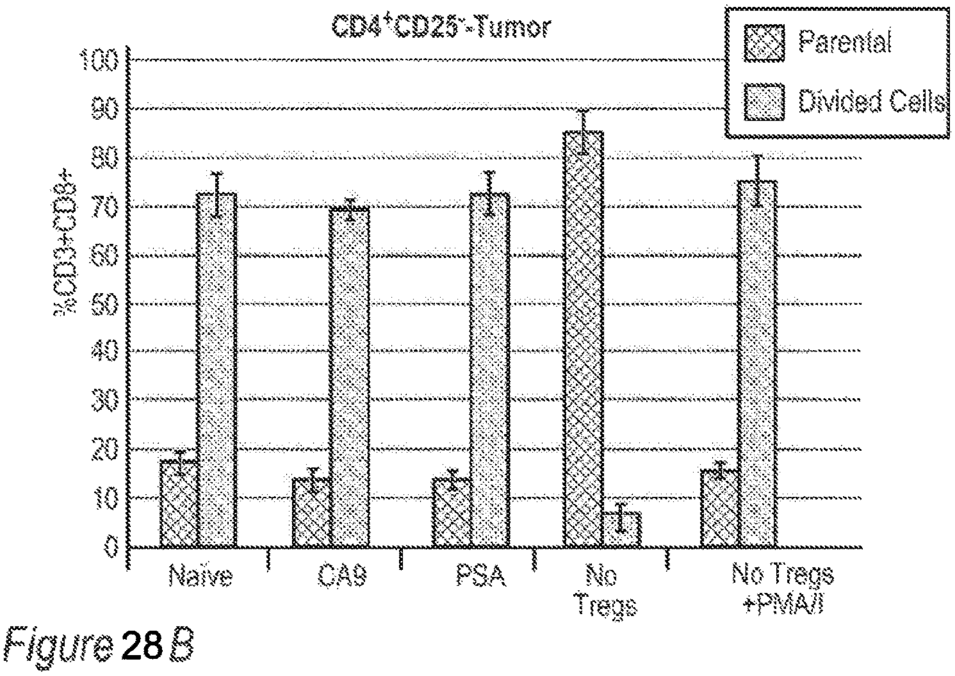
Figure 28:
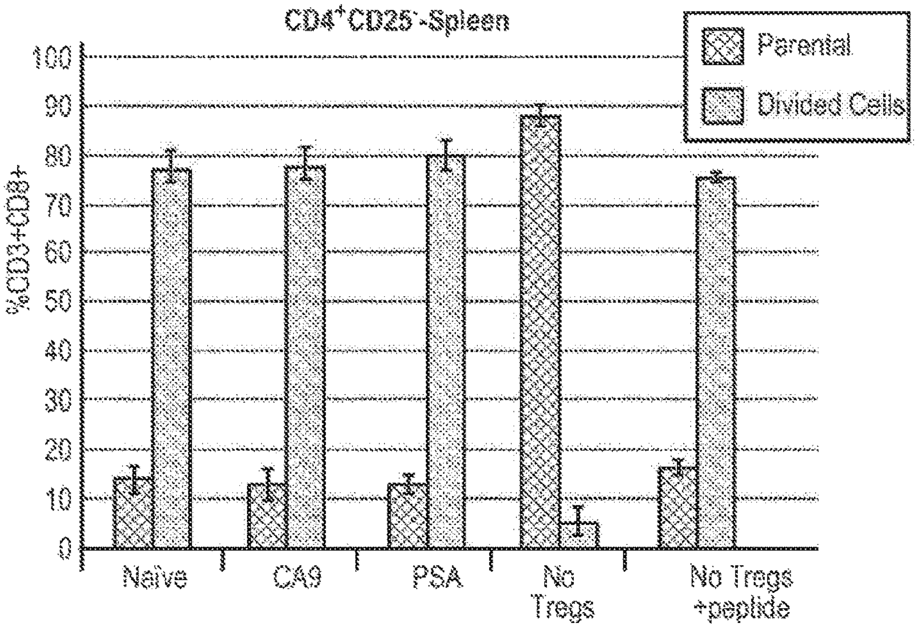
Figure 28:
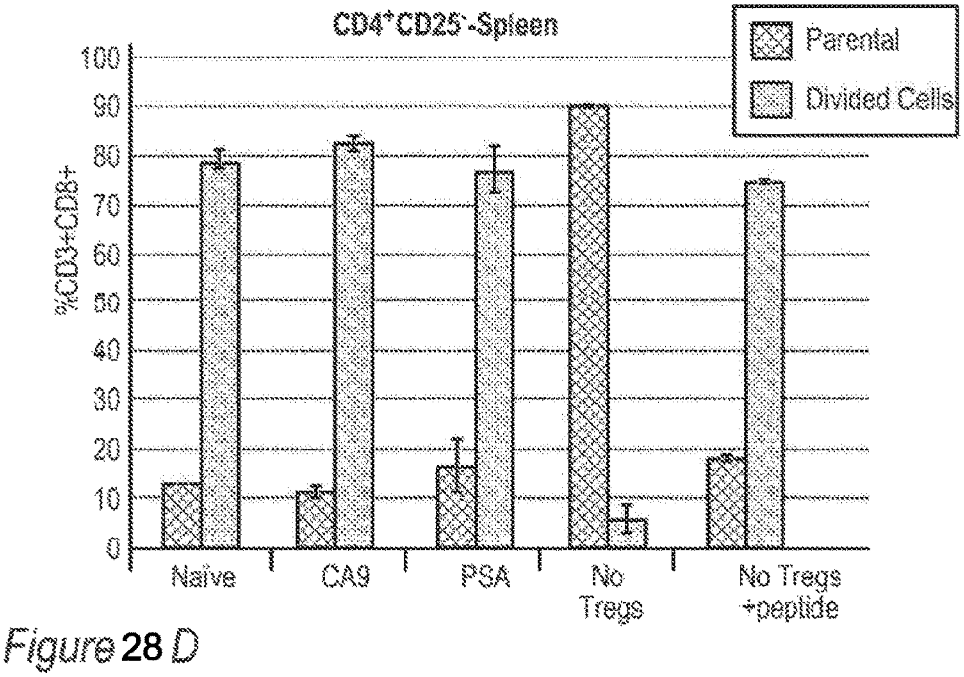
Figure 29:
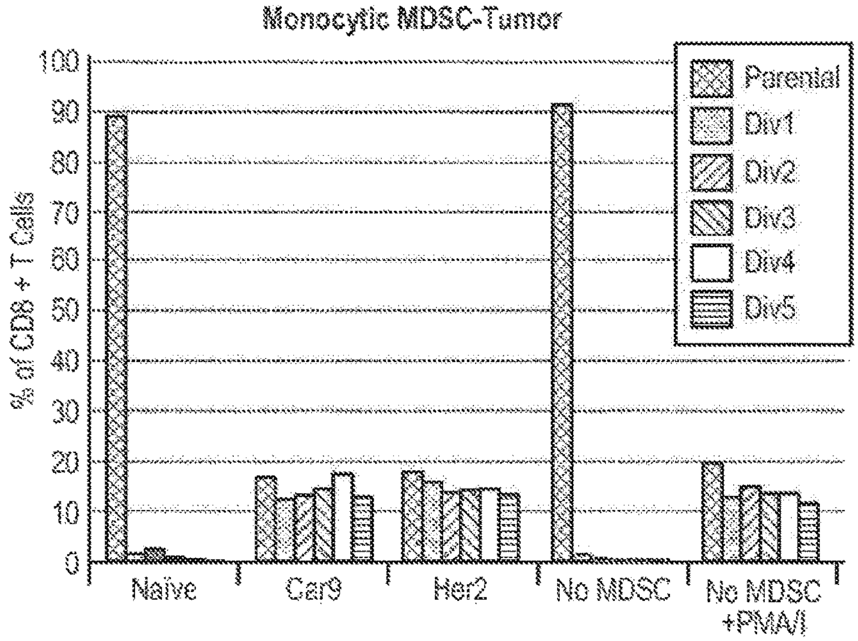
FIGS. 29A-29D show suppressor assay data demonstrating that monocytic MDSCs from 4T1 tumors (Her2 expressing tumors) have decreased suppressive ability after *Listeria* vaccination. This change in the suppressive ability of the MDSCs is not antigen specific as the same decrease in suppression is seen with Her2/neu-antigen specific T cells and also with non-specifically stimulated T cells.
Figure 29:
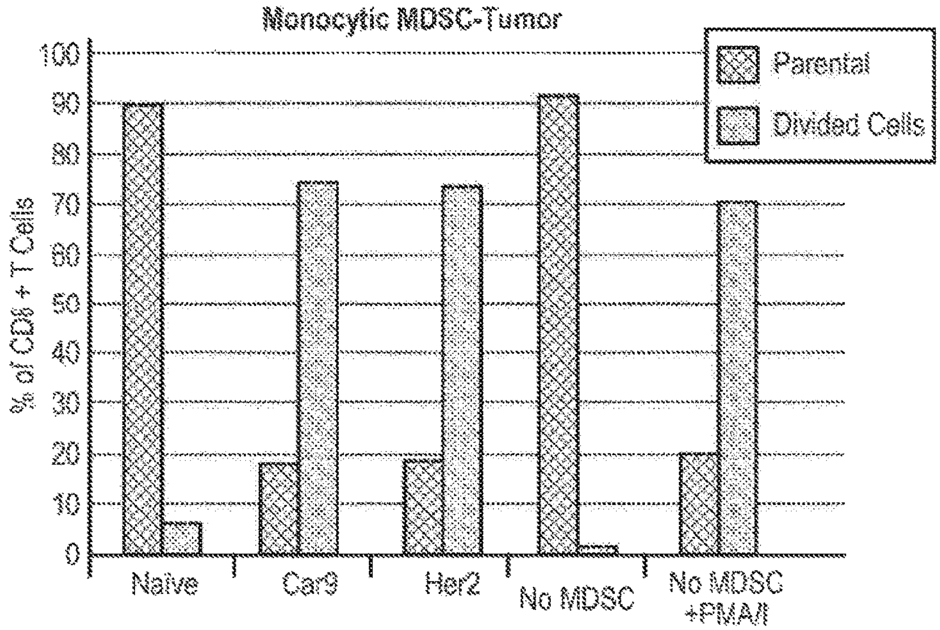
Figure 29:
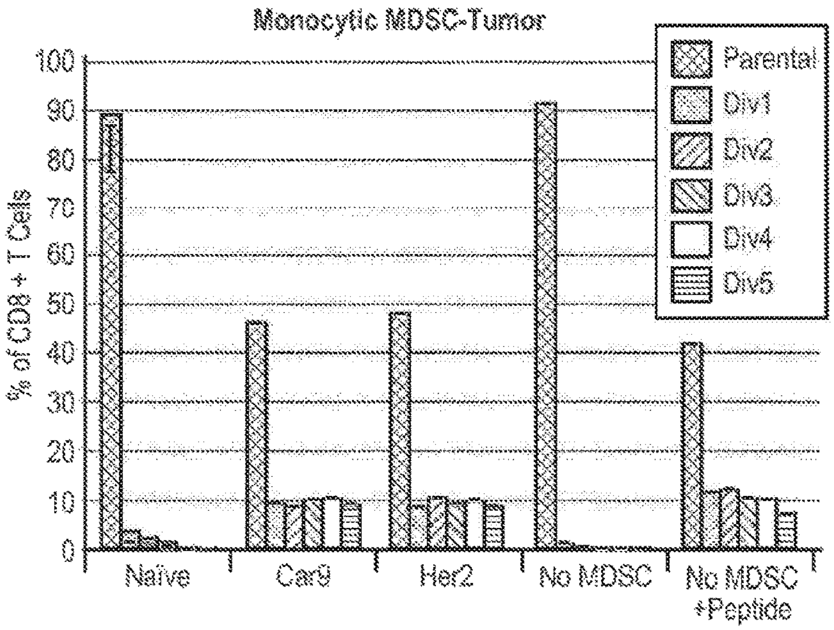
Figure 29:
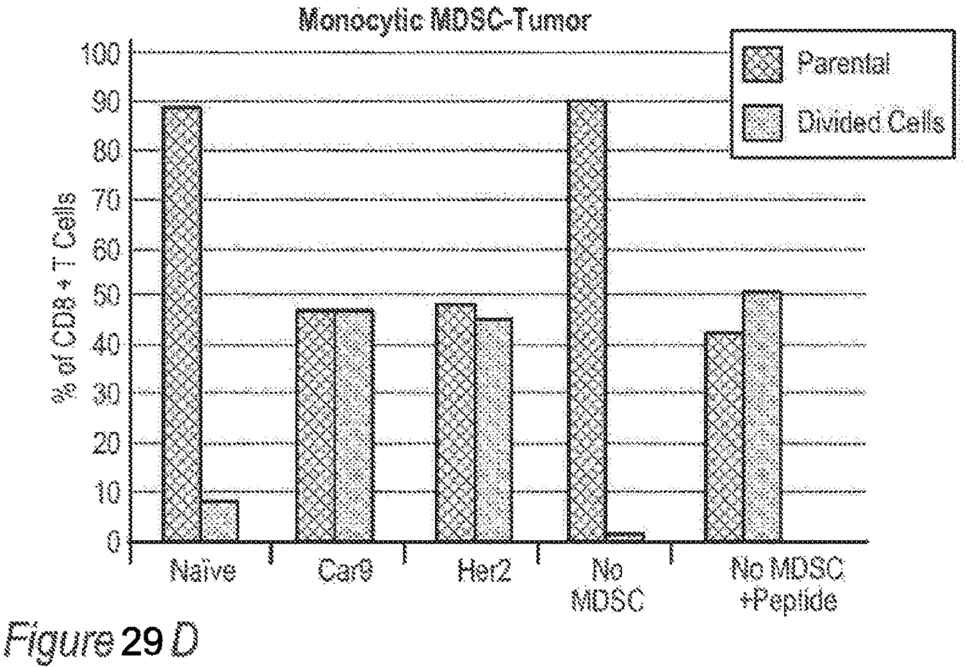
Figure 30:
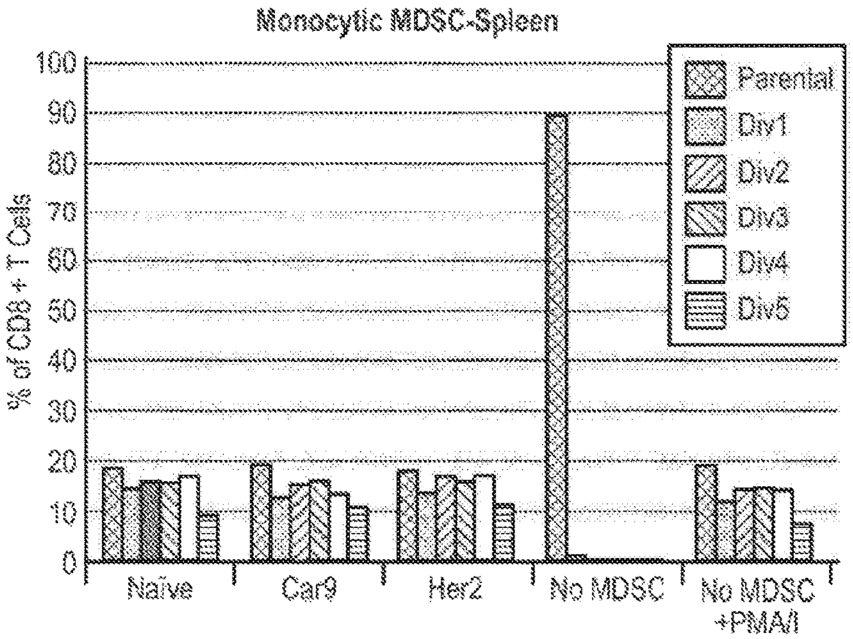
FIGS. 30A-30D show suppressor assay data demonstrating that there is no *Listeria*-specific effect on splenic monocytic MDSCs.
Figure 30:
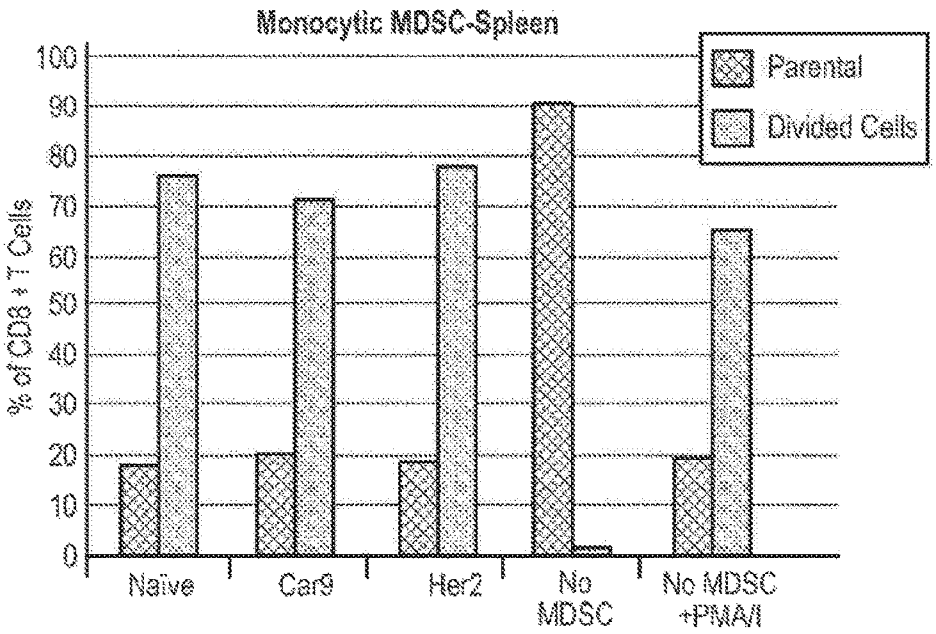
Figure 31:
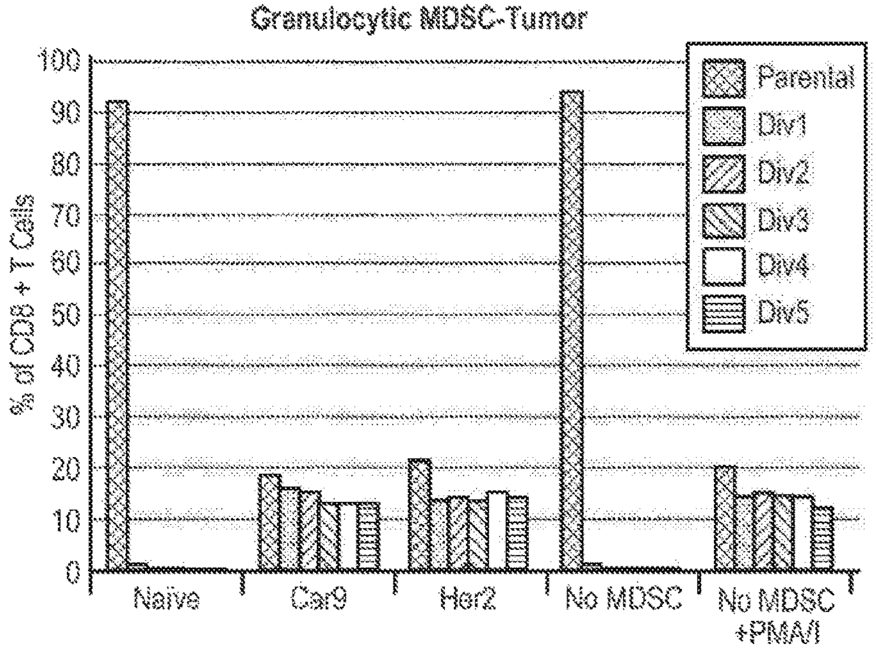
FIGS. 31A-31D show suppressor assay data demonstrating that granulocytic MDSCs from 4T1 tumors (Her2 expressing tumors) have decreased suppressive ability after *Listeria* vaccination. This change in the suppressive ability of the MDSCs is not antigen specific as the same decrease in suppression is seen with Her2/neu-antigen specific T cells and also with non-specifically stimulated T cells.
Figure 31:
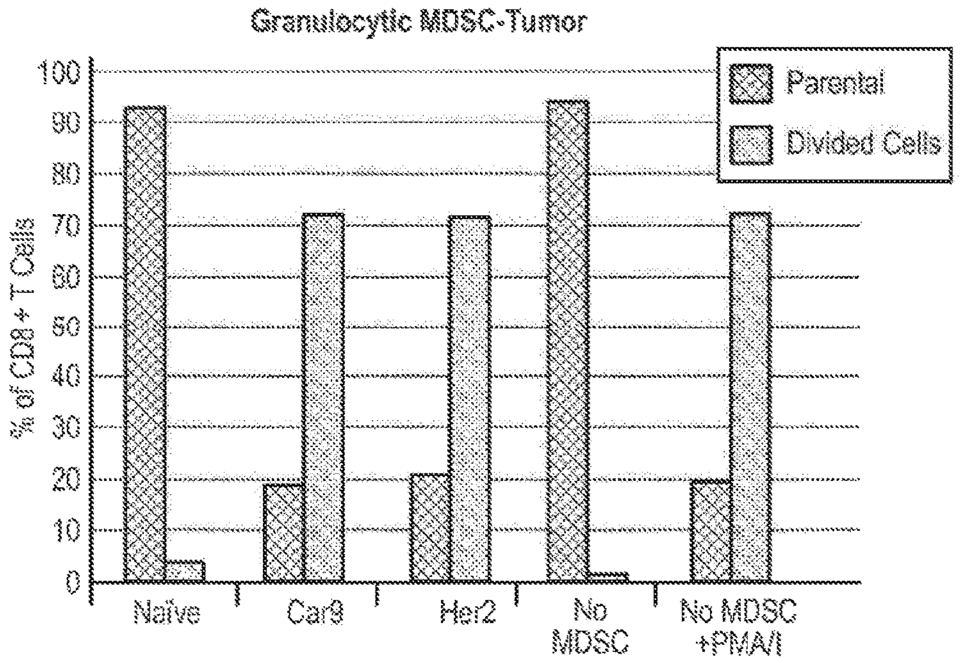
Figure 32:
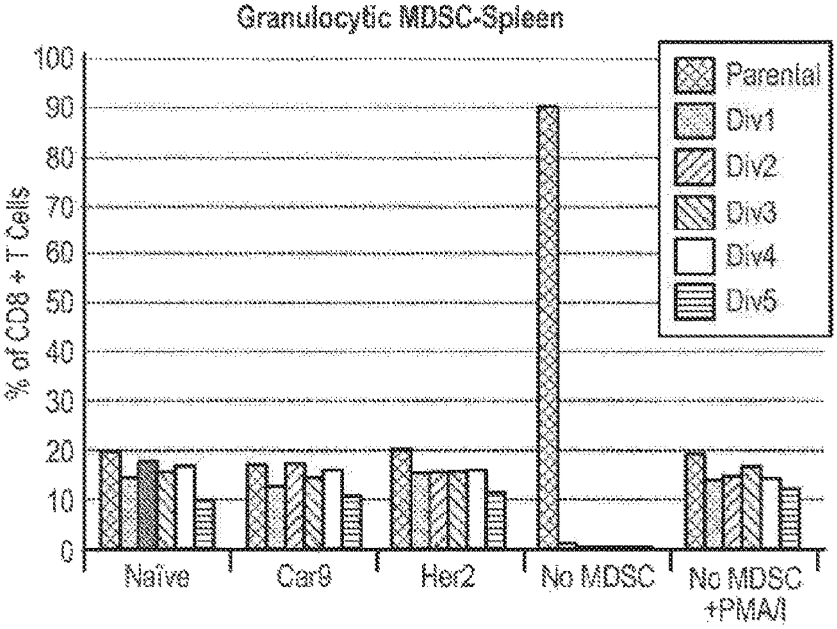
FIGS. 32A-32D showed suppressor assay data demonstrating that there is no *Listeria*-specific effect on splenic granulocytic MDSCs.
Figure 32:
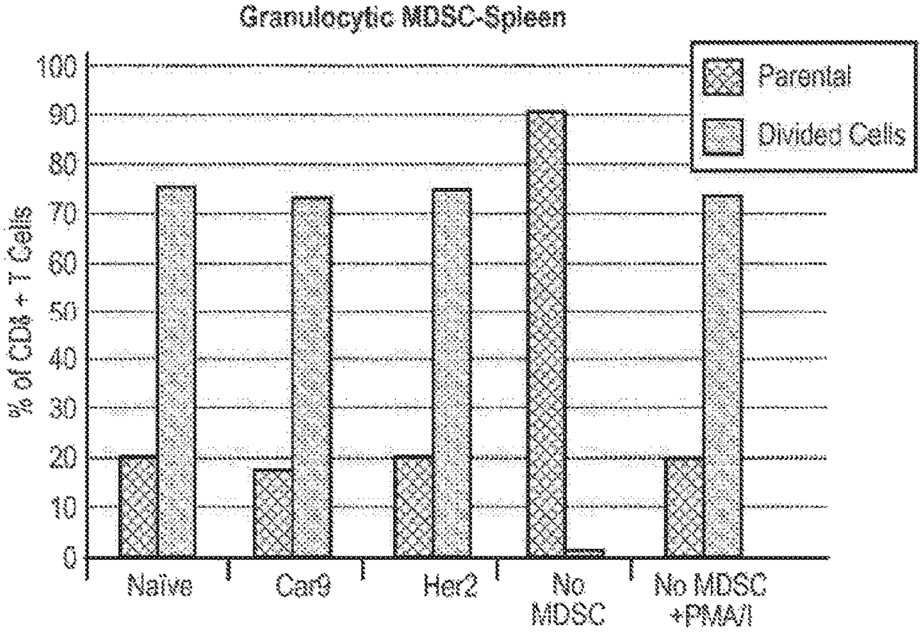
Figure 32:
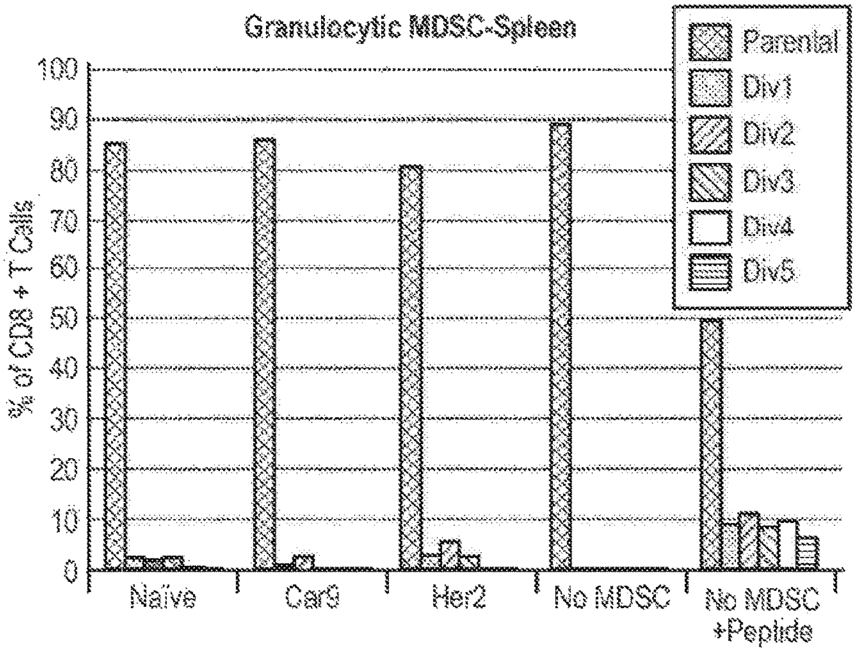
Figure 32:
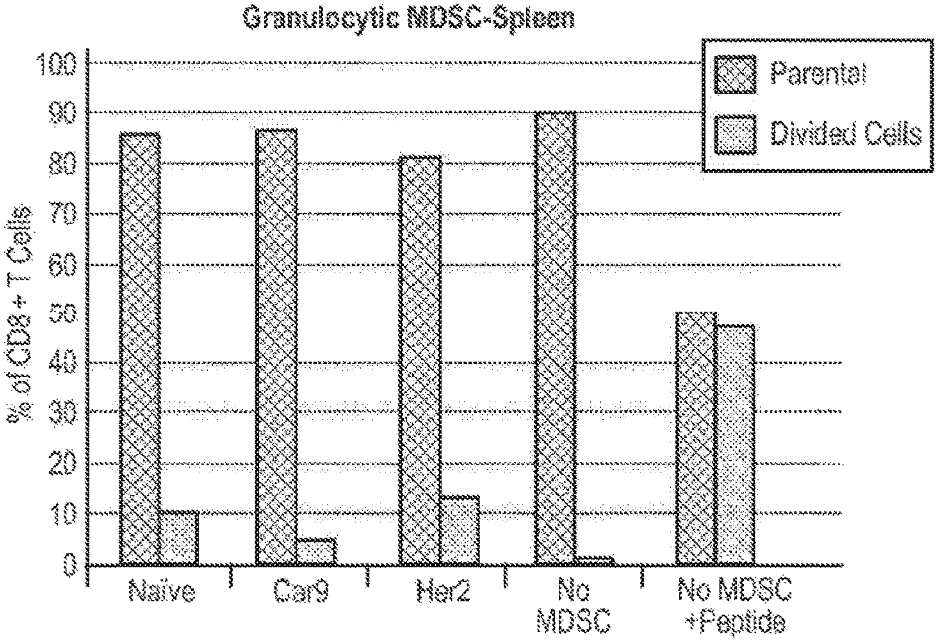
Figure 33:
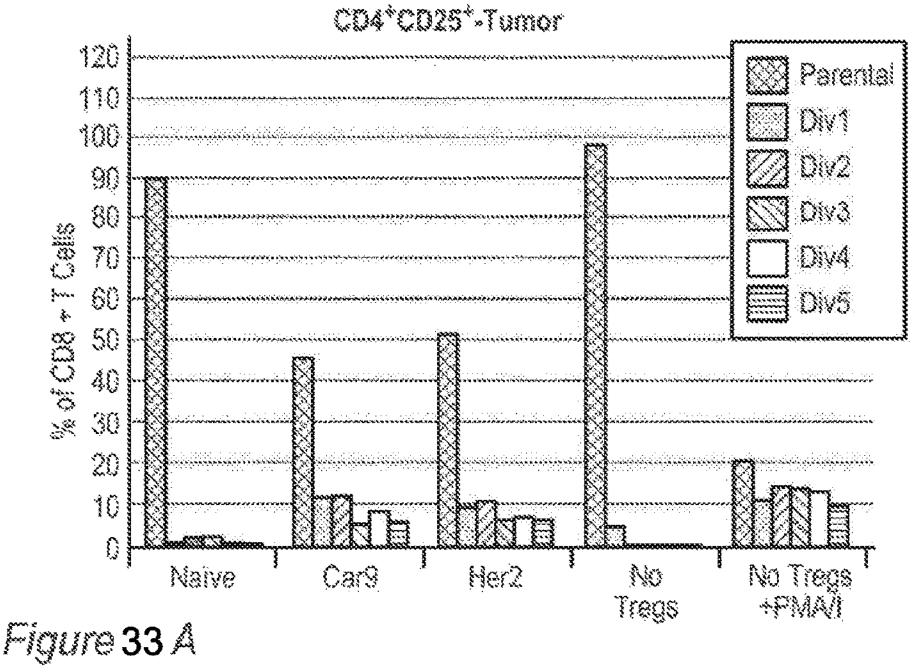
FIGS. 33A-33D show suppressor assay data demonstrating that decrease in the suppressive ability of Tregs from 4T1 tumors (Her2 expressing tumors) after *Listeria* vaccination.
Figure 33:
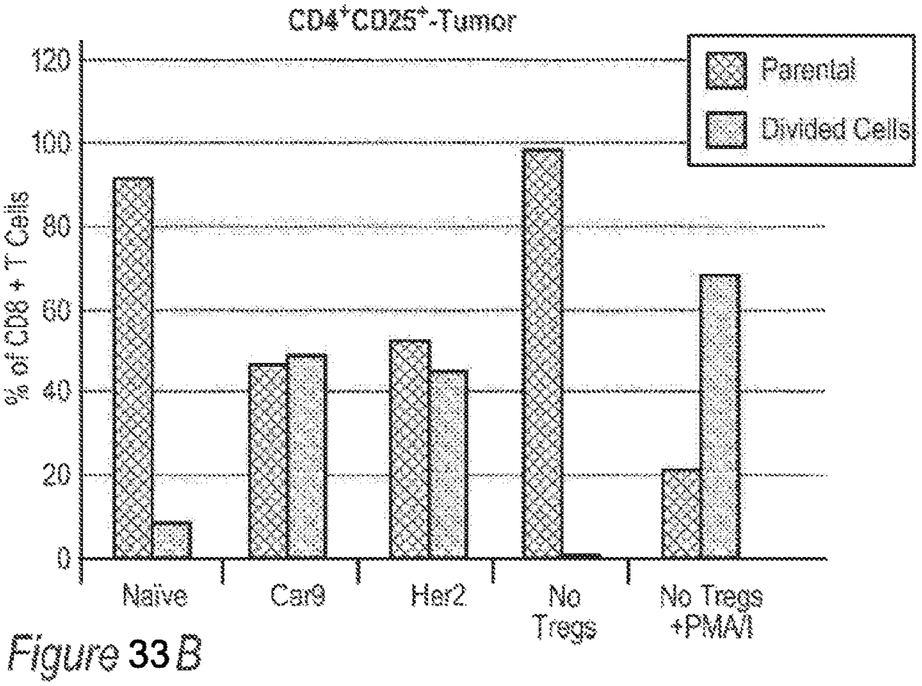
Figure 33:
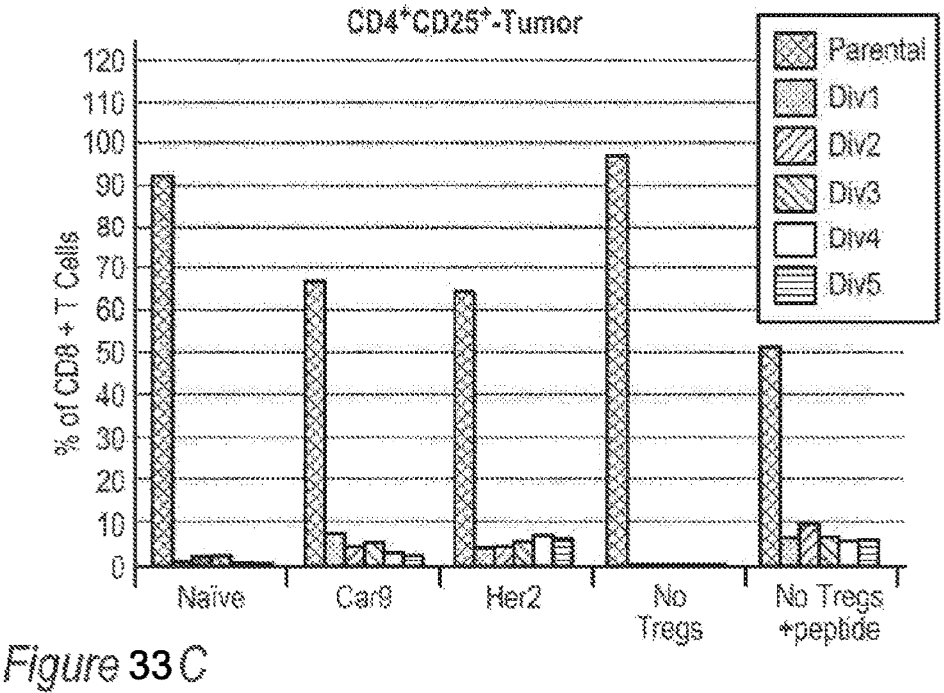
Figure 33:
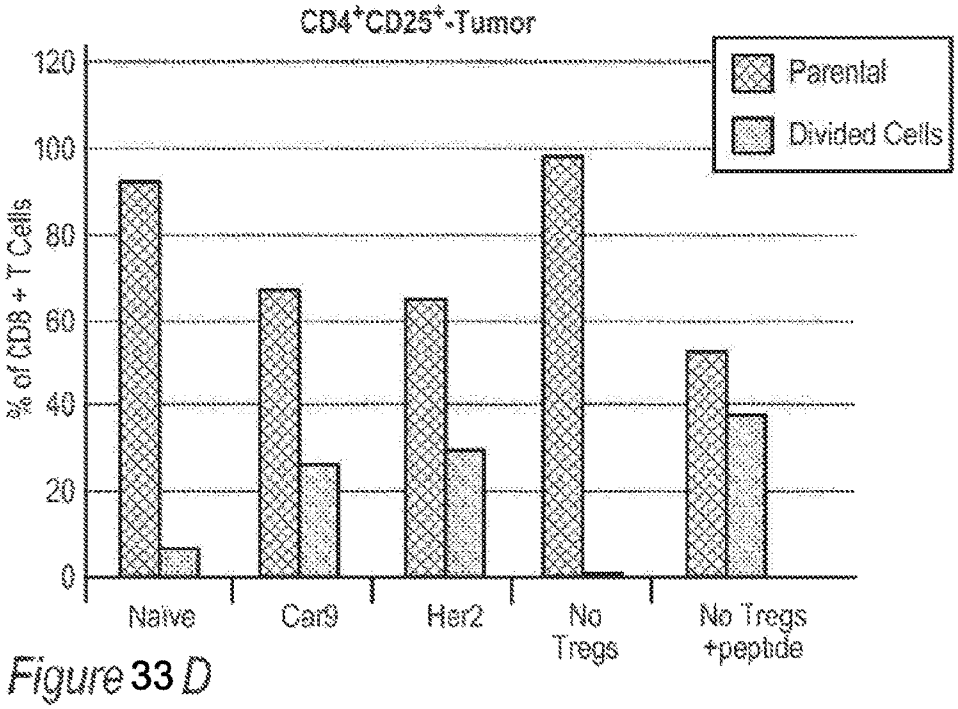

As a control conventional CD4+ T cells were used in place of MDSCs or Tregs and were found not to have an effect on cell division (FIG. 28).

Example 20

Figure 34:
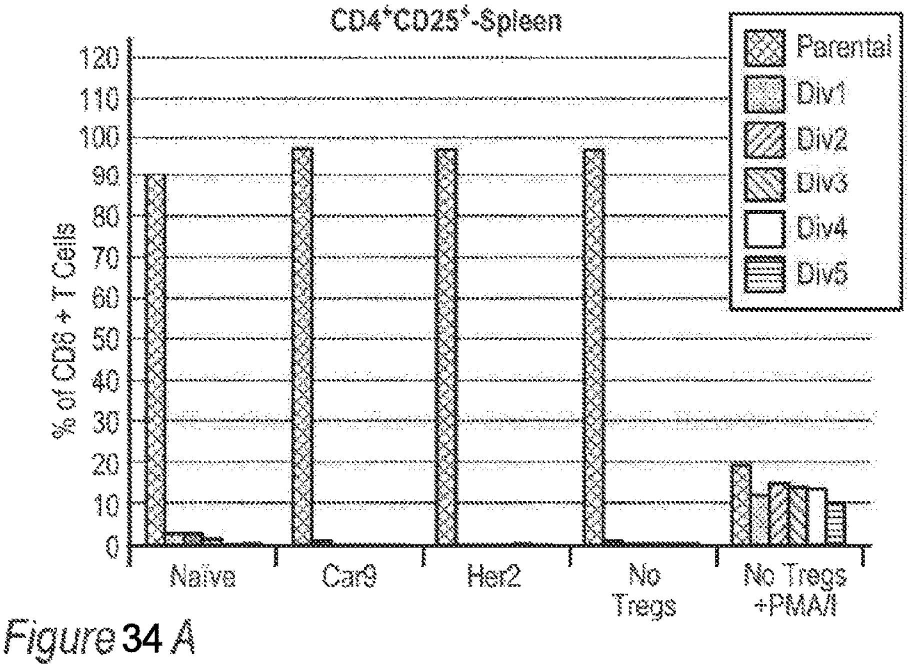
FIGS. 34A-34D show suppressor assay data demonstrating that there is no *Listeria*-specific effect on splenic Tregs. The responder T cells are all capable of dividing, regardless of the whether or not they are antigen specific.
Figure 34:
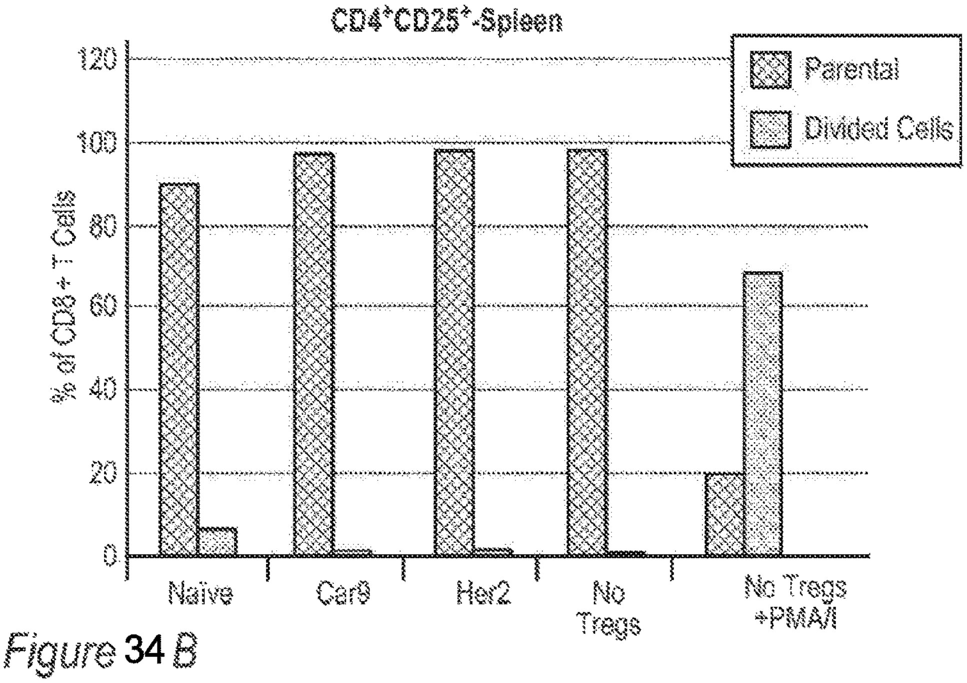
Figure 34:
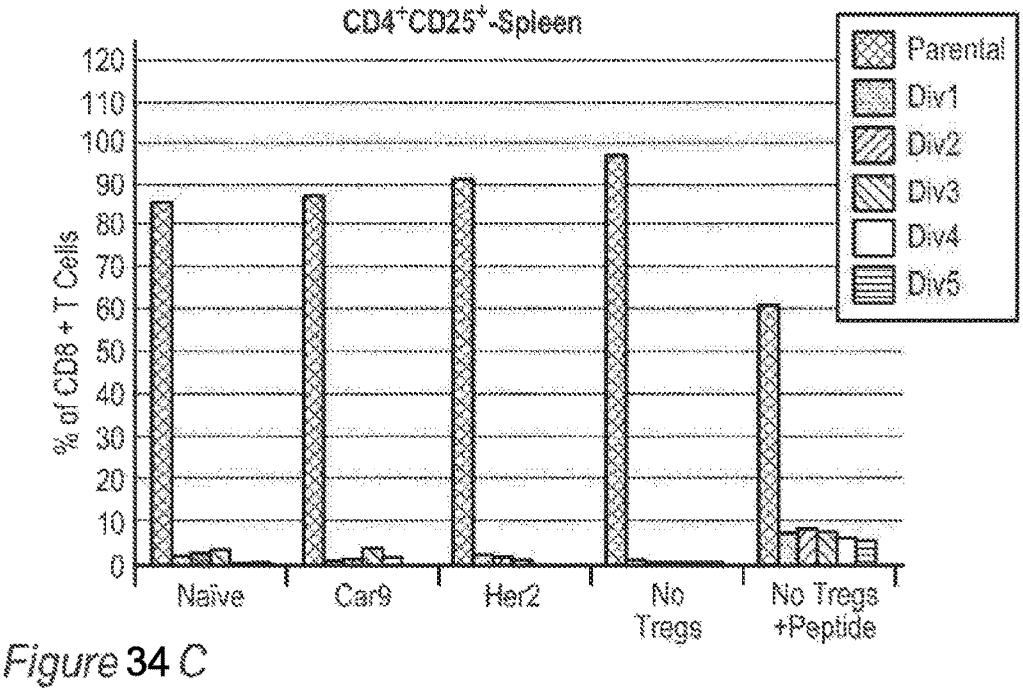
Figure 34:
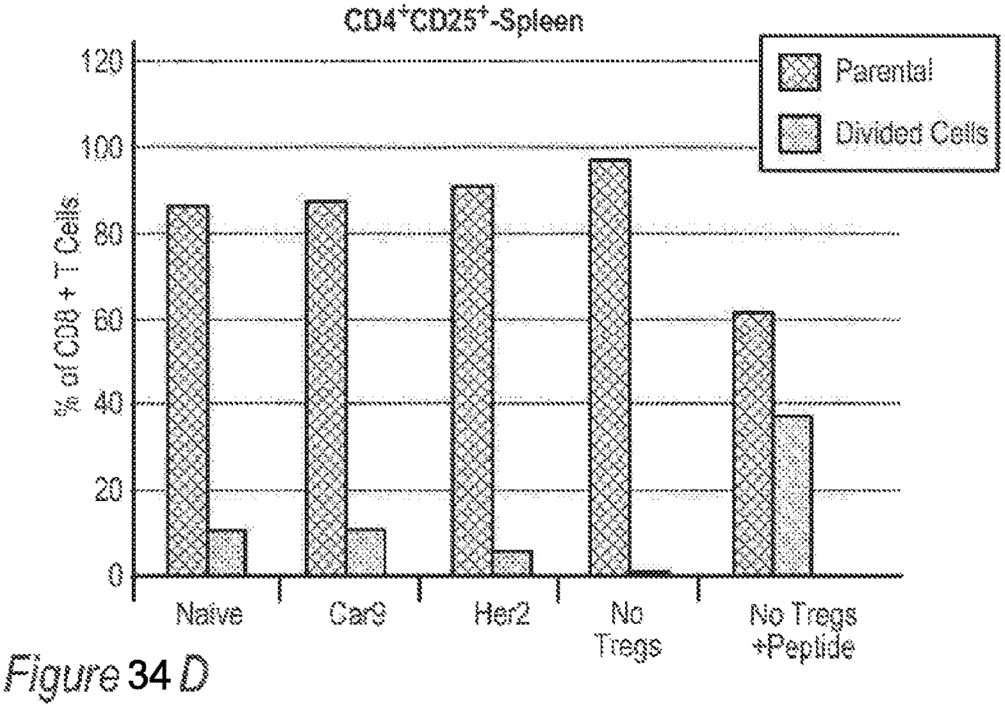

MDSCS and Tregs from 4T1 Tumors but not Spleen are Less Suppressive after *Listeria* Vaccination As in the above, the same experiments were carried out using 4T1 tumors and the same observations were made, namely, that MDSCs are less suppressive after *Listeria* vaccination (FIGS. 29 & 31), that *Listeria* has no specific effect on splenic monocytic MDSCs (FIGS. 30 & 32), that there is a decrease in the suppressive ability of Tregs from 4T1 tumors after *Listeria* vaccination (FIG. 33), and that *Listeria* has no effect on the suppressive ability of splenic Tregs (FIG. 34).

Finally, it was observed that *Listeria* has no effect on the suppressive ability of splenic Tregs.

Example 21

Figure 35:
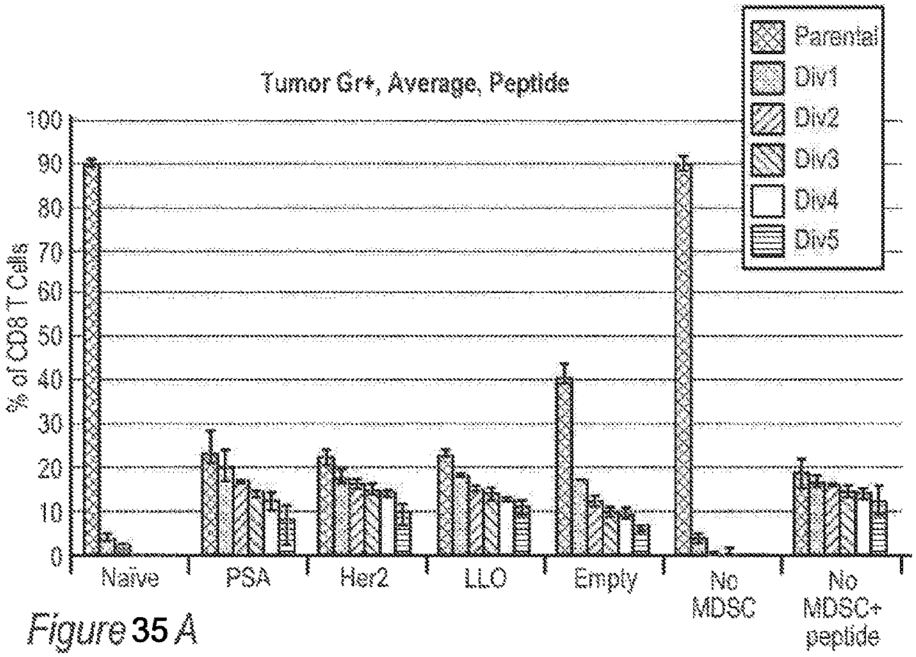
FIGS. 35A-35D show suppressor assay data demonstrating that suppressive ability of the granulocytic MDSC is due to the overexpression of tLLO and is independent of the partnering fusion antigen. Left-hand panels (FIGS. 35A and 35C) show individual cell division cycles for each group. Right-hand panels (FIGS. 35B and 35D) show pooled percentage division.
Figure 35:
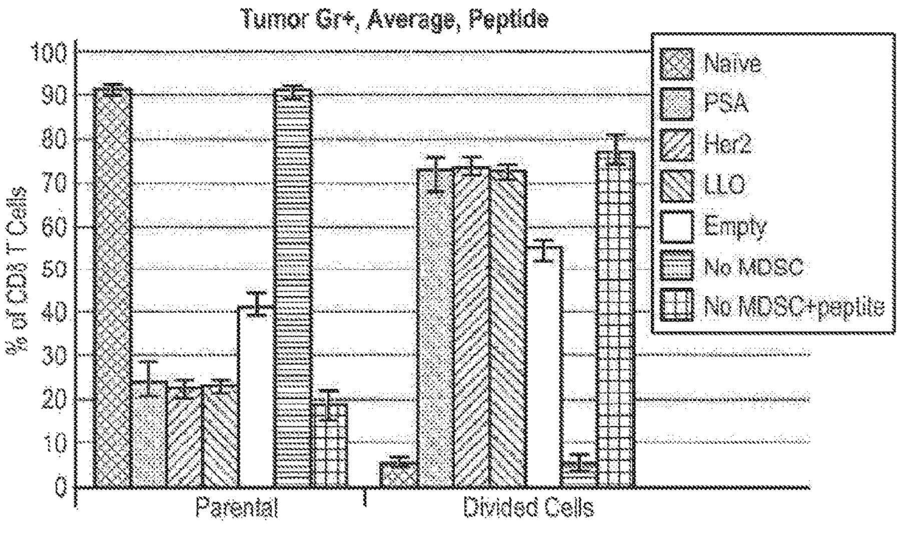
Figure 35:
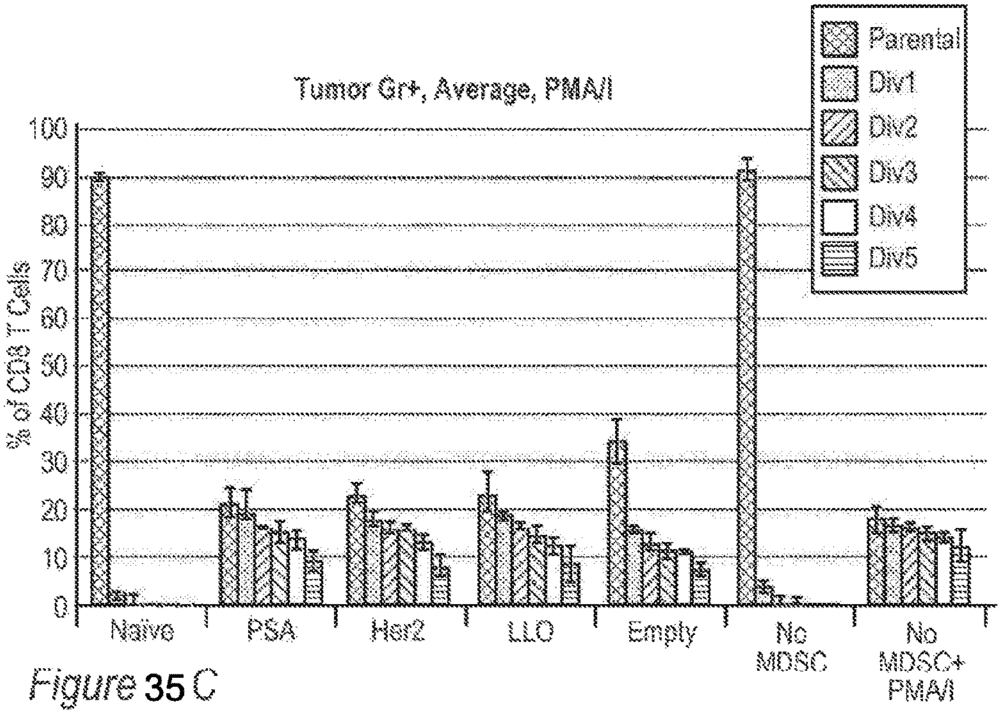
Figure 35:
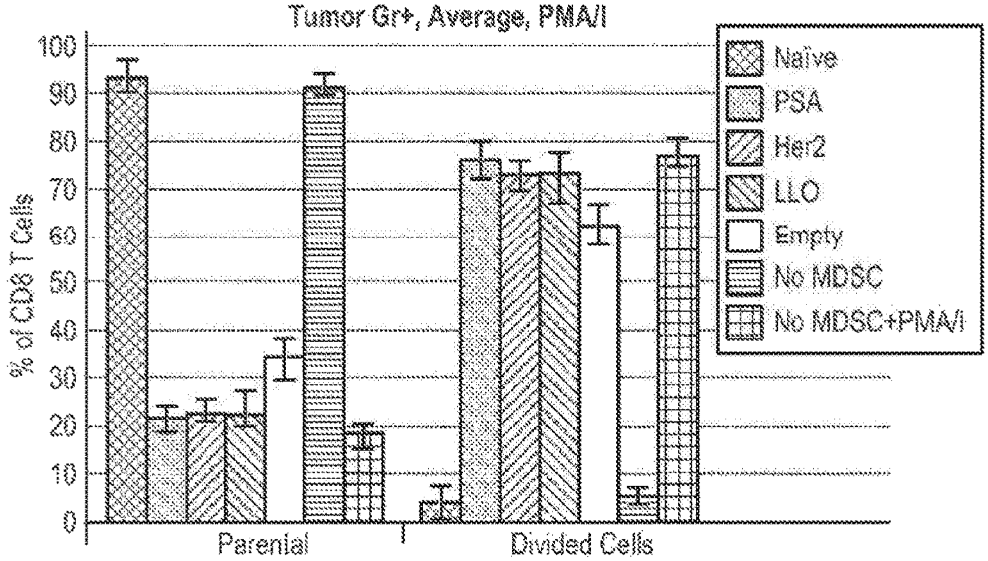

Change in the Suppressive Ability of the Granulocity and Monocytic MDSC is Due to the Overexpression of tLLo The LLO plasmid shows similar results as the *Listeria* vaccines with either the TAA or an irrelevant antigen (FIG. 35). This means that the change in the suppressive ability of the granulocytic MDSC is due to the overexpression of tLLO and is independent of the partnering fusion antigen. The empty plasmid construct alone also led to a change in the suppressive ability of the MDSC, although not to exactly the same level as any of the vaccines that contain the truncated LLO on the plasmid. The average of the 3 independent experiments show that the difference in suppression between the empty plasmid and the other plasmids with tLLO (with and without a tumor antigen) are significant.

Reduction in MDSC suppressive ability was identical regardless of the fact if antigen specific or non-specific stimulated responder T cells were used.

Figure 36:
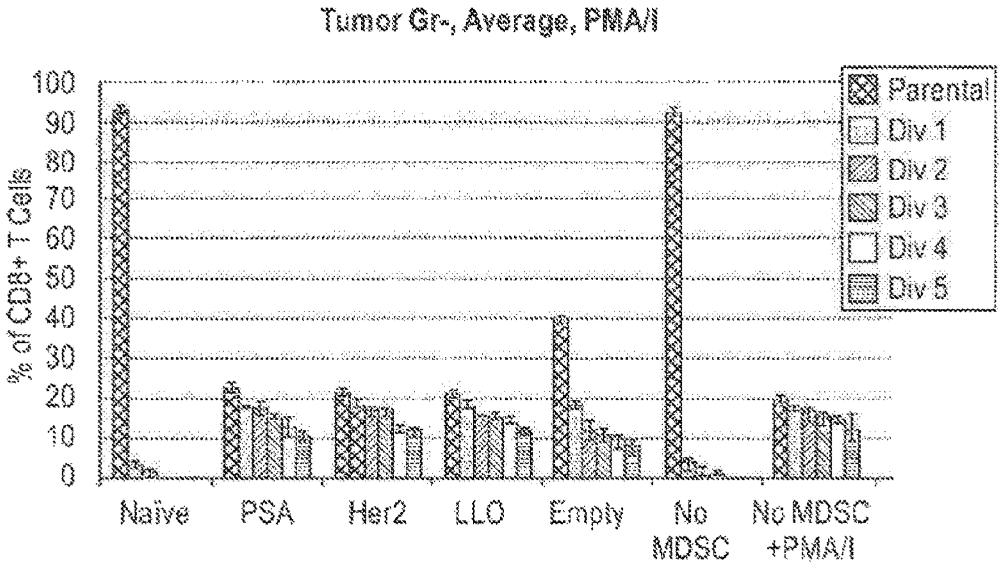
FIGS. 36A-36D show suppressor assay data also demonstrating that suppressive ability of the monocytic MDSC is due to the overexpression of tLLO and is independent of the partnering fusion antigen. Left-hand panels (FIGS. 36A and 36C) show individual cell division cycles for each group. Right-hand panels (FIGS. 36B and 36D) show pooled percentage division.
Figure 36:
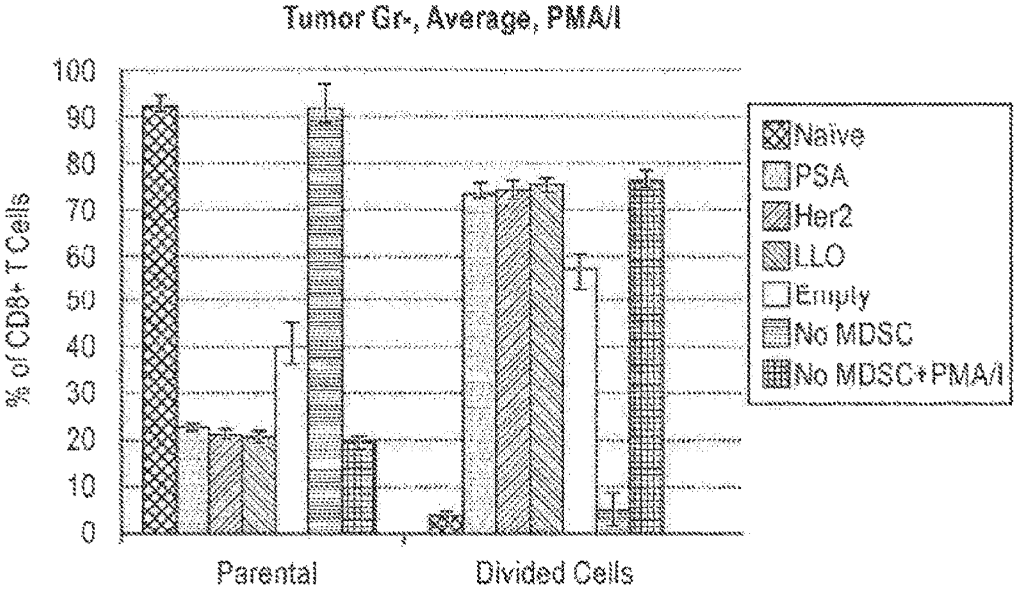

Similar to the granulocytic MDSC, the average of the 3 independent experiments shows that the differences observed in the suppressive ability of the monocytic MDSCs purified from the tumors after vaccination with the Lm-empty plasmid vaccine are significant when compared to the other vaccine constructs (FIG. 36).

Figure 37:
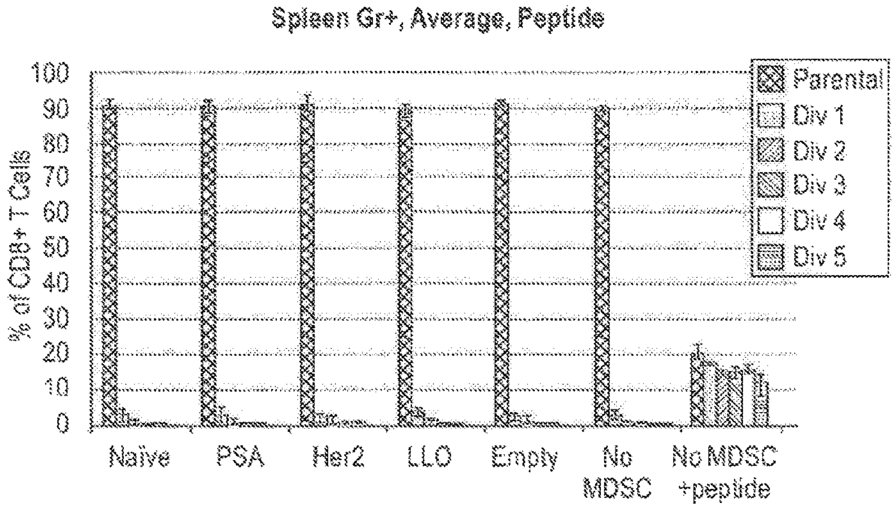
FIGS. 37A-37D show suppressor assay data demonstrating that granulocytic MDSC purified from the spleen retain their ability to suppress the division of the antigen-specific responder T cells after Lm vaccination (FIGS. 37A and 37B). However, after non-specific stimulation, activated T cells (with PMA/ionomycin) are still capable of dividing (FIGS. 37C and 37D). Left-hand panels show individual cell division cycles for each group. Right-hand panels show pooled percentage division.
Figure 37:
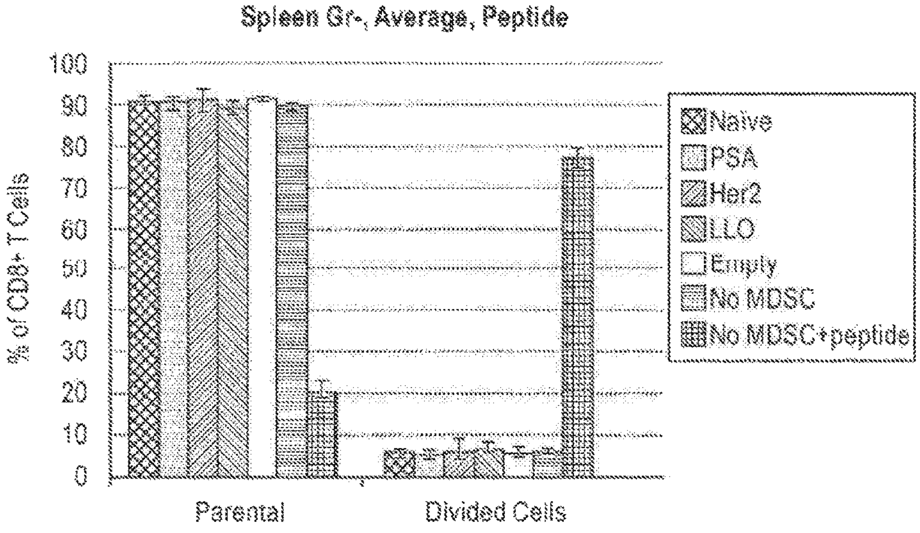

Similar to the above observations, granulocytic MDSC purified from the spleen retain their ability to suppress the division of the antigen-specific responder T cells after Lm vaccination (FIG. 37). However, after non-specific stimulation, activated T cells (with PMA/ionomycin) are still capable of dividing. None of these results are altered with the use of the LLO only or the empty plasmid vaccines showing that the Lm-based vaccines are not affecting the splenic granulocytic MDSC (FIG. 37).

Figure 38:
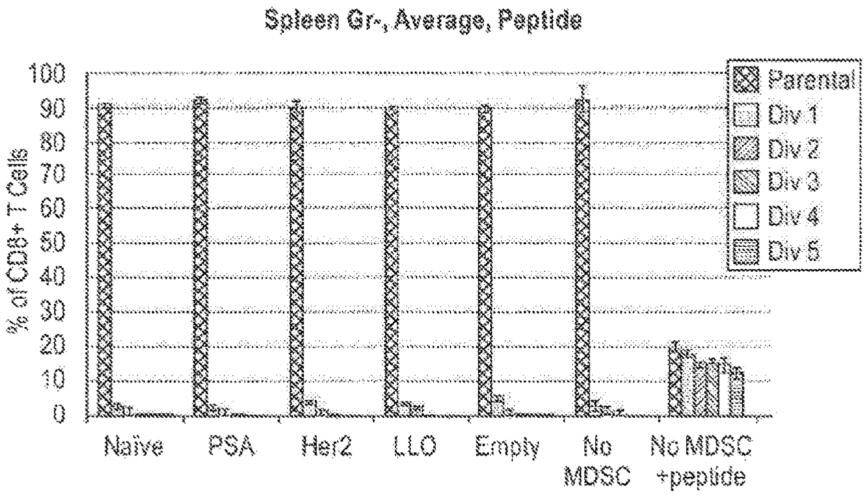
FIGS. 38A-38D show suppressor assay data demonstrating that monocytic MDSC purified from the spleen retain their ability to suppress the division of the antigen-specific responder T cells after Lm vaccination (FIGS. 38A and 38B). However, after non-specific activation (stimulated by PMA/ionomycin), T cells are still capable of dividing (FIGS. 38C and 38D). Left-hand panels show individual cell division cycles for each group. Right-hand panels show pooled percentage division.
Figure 38:
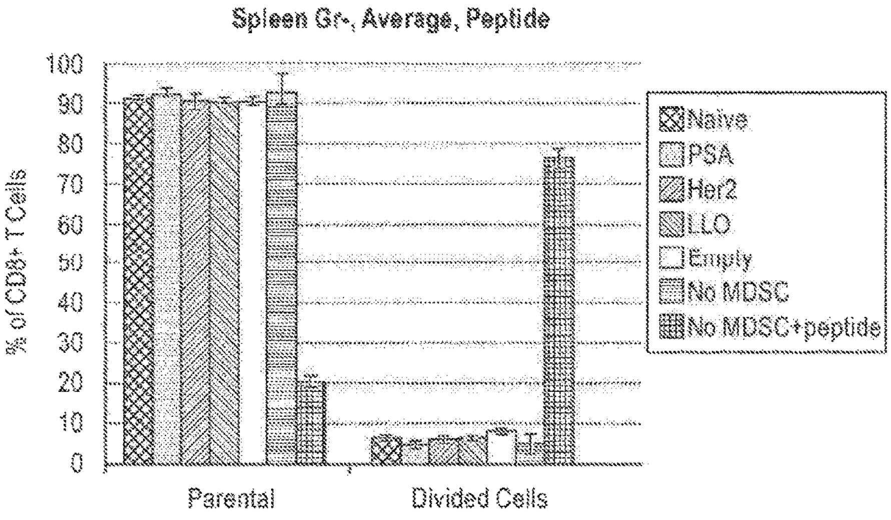

Similarly, monocytic MDSC purified from the spleen retain their ability to suppress the division of the antigen-specific responder T cells after Lm vaccination. However, after non-specific activation (stimulated by PMA/ionomycin), T cells are still capable of dividing. None of these results are altered with the use of the LLO only or the empty plasmid vaccines showing that the Lm vaccines are not affecting the splenic monocytic MDSC (FIG. 38).

Figure 39:
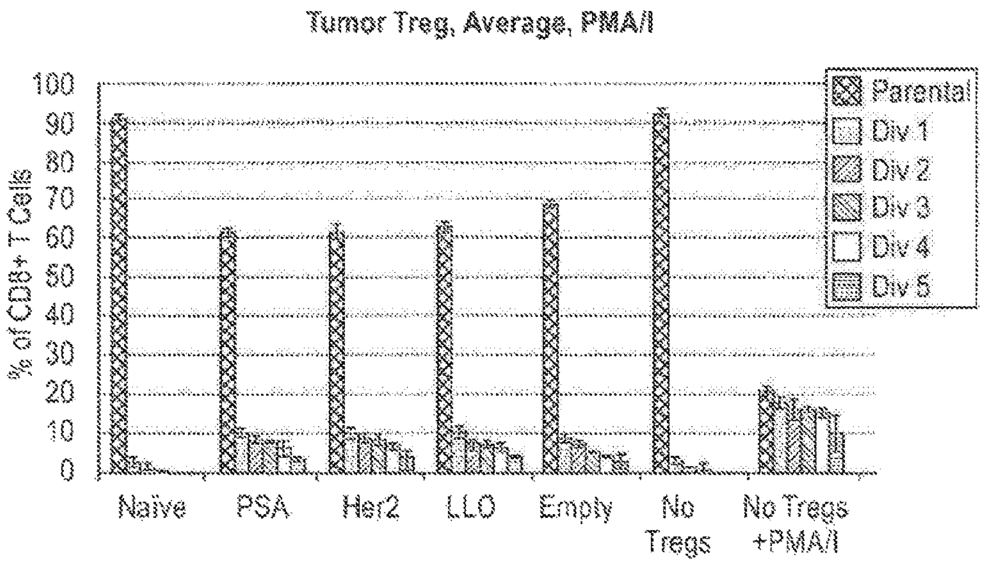
FIGS. 39A-39D show suppressor assay data demonstrating that Tregs purified from the tumors of any of the Lm-treated groups have a slightly diminished ability to suppress the division of the responder T cells, regardless of whether the responder cells are antigen specific (FIGS. 39A and 39B) or non-specifically (FIGS. 39C and 39D) activated. Left-hand panels show individual cell division cycles for each group. Right-hand panels show pooled percentage division.
Figure 39:
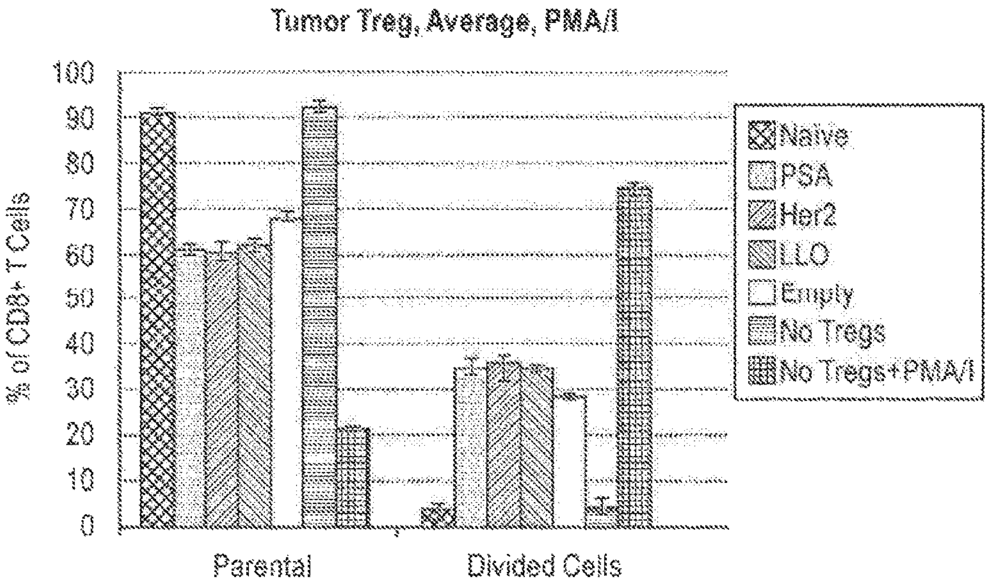

Tregs purified from the tumors of any of the Lm-treated groups have a slightly diminished ability to suppress the division of the responder T cells, regardless of whether the responder cells are antigen specific or non-specifically activated. Especially for the non-specifically activated responder T cells, it looks as though the vaccine with the empty plasmid shows the same results as all the vaccines that contain LLO on the plasmid. Averaging this experiment with the others shows that the differences are not significant (FIG. 39).

Figure 40:
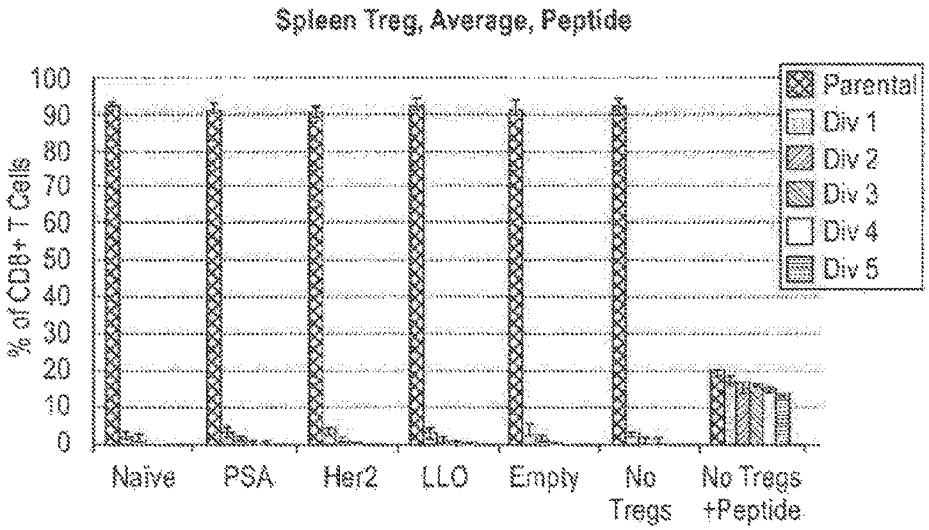
FIGS. 40A-40D show suppressor assay data demonstrating that Tregs purified from the spleen are still capable of suppressing the division of both antigen specific (FIGS. 40A-40B) and non-specifically (FIGS. 40C and 40D) activated responder T cells.
Figure 40:
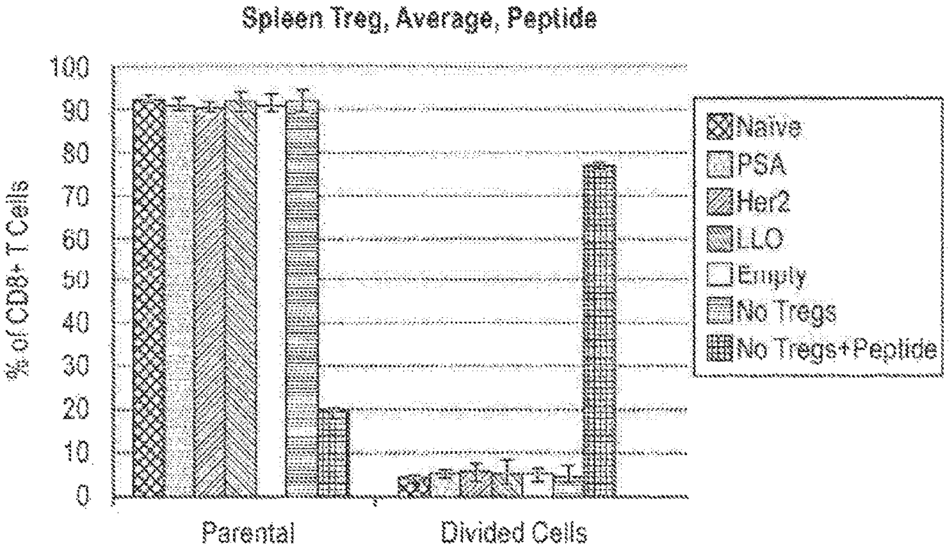

Tregs purified from the spleen are still capable of suppressing the division of both antigen specific and non-specifically activated responder T cells. There is no effect of Lm treatment on the suppressive ability of splenic Tregs (FIG. 40).

Tcon cells are not capable of suppressing the division of T cells regardless of whether the responder cells are antigens specific or non-specifically activated, which is consistent with the fact that these cells are non-suppressive. Lm has no effect on these cells and there was no difference if the cells were purified from the tumors or the spleen of mice (FIGS. 41-42).

Materials and Methods (Examples 22-28)

Mice

Balb/c female mice (6-8 week old) from Charles River Laboratories were utilized for all experiments involving the 4T1 tumor line. FVB/NJ female mice (6-8 week old) from Jackson Laboratories were utilized for all experiments involving the NT2 tumor line. A rat Her2/neu transgenic mouse strain in the FVB/NJ background was utilized in studies involving spontaneous tumor formation and for prevention studies of autochthonous mammary tumor formation was housed and bred at the animal core facility at the University of Pennsylvania. All mouse experiments were performed in accordance with the regulations of the Institutional Animal Care and Use Committee of the University of Pennsylvania.

*Listeria* Strains

To construct an attenuated *Listeria*-based ISG15 vaccine, first the gene encoding murine ISG15 was amplified from a construct containing murine ISG15 cDNA from Balb/c mice with the following primers: Lm-LLO-ISG15.FOR 5'-TAAT-<u>CTCGAG</u>-ATGGCCTGGGACCTAAAG-3' (SEQ ID NO: 83) and Lm-LLO-ISG15.REV 5'-ATTA-<u>ACTAGT</u>-TTAGGCACACTGGTCCCC-3' (SEQ ID NO: 84). The XhoI sequence underlined in the forward primer and the SpeI sequence underlined in the reverse primer were utilized for ligation. Each fragment amplicon was restriction-enzyme digested and ligated into the *Listeria* expression plasmid, pGG34. Each sequence was genetically fused downstream to the sequence encoding truncated Listeriolysin O (tLLO) under the control of the hly promoter. Subsequently, pGG34-LLO-ISG15 was electroporated into the attenuated *Listeria monocytogenes* (Lm) strain, XFL7, and plasmid containing colonies were selected for resistance on BHI-chloramphenicol plates. To confirm proper construction of Lm-LLO-ISG15, the attenuated *Listeria*-based vaccine was grown in BHI-chloramphenicol selection media and secreted proteins were precipitated with trichloroacetic acid. After boiling in SDS sample buffer, secreted proteins were subject to SDS-PAGE analysis and transferred to a PVDF membrane. Western analysis on the membrane was performed with anti-mouse ISG15 antibody (Santa Cruz Biotech, Santa Cruz, Calif.) to confirm secretion of the tLLO-ISG15 fusion protein, anti-chicken ovalbumin with 3A11.2 monoclonal antibody and wild-type LLO with B3-19 monoclonal antibody. The control vaccine, Lm-LLO-OVA, consisting of tLLO genetically fused to chicken ovalbumin was similarly constructed. All *Listeria*-based vaccines were administered intraperitoneally (i.p.) at either $2\times10^8$ or $5\times10^8$ CFU in 200 μl of PBS. The control vaccines Lm-LLO-OVA and Lm-LLO-NYESO-1 were similarly constructed.

Cell Lines

The metastatic breast cancer tumor line 4T1 was utilized in tumor implantation studies in Balb/c mice. The NT2 breast cancer cell line that overexpresses rat Her2/neu was utilized for tumor implantation studies in FVB mice. 4T1-Luc was maintained in DMEM supplemented with 10% fetal calf serum, 2 mM $_L$-glutamine, 1 mM sodium pyruvate, 50 U/mL penicillin, and 50 μg/mL streptomycin. NT2 cells were maintained in RPMI 1640 medium supplemented with 10% fetal calf serum, 20 μg/mL insulin, 2 mM $_L$-glutamine, 1 mM sodium pyruvate, 50 U/mL penicillin, and 50 μg/mL streptomycin. The non-transformed NIH-3T3 fibroblast cell line obtained from ATCC. NIH-3T3 cells were maintained in DMEM supplemented with 10% fetal calf serum, 2 mM $_L$-glutamine, 1 mM sodium pyruvate, 50 U/mL penicillin, and 50 μg/mL streptomycin.

ISG15 Expression in Normal and Tumor Murine Tissue

Figure 43:
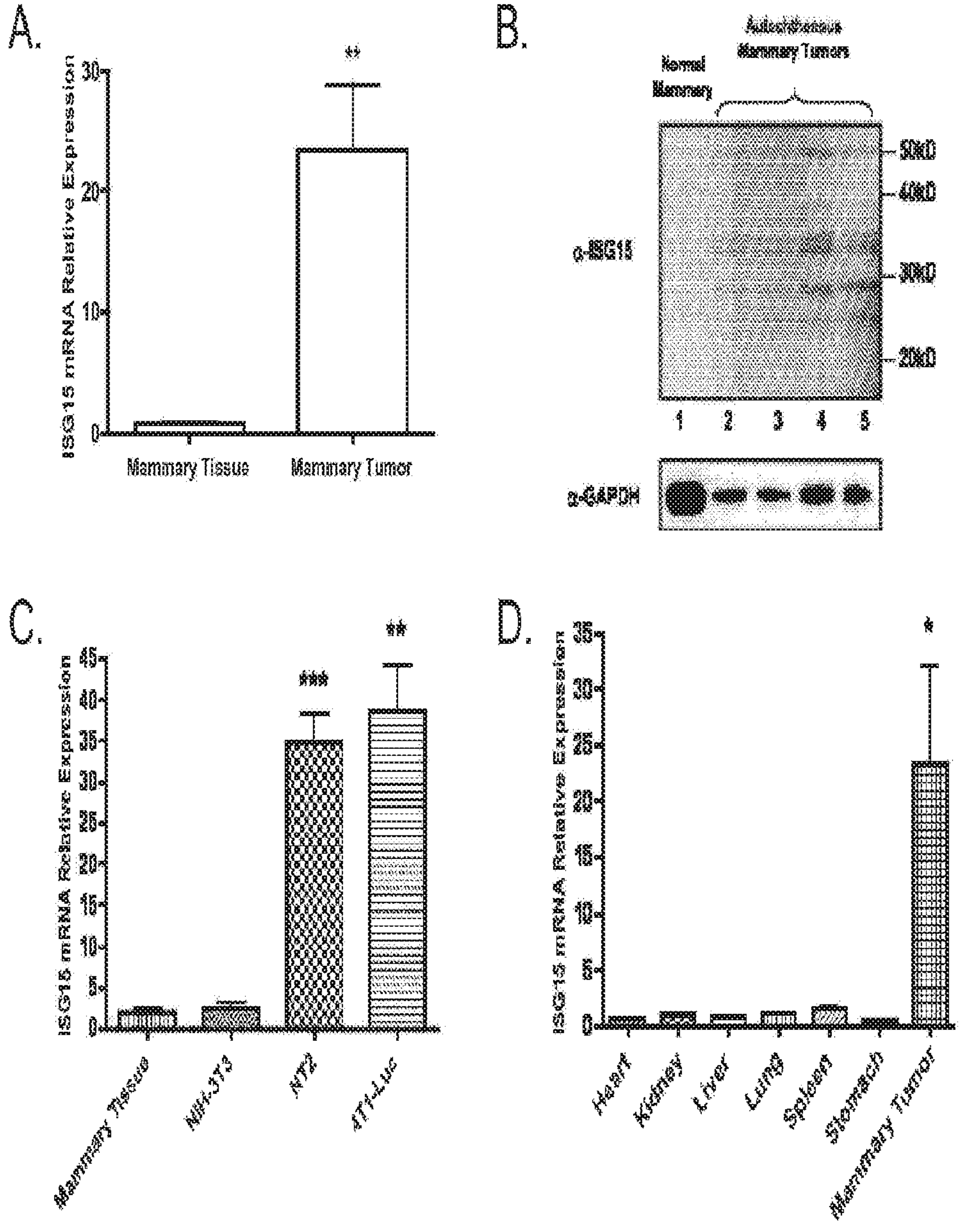
FIG. 43. Elevated expression of ISG15 in mouse mammary tumors. (A) mRNA was extracted from autochthonous mouse mammary tumors (n=9) from FVB/N HER2/neu transgenic mice and normal mammary tissues (n=4) from FVB/N mice. After cDNA conversion, qPCR analysis was performed to determine relative ISG15 mRNA expression. (B) Western blot analysis of tissue lysates from normal mammary tissue and HER2/neu mammary tumor tissues with anti-ISG15 antibody, top panel, and anti-GAPDH antibody to demonstrate equivalent protein loading, bottom panel. (C) qPCR of cDNA from mammary tumor cell lines NT2 and 4T1-Luc were compared against normal mammary tissue and non-transformed cell line NIH-3T3 for expression of ISG15 mRNA (n=3). (D) qPCR analysis of ISG15 expression in a panel of normal tissues (n=3) compared to autochthonous mammary tumors from HER2/neu transgenic mice (n=7).

RNA was extracted from tissue or cells using the RNeasy RNA extraction kit from Qiagen and converted to cDNA. The cDNA was then subjected to qPCR analysis with primers specific for ISG15 qISG15.FOR 5'-ATGGC-CTGGGACCTAAAG-3' (SEQ ID NO: 85) and qISG15.REV 5'-TTAGGCACACTGGTCCCC-3' (SEQ ID NO: 86), 18S rRNA 18SRNA.FOR 5'-CGGCTACCA-CATCCAAGGAA-3' (SEQ ID NO: 87) and 18SRNA.REV 5'-GCTGGAATTACCGCGGCT-3' (SEQ ID NO: 88), and β-actin ACTIN.FOR 5'-GTGGGCCGCTCTAGGCAC-CAA-3' (SEQ ID NO: 89) and ACTIN.REV 5'-CTCTTT-GATGTCACGCACGATTTC-3' (SEQ ID NO: 90). ISG15 expression was normalized to either 18S rRNA (FIGS. 43C and D) or β-actin (FIG. 43A).

Western Blot Analysis of Mammary Tissue Lysates

Normal mammary tissue from FVB/N mice (n=4) and autochthonous mammary tumor tissue from HER2/neu transgenic mice in the FVB/N background (n=9) were excised and processed into lysates. Briefly, tissue samples were snap-frozen in liquid $N_2$, pulverized, and solubilized in lysis buffer (PBS with 2% Triton X-100 and 0.02% saponin) supplemented with protease inhibitor cocktail. Lysates were mixed with 4×LDS Sample Loading Buffer and subjected to SDS-PAGE. After transfer of separated proteins to a PVDF membrane, western blot analysis was performed with anti-mouse ISG15 antibody. Separately, the same lysates were subjected to SDS-PAGE and the gel stained with Coomassie stain to visualize total proteins as a measure of protein loading.

Tumor Immunotherapy with ISG15 Peptides.

4T1-Luc tumor cells ($10^5$) were implanted into the mammary tissue of Balb/c mice and mice were subsequently vaccinated on day 5, 12, and 19 with either 100 μl of PBS or 50 μg CpG oligodeoxynucleotides (ODN) mixed with control, HIV-gag H-$2K^d$ CTL epitope peptide (AMQMLKETI) (SEQ ID NO: 91), or ISG15-specific peptides (100 μg), pISG15 d1(RGHSNIYEV) (SEQ ID NO: 92) and pISG15 d2(LGPSSTVML) (SEQ ID NO: 93), in 100 μL of PBS s.c. proximal to the cervical lymph nodes. Tumor volume was monitored by perpendicular caliper measurements throughout the course of the experiment. Tumor volume was calculated as (tumor diameter)$^3$/2.

ISG15 Peptide Tumor Load Study

4T1-Luc tumor cells ($10^5$) were implanted into the mammary tissue and mice were subsequently vaccinated on day 4, 11, and 18 with either 50 ug of CpG alone in 100 ul of PBS or CpG (50 ug) along with control or ISG15-specific peptides (100 ug) in 100 ul of PBS subcutaneously proximal to the cervical lymph nodes. At experimental end on day 32, tumor mass of each vaccinated group was measured, tumors were analyzed for ISG15-specific IFN-γ responses as described in ELISpot Analysis and lung metastases measured as described in Metastatic Tumor Study.

Metastatic Tumor Study

4T1-Luc tumor cells ($10^5$) were implanted into the mammary tissue and mice were subsequently vaccinated on day 4, 11, and 18 with either peptide or *Listeria*-based vaccines. Mice were then sacrificed on day 32 and lungs isolated and perfused with PBS. Lung surface metastatic nodules per lung were then counted with a Nikon SMZ1B Zoom Stereomicroscope attached to a Fostec 8375 Illuminator and Ringlight.

ELISpot Analysis

The 96-well filtration plates (Millipore, Bedford, Mass.) were coated with 15 μg/ml rat anti-mouse IFN-γ antibody in 100 μl of PBS. After overnight incubation at 4° C., the wells were washed and blocked with DMEM supplemented with 10% fetal calf serum. For FIG. 2C, splenocytes from each experimental group were added to the wells along with HIV-gag H-$2K^d$ CTL epitope peptide (AMQMLKETI) (SEQ ID NO: 91) or predicted ISG15-specific H-$2K^d$ CTL epitope peptides, ISG15-d1(RGHSNIYEV) (SEQ ID NO: 92) and ISG15-d2(LGPSSTVML) (SEQ ID NO: 93) (5 μg/ml) plus IL-2 (5 U/ml). ISG15-specific H-$2K^d$ CTL epitope were predicted from the ISG15 protein sequence in Balb/c mice using RANKPEP prediction software at http://bio.dfci.harvard.edu/Tools/rankpep.html. For FIG. 47B, splenocytes from each experimental group were added to the wells along with HIV-gag H-$2K^d$ CTL epitope peptide (AMQMLKETI) (SEQ ID NO: 91) or Her2/neu-specific H-$2K^d$ epitope peptides Her2-EC1 (PYNYLSTEV) (SEQ ID NO: 94), Her2-EC2 (LFRNPHQALL) (SEQ ID NO: 95), and Her2-IC1 (PYVSRLLGI) (SEQ ID NO: 96). Cells were incubated at 37° C. for 24 h. The plate was washed followed by incubation with 1 μg/ml biotinylated IFN-γ antibody (clone R4-6A2, MABTECH, Mariemont, Ohio) in 100 μl PBS at 4° C. overnight. After washing, 1:100 streptavidin-horseradish peroxidase in 100 μl PBS were added and incubated for 1 hr at room temperature. Spots were developed by adding 100 μl of substrate after washing and incubated at room temperature for 15 min. Color development was stopped by washing extensively in $dH_2O$ and spot-forming cells (SFC) were counted with an ELISpot reader.

Depletion Experiment $CD8^+$ cells were depleted in 4T1-Luc tumor-bearing mice by injecting the mice with 0.5 mg of a-CD8 antibody (monoclonal antibody clone 2.43) on days 6, 7, 8, 10, 12, and 14 post-tumor implantation. A control group of mice were also treated under the same conditions but with an isotype matched, control antibody specific for beta-galactosidase. The concurrent tumor load study was adhered to as described in "Tumor immunotherapy with Lm-LLO-ISG15" in the method section herein.

Winn Assay for In Vivo Determination of Effector Cell.

The Winn assay was performed as previously described with some modification. Briefly, 4T1-Luc tumor cells ($2\times10^5$) mixed with CD4-depleted splenocytes (depletion with $CD4^+$ Dynabeads and confirmed by FACS analysis) from either twice control Lm vaccinated or twice Lm-LLO-ISG15 vaccinated Balb/c mice ($2\times10^7$) at a ratio of 1 tumor cell to 100 CD4-depleted splenocytes were implanted in the mammary tissue. Tumor development was then measured as described in "Tumor immunotherapy with Lm-LLO-ISG15" in the methods section herein.

Detection of HER2/Neu-specific Tumor Infiltrating Lymphocytes (TILs)

Balb/c mice were implanted with 4T1-Luc tumors and immunized i.p. with control Lm or Lm-LLO-ISG15 and boosted 7 days later. Tumors were harvested 9 days after boosting and manually dissociated into a single-cell suspension. The tumor cell suspension was then Ficoll-purified to remove dead cells and cellular debris by excluding the low-density fraction after centrifugation. The remaining tumor cells were then subjected to three-color flow cytometry for CD8 (53-6.7, FITC conjugated), CD62 ligand (CD62L; MEL-14, APC conjugated), and HER2/neu-EC2 H-$2D^q$ tetramer-PE conjugated (specific for PDSLRDLSVF, SEQ ID NO: 97) using a FACSCalibur flow cytometer with Cell Quest software. Tetramers were provided by the National Institute of Allergy and Infectious Diseases Tetramer Core Facility and used at a 1/200 dilution. Results were analyzed as described above to compare the ability of Lm-LLO-ISG15 to induce tetramer$^+$, $CD8^+$, $CD62L^-$, Her2/neu-specific TILs in comparison to control Lm vaccination.

Statistical Analyses

One-tailed student's t-tests were performed for all final tumor volume, metastatic load and immune response studies with Welch's correction applied for gene expression studies with autochthonous HER2/neu mammary tumors. Log rank test was performed for autochthonous HER2/neu mammary tumor incidence studies. Statistical analyses were performed using GraphPad Prism version 4.0a for Macintosh (www.graphpad.com). Significant p-values for all comparisons are depicted in figures as follows: *=p-value<0.05, =p-value<0.01, and *=p-value<0.001.

Results

Example 22

Elevated Expression of ISG15 in Murine Breast Tumors

The elevated expression of ISG15 in human malignancies is well-characterized in numerous tumor models. However, there is a lack of evidence for similar increased levels of ISG15 in murine tumor models. To determine if ISG15 expression is elevated in a murine model for breast cancer, ISG15 expression was assayed in autochthonous mouse mammary tumors from HER2/neu transgenic mice, mouse mammary tumor cell lines and a panel of normal and non-transformed mammary tissues and cell lines. As observed in human breast cancer, expression of ISG15 mRNA is significantly elevated in the autochthonous mouse mammary tumors in comparison to normal mouse mammary tissue (FIG. 43A). To confirm the elevated ISG15 mRNA expression results in elevated protein production, Western blot analysis with anti-ISG15 antibody was performed with lysates of normal and HER2/neu tumor mouse mammary tissue. In comparison to normal mouse mammary tissue (FIG. 43B, top panel, lane 1), the conjugated form of ISG15 protein (bands above 20 kD marker) is elevated in HER2/neu mammary tumor tissue (FIG. 43B, top panel, lanes 2-5). Elevated expression of the unconjugated form of ISG15 protein is also evident in mouse mammary tumor tissue (FIG. 43B, top panel, lanes 2 and 4) in comparison to normal mammary tissue (FIG. 43B, top panel, lane 1). Equivalent protein loading is evident by probing for expression of the housekeeping protein, GAPDH, with the same lysates (FIG. 43B, bottom panel, lanes 1-5). ISG15 mRNA expression was similarly elevated in mouse mammary tumor cell lines, 4T1-Luc and NT2, in comparison to normal mouse mammary tissue and a non-transformed mouse cell line, NIH-3T3 (FIG. 43C). To alleviate concerns of elevated ISG15 expression in non-malignant tissues, ISG15 mRNA expression was analyzed in a panel of normal mouse tissues in comparison to HER2/neu mammary mouse tumor tissue. Significantly elevated expression of ISG15 mRNA in mammary tumor tissue was similarly observed when compared against each normal tissue type (FIG. 43D). This expression analysis confirms that ISG15 expression is significantly elevated in mouse models of breast cancer. Together with the finding that ISG15 mRNA is nominally expressed in a panel of normal tissues, this suggests that ISG15 may be a promising novel tumor-associated antigen (TAA).

Example 23

Construction of an ISG15-Specific CTL Vaccine

Figure 44:
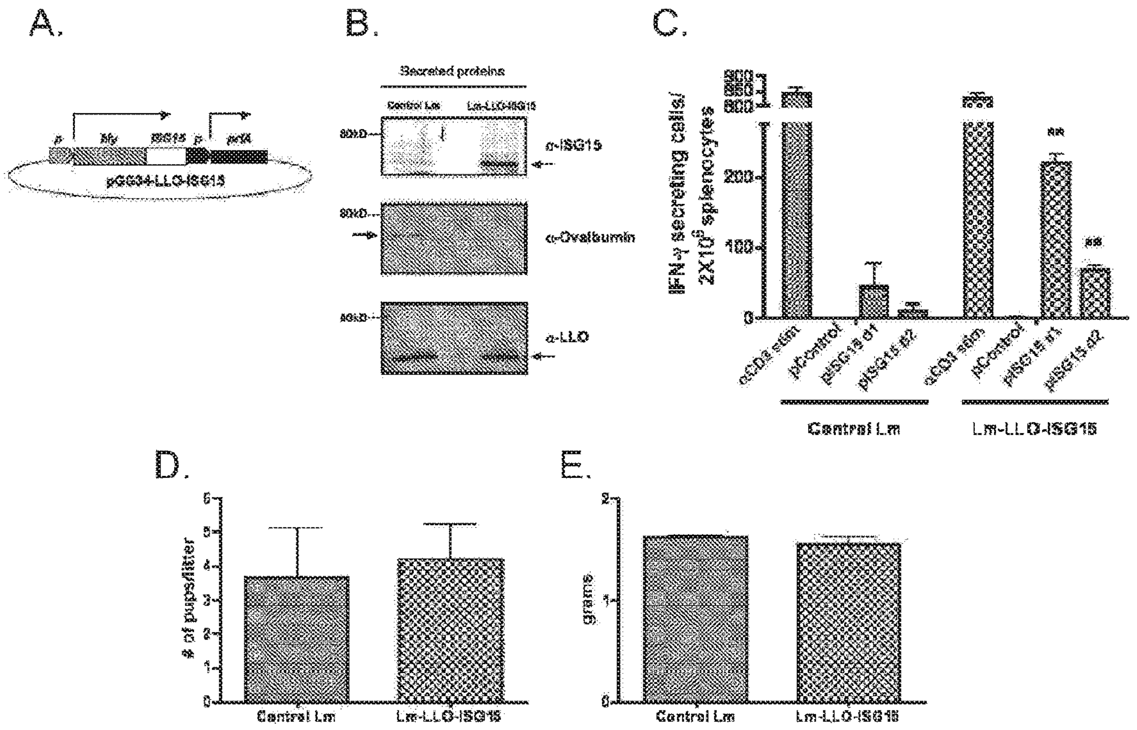
FIG. 44. Construction of a *Listeria*-based CTL vaccine against ISG15. (A) Illustration depicting the *Listeria* expression vector, pGG34-LLO-ISG15, that was electroporated into the $prfA^-$ XFL7 *Listeria* strain to construct the attenuated *Listeria* vaccine, Lm-LLO-ISG15. (B) Western blot analysis of TCA-precipitated proteins from the media of Lm-LLO-ISG15 and control Lm vaccine, Lm-LLO-OVA, cultures. Precipitated proteins were subjected to SDS-PAGE and western blot analysis with antibodies against mouse ISG15 (top panel), chicken ovalbumin (middle panel), and Listeriolysin O (bottom panel). (C) ELISpot analysis of ISG15-specific IFNγ responses from splenocytes of 8-week old Balb/c mice that were vaccinated i.p. twice with either Lm-LLO-ISG15 or control Lm. Results are depicted as IFNγ-secreting SFCs per $2\times10^6$ splenocytes. (D) Number of pups per litter for female mice vaccinated with either a control Lm vaccine ($2\times10^8$ CFU) or Lm-LLO-ISG15 ($2\times10^8$ CFU). (E) Mean pup weight of littermates from each vaccinated group of females on day one post-birth depicted in grams.

To assess the potential for ISG15 as a novel TAA, a *Listeria*-based CTL vaccine was developed to target tumors with elevated ISG15 expression. Construction of the vaccine, Lm-LLO-ISG15, was accomplished by genetically fusing the mouse ISG15 gene from Balb/c mice downstream of the gene encoding a truncated form of Listeriolysin O (tLLO), already present in the *Listeria monocytogenes* (Lm) expression vector pGG34, which contains a signal sequence to allow for proper secretion of the fusion protein. The pGG34-LLO-ISG15 construct was subsequently electroporated into the attenuated competent Lm strain, XFL7 (FIG. 44A). Proper secretion of the tLLO-ISG15 fusion protein was confirmed by Western blot analysis with anti-mouse ISG15 antibody against TCA-precipitated proteins from the media of an Lm-LLO-ISG15 growth culture (FIG. 44B, top panel). Similar production and secretion of a fusion protein of tLLO fused to chicken ovalbumin was observed from our control Lm when probed with anti-ovalbumin antibody (FIG. 44B, middle panel). Secreted proteins from Lm-LLO-ISG15 and the control Lm were also probed with wild-type LLO antibody to confirm equivalent secreted protein loading (FIG. 44B, bottom panel). Generation of ISG15-specific CTL responses was assayed by administering both Lm-LLO-ISG15 and a control Lm vaccine to female Balb/c mice, weekly, starting at week 6. One week after the third vaccination, splenocytes from each vaccination group were subjected to ELISpot analysis to investigate IFN-γ responses against a control epitope and two ISG15-specific H2-$K^d$-restricted CD8+ T-cell epitopes predicted by RANKPEP. A significant increase in IFN-γ secreting SFCs was observed only in the splenocytes from the Lm-LLO-ISG15 vaccinated mice after stimulation with each predicted ISG15-specific CTL epitope in comparison to control peptide stimulation (FIG. 44C). These results suggest that an ISG15-specific adaptive response can be generated by an attenuated Lm-based CTL vaccine against ISG15.

While under normal conditions, ISG15 expression is at low or undetectable levels in normal tissues, however, there is evidence for elevated ISG15 expression at the placental implantation site during pregnancy. To determine if an ISG15-specific immune response may severely impact fertility in Lm-LLO-ISG15 vaccinated female mice, a pregnancy study was performed. In comparison to control Lm vaccinated female mice, the fertility of Lm-LLO-ISG15 vaccinated female mice was not significantly impaired as measured by litter size and pup weight (FIGS. 44D and E, respectively). Generation of an ISG15-specific adaptive immune response with no obvious adverse effects encouraged examination of its efficacy in mouse models for breast cancer.

Example 24

Therapeutic Impact on Murine Breast Tumors after LM-LLO-ISG15 Vaccination

Figure 45:
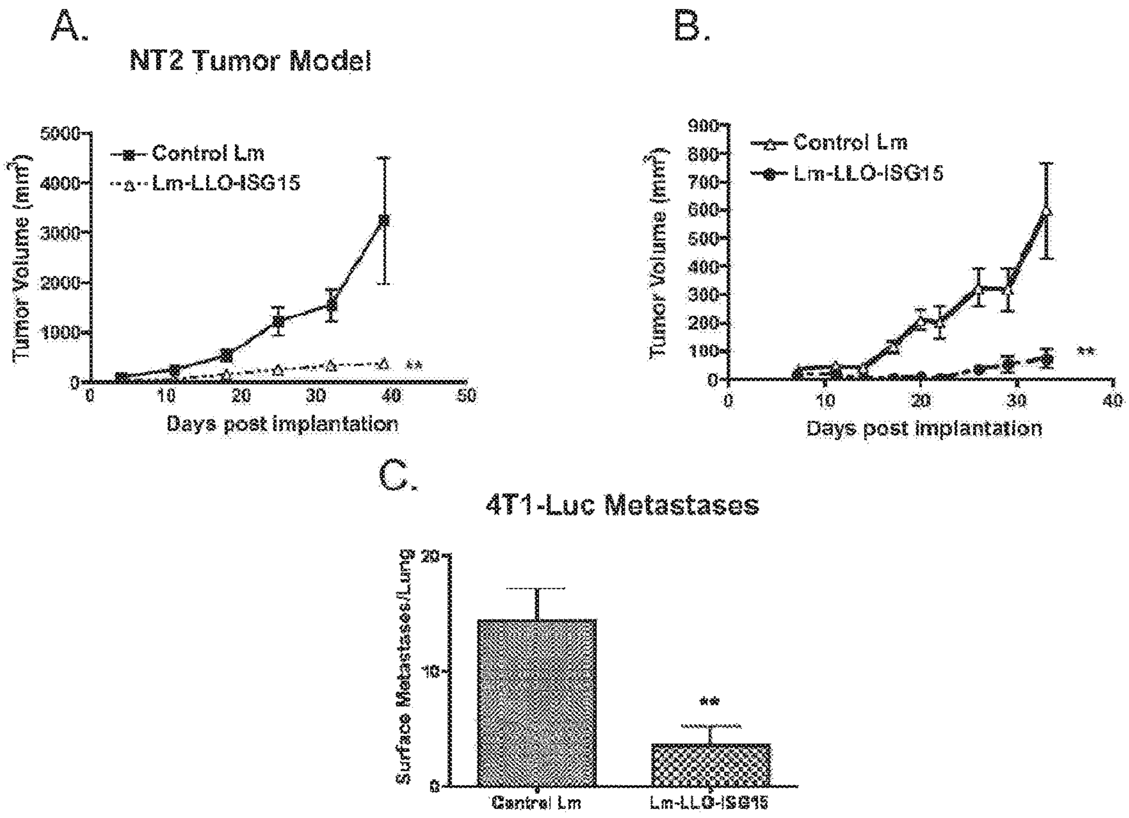
FIG. 45. Therapeutic impact on mouse mammary tumors after Lm-LLO-ISG15 vaccination. (A) Tumor load study to determine the effectiveness of Lm-LLO-ISG15 against implanted NT2 mammary tumors. NT2 tumor cells were implanted s.c. in the hind flank of FVB/N mice and subsequently vaccinated with Lm-LLO-ISG15 or control Lm. Tumor size was monitored with calipers until experiment end and tumor volume calculated. (B) Tumor load study to determine the ability of Lm-LLO-ISG15 vaccination to control the growth of implanted primary 4T1-Luc mammary tumors. 4T1-Luc tumor cells were implanted in the mammary tissue of Balb/c mice and mice were subsequently vaccinated with Lm-LLO-ISG15 or control Lm. (C) Metastatic tumor study to determine the ability of Lm-LLO-ISG15 vaccination to control metastatic spread of 4T1-Luc after implantation in the mammary gland. Briefly, 4T1-Luc cells are implanted into the mammary tissue of Balb/c mice and mice are subsequently vaccinated with Lm-LLO-ISG15 or control Lm. After 32 days post implantation, lungs from vaccinated tumor-bearing mice are removed and perfused with PBS. Lung surface metastatic nodules were then counted with a light microscope.

The therapeutic potential of an ISG15-specific adaptive immune response generated by Lm-LLO-ISG15 against breast cancer was initially investigated against implanted primary and metastatic mouse models of breast cancer. Implantation of NT2 tumor cells s.c. in the hind flank of FVB/N mice and subsequent vaccination with Lm-LLO-ISG15 resulted in significantly reduced tumor volume as compared to control vaccination (FIG. 45A). Similarly, Lm-LLO-ISG15 therapeutic vaccination significantly inhibited the growth of mammary tissue-implanted 4T1-Luc primary tumors (FIG. 45B). The ability of 4T1-Luc tumors to naturally metastasize after implantation in the mammary gland allowed further investigation into the efficacy of an ISG15-specific CTL response against a more aggressive model for breast cancer. Significant reductions in the appearance of 4T1-Luc metastatic lung lesions were observed after Lm-LLO-ISG15 administration in comparison to control Lm (FIG. 45C).

Example 25

Delayed Progression of HER2/Neu+ Autochthonous Mammary Tumors and Epitope Spreading by Lm-LLO-ISG15

Figure 46:
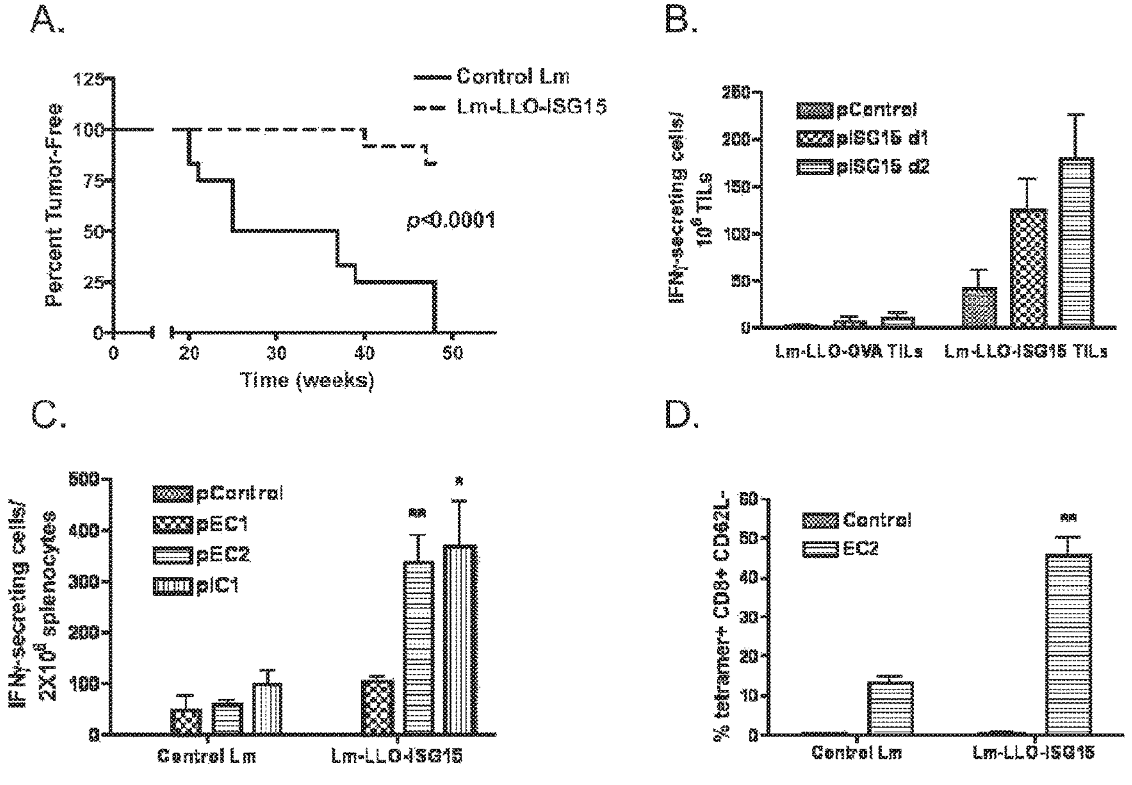
FIG. 46. Delayed progression of HER2/neu+autochthonous mammary tumors and epitope spreading by Lm-LLO-ISG15. (A) The FVB/N Her2/neu transgenic mouse model was used to determine if Lm-LLO-ISG15 vaccination can delay autochthonous mammary tumor progression in comparison to control Lm vaccination. FVB/N HER2/neu transgenic mice were injected six times with either Lm-LLO-ISG15 ($2\times10^8$ CFU) or the control Lm vaccine, Lm-LLO-OVA ($2\times10^8$ CFU), starting at 6 wk of age and continued every 3 weeks until week 21. Tumor incidence was monitored on a weekly basis. (B) ELISpot analysis of ISG15-specific IFN-γ responses in the spontaneous breast tumors from naïve mice. After allowing for tumor formation, tumor-bearing mice were vaccinated twice (day 0 and 7) with Control Lm and Lm-LLO-ISG15 followed by removal of tumors and ELISpot analysis on day 14. (C) ELISpot analysis demonstrating epitope spreading to HER2/neu in splenocytes of Lm-LLO-ISG15 vaccinated NT2 tumor-bearing FVB/N HER2/neu transgenic mice at the completion of the experiment. (D) TIL tetramer analysis demonstrating an increased percentage of HER2/neu-specific CD8+62L− in the tumors of Lm-LLO-ISG15 vaccinated 4T1-Luc tumor bearing mice in comparison to control Lm vaccinated mice.

To determine if Lm-LLO-ISG15 could also provide therapeutic efficacy in a more clinically relevant model of human breast tumor development, we utilized a FVB/N HER2/neu transgenic mouse model that, in the absence of therapeutic intervention, develops autochthonous mammary tumors past 4 months of age. Transgenic female mice were vaccinated every three weeks with Lm-LLO-ISG15 or a control Lm from week 6 to 21 after birth and subsequently monitored for mammary tumor incidence. Mice administered Lm-LLO-ISG15 demonstrated a significant delay to tumor progression in comparison to a control Lm vaccinated group ($p<0.0001$) (FIG. 46A). In fact, greater than 80 percent of Lm-LLO-ISG15 vaccinated mice are still tumor-free by week 49 after birth while all control Lm vaccinated mice have developed mammary tumors with a median time to progression of 31 weeks. To determine if the infiltration of ISG15-specific CTLs into autochthonous tumors after Lm-LLO-ISG15 vaccination could be a possible mechanism for this delayed progression, an IFNγELISpot analysis was performed on TILs of these tumors after Lm-LLO-ISG15 vaccination. After allowing for autochthonous tumors to form, tumor-bearing mice were vaccinated twice on day 0 and 7 with either a Control Lm vaccine or Lm-LLO-ISG15. One week after the last vaccination, tumors were excised and TILs purified and processed for ELISpot analysis. As expected, the tumors of Lm-LLO-ISG15 vaccinated contain a significantly greater number of TILs specific for ISG15, as measured by their ability to secrete IFNγ after ISG15 epitope peptide stimulation, than the tumors of Control Lm vaccinated mice (FIG. 46B). These results suggest that the delayed progression of autochthonous mammary tumors by Lm-LLO-ISG15 is, in part, mediated by infiltration of ISG15-specific CTLs.

Recent studies demonstrate that the clinical efficacy of cancer vaccines significantly correlates with their ability to stimulate cross-priming and epitope spreading to additional TAAs. Similar results were observed previously using Lm-based cancer vaccines where development of epitope spreading to additional TAAs was associated with vaccine efficacy. To assess whether epitope spreading is developing after Lm-LLO-ISG15 vaccination, an ELISpot to detect HER2/neu-specific responses was performed with splenocytes from NT2 tumor-bearing mice after administration of either control Lm or Lm-LLO-ISG15. Splenocytes of Lm-LLO-ISG15 vaccinated mice contained significantly greater numbers of SFCs specific for known CTL epitopes within HER2/neu compared to control Lm vaccinated mice (FIG. 46C). This result suggests that Lm-LLO-ISG15 vaccination results in epitope spreading to additional TAAs. In fact, evidence for epitope spreading was also observed after Lm-LLO-ISG15 vaccination against 4T1-Luc tumors, a tumor cell line that expresses Her2/neu very weakly. 4T1-Luc tumors from Lm-LLO-ISG15 vaccinated mice contained a significantly higher percentage of Her2/neu-specific $CD8^{+}62L^{-}$ TILs than 4T1-Luc tumors from control Lm vaccinated mice (FIG. 46D). While epitope spreading to HER2/neu may provide some therapeutic efficacy, it is unclear if this secondary response is robust enough to warrant cardiotoxicity safety concerns. In summary, these tumor load studies demonstrate that vaccination against ISG15 can inhibit the growth of primary implanted mouse mammary tumors, inhibit metastatic spread, delay progression of autochthonous mammary tumors and generate epitope spreading to additional TAAs.

Example 26

Therapeutic Impact of ISG15 Vaccination is CD-8 Dependent

Figure 47:
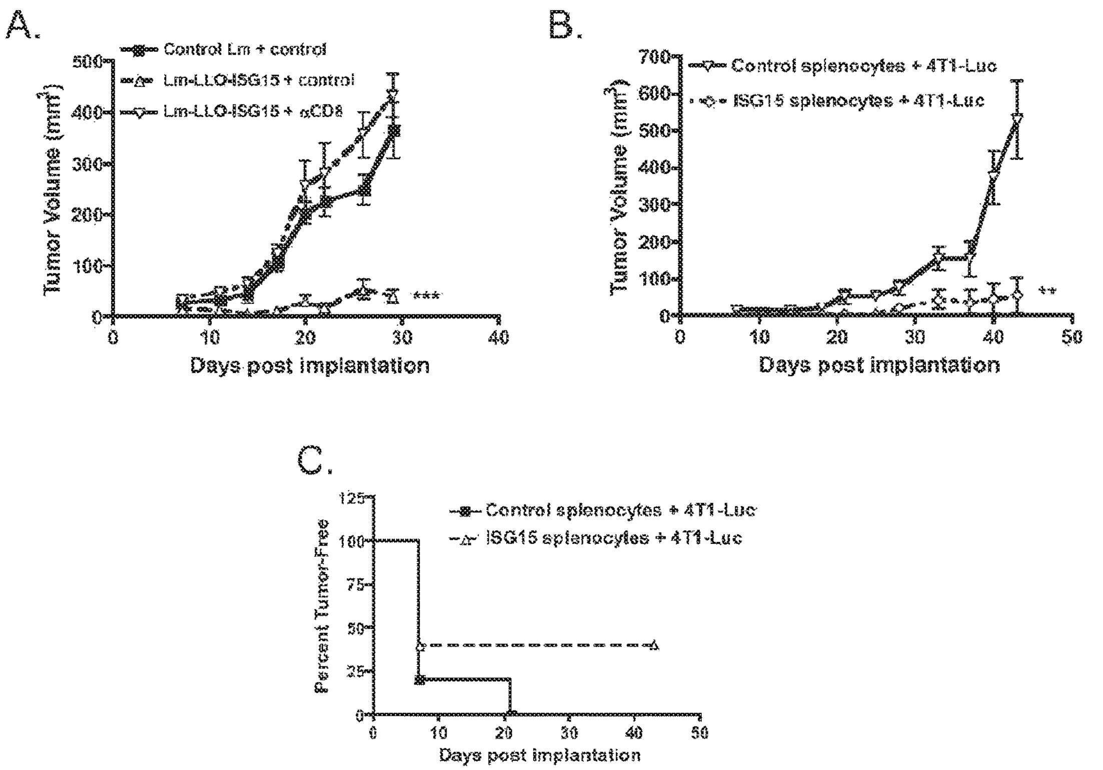
FIG. 47. Therapeutic impact of ISG15 vaccination is CD8-dependent. (A) CD8 depletion experiment of 4T1-Luc tumor-bearing mice. Briefly, Balb/c mice were implanted with 4T1-Luc tumor cells and depleted of $CD8^+$ cells or mock depleted in addition to vaccination with Lm-LLO-ISG15 or control Lm. (B) Winn assay performed to measure direct cytolytic activity of Lm-LLO-ISG15 CD8-enriched splenocytes. CD4-depleted splenocytes from Lm-LLO-ISG15 or control Lm vaccinated mice were mixed with 4T1-Luc cells and implanted in naïve Balb/c mice. (C) Graph depicting percent tumor-free survival of Balb/c mice from the experiment depicted in FIG. 47B.

While the generation of robust IFN-γ responses and significant therapeutic tumor impact are suggestive of strong CTL responses, the dependence of ISG15-specific CD8+ T cell function in Lm-LLO-ISG15 efficacy was investigated. Depletion of $CD8^{+}$ cells in 4T1-Luc tumor-bearing mice completely abrogates the anti-tumor efficacy of Lm-LLO-ISG15 compared to mock depletion with a control antibody (FIG. 47A). As an in vivo measure of ISG15-specific CTL tumor cell lysis, we performed a Winn assay to assess whether splenocytes enriched for $CD8^{+}$ T cells from Lm-LLO-ISG15 vaccinated mice could directly inhibit 4T1-Luc tumor formation. Splenocytes from mice twice-vaccinated with either Lm-LLO-ISG15 or a control Lm were depleted of $CD4^{+}$ cells and incubated briefly with 4T1-Luc tumor cells. The tumor cell and splenocyte mixture was then implanted into the mammary tissue of Balb/c mice and tumor progression monitored. $CD8^{+}$ T-cell-enriched splenocytes from Lm-LLO-ISG15 vaccinated mice significantly inhibited tumor growth in comparison to those from control Lm vaccinated mice (FIG. 47B). Additionally, all control Lm splenocyte-receiving mice developed tumors by day 21 post-implantation while 40% of mice receiving ISG15-specific splenocytes were still tumor-free at day 43 (FIG. 47C). This result suggests that Lm-LLO-ISG15 induces a CD8-dependent adaptive immune response that results in direct lysis of tumor cells and is likely mediated by $CD8^{+}$ T cells.

Example 27

Figure 48:
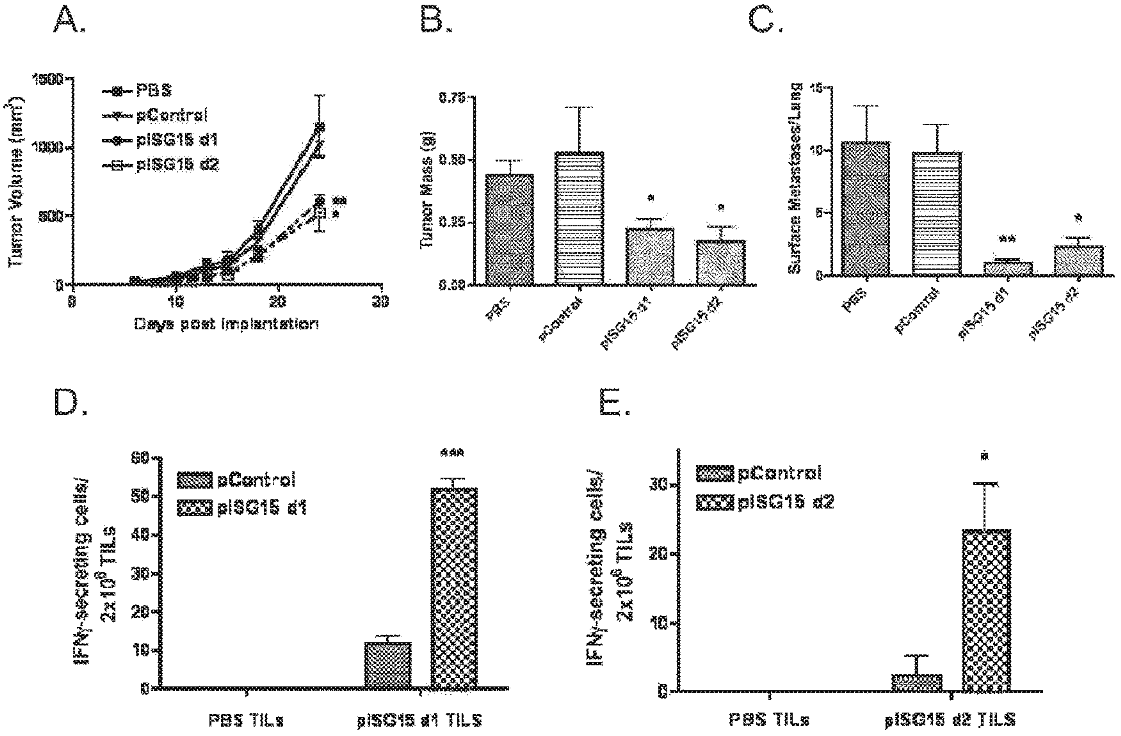
FIG. 48. Expansion of ISG15-specific CTL clones in vivo results in anti-tumor responses. After implantation of 4T1-Luc tumor cells in the mammary tissue of female Balb/c mice, mice were subsequently vaccinated with PBS or CpG along with either a control or an ISG15 epitope peptide. (A) Tumor volume for each group was measured throughout the course of the experiment. (B) At the conclusion of the experiment, primary tumors were removed and mean tumor mass for each vaccinated group was calculated. (C) Additionally, lungs from mice of each vaccinated group were also removed at the conclusion of the experiment for inspection of surface metastases. Mean number of lung surface metastases was calculated for vaccinated group. (D) ELISpot analysis of ISG15 d1-specific IFN-γ responses by tumor-infiltrating lymphocytes (TILs) from PBS and pISG15 d1/CPG vaccinated mice. (E) ELISpot analysis of ISG15 d2-specific IFN-γ responses by TILs from PBS and pISG15 d2/CPG vaccinated mice.

Expansion of ISG15-Specific CTL Clones In Vivo Results in Anti-Tumor Responses To assess whether expansion of a single ISG15-specific $CD8^{+}$ T cell clone can result in anti-tumor efficacy, mice were implanted with 4T1-Luc tumor cells and vaccinated with either PBS alone or an adjuvant, CpG ODN, mixed with each ISG15 $H2K^{d}$ epitope peptide or a control peptide. In mice vaccinated with CpG ODN and ISG15 $H2K^{d}$ peptides, 4T1-Luc tumor volume and tumor mass were significantly reduced in comparison to PBS alone and control peptide vaccination (FIGS. 48A and B, respectively). 4T1-Luc tumor lung metastases were also significantly reduced after vaccination with each ISG15 peptide in comparison to PBS alone or control peptide vaccination (FIG. 48C). Additionally, IFNγ secretion in response to stimulation with each ISG15 $H2K^{d}$ epitope peptides was observed in TILs only from mice that were vaccinated with their respective ISG15 $H2K^{d}$ epitope peptide suggesting that there was a successful expansion ISG15-specific CTLs that trafficked to the targeted tumor (FIGS. 48D and E). These data strongly suggest that expansion of ISG15-specific $CD8^{+}$ T cells can directly inhibit growth of tumors with elevated expression of ISG15.

Materials and Methods (Examples 28-37)

Mice.

Female FVB/N mice were purchased from Charles River Laboratories. The FVB/N Her-2/neu transgenic mice were housed and bred at the animal core facility at the University of Pennsylvania. Mice were six to eight weeks old at the start of the experiments, which were done in accordance with regulations by the Institutional Animal Care and Use Committee of the University of Pennsylvania.

Peptides and Antibodies.

Anti-mouse CD31, anti-mouse CD8α-PE, rat $IgG_{2a}$-PE isotype controls were purchased from BD Biosciences (San Jose, Calif.). Rabbit anti-*Listeria* antiserum polyclonal antibody, serotypes 1, 4 was purchased from Difco BD Biosciences. Rabbit anti-HIF-1α was purchased from Novus Biologicals (Littleton, Colo.). Goat anti-Rabbit-Alexa-488 secondary antibody was purchased from Invitrogen. DAPI was purchased from Sigma (St. Louis, Mo.). Rat anti-mouse IFN-g (clone AN18) was purchased from MABTECH (Mariemont, Ohio). Rat anti-mouse IFN-g (clone XMG1.2) was purchased from eBioscience (San Diego, Calif.). The antibodies used in the Western blot for fusion protein expression was either a polyclonal rabbit serum raised to the first thirty residues (PEST) of LLO protein (Sewell et al., 2004, Cancer research. 64:8821-8825) or an anti-LLO mouse antibody, specific for full-length LLO, generated from hybridoma supernatant, clone #B5-19 (Edelson et al., 2001, Immunity. 14:503-512). All peptides were purchased from EZBiolabs (Westfield, Ind.). Tetramers were provided by Dr. Amy Stout of the National Institutes of Health AIDS Research and Reference Reagent Program. Tetramers used were all PE-conjugated H-$2D^q$ and contained either peptides for Her-2/neu region EC1 (ASPETHLDML; SEQ ID NO: 98), or EC2 (PDSLRDLSVF; SEQ ID NO: 97) or IC1 (GSGAFGTVYK; SEQ ID NO: 99). Peptides used in these studies were as follows: Flk-$E1_{210-219}$ (TYQSIMYIV; SEQ ID NO: 100), Flk-$E2_{613-622}$ (MFSNSTNDI; SEQ ID NO: 101), Flk-$I1_{906-915}$ (PGGPLMVIV; SEQ ID NO: 102), Flk-$I1_{839-848}$ (GRGAFGQVI; SEQ ID NO: 103); (HER2-$pEC1_{302-310}$ (PYNYLSTEV; SEQ ID NO: 94), Her2-$pEC2_{420}$-429 (PDSLRDLSVF; SEQ ID NO:97), Her2-$pIC1_{732-741}$ (GSGAFGTVYK; SEQ ID NO: 99); HIV-pGag (AMQMLKETI; SEQ ID NO: 91).

ELISpots

Secretion of IFN-g by mouse splenocytes in response to peptide stimulation was tested by enzyme-linked immunospot (ELISpot) assay. We preferred to use ELISpots over other assays because of the level of sensitivity that could be obtained for low frequency, antigen specific cells and also because we could test for anti-Her-2/neu and anti-Flk-1 specific T cells directly ex vivo without in vitro manipulation. Briefly, isolated splenocytes were plated at $1\times10^6$ cells per well or titrated across a 96 well plate coated with 7 μg/ml of rat anti-mouse IFN-γ antibody (clone AN18, MABTECH, Mariemont, Ohio), in the presence of 10 μg/ml peptide and 5 U/ml of IL-2. Secondary, biotinylated, anti-IFN-g antibody (clone XMG1.2, eBioscience) was added to each well at a final concentration of 2 μg/ml. After overnight incubation at 37° C. plates were developed for 1 hour at room temperature with Streptavidin-horseradish peroxidase (1:1000 dilution) followed by substrate TMB (Vector laboratories, ABC kit). Spots were counted using the Immunospot C.T.L. scanner and counting software (CTL, Cleveland, Ohio).

Cell lines.

Cell culture media and supplements were purchased from Gibco (Invitrogen). NT-2 and J774A.1 cells were maintained as previously described. All cell cultures were kept at 37° C. and 5% $CO_2$. 4T1 and 4T1 cells stably expressing the firefly luciferase gene (4T1-Luc) were the kind gift of Dr. Ellen Pure (Wistar Institute) and were maintained in cell culture medium.

Construction of Lm-LLO-Flk-1 Vaccines.

The source of the Flk-1 gene was a DNA vaccine plasmid generously provided by Dr. Ralph Reisfeld (The Scripps Research Institute, La Jolla, Calif.). Fragments corresponding to residues 68 to 1081 were amplified by PCR using the following primers: Flk-E1 (F): 5'-GGG CTCGAGCGTGATTCTGAGGAAAGGGTATT-3' (SEQ ID NO: 104), Flk-E1 (R): 5' GGG ACTAGTTTACCCGGTTTACAATCTTCTTAT-3' (SEQ ID NO: 105), (AA 68-277); Flk-E2 (F): 5'-GGG CTCGAGGTGATCAGGGGTCCTGAAATTA-3' (SEQ ID NO: 106), Flk-E2 (R): 5'-GGG ACTAGTTTAGCCTCCATCCTCCTTCCT-3' (SEQ ID NO: 107), (AA 545-730); Flk-I1 (F): 5'-GGG CTCGAGGAAGGGGAACTGAAGACAGCC-3' (SEQ ID NO: 108), Flk-I1 (R): 5'-GGGACTAGTTTATGTG-TATACTCTGTCAAAAATGGTTTC-3' (SEQ ID NO: 109), (AA 792-1081). XhoI sequence underlined for forward (F) primer, SpeI sequence underlined for reverse (R) primer, stop codon in bold. The PCR product was ligated into pCR2.1-TOPO plasmid (Invitrogen), confirmed by sequencing and subsequently excised by double digestion with XhoI and SpeI (New England Biolabs). The fragment was ligated into a pGG34-based plasmid downstream and fused to a gene encoding for the first 441 residues of the LLO protein, whose expression is driven by the hly promoter. The construction of the pGG34 plasmid has been described in detail elsewhere. The resultant plasmid was electroporated into the PrfA-defective Lm strain XFL-7, which is derived from the Lm strain 10403S. Positive clones were selected on Brain Heart Infusion (BHI, Difco) plates supplemented with 34 μg/ml of chloramphenicol and 250 μg/ml of streptomycin. The resultant stains were named Lm-LLO-Flk-E1, Lm-LLO-Flk-E2, and Lm-LLO-Flk-I1.

Growth and Preparation of Lm Vaccine Doses

Vaccine stocks were kept at −80° C. in 10% glycerol in 1×PBS. Each stock was streaked over a chloramphenicol/streptomycin plate and grown overnight. A single colony was used for growth in an overnight culture of 5 mls BHI media under antibiotic selection. This culture was further expanded for 4 hrs in a shaking incubator at 37° C. and grown until the microbial density reached 0.4-0.8 $OD_{600}$ at which time the microbes were washed and frozen sterile in 10% glycerol and kept at −80° C. until use. Stocks were titered for each lot generated. Single lots were used for one continuous experiment, different lots were used for each repetition, lot-to-lot variation was not observed. Each lot was checked for fusion protein expression by Western Blot with an anti-PEST and anti-LLO antibody. For each dose, one vial is selected, thawed and washed twice in 1×PBS before dilution and use; unused microbes are discarded.

Effect of Lm-LLO-Flk-1 Vaccines on Tumor Growth $1\times10^6$ of NT-2 tumor cells were injected s.c. in 200 μl of PBS on the flank of FVB/N mice. On day 4 after tumor inoculation, mice were immunized i.p. with $5\times10^8$ CFUs of either Lm-LLO-Flk-E1, Lm-LLO-Flk-E2 or Lm-LLO-Flk-I1. This dose was determined as one-tenth of the minimum dose observed to have adverse effects on the mice and was used in all experiments. Immunizations were repeated weekly totaling 3 doses of the vaccine for all experiments. In the control groups, mice received a control Lm vaccine—Lm-LLO-NY-ESO-$1_{101-156}$. Lm-LLO-NY-ESO-$1_{101}$-156 acts as an irrelevant or third party Lm vaccine to control for immune responses to LLO or the listerial infection, we commonly use this vaccine as a control at comparable concentrations to the test vaccine. Tumors were measured every 3 days with calipers and the shortest (width) and longest surface diameters were recorded for each individual tumor. Calculated tumor volumes were performed using the following equation: $[(\text{width})^2\times\text{length}\times0.52]$. Mice were sacrificed if they developed open wounds or tumors reached 20 mm in diameter. Tumor-free surviving mice challenged with NT-2 were re-challenged in the opposite flank with the same cell line at least 10 weeks after the first inoculation.

Tumor Immunofluorescence

On day 64 post-tumor inoculation, mice were sacrificed and the NT-2 tumors were surgically excised, cryopreserved in OCT freezing medium and cryosectioned to provide 8-10 mm thick sections. For immunofluorescence, samples were thawed and fixed using 4% formalin. After blocking (2.4G2 conditioned medium/10% FBS/5% normal rat and mouse serum), sections were stained with primary antibodies in blocking solution in a humidified chamber at 37° C. for 1 hour. Samples were stained with secondary antibody following the same procedure as used for primary staining. DAPI (Invitrogen) staining was performed according to manufacturer's instructions. Intracellular staining for HIF-1α was done in PBS/0.1% Tween/1% BSA solution. Slides were cover-slipped using mounting solution (Biomeda) with anti-fading agents, set for 24 hours and kept at 4° C. until imaged using Spot Image Software (vs. 2006) and a BX51 series Olympus fluorescent microscope. Images were merged using Spot Image Software and quantitation was performed after an ROI was gated using Image Pro Software (vs. 2006). All images are a merged series of three different channels captured for the same exposure time. For the quantitation of microvascular density using anti-CD31 we based our analysis on previously published works using similar strategies for measuring MVD in mouse tumor models.

Metastasis Studies and Bioluminescent Imaging

Mice were given a total of three vaccinations prior to i.v. injection, 7 days post-final vaccination, with 50,000 4T1 cells expressing the integrated luciferase reporter gene (4T1-Luc). The corresponding substrate, D-Luciferin was injected i.p. at 5-10 mg/mouse in 200 ul of PBS before imaging. The mice were placed in the dark chamber of a Xenogen IVIS imaging system (X-100) (Xenogen Corporation, Alameda, Calif.), under anesthesia following i.p. injection of ketamine (80 mg/kg)/xylazine (12 mg/kg) (Sigma, St. Louis, Mo.). Photographic and luminescence images were captured with a CCD camera and the luminescence intensity was quantitated using Living Image software (version 2.11) from Xenogen according to the manufacturer's instructions. Longitudinal imaging was performed on a weekly basis until at least 4 weeks post tumor inoculation. All mice were imaged for the same exposure and length of time. Images show normalized graphics. For the pathology study, the identical experiment was performed except lung tissue was perfused, extracted, wax embedded and stained with H+E before being counted (by hand) for tumors.

Pregnancy and Wound Healing Safety Studies.

Six to eight week old FVB/N female mice were immunized three consecutive times weekly with either a control Lm vaccine or Lm-LLO-Flk-1 vaccines. On the fourth week safety studies were conducted. For pregnancy and fertility, 5 mice per group were allowed to mate with individually housed males. Coitus was monitored and confirmed by the presence of a vaginal plug. Time to gestation, pup weight at birth and total litter size were measured. The wound-healing assay utilized in this study was done according to previously described methods. Briefly, mice were anesthetized, hair removed and skin-cleaned with an aseptic wipe. Two circular 3 mm in diameter wounds were punched from the skin using a sterile skin biopsy tool (Acuderm). Wounds were not treated and no infection was observed. Average time to wound closure was monitored and considered complete when a scar was formed without any visible scab left.

Statistical Analysis and Methods of Quantitation.

Data were analyzed using the non-parametric Mann-Whitney test. The log-rank chi-squared test was used for all survival data. All statistical analysis was done with Prism software, vs. 4.0a (2006). Statistical significance was based on a value of p≤0.05. In all non-transgenic studies we included at least 8 mice per group. All studies were repeated at least once.

Example 28

Construction of LLO-FLK-1 Constructs

Figure 49A:
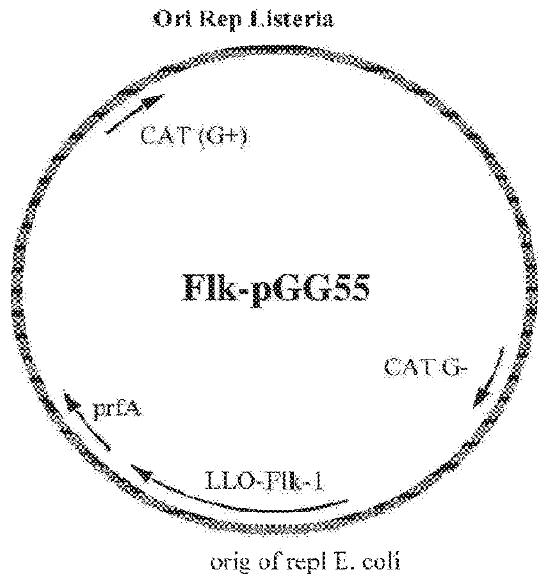
FIG. 49A shows the design of the Flk-1/VEGFR2 expressing Lm-based constructs. Each gene fragment was cloned into the expression vector pGG34 fused to LLO and placed under the control of the hly promoter.
Figure 50B:
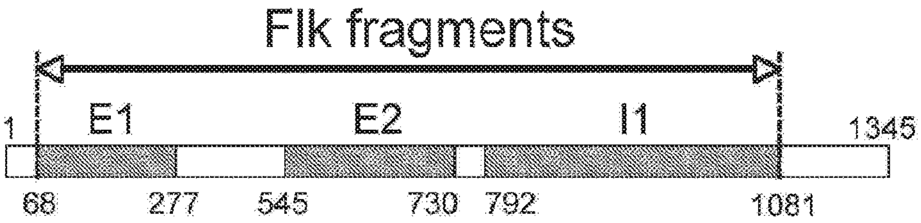
FIG. 50B shows the Map of the flk gene showing one embodiment of the fragments used in the present invention.
Figure 50C:
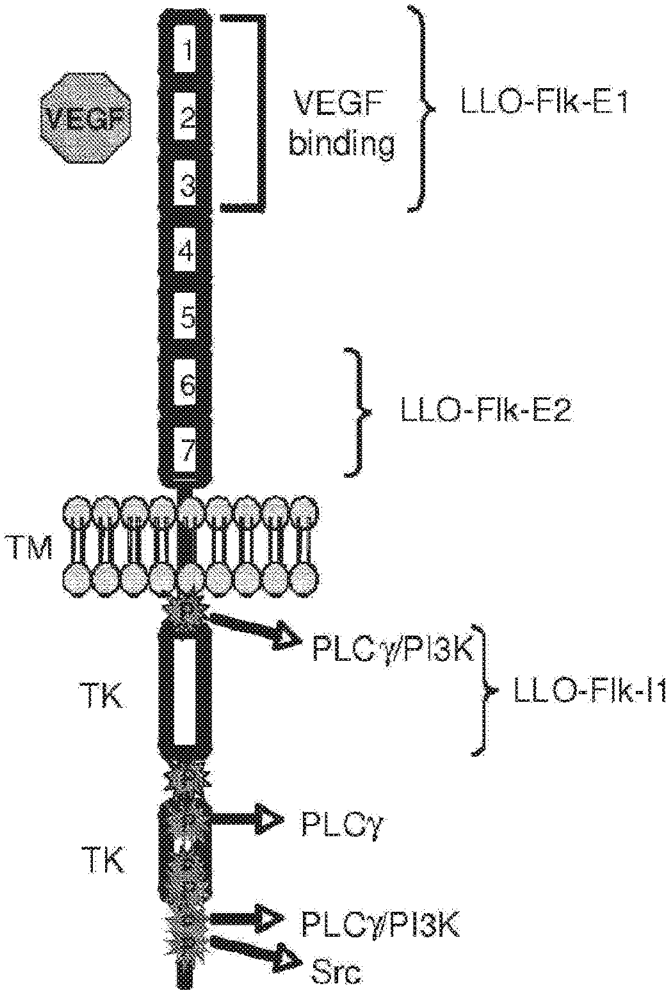
FIG. 50C shows a cartoon showing how the flk fragments used in one embodiment of the present invention related to the various domains of the flk gene.

A total of three constructs were tested, each containing a different region of Flk-1: E1 (AA 68-277), E2 (AA 545-730) and I1 (792-1081) (FIG. 49A). Regions were selected based on predicted epitopes. Since we were interested in testing these vaccines in the FVB/N-based breast cancer model, we decided to clone fragments that would be most appropriate for the model haplotype used for testing (i.e., FVB/N, $H2^q$). The E1, E2 and I1 domains selected contained several potential epitopes for the H-$2^q$ mouse MHC I haplotype (FIG. 50A).

Figure 49B:
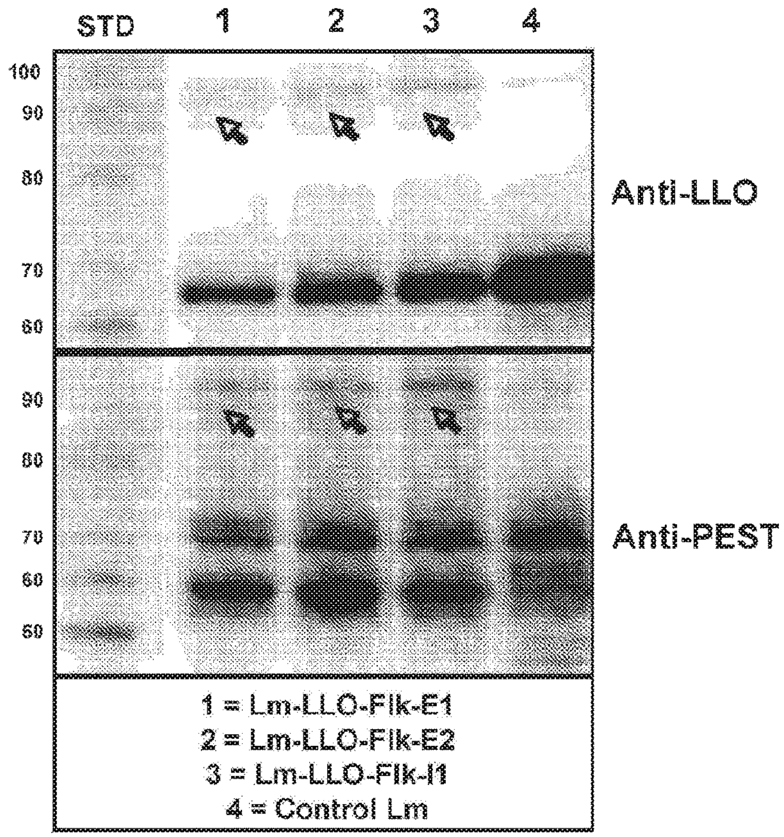
FIG. 49B shows the design of the Flk-1/VEGFR2 expressing Lm-based constructs. Western blot from culture supernatants showing expression of each fusion protein from the constructs listed. Polyclonal, rabbit, anti-PEST antibody was used for fusion protein detection (bottom), and mouse anti-LLO antibody was used for confirmation (top). Note that all lanes were taken from the same Western blot.
Figure 50D:
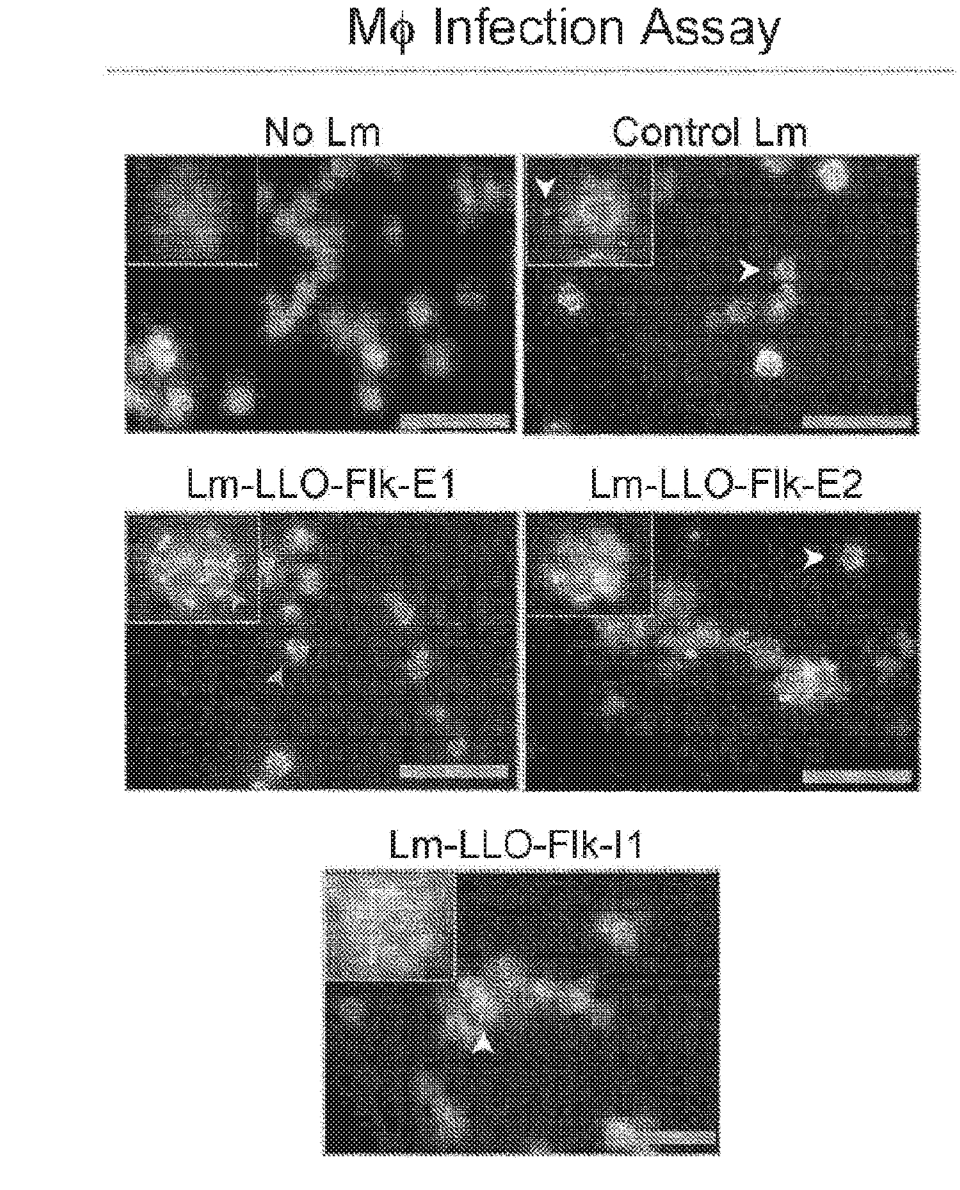
FIG. 50D shows a macrophage infection assay was performed as described in the methods. J774A.1 cells were incubated with *Listeria* constructs, washed, then incubated with Gentimycin, bacteria that were able to infect the macrophage and escape into the cytoplasm are shown in Alexa-488 (green), the PE $CD11b^+$ halo (red) demarks the cell shape and size.

Each fragment was cloned as a fusion protein with the truncated LLO protein (FIG. 49A). To test whether the LLO-Flk-1 fusion proteins were produced and secreted by the Lm-LLO-Flk-1 constructs, we analyzed protein from culture supernatants by Western-Blot (Figure. 49B) using a polyclonal anti-PEST antibody (FIG. 49B bottom) or anti-LLO antibody (FIG. 49B top). A band for each fusion construct was detected, LLO-Flk-E1 (~81 kDa), LLO-Flk-E2 (~78 kDa), and LLO-Flk-I1 (~89 kDa). The band around 60-70 kDa is endogenous LLO; the truncated fusion protein LLO is found around 60-50 kDa. The anti-LLO blot was used as a control to show that our fusion proteins are LLO-Flk linked. All three constructs were able to infect, grow, and escape the phagolysosome as evidenced by replication in J774A.1 macrophages (FIG. 50D). Also, each vaccine was able to immunize mice against cloned Flk-1 regions as shown by IFN-g splenocyte responses ex vivo (FIG. 49C). Peptides used for re-challenge in these FVB/N ELISpot experiments were originally mapped in the $H2^d$ Balb/c mouse as immunodominant Flk-1 epitopes. We routinely use $H2^d$ mapped epitopes in $H2^q$ models as $H2^d$ identified epitopes can also serve as $H2^q$ epitopes presumably due to the high homology of the $H2^d$ and $H2^q$ molecules.

Example 29

Figure 51A:
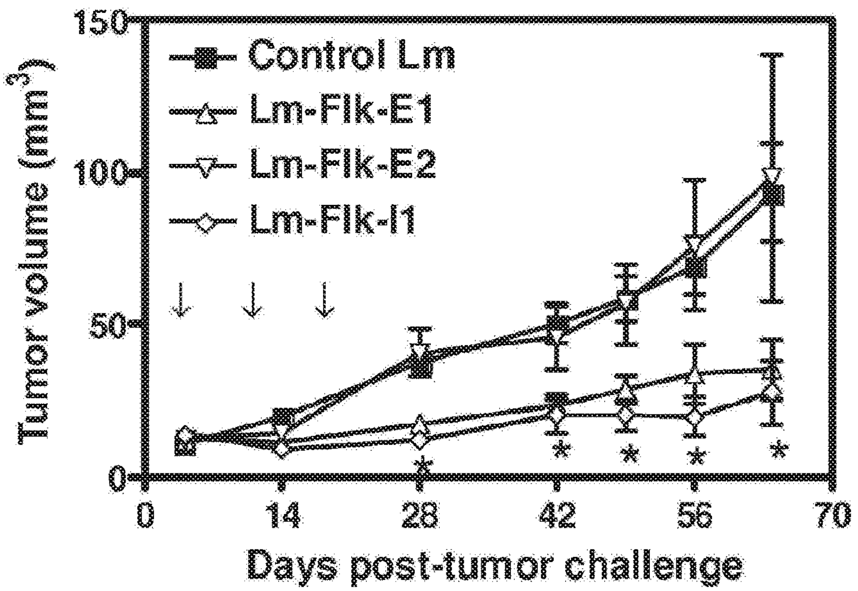
FIG. 51A shows Lm-LLO-Flk-1 vaccines can induce regression of established Her-2/neu+tumors in vivo. NT-2 tumor volume ($mm^3$) from mice treated with each construct. Graph shows Mean±SEM; *$p<0.05$, Mann-Whitney statistical test, N=8 mice per group, experiment repeated twice.
Figure 52A:
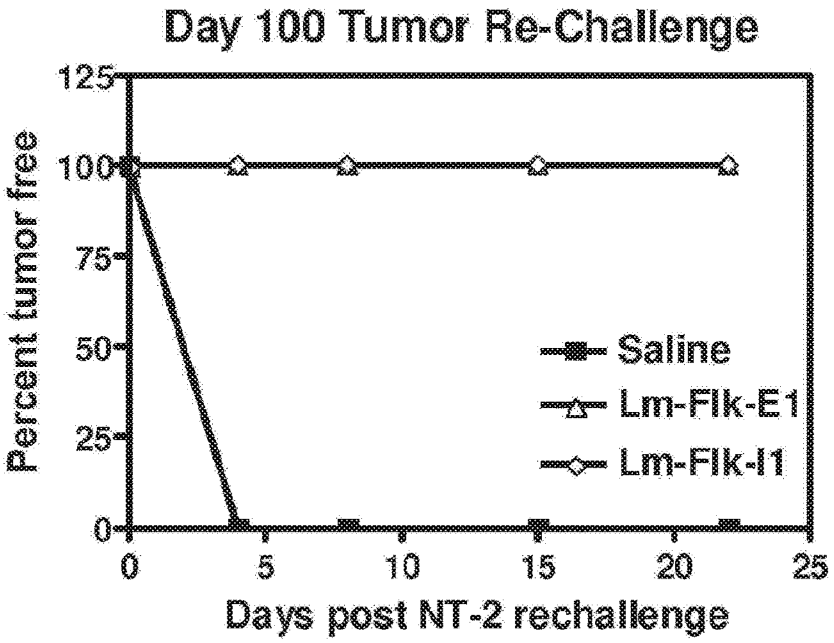
FIG. 52A shows mice with fully regressed tumors show long-term memory to tumor re-challenge. Mice that had fully regressed tumors were re-challenged with NT-2 in the contra-lateral flank on day 100. A saline treated group was used as our negative control for tumor growth.
Figure 52B:
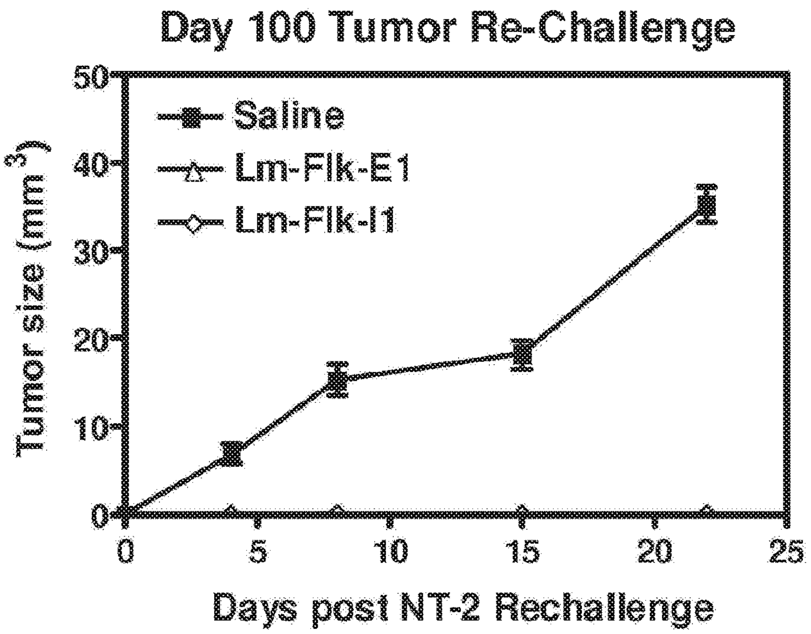
FIG. 52B shows tumor volume for mice that grew tumors after re-challenge on day 100 of tumor free mice. Both graphs refer to a single experiment. Number of tumor free mice was 2/8 for Flk-E1 and Flk-I1 groups, the saline group had 5 mice.

Therapeutic Efficacy of LM-LLO-FLK-1 Vaccines in a Her-2/Neu-Expressing Tumor Model To test the ability of our vaccines to induce the regression of Her-2/neu$^+$ breast tumors, we used the NT-2 tumor model, which overexpresses the rat Her-2/neu as a transgene and was originally derived from a spontaneous mammary tumor in the FVB/N Her-2/neu transgenic mouse. The NT-2 cell line does not express the Flk-1 molecule, and thus our antigen of interest is only located on the host vasculature. Cells were grown in vitro and transplanted subcutaneously into the flank of FVB/N mice. On day 4, when palpable (~4-5 mm in diameter) tumors had formed, mice were vaccinated and then boosted weekly for a total of three vaccinations. Vaccines Flk-E1 and Flk-I1 were able to induce regression, and in some mice complete eradication (Flk-E1: 2/8; Flk-I1: 2/8) of transplanted tumors by day 64 post-inoculation (FIG. 51A). However, Flk-E2 was unable to control tumor growth, which was similar to the group treated with the control Lm. Mice with completely regressed tumors were re-challenged with NT-2 on the contra-lateral side at 100 days post-tumor inoculation and re-growth of the new tumor was not observed suggesting long-lived anti-tumor immunity (FIGS. 52A & B).

Figure 51B:
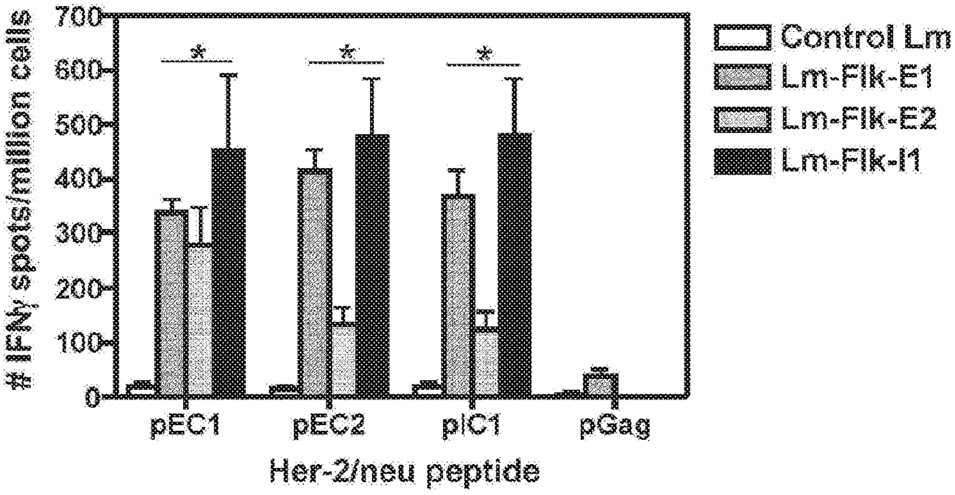
FIG. 51B shows IFN-g ELISpots showing epitope spreading to various Her-2/neu regions. Splenocytes from the 64-day time point were restimulated ex vivo with Her-2/neu peptide epitopes. Graph shows Mean±SEM; *$p<0.05$, Mann-Whitney statistical test, N=5 mice per group, experiment repeated once.
Figure 51C:
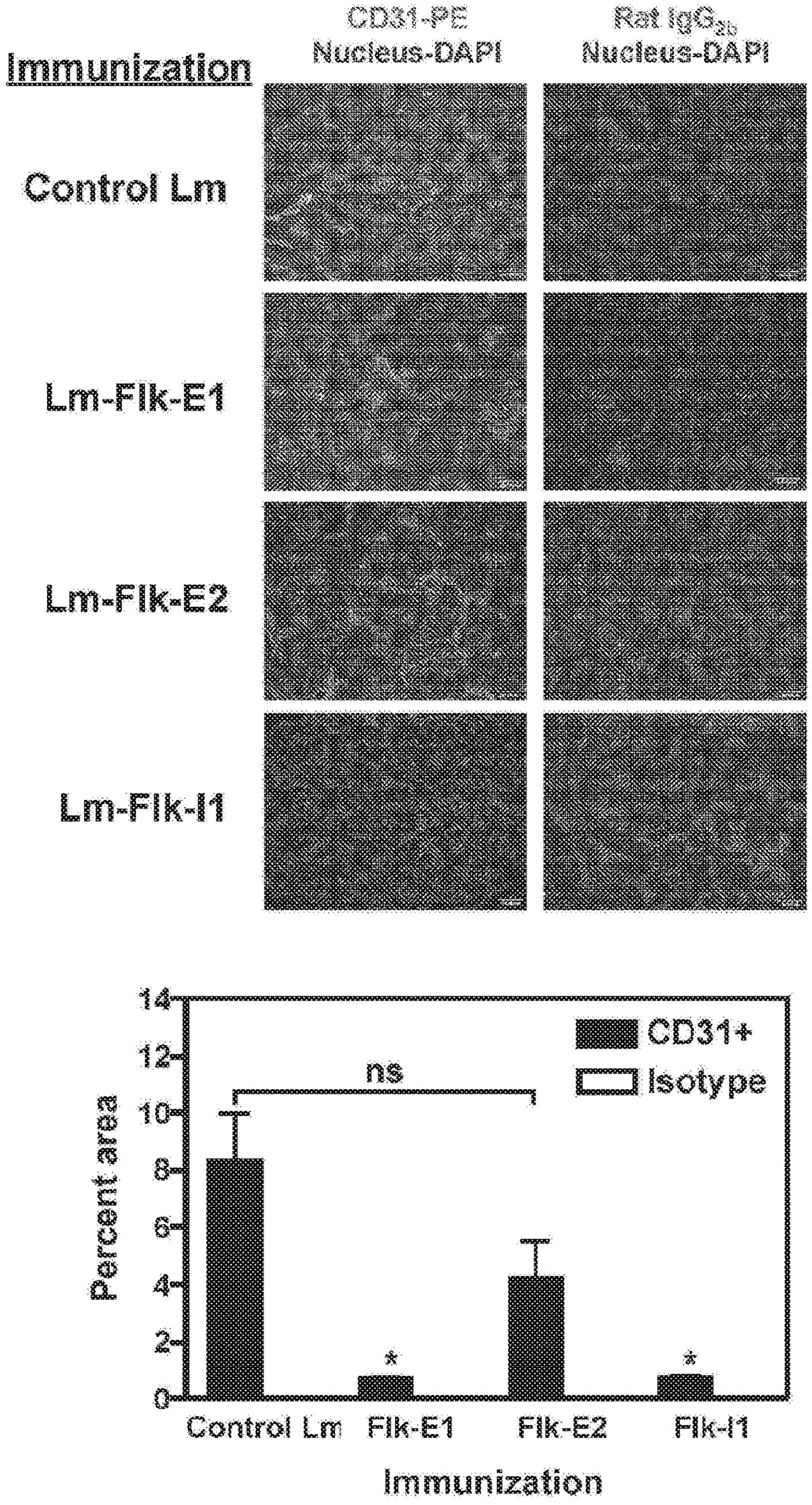
FIG. 51C Shows mice were immunized thrice over the course of three weeks after the initial establishment of NT-2 tumors. In this figure we show staining for the pan-endothelial marker CD31-PE and nucleus using DAPI. Isotype controls were used on sequential sections as shown to the right. Quantitation of vessel density performed by Image Pro software. Graph shows Mean±SEM, *$p<0.05$, Mann-Whitney test, ns=not significant.
Figure 51D:
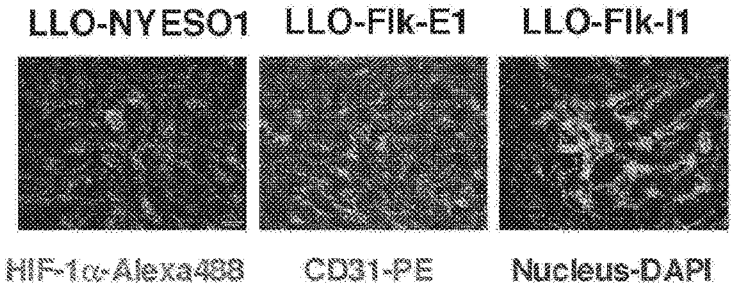
FIG. 51D Shows staining for the pan-endothelial marker CD31-PE, the nucleus using DAPI, and the nuclear hypoxic marker Hypoxia Inducible Factor-1α(HIF-1α).

Microvascular density (MVD) of day 64 tumors was assessed by staining with the pan-endothelial cell marker CD31 and counterstained with the nuclear marker DAPI. As expected, MVD in tumors from the Flk-E2 treated group resembled those from control treated mice. However, a reduction in the density of $CD31^+$ vessels was seen in Flk-I1 treated mice and a further reduction was observed using the Flk-E1 vaccination (FIG. 51C). This reduction in $CD31^+$ vessels correlated with an increase in staining for the nuclear hypoxic marker, Hypoxia Inducible Factor-1α (HIF-1α) in the Flk-E1 and Flk-I1 treated groups, but not for the control group (FIG. 51D). It is possible to hypothesize that regression of these Her-2/neu$^+$ tumors, in addition to the reduction of tumor MVD, was due to anti-VEGFR2 cytotoxic T cells killing endothelial cells involved in tumor angiogenesis, possibly leading to tumor damage or growth restriction resulting in the observed regression. Subsequently, phagocytosed tumor debris could be cross-presented by local dendritic cells in draining lymph nodes and presented to anti-Her-2/neu CTLs, whose epitopes have been previously mapped in the FVB/N mouse. If this inter-molecular epitope spreading occurred, we would expect that mice that exhibited the greatest regression would also have a high frequency of anti-Her-2/neu $CD8^+$ T cells. To test this hypothesis, we harvested splenocytes from day 64 mice, and performed an IFN-g ELISpot, re-challenging with three known epitopes from three different regions of Her-2/neu. We decided to use an ELISpot assay to measure anti-Her-2/neu responses because we had previously mapped CTL epitopes for different regions of the Her-2/neu molecule and the ELISpot assay is sensitive enough to detect a low frequency of specific T cells, unlike several cytotoxic assays that require in vitro stimulation and expansion. We found that Flk-E1 and Flk-I1 showed the greatest epitope spreading, while Flk-E2 showed the least (FIG. 51B, $*p<0.05$), strongly correlating with the extent of tumor regression found in vivo (FIG. 51A).

Example 30

Figure 53A:
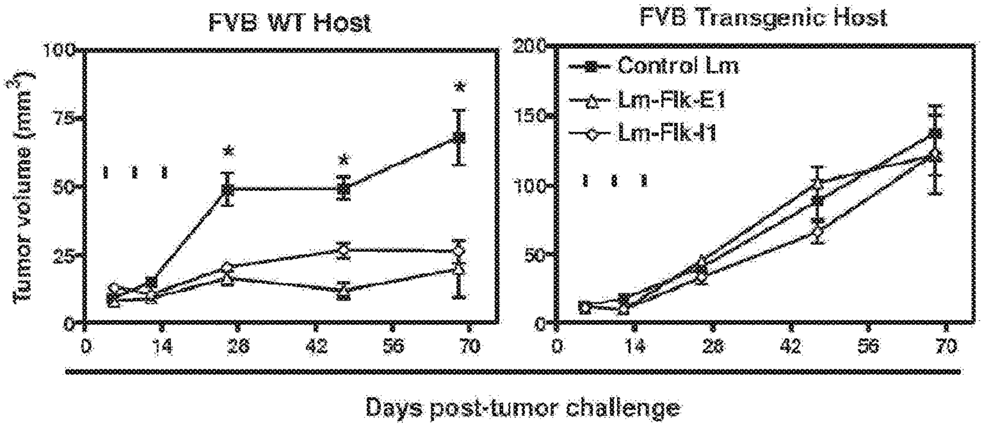
FIG. 53A shows anti-angiogenesis vaccines are not effective in mice tolerant to HER-2/neu. A. FVB/N wild-type (WT) or FVB/N transgenic (Tg) mice were injected with $1\times10^6$ NT-2 cells s.c., tumors were allowed to grow until palpable before treatment started. Mice were immunized a total of three times, mean tumor sizes are shown here for up to 69 days post tumor inoculation. Graphs show Mean±SEM; *$p<0.05$, Mann-Whitney test, experiment repeated twice.
Figure 53B:
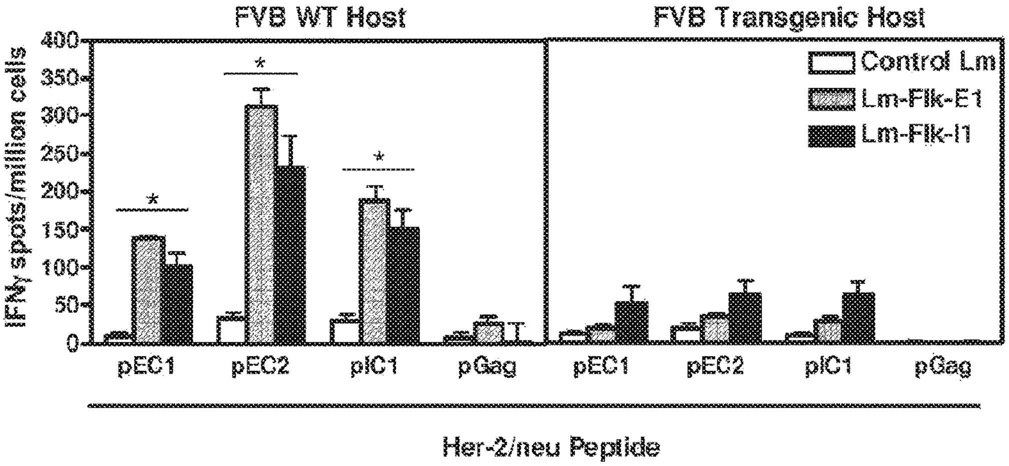
FIG. 53B shows spleens were processed for IFN-g ELISpots, stimulated with various Her-2/neu peptides ex vivo, or a third party peptide as a negative control (pGag). Graphs show Mean±SEM; *$p<0.05$, Mann-Whitney test, experiment repeated once.
Figure 53C:
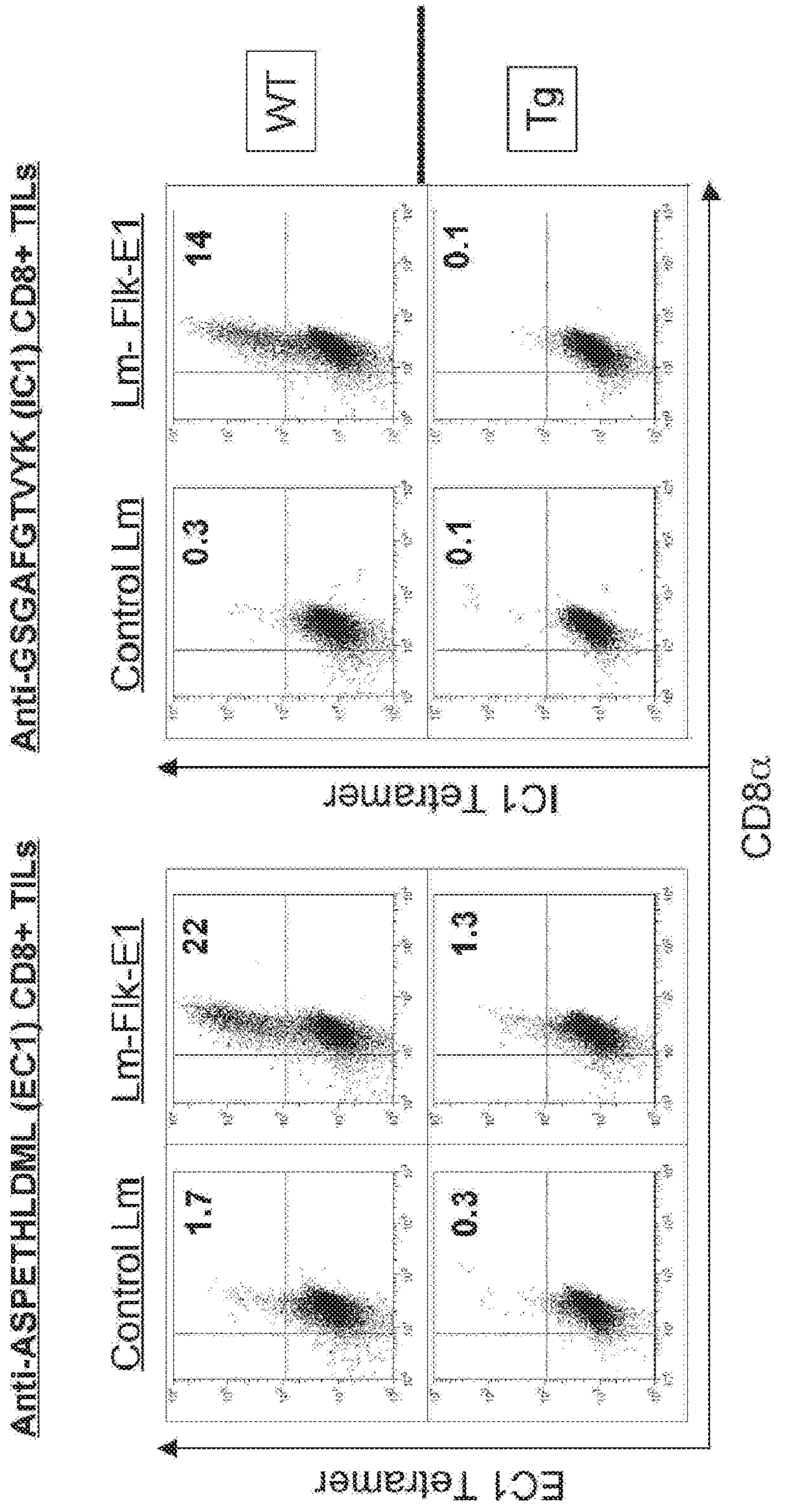
FIG. 53C shows tumors from each group were pooled and digested for TILs; here we show Her-2/neu specific T cells staining for CD8α and EC1 or IC1 specific tetramers. Significantly more Her-2/neu specific T cells are found in the wild type (WT) but not transgenic (Tg) mice; control Lm group shows low background. Experiment repeated once giving similar results.
Figure 54A:
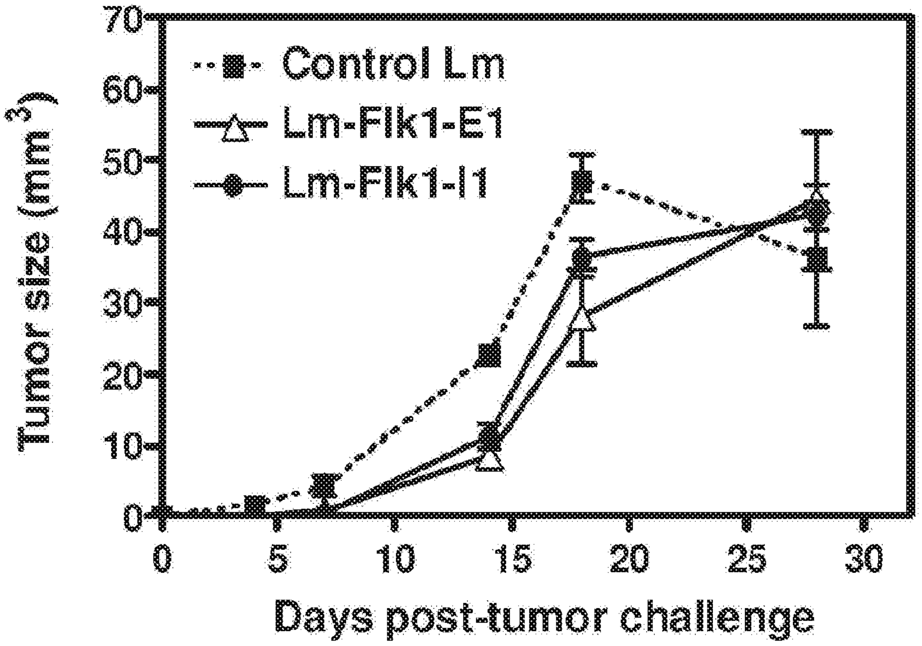
FIG. 54A shows mice protected with anti-Flk-1 Lm-vaccines show reduced primary tumor growth, tumor burden, and reduced morbidity and mortality when challenged with 4T1 experimental metastases. A. Primary subcutaneous 4T1 tumors grow slower in Lm-LLO-Flk-1 protected animals. Mice were immunized thrice with each vaccine then injected with s.c. and i.v. with 50,000 4T1 cells. Graph shows Mean±SEM for tumor volume.
Figure 54B:
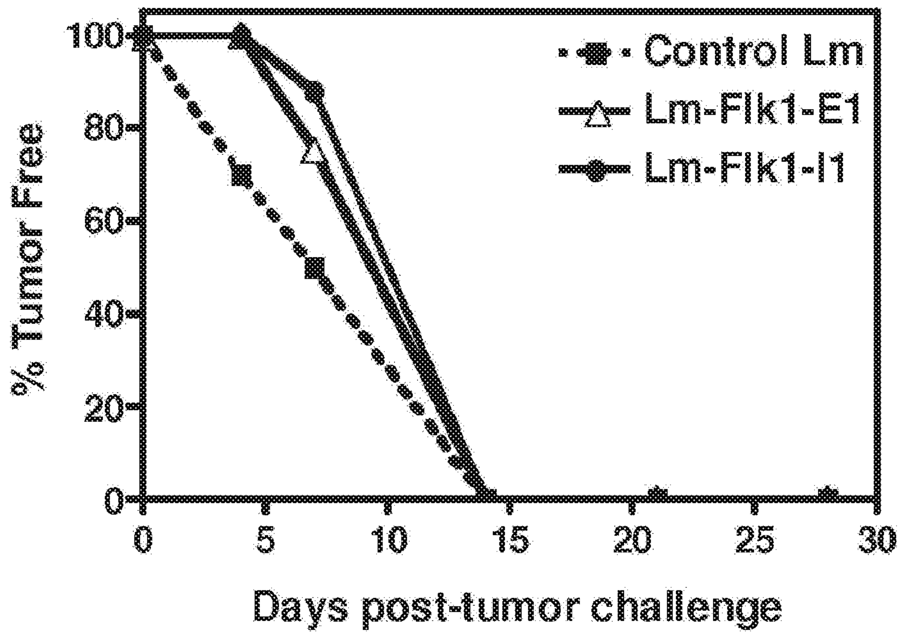
FIG. 54B shows tumor burden shown as percent of tumor free mice after challenge with 4T1 cells s.c. Graph shows mean of 8 mice per treated group.
Figure 54C:
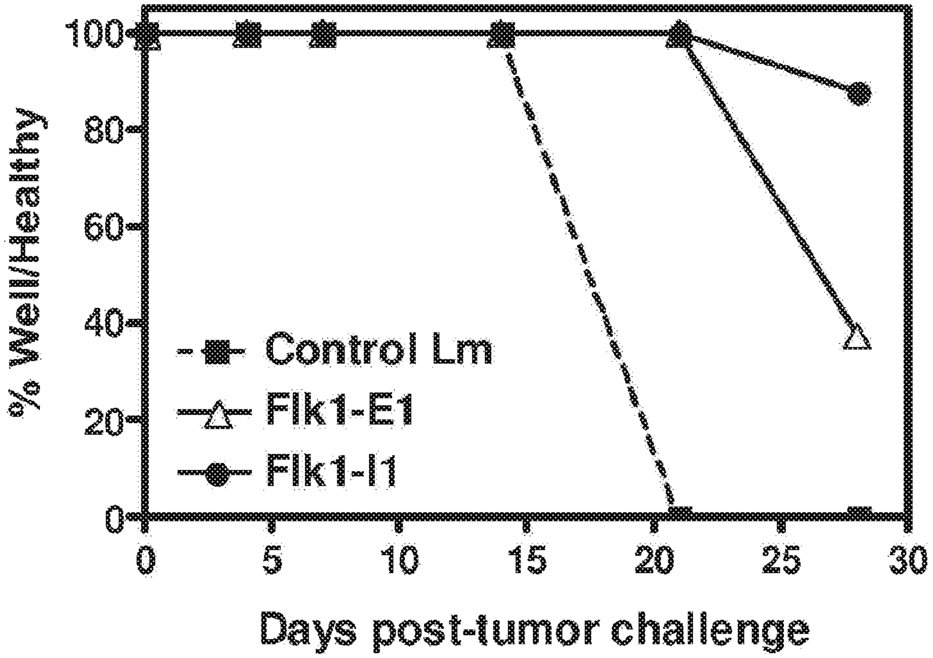
FIG. 54C displays a graph that shows percentage of well/healthy mice based on visual inspection and observation. N=8 mice per group.
Figure 54D:
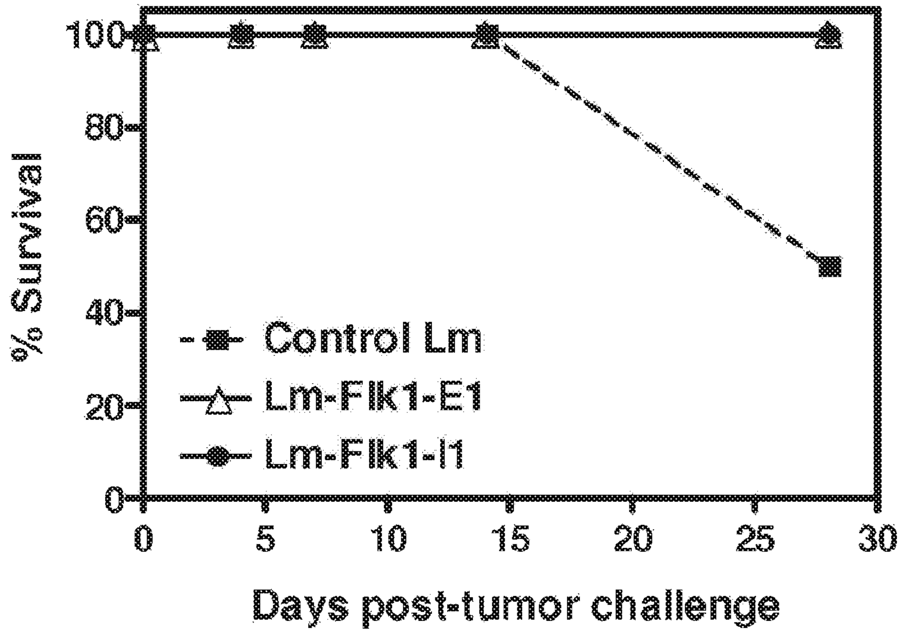
FIG. 54D displays a graph that shows percent survival relative to days post-tumor challenge for control Lm, Lm-Flk1-E1-treated mice, and Lm-Flk1-I1-treated mice.

Anti-Angiogenesis Induced Tumor Regression is Dependent on Epitope Spreading to an Endogenous Tumor Antigen The presence of Her-2/neu epitope spreading suggested that tumor regression may not solely depend on anti-vascular events, but also on the immune response to the tumor antigen HER-2/neu. To test this hypothesis we repeated the same experiment using the two most potent vaccines, Flk-E1 and Flk-I1 but, in addition to inoculation of wild-type FVB/N mice, we also injected the NT-2 cells subcutaneously into its syngeneic progenitor strain, FVB/N Her-2/neu transgenic, which exhibits profound tolerance to the rat Her-2/neu molecule. Again, Flk-E1 and Flk-I1 slowed the growth of the NT-2 tumors in wild type FVB/N mice, as previously demonstrated (FIG. 53A, left panel). However, in the transgenic host where anti-HER-2/neu responses are limited by tolerance, we observed outgrowth of all tumors (FIG. 53A, right panel). Both these results reflected the epitope spreading observed towards the endogenous Her-2/neu protein demonstrated in the spleen (FIG. 53B) and at the tumor site as shown for the Flk-E1 vaccination (FIG. 53C). This suggests that anti-vascular events are not enough for tumor regression, but rather the combined effect on both the tumor's vasculature and directly on tumor cells is required for tumor death and ultimately regression.

Example 31

Figure 55A:
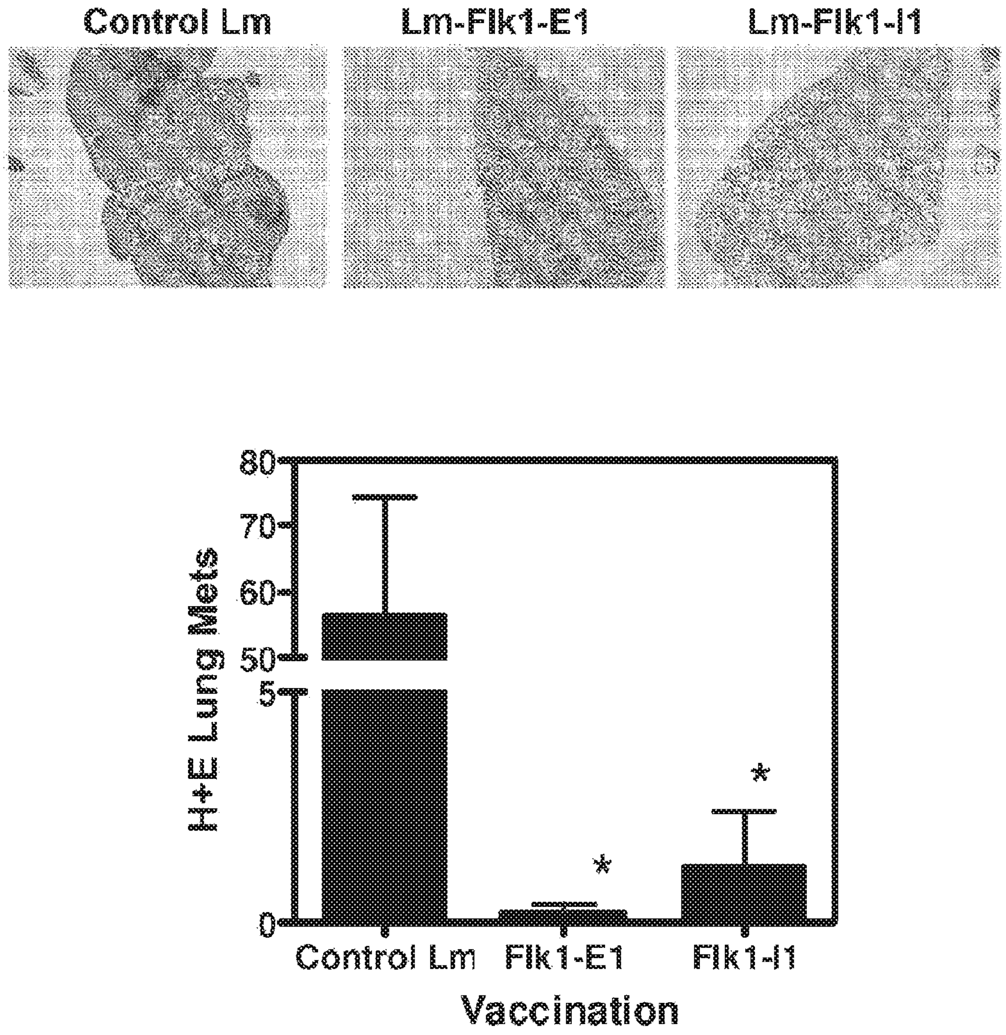
FIG. 55A shows that Flk-1 vaccines can protect mice from experimental metastases and induce weak Her-2/neu epitope spreading in a more aggressive tumor model for breast cancer. A. Mice were immunized thrice with each vaccine then injected with 50,000 4T1 cells i.v., tumors were allowed to grow for 25 days then mice were sacrificed. H+E stained sections were performed on lung tissues, tumor nodes were counted by hand. Graph shows the number of lung metastases per lobe per animal, Mean±SEM; *$p<0.05$, Mann-Whitney test, experiment repeated once, N=5 mice shown.
Figure 55B:
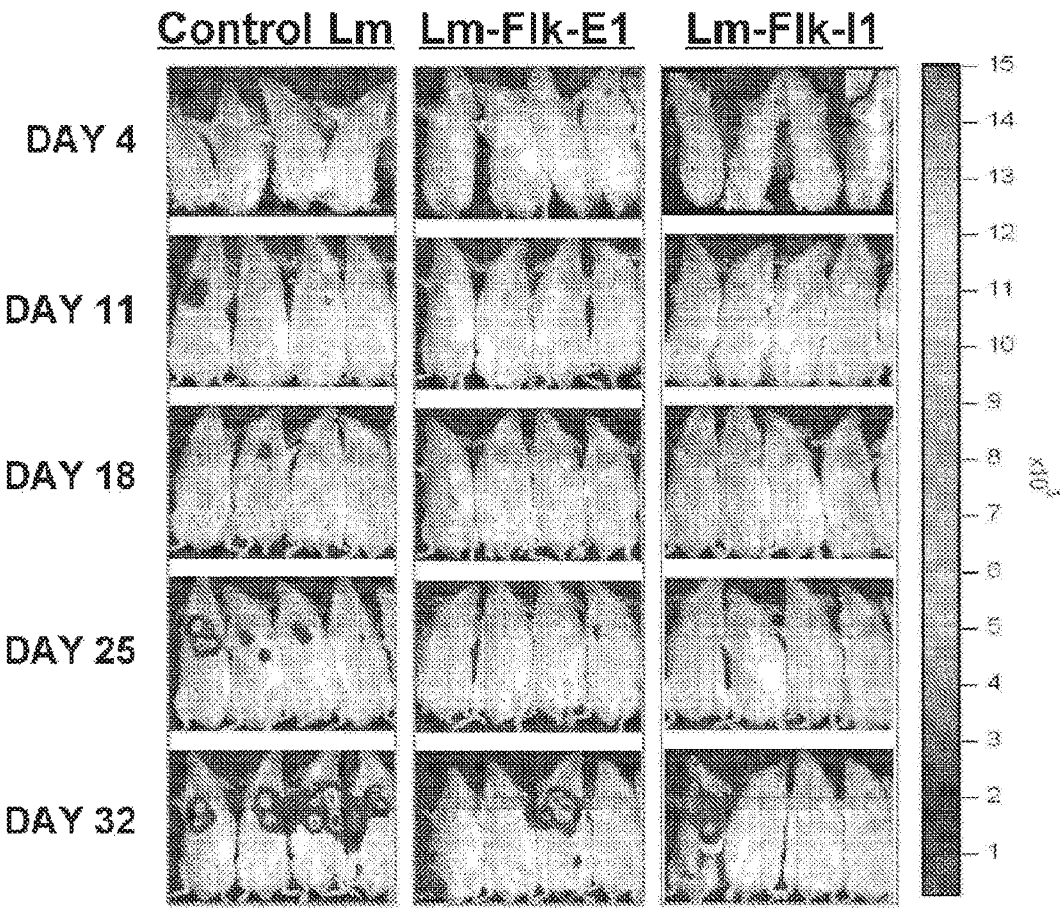
FIG. 55B shows that spleens from these animals were processed and re-challenged ex vivo in IFN-g ELISpot assays for Her-2/neu epitope spreading. The 4T1 cell line does express low levels of mouse Her-2/neu. Spreading is seen only in the Flk-1-E1 immunized mice. Graph shows Mean±SEM for spot number per well as compared to control Lm group; *$p<0.05$, Mann-Whitney test, experiment repeated once, N=5 per group.

Vaccination with LM-LLO-FLK-1 Vaccine Fragments can Prevent the Growth of Experimental Metastases An important use for anti-angiogenesis vaccines could be for the treatment or prevention of breast cancer metastasis. Tumor cells that metastasize are highly dependent on the development of new vessels, although smaller tumors do not completely rely on new vasculature. However, it has been hypothesized that once they have grown beyond a certain size, tumors become highly dependent on the formation of new vessels and thus become a possible target for anti-VEGFR2 CTLs. To test if our vaccines could protect against breast tumor dissemination we used an experimental metastasis system involving the direct inoculation of in vitro cultured tumor cells into the tail vein of mice allowing for rapid colonization of several downstream organs, especially the lung. Since after tail vein vaccination, the NT-2 model does not well colonize the lung (data not shown) we used 4T1, which is an aggressive, mouse breast carcinoma cell line from the Balb/c mouse. Balb/c mice were immunized thrice over the course of three weeks with either Lm-LLO-Flk-E1, or Lm-LLO-Flk-I1 or a control Lm vaccine. Mice were then injected with 50,000 4T1 cells i.v. and also s.c. within the same animal. The s.c. site injection was performed so that we could measure primary tumor growth, while the i.v. injection mimicked metastasis. Mice treated with the Flk-1 vaccines had prolonged tumor growth, slowed primary s.c. tumor size, increased survival, and reduced morbidity as compared to control mice (FIG. 54). Unlike the poor responses seen against the primary 4T1 tumor, the rate of seeding and total metastases found in each animal was significantly lower in treated animals compared to control mice (FIG. 55A). A low level of epitope spreading to Her-2/neu was observed (FIG. 55B), probably because 4T1 weakly expresses the mouse Her-2/neu.

Figure 55C:
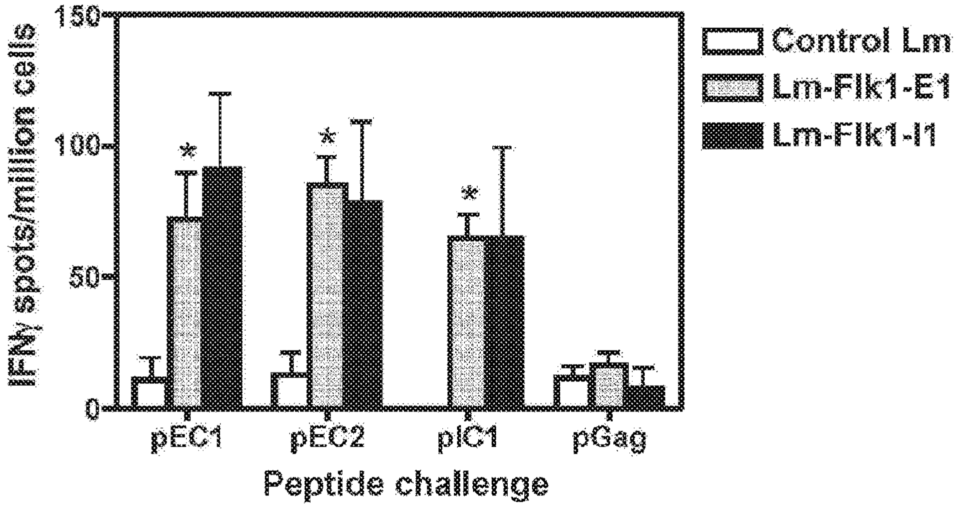
FIG. 55C. Shows an experiment where mice were protected via immunization with each vaccine for a series of three weeks then injected with 50,000 4T1-Luc cells i.v., mice were imaged longitudinally over the course of four weeks looking for the incidence of lung seeding and rate of metastasis.
Figure 55D:
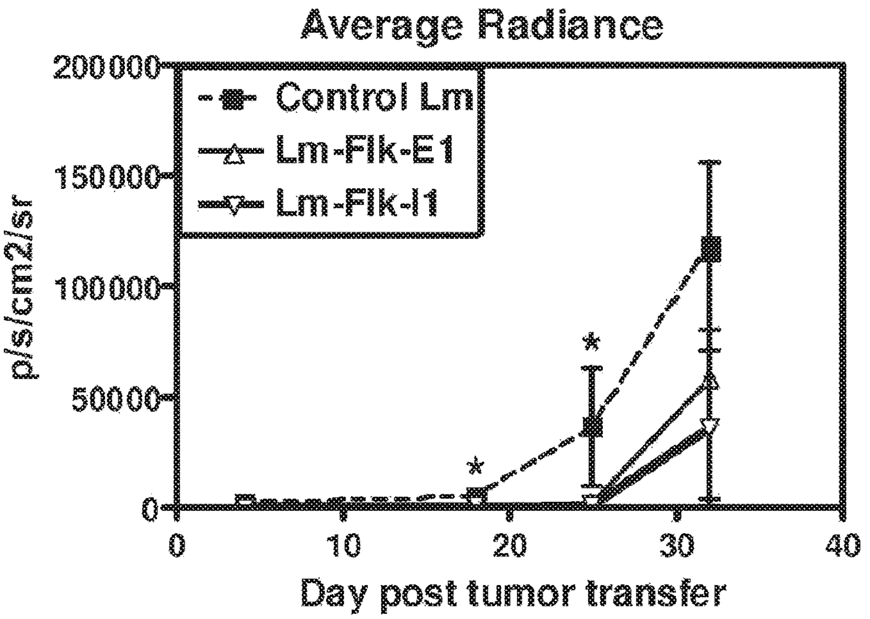
FIG. 55D shows that average radiance in photons (p) captured per second (s) per $cm^2$ for the surface area (sr) gated in the ROI. Graph shows Mean±SEM; *$p<0.05$, Mann-Whitney test. Significance for mice as follows: Day 18, only Flk-E1 significant; Day 25, both Flk-E1 and Flk-I1 significantly different when compared to control Lm.

To more stringently test the hypothesis that immunizing against Flk-1 can prevent the seeding of lung tissue with experimental metastases, we used a bioluminescent model where individual tumor cells and masses can be visualized using non-invasive imaging. Mice were injected i.v. with 50,000 4T1 cells expressing the firefly luciferase gene (4T1-Luc) after several rounds of vaccination with the Lm-Flk-E1 and –I1 vaccines. On a weekly basis, mice were anesthetized and injected with a luciferase substrate (D-Luciferin) and imaged. Lung seeding was apparent by day 11 and control treated mice rapidly become colonized with 4T1-Luc cells by day 25 whereas none of the Lm-LLO-Flk-E1 and Lm-LLO-Flk-I1 treated mice showed any signs of lung seeding until at least day 32 at which point the control treated mice had become ill and were sacrificed (FIG. 55C). At day 32, only 25% of the Flk-1 vaccinated mice showed any lung tumors. It is possible that tumor masses were undetectable at this time point by this bioluminescent method since a signal for tumor cells was observed on day 25 but not day 32 for the Lm-Flk-E1 treated group. This very small signal on day 25 is below the 1000 cell threshold and may have lost some cellular mass within the following week to fall below the limit of detection for the system. Mice immunized with the control Lm rapidly became diseased by lung tumors, but the Flk-E1 and Flk-I1 Lm vaccinations delayed tumor burden, time to progression (day 25 for control treated versus day 32 for Flk-1 treated), and eventual disease (reduced morbidity as shown in FIG. 54).

Example 32

Figure 56A:
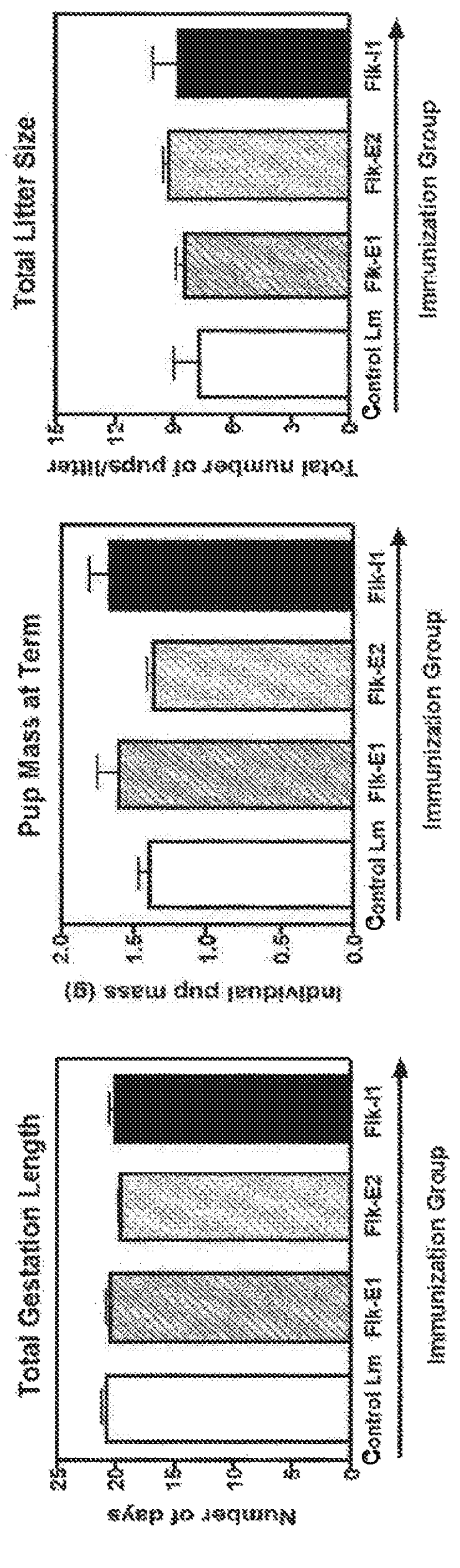
FIG. 56A shows safety studies using the anti-angiogenesis Flk-1 vaccines. Mice were immunized thrice as performed in all previous experiments then were allowed to either mate or entered into wound-healing studies. Mice (n=5/group) were mated with syngeneic FVB/N males, gestation was confirmed upon the observance of a vaginal plug following coitus. This was considered as day 0.5 dpc. Total gestation length, pup mass at term, and total litter size was measured, graphs show Mean±SEM; *$p<0.05$.
Figure 56B:
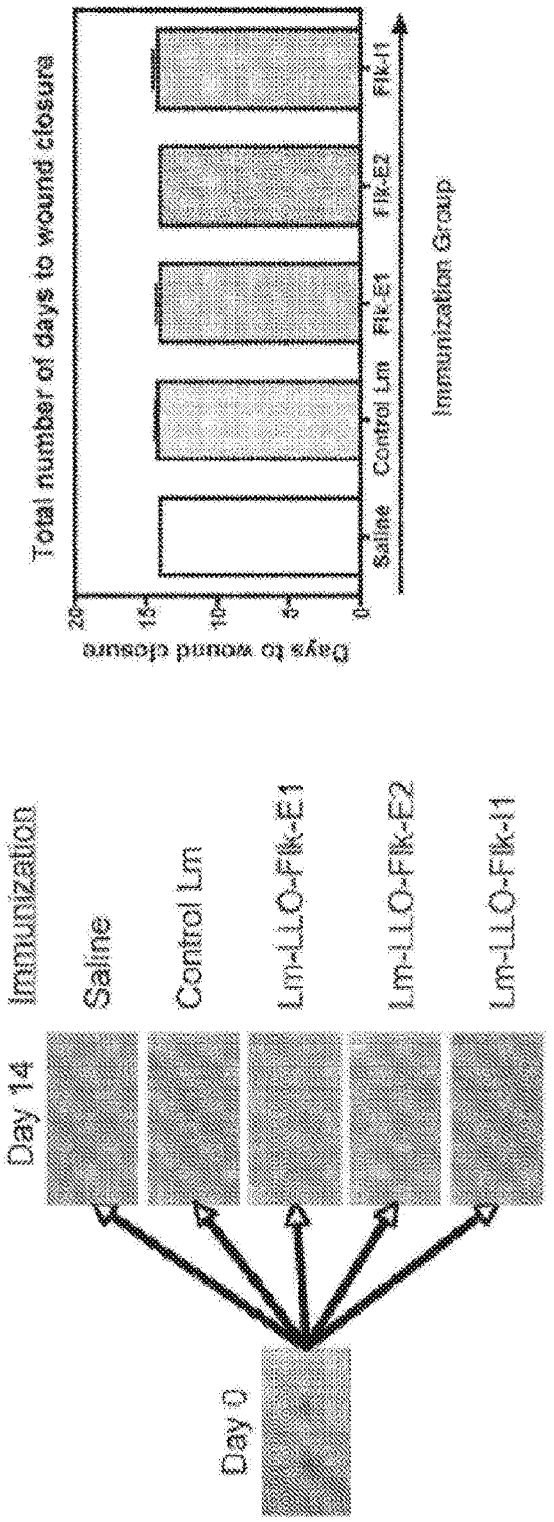
FIG. 56B. A pair of sterile skin biopsies were produced on the back of each vaccinated mouse (N=5/group). Healing was observed on a daily basis. On day 14 healing was complete for all groups tested, near identical healing was observed for all groups. Graph shows the number of days until wound closure, Mean±SEM; *$p<0.05$, Mann-Whitney test.

Immunization with Flk-1 has No Impact on Wound Healing, Pregnancy or Fertility in Mice To evaluate whether Lm-LLO-Flk-1 vaccines cause toxicity that is associated with angiogenesis inhibition, we studied wound healing, pregnancy and fertility in immunized mice. Mice were immunized thrice with Lm-LLO-Flk-E1, Lm-LLO-Flk-E2, Lm-LLO-Flk-I1, control Lm or saline alone before being mated or given sterile wound punches. We observed mice that were mated for length of gestation from coitus, mean pup mass at term, and total litter size. Wound punches were sterile but mice were caged together. Wound healing technique was followed according to previously described methods. Five mice from each immunization group were shaved and given sterile wound punches, two per animal then allowed to heal over time. Time to wound closure was measured. Full wound healing was considered complete, no scabs were left at time of wound closure. Immunization with Lm-LLO-Flk-E1, Lm-LLO-Flk-E2, or Lm-LLO-Flk-I1 had no impact on fertility, gestation length or pup mass at birth (FIG. 56A). Similarly, immunization had no significant impact on the time required for wound closure (FIG. 56B).

Figure 57:
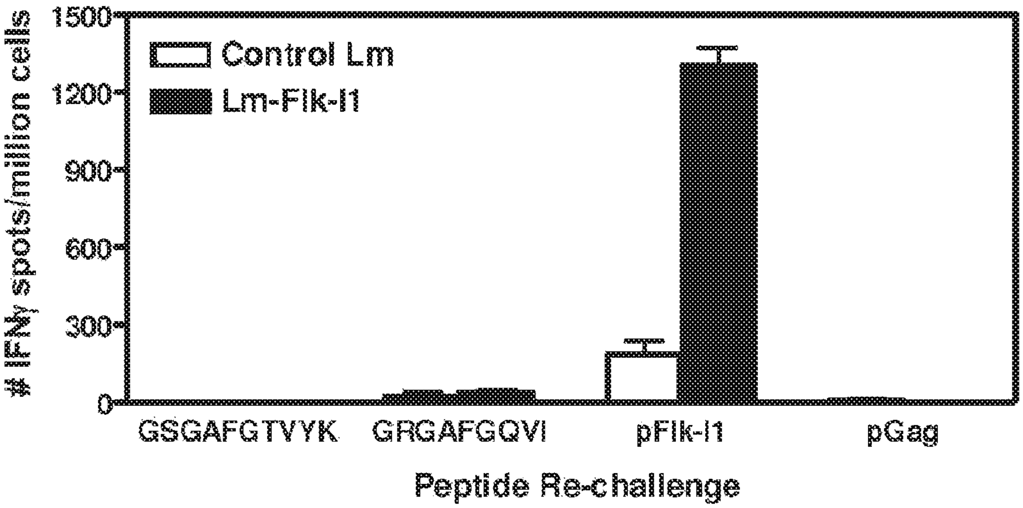
FIG. 57. Flk-1 vaccine induced epitope spreading may not be due to cross reactivity between Flk-1 and Her-2/neu shared domains. Mice were immunized thrice with either control Lm or Flk-I1 vaccine. Splenocytes were processed and re-challenged ex vivo for the secretion of IFN-g in response to peptide challenge. Peptides included were the previously mapped pFlk-I1 epitope (PGGPLMVIV; SEQ ID NO: 102), a putative pIC1 epitope for Her-2/neu (GSGAFGTVYK; SEQ ID NO: 99) or the epitope in question, a putative shared epitope between the Her-2/neu and Flk-1 kinase domains (GRGAFGQVI; SEQ ID NO: 103), and a third party epitope used as a negative control (pGag). Graph shows Mean±SEM, N=3/group.

To evaluate if the immune responses to Her-2/neu observed after Flk-I1 immunization was due to cross-reactivity between shared epitopes between Flk-1 and Her-2/neu, FVB/N mice immunized with Flk-I1 vaccine were evaluated for immunity to FLK-$I1_{839-848}$, which is cross-reactive to the rat Her-2/neu epitope GSGAFGTVYK (SEQ ID NO: 99). Vaccination of mice with Lm-LLO-Flk-I1 lead to excellent responses against the previously mapped Flk-I1 epitope PGGPLMVIV (SEQ ID NO:102). However no significant responses were seen against either the mouse Flk-$I1_{839-848}$ epitope or the homologous rat Her-2/neu $IC1_{732-741}$ epitope (FIG. 57). Thus the immune responses to Her-2/neu observed after Flk-I1 immunization were most likely due to epitope spreading and not due to cross-reactivity between shared epitopes.

Taken together, Lm-LLO-Flk-1 vaccines were able to eradicate some established breast tumors, reduce microvascular density in the remaining tumors, protect against tumor re-challenge and experimental metastases and induce epitope spreading to various regions of the tumor-associated antigen Her-2/neu. Tumor eradication was found to be dependent on epitope spreading to HER-2/neu and was not solely due to the reduction of tumor vasculature. However, vaccine efficacy did not affect normal wound healing nor have toxic side effects on pregnancy. Thus, an anti-angiogenesis vaccine can overcome tolerance to the host vasculature driving epitope spreading to an endogenous tumor protein and drive active tumor regression. Therefore, presented herein is a novel method of targeting both the tumor vasculature and an endogenous tumor antigen (Her-2/neu) using a single vaccine.

Example 33

Mutations Arise in Escape Mutants

Mice

The FVB/N Her-2/neu transgenic mice were housed and bred at the animal core facility at the University of Pennsylvania. Mice were six to eight weeks old when used at the start of the experiments, which were done in accordance with regulations by the Institutional Animal Care and Use Committee of the University of Pennsylvania.

*Listeria* Vaccine Strains.

Strains used were Lm-LLO-Flk-E1 and Lm-LLO-Flk-I1. The strain Lm-LLO-NYESO1 was used as a third party control vaccine for antigen specificity. Bacteria were selected on Brain Heart Infusion (BHI, Difco) plates supplemented with 34 μg/ml of chloramphenicol and 250 μg/ml of streptomycin, then grown in liquid culture and frozen in 1 ml aliquots at −80° C. For injection, the vaccines were washed twice with sterile PBS before administration.

Autochthonous Tumor Protection.

To test the ability of the anti-Flk-1 *Listeria* vaccines to impact on spontaneously arising tumors we used the FVB/N rat Her-2/neu transgenic female mouse which overexpresses the rat Her-2/neu molecule and spontaneously develops mammary tumors. For these long-term protection studies, we immunized female mice (N=15) a total of six times starting at 6 weeks of age and immunizing i.p. every three weeks until 21 weeks of age. Vaccines Lm-LLO-Flk-E1, Lm-LLO-Flk-I1, or Lm-LLO-NYESO-1 were injected at 0.1 LD50 suspended in PBS. Tumor burden was followed on a weekly basis. Once tumors were beyond 10 mm in size the animals were sacrificed and tumors were removed for analysis. Statistical analysis of differences in autochthonous tumor growth was done using the Kaplan-Meier log-rank test using GraphPad Prism Software, comparing the time of onset of tumor growth between each vaccine group and control groups.

Analysis and Mapping of Mutations.

Tumors were excised fresh and placed into RNAlater solution, stored at 4° C. for less than 2 weeks. We extracted mRNA from stored tumors using a Qiagen mRNA kit (Invitrogen), then generated cDNA via PCR. Individual PCR samples were further divided to allow sequencing of each individual fragment of Her-2/neu in stretches of 500-800 bp each (EC1, EC2, EC3, IC1, IC2) as was described elsewhere (Singh, 2007). Sequencing was done by the Children's Hospital of Philadelphia (CHOP) Sequencing Facility and then analyzed using 4Peaks software 1.7.2. Mutations that did not occur in four or more individual PCR and sequencing reactions were discarded as PCR-induced mutations. Molecular modeling was done using MacPyMol.

PCR primer sequences:

```
EC1 FP:
                              (SEQ ID NO: 110)
AGGGCTGTCAGGTAGTGC

EC1 RP:
                              (SEQ ID NO: 111)
TGACCTCTTGGTTATTCG

EC2 FP:
                              (SEQ ID NO: 112)
ACCTGCCCCTACAACTAC

EC2 RP:
                              (SEQ ID NO: 113)
GACGCCCTCTACAGTTGC

EC3 FP:
                              (SEQ ID NO: 114)
GTGGATTGGCTCTGATTC

EC3 RP:
                              (SEQ ID NO: 115)
TGAGTTACAGACCAAGCC

IC1 FP:
                              (SEQ ID NO: 116)
CAAACGAAGGAGACAGAAG
```

-continued

```
IC1 RP:
                                    (SEQ ID NO: 117)
CACCATCAAACACATCGG

IC2 FP:
                                    (SEQ ID NO: 118)
CACTGCTGGAAGATGATG

IC2 RP:
                                    (SEQ ID NO: 119)
TTTGTGGCGATGGAGACC
```

Figure 58A:
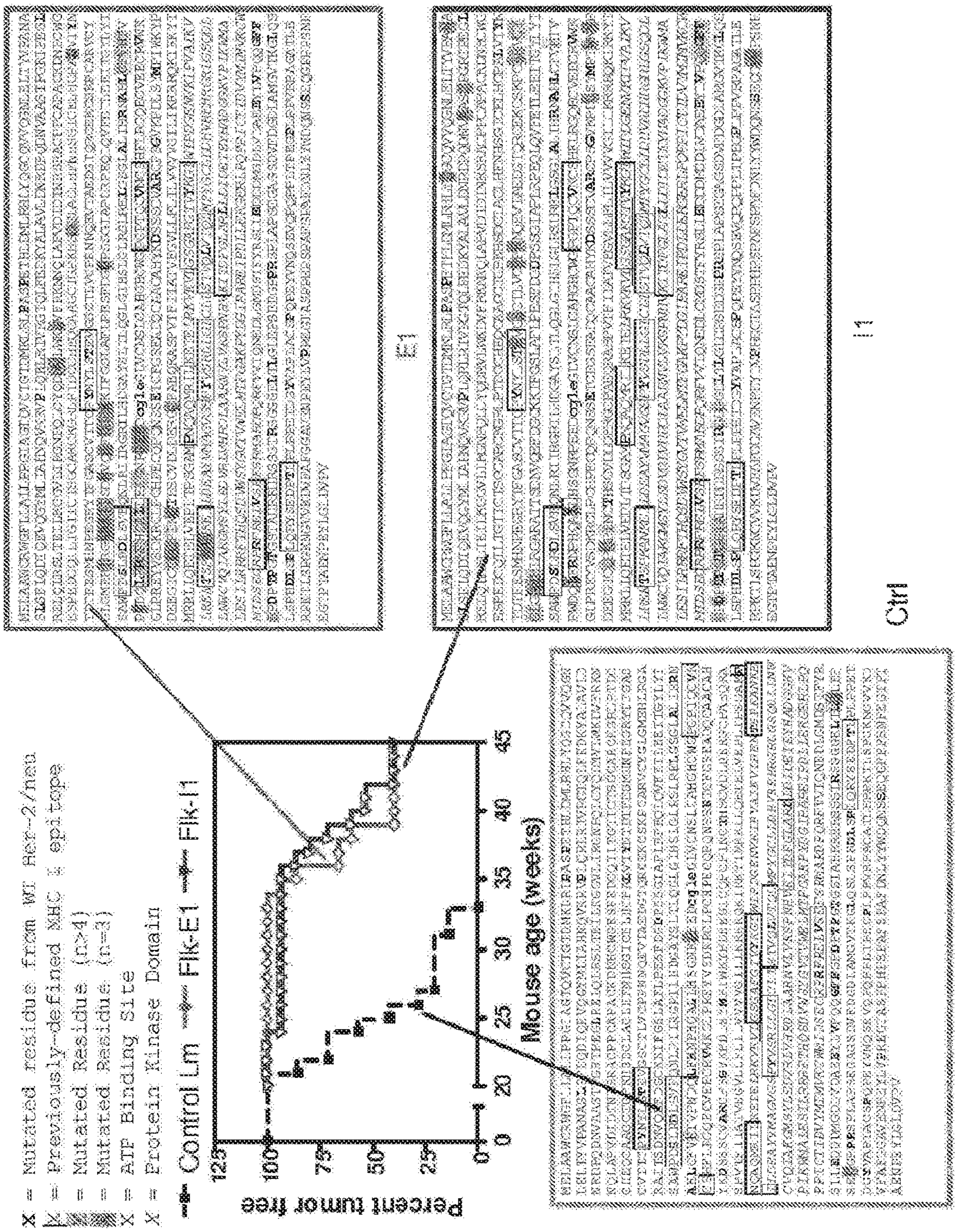
FIG. 58A. Flk-1 vaccines can significantly delay tumor outgrowth in spontaneous, orthotopic models for Her-2/neu breast cancer. Transgenic FVB-rHer-2/neu mice were immunized thrice with each Flk vaccine or control Lm alone. Tumors from each mouse were examined for mutated Her-2/neu message. Message RNA was collected, cDNA synthesized and sequenced. The resulting sequence was paired alongside the wild-type sequence to determine mutated residues. Only mutations that arose 4 times or more were considered true mutations. A summary of all mutations is found on the left, this shows an N of at least 3, but not more than 5 mice, per group. All mutational data is combined and overlayed onto the rat Her-2/neu wild-type sequence. The bold aa residues are mutations that arise when vaccines are against Her-2/neu domains. The red-highlighted aa residues are mutations that arise when Flk-1 vaccines are used. The blue-highlighted region shows the Her-2/neu kinase domain. The green-highlighted region shows the ATP-binding domain.
Figure 58B:
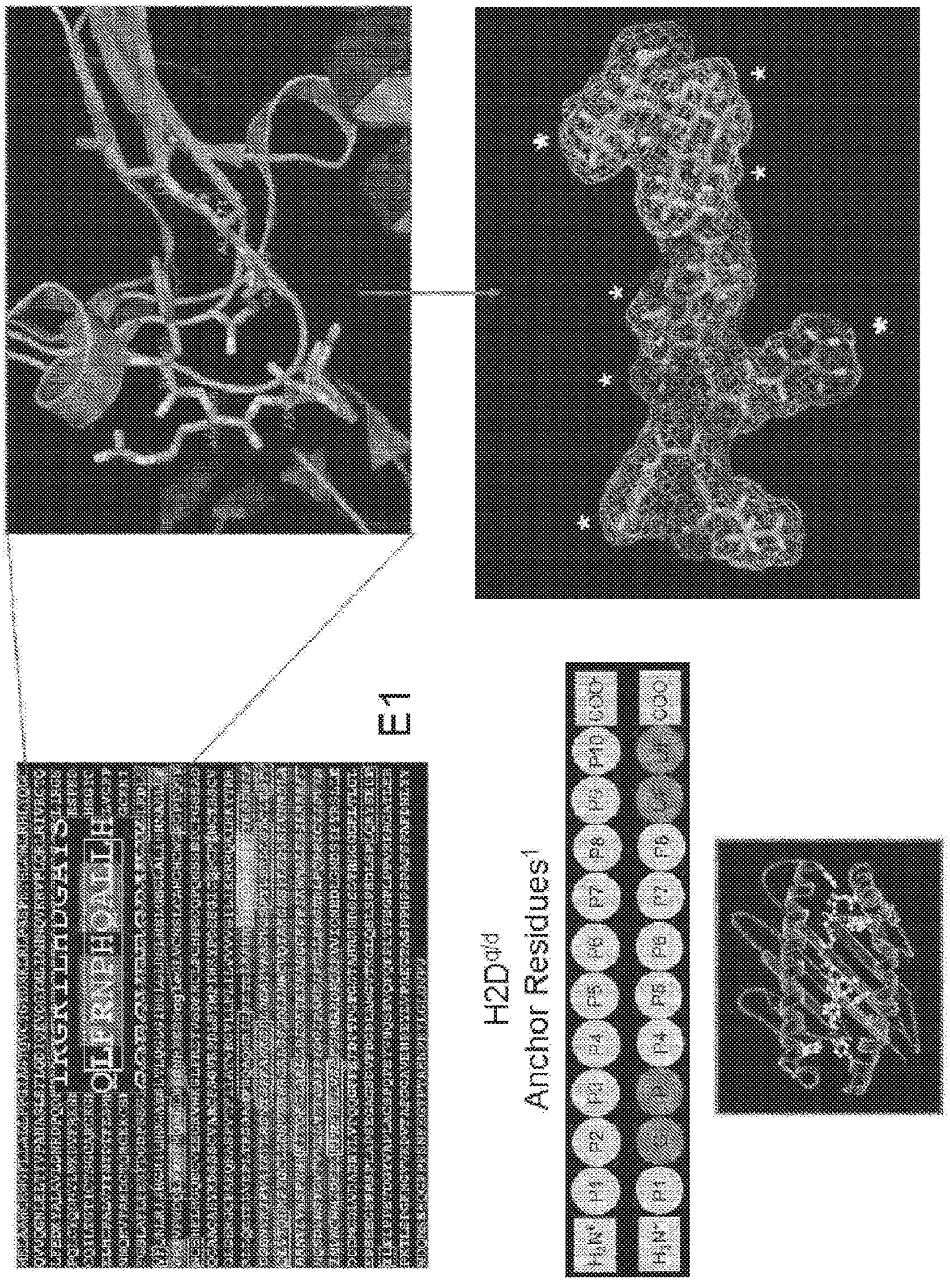
FIG. 58B. Tumor outgrowth is due to mutations arising in key CTL epitopes responsible keeping the tumor in check. Looking closer at "hot-spots" or strings of mutated residues, we found that several mutated residues are found within previously mapped CTL epitopes. One such epitope shows mutations in key amino acids responsible for anchoring the epitope to the H2Dq MHC I molecule. Other "hot-spots" are being investigated for new CTL epitopes.

Transgenic FVB/N mice expressing rat Her-2/neu were vaccinated with Flk-E1, Flk-I1, or control Lm every 3 weeks starting at 6 weeks old, and tumors were measured weekly after the final vaccination. Vaccination with Flk-E1 and Flk-I1 increased the percentage of tumor-free mice compared to control Lm-vaccination. Between week 35 and 40, there were a number of mice in the Flk-E1 and Flk-I1-vaccinated mice that developed tumors. Tumors from each mouse were examined for mutated Her-2/neu message. Message RNA was collected, cDNA synthesized and sequenced. The resulting sequence was paired alongside the wild-type sequence to determine mutated residues. Only mutations that arose 4 times or more were considered true mutations (FIG. 58A). Several of the mutated residues within the "hot-spots" or strings of mutated residues were within previously mapped CTL epitopes. One such epitope shows mutations in key amino acids responsible for anchoring the epitope to the H2Dq MHC I molecule (FIG. 58B).

Example 34

Targeting of Breast and Melanoma Brain Metastases

Experiments were performed using the methods as described hereinabove.

Figure 59A:
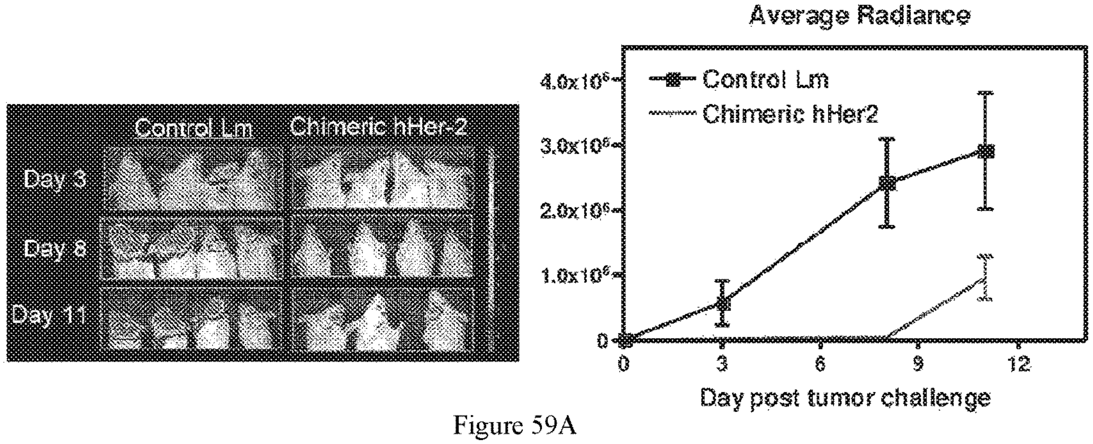
FIG. 59A. Anti-Her-2/neu human chimeric vaccine can delay the growth of a metastatic breast cancer line in the brain of protected mice. Balb/c mice were immunized thrice with each vaccine, either anti-human Her-2/neu or control vaccination NYESO1. EMT6-Luc cells were grown in vitro then injected into the brain of anesthetized mice at 5,000 cell per mouse. EMT6-Luc cells express low levels of mouse Her-2/neu (data not shown) Cells were allowed to grow before being imaged on the indicated days. EMT6-Luc cells produce the enzyme luciferase and when they metabolize D-Luciferin in vivo the by-product are photons that are captured ex vivo using a Xenogen X-100 camera and displayed using a heat map. Pixel intensity is graphed as number of photons per second per cm^2 per cm of surface area, presented as average radiance.

Balb/c mice were immunized thrice with each vaccine, either anti-human Her-2/neu or control vaccination NYESO1. Murine breast carcinoma cells stably expressing the firefly luciferase gene (EMT6-Luc cells from John Ohlfest's lab at University of Minnesota) were grown in vitro then injected into the brain of anesthetized mice at 5,000 cell per mouse. EMT6-Luc cells express low levels of mouse Her-2/neu (data not shown) Cells were allowed to grow before being imaged on the indicated days. While brain metastases were clearly seen in NYESO1-vaccinated mice, anti-human Her-2/neu vaccination controlled brain tumors on days 3, 8 and 11 after experimental induction of metastases (FIG. 59A).

Figure 59B:
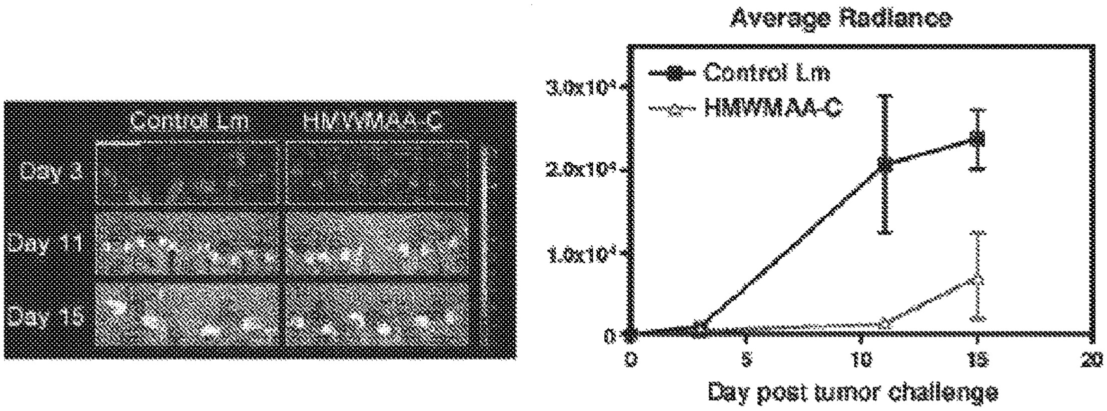
FIG. 59B. Anti-HMWMAA human vaccine can delay the growth of a metastatic melanoma line in the brain of protected mice. C57B⅙ mice were immunized thrice with each vaccine, either anti-human HMWMAA-C or control vaccination NYESO1. B16F10-Luc cells were grown in vitro then injected into the brain of anesthetized mice at 5,000 cells per mouse. B16F10 parental line do not express HMWMAA, thus the only source of HMWMAA is on pericytes and glial cells. Luciferase mechanism and image capture the same as in FIG. 59A.

C57Bl/6 mice were immunized thrice with each vaccine, either anti-human HMWMAA-C or control vaccination NYESO1. B16F10-Luc mouse melanoma cells (from Jeff Miller's lab at UCSF) were grown in vitro then injected into the brain of anesthetized mice at 5,000 cells per mouse. B16F10 parental line do not express HMWMAA (personal communication), thus the only source of HMWMAA is on pericytes and glial cells. Vaccination of mice with anti-human HMW-MAA-C reduced brain tumors on days 11 and 15 after experimental induction of metastases (FIG. 59B). Thus, vaccination with either HMW-MAAC or Her-2/neu is protective against brain metastases, even if the tumor cells do not express HMW-MAA.

Example 35

Construction of Novel Anti-CD105/Endoglin *Listeria*-Based Vaccine-Therapeutic

Figure 62:
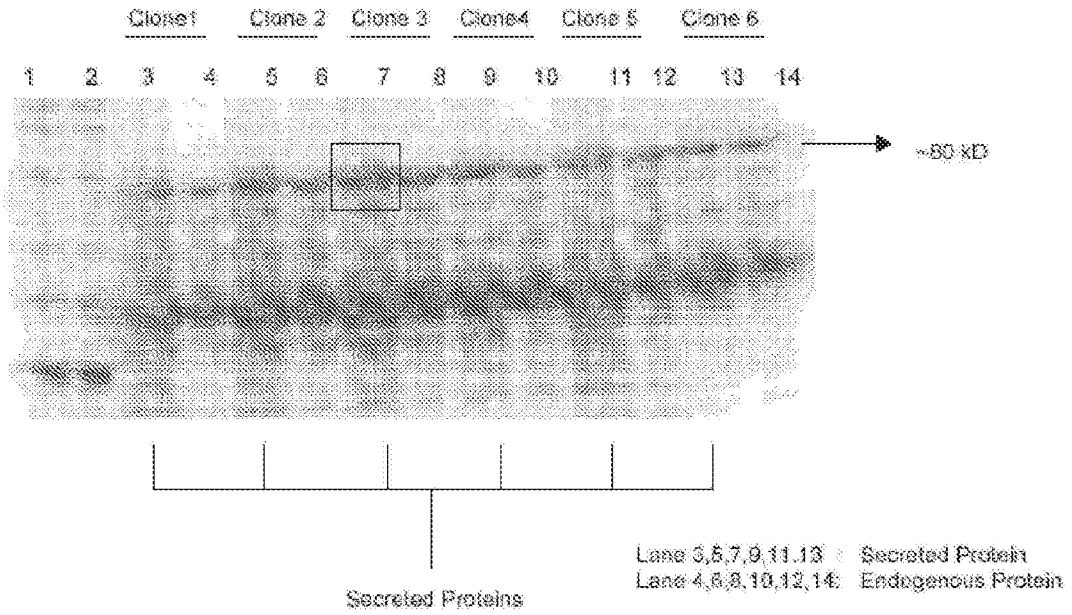
FIG. 62. Lm-LLO-CD105A expresses and secretes a protein of appropriate size (~80 kD) detected by an anti-LLO antibody and Western blotting: The XFL7 strains were transformed with CD105A plasmid using electroporation. The transformed XFL7 cells were plated on 37 ug/mL and 250 ug/uL of chloramphenicol and streptomycin. The colonies that formed during the two day incubation period were grown in LB media, spun down and the supernatant and cell lysate were subjected to Western blotting to detect the fusion protein either as a secreted protein in the supernatant or n endogenous protein trapped within the bacterial cell.
Figure 63:
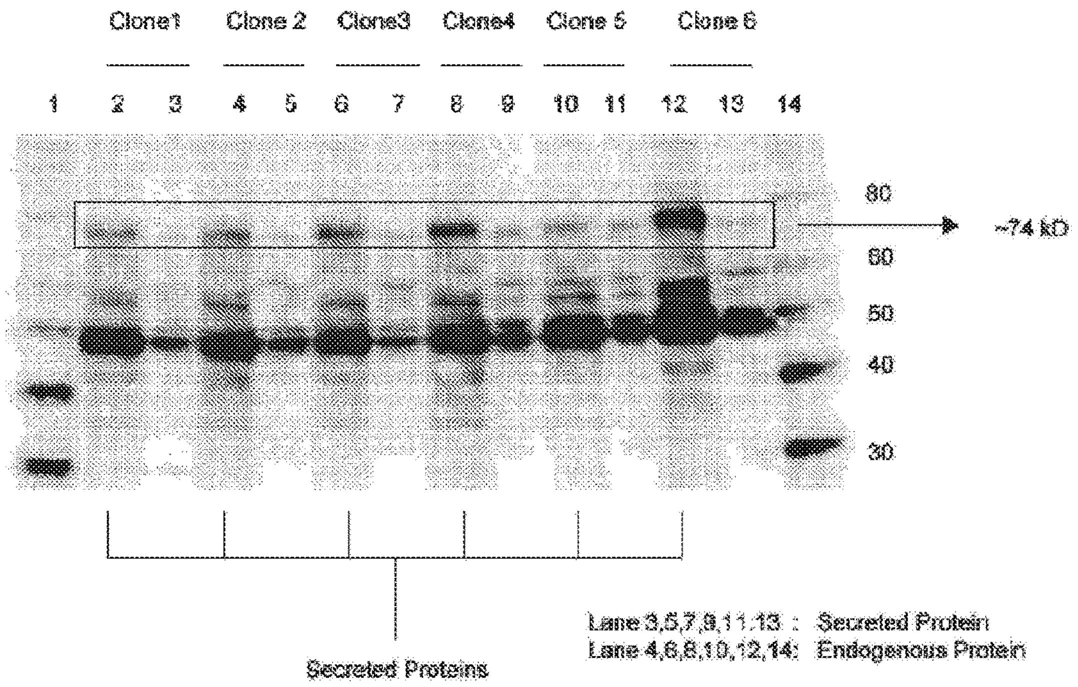
FIG. 63. Lm-LLO-CD105B expresses and secretes a protein of appropriate size (~74 kD) detected by an anti-LLO antibody and Western blotting: The XFL7 strains were transformed with CD105A plasmid using electroporation. The transformed XFL7 cells were plated on 37 ug/mL and 250 ug/uL of chloraphenicol and streptomycine. The colonies that formed during the two day incubation period were grown in LB media, spun down and the supernatant and cell lysate were subjected to Western blotting to detect the fusion protein either as a secreted protein in the supernatant or n endogenous protein trapped within the bacterial cell.

A construct of an Lm strain that expressed a rather large fragment of endoglin (FIG. 60) did not secrete the fragment when fused to LLO, therefore it was redesigned to two novel Lm constructs, Lm-LLO-CD105A (aa17-319) and Lm-LLO-CD105B (359-588) that span nearly the entire endoglin gene (FIG. 61A) and include putative CTL epitopes, determined using RANKpep, that lie outside the region of endoglin that had been previously targeted (FIG. 60). By potentially including more immunodominant epitopes within these novel constructs expansion of the pool of CTL epitopes were used to enhance vaccine efficacy. Further by making the fusion proteins smaller and removing regions of high hydrophobicity from the constructs, these fusion proteins were better secreted by Lm. Genes encoding these fragment were cloned into CD105pGG-34 (FIG. 61B). Both Lm-LLO-CD105A (FIG. 62) and Lm-LLO-CD105B (FIG. 63) expressed and secreted fragments of the appropriate size.

Example 36

Figure 64:
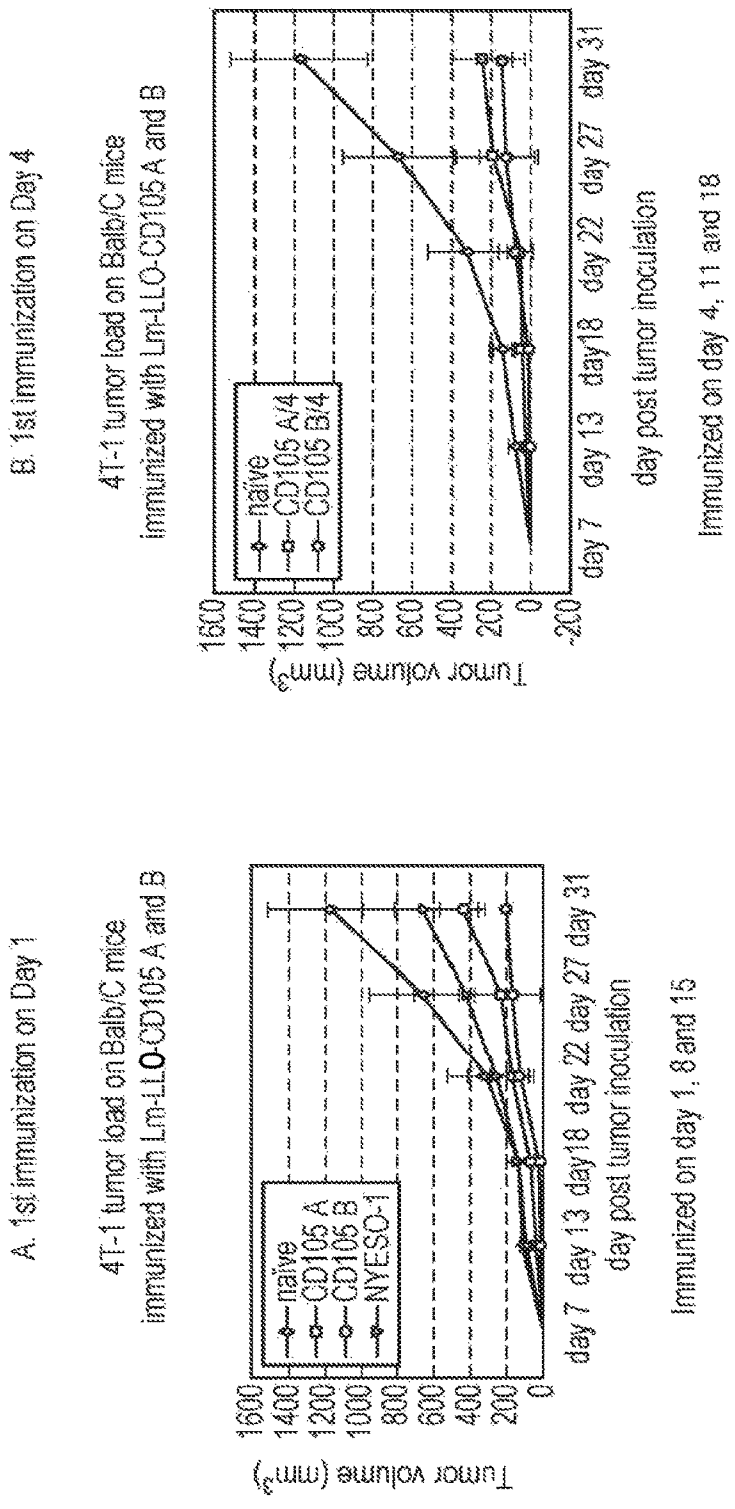
FIG. 64. Growth of 4T1 tumors ($2\times10^5$ cells implanted in the mammary fat pad) in Balb/c mice immunized with Lm-LLO-CD105 A and B compared to a control vaccine Lm-LLO-NY-ESO-1. Mice were vaccinated with $2\times10^8$ cfu of each vaccine on the days indicated.
Figure 65:
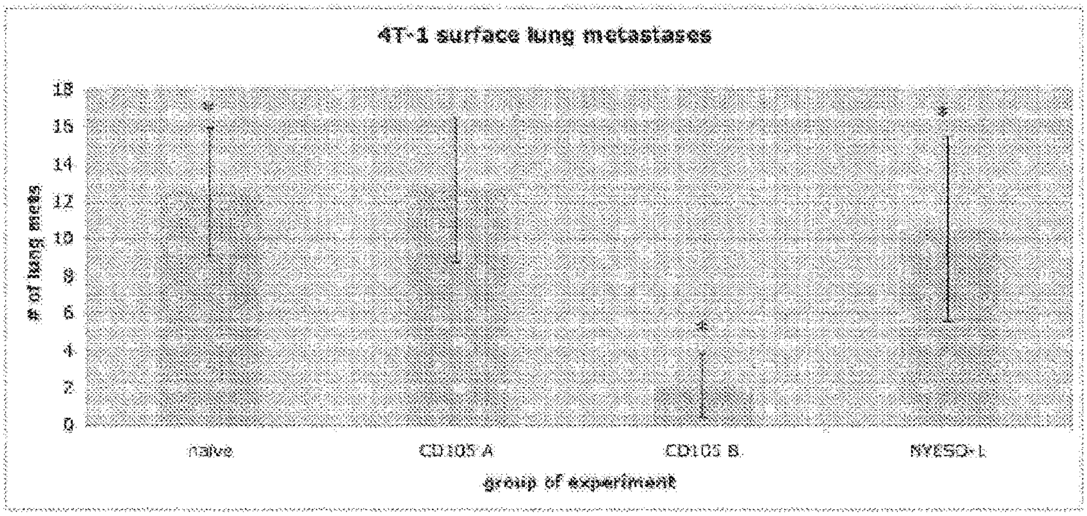
FIG. 65. Mice from the experiment shown in FIG. 53B were sacrificed on day 32 and lungs were removed and inflated with PBS. The visible surface metastases were counted under a dissecting microscope. A significant decrease was observed only for Lm-LLO-CD105B compared to naive ($p<0.01$) or Lm-LLO-NY-ESO1 ($p<0.05$).

LM-LLO-CD105A and B Impact on Primary and Metastatic Growth of Breast Tumor 4T1 in the Balb/C Mouse The BALB/c mouse 4T1 breast tumor, the more malignant of our breast tumor models since it rapidly metastasizes when implanted into the mammary gland, was chosen as the first test of the vaccines shown in Example 8. $2\times10^5$ 4 T1 cells were implanted in the mammary fat pad in Balb/c mice. Mice were vaccinated with $2\times10^8$ cfu of each vaccine on either day 1, 8 and 15 or on days 4, 11 and 18. Both vaccine regimens showed a significant slowing of tumor growth compared with naive or control vaccinated mice (FIG. 64). On day 32, the mice were sacrificed and their lungs were removed and examined for metastatic spread. Interestingly, only Lm-LLO-CD105B showed a statistically significant reduction in surface lung metastases (FIG. 65).

Next, CTL responses in these mice were examined. As an initial attempt to determine the immunogenic regions of the endoglin molecule that could be recognized by $CD8^+$ T cells, the two fragments were subjected to analysis by RANKpep (http://bio.dfci.harvard.edu/RANKPEP/) and SYFPEITHI (http://www.syfpeithi.de/). From this the two most promising peptides for CD105A: AGPRTVTVM (SEQ ID NO: 120) (a $D^d$ binder) and for CD105B: AYSSCGMKV (SEQ ID NO: 121) (a $K^d$ binder) were selected Their positions in the endoglin sequence are underlined in FIG. 61A.

These two peptides were used in ELISpot analyses to stimulate splenocytes taken from mice shown in FIG. 16B, that had been vaccinated on days 4, 11 and 18, four days following their last vaccination. However they did not stimulate T cells to secrete interferon-gamma, compared to a control H-$2^d$ restricted peptide from HIV Gag, which suggests that they are not CTL epitopes (FIG. 55). Epitope spreading to two endogenous tumor antigens expressed at low levels by 4T1 was also analyzed. The first is an envelope glycoprotein, gp70, from the endogenous ecotropic murine leukemia virus. An epitope, designated AH1, SPSYVYHQF (SEQ ID NO:122), from gp70, with $L^d$ restriction, has been mapped for the BALB/c mouse. Interestingly it was found that both Lm-LLO-CD105A and B induced epitope spreading to this antigen. Epitope spreading to HER-2/neu, was also investigated. Two known epitopes in the extracellular domain of HER-2/neu, EC1 and EC2 and one from the intracellular domain were used. Although no significant increase in IFN-gamma ELISpots against IC1 for either endoglin vaccine compared to the control vaccine Lm-LLO- NY-ESO-1 was observed, spreading to EC1 and EC2 using the Lm-LLO-CD105A vaccine was witnessed (FIG. 65).

Figure 66:
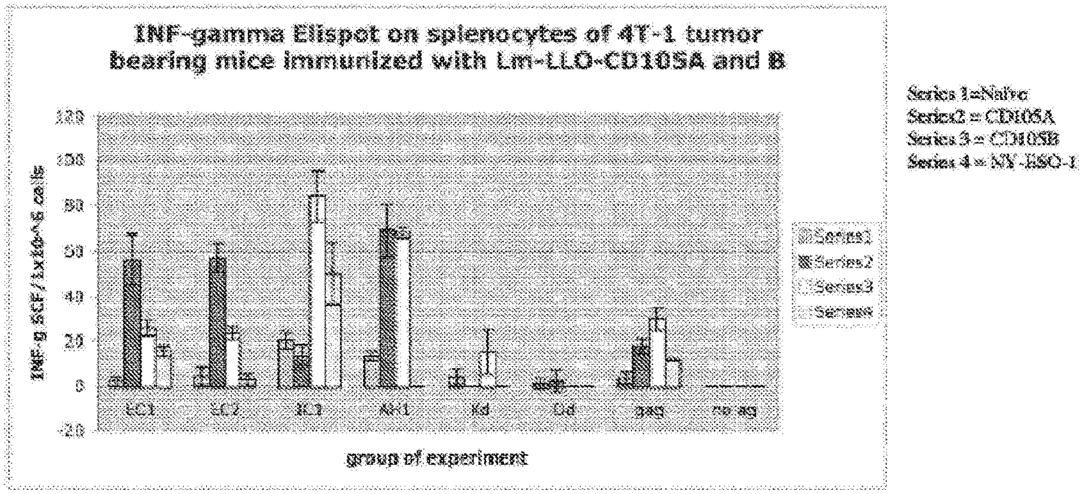
FIG. 66. Immunization with Lm-LLO-CD105A and B induces epitope spreading to endogenous antigens HER-2/neu and gp70 and the induction of antigen-specific T cells in the spleen. On day 22 post tumor implantation in the experiment shown in FIG. 53B, spleens were removed from 3 mice, pooled, and a single cell suspension was analyzed by ELISpot after stimulation with the peptides shown. Note that Kd and Dd are two peptides from the endoglin sequence that were predicted to bind to these MHC class I molecules. They reside in CD105A: AGPRTVTVM (Dd) (SEQ ID NO: 120) and in CD105B AYSSCGMKV (Kd) (SEQ ID NO: 121).

Tumors from the mice were examined for antigen-specific infiltrating T-cells, from which the splenocytes were harvested for HER-2/neu and gp70 specific T cells using FACS and tetramer analysis. Significant increases in EC1, EC2 and AH1 specific T cells in tumors were observed, and modest increases in IC1 specific T cells, from Lm-LLO-CD105 vaccinated mice compared to those vaccinated with Lm-LLO-NY-ESO-1 were also observed (FIG. 66).

Example 37

Figure 67:
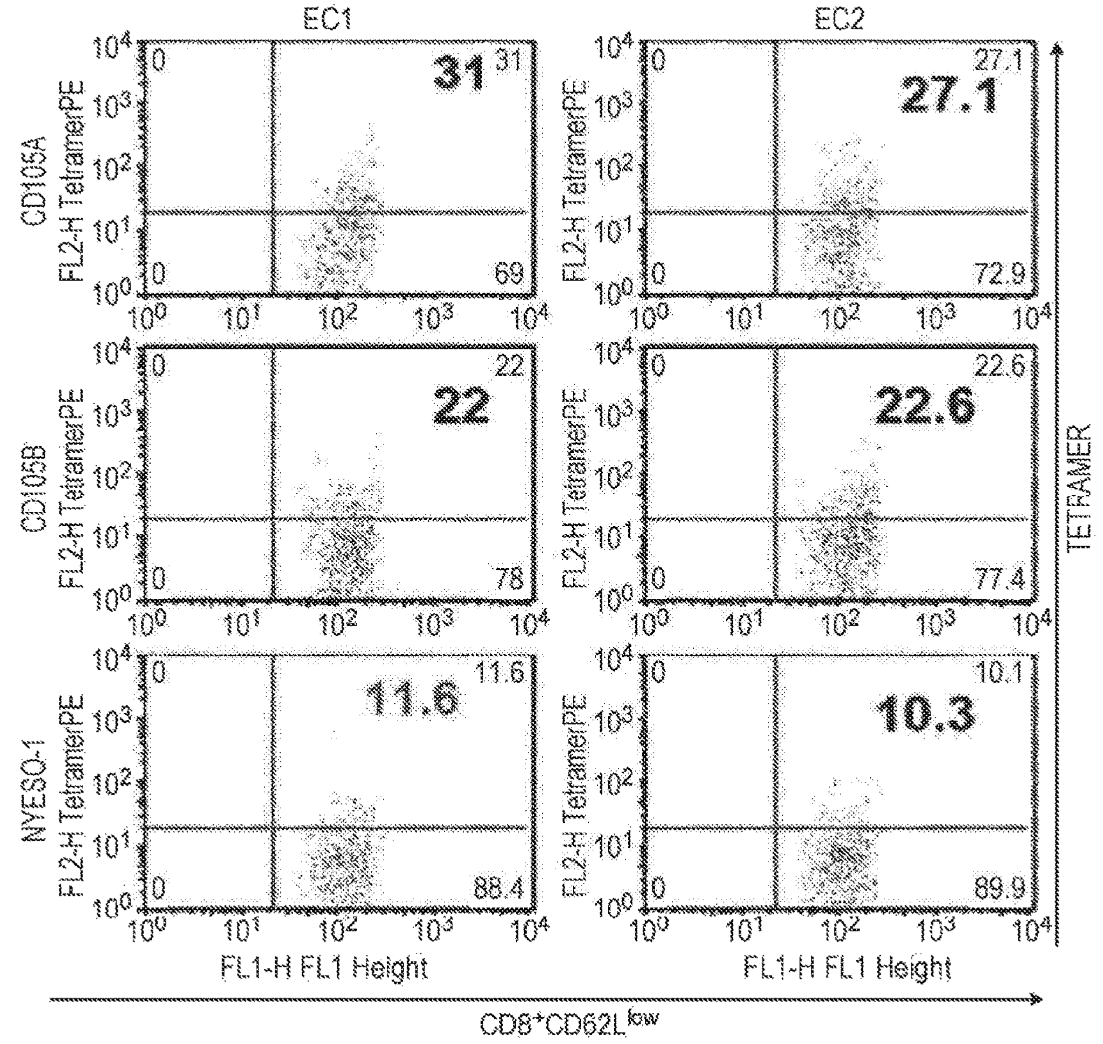
FIG. 67. Immunization with Lm-LLO-CD105A and B induces epitope spreading to endogenous antigens HER-2/neu and gp70 and the induction of antigen-specific T cells that infiltrate the tumor. On day 22 post tumor implantation in the experiment shown in FIG. 53B, tumors were removed from 3 mice, pooled and processed for FACS analysis and stained with EC1, EC2, IC1 and AH1 tetramers, anti CD8 and CD62L, CD11B. The CD11B-population was gated on CD8+, CD62L low and analyzed for antigen specificity using the tetramers shown.
Figure 67:
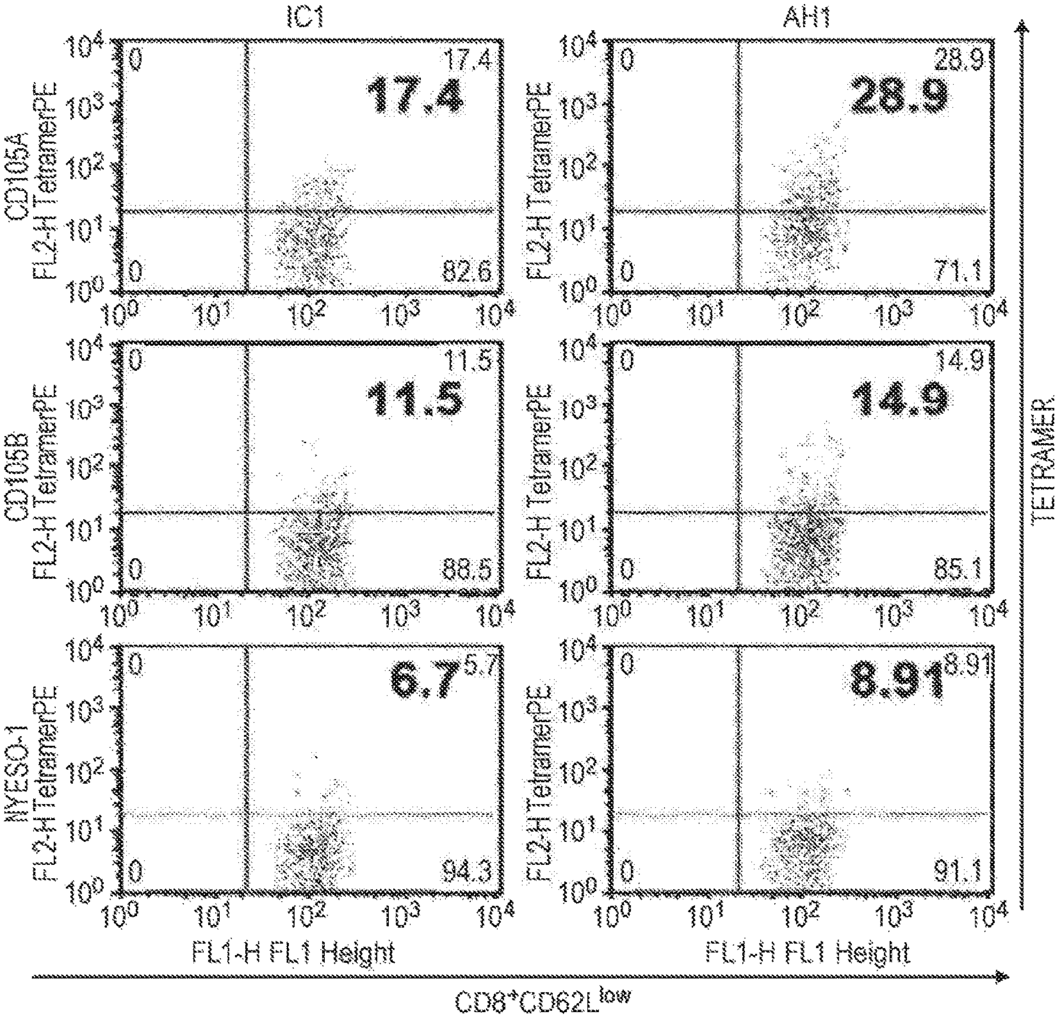
Figure 68:
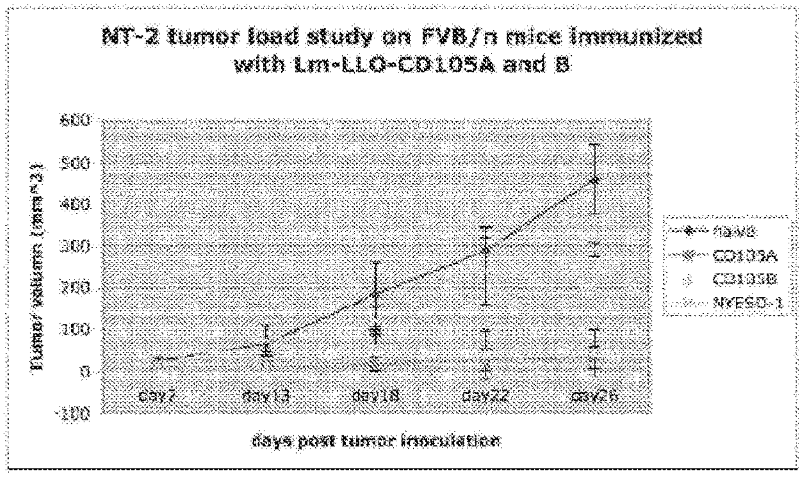
FIG. 68. Growth of NT-2 ($1\times10^6$ cells) tumors implanted sub-cutaneously in FVB mice, which were subsequently immunized with Lm-LLO-CD105 A and B or a control vaccine Lm-LLO-NY-ESO-1 on days 4, 11 and 18, with $2\times10^8$ cfu of each vaccine.

Studies on the Use of LM-LLO-CD105A and B to Impact on the Growth of the Her-2/Neu Positive Breast Tumor Nt2 Derived from the Fvb Her-2/Neu Transgenic Mouse The endoglin vaccines were tested in other breast tumor model in the FVB mouse using the transplantable HER-2/neu tumor NT2. Further, $1\times10^6$ tumor cells were implanted sub-cutaneously in FVB mice and they were immunized with Lm-LLO-CD105 A and B on days 4, 11 and 18, with $2\times10^8$ cfu of each vaccine. Lm-LLO-NY-ESO-1 was used as the control vaccine. Both vaccines significantly impacted tumor growth (FIG. 67) and at day 60, 50% of the mice immunized with Lm-LLO-CD105A were tumor free and 25% of the mice vaccinated with Lm-LLO-CD 105B were tumor free compared to none in the unvaccinated group or the group vaccinated with Lm-LLO-NYESO1.

Example 38

Site-Directed Mutagenesis of the LLO Cholesterol-Binding Domain

Site-directed mutagenesis was performed on LLO to introduce inactivating point mutations in the CBD, using the following strategy. The resulting protein is termed "mutLLO":

Subcloning of LLO into pET29b

The amino acid sequence of wild-type LLO is:

(SEQ ID NO: 123)

MKKIMLVFITLILVSLPIAQQTEAKDASAFNKENSISSVAPPASPPAS

PKTPIEKKHADEIDKYIQGLDYNKNNVLVYHGDAVTNVPPRKGYKDGN

EYIVVEKKKKSINQNNADIQVVNAISSLTYPGALVKANSELVENQPDV

LPVKRDSLTLSIDLPGMTNQDNKIVVKNATKSNVNNAVNTLVERWNEK

YAQAYSNVSAKIDYDDEMAYSESQLIAKFGTAFKAVNNSLNVNFGAIS

EGKMQEEVISFKQIYYNVNVNEPTRPSRFFGKAVTKEQLQALGVNAEN

PPAYISSVAYGRQVYLKLSTNSHSTKVKAAFDAAVSGKSVSGDVELTN

IIKNSSFKAVIYGGSAKDEVQIIDGNLGDLRDILKKGATFNRETPGVP

IEAYTTNFLKDNELAVIKNNSEYIETTSKAYTDGKINIDHSGGYVAQF

NISWDEVNYDPEGNEIVQHKNWSENNKSKLAHFTSSIYLPGNARNINV

YAKECTGLAWEWWRTVIDDRNLPLVKNRISIWGTTLYPKYSNKVDNP

IE.

The signal peptide and the cholesterol-binding domain (CBD) are underlined, with 3 critical residues in the CBD (C484, W491, and W492) in bold-italics.

A 6×His tag (HHHHHH) was added to the C-terminal region of LLO. The amino acid sequence of His-tagged LLO is:

(SEQ ID NO: 124)

MKKIMLVFITLILVSLPIAQQTEAKDASAFNKENSISSVAPPASPPAS

PKTPIEKKHADEIDKYIQGLDYNKNNVLVYHGDAVTNVPPRKGYKDGN

EYIVVEKKKKSINQNNADIQVVNAISSLTYPGALVKANSELVENQPDV

LPVKRDSLTLSIDLPGMTNQDNKIVVKNATKSNVNNAVNTLVERWNEK

YAQAYSNVSAKIDYDDEMAYSESQLIAKFGTAFKAVNNSLNVNGFAIS

EGKMQEEVISFKQIYYNVNVNEPTRPSRFFGKAVTKEQLQALGVNAEN

PPAYISSVAYGRQVYLKLSTNSHSTKVKAAFDAAVSGKSVSGDVELTN

IIKNSSFKAVIYGGSAKDEVQIIDGNLGDLRDILKKGATFNRETPGVP

IAYTTNFLKDNELAVIKNNSEYIETTSKAYTDGKINIDHSGGYVAQFN

ISWDEVNYDPEGNEIVQHKNWSENNKSKLAHFTSSIYLPGNARNINVY

AKECTGLAWEWWRTVIDDRNLPLVKNRNISIWGTTLYPKYSNKVDNP

IEHHHHHH.

A gene encoding a His-tagged LLO protein was digested with NdeI/BamHI, and the NdeI/BamHI was subcloned into the expression vector pET29b, between the NdeI and BamHI sites. The sequence of the gene encoding the LLO protein is:

(SEQ ID NO: 125)

catatgaaggatgcatctgcattcaataaagaaaattcaatttcatcc gtggcaccaccagcatctccgcctgcaagtcctaagacgccaatcgaa aagaaacacgcggatgaaatcgataagtatatacaaggattggattac aataaaaacaatgtattagtataccacggagatgcagtgacaaatgtg ccgccaagaaaaggttacaaagatggaaatgaatatattgttgtggag aaaaagaagaaatccatcaatcaaaataatgcagacattcaagttgtg aatgcaatttcgagcctaacctatccaggtgctctcgtaaaagcgaat tcggaattagtagaaaatcaaccagatgttctccctgtaaaacgtgat tcattaacactcagcattgatttgccaggtatgactaatcaagacaat aaaatagttgtaaaaaatgccactaaatcaaacgttaacaacgcagta aatacattagtggaaagatggaatgaaaaatatgctcaagcttattca aatgtaagtgcaaaaattgattatgatgacgaaatggcttacagtgaa tcacaattaattgcgaaatttggtacagcatttaaagctgtaaataat agcttgaatgtaaacttcggcgcaatcagtgaagggaaaatgcaagaa gaagtcattagttttaaacaaatttactataacgtgaatgttaatgaa cctacaagaccttccagatttttcggcaaagctgttactaaagagcag ttgcaagcgcttggagtgaatgcagaaaatcctcctgcatatatctca agtgtggcgtatggccgtcaagtttatttgaaattatcaactaattcc catagtactaaagtaaaagctgcttttgatgctgccgtaagcggaaaa tctgtctcaggtgatgtagaactaacaaatatcatcaaaaattcttcc ttcaaagccgtaatttacggaggttccgcaaaagatgaagttcaaatc -continued

```
atcgacggcaacctcggagacttacgcgatatttgaaaaaaggcgct
acttttaatcgagaaacaccaggagttcccattgcttatacaacaaac
ttcctaaaagacaatgaattagctgttattaaaaacaactcagaatat
attgaaacaacttcaaaagcttatacagatggaaaaattaacatcgat
cactctggaggatacgttgctcaattcaacatttcttgggatgaagta
aattatgatcctgaaggtaacgaaattgttcaacataaaaactggagc
gaaaacaataaaagcaagctagctcatttcacatcgtccatctatttg
cctggtaacgcgagaaatattaatgtttacgctaaa
```

**gaa*tgc*actggtttagcttgggaa*tggtg***gagaacggtaattgatg

```
accggaacttaccacttgtgaaaaatagaaatatctccatctggggca
ccacgctttatccgaaatatagtaataaagtagataatccaatcgaac
accaccaccaccaccactaataaggatcc.
```

The underlined sequences are, starting from the beginning of the sequence, the NdeI site, the NheI site, the CBG-encoding region, the 6×His tag, and the BamHI site. The CBD resides to be mutated in the next step are in bold-italics.

Splicing by Overlap Extension (SOE) PCR

Figure 69A:
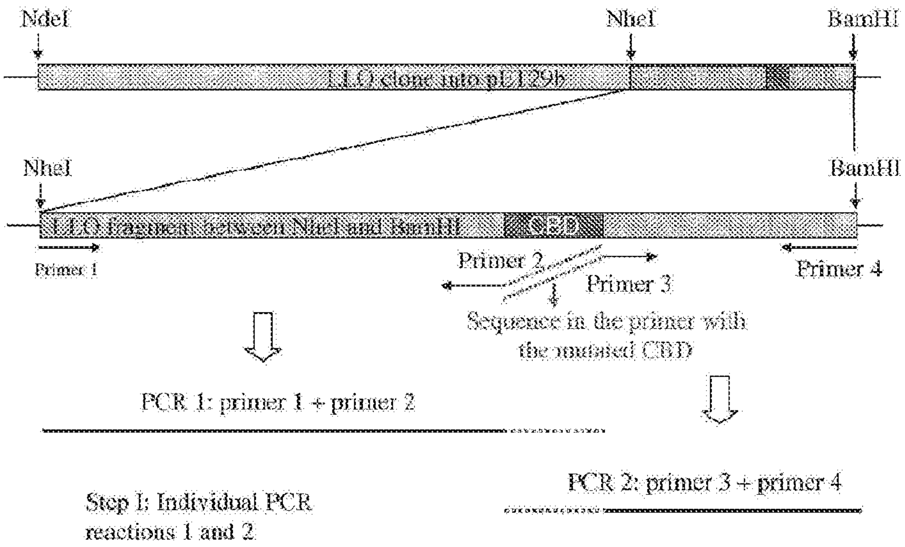
FIG. 69A-B. SOE mutagenesis strategy. Decreasing/lowering the virulence of LLO was achieved by mutating the 4th domain of LLO. This domain contains a cholesterol binding site allowing it to bind to membranes where it oligomerizes to form pores.
Figure 69B:
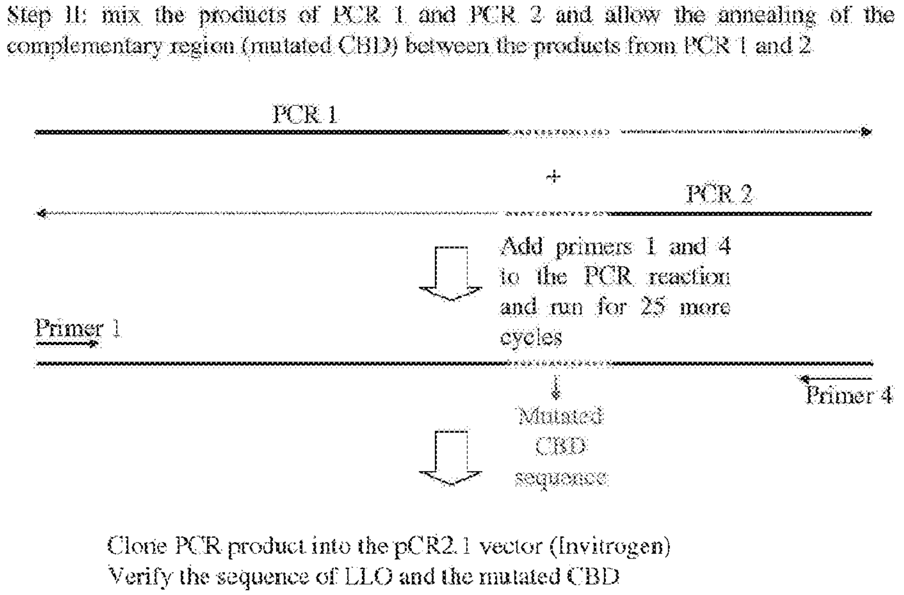

Step 1: PCR reactions #1 and #2 were performed on the pET29b-LLO template. PCR reaction #1, utilizing primers #1 and #2, amplified the fragment between the NheI site and the CBD, inclusive, introducing a mutation into the CBD. PCR reaction #2, utilizing primers #3 and #4, amplified the fragment between the CBD and the BamHI site, inclusive, introducing the same mutation into the CBD (FIG. 69A).

PCR reaction #1 cycle: A) 94° C. 2 min 30 sec, B) 94° C. 30 sec, C) 55° C. 30 sec, D) 72° C. 1 min, Repeat steps B to D 29 times (30 cycles total), E) 72° C. 10 min.

PCR reaction #2 cycle: A) 94° C. 2 min 30 sec, B) 94° C. 30 sec, C) 60° C. 30 sec, D) 72° C. 1 min, Repeat steps B to D 29 times (30 cycles total), E) 72° C. 10 min.

Step 2: The products of PCR reactions #1 and #2 were mixed, allowed to anneal (at the mutated CBD-encoding region), and PCR was performed with primers #1 and #4 for 25 more cycles (FIG. 8B). PCR reaction cycle: A) 94° C. 2 min 30 sec, B) 94° C. 30 sec, C) 72° C. 1 min, Repeat steps B to C 9 times (10 cycles total), Add primers #1 and #4, D) 94° C. 30 sec, E) 55° C. 30 sec, F) 72° C. 1 min, Repeat steps D to F 24 times (25 cycles total), G) 72° C. 10 min.

Primer sequences:

Primer 1: GCTAGCTCATTTCACATCGT (SEQ ID NO: 126; NheI sequence is underlined).

Primer 2:

(SEQ ID NO: 127

TCT*TGCAGC*TTCCCAAGCTAAACCAGT*CGC*TTC

TTTAGCGTAAACATTAATATT;

CBD-encoding sequence is underlined; mutated codons are in bold-italics).

Primer 3:

(SEQ ID NO: 128

GAA*GCG*ACTGGTTTAGCTTGGGAA*GCTGCA*AGA

ACGGTAATTGATGACCGGAAC;

CBD-encoding sequence is underlined; mutated codons are in bold-italics).

Primer 4: GGATCCTTATTAGTGGTGGTGGTGGTG-GTGTTCGATTGG (SEQ ID NO: 129; BamHI sequence is underlined).

The wild-type CBD sequence is ECTGLAWEWWR (SEQ ID NO: 130).

The mutated CBD sequence is EATGLAWEAAR (SEQ ID NO: 131).

The sequence of the mutated NheI-BamHI fragment is (SEQ ID NO: 132)

GCTAGCTCATTTCACATCGTCCATCTATTTGCCTGGTAACGCGAGAAA

TATTAATGTTTACGCTAAA

GAA*GCG*ACTGGTTTAGCTTGGGAA*GCTGCA*AGA

ACGGTAATTGATGACCGGAACTTACCACTTGTGAAAAATAG

AAATATCTCCATCTGGGGCACCACGCTTTATCCGA

AATATAGTAATAAAGTAGATAATCCAATCGAACACCAC

CACCACCACCACTAATAAGGATCC.

Example 39

Replacement of Part of the LLO CBD with a CTL Epitope

Site-directed mutagenesis was performed on LLO to replace 9 amino acids (AA) of the CBD with a CTL epitope from the antigen NY-ESO-1. The sequence of the CBD (SEQ ID NO: 130) was replaced with the sequence E SLLMWITQCR (SEQ ID NO: 133; mutated residues underlined), which contains the HLA-A2 restricted epitope 157-165 from NY-ESO-1, termed "ctLLO."

The subcloning strategy used was similar to the previous Example.

The primers used were as follows:

Primer 1: GCTAGCTCATTTCACATCGT (SEQ ID NO: 126; NheI sequence is underlined).

Primer 2:

(SEQ ID NO: 134

TCT*GCACTGGGTGATCCACATCAGCAGGCT*TTC

TTTAGCGTAAACATTAATATT;

CBD-encoding sequence is underlined; mutated (NY-ESO-1) codons are in bold-italics).

Primer 3:

(SEQ ID NO: 135

GAA*AGCCTGCTGATGTGGATCACCCAGTGC*AGA

ACGGTAATTGATGACCGGAAC;

CBD-encoding sequence is underlined; mutated (NY-ESO-1) codons are in bold-italics).

Primer 4: GGATCCTTATTAGTGGTGGTGGTGGTG-GTGTTCGATTGG (SEQ ID NO: 129; BamHI sequence is underlined).

The sequence of the resulting NheI/BamHI fragment is as follows:

```
                                  (SEQ ID NO: 136)
GCTAGCTCATTTCACATCGTCCATCTATTTGCCTGGTAACGCGAGAAA

TATTAATGTTTACGCTAAA

GAAAGCCTGCTGATGTGGATCACCCAGTGCAGAACGGTAATTGATGA

CCGGAACTTACCACTTGTGAAAAATAGAAATATCTCCATCTGGGGCAC

CACGCTTTATCCGAAATATAGTAATAAAGTAGATAATCCAATCGAACA

CCACCACCACCACCACTAATAAGGATCC.
```

Example 40

Anti-Tumor Efficacy of a Dual CHER2-CA9 *Listeria* Vaccine on the Growth of 4T1 Tumors Implanted in the Mammary Glands of Balb/C Mice Experimental Details:

A recombinant Lm (LmddA-cHer2/CA9) was generated. This Lm strain expresses and secretes a chimeric Her2 (cHer2) protein chromosomally as fusion to genomic Listeriolysin O (LLO) and a fragment of human Carbonic Anhydrase 9 (CA9) using a plasmid as fusion to truncated LLO (tLLO), to multiply target tumor cells.

| Group | 4T1 Tumor Implantation ($7 \times 10^3$) | Vaccine Dose 1 ($1 \times 10^8$ CFU) | Vaccine Boost ($1 \times 10^8$ CFU) | Measurement Dates |
|---|---|---|---|---|
| Naïve-PBS | Jan. 9, 2012 | Jan. 12, 2012 | Jan. 19, 2012 | Jan. 13, 2012, Jan. 20, 2012, Jan. 27, 2012, Jan. 30, 2012 |
| LmddA-PSA | Jan. 9, 2012 | Jan. 12, 2012 | Jan. 19, 2012 | Jan. 13, 2012, Jan. 20, 2012, Jan. 27, 2012, Jan. 30, 2012 |
| LmddA-cHER2 | Jan. 9, 2012 | Jan. 12, 2012 | Jan. 19, 2012 | Jan. 13, 2012, Jan. 20, 2012, Jan. 27, 2012, Jan. 30, 2012 |
| LmddA-CA9 | Jan. 9, 2012 | Jan. 12, 2012 | Jan. 19, 2012 | Jan. 13, 2012, Jan. 20, 2012, Jan. 27, 2012, Jan. 30, 2012 |
| LmddA-cHER2-CA9 | Jan. 9, 2012 | Jan. 12, 2012 | Jan. 19, 2012 | Jan. 13, 2012, Jan. 20, 2012, Jan. 27, 2012, Jan. 30, 2012 |

Vaccine Titers:

LmddA-PSA—$6.5\times10^8$

LmddA-CA9—$1.4\times10^{10}$

LmddA-cHER2—$1.05\times10^{10}$

Dual cHer2-CA9 (LmddA)—$1.5\times10^9$

Experimental Protocols:

4T1 cells were grown in RPMI containing 10% FBS, 2 mM L-Glu, 1.5 g/L sodium bicarbonate, 4.5 g/L glucose, 1 mM sodium pyruvate, and 10 mM HEPES. On the day of injection, cells were trypsinized then washed 2× in PBS. Cells were counted and resuspended at $7\times10^3$ cells/50 μl.

Tumors were implanted in the mammary glands of each of the mice. There are 16 mice per group. The mice were vaccinated 3 days later. On day 4, 4 mice in each group were euthanized and examined for tumor growth. Mice were given the boost of each vaccine on day 10. On day 11, 4 mice in each group were euthanized and tumors were measured. On day 18, 4-5 mice in each group were euthanized and tumors were measured. On day 21, the remaining mice in each group were euthanized and the tumors were measured.

Results

On day 4, the tumors are barely palpable, so no measurements were made.

| PBS Average | PSA | PSA Average | CA9 | CA9 Average | HER2 | Her2 Average | Dual | Dual Average |
|---|---|---|---|---|---|---|---|---|
| Day 11 | | | | | | | | |
| 3.915 | 3.99 × 2.73 | 3.36 | 1.3 × 2.1 | 1.7 | 2.3 × 3.2 | 2.75 | 0 | 0 |
| 1.75 | 3.58 × 4.91 | 4.245 | 3.3 × 4.1 | 3.7 | 1.3 × 3.2 | 2.25 | 0 | 0 |
| 2.8 | 1.93 × 2.3 | 2.115 | 2.2 × 3.1 | 2.65 | 2.1 × 2.2 | 2.15 | 1.1 × 1.3 | 1.2 |

-continued

| PBS Average | PSA | PSA Average | CA9 | CA9 Average | HER2 | Her2 Average | Dual | Dual Average |
|---|---|---|---|---|---|---|---|---|
| 2.15 | 2.2 × 3.1 | 2.65 | 2.2 × 1.4 | 1.8 | 1.2 × 3.1 | 2.15 | 2.1 × 3.2 | 2.65 |
| 2.65 | | 3.09 | | 2.46 | | 2.33 | | 0.96 |
| | | | | Day 18 | | | | |
| 9.465 | 5.8 × 11.12 | 8.46 | 4.18 × 3.49, 2.75 × 3.34 | 6.88 | 4.74 × 6.34 | 5.54 | 5.24 × 4.59 | 4.915 |
| 7.27 | 6.02 × 7.5, 3.54 × 6.74 | 11.9 | 5.72 × 7.23 | 6.475 | 3.73 × 7.34 | 5.535 | 4.92 × 4.87 | 4.895 |
| 11.335 | 5.06 × 7.18, 3.72 × 3.44 | 9.7 | 4.08 × 7.64 | 5.86 | 2.97 × 5.34 | 4.155 | 3 × 5.55 | 4.275 |
| 6.645 | 9.17 × 10.49 | 9.83 | 4.08 × 3.54 | 3.81 | 7.41 × 5.05 | 6.23 | 2.89 × 6.73, 2.87 × 4.37 | 8.43 |
| 10.375 | 1 found dead | | 1 found dead | | 5.7 × 5.95 | 5.825 | 2.82 × 5.27 | 4.045 |
| 9.018 | | 9.9725 | | 5.76 | | 5.42 | | 5.312 |
| | | | | Day 21 | | | | |
| 11.615 | 7.53 × 10.63 | 9.08 | 4.86 × 9.68 | 7.24 | 8.72 × 10.78, 1.3 × 2.41 | 11.605 | 4.12 × 6.18 | 5.15 |
| 8.945 | 8.38 × 11.61 | 9.995 | 5.03 × 8.38 | 6.705 | 6.8 × 5.91 | 6.355 | 4.76 × 6.36 | 5.56 |
| | 8.66 × 9.41 | 9.035 | 1 found dead | | 1 found dead | | 1 found dead | |
| 10.28 | | 9.37 | | 6.97 | | 8.98 | | 5.355 |

Figure 70:
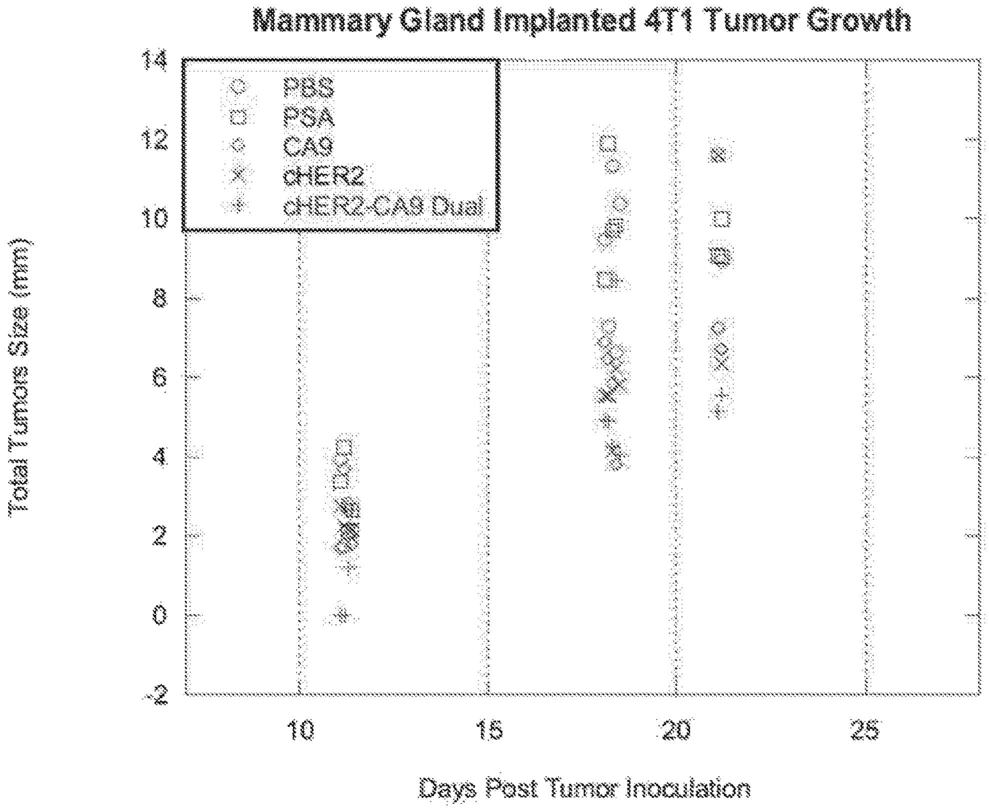
FIG. 70. Graph showing the individual mice and the tumor sizes on the days of tumor measurement: days 11, 18, and 21 following administration of various *Listeria*-based constructs.

The numbers show that the dual vaccine (recombinant *Listeria* expressing two heterologous antigens) initially (day 11) has a large impact on the tumor mass (FIG. 70). Two of the mice euthanized had no tumors and the others were smaller than the control and around the size of the mono-CA9 and cHER2 vaccinated mice. By day 18, multiple tumors can be measured in some of the mice in several of the groups. The PBS and PSA control mice have much larger tumors than the mono-CA9 and cHER2 or the dual vaccine groups. The dual vaccine group has one outlier with a large tumor burden, otherwise the average for that group would have been the smallest. The experiment was terminated early as the mice in several groups were looking very sick and had been dying. However, at the last measurement, the mice in the dual vaccine group had the smallest tumors (FIG. 70). This may be due to the level of control on tumor growth that was seen early on.

In conclusion, the dual vaccine shows an initial level of tumor control in the 4T1 model that is higher than levels achieved with the mono-vaccines or the control mice as the dual vaccine groups have the smallest tumor burden at the end of the experiment (see FIG. 70).

The preceding examples are presented in order to more fully illustrate the embodiments of the invention. They should in no way be construed, however, as limiting the broad scope of the invention.

Example 41

Development of a Recombinant *L. Monocytogenes* Vector with Enhanced Anti-Tumor Activity by Concomitant Expression and Secretion of LLO-PSA and TLLO-HMW-$MAA_{2160-2258}$ Fusion Proteins, Eliciting Immune Responses to Both Heterologous Antigens Materials and Methods:

Construction of the pADV168 plasmid. The HMW-MAA-C fragment is excised from a pCR2.1-HMW-$MAA_{210-2258}$ plasmid by double digestion with XhoI and XmaI restriction endonucleases. This fragment is cloned in the pADV134 plasmid already digested with XhoI and XmaI to excise the E7 gene. The pADV168 plasmid is electroporated into electrocompetent the $dal^{(-)}$ $dat^{(-)}$ *E. coli* strain MB2159 and positive clones screened for RFLP and sequence analysis.

Construction of Lmdd-143/168, LmddA-143/168 and the control strains LmddA-168, Lmdd-143/134 and LmddA-143/134. Lmdd, Lmdd-143 and LmddA-143 is transformed with either pADV168 or pADV134 plasmid. Transformants are selected on Brain-Heart Infusion-agar plates supplemented with streptomycin (250 μg/ml) and without D-alanine (BHIs medium). Individual clones are screened for LLO-PSA, tLLO-HMW-$MAA_{2160-2258}$ and tLLO-E7 secretion in bacterial culture supernatants by Western-blot using an anti-LLO, anti-PSA or anti-E7 antibody. A selected clone from each strain will be evaluated for in vitro and in vivo virulence. Each strain is passaged twice in vivo to select the most stable recombinant clones. Briefly, a selected clone from each construct is grown and injected i.p to a group of 4 mice at $1\times10^8$ CFU/mouse. Spleens are harvested on days 1 and 3, homogenized and plated on BHIs-agar plates. After the first passage, one colony from each strain is selected and passaged in vivo for a second time. To prevent further attenuation of the vector, to a level impairing its viability, constructs in two vectors with distinct attenuation levels (Lmdd-143/168, LmddA-143/168) are generated.

Figure 71A:
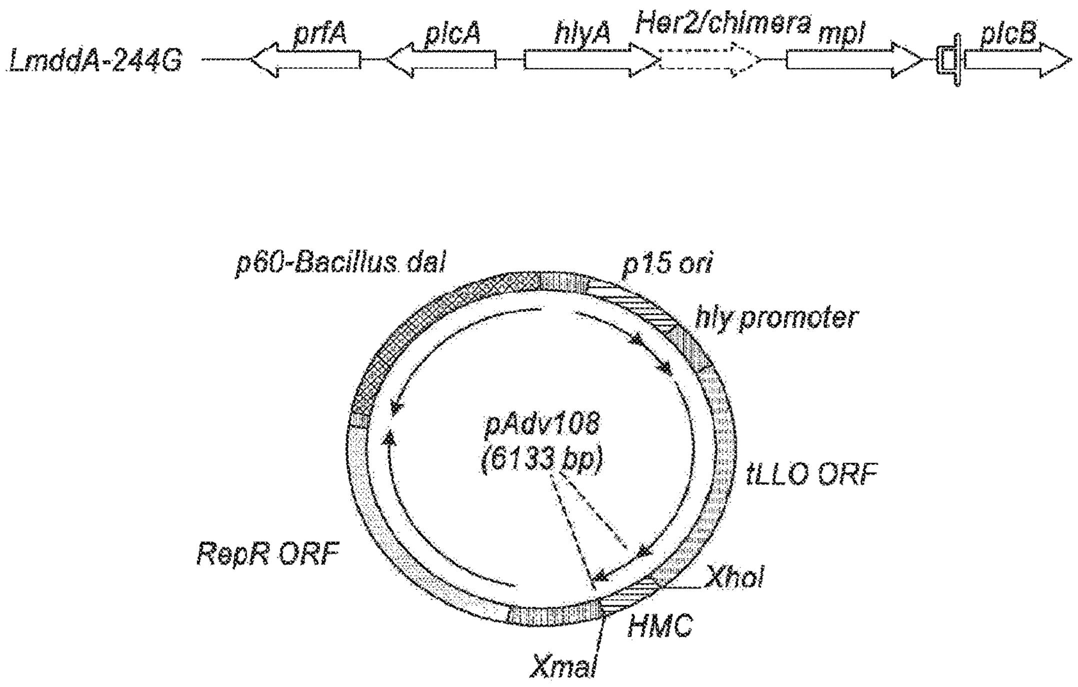
FIG. 71. A Construction of *Listeria* strain engineered to express and secrete two antigens as fusion protein, LmddA244G. The antigen Her2 chimera was genetically fused to the genomic Listeriolysin O and the second antigen HMW-MAA-C(HMC) was fused to truncated Listeriolysin O in the plasmid. B. The secretion of fusion proteins LLO-ChHer2 and tLLO-HMC was detected by western blot using anti-LLO and anti-FLAG antibodies respectively.
Figure 71B:
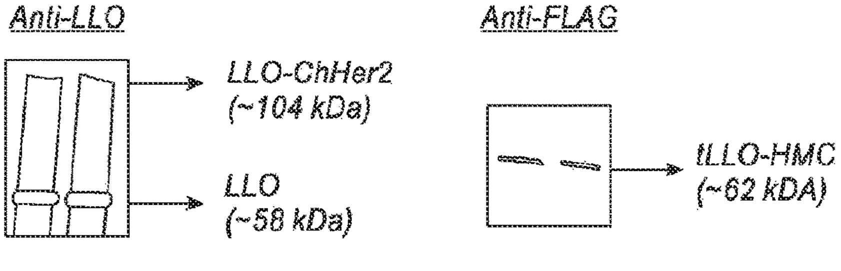

Construction of *Listeria* strain engineered to express and secrete two Antigens as fusion proteins, LmddA244G. The antigen Her2 chimera was genetically fused to the genomic Listeriolysin O and the second antigen HMW-MAA-C (HMC) was fused to a truncated Listeriolysin O in the plasmid (FIG. 71 A). The secretion of fusion proteins LLO-ChHer2 and tLLO-HMC were detected by western blot using anti-LLO and anti-FLAG antibodies respectively (see FIG. 71B).

Hemolytic assay. To determine the ability of genomic LLO to cause phagolysosomal escape a hemolytic assay was performed using secreted supernatant of control wild type 10403S and LmddA244G-168 and sheep red blood cells as target cells.

In vitro intracellular replication in J774 cells. An in vitro intracellular growth assay was performed using a murine macrophage-like J774 cell line. Briefly, J774 cells were infected for 1 hour in medium without antibiotics at MOI of 1:1 with either one of the mono vaccines (LmddA164 and LmddA168) or bivalent immunotherapy. At 1 h post-infection, cells were treated with 10 μg/ml of gentamicin to kill extracellular bacteria. Samples were harvested at regular time intervals and cells lysed with water to quantify the number of intracellular CFU. Ten-fold serial dilutions of the lysates are plated in duplicates on BHI plates and colony-forming units (CFU) were counted in each sample.

In vivo virulence studies. Groups of four C57BL/6 mice (7 weeks old) are injected i.p. with two different doses ($1\times10^8$ and $1\times10^9$ CFUs/dose) of Lmdd-143/168, LmddA-143/168, LmddA-168, Lmdd-143/134 or LmddA-143/134 strains. Mice are followed-up for 2 weeks for survival and $LD_{50}$ estimation. An $LD_{50}$ of $>1\times10^8$ constitutes an acceptable value based on previous experience with other Lm-based vaccines.

Results

Once the pADV168 plasmid is successfully constructed, it is sequenced for the presence of the correct HMW-MAA sequence. This plasmid in these new strains express and secrete the LLO fusion proteins specific for each construct. These strains are highly attenuated, with an LD50 of at least $1\times10^8$ CFU and likely higher than $1\times10^9$ CFU for the actA-deficient (LmddA) strains, which lack the actA gene and consequently the ability of cell-to-cell spread.

A recombinant Lm (LmddA-cHer2/HMC) was generated. This Lm strain expresses and secretes a chimeric Her2 (cHer2) protein chromosomally as fusion to genomic Listeriolysin O (LLO) and a fragment of $HMW\text{-}MAA_{2160\text{-}2258}$ (also named HMW-MAA C or HMC) using a plasmid as fusion to truncated LLO (tLLO), to target tumor cells and tumor vasculature concomitantly referred as LmddA244G-168. The expression and secretion of both the fusion proteins tLLO-HMC and LLO-cHer2 from LmddA244G-168 was detected by western blot using anti-FLAG and anti-LLO specific antibodies (FIG. 71B). Furthermore, the vaccine LmddA244G-168 was passaged twice in vivo in mice to stabilize the virulence of LmddA-244G and to confirm that it retained the expression of recombinant fusion proteins (FIG. 71B). The vaccine LmddA244G-168 retained its ability to express and secrete both the fusion proteins, tLLO-HMC and LLO-cHer2 after two in vivo mice passages.

Figure 72A:
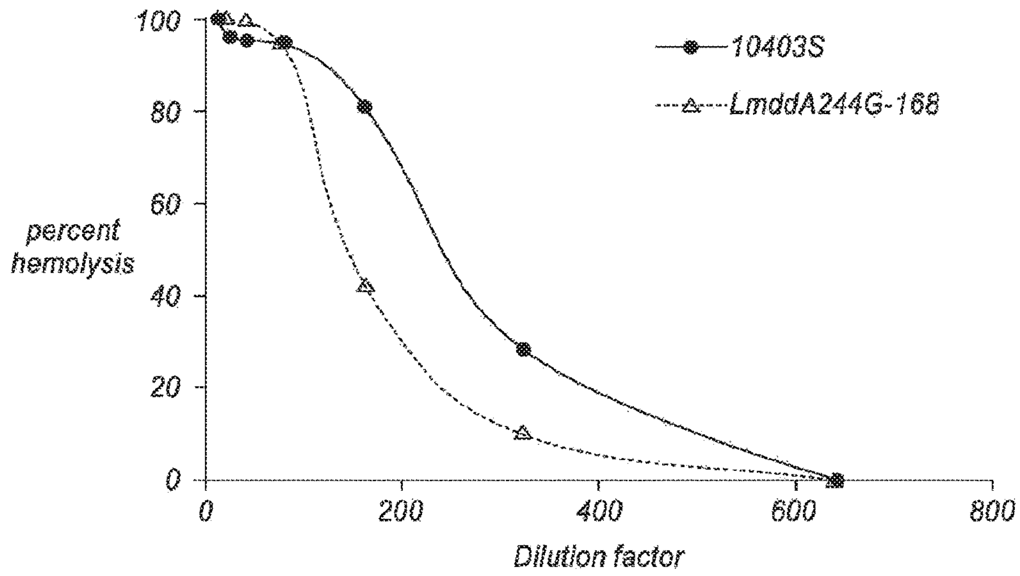
FIG. 72. Hemolytic activity of LmddA244G-168 was quantified using Sheep Red Blood cells. A 1.5 fold reduction in the hemolytic activity of bivalent immunotherapy LmddA244G-168 was observed when compared to 10403S. B. Intracellular growth of both bivalent and monovalent immunotherapies in J774 cell line. The intracellular growth of LmddA244G-168 was similar to monovalent immunotherapies LmddA164 and LmddA168.

The strain LmddA244G-168, expresses chromosomal LLO as fusion protein LLO-cHer2 which may impact the functional ability of LLO to cause phagolysosomal escape. To determine this hemolytic assay was performed using secreted supernatant of control wild type 10403S and LmddA244G-168 and sheep red blood cells as target cells. As indicated in FIG. 72A, there was a 1.5 fold reduction in the hemolytic ability of LmddA244G-168 when compared to wild type highly virulent Lm strain 10403S.

Figure 72B:
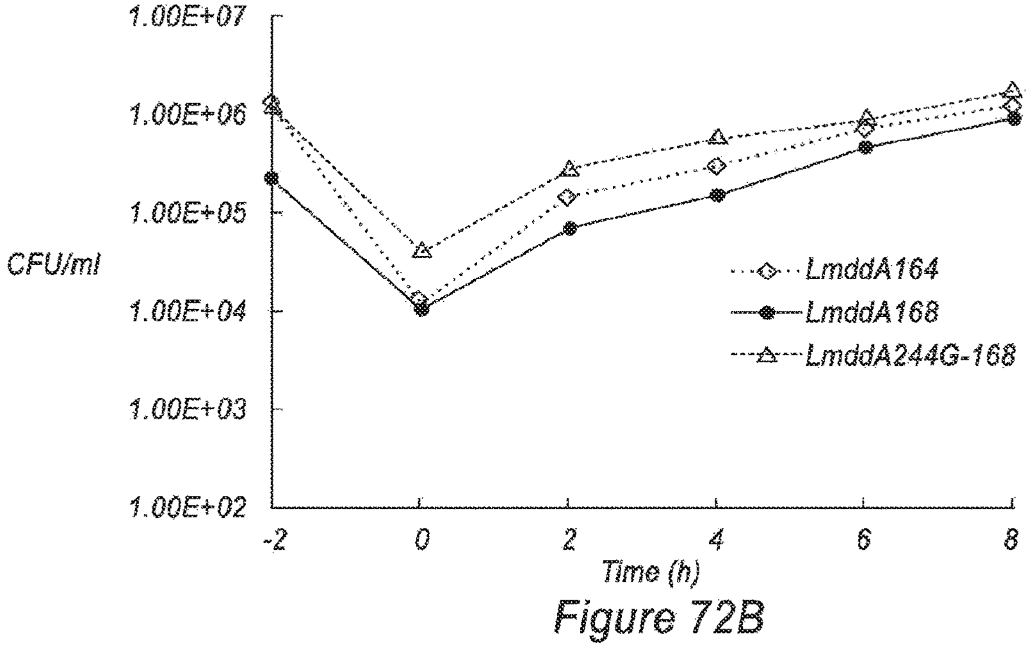

Additionally, to examine if the expression of fusion protein LLO-cHer2 did not cause any deleterious effect on the ability of LmddA-cHer2/HMC to infect macrophages and its intracellular growth, a cell infection assay was performed using mouse macrophage like cells J774. The results as specified in FIG. 72B showed that intracellular growth behavior of different *Listeria*-based immunotherapies expressing either single or dual antigens were similar suggesting that the co-expression of two antigens did not cause any change in the ability of LmddA244G-168 to present target intracellular proteins for immunological responses.

Example 42

Detection of Immune Responses and Anti-tumor Effects Elicited Upon Immunization with Lmdd-244G/168

Immune responses to cHer2 and HMW-MAA are studied in mice upon immunization with Lmdd-244G-168 strain using standard methods, such as detection of IFN-γ production against these antigens. The therapeutic efficacy of dual-expression vectors are tested in the NT2 breast tumor model.

IFN-γ ELISpot. We evaluated the ability of bivalent immunotherapy to generate immune responses specific for the two antigens Her2 and HMW-MAA in FvB mice. Mice (3/group) were immunized with different immunotherapies such as LmddA134 (Lm-control), LmddA164 and LmddA244G/168 on day 0 and boosted on day 14. Her2/neu specific immune responses were detected in the spleens harvested on day 21. The IFN-γ ELispot assay was done according to the kit instructions and spleen cells were stimulated with peptide epitope specific for the intracellular region (RLLQETELV) (SEQ ID NO. 76).

IFN-γ ELISA. The generation of HMW-MAA-C specific immune responses in the splenocytes of immunized mice was determined by stimulating cells with HMA-MAA-C protein for 2 days. The IFN-γ release was detected by ELISA performed using mouse interferon-gamma ELISA kit.

Anti-tumor efficacy. The antitumor efficacy was examined using mouse NT2 breast tumor model. FvB mice were implanted with $1\times10^6$ NT2 cells on day 0 and established tumors on right flank were treated starting day 6 with three immunizations at weekly intervals with different immunotherapies. Tumors were monitored twice a week until the end of the study. Mice were euthanized if the tumor diameter was greater than 1.5 cm.

Results

Figure 73A:
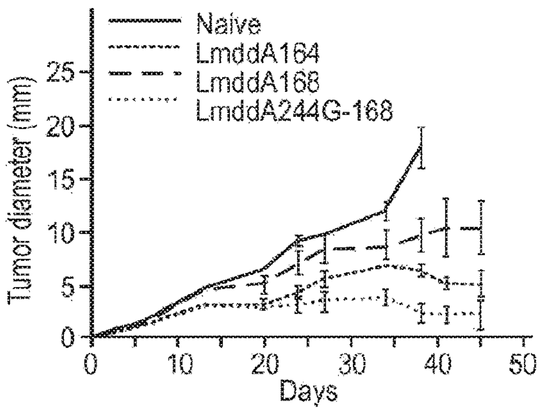
FIG. 73. A. Established NT2 tumors were implanted with treated with mono therapies and bivalent therapy on days 6, 13 and 20. The naïve group is untreated mice. B. The percent tumor free mice in different treatment and untreated naïve group. C. The volume of established NT2 tumors after of LmddA244G-168 treatment.
Figure 73B:
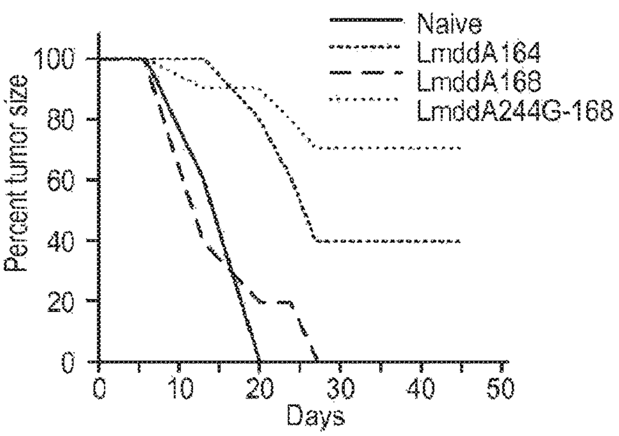
Figure 73C:
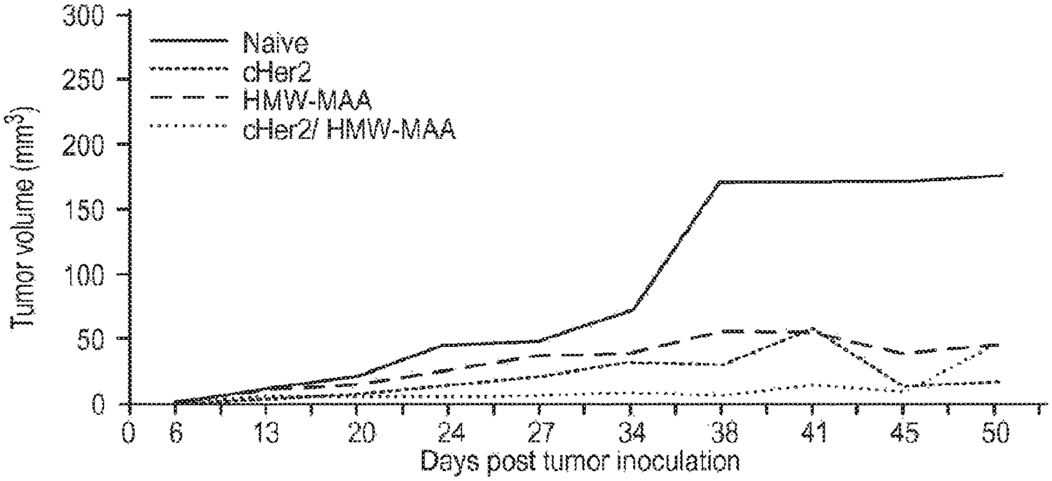

Next, the anti-tumor therapeutic efficacy of LmddA244G was examined using mouse NT2 breast tumor model. The FvB mice bearing established NT2 tumors on right flank were treated with three immunizations at one week interval with different immunotherapies expressing either mono antigens LmddA164 (ChHer2), LmddA168 (HMC) or bivalent immunotherapy LmddA244G-168. Treatment with both mono- and bivalent-immunotherapy caused a reduction of NT2 tumor as indicated in FIGS. 73A and 73C. However, a stronger impact on the control of NT2 tumor growth was observed after treatment with bivalent-immunotherapy. Additional analysis on the percent tumor free mice in each group confirmed that treatment with bivalent immunotherapy generated maximum tumor-free mice (70%) when compared to mono-immunotherapy (less than 40%) treated groups. These observations support that targeting two antigens concurrently using *Listeria monocytogenes* as vector for therapy resulted in enhanced anti-tumor efficacy.

Figure 74A:
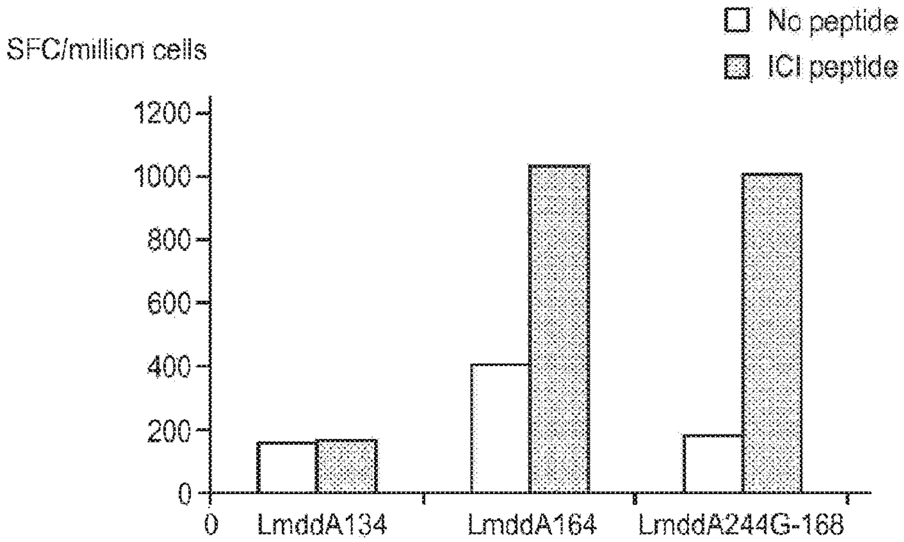
FIG. 74. A. Generation of Her2 specific immune responses in mice after administration of monovalent (LmddA164) as well as bivalent immunotherapy (LmddA244G-168) expressing chimera Her2. The Her2 specific immune responses were evaluated in an ELIspot based assay using FvB IC1 peptide epitope-RLLQETELV (Seavey et al 2009, Clin Cancer Res. 2009 Feb. 1; 15(3): 924-32. B. Generation of HMW-MAA-C specific immune responses in mice after administration of monovalent (LmddA168) as well as bivalent immunotherapy (LmddA244G-168) expressing HMW-MAA-C. The Her2 specific immune responses were evaluated in an ELISA based assay using affinity purified HMA-MAA-C protein fragment.
Figure 74B:
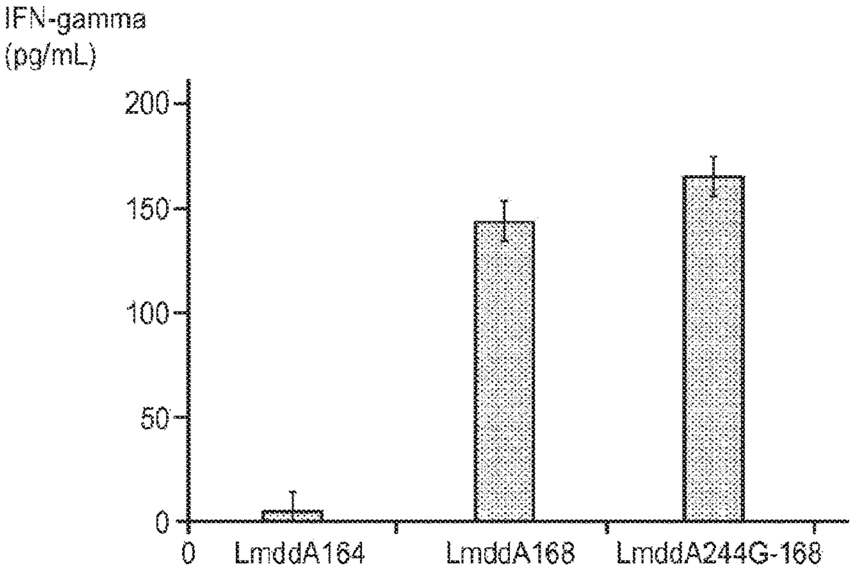

The ability of bivalent immunotherapy was evaluated to generate immune responses specific for the two antigens Her2 and HMW-MAA in FvB mice. Mice were immunized with different immunotherapies such as LmddA134 (irrelevant control), LmddA164 and LmddA244G/168 on day 0 and boosted on day 14. Her2/neu specific immune responses were detected using an ELISpot based assay using peptide epitope specific for intracellular region. Both mono and bivalent-immunotherapy expressing Her2 generated comparable levels of immune responses detected using ELISpot-based assay (see FIG. 74).

The generation and for HMW-MAA-C specific immune responses in the splenocytes of immunized mice was detected using ELISA. The expression of tumor antigen from Lm using either single copy (mono immunotherapy) or multicopy (bivalent immunotherapy) based expression generates comparable level of antigen-specific immune responses (see FIG. 74).

Example 43

Anti-tumor Efficacy of a Dual cHER2-Hmw-Maa *Listeria* Vaccine on the Growth of 4T1 Tumors Implanted in the Mammary Glands of Balb/c Mice.

Experimental Details:

A recombinant Lm (LmddA-cHer2/HMW-MAA) was generated. This Lm strain expresses and secretes a chimeric Her2 (cHer2) protein chromosomally as fusion to genomic Listeriolysin O (LLO) and high molecular weight melanoma associated antigen (HMW-MAA) using a plasmid as fusion to truncated LLO (tLLO), to multiply target tumor cells.

TABLE 4

| | 4T1-HMW- | Immunotherapy | | | |
|---|---|---|---|---|---|
| Groups | MAA Tumor Implantation ($1 \times 10^4$) | Dose 1 ($1 \times 10^8$ CFU) | Dose 2 ($1 \times 10^8$ CFU) | Dose 3 ($1 \times 10^8$ CFU) | Measurement Dates |
| Naïve-PBS | Day 0 | Day 1 | Day 8 | Day 15 | 1X/Week |
| cHer2 | Day 0 | Day 1 | Day 8 | Day 15 | 1X/Week |
| HMW-MAA | Day 0 | Day 1 | Day 8 | Day 15 | 1X/Week |
| cHer2/ HMW-MAA | Day 0 | Day 1 | Day 8 | Day 15 | 1X/Week |

Vaccine Titers:

LmddA-PSA—$6.5 \times 10^8$

LmddA-HMW-MMA—$1.4 \times 10^{10}$

LmddA-cHER2—$1.05 \times 10^{10}$

Dual cHer2- HMW-MMA (LmddA)—$1.5 \times 10^9$

Experimental Protocols:

4T1 cells were grown in RPMI containing 10% FBS, 2 mM L-Glu, 1.5 g/L sodium bicarbonate, 4.5 g/L glucose, 1 mM sodium pyruvate, and 10 mM HEPES. On the day of injection, cells were trypsinized then washed 2× in PBS. Cells were counted and resuspended at $7 \times 10^3$ cells/50 µl.

Tumors were implanted in the mammary glands of each of the mice. There are 16 mice per group. The mice were vaccinated 3 days later. On day 8, 4 mice in each group were euthanized and examined for tumor growth. Mice were given the boost of each vaccine on day 8. On day 15, 4 mice in each group were euthanized and tumors were measured.

Mice were given another boost of each vaccine on day 15. On day 15, 21, 28 and 35, 4-5 mice in each group were euthanized and tumors were measured. On days 42, the remaining mice in each group were euthanized and the tumors were measured.

Results

Figure 75:
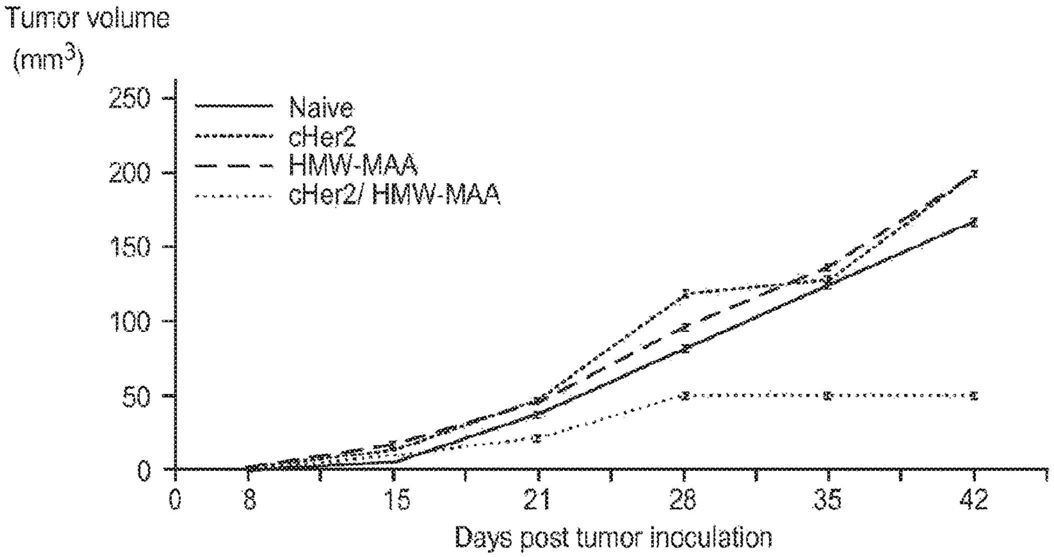
FIG. 75. Established 4T1 tumors were treated with mono therapies and bivalent therapy on days 1, 8, and 15. The naïve group is untreated mice.

The results are summarized in FIG. 75. The graphs show that the dual vaccine (recombinant *Listeria* expressing two heterologous antigens) has a large impact on the tumor volume (FIG. 75). The volumes of tumors in mice receiving bivalent therapy were smaller than both the control and the mono-HMW-MMA and cHER2 vaccinated mice. The PBS and PSA control mice have tumors that are comparable in volume to the mono-HMW-MMA and cHER2 groups.

In conclusion, the dual vaccine shows an initial level of tumor control in the 4T1 model that is higher than levels achieved with the mono-vaccines or the control mice as the dual vaccine groups have the smallest tumor burden at the end of the experiment (see FIG. 75).

Example 44

Comparative Study of Anti-Tumor Efficacy of a Dual and Sequential Cher2-Hmw-Maa *Listeria* Vaccine on the Growth of Nt2 Breast Tumor Model Experimental Details:

The antitumor efficacy was examined using mouse NT2 breast tumor model. FvB mice were implanted with $1 \times 10^6$ NT2 cells on day 0 and established tumors on right flank were treated starting day 6 with three immunizations at weekly intervals with different immunotherapies. Tumors were monitored twice a week until the end of the study. Mice were euthanized if the tumor diameter was greater than 1.5 cm.

TABLE 5

| Groups | NT2 Tumor Implantation ($1 \times 10^6$) | Immunotherapy Doses ($1 \times 10^8$ CFU) starting on Day 7 | Measurement Dates |
|---|---|---|---|
| Naïve-PBS | Day 0 | PBS; 5 doses; one week apart | 2X/Week |
| cHer2 | Day 0 | 5 doses; one week apart | 2X/Week |
| HMW-MAA | Day 0 | 5 doses; one week apart | 2X/Week |
| cHer2 + HMW-MAA | Day 0 | 5 doses; one week apart | 2X/Week |
| cHer2 followed by HMW-MAA | Day 0 | Doses one week apart; 3 doses of cHer2 followed by 3 doses of HMW-MAA | 2X/Week |

Results

The anti-tumor therapeutic efficacy of different *listeria* vaccine regiments was examined using mouse NT2 breast tumor model. The FvB mice bearing established NT2 tumors on right flank were treated with five immunizations of $1 \times 10^8$ at one week intervals with different immunotherapies expressing either mono antigens LmddA164 (ChHer2), LmddA168 (HMC), or combination of therapies expressing both antigens administered simultaneously (bivalent therapy). In addition, a combination vs sequential therapy was carried out with different immunotherapies expressing either mono antigens LmddA164 (ChHer2), LmddA168

Figure 76:
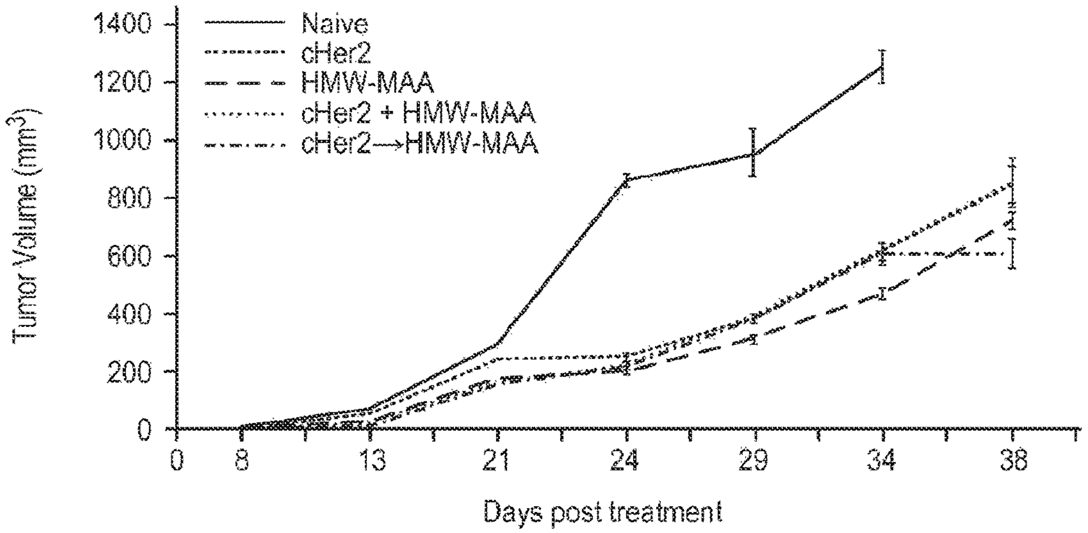
FIG. 76. Established NT2 tumors were treated with mono therapies, bivalent therapy, or sequential mono therapies. The naïve group is untreated mice.

(HMC), a combination of therapies expressing both antigens administered simultaneously (bivalent therapy), or a combination of sequential administration of each mono antigen (cHer2 followed by HMW-MAA). In the latter, 3 weekly doses of LmddA164 (ChHer2) were administered and were followed by 3 weekly doses of LmddA168 (HMC). The results are summarized in FIG. 76. All the regiments caused approximately equivalent reduction of NT2 tumor volume as indicated in FIG. 76. These observations show that simultaneous or sequential administration of two monovalent constructs was at least comparable to bivalent constructs in controlling tumor growth (FIG. 76).

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of inducing a multi-target immune response in a subject having a disease, comprising:

(a) evaluating the expression or presence of two or more biomarker peptides associated with the disease or genes encoding the biomarker peptides in a biological sample from the subject; and (b) administering to the subject a composition comprising a recombinant *Listeria* strain comprising a nucleic acid encoding a fusion protein, wherein the fusion protein comprises the two or more biomarker peptides identified in the biological sample fused to a peptide containing a sequence rich in proline (P), glutamic acid (E), serine (S), and threonine (T) residues (PEST-containing peptide), thereby inducing the multi-target immune response in the subject, wherein the multi-target immune response comprises an immune response against the two or more biomarker peptides.

2. The method of claim 1, wherein step (a) comprises evaluating expression of the two or more biomarker peptides associated with the disease in the biological sample.

3. The method of claim 1, wherein step (a) comprises:
(i) obtaining the biological sample from the subject; and
(ii) evaluating the expression or presence of the two or more biomarker peptides associated with the disease or the genes encoding the biomarker peptides in the biological sample.

4. The method of claim 1, wherein the antigenic biomarker peptides are overexpressed in subjects having the disease as compared to normal levels of expression of the antigenic biomarker peptides in healthy subjects.

5. The method of claim 1, wherein the disease is a congenital disease, and infectious disease, a cancer, or a tumor growth.

6. The method of claim 1, wherein the biological sample is blood, tissue, deoxyribonucleic acid (DNA), ribonucleic acid (RNA), sperm, cerebrospinal fluid, sputum, or serum.

7. The method of claim 1, further comprising administering to the subject a booster dose of the composition comprising the recombinant *Listeria* strain.

8. The method of claim 1, further comprising administering an additional composition prior to, concurrently with, or following administration of the composition comprising the recombinant *Listeria* strain.

9. The method of claim 8, wherein the additional composition is a DNA vaccine encoding an additional fusion protein comprising an additional antigenic biomarker peptide expressed in the biological sample, a viral vector comprising the additional fusion protein, a virus-like particle comprising the additional fusion protein, or a live, recombinant, non-*Listeria* bacterial vector expressing the additional fusion protein.

10. The method of claim 8, further comprising administering to the subject a booster dose of the additional composition.

11. The method of claim 1, further comprising administering an active agent.

12. The method of claim 11, wherein the active agent is an immune checkpoint inhibitor, an antibody or fragment thereof, a chimeric antigen receptor engineered T cell, or a combination thereof.

13. The method of claim 1, wherein the fusion protein in the recombinant *Listeria* strain in step (b) comprises two to ten antigenic biomarker peptides.

14. The method of claim 1, wherein the PEST-containing peptide is an N-terminal listeriolysin O (LLO) peptide or an N-terminal ActA peptide.

15. The method of claim 1, wherein the recombinant *Listeria* strain comprises a genomic mutation or deletion of a dal gene and a dat gene.

16. The method of claim 15, wherein the nucleic acid in the recombinant *Listeria* strain comprises an open reading frame encoding an alanine racemase enzyme or a D-amino acid transferase enzyme.

17. The method of claim 1, wherein the recombinant *Listeria* strain comprises a genomic mutation or a deletion of an actA gene.

18. The method of claim 1, wherein the recombinant *Listeria* strain comprises a genomic mutation or a deletion of a prfA gene.

19. The method of claim 1, wherein the nucleic acid in the recombinant *Listeria* strain is present in a stable extrachromosomal plasmid.

20. The method of claim 1, wherein the nucleic acid in the recombinant *Listeria* strain is present in a plasmid comprising sequences that encode for integration of the plasmid into a *Listeria* chromosome.

21. The method of claim 1, wherein the *Listeria* is *Listeria monocytogenes*.

22. The method of claim 1, wherein the disease is a tumor, and the biomarker is a tumor antigen expressed by the tumor or its vasculature.

23. The method of claim 22, wherein the tumor antigen is associated with the formation of or proliferation of the tumor.

24. The method of claim 1, wherein the method results in an increase of a cluster of differentiation 8 (CD8±T-cell to T-regulatory cell suppressor ratio.

25. The method of claim 1, wherein the method treats or prevents the recurrence of the disease.

26. The method of claim 1, wherein the recombinant *Listeria* strain is a recombinant, attenuated, auxotrophic *Listeria monocytogenes*strain comprising a genomic mutation or deletion of a dal gene, a dat gene, and an actA gene, wherein the PEST-containing peptide is an N-terminal listeriolysin O (LLO) peptide, and wherein the nucleic acid in the recombinant *Listeria* strain is present in a stable extrachromosomal plasmid and further comprises an open reading frame encoding an alanine racemase enzyme or a D-amino acid transferase enzyme.

27. The method of claim 26, wherein the disease is a tumor, and the biomarker is a tumor antigen expressed by the tumor or its vasculature.

28. A method of inducing a multi-target immune response in a subject having a disease, comprising:
(a) evaluating the expression or presence of two or more biomarker peptides associated with the disease or genes encoding the biomarker peptides in a biological sample from the subject; and
(b) administering to the subject a composition comprising a recombinant *Listeria* strain comprising a nucleic acid encoding two or more fusion proteins, wherein each of the two or more fusion proteins comprises a different biomarker peptide identified in the biological sample fused to a peptide containing a sequence rich in proline (P), glutamic acid (E), serine (S), and threonine (T) residues (PEST-containing peptide), thereby inducing the multi-target immune response in the subject, wherein the multi-target immune response comprises an immune response against the two or more biomarker peptides.

29. A method of inducing a multi-target immune response in a subject having a disease, comprising:
(a) evaluating the expression or presence of two or more biomarker peptides associated with the disease or genes encoding the biomarker peptides in a biological sample from the subject; and
(b) administering to the subject a mixture of two or more compositions, each comprising a recombinant *Listeria* strain comprising a nucleic acid encoding a fusion protein, wherein each fusion protein comprises a different biomarker peptide identified in the biological sample fused to a peptide containing a sequence rich in proline (P), glutamic acid (E), serine (S), and threonine (T) residues (PEST-containing peptide), thereby inducing the multi-target immune response in the subject, wherein the multi-target immune response comprises an immune response against the two or more biomarker peptides.

* * * * *

UNITED STATES PATENT AND TRADEMARK OFFICE
CERTIFICATE OF CORRECTION

PATENT NO. : 10,143,734 B2
APPLICATION NO. : 15/119661
DATED : December 4, 2018
INVENTOR(S) : Petit Page 1 of 1

It is certified that error appears in the above-identified patent and that said Letters Patent is hereby corrected as shown below:

In the Claims

Column 246, Claim 26, Line 17:
"*monocytogenes*strain" should read --*monocytogenes* strain--

Signed and Sealed this
Nineteenth Day of February, 2019

Andrei Iancu
*Director of the United States Patent and Trademark Office*